US011492651B2

(12) United States Patent
Gabant

(10) Patent No.: US 11,492,651 B2
(45) Date of Patent: Nov. 8, 2022

(54) METHODS AND COMPOSITIONS FOR MAKING BACTERIOCINS AND ANTIMICROBIAL PEPTIDES

(71) Applicant: Syngulon SA, Seraing (BE)

(72) Inventor: Philippe Gabant, Ottignies Louvain-la-Neuve (BE)

(73) Assignee: Syngulon SA, Seraing (BE)

( * ) Notice: Subject to any disclaimer, the term of this patent is extended or adjusted under 35 U.S.C. 154(b) by 0 days.

(21) Appl. No.: 16/642,342

(22) PCT Filed: Aug. 30, 2018

(86) PCT No.: PCT/US2018/048846
§ 371 (c)(1),
(2) Date: Feb. 26, 2020

(87) PCT Pub. No.: WO2019/046577
PCT Pub. Date: Mar. 7, 2019

(65) Prior Publication Data
US 2020/0263221 A1 Aug. 20, 2020

Related U.S. Application Data

(60) Provisional application No. 62/720,804, filed on Aug. 21, 2018, provisional application No. 62/552,835, filed on Aug. 31, 2017.

(51) Int. Cl.
*C12P 21/02* (2006.01)
*A01N 63/50* (2020.01)
*B01L 3/00* (2006.01)
*C07K 14/195* (2006.01)
*C12M 1/40* (2006.01)
*C12M 3/06* (2006.01)
*C12M 1/00* (2006.01)
*C12M 1/34* (2006.01)
*C12M 1/36* (2006.01)
*C07K 14/32* (2006.01)

(52) U.S. Cl.
CPC .............. *C12P 21/02* (2013.01); *A01N 63/50* (2020.01); *B01L 3/502738* (2013.01); *C07K 14/195* (2013.01)

(58) Field of Classification Search
CPC ..... C12Q 1/04; C07K 14/4723; C07K 14/195
See application file for complete search history.

(56) References Cited

U.S. PATENT DOCUMENTS

| 5,910,438 | A | 6/1999 | Bernard et al. |
| 6,180,407 | B1 | 1/2001 | Bernard et al. |
| 7,176,029 | B2 | 2/2007 | Bernard et al. |
| 7,183,097 | B1 | 2/2007 | Gerdes et al. |
| 9,333,227 | B2 | 5/2016 | Philippe |
| 9,737,592 | B1 * | 8/2017 | Bermudes ............. A61K 38/55 |
| 10,188,114 | B2 | 1/2019 | Philippe |
| 2003/0096365 | A1 * | 5/2003 | Faye .................... C07K 14/195 435/69.1 |
| 2004/0052814 | A1 | 3/2004 | Shi et al. |
| 2006/0229244 | A1 * | 10/2006 | Dorit .................... A61K 38/164 514/2.8 |
| 2010/0286030 | A1 * | 11/2010 | Farris .................... A01N 63/50 514/2.8 |
| 2013/0052182 | A1 | 2/2013 | Miller |
| 2015/0050253 | A1 | 2/2015 | Philippe |
| 2016/0145558 | A1 * | 5/2016 | Boedicker ............... C12M 1/14 435/289.1 |
| 2016/0235774 | A1 * | 8/2016 | Vournakis ............... A61P 11/00 |
| 2019/0191709 | A1 | 6/2019 | Philippe |
| 2020/0263221 | A1 | 8/2020 | Philippe |
| 2021/0238645 | A1 | 8/2021 | Philippe |

FOREIGN PATENT DOCUMENTS

| CN | 1807645 A | 7/2006 |
| CN | 101974546 A | 2/2011 |
| WO | WO 2016028700 | 2/2016 |

OTHER PUBLICATIONS

Damiati et al. (2018) Cell-Free Approaches in Synthetic Biology Utilizing Microfluidics Genes, vol. 9, issue 144), pp. 1-17.*
Georgi et al. (2016) On-chip automation of cell-free protein synthesis: New opportunities due to a novel reaction mode. Lab Chip vol. 16, pp. 269-281.*
Gajic et al., (2003) Novel Mechanism of Bacteriocin Secretion and Immunity Carried Out by Lactococcal Multidrug Resistance Proteins, J. Biol. Chem., vol. 278, No. 36, pp. 34291-34298.*
Shukla et al. (2010) Controlling the release of peptide antimicrobial agents from surfaces, Biomater., pp. 2348-1357.*
Montalban-Lopez Manuel et al., Employing the promiscuity of lantibiotic biosynthetic machineries to produce novel antimicrobials FEMS Microbiology Reviews, vol. 41, No. 1, Sep. 2, 2016, pp. 5-18.
Van Heel Auke J. et al., Discovery, Production and Modification of Five Novel Lantibiotics Using the Promiscuous Nisin Modification Machinery, ACS Synthetic Biology, vol. 5, No. 10, Jul. 7, 2016, pp. 1146-1154.
Lohans Christopher T. et al., Development 1-4,6-H of Class IIa Bacteriocins as Therapeutic Agents,International Journal of Microbiology, vol. 2012, 386410,Jan. 1, 2012, pp. 1-13.
Michael Klocke et al., Heterologous Expression of Enterocin A, a Bacteriocin From Enterococcus Faecium, Fused to a Cellulose-Binding Domain in *Escherichia coli* Results in a Functional Protein With Inhibitory Activity Against Listeria., Applied Microbiology And Biotechnology, vol. 67, No. 4, Jun. 1, 2005, pp. 532-538.

(Continued)

*Primary Examiner* — Suzanne M Noakes
*Assistant Examiner* — Jae W Lee
(74) *Attorney, Agent, or Firm* — Knobbe, Martens, Olson & Bear, LLP

(57) ABSTRACT

Methods and compositions for making bacteriocins are described in some embodiments herein. In some embodiments, pro-polypeptide comprising the bacteriocins in the desired ratios in cis, and separated by cleavage sited can be produced by a microbial cell comprising a nucleic acid encoding the pro-polypeptide. In some embodiments microfluidic devices and methods for making specified mixtures of antimicrobial peptides and/or bacteriocins are described.

16 Claims, 8 Drawing Sheets
Specification includes a Sequence Listing.

(56) References Cited

OTHER PUBLICATIONS

Qingshan Ma et al., Expression and purification of lacticin Q by small ubiquitin-related modifier fusion in *Escherichia coli*, The Journal of Microbiology, The Microbiological Society of Korea, Heidelberg, vol. 50, No. 2, Apr. 27, 2012, pp. 326-331.
Leonardo Acuna et al., A new hybrid bacteriocin, Ent35-MccV, displays antimicrobial activity against pathogenic Gram-positive and Gram-negative bacteria, FEBS Open Bio, vol. 2, No. 1, Jan. 1, 2012, pp. 12-19.
Extended European Search Report in European Application No. 18852336.9 in 17 pages.
File History of U.S. Appl. No. 14/459,810, filed Jun. 14, 2014.
File History of U.S. Appl. No. 16/227,371, filed Dec. 20, 2018.
File History of U.S. Appl. No. 15/087,706, filed Mar. 31, 2016.
Sahl et al. Biosynthesis and biological activities of lantibiotics with unique post-translational modifications. Eur J Biochem, Jun. 15, 1995, vol. 230, No. 3, pp. 827-853.
Li. Recombinant production of antimicrobial peptides in *Escherichia coli*: a review. Protein Expr Purif, Dec. 2011, vol. 80, No. 2, pp. 260-267.
International Search Report and Written Opinion in International Application No. PCT/US2018/048846 dated Dec. 20, 2018 in 12 pages.
Office Action with English Translation dated Jul. 22, 2022, in Japanese Patent Application No. 2020-512860 in 11 pages.
Adetunji et al., Fungicidal effect of bacteriocins harvested from Bacillus spp., Malaysian Journal of Microbiology, vol. 9, No. 2, pp. 130-134, 2013.
Altschul, S.F., et al. Basic local alignment search tool, Journal of Molecular Biology, vol. 215, pp. 403-410, 1990.
Cotter, P.D. et al., Bacteriocins—a viable alternative to antibiotics, Nature Reviews Microbiology, vol. 11, pp. 95-105, 2013.
Gibson et al., Creation of a Bacterial Cell Controlled by a Chemically Synthesized Genome, Science, vol. 329, pp. 52-56, 2010.
Goñi-Moreno, et al., Multicellular Computing Using Conjugation for Wiring. PLoSONE, vol. 8, No. 6, e65986, 2013.
Jain et al. Current ADC Linker Chemistry, Pharmaceutical Research, vol. 32, pp. 3526-3540, 2015.
Jaramillo A., et al., Engineered Stable Ecosystems, Synthetic Biology, No. 2, vol. 17119, 2017.
Mead et al. Nucleic Acids Res. Dec. 11, 1990; 18(23): 7167.
Nielsen et al., Genetic circuit design automation, Science, vol. 352, No. 6281, aac7341,2016.
Rajput A. et al., Prediction and Analysis of Quorum Sensing Peptides Based on Sequence Features, PLoSOne, vol. 10, No. 3, 2015.
Shekh, R.M. et al., Biochemical characterization of an anti-Candida factor produced by Enterococcus, BMC Microbiology, vol. 12, No. 132, 2012.
Shenin et al., "Characteristics of Alirin B1, the major component of a fungicidal substance produced by Bacillus subtilis 10-VIZR". Antibiot Khimioter, vol. 50: pp. 3-7, 1995.
Srivastava, S. et al., Antifungal Activity of Pseudomonas fluorescens Against Different Plant Pathogenic Fungi,The Internet Journal of Microbiology, vol. 7 No. 2, 2008.
Tomita et al. Twenty-Five Years of Research on Bovine Lactoferrin Applications, Biochimie, vol. 91, No. 1, pp. 52-57, 2009.
Wang et al. APD3: The Antimicrobial Peptide Database as a Tool for Research and Education, Nucleic Acids Research, vol. 44, Issue D1, pp. D1087-D1093, 2016.
Wang et al. Genome Mining Demonstrates the Widespread Occurrence of Gene Clusters Encoding Bacteriocins in Cyanobacteria, PLoS ONE 6(7): e22384, 2011.
Wright, et al., Building-in biosafety for synthetic biology, Microbiology, vol. 159, pp. 1221-1235, 2013.
Zuber, P et al. Peptide Antibiotics, Bacillus subtilis and Other Gram-Positive Bacteria: Biochemistry, Physiology, and Molecular Genetics ed Sonenshein et al., pp. 897-916, American Society for Microbiology, 1993.

* cited by examiner

SEQUENCE LISTING

```
<160> NUMBER OF SEQ ID NOS: 750

<210> SEQ ID NO 1
<211> LENGTH: 40
<212> TYPE: PRT
<213> ORGANISM: Enterococcus faecalis

<400> SEQUENCE: 1

Trp Leu Pro Pro Ala Gly Leu Leu Gly Arg Cys Gly Arg Trp Phe Arg
1               5                   10                  15

Pro Trp Leu Leu Trp Leu Gln Ser Gly Ala Gln Tyr Lys Trp Leu Gly
            20                  25                  30

Asn Leu Phe Gly Leu Gly Pro Lys
        35                  40
```

<210> SEQ ID NO 2
<211> LENGTH: 5
<212> TYPE: PRT
<213> ORGANISM: Artificial Sequence
<220> FEATURE:
<223> OTHER INFORMATION: N-terminal motif of class terminal IIa
<220> FEATURE:
<221> NAME/KEY: VARIANT
<222> LOCATION: 3
<223> OTHER INFORMATION: Xaa = any amino acid

<400> SEQUENCE: 2

Tyr Gly Xaa Gly Val
1               5

<210> SEQ ID NO 3
<211> LENGTH: 135
<212> TYPE: PRT
<213> ORGANISM: Artificial Sequence
<220> FEATURE:
<223> OTHER INFORMATION: Hybrid bacteriocin Ent35-MccV

<400> SEQUENCE: 3

Gly Lys Tyr Tyr Gly Asn Gly Val Ser Cys Asn Lys Lys Gly Cys Ser
1               5                   10                  15

Val Asp Trp Gly Arg Ala Ile Gly Ile Ile Gly Asn Asn Ser Ala Ala
            20                  25                  30

Asn Leu Ala Thr Gly Gly Ala Ala Gly Trp Lys Ser Gly Gly Gly Ala
        35                  40                  45

Ser Gly Arg Asp Ile Ala Met Ala Ile Gly Thr Leu Ser Gly Gln Phe
    50                  55                  60

Val Ala Gly Gly Ile Gly Ala Ala Gly Gly Val Ala Gly Gly Ala
65                  70                  75                  80

Ile Tyr Asp Tyr Ala Ser Thr His Lys Pro Asn Pro Ala Met Ser Pro
                85                  90                  95

Ser Gly Leu Gly Gly Thr Ile Lys Gln Lys Pro Glu Gly Ile Pro Ser
            100                 105                 110

Glu Ala Trp Asn Tyr Ala Ala Gly Arg Leu Cys Asn Trp Ser Pro Asn
        115                 120                 125

Asn Leu Ser Asp Val Cys Leu
    130                 135

<210> SEQ ID NO 4
<211> LENGTH: 46
<212> TYPE: PRT
<213> ORGANISM: Lactobacillus acidophilus

<400> SEQUENCE: 4

Met Ile Ser Ser His Gln Lys Thr Leu Thr Asp Lys Glu Leu Ala Leu
1               5                   10                  15

Ile Ser Gly Gly Lys Thr His Tyr Pro Thr Asn Ala Trp Lys Ser Leu
            20                  25                  30

Trp Lys Gly Phe Trp Glu Ser Leu Arg Tyr Thr Asp Gly Phe
        35                  40                  45

<210> SEQ ID NO 5
<211> LENGTH: 141
<212> TYPE: DNA
<213> ORGANISM: Lactobacillus acidophilus

<400> SEQUENCE: 5

```
atgatttcat ctcatcaaaa aacgttaact gataaagaat tagcattaat ttctgggggg      60
aaaacgcact acccgactaa tgcatggaaa agtctttgga aaggtttctg ggaaagcctt     120
cgttatactg acggttttta g                                               141
```

<210> SEQ ID NO 6
<211> LENGTH: 81
<212> TYPE: PRT
<213> ORGANISM: Lactobacillus acidophilus

<400> SEQUENCE: 6

```
Met Ile Ser Met Ile Ser Ser His Gln Lys Thr Leu Thr Asp Lys Glu
1               5                   10                  15

Leu Ala Leu Ile Ser Gly Gly Lys Thr Tyr Tyr Gly Thr Asn Gly Val
            20                  25                  30

His Cys Thr Lys Lys Ser Leu Trp Gly Lys Val Arg Leu Lys Asn Val
        35                  40                  45

Ile Pro Gly Thr Leu Cys Arg Lys Gln Ser Leu Pro Ile Lys Gln Asp
    50                  55                  60

Leu Lys Ile Leu Leu Gly Trp Ala Thr Gly Ala Phe Gly Lys Thr Phe
65                  70                  75                  80

His
```

<210> SEQ ID NO 7
<211> LENGTH: 246
<212> TYPE: DNA
<213> ORGANISM: Lactobacillus acidophilus

<400> SEQUENCE: 7

```
atgatttcaa tgatttcatc tcatcaaaaa acgttaactg ataaagaatt agcattaatt      60 tctggggga aaacgtacta tggtactaat ggtgtgcatt gtactaaaaa gagtctttgg     120
ggtaaagtac gcttaaaaaa cgtgattcct ggaactcttt gtcgtaagca atcgttgccg     180
atcaaacagg atttaaaaat tttactgggc tgggctacag gtgcttttgg caagacattt     240
cattaa                                                                246
```

<210> SEQ ID NO 8
<211> LENGTH: 60
<212> TYPE: PRT
<213> ORGANISM: Lactobacillus acidophilus

<400> SEQUENCE: 8

```
Met Asp Lys Lys Thr Lys Ile Leu Phe Glu Val Leu Tyr Ile Ile Cys
1               5                   10                  15

Ile Ile Gly Pro Gln Phe Ile Leu Phe Val Thr Ala Lys Asn Asn Met
            20                  25                  30

Tyr Gln Leu Val Gly Ser Phe Val Gly Ile Val Trp Phe Ser Tyr Ile
        35                  40                  45

Phe Trp Tyr Ile Phe Phe Lys Gln His Lys Lys Met
    50                  55                  60
```

<210> SEQ ID NO 9
<211> LENGTH: 183
<212> TYPE: DNA
<213> ORGANISM: Lactobacillus acidophilus

<400> SEQUENCE: 9

```
atggataaga aaacaaaaat attatttgaa gtattataca tcatctgtat aataggccct      60
```

```
caatttatat tatttgtgac tgcaaaaaac aatatgtatc agttggtggg ttcgtttgtt    120
ggaatagtat ggttttcgta tattttttgg tattttttt tcaaacaaca taaaaaatg     180 tag                                                                  183
```

```
<210> SEQ ID NO 10
<211> LENGTH: 65
<212> TYPE: PRT
<213> ORGANISM: Lactobacillus gasseri

<400> SEQUENCE: 10
```

Met Ala Leu Lys Thr Leu Glu Lys His Glu Leu Arg Asn Val Met Gly
1               5                   10                  15

Gly Asn Lys Trp Gly Asn Ala Val Ile Gly Ala Ala Thr Gly Ala Thr
            20                  25                  30

Arg Gly Val Ser Trp Cys Arg Gly Phe Gly Pro Trp Gly Met Thr Ala
        35                  40                  45

Cys Ala Leu Gly Gly Ala Ala Ile Gly Gly Tyr Leu Gly Tyr Lys Ser
    50                  55                  60

Asn
65

```
<210> SEQ ID NO 11
<211> LENGTH: 198
<212> TYPE: DNA
<213> ORGANISM: Lactobacillus gasseri

<400> SEQUENCE: 11
atggctttaa aaacattaga aaaacatgaa ttaagaaatg taatgggtgg aaacaagtgg    60
gggaatgctg taataggagc tgctacggga gctactcgcg gagtaagttg gtgcagagga   120
ttcggaccat ggggaatgac tgcctgtgcg ttaggaggtg ctgcaattgg aggatatctg   180
ggatataaga gtaattaa                                                 198
```

```
<210> SEQ ID NO 12
<211> LENGTH: 51
<212> TYPE: PRT
<213> ORGANISM: Staphylococcus aureus

<400> SEQUENCE: 12
```

Met Ser Trp Leu Asn Phe Leu Lys Tyr Ile Ala Lys Tyr Gly Lys Lys
1               5                   10                  15

Ala Val Ser Ala Ala Trp Lys Tyr Lys Gly Lys Val Leu Glu Trp Leu
            20                  25                  30

Asn Val Gly Pro Thr Leu Glu Trp Val Trp Gln Lys Leu Lys Lys Ile
        35                  40                  45

Ala Gly Leu
    50

```
<210> SEQ ID NO 13
<211> LENGTH: 156
<212> TYPE: DNA
<213> ORGANISM: Staphylococcus aureus

<400> SEQUENCE: 13
atgagttggt taaattttt aaaatacatc gctaaatatg gcaaaaaagc ggtatctgct     60
gcttggaagt acaaaggtaa agtattagaa tggcttaatg ttggtcctac tcttgaatgg   120
gtatggcaaa aattaaagaa aattgctgga ttataa                             156
```

<210> SEQ ID NO 14
<211> LENGTH: 61
<212> TYPE: PRT
<213> ORGANISM: Enterococcus avium

<400> SEQUENCE: 14

Met Thr Arg Ser Lys Lys Leu Asn Leu Arg Glu Met Lys Asn Val Val
1               5                   10                  15

Gly Gly Thr Tyr Tyr Gly Asn Gly Val Ser Cys Asn Lys Lys Gly Cys
            20                  25                  30

Ser Val Asp Trp Gly Lys Ala Ile Ser Ile Ile Gly Asn Asn Ser Ala
        35                  40                  45

Ala Asn Leu Ala Thr Gly Gly Ala Ala Gly Trp Lys Ser
    50                  55                  60

<210> SEQ ID NO 15
<211> LENGTH: 186
<212> TYPE: DNA
<213> ORGANISM: Enterococcus avium

<400> SEQUENCE: 15
atgacaagat caaaaaaatt aaatttacgc gaaatgaaga atgttgttgg tggtacctac      60
tatggaaatg gtgtatcttg taacaagaaa ggctgttcag ttgactgggg caaagccatc     120
agtattatag gaataattc cgcagcaaac ttagcaactg gtggtgctgc tggttggaag     180
tcataa                                                                186

<210> SEQ ID NO 16
<211> LENGTH: 67
<212> TYPE: PRT
<213> ORGANISM: Enterococcus faecalis

<400> SEQUENCE: 16

Met Lys Lys Lys Leu Val Ile Cys Gly Ile Ile Gly Ile Gly Phe Thr
1               5                   10                  15

Ala Leu Gly Thr Asn Val Glu Ala Ala Thr Tyr Tyr Gly Asn Gly Leu
            20                  25                  30

Tyr Cys Asn Lys Gln Lys Cys Trp Val Asp Trp Asn Lys Ala Ser Arg
        35                  40                  45

Glu Ile Gly Lys Ile Ile Val Asn Gly Trp Val Gln His Gly Pro Trp
    50                  55                  60

Ala Pro Arg
65

<210> SEQ ID NO 17
<211> LENGTH: 204
<212> TYPE: DNA
<213> ORGANISM: Enterococcus faecalis

<400> SEQUENCE: 17
atgaaaaaga aattagttat ttgtggcatt attgggattg gttttacagc attaggaaca      60
aatgtagaag ctgctacgta ttacggaaat ggtttatatt gtaataagca aaaatgttgg     120
gtagactgga ataaagcttc aagggaaatt ggaaaaatta ttgttaatgg ttgggtacaa     180
catggccctt gggctcctag atag                                            204

<210> SEQ ID NO 18
<211> LENGTH: 51

<212> TYPE: PRT
<213> ORGANISM: Lactococcus lactis

<400> SEQUENCE: 18

Met Lys Glu Gln Asn Ser Phe Asn Leu Leu Gln Glu Val Thr Glu Ser
1               5                   10                  15

Glu Leu Asp Leu Ile Leu Gly Ala Lys Gly Gly Ser Gly Val Ile His
            20                  25                  30

Thr Ile Ser His Glu Val Ile Tyr Asn Ser Trp Asn Phe Val Phe Thr
        35                  40                  45

Cys Cys Ser
    50

<210> SEQ ID NO 19
<211> LENGTH: 156
<212> TYPE: DNA
<213> ORGANISM: Lactococcus lactis

<400> SEQUENCE: 19
atgaaagaac aaaactcttt taatcttctt caagaagtga cagaaagtga attggacctt      60
attttaggtg caaaaggcgg cagtggagtt attcatacaa tttctcatga agtaatatat     120
aatagctgga actttgtatt tacttgctgc tcttaa                              156

<210> SEQ ID NO 20
<211> LENGTH: 74
<212> TYPE: PRT
<213> ORGANISM: Enterococcus faecium

<400> SEQUENCE: 20

Met Lys Lys Lys Val Leu Lys His Cys Val Ile Leu Gly Ile Leu Gly
1               5                   10                  15

Thr Cys Leu Ala Gly Ile Gly Thr Gly Ile Lys Val Asp Ala Ala Thr
            20                  25                  30

Tyr Tyr Gly Asn Gly Leu Tyr Cys Asn Lys Glu Lys Cys Trp Val Asp
        35                  40                  45

Trp Asn Gln Ala Lys Gly Glu Ile Gly Lys Ile Ile Val Asn Gly Trp
    50                  55                  60

Val Asn His Gly Pro Trp Ala Pro Arg Arg
65                  70

<210> SEQ ID NO 21
<211> LENGTH: 225
<212> TYPE: DNA
<213> ORGANISM: Enterococcus faecium

<400> SEQUENCE: 21
atgaaaaaga agtattaaa acattgtgtt attctaggaa tattaggaac ttgtctagct       60
ggcatcggta caggaataaa agttgatgca gctacttact atggaaatgg tctttattgt    120
aacaaagaaa aatgttgggt agattggaat caagctaaag gagaaattgg aaaaattatt    180
gttaatggtt gggttaatca tggtccatgg gcacctagaa ggtag                    225

<210> SEQ ID NO 22
<211> LENGTH: 50
<212> TYPE: PRT
<213> ORGANISM: Clostridium botulinum

<400> SEQUENCE: 22

Met Gln Lys Pro Glu Ile Ile Ser Ala Asp Leu Gly Leu Cys Ala Val

```
1               5                   10                  15
Asn Glu Phe Val Ala Leu Ala Ala Ile Pro Gly Gly Ala Ala Thr Phe
                    20                  25                  30
Ala Val Cys Gln Met Pro Asn Leu Asp Glu Ile Val Ser Asn Ala Ala
        35                  40                  45
Tyr Val
    50

<210> SEQ ID NO 23
<211> LENGTH: 153
<212> TYPE: DNA
<213> ORGANISM: Clostridium botulinum

<400> SEQUENCE: 23
atgcaaaaac cagaaattat tagtgctgat ttagggcttt gtgcagttaa tgaatttgta      60
gctcttgctg ccattcctgg tggtgctgct acatttgcag tatgccaaat gccaaacttg     120
gatgagattg ttagtaatgc agcatatgtt taa                                  153

<210> SEQ ID NO 24
<211> LENGTH: 58
<212> TYPE: PRT
<213> ORGANISM: Streptococcus equinus

<400> SEQUENCE: 24

Met Met Asn Ala Thr Glu Asn Gln Ile Phe Val Glu Thr Val Ser Asp
1               5                   10                  15
Gln Glu Leu Glu Met Leu Ile Gly Gly Ala Asp Arg Gly Trp Ile Lys
                    20                  25                  30
Thr Leu Thr Lys Asp Cys Pro Asn Val Ile Ser Ser Ile Cys Ala Gly
        35                  40                  45
Thr Ile Ile Thr Ala Cys Lys Asn Cys Ala
    50                  55

<210> SEQ ID NO 25
<211> LENGTH: 177
<212> TYPE: DNA
<213> ORGANISM: Streptococcus equinus

<400> SEQUENCE: 25
atgatgaatg ctactgaaaa ccaaattttt gttgagactg tgagtgacca agaattagaa      60
atgttaattg gtggtgcaga tcgtggatgg attaagactt taacaaaaga ttgtccaaat     120
gtaatttctt caatttgtgc aggtacaatt attacagctt gtaaaaattg tgcttaa        177

<210> SEQ ID NO 26
<211> LENGTH: 77
<212> TYPE: PRT
<213> ORGANISM: Brochothrix campestris

<400> SEQUENCE: 26

Met His Lys Val Lys Lys Leu Asn Asn Gln Glu Leu Gln Gln Ile Val
1               5                   10                  15
Gly Gly Tyr Ser Ser Lys Asp Cys Leu Lys Asp Ile Gly Lys Gly Ile
                    20                  25                  30
Gly Ala Gly Thr Val Ala Gly Ala Ala Gly Gly Gly Leu Ala Ala Gly
        35                  40                  45
Leu Gly Ala Ile Pro Gly Ala Phe Val Gly Ala His Phe Gly Val Ile
    50                  55                  60
```

Gly Gly Ser Ala Ala Cys Ile Gly Gly Leu Leu Gly Asn
65                  70                  75

<210> SEQ ID NO 27
<211> LENGTH: 234
<212> TYPE: DNA
<213> ORGANISM: Brochothrix campestris

<400> SEQUENCE: 27
atgcacaagg taaaaaaatt aaacaatcaa gagttacaac agatcgtggg aggttacagt    60
tcaaaagatt gtctaaaaga tattggtaaa ggaattggtg ctggtacagt agctggggca   120
gccggcggtg gcctagctgc aggattaggt gctatcccag gagcattcgt tggagcacat   180
tttggagtaa tcggcggatc tgccgcatgc attggtggat tattaggtaa ctag         234

<210> SEQ ID NO 28
<211> LENGTH: 80
<212> TYPE: PRT
<213> ORGANISM: Butyrivibrio fibrisolvens

<400> SEQUENCE: 28

Met Ser Lys Lys Gln Ile Met Ser Asn Cys Ile Ser Ile Ala Leu Leu
1               5                   10                  15

Ile Ala Leu Ile Pro Asn Ile Tyr Phe Ile Ala Asp Lys Met Gly Ile
            20                  25                  30

Gln Leu Ala Pro Ala Trp Tyr Gln Asp Ile Val Asn Trp Val Ser Ala
        35                  40                  45

Gly Gly Thr Leu Thr Thr Gly Phe Ala Ile Ile Val Gly Val Thr Val
    50                  55                  60

Pro Ala Trp Ile Ala Glu Ala Ala Ala Ala Phe Gly Ile Ala Ser Ala
65                  70                  75                  80

<210> SEQ ID NO 29
<211> LENGTH: 243
<212> TYPE: DNA
<213> ORGANISM: Butyrivibrio fibrisolvens

<400> SEQUENCE: 29
atgagtaaaa aacaaattat gagtaactgt atatcaattg cattattaat agcactaatt    60
cctaatatct attttattgc agataaaatg gaattcagt tagcacctgc ttggtatcaa   120
gatattgtga attgggtatc tgctggtgga acacttacta ctggttttgc gattattgta   180
ggagttacag taccggcatg gatagcagaa gcagctgcag cttttggtat agcttcagca   240
tga                                                                 243

<210> SEQ ID NO 30
<211> LENGTH: 48
<212> TYPE: PRT
<213> ORGANISM: Butyrivibrio fibrisolvens

<400> SEQUENCE: 30

Met Asn Lys Glu Leu Asn Ala Leu Thr Asn Pro Ile Asp Glu Lys Glu
1               5                   10                  15

Leu Glu Gln Ile Leu Gly Gly Gly Asn Gly Val Ile Lys Thr Ile Ser
            20                  25                  30

His Glu Cys His Met Asn Thr Trp Gln Phe Ile Phe Thr Cys Cys Ser
        35                  40                  45

<210> SEQ ID NO 31

-continued

```
<211> LENGTH: 147
<212> TYPE: DNA
<213> ORGANISM: Butyrivibrio fibrisolvens

<400> SEQUENCE: 31
atgaacaaag aacttaatgc acttacaaat cctattgacg agaaggagct tgagcagatc    60
ctcggtggtg gcaatggtgt catcaagaca atcagccacg agtgccacat gaacacatgg   120
cagttcattt tcacatgttg ctcttaa                                       147

<210> SEQ ID NO 32
<211> LENGTH: 66
<212> TYPE: PRT
<213> ORGANISM: Carnobacterium maltaromaticum

<400> SEQUENCE: 32
```

Met Asn Ser Val Lys Glu Leu Asn Val Lys Glu Met Lys Gln Leu His
1               5                   10                  15

Gly Gly Val Asn Tyr Gly Asn Gly Val Ser Cys Ser Lys Thr Lys Cys
            20                  25                  30

Ser Val Asn Trp Gly Gln Ala Phe Gln Glu Arg Tyr Thr Ala Gly Ile
        35                  40                  45

Asn Ser Phe Val Ser Gly Val Ala Ser Gly Ala Gly Ser Ile Gly Arg
    50                  55                  60

Arg Pro
65

```
<210> SEQ ID NO 33
<211> LENGTH: 201
<212> TYPE: DNA
<213> ORGANISM: Carnobacterium maltaromaticum

<400> SEQUENCE: 33
atgaatagcg taaaagaatt aaacgtgaaa gaaatgaaac aattacacgg tggagtaaat    60
tatggtaatg gtgtttcttg cagtaaaaca aaatgttcag ttaactgggg acaagccttt   120
caagaaagat acacagctgg aattaactca tttgtaagtg gagtcgcttc tggggcagga   180
tccattggta ggagaccgta a                                             201

<210> SEQ ID NO 34
<211> LENGTH: 61
<212> TYPE: PRT
<213> ORGANISM: Carnobacterium maltaromaticum

<400> SEQUENCE: 34
```

Met Lys Ser Val Lys Glu Leu Asn Lys Lys Glu Met Gln Gln Ile Asn
1               5                   10                  15

Gly Gly Ala Ile Ser Tyr Gly Asn Gly Val Tyr Cys Asn Lys Glu Lys
            20                  25                  30

Cys Trp Val Asn Lys Ala Glu Asn Lys Gln Ala Ile Thr Gly Ile Val
        35                  40                  45

Ile Gly Gly Trp Ala Ser Ser Leu Ala Gly Met Gly His
    50                  55                  60

```
<210> SEQ ID NO 35
<211> LENGTH: 186
<212> TYPE: DNA
<213> ORGANISM: Carnobacterium maltaromaticum

<400> SEQUENCE: 35
```

```
atgaaaagcg ttaaagaact aaataaaaaa gaaatgcaac aaattaatgg tggagctatc    60
tcttatggca atggtgttta ttgtaacaaa gagaaatgtt gggtaaacaa ggcagaaaac   120
aaacaagcta ttactggaat agttatcggt ggatgggctt ctagtttagc aggaatggga   180
cattaa                                                              186
```

<210> SEQ ID NO 36
<211> LENGTH: 71
<212> TYPE: PRT
<213> ORGANISM: Carnobacterium maltaromaticum

<400> SEQUENCE: 36

```
Met Asn Asn Val Lys Glu Leu Ser Ile Lys Glu Met Gln Gln Val Thr
1               5                   10                  15

Gly Gly Asp Gln Met Ser Asp Gly Val Asn Tyr Gly Lys Gly Ser Ser
            20                  25                  30

Leu Ser Lys Gly Gly Ala Lys Cys Gly Leu Gly Ile Val Gly Gly Leu
        35                  40                  45

Ala Thr Ile Pro Ser Gly Pro Leu Gly Trp Leu Ala Gly Ala Ala Gly
    50                  55                  60

Val Ile Asn Ser Cys Met Lys
65                  70
```

<210> SEQ ID NO 37
<211> LENGTH: 216
<212> TYPE: DNA
<213> ORGANISM: Carnobacterium maltaromaticum

<400> SEQUENCE: 37

```
atgaataatg taaagagtt aagtattaaa gaaatgcaac aagttactgg tggagaccaa    60
atgtcagatg gtgtaaatta tggaaaaggc tctagcttat caaaaggtgg tgccaaatgt   120
ggtttaggga tcgtcggcgg attagctact atcccttcag gtcctttagg ctggttagcc   180
ggagcagcag gtgtaattaa tagctgtatg aaataa                             216
```

<210> SEQ ID NO 38
<211> LENGTH: 64
<212> TYPE: PRT
<213> ORGANISM: Carnobacterium maltaromaticum

<400> SEQUENCE: 38

```
Met Leu Tyr Glu Leu Val Ala Tyr Gly Ile Ala Gln Gly Thr Ala Glu
1               5                   10                  15

Lys Val Val Ser Leu Ile Asn Ala Gly Leu Thr Val Gly Ser Ile Ile
            20                  25                  30

Ser Ile Leu Gly Gly Val Thr Val Gly Leu Ser Gly Val Phe Thr Ala
        35                  40                  45

Val Lys Ala Ala Ile Ala Lys Gln Gly Ile Lys Lys Ala Ile Gln Leu
    50                  55                  60
```

<210> SEQ ID NO 39
<211> LENGTH: 195
<212> TYPE: DNA
<213> ORGANISM: Carnobacterium maltaromaticum

<400> SEQUENCE: 39

```
atgttatatg aattagttgc atatggtatc gcacaaggta cagctgaaaa ggttgtaagt    60
ctaattaacg caggtttaac agtagggtct attatttcaa ttttgggtgg ggtcacagtc   120
```

```
ggtttatcag gtgtcttcac agcagttaaa gcagcaattg ctaaacaagg aataaaaaaa      180
gcaattcaat tataa                                                       195
```

<210> SEQ ID NO 40
<211> LENGTH: 836
<212> TYPE: PRT
<213> ORGANISM: Pectobacterium carotovorum subsp. carotovorum

<400> SEQUENCE: 40

```
Met Ile Lys Tyr Arg Leu Tyr Ala Pro Asn Asp Gly Asp Thr Met Thr
 1               5                  10                  15

Val Ser Gly Gly Gly Gly Trp Val Ser Asn Asp Arg Lys Gly Gly
                20                  25                  30

Asn Asp Arg Asp Asn Gly Lys Gly Gly Ser Ala Val Asp Phe Ser Lys
             35                  40                  45

Asn Pro Glu Lys Gln Ala Ile Val Asn Pro Tyr Leu Ala Ile Ala Ile
         50                  55                  60

Pro Met Pro Val Tyr Pro Leu Tyr Gly Lys Leu Gly Phe Thr Ile Asn
 65                  70                  75                  80

Thr Thr Ala Ile Glu Thr Glu Leu Ala Asn Val Arg Ala Ala Ile Asn
                 85                  90                  95

Thr Lys Leu Ala Thr Leu Ser Ala Val Ile Gly Arg Ser Leu Pro Val
            100                 105                 110

Val Gly Arg Val Phe Gly Val Thr Ala Ala Gly Met Trp Pro Ser Ser
        115                 120                 125

Thr Ala Pro Ser Ser Leu Asp Ser Ile Tyr Asn Gln Ala His Gln Gln
130                 135                 140

Ala Leu Ala Gln Leu Ala Ala Gln Gln Gly Val Leu Asn Lys Gly Tyr
145                 150                 155                 160

Asn Val Thr Ala Met Pro Ala Gly Phe Val Ser Ser Leu Pro Val Ser
                165                 170                 175

Glu Ile Lys Ser Leu Pro Thr Ala Pro Ala Ser Leu Leu Ala Gln Ser
            180                 185                 190

Val Ile Asn Thr Glu Leu Ser Gln Arg Gln Leu Ala Leu Thr Gln Pro
        195                 200                 205

Thr Thr Asn Ala Pro Val Ala Asn Ile Pro Val Val Lys Ala Glu Lys
210                 215                 220

Thr Ala Met Pro Gly Val Tyr Ser Ala Lys Ile Ile Ala Gly Glu Pro
225                 230                 235                 240

Ala Phe Gln Ile Lys Val Asp Asn Thr Lys Pro Ala Leu Ala Gln Asn
                245                 250                 255

Pro Pro Lys Val Lys Asp Asp Ile Gln Val Ser Ser Phe Leu Ser Ser
            260                 265                 270

Pro Val Ala Asp Thr His His Ala Phe Ile Asp Phe Gly Ser Asp His
        275                 280                 285

Glu Pro Val Tyr Val Ser Leu Ser Lys Ile Val Thr Ala Glu Glu Glu
    290                 295                 300

Lys Lys Gln Val Glu Glu Ala Lys Arg Arg Glu Gln Glu Trp Leu Leu
305                 310                 315                 320

Arg His Pro Ile Thr Ala Ala Glu Arg Lys Leu Thr Glu Ile Arg Gln
                325                 330                 335

Val Ile Ser Phe Ala Gln Gln Leu Lys Glu Ser Ser Val Ala Thr Ile
            340                 345                 350

Ser Glu Lys Thr Lys Thr Val Ala Val Tyr Gln Glu Gln Val Asn Thr
```

-continued

```
            355                 360                 365
Ala Ala Lys Asn Arg Asp Asn Phe Tyr Asn Gln Asn Arg Gly Leu Leu
        370                 375                 380
Ser Ala Gly Ile Thr Gly Gly Pro Gly Tyr Pro Ile Tyr Leu Ala Leu
385                 390                 395                 400
Trp Gln Thr Met Asn Asn Phe His Gln Ala Tyr Phe Arg Ala Asn Asn
                    405                 410                 415
Ala Leu Glu Gln Glu Ser His Val Leu Asn Leu Ala Arg Ser Asp Leu
                420                 425                 430
Ala Lys Ala Glu Gln Leu Leu Ala Glu Asn Asn Arg Leu Gln Val Glu
            435                 440                 445
Thr Glu Arg Thr Leu Ala Glu Glu Lys Glu Ile Lys Arg Asn Arg Val
        450                 455                 460
Asn Val Ser Thr Phe Gly Thr Val Gln Thr Gln Leu Ser Lys Leu Leu
465                 470                 475                 480
Ser Asp Phe Tyr Ala Val Thr Ser Leu Ser Gln Ser Val Pro Ser Gly
                    485                 490                 495
Ala Leu Ala Ser Phe Ser Tyr Asn Pro Gln Gly Met Ile Gly Ser Gly
                500                 505                 510
Lys Ile Val Gly Lys Asp Val Asp Val Leu Phe Ser Ile Pro Val Lys
            515                 520                 525
Asp Ile Pro Gly Tyr Lys Ser Pro Ile Asn Leu Asp Asp Leu Ala Lys
        530                 535                 540
Lys Asn Gly Ser Leu Asp Leu Pro Ile Arg Leu Ala Phe Ser Asp Glu
545                 550                 555                 560
Asn Gly Glu Arg Val Leu Arg Ala Phe Lys Ala Asp Ser Leu Arg Ile
                    565                 570                 575
Pro Ser Ser Val Arg Gly Val Ala Gly Ser Tyr Asp Lys Asn Thr Gly
                580                 585                 590
Ile Phe Ser Ala Glu Ile Asp Gly Val Ser Ser Arg Leu Val Leu Glu
            595                 600                 605
Asn Pro Ala Phe Pro Pro Thr Gly Asn Val Gly Asn Thr Gly Asn Thr
        610                 615                 620
Ala Pro Asp Tyr Lys Ala Leu Leu Asn Thr Gly Val Asp Val Lys Pro
625                 630                 635                 640
Val Asp Lys Ile Thr Val Thr Val Thr Pro Val Ala Asp Pro Val Asp
                    645                 650                 655
Ile Asp Asp Tyr Ile Ile Trp Leu Pro Thr Ala Ser Gly Ser Gly Val
                660                 665                 670
Glu Pro Ile Tyr Val Val Phe Asn Ser Asn Pro Tyr Gly Gly Thr Glu
            675                 680                 685
Lys Gly Lys Tyr Ser Lys Arg Tyr Tyr Asn Pro Asp Lys Ala Gly Gly
        690                 695                 700
Pro Ile Leu Glu Leu Asp Trp Lys Asn Val Lys Ile Asp His Ala Gly
705                 710                 715                 720
Val Asp Asn Val Lys Leu His Thr Gly Arg Phe Lys Ala Ser Val Glu
                    725                 730                 735
Asn Lys Val Met Ile Glu Arg Leu Glu Asn Ile Leu Asn Gly Gln Ile
                740                 745                 750
Thr Ala Thr Asp Thr Asp Lys Arg Phe Tyr Thr His Glu Leu Arg Glu
            755                 760                 765
Leu Asn Arg Tyr Arg Asn Leu Gly Ile Lys Asp Gly Glu Val Pro Ser
        770                 775                 780
```

```
Ser Ile Gln Glu Glu Ser Ala Val Trp Asn Asp Thr His Thr Ala Thr
785                 790                 795                 800

Leu Glu Asp Tyr Lys Ile Asn Glu Lys Glu Gln Pro Leu Tyr Thr Asp
            805                 810                 815

Ala Ala Leu Gln Ala Ala Tyr Glu Gln Glu Leu Lys Asp Ala Leu Gly
        820                 825                 830

Gly Lys His Gly
        835

<210> SEQ ID NO 41
<211> LENGTH: 2511
<212> TYPE: DNA
<213> ORGANISM: Pectobacterium carotovorum subsp. carotovorum

<400> SEQUENCE: 41
```

| | | | | | |
|---|---|---|---|---|---|
| atgattaaat | accgtttata | tgctccaaat | gatggagaca | ccatgacagt | gagtggtggt | 60 |
| ggtggttggg | tttcaaacga | tgatcgcaaa | ggtggtaatg | acagggacaa | tggcaaaggt | 120 |
| ggttctgccg | ttgattttag | taaaaatcca | gaaaagcagg | ctatcgttaa | tccctatttg | 180 |
| gcaatcgcga | taccgatgcc | ggtctaccct | ctttatggaa | agctagggtt | cacaataaat | 240 |
| acgacggcaa | ttgagactga | actcgcaaat | gtcagagcag | caattaacac | taaacttgca | 300 |
| acactcagtg | cagtgattgg | cagatcactt | ccggtcgttg | ggcgggtatt | tggtgttact | 360 |
| gccgccggaa | tgtggccttc | tagtaccgct | cccagtagtc | tcgattctat | atacaatcaa | 420 |
| gcacatcagc | aggctttagc | ccagttagct | gctcaacagg | gagtattaaa | taagggtat | 480 |
| aacgttacag | caatgcctgc | aggtttcgtc | agcagtttgc | ctgttagtga | aatcaaatca | 540 |
| ttgccaacag | ctcccgccag | tttactggca | caaagtgtga | ttaataccga | actttcccag | 600 |
| cgtcaactgg | ctcttactca | gcccacgacg | aatgcaccag | tcgcgaatat | tcccgtagtt | 660 |
| aaagcagaga | aaacagcaat | gccaggtgtg | tattcagcga | aaattattgc | tggtgagcct | 720 |
| gcattccaaa | tcaaggtcga | taataccaaa | cctgctttgg | cacagaatcc | gccgaaagta | 780 |
| aaagatgata | ttcaggtatc | ttctttcctt | tcctcgccag | tagctgatac | gcaccatgca | 840 |
| tttattgatt | ttggcagcga | tcatgaaccg | gtatacgtgt | ctctttcaaa | gatcgtgaca | 900 |
| gccgaggagg | agaaaaaaca | ggttgaagag | gccaagcgcc | gtgagcagga | gtggttgttg | 960 |
| cgtcatccaa | ttacagctgc | ggagcgaaaa | ttaactgaaa | tccgccaagt | gatctctttt | 1020 |
| gctcaacagc | taaagaaag | ctctgtcgca | accatttcag | aaaaaactaa | aactgttgcg | 1080 |
| gtttaccaag | aacaggtgaa | taccgctgca | aaaaatcgcg | acaatttta | taatcaaaat | 1140 |
| agaggtctgt | taagtgcggg | tataactggg | ggaccgggat | atcctattta | tcttgcttta | 1200 |
| tggcaaacga | tgaataactt | tcatcaggct | tatttcagag | caataatgc | attggaacaa | 1260 |
| gagagtcatg | ttctgaacct | ggctcgttct | gatctggcta | aggctgagca | attgcttgct | 1320 |
| gagaataatc | gacttcaggt | tgaaacggag | cgaacgcttg | ccgaagaaaa | agagataaaa | 1380 |
| cgcaacaggg | ttaatgtatc | aacatttggc | acagtgcaaa | ctcaacttag | taaattgctg | 1440 |
| tcagattttt | atgctgttac | atcactttcc | caaagtgttc | cttcgggggc | attagcctct | 1500 |
| ttttcatata | atccacaagg | gatgattggc | agcggtaaga | ttgttgggaa | ggatgtcgat | 1560 |
| gttttatttt | ccatcccagt | aaaagatatt | ccgggatata | atctcctat | taacttggac | 1620 |
| gatttagcca | agaaaaatgg | aagtctggat | cttcccattc | gtctggcatt | ttctgatgag | 1680 |
| aatggagaaa | gggttcttcg | ggcattcaaa | gcggatagtc | tgcgaatccc | ttcgagtgtc | 1740 |

```
agaggtgtag cgggcagtta tgacaaaaat acgggtattt ttagtgcaga aattgatggt   1800
gtttcatctc gccttgtact ggaaaaccca gcgtttcctc cgaccggaaa tgtcggtaat   1860
acgggtaata ctgcacctga ctataaagca ttactgaata ctggtgttga tgttaaacct   1920
gttgataaaa tcacagttac ggtaacacca gttgctgatc cagtggatat tgatgactat   1980
ataatctggt tgccaactgc gtctggttct ggcgtggaac ccatttatgt cgtgtttaac   2040
agtaatccgt atggtgggac ggaaaaagga aaatatagca aacgttatta taatccagat   2100
aaggcaggcg gtccgatctt ggagctggat tggaaaaacg ttaagattga ccatgcaggt   2160
gtggacaatg ttaaattaca cacagggcgt ttcaaagcgt cggttgaaaa caaagtgatg   2220
attgaacgtt tggaaaacat actgaatggt caaatcacgg ccacggatac tgacaagcga   2280
ttctatacgc atgaattaag agagttaaac cgctacagaa atttaggcat caaagacggt   2340
gaagtgccta gtagcattca agaagaaagc gctgtttgga acgacacaca cacagcgacg   2400
cttgaagact acaaaattaa tgagaaagag caaccgttgt acactgatgc tgctttgcag   2460
gcagcctacg aacaggaact caaagacgca ttaggaggga aacatggcta a            2511
```
<210> SEQ ID NO 42
<211> LENGTH: 74
<212> TYPE: PRT
<213> ORGANISM: Bacillus cereus

<400> SEQUENCE: 42

```
Met Glu Asn Leu Gln Met Leu Thr Glu Glu Glu Leu Met Glu Ile Glu
1               5                   10                  15

Gly Gly Gly Trp Trp Asn Ser Trp Gly Lys Cys Val Ala Gly Thr Ile
            20                  25                  30

Gly Gly Ala Gly Thr Gly Gly Leu Gly Gly Ala Ala Ala Gly Ser Ala
        35                  40                  45

Val Pro Val Ile Gly Thr Gly Ile Gly Gly Ala Ile Gly Gly Val Ser
    50                  55                  60

Gly Gly Leu Thr Gly Ala Ala Thr Phe Cys
65                  70
```

<210> SEQ ID NO 43
<211> LENGTH: 225
<212> TYPE: DNA
<213> ORGANISM: Bacillus cereus

<400> SEQUENCE: 43

```
atggaaaact tacaaatgtt aactgaagaa gaattaatgg aaattgaagg tggaggctgg     60
tggaatagct ggggtaaatg tgttgctgga actatcggtg gagctggaac tggtggttta    120
ggtggagctg ctgcaggttc agctgttccg gttattggta ctggtattgg tggcgctatt    180
ggtggagtta gcggtggcct tacaggtgca gctacttttt gctaa                    225
```

<210> SEQ ID NO 44
<211> LENGTH: 78
<212> TYPE: PRT
<213> ORGANISM: Streptoverticillium griseoverticillatum

<400> SEQUENCE: 44

```
Met Thr Ala Ser Ile Leu Gln Gln Ser Val Val Asp Ala Asp Phe Arg
1               5                   10                  15

Ala Ala Leu Leu Glu Asn Pro Ala Ala Phe Gly Ala Ser Ala Ala Ala
            20                  25                  30
```

Leu Pro Thr Pro Val Glu Ala Gln Asp Gln Ala Ser Leu Asp Phe Trp
            35                  40                  45

Thr Lys Asp Ile Ala Ala Thr Glu Ala Phe Ala Cys Arg Gln Ser Cys
    50                  55                  60

Ser Phe Gly Pro Phe Thr Phe Val Cys Asp Gly Asn Thr Lys
65                  70                  75

<210> SEQ ID NO 45
<211> LENGTH: 237
<212> TYPE: DNA
<213> ORGANISM: Streptoverticillium griseoverticillatum

<400> SEQUENCE: 45
atgaccgctt ccattcttca gcagtccgtc gtggacgccg acttccgcgc ggcgctgctt      60
gagaaccccg ccgccttcgg cgcttccgcc gcggccctgc ccacgcccgt cgaggcccag     120
gaccaggcgt cccttgactt ctggaccaag gacatcgccg ccacggaagc cttcgcctgc     180
cgccagagct gcagcttcgg cccgttcacc ttcgtgtgcg acggcaacac caagtaa       237

<210> SEQ ID NO 46
<211> LENGTH: 76
<212> TYPE: PRT
<213> ORGANISM: Geobacillus kaustophilus

<400> SEQUENCE: 46

Met Ser Leu Leu Ala Leu Val Ala Gly Thr Leu Gly Val Ser Gln Ser
1               5                   10                  15

Ile Ala Thr Thr Val Val Ser Ile Val Leu Thr Gly Ser Thr Leu Ile
            20                  25                  30

Ser Ile Ile Leu Gly Ile Thr Ala Ile Leu Ser Gly Gly Val Asp Ala
        35                  40                  45

Ile Leu Glu Ile Gly Trp Ser Ala Phe Val Ala Thr Val Lys Lys Ile
    50                  55                  60

Val Ala Glu Arg Gly Lys Ala Ala Ala Ile Ala Trp
65                  70                  75

<210> SEQ ID NO 47
<211> LENGTH: 231
<212> TYPE: DNA
<213> ORGANISM: Geobacillus kaustophilus

<400> SEQUENCE: 47
atgagtttgc tggcgcttgt tgccgggacg ctcggcgtgt cacagtcaat cgcgacgacg      60
gttgtttcga ttgtgttgac cggctccact ctcatttcta ttattcttgg gatcaccgct     120
attttgtcag gtggagtcga cgccattttg gaaattgggt ggtcagcttt tgtcgcgacg     180
gtgaaaaaaa tagtggcgga acgaggaaaa gcggcagcga ttgcatggta a              231

<210> SEQ ID NO 48
<211> LENGTH: 309
<212> TYPE: PRT
<213> ORGANISM: Clostridium tyrobutyricum

<400> SEQUENCE: 48

Met Arg Lys Val Phe Leu Arg Ser Ile Ile Ser Thr Leu Val Met Cys
1               5                   10                  15

Ala Phe Val Ser Ser Ser Phe Ser Val Asn Ala Asp Glu Ser Lys Pro
            20                  25                  30

Asn Asp Glu Lys Ile Ile Asn Asn Ile Glu Asn Val Thr Thr Thr Lys

```
                   35                  40                  45

Asp Ile Lys Ser Asn Lys Asn Asn Ile Val Tyr Leu Asp Glu Gly
    50                  55                  60

Val Met Ser Ile Pro Leu Ser Gly Arg Lys Pro Ile Ala Ile Lys Asp
65                  70                  75                  80

Asp Asn Asn Lys Glu Asp Leu Thr Val Thr Leu Pro Ile Lys Asn Thr
                85                  90                  95

Gly Asp Ile Ser Lys Ile Ser Ser Asn Gly Thr Ile Leu Tyr Lys Asn
            100                 105                 110

Asn Ser Ser Asn Ser Asn Ile Ala Leu Gln Pro Lys Asn Asp Gly
        115                 120                 125

Phe Lys Ala Leu Ile Asn Ile Asn Asp Lys Leu Ala Asn Lys Glu Tyr
    130                 135                 140

Glu Phe Thr Phe Asn Leu Pro Lys Asn Ser Lys Leu Ile Ser Ala Ala
145                 150                 155                 160

Thr Tyr Leu Gly Lys Glu Tyr Asp Thr Lys Glu Val Phe Val Val Asp
                165                 170                 175

Lys Asn Asn Ile Ile Thr Ser Ile Ile Ser Pro Ala Trp Ala Lys Asp
            180                 185                 190

Ala Asn Gly His Asn Val Ser Thr Tyr Tyr Lys Ile Val Ser Asn Asn
        195                 200                 205

Lys Leu Val Gln Val Val Glu Phe Thr Glu Asn Thr Ala Phe Pro Val
    210                 215                 220

Val Ala Asp Pro Asn Trp Thr Lys Ile Gly Lys Cys Ala Gly Ser Ile
225                 230                 235                 240

Ala Trp Ala Ile Gly Ser Gly Leu Phe Gly Gly Ala Lys Leu Ile Lys
                245                 250                 255

Ile Lys Lys Tyr Ile Ala Glu Leu Gly Gly Leu Gln Lys Ala Ala Lys
            260                 265                 270

Leu Leu Val Gly Ala Thr Thr Trp Glu Glu Lys Leu His Ala Gly Gly
        275                 280                 285

Tyr Ala Leu Ile Asn Leu Ala Ala Glu Leu Thr Gly Val Ala Gly Ile
    290                 295                 300

Gln Ala Asn Cys Phe
305

<210> SEQ ID NO 49
<211> LENGTH: 930
<212> TYPE: DNA
<213> ORGANISM: Clostridium tyrobutyricum

<400> SEQUENCE: 49
ttgagaaaag tattttaag atcaataatt tcaacattag ttatgtgtgc atttgtttca       60
agcagctttt cagtaaatgc ggatgaaagc aaaccaaatg atgaaaaaat aattaataac      120
atagaaaacg ttactactac taaagatatt gtaaaaagta ataaaaataa tattgtatat      180
ttagatgaag gtgtaatgag tattccattg tctgggagaa aacccattgc tattaaagat      240
gataataata agaagatt aactgttaca ttacctatta gaatactgg agatatatct        300 aaaattagta gtaatggtac tattctgtat aaaaataata gtagtaattc atctaatata      360
gctttacaac ctaaaaatga tggatttaag gctttaataa atattaatga taagttagct      420
aataaagaat atgaatttac atttaattta cccaaaaaca gtaaattaat tagtgctgcc      480
acatatttgg gtaaagaata tgatacaaaa gaagtatttg tagtagacaa aaataatata      540
```

```
attacgagta ttattagtcc agcttgggct aaagatgcaa atggacataa tgtttctact    600
tattataaga tagtatcgaa taataaatta gtacaagttg ttgaattcac agaaaatact    660
gcattcccgg tggtagctga tcctaattgg actaaaattg ggaaatgcgc tgggtcaata    720
gcatgggcta taggttctgg cctttttggt ggagcaaagc taattaaaat aaaaaaatat    780
atagcagagc ttgaggcact tcaaaaagca gctaaattat tagttggtgc aaccacttgg    840
gaagaaaaat tacacgcagg cggttatgca ttaattaact tagctgctga gctaacaggt    900
gtagcaggta tacaagcaaa ttgttttttaa                                    930
```

<210> SEQ ID NO 50
<211> LENGTH: 62
<212> TYPE: PRT
<213> ORGANISM: Bacillus coagulans

<400> SEQUENCE: 50

```
Met Lys Lys Ile Glu Lys Leu Thr Glu Lys Glu Met Ala Asn Ile Ile
1               5                   10                  15

Gly Gly Lys Tyr Tyr Gly Asn Gly Val Thr Cys Gly Lys His Ser Cys
            20                  25                  30

Ser Val Asp Trp Gly Lys Ala Thr Thr Cys Ile Ile Asn Asn Gly Ala
        35                  40                  45

Met Ala Trp Ala Thr Gly Gly His Gln Gly Thr His Lys Cys
    50                  55                  60
```

<210> SEQ ID NO 51
<211> LENGTH: 189
<212> TYPE: DNA
<213> ORGANISM: Bacillus coagulans

<400> SEQUENCE: 51

```
atgaaaaaaa ttgaaaaatt aactgaaaaa gaaatggcca atatcattgg tggtaaatac    60
tacggtaatg gggttacttg tggcaaacat tcctgctctg ttgactgggg taaggctacc   120
acctgcataa tcaataatgg agctatggca tgggctactg gtggacatca aggtactcat   180
aaatgctag                                                           189
```

<210> SEQ ID NO 52
<211> LENGTH: 490
<212> TYPE: PRT
<213> ORGANISM: Escherichia coli

<400> SEQUENCE: 52

```
Met Asp Lys Val Thr Asp Asn Ser Pro Asp Val Glu Ser Thr Glu Ser
1               5                   10                  15

Thr Glu Gly Ser Phe Pro Thr Val Gly Val Asp Thr Gly Asp Thr Ile
            20                  25                  30

Thr Ala Thr Leu Ala Thr Gly Thr Glu Asn Val Gly Gly Gly Gly Gly
        35                  40                  45

Ala Phe Gly Gly Ala Ser Glu Ser Ser Ala Ala Ile His Ala Thr Ala
    50                  55                  60

Lys Trp Ser Thr Ala Gln Leu Lys Lys His Gln Ala Glu Gln Ala Ala
65                  70                  75                  80

Arg Ala Ala Ala Ala Glu Ala Ala Leu Ala Lys Ala Lys Ser Gln Arg
                85                  90                  95

Asp Ala Leu Thr Gln Arg Leu Lys Asp Ile Val Asn Asp Ala Leu Arg
            100                 105                 110
```

Ala Asn Ala Ala Arg Ser Pro Ser Val Thr Asp Leu Ala His Ala Asn
            115                 120                 125

Asn Met Ala Met Gln Ala Glu Ala Glu Arg Leu Arg Leu Ala Lys Ala
        130                 135                 140

Glu Gln Lys Ala Arg Glu Ala Glu Ala Glu Lys Ala Leu Arg
145                 150                 155                 160

Glu Ala Glu Arg Gln Arg Asp Glu Ile Ala Arg Gln Ala Glu Thr
                165                 170                 175

Ala His Leu Leu Ala Met Ala Glu Ala Ala Glu Lys Asn Arg
            180                 185                 190

Gln Asp Ser Leu Asp Glu Glu His Arg Ala Val Glu Val Ala Glu Lys
            195                 200                 205

Lys Leu Ala Glu Ala Lys Ala Glu Leu Ala Lys Ala Glu Ser Asp Val
            210                 215                 220

Gln Ser Lys Gln Ala Ile Val Ser Arg Val Ala Gly Glu Leu Glu Asn
225                 230                 235                 240

Ala Gln Lys Ser Val Asp Val Lys Val Thr Gly Phe Pro Gly Trp Arg
                245                 250                 255

Asp Val Gln Lys Lys Leu Glu Arg Gln Leu Gln Asp Lys Lys Asn Glu
            260                 265                 270

Tyr Ser Ser Val Thr Asn Ala Leu Asn Ser Ala Val Ser Ile Arg Asp
        275                 280                 285

Ala Lys Lys Thr Glu Val Gln Asn Ala Glu Ile Lys Leu Lys Glu Ala
        290                 295                 300

Lys Asp Ala Leu Glu Lys Ser Gln Val Lys Asp Ser Val Asp Thr Met
305                 310                 315                 320

Val Gly Phe Tyr Gln Tyr Ile Thr Glu Gln Tyr Gly Glu Lys Tyr Ser
                325                 330                 335

Arg Ile Ala Gln Asp Leu Ala Glu Lys Ala Lys Gly Ser Lys Phe Asn
            340                 345                 350

Ser Val Asp Glu Ala Leu Ala Ala Phe Glu Lys Tyr Lys Asn Val Leu
        355                 360                 365

Asp Lys Lys Phe Ser Lys Val Asp Arg Asp Asp Ile Phe Asn Ala Leu
370                 375                 380

Glu Ser Ile Thr Tyr Asp Glu Trp Ala Lys His Leu Glu Lys Ile Ser
385                 390                 395                 400

Arg Ala Leu Lys Val Thr Gly Tyr Leu Ser Phe Gly Tyr Asp Val Trp
                405                 410                 415

Asp Gly Thr Leu Lys Gly Leu Lys Thr Gly Asp Trp Lys Pro Leu Phe
            420                 425                 430

Val Thr Leu Glu Lys Ser Ala Val Asp Phe Gly Val Ala Lys Ile Val
        435                 440                 445

Ala Leu Met Phe Ser Phe Ile Val Gly Ala Pro Leu Gly Phe Trp Gly
        450                 455                 460

Ile Ala Ile Ile Thr Gly Ile Val Ser Ser Tyr Ile Gly Asp Asp Glu
465                 470                 475                 480

Leu Asn Lys Leu Asn Glu Leu Leu Gly Ile
                485                 490

<210> SEQ ID NO 53
<211> LENGTH: 1473
<212> TYPE: DNA
<213> ORGANISM: Escherichia coli

<400> SEQUENCE: 53

```
atggataaag tcactgataa ttctccagat gtggagagca cagaatctac tgaggggtca      60
ttcccaactg ttggggttga tactggcgat acgattacag cgacgcttgc aactggaact     120
gaaaatgttg gtggaggcgg tggagcattt ggtggggcca gtgaaagttc tgctgcgata     180
catgcaaccg ctaaatggtc taccgcgcag ttgaaaaaac atcaggctga acaggctgcc     240
cgtgctgctg cggctgaggc agcattggca aaagcgaaat ctcagcgtga tgccctgact     300
caacgtctca aggatattgt taatgacgct ttacgtgcta atgccgctcg tagtccatca     360
gtaactgacc ttgctcatgc caataatatg gcaatgcagg cagaggctga gcgtttgcgc     420
cttgcgaagg cagagcaaaa agcccgtgaa gaagctgaag cagcagaaaa agcgctccgg     480
gaagcagaac gccaacgtga tgagattgcc cgccaacagg ctgaaaccgc gcatttgtta     540
gcaatggcgg aggcagcaga ggctgagaaa atcgacagg attctcttga tgaagagcat     600
cgggctgtgg aagtggcaga agaagctg gctgaggcta aagctgaact ggcgaaggcc     660
gaaagcgatg tacagagtaa gcaagcgatt gtttccagag ttgcagggga gcttgaaaac     720
gctcaaaaaa gtgttgatgt gaaggttacc ggatttcctg gatggcgtga tgttcagaaa     780
aaactggaga gacaattgca ggataagaag aatgaatatt cgtcagtgac gaatgctctt     840
aattctgctg ttagcattag agatgctaaa aaaacagaag ttcagaatgc tgagataaaa     900
ttaaaagaag ctaaggatgc tcttgagaag agtcaggtaa aagactctgt tgatactatg     960
gttgggtttt atcaatatat aaccgaacaa tatggggaaa atattccag aatagctcag    1020
gatttagctg aaaaggcgaa gggtagtaaa tttaatagtg ttgatgaagc acttgctgca    1080
tttgaaaagt ataaaaatgt actggataag aaattcagta aggttgatag ggatgatatt    1140
tttaatgctt tagagtctat tacttatgat gagtgggcca agcatctaga aaagatctct    1200
agggctctta aggttactgg atatttgtct ttcgggtatg atgtatggga tggtacccta    1260
aagggattaa aaacaggaga ctggaagcct ttatttgtca ctctggagaa gagcgcggta    1320
gatttcggcg tggcaaaaat tgtggcatta atgtttagtt ttattgttgg tgcgcctctt    1380
ggcttctggg gaattgcaat tatcacaggt attgtttctt cttacatagg ggatgatgag    1440
ttgaacaagc ttaatgaatt actaggtatt taa                                1473
```

<210> SEQ ID NO 54
<211> LENGTH: 522
<212> TYPE: PRT
<213> ORGANISM: Escherichia coli

<400> SEQUENCE: 54

```
Met Glu Thr Ala Val Ala Tyr Tyr Lys Asp Gly Val Pro Tyr Asp Asp
1               5                   10                  15

Lys Gly Gln Val Ile Ile Thr Leu Leu Asn Gly Thr Pro Asp Gly Ser
            20                  25                  30

Gly Ser Gly Gly Gly Gly Gly Lys Gly Gly Ser Lys Ser Glu Ser Ser
        35                  40                  45

Ala Ala Ile His Ala Thr Ala Lys Trp Ser Thr Ala Gln Leu Lys Lys
    50                  55                  60

Thr Gln Ala Glu Gln Ala Ala Arg Ala Lys Ala Ala Glu Ala Gln
65                  70                  75                  80

Ala Lys Ala Lys Ala Asn Arg Asp Ala Leu Thr Gln Arg Leu Lys Asp
                85                  90                  95

Ile Val Asn Glu Ala Leu Arg His Asn Ala Ser Arg Thr Pro Ser Ala
            100                 105                 110
```

```
Thr Glu Leu Ala His Ala Asn Asn Ala Ala Met Gln Ala Glu Asp Glu
        115                 120                 125
Arg Leu Arg Leu Ala Lys Ala Glu Glu Lys Ala Arg Lys Glu Ala Glu
        130                 135                 140
Ala Ala Glu Lys Ala Phe Gln Glu Ala Glu Gln Arg Arg Lys Glu Ile
145                 150                 155                 160
Glu Arg Glu Lys Ala Glu Thr Glu Arg Gln Leu Lys Leu Ala Glu Ala
                165                 170                 175
Glu Glu Lys Arg Leu Ala Ala Leu Ser Glu Ala Lys Ala Val Glu
            180                 185                 190
Ile Ala Gln Lys Lys Leu Ser Ala Gln Ser Glu Val Val Lys Met
        195                 200                 205
Asp Gly Glu Ile Lys Thr Leu Asn Ser Arg Leu Ser Ser Ile His
        210                 215                 220
Ala Arg Asp Ala Glu Met Lys Thr Leu Ala Gly Lys Arg Asn Glu Leu
225                 230                 235                 240
Ala Gln Ala Ser Ala Lys Tyr Lys Glu Leu Asp Glu Leu Val Lys Lys
                245                 250                 255
Leu Ser Pro Arg Ala Asn Asp Pro Leu Gln Asn Arg Pro Phe Phe Glu
            260                 265                 270
Ala Thr Arg Arg Val Gly Ala Gly Lys Ile Arg Glu Glu Lys Gln
        275                 280                 285
Lys Gln Val Thr Ala Ser Glu Thr Arg Ile Asn Arg Ile Asn Ala Asp
        290                 295                 300
Ile Thr Gln Ile Gln Lys Ala Ile Ser Gln Val Ser Asn Asn Arg Asn
305                 310                 315                 320
Ala Gly Ile Ala Arg Val His Glu Ala Glu Asn Leu Lys Lys Ala
                325                 330                 335
Gln Asn Asn Leu Leu Asn Ser Gln Ile Lys Asp Ala Val Asp Ala Thr
            340                 345                 350
Val Ser Phe Tyr Gln Thr Leu Thr Glu Lys Tyr Gly Glu Lys Tyr Ser
        355                 360                 365
Lys Met Ala Gln Glu Leu Ala Asp Lys Ser Lys Gly Lys Ile Gly
        370                 375                 380
Asn Val Asn Glu Ala Leu Ala Ala Phe Glu Lys Tyr Lys Asp Val Leu
385                 390                 395                 400
Asn Lys Lys Phe Ser Lys Ala Asp Arg Asp Ala Ile Phe Asn Ala Leu
                405                 410                 415
Ala Ser Val Lys Tyr Asp Asp Trp Ala Lys His Leu Asp Gln Phe Ala
            420                 425                 430
Lys Tyr Leu Lys Ile Thr Gly His Val Ser Phe Gly Tyr Asp Val Val
        435                 440                 445
Ser Asp Ile Leu Lys Ile Lys Asp Thr Gly Asp Trp Lys Pro Leu Phe
        450                 455                 460
Leu Thr Leu Glu Lys Lys Ala Ala Asp Ala Gly Val Ser Tyr Val Val
465                 470                 475                 480
Ala Leu Leu Phe Ser Leu Leu Ala Gly Thr Thr Leu Gly Ile Trp Gly
                485                 490                 495
Ile Ala Ile Val Thr Gly Ile Leu Cys Ser Tyr Ile Asp Lys Asn Lys
            500                 505                 510
Leu Asn Thr Ile Asn Glu Val Leu Gly Ile
        515                 520
```

<210> SEQ ID NO 55
<211> LENGTH: 1569
<212> TYPE: DNA
<213> ORGANISM: Escherichia coli

<400> SEQUENCE: 55

| | | | | | |
|---|---|---|---|---|---|
| atggaaaccg | cggtagcgta | ctataaagat | ggtgttcctt | atgatgataa | gggacaggta | 60 |
| attattactc | ttttgaatgg | tactcctgac | gggagtggct | ctggcggcgg | aggtggaaaa | 120 |
| ggaggcagta | aaagtgaaag | ttctgcagct | attcatgcaa | ctgctaaatg | gtctactgct | 180 |
| caattaaaga | aaacacaggc | agagcaggct | gcccgggcaa | aagctgcagc | ggaagcacag | 240 |
| gcgaaagcaa | aggcaaacag | ggatgcgctg | actcagcgcc | tgaaggatat | cgtgaatgag | 300 |
| gctcttcgtc | acaatgcctc | acgtacgcct | tcagcaacag | agcttgctca | tgctaataat | 360 |
| gcagctatgc | aggcggaaga | cgagcgtttg | cgccttgcga | aagcagaaga | aaaagcccgt | 420 |
| aaagaagcgg | aagcagcaga | aaaggctttt | caggaagcag | aacaacgacg | taaagagatt | 480 |
| gaacgggaga | aggctgaaac | agaacgccag | ttgaaactgg | ctgaagctga | agagaaacga | 540 |
| ctggctgcat | tgagtgaaga | agctaaagct | gttgagatcg | cccaaaaaaa | actttctgct | 600 |
| gcacaatctg | aagtggtgaa | aatggatgga | gagattaaga | ctctcaattc | tcgtttaagc | 660 |
| tccagtatcc | atgcccgtga | tgcagaaatg | aaaacgctcg | ctggaaaacg | aaatgaactg | 720 |
| gctcaggcat | ccgctaaata | taagaactg | gatgagctgg | tcaaaaaact | atcaccaaga | 780 |
| gccaatgatc | cgcttcagaa | ccgtcctttt | tttgaagcaa | ccagacgacg | ggttggggcc | 840 |
| ggtaagatta | gaagaaaa | acaaaaacag | gtaacagcat | cagaaacacg | tattaaccgg | 900 |
| ataaatgctg | atataactca | gatccagaag | gctatttctc | aggtcagtaa | taatcgtaat | 960 |
| gccggtatcg | ctcgtgttca | tgaagctgaa | gaaaatttga | aaaaagcaca | gaataatctc | 1020 |
| cttaattcac | agattaagga | tgctgttgat | gcaacagtta | gcttttatca | aacgctgact | 1080 |
| gaaaaatatg | tgaaaaata | ttcgaaaatg | gcacaggaac | ttgctgataa | gtctaaaggt | 1140 |
| aagaaaatcg | gcaatgtgaa | tgaagctctc | gctgcttttg | aaaaatacaa | ggatgtttta | 1200 |
| aataagaaat | tcagcaaagc | cgatcgtgat | gctatttta | atgcgttggc | atcggtgaag | 1260 |
| tatgatgact | gggctaaaca | tttagatcag | tttgccaagt | acttgaagat | tacggggcat | 1320 |
| gtttcttttg | gatatgatgt | ggtatctgat | atcctaaaaa | ttaaggatac | aggtgactgg | 1380 |
| aagccactat | ttcttacatt | agagaagaaa | gctgcagatg | caggggtgag | ttatgttgtt | 1440 |
| gctttactt | ttagcttgct | tgctggaact | acattaggta | tttggggtat | tgctattgtt | 1500 |
| acaggaattc | tatgctccta | tattgataag | aataaactta | atactataaa | tgaggtgtta | 1560 |
| gggatttaa | | | | | | 1569 |

<210> SEQ ID NO 56
<211> LENGTH: 626
<212> TYPE: PRT
<213> ORGANISM: Escherichia coli

<400> SEQUENCE: 56

Met Ser Asp Pro Val Arg Ile Thr Asn Pro Gly Ala Glu Ser Leu Gly
1               5                   10                  15

Tyr Asp Ser Asp Gly His Glu Ile Met Ala Val Asp Ile Tyr Val Asn
                20                  25                  30

Pro Pro Arg Val Asp Val Phe His Gly Thr Pro Ala Trp Ser Ser
            35                  40                  45

-continued

```
Phe Gly Asn Lys Thr Ile Trp Gly Gly Asn Glu Trp Val Asp Asp Ser
        50                  55                  60

Pro Thr Arg Ser Asp Ile Glu Lys Arg Asp Lys Glu Ile Thr Ala Tyr
 65                  70                  75                  80

Lys Asn Thr Leu Ser Ala Gln Gln Lys Glu Asn Glu Asn Lys Arg Thr
                 85                  90                  95

Glu Ala Gly Lys Arg Leu Ser Ala Ala Ile Ala Ala Arg Glu Lys Asp
            100                 105                 110

Glu Asn Thr Leu Lys Thr Leu Arg Ala Gly Asn Ala Asp Ala Ala Asp
            115                 120                 125

Ile Thr Arg Gln Glu Phe Arg Leu Leu Gln Ala Glu Leu Arg Glu Tyr
130                 135                 140

Gly Phe Arg Thr Glu Ile Ala Gly Tyr Asp Ala Leu Arg Leu His Thr
145                 150                 155                 160

Glu Ser Arg Met Leu Phe Ala Asp Ala Asp Ser Leu Arg Ile Ser Pro
                165                 170                 175

Arg Glu Ala Arg Ser Leu Ile Glu Gln Ala Glu Lys Arg Gln Lys Asp
            180                 185                 190

Ala Gln Asn Ala Asp Lys Lys Ala Ala Asp Met Leu Ala Glu Tyr Glu
            195                 200                 205

Arg Arg Lys Gly Ile Leu Asp Thr Arg Leu Ser Glu Leu Glu Lys Asn
210                 215                 220

Gly Gly Ala Ala Leu Ala Val Leu Asp Ala Gln Gln Ala Arg Leu Leu
225                 230                 235                 240

Gly Gln Gln Thr Arg Asn Asp Arg Ala Ile Ser Glu Ala Arg Asn Lys
                245                 250                 255

Leu Ser Ser Val Thr Glu Ser Leu Asn Thr Ala Arg Asn Ala Leu Thr
            260                 265                 270

Arg Ala Glu Gln Gln Leu Thr Gln Gln Lys Asn Thr Pro Asp Gly Lys
            275                 280                 285

Thr Ile Val Ser Pro Glu Lys Phe Pro Gly Arg Ser Ser Thr Asn His
290                 295                 300

Ser Ile Val Val Ser Gly Asp Pro Arg Phe Ala Gly Thr Ile Lys Ile
305                 310                 315                 320

Thr Thr Ser Ala Val Ile Asp Asn Arg Ala Asn Leu Asn Tyr Leu Leu
                325                 330                 335

Ser His Ser Gly Leu Asp Tyr Lys Arg Asn Ile Leu Asn Asp Arg Asn
            340                 345                 350

Pro Val Val Thr Glu Asp Val Glu Gly Asp Lys Lys Ile Tyr Asn Ala
            355                 360                 365

Glu Val Ala Glu Trp Asp Lys Leu Arg Gln Arg Leu Leu Asp Ala Arg
370                 375                 380

Asn Lys Ile Thr Ser Ala Glu Ser Ala Val Asn Ser Ala Arg Asn Asn
385                 390                 395                 400

Leu Ser Ala Arg Thr Asn Glu Gln Lys His Ala Asn Asp Ala Leu Asn
                405                 410                 415

Ala Leu Leu Lys Glu Lys Glu Asn Ile Arg Asn Gln Leu Ser Gly Ile
            420                 425                 430

Asn Gln Lys Ile Ala Glu Glu Lys Arg Lys Gln Asp Glu Leu Lys Ala
            435                 440                 445

Thr Lys Asp Ala Ile Asn Phe Thr Thr Glu Phe Leu Lys Ser Val Ser
450                 455                 460

Glu Lys Tyr Gly Ala Lys Ala Glu Gln Leu Ala Arg Glu Met Ala Gly
```

|     |     |     |     |     |     |     |     |     |     |     |     |     |     |     |
| --- | --- | --- | --- | --- | --- | --- | --- | --- | --- | --- | --- | --- | --- | --- |
| 465 |     |     |     |     | 470 |     |     |     |     | 475 |     |     |     | 480 |
| Gln | Ala | Lys | Gly | Lys | Lys | Ile | Arg | Asn | Val | Glu | Glu | Ala | Leu | Lys | Thr |
|     |     |     |     | 485 |     |     |     |     | 490 |     |     |     |     | 495 |
| Tyr | Glu | Lys | Tyr | Arg | Ala | Asp | Ile | Asn | Lys | Lys | Ile | Asn | Ala | Lys | Asp |
|     |     |     |     | 500 |     |     |     |     | 505 |     |     |     |     | 510 |
| Arg | Ala | Ala | Ile | Ala | Ala | Ala | Leu | Glu | Ser | Val | Lys | Leu | Ser | Asp | Ile |
|     |     |     | 515 |     |     |     |     | 520 |     |     |     |     | 525 |
| Ser | Ser | Asn | Leu | Asn | Arg | Phe | Ser | Arg | Gly | Leu | Gly | Tyr | Ala | Gly | Lys |
|     | 530 |     |     |     |     | 535 |     |     |     |     | 540 |

Phe Thr Ser Leu Ala Asp Trp Ile Thr Glu Phe Gly Lys Ala Val Arg
545             550                 555                 560

Thr Glu Asn Trp Arg Pro Leu Phe Val Lys Thr Glu Thr Ile Ile Ala
                565                 570                 575

Gly Asn Ala Ala Thr Ala Leu Val Ala Leu Val Phe Ser Ile Leu Thr
            580                 585                 590

Gly Ser Ala Leu Gly Ile Ile Gly Tyr Gly Leu Leu Met Ala Val Thr
            595                 600                 605

Gly Ala Leu Ile Asp Glu Ser Leu Val Glu Lys Ala Asn Lys Phe Trp
    610                 615                 620

Gly Ile
625

<210> SEQ ID NO 57
<211> LENGTH: 1881
<212> TYPE: DNA
<213> ORGANISM: Escherichia coli

<400> SEQUENCE: 57

```
atgtctgacc ctgtacgtat tacaaatccc ggtgcagaat cgctggggta tgattcagat    60
ggccatgaaa ttatggccgt tgatatttat gtaaaccctc acgtgtcga tgtctttcat   120
ggtaccccgc ctgcatggag ttccttcggg aacaaaacca tctggggcgg aaacgagtgg   180
gttgatgatt ccccaacccg aagtgatatc gaaaaaaggg acaaggaaat cacagcgtac   240
aaaaacacgc tcagcgcgca gcagaaagag aatgagaata gcgtactga agccggaaaa   300
cgcctctctg cggcgattgc tgcaagggaa aaagatgaaa acacactgaa aacactccgt   360
gccggaaacg cagatgccgc tgatattaca cgacaggagt tcagactcct gcaggcagag   420
ctgagagaat acggattccg tactgaaatc gccggatatg acgccctccg gctgcataca   480
gagagccgga tgctgtttgc tgatgctgat tctcttcgta tatctccccg ggaggccagg   540
tcgttaatcg aacaggctga aaacggcag aaggatgcgc agaacgcaga caagaaggcc   600
gctgatatgc ttgctgaata cgagcgcaga aaaggtattc tggacacccg gttgtcagag   660
ctggaaaaaa atggcggggc agcccttgcc gttcttgatg cacaacaggc ccgtctgctc   720
gggcagcaga cacggaatga cagggccatt tcagaggccc ggaataaact cagttcagtg   780
acggaatcgc ttaacacggc ccgtaatgca ttaaccagag ctgaacaaca gctgacgcaa   840
cagaaaaaca cgcctgacgg caaaacgata gtttcccctg aaaaattccc ggggcgttca   900
tcaacaaatg attctattgt tgtgagcggt gatccgagat tgccggtac gataaaaatc   960
acaaccagcg cagtcatcga taaccgtgca aacctgaatt atcttctgag ccattccggt  1020
ctggactata acgcaatat tctgaatgac cggaatccgg tggtgacaga ggatgtggaa  1080
ggtgacaaga aaatttataa tgctgaagtt gctgaatggg ataagttacg gcaaagattg  1140
cttgatgcca gaaataaaat cacctctgct gaatctgcgg taaattcggc gagaaataac  1200
```

-continued

```
ctcagtgcca gaacaaatga gcaaaagcat gcaaatgacg ctcttaatgc cctgttgaag    1260 gaaaagaga atatccgtaa ccagctttcc ggcatcaatc agaagatagc ggaagagaaa    1320
agaaaacagg atgaactgaa ggcaacgaaa gacgcaatta atttcacaac agagttcctg    1380
aaatcagttt cagaaaaata tggtgcaaaa gctgagcagt tagccagaga gatggccggg    1440
caggctaaag ggaagaaaat acgtaatgtt gaagaggcat taaaaacgta tgaaaagtac    1500
cgggctgaca ttaacaaaaa aattaatgca aaagatcgtg cagcgattgc cgcagcccct    1560
gagtctgtga agctgtctga tatatcgtct aatctgaaca gattcagtcg gggactggga    1620
tatgcaggaa aatttacaag tcttgctgac tggatcactg agtttggtaa ggctgtccgg    1680
acagagaact ggcgtcctct ttttgttaaa acagaaacca tcatagcagg caatgccgca    1740
acggctcttg tggcactggt cttcagtatt cttaccggaa gcgctttagg cattatcggg    1800
tatggtttac tgatggctgt caccggtgcg ctgattgatg aatcgcttgt ggaaaaagcg    1860
aataagttct ggggtattta a                                             1881
```

<210> SEQ ID NO 58
<211> LENGTH: 626
<212> TYPE: PRT
<213> ORGANISM: Escherichia coli

<400> SEQUENCE: 58

```
Met Ser Asp Pro Val Arg Ile Thr Asn Pro Gly Ala Glu Ser Leu Gly
1               5                   10                  15

Tyr Asp Ser Asp Gly His Glu Ile Met Ala Val Asp Ile Tyr Val Asn
            20                  25                  30

Pro Pro Arg Val Asp Val Phe His Gly Thr Pro Ala Trp Ser Ser
        35                  40                  45

Phe Gly Asn Lys Thr Ile Trp Gly Gly Asn Glu Trp Val Asp Asp Ser
    50                  55                  60

Pro Thr Arg Ser Asp Ile Glu Lys Arg Asp Lys Glu Ile Thr Ala Tyr
65                  70                  75                  80

Lys Asn Thr Leu Ser Ala Gln Gln Lys Glu Asn Glu Asn Lys Arg Thr
                85                  90                  95

Glu Ala Gly Lys Arg Leu Ser Ala Ala Ile Ala Ala Arg Glu Lys Asp
            100                 105                 110

Glu Asn Thr Leu Lys Thr Leu Arg Ala Gly Asn Ala Asp Ala Ala Asp
        115                 120                 125

Ile Thr Arg Gln Glu Phe Arg Leu Leu Gln Ala Glu Leu Arg Glu Tyr
    130                 135                 140

Gly Phe Arg Thr Glu Ile Ala Gly Tyr Asp Ala Leu Arg Leu His Thr
145                 150                 155                 160

Glu Ser Arg Met Leu Phe Ala Asp Ala Asp Ser Leu Arg Ile Ser Pro
                165                 170                 175

Arg Glu Ala Arg Ser Leu Ile Glu Gln Ala Lys Arg Gln Lys Asp
            180                 185                 190

Ala Gln Asn Ala Asp Lys Lys Ala Ala Asp Met Leu Ala Glu Tyr Glu
        195                 200                 205

Arg Arg Lys Gly Ile Leu Asp Thr Arg Leu Ser Glu Leu Glu Lys Asn
    210                 215                 220

Gly Gly Ala Ala Leu Ala Val Leu Asp Ala Gln Gln Ala Arg Leu Leu
225                 230                 235                 240

Gly Gln Gln Thr Arg Asn Asp Arg Ala Ile Ser Glu Ala Arg Asn Lys
```

```
                245                 250                 255
Leu Ser Ser Val Thr Glu Ser Leu Lys Thr Ala Arg Asn Ala Leu Thr
            260                 265                 270
Arg Ala Glu Gln Gln Leu Thr Gln Gln Lys Asn Thr Pro Asp Gly Lys
        275                 280                 285
Thr Ile Val Ser Pro Glu Lys Phe Pro Gly Arg Ser Ser Thr Asn His
    290                 295                 300
Ser Ile Val Val Ser Gly Asp Pro Arg Phe Ala Gly Thr Ile Lys Ile
305                 310                 315                 320
Thr Thr Ser Ala Val Ile Asp Asn Arg Ala Asn Leu Asn Tyr Leu Leu
                325                 330                 335
Thr His Ser Gly Leu Asp Tyr Lys Arg Asn Ile Leu Asn Asp Arg Asn
            340                 345                 350
Pro Val Val Thr Glu Asp Val Glu Gly Asp Lys Lys Ile Tyr Asn Ala
        355                 360                 365
Glu Val Ala Glu Trp Asp Lys Leu Arg Gln Arg Leu Leu Asp Ala Arg
    370                 375                 380
Asn Lys Ile Thr Ser Ala Glu Ser Ala Ile Asn Ser Ala Arg Asn Asn
385                 390                 395                 400
Val Ser Ala Arg Thr Asn Glu Gln Lys His Ala Asn Asp Ala Leu Asn
                405                 410                 415
Ala Leu Leu Lys Glu Lys Glu Asn Ile Arg Ser Gln Leu Ala Asp Ile
            420                 425                 430
Asn Gln Lys Ile Ala Glu Glu Lys Arg Lys Arg Asp Glu Ile Asn Met
        435                 440                 445
Val Lys Asp Ala Ile Lys Leu Thr Ser Asp Phe Tyr Arg Thr Ile Tyr
    450                 455                 460
Asp Glu Phe Gly Lys Gln Ala Ser Glu Leu Ala Lys Glu Leu Ala Ser
465                 470                 475                 480
Val Ser Gln Gly Lys Gln Ile Lys Ser Val Asp Asp Ala Leu Asn Ala
                485                 490                 495
Phe Asp Lys Phe Arg Asn Asn Leu Asn Lys Lys Tyr Asn Ile Gln Asp
            500                 505                 510
Arg Met Ala Ile Ser Lys Ala Leu Glu Ala Ile Asn Gln Val His Met
        515                 520                 525
Ala Glu Asn Phe Lys Leu Phe Ser Lys Ala Phe Gly Phe Thr Gly Lys
    530                 535                 540
Val Ile Glu Arg Tyr Asp Val Ala Val Glu Leu Gln Lys Ala Val Lys
545                 550                 555                 560
Thr Asp Asn Trp Arg Pro Phe Val Lys Leu Glu Ser Leu Ala Ala
                565                 570                 575
Gly Arg Ala Ala Ser Ala Val Thr Ala Trp Ala Phe Ser Val Met Leu
            580                 585                 590
Gly Thr Pro Val Gly Ile Leu Gly Phe Ala Ile Met Ala Ala Val
        595                 600                 605
Ser Ala Leu Val Asn Asp Lys Phe Ile Glu Gln Val Asn Lys Leu Ile
    610                 615                 620
Gly Ile
625

<210> SEQ ID NO 59
<211> LENGTH: 1881
<212> TYPE: DNA
<213> ORGANISM: Escherichia coli
```

<400> SEQUENCE: 59

```
atgtctgacc ctgtacgtat tacaaatccc ggtgcagaat cgctgggata tgattcagat      60
ggccatgaaa ttatggccgt tgatatttat gtaaaccctc cacgtgtcga tgtctttcat     120
ggtaccccgc ctgcatggag ttccttcggg aacaaaacca tctggggtgg aaacgagtgg     180
gtcgatgatt ccccaacccg aagtgatatc gaaaaaggg acaaggaaat cacagcgtac      240
aaaaacacgc tcagcgcgca gcagaaagag aatgagaata gcgtactga agctggaaaa      300
cgcctttctg cggcaattgc tgcaagggaa aaagatgaaa acacactgaa aacactccgt     360
gccggaaacg cagatgccgc tgatattaca cgacaggagt tcagactcct gcaggcagag     420
ctgagagaat acggattccg tactgaaatc gccggatatg atgccctccg gctgcataca     480
gagagccgga tgctgtttgc tgatgctgat tctcttcgta tatctccccg cgaggccagg     540
tcgttaatcg aacaggctga aaacggcag aaggatgcgc agaacgcaga caagaaggcc      600
gctgatatgc ttgctgaata cgagcgcaga aaggtattc tggacacgcg gttgtcagag      660
ctggaaaaaa atggcgggc agcccttgcc gttcttgatg cacaacaggc ccgtctgctc      720
gggcagcaga cacggaatga cagggccatt tcagaggccc ggaataaact cagttcggtg     780
acggaatcgc ttaagacggc ccgtaatgca ttaaccagag ctgaacaaca gctgacgcaa     840
cagaaaaaca cgcctgacgg caaaacgata gtttcccctg aaaaattccc ggggcgttca     900
tcaacaaatc attctattgt tgtgagtggt gatccgaggt ttgccggtac gataaaaatc     960
acaaccagcg cggtcatcga taaccgtgca aacctgaatt atcttctgac ccattccggt    1020
ctggactata aacgcaatat tctgaatgac cggaatccgg tggtgacaga ggatgtggaa    1080
ggtgacaaga aaatttataa tgctgaagtt gctgaatggg ataagttacg gcaacgattg    1140
cttgatgcca gaaataaaat cacctctgct gaatctgcga taaattcggc gagaaataac    1200
gtcagtgcca gaacaaatga acaaaagcat gcaaatgacg ctcttaatgc cctgttgaag    1260
gaaaagagag atatccgtag ccagcttgct gacatcaatc agaaaatagc tgaagagaaa    1320
agaaaaaggg atgaaataaa tatggtaaag gatgccataa aactcacctc tgatttctac    1380
agaacgatat atgatgagtt cggtaaacaa gcatccgaac ttgctaagga gctggcttct    1440
gtatctcaag ggaaacagat taagagtgtg gatgatgcac tgaacgcttt tgataaattc    1500
cgtaataatc tgaacaagaa atataacata caagatcgca tggccatttc taaagccctg    1560
gaagctatta atcaggtcca tatggcggag aattttaagc tgttcagtaa ggcatttggt    1620
tttaccggaa aagttattga acgttatgat gttgctgtgg agttacaaaa ggctgtaaaa    1680
acggacaact ggcgtccatt ttttgtaaaa cttgaatcac tggcagcagg aagagctgct    1740
tcagcagtta cagcatgggc gttttccgtc atgctgggaa cccctgtagg tattctgggt    1800
tttgcaatta ttatggcggc tgtgagtgcg cttgttaatg ataagtttat tgagcaggtc    1860
aataaactta ttggtatctg a                                              1881
```

<210> SEQ ID NO 60  
<211> LENGTH: 271  
<212> TYPE: PRT  
<213> ORGANISM: Escherichia coli

<400> SEQUENCE: 60

```
Met Glu Thr Leu Thr Val His Ala Pro Ser Pro Ser Thr Asn Leu Pro
  1               5                  10                  15

Ser Tyr Gly Asn Gly Ala Phe Ser Leu Ser Ala Pro His Val Pro Gly
```

```
            20                  25                  30
Ala Gly Pro Leu Leu Val Gln Val Val Tyr Ser Phe Phe Gln Ser Pro
             35                  40                  45

Asn Met Cys Leu Gln Ala Leu Thr Gln Leu Glu Asp Tyr Ile Lys Lys
 50                  55                  60

His Gly Ala Ser Asn Pro Leu Thr Leu Gln Ile Ile Ser Thr Asn Ile
 65                  70                  75                  80

Gly Tyr Phe Cys Asn Ala Asp Arg Asn Leu Val Leu His Pro Gly Ile
                 85                  90                  95

Ser Val Tyr Asp Ala Tyr His Phe Ala Lys Pro Ala Pro Ser Gln Tyr
            100                 105                 110

Asp Tyr Arg Ser Met Asn Met Lys Gln Met Ser Gly Asn Val Thr Thr
            115                 120                 125

Pro Ile Val Ala Leu Ala His Tyr Leu Trp Gly Asn Gly Ala Glu Arg
        130                 135                 140

Ser Val Asn Ile Ala Asn Ile Gly Leu Lys Ile Ser Pro Met Lys Ile
145                 150                 155                 160

Asn Gln Ile Lys Asp Ile Ile Lys Ser Gly Val Val Gly Thr Phe Pro
                165                 170                 175

Val Ser Thr Lys Phe Thr His Ala Thr Gly Asp Tyr Asn Val Ile Thr
            180                 185                 190

Gly Ala Tyr Leu Gly Asn Ile Thr Leu Lys Thr Glu Gly Thr Leu Thr
        195                 200                 205

Ile Ser Ala Asn Gly Ser Trp Thr Tyr Asn Gly Val Val Arg Ser Tyr
    210                 215                 220

Asp Asp Lys Tyr Asp Phe Asn Ala Ser Thr His Arg Gly Ile Ile Gly
225                 230                 235                 240

Glu Ser Leu Thr Arg Leu Gly Ala Met Phe Ser Gly Lys Glu Tyr Gln
                245                 250                 255

Ile Leu Leu Pro Gly Glu Ile His Ile Lys Glu Ser Gly Lys Arg
            260                 265                 270

<210> SEQ ID NO 61
<211> LENGTH: 816
<212> TYPE: DNA
<213> ORGANISM: Escherichia coli

<400> SEQUENCE: 61
atggaaacct taactgttca tgcaccatca ccatcaacta acttaccaag ttatggcaat     60
ggtgcatttt ctctttcagc accacatgtg cctggtgctg ccctcttttt agtccaggtt    120
gtttatagtt ttttccagag tccaaacatg tgtcttcagg ctttaactca acttgaggat    180
tacatcaaaa acatggggc cagcaaccct ctcacattgc agatcatatc gacaaatatt    240
ggttacttct gtaacgccga ccgaaatctg gttcttcacc ctggtaataag cgtttatgac    300 gcttaccact cgcaaaaacc agcgccaagt caatatgact atcgctcaat gaatatgaaa    360
caaatgagcg gtaatgtcac taccaattgtg gcgcttgctca ctcactattt atggggtaat    420
ggcgctgaaa ggagcgttaa tatcgccaac attggtctta aaatttcccc tatgaaaatt    480
aatcagataa aagacattat aaaatctggt gtagtaggca cattccctgt ttctacaaag    540
ttcacacatg ccactggtga ttataatgtt attaccggtg catatcttgg taatatcaca    600
ctgaaaacag aaggtacttt aactatctct gccaatggct cctggactta aatggcgtt    660 gttcgttcat atgatgataa atacgatttt aacgccagca ctcaccgtgg cattatcgga    720
```

```
gagtcgctca caaggctcgg ggcgatgttt tctggtaaag agtaccagat actgcttcct    780
ggtgaaattc acattaaaga aagtggtaag cgataa                              816
```

<210> SEQ ID NO 62
<211> LENGTH: 387
<212> TYPE: PRT
<213> ORGANISM: Escherichia coli

<400> SEQUENCE: 62

```
Met Gly Ser Asn Gly Ala Asp Asn Ala His Asn Asn Ala Phe Gly Gly
1               5                   10                  15

Gly Lys Asn Pro Gly Ile Gly Asn Thr Ser Gly Ala Gly Ser Asn Gly
            20                  25                  30

Ser Ala Ser Ser Asn Arg Gly Asn Ser Asn Gly Trp Ser Trp Ser Asn
        35                  40                  45

Lys Pro His Lys Asn Asp Gly Phe His Ser Asp Gly Ser Tyr His Ile
    50                  55                  60

Thr Phe His Gly Asp Asn Asn Ser Lys Pro Lys Pro Gly Gly Asn Ser
65                  70                  75                  80

Gly Asn Arg Gly Asn Asn Gly Asp Gly Ala Ser Ala Lys Val Gly Glu
                85                  90                  95

Ile Thr Ile Thr Pro Asp Asn Ser Lys Pro Gly Arg Tyr Ile Ser Ser
            100                 105                 110

Asn Pro Glu Tyr Ser Leu Leu Ala Lys Leu Ile Asp Ala Glu Ser Ile
        115                 120                 125

Lys Gly Thr Glu Val Tyr Thr Phe His Thr Arg Lys Gly Gln Tyr Val
    130                 135                 140

Lys Val Thr Val Pro Asp Ser Asn Ile Asp Lys Met Arg Val Asp Tyr
145                 150                 155                 160

Val Asn Trp Lys Gly Pro Lys Tyr Asn Asn Lys Leu Val Lys Arg Phe
                165                 170                 175

Val Ser Gln Phe Leu Leu Phe Arg Lys Glu Glu Lys Glu Lys Asn Glu
            180                 185                 190

Lys Glu Ala Leu Leu Lys Ala Ser Glu Leu Val Ser Gly Met Gly Asp
        195                 200                 205

Lys Leu Gly Glu Tyr Leu Gly Val Lys Tyr Lys Asn Val Ala Lys Glu
    210                 215                 220

Val Ala Asn Asp Ile Lys Asn Phe His Gly Arg Asn Ile Arg Ser Tyr
225                 230                 235                 240

Asn Glu Ala Met Ala Ser Leu Asn Lys Val Leu Ala Asn Pro Lys Met
                245                 250                 255

Lys Val Asn Lys Ser Asp Lys Asp Ala Ile Val Asn Ala Trp Lys Gln
            260                 265                 270

Val Asn Ala Lys Asp Met Ala Asn Lys Ile Gly Asn Leu Gly Lys Ala
        275                 280                 285

Phe Lys Val Ala Asp Leu Ala Ile Lys Val Glu Lys Ile Arg Glu Lys
    290                 295                 300

Ser Ile Glu Gly Tyr Asn Thr Gly Asn Trp Gly Pro Leu Leu Leu Glu
305                 310                 315                 320

Val Glu Ser Trp Ile Ile Gly Gly Val Val Ala Gly Val Ala Ile Ser
                325                 330                 335

Leu Phe Gly Ala Val Leu Ser Phe Leu Pro Ile Ser Gly Leu Ala Val
            340                 345                 350

Thr Ala Leu Gly Val Ile Gly Ile Met Thr Ile Ser Tyr Leu Ser Ser
```

```
                355                 360                 365
Phe Ile Asp Ala Asn Arg Val Ser Asn Ile Asn Asn Ile Ser Ser
            370                 375                 380

Val Ile Arg
385

<210> SEQ ID NO 63
<211> LENGTH: 51
<212> TYPE: DNA
<213> ORGANISM: Escherichia coli

<400> SEQUENCE: 63
gcaaatcgag tttcgaatat aaataacatt atatctagtg ttattcgatg a            51

<210> SEQ ID NO 64
<211> LENGTH: 103
<212> TYPE: PRT
<213> ORGANISM: Escherichia coli

<400> SEQUENCE: 64

Met Arg Thr Leu Thr Leu Asn Glu Leu Asp Ser Val Ser Gly Gly Ala
1               5                   10                  15

Ser Gly Arg Asp Ile Ala Met Ala Ile Gly Thr Leu Ser Gly Gln Phe
            20                  25                  30

Val Ala Gly Gly Ile Gly Ala Ala Gly Val Ala Gly Gly Ala
        35                  40                  45

Ile Tyr Asp Tyr Ala Ser Thr His Lys Pro Asn Pro Ala Met Ser Pro
    50                  55                  60

Ser Gly Leu Gly Gly Thr Ile Lys Gln Lys Pro Glu Gly Ile Pro Ser
65                  70                  75                  80

Glu Ala Trp Asn Tyr Ala Ala Gly Arg Leu Cys Asn Trp Ser Pro Asn
                85                  90                  95

Asn Leu Ser Asp Val Cys Leu
            100

<210> SEQ ID NO 65
<211> LENGTH: 312
<212> TYPE: DNA
<213> ORGANISM: Escherichia coli

<400> SEQUENCE: 65
atgagaactc tgactctaaa tgaattagat tctgtttctg gtggtgcttc agggcgtgat       60
attgcgatgg ctataggaac actatccgga caatttgttg caggaggaat tggagcagct      120
gctgggggtg tggctggagg tgcaatatat gactatgcat ccactcacaa acctaatcct      180
gcaatgtctc catccggttt aggaggaaca attaagcaaa aacccgaagg gataccttca      240
gaagcatgga actatgctgc gggaagattg tgtaattgga gtccaaataa tcttagtgat      300
gtttgtttat aa                                                         312

<210> SEQ ID NO 66
<211> LENGTH: 58
<212> TYPE: PRT
<213> ORGANISM: Enterococcus columbae

<400> SEQUENCE: 66

Met Met Asn Ala Thr Glu Asn Gln Ile Phe Val Glu Thr Val Ser Asp
1               5                   10                  15

Gln Glu Leu Glu Met Leu Ile Gly Gly Ala Gly Arg Gly Trp Ile Lys
```

```
                20                  25                  30

Thr Leu Thr Lys Asp Cys Pro Asn Val Ile Ser Ser Ile Cys Ala Gly
            35                  40                  45

Thr Ile Ile Thr Ala Cys Lys Asn Cys Ala
        50                  55

<210> SEQ ID NO 67
<211> LENGTH: 177
<212> TYPE: DNA
<213> ORGANISM: Enterococcus columbae

<400> SEQUENCE: 67
atgatgaatg ctactgaaaa ccaaattttt gttgagactg tgagtgacca agaattagaa      60
atgttaattg gtggtgcagg tcgtggatgg attaagactt taacaaaaga ttgtccaaat     120
gtgatttctt caatttgtgc aggtacaatt attacagctt gtaaaaattg tgcttaa       177

<210> SEQ ID NO 68
<211> LENGTH: 59
<212> TYPE: PRT
<213> ORGANISM: Lactobacillus curvatus

<400> SEQUENCE: 68

Met Asn Asn Val Lys Glu Leu Ser Met Thr Glu Leu Gln Thr Ile Thr
1               5                   10                  15

Gly Gly Ala Arg Ser Tyr Gly Asn Gly Val Tyr Cys Asn Asn Lys Lys
            20                  25                  30

Cys Trp Val Asn Arg Gly Glu Ala Thr Gln Ser Ile Ile Gly Gly Met
        35                  40                  45

Ile Ser Gly Trp Ala Ser Gly Leu Ala Gly Met
    50                  55

<210> SEQ ID NO 69
<211> LENGTH: 180
<212> TYPE: DNA
<213> ORGANISM: Lactobacillus curvatus

<400> SEQUENCE: 69
atgaataatg taaagaatt aagtatgaca gaattacaaa caattaccgg cggtgctaga       60
tcatatggca acggtgttta ctgtaataat aaaaaatgtt gggtaaatcg gggtgaagca    120
acgcaaagta ttattggtgg tatgattagc ggctgggcta gtggtttagc tggaatgtaa    180

<210> SEQ ID NO 70
<211> LENGTH: 64
<212> TYPE: PRT
<213> ORGANISM: Streptomyces sp.

<400> SEQUENCE: 70

Met Arg Ser Glu Met Thr Leu Thr Ser Thr Asn Ser Ala Glu Ala Leu
1               5                   10                  15

Ala Ala Gln Asp Phe Ala Asn Thr Val Leu Ser Ala Ala Pro Gly
            20                  25                  30

Phe His Ala Asp Cys Glu Thr Pro Ala Met Ala Thr Pro Ala Thr Pro
        35                  40                  45

Thr Val Ala Gln Phe Val Ile Gln Gly Ser Thr Ile Cys Leu Val Cys
    50                  55                  60

<210> SEQ ID NO 71
<211> LENGTH: 195
```

<212> TYPE: DNA
<213> ORGANISM: Streptomyces sp.

<400> SEQUENCE: 71

```
gtgcgatctg agatgactct tacgagcacg aattccgctg aggctctggc ggcgcaggac        60
tttgcgaaca ccgttctcag cgcggcggcc ccgggcttcc acgcggactg cgagacgccg       120
gccatggcca ccccggccac gccgaccgtc gcccagttcg tgatccaggg cagcacgatc       180
tgcctggtct gctga                                                        195
```

<210> SEQ ID NO 72
<211> LENGTH: 65
<212> TYPE: PRT
<213> ORGANISM: Bacillus halodurans

<400> SEQUENCE: 72

```
Met Val Asn Ser Lys Asp Leu Arg Asn Pro Glu Phe Arg Lys Ala Gln
1               5                   10                  15
Gly Leu Gln Phe Val Asp Glu Val Asn Glu Lys Glu Leu Ser Ser Leu
            20                  25                  30
Ala Gly Ser Gly Asp Val His Ala Gln Thr Thr Trp Pro Cys Ala Thr
        35                  40                  45
Val Gly Val Ser Val Ala Leu Cys Pro Thr Thr Lys Cys Thr Ser Gln
    50                  55                  60
Cys
65
```

<210> SEQ ID NO 73
<211> LENGTH: 198
<212> TYPE: DNA
<213> ORGANISM: Bacillus halodurans

<400> SEQUENCE: 73

```
atggtaaatt caaaagattt gcgtaatcct gaattccgca aagcccaagg tctacaattc        60
gttgacgagg tgaacgagaa ggaactttcg tctctagctg gttcaggaga tgtgcatgca       120
caaacaactt ggccttgcgc tacagttggt gtctccgtag ccttgtgccc aactacaaag       180
tgtacaagcc agtgctaa                                                    198
```

<210> SEQ ID NO 74
<211> LENGTH: 66
<212> TYPE: PRT
<213> ORGANISM: Carnobacterium divergens

<400> SEQUENCE: 74

```
Met Lys Asn Leu Lys Glu Gly Ser Tyr Thr Ala Val Asn Thr Asp Glu
1               5                   10                  15
Leu Lys Ser Ile Asn Gly Gly Thr Lys Tyr Tyr Gly Asn Gly Val Tyr
            20                  25                  30
Cys Asn Ser Lys Lys Cys Trp Val Asp Trp Gly Gln Ala Ser Gly Cys
        35                  40                  45
Ile Gly Gln Thr Val Val Gly Gly Trp Leu Gly Gly Ala Ile Pro Gly
    50                  55                  60
Lys Cys
65
```

<210> SEQ ID NO 75
<211> LENGTH: 201
<212> TYPE: DNA

<213> ORGANISM: Carnobacterium divergens

<400> SEQUENCE: 75

```
atgaaaaact taaaagaagg ttcatacact gctgttaata ctgatgaatt aaaaagtatc    60
aatggtggaa caaatatta tgggaatggc gtttattgca attctaaaaa atgttgggta   120
gattggggac aagcttcagg ttgtatcggt caaactgttg ttggcggatg gctaggcgga   180
gctataccag gtaaatgcta a                                             201
```

<210> SEQ ID NO 76
<211> LENGTH: 63
<212> TYPE: PRT
<213> ORGANISM: Carnobacterium divergens

<400> SEQUENCE: 76

```
Met Ile Lys Arg Glu Lys Asn Arg Thr Ile Ser Ser Leu Gly Tyr Glu
1               5                   10                  15
Glu Ile Ser Asn His Lys Leu Gln Glu Ile Gln Gly Gly Lys Gly Ile
            20                  25                  30
Leu Gly Lys Leu Gly Val Val Gln Ala Gly Val Asp Phe Val Ser Gly
        35                  40                  45
Val Trp Ala Gly Ile Lys Gln Ser Ala Lys Asp His Pro Asn Ala
    50                  55                  60
```

<210> SEQ ID NO 77
<211> LENGTH: 192
<212> TYPE: DNA
<213> ORGANISM: Carnobacterium divergens

<400> SEQUENCE: 77

```
atgattaaaa gagaaaagaa cagaacaatt tcttcccttg gttatgaaga aatttctaat    60
cataaattgc aagaaataca aggtggaaaa ggaattcttg gtaaactagg agtagtacag   120
gcaggagtgg attttgtatc aggagtgtgg gctggaataa aacagtctgc caaagatcat   180
cctaatgcgt aa                                                       192
```

<210> SEQ ID NO 78
<211> LENGTH: 75
<212> TYPE: PRT
<213> ORGANISM: Carnobacterium divergens

<400> SEQUENCE: 78

```
Met Lys Lys Gln Ile Leu Lys Gly Leu Val Ile Val Val Cys Leu Ser
1               5                   10                  15
Gly Ala Thr Phe Phe Ser Thr Pro Gln Gln Ala Ser Ala Ala Ala Pro
            20                  25                  30
Lys Ile Thr Gln Lys Gln Lys Asn Cys Val Asn Gly Gln Leu Gly Gly
        35                  40                  45
Met Leu Ala Gly Ala Leu Gly Gly Pro Gly Gly Val Val Leu Gly Gly
    50                  55                  60
Ile Gly Gly Ala Ile Ala Gly Gly Cys Phe Asn
65                  70                  75
```

<210> SEQ ID NO 79
<211> LENGTH: 228
<212> TYPE: DNA
<213> ORGANISM: Carnobacterium divergens

<400> SEQUENCE: 79

-continued

```
atgaaaaaac aaattttaaa agggttggtt atagttgttt gtttatctgg ggcaacattt      60
ttctcaacac cacaacaagc ttctgctgct gcaccgaaaa ttactcaaaa acaaaaaaat     120
tgtgttaatg gacaattagg tggaatgctt gctggagctt tgggtggacc tggcggagtt    180
gtgttaggtg gtataggtgg tgcaatagca ggaggttgtt ttaattaa                 228
```

<210> SEQ ID NO 80
<211> LENGTH: 72
<212> TYPE: PRT
<213> ORGANISM: Enterococcus durans

<400> SEQUENCE: 80

```
Met Gln Thr Ile Lys Glu Leu Asn Thr Met Glu Leu Gln Glu Ile Ile
1               5                   10                  15

Gly Gly Glu Asn Asp His Arg Met Pro Tyr Glu Leu Asn Arg Pro Asn
            20                  25                  30

Asn Leu Ser Lys Gly Gly Ala Lys Cys Ala Ala Gly Ile Leu Gly Ala
        35                  40                  45

Gly Leu Gly Ala Val Gly Gly Pro Gly Gly Phe Ile Ser Ala Gly
    50                  55                  60

Ile Ser Ala Val Leu Gly Cys Met
65                  70
```

<210> SEQ ID NO 81
<211> LENGTH: 219
<212> TYPE: DNA
<213> ORGANISM: Enterococcus durans

<400> SEQUENCE: 81

```
atgcaaacga tcaaagaatt gaacacgatg gaattacaag aaataattgg aggtgaaaat      60
gaccatcgga tgccttacga attgaaccgt ccaaataatt tatccaaagg tggggctaag    120
tgtgctgctg gaatacttgg cgctggacta ggcgcagtag gcggtggacc tggcggattt    180
attagtgccg gaatcagtgc tgttcttggt tgtatgtaa                           219
```

<210> SEQ ID NO 82
<211> LENGTH: 72
<212> TYPE: PRT
<213> ORGANISM: Enterococcus durans

<400> SEQUENCE: 82

```
Met Gln Thr Ile Lys Glu Leu Asn Thr Met Glu Leu Gln Lys Ile Ile
1               5                   10                  15

Gly Gly Glu Asn Asp His Arg Met Pro Tyr Glu Leu Asn Arg Pro Asn
            20                  25                  30

Asn Leu Ser Lys Gly Gly Ala Lys Cys Ala Ala Gly Ile Leu Gly Ala
        35                  40                  45

Gly Leu Gly Ala Val Gly Gly Pro Gly Gly Phe Ile Ser Ala Gly
    50                  55                  60

Ile Ser Ala Val Leu Gly Cys Met
65                  70
```

<210> SEQ ID NO 83
<211> LENGTH: 219
<212> TYPE: DNA
<213> ORGANISM: Enterococcus durans

<400> SEQUENCE: 83

```
atgcaaacga tcaaagaatt gaacacgatg gaattacaaa aaataattgg aggtgaaaat      60
```

```
gaccatcgga tgccttacga attgaaccgt ccaaataatt tatccaaagg tggagctaag    120
tgcgctgccg gaatacttgg tgctggatta ggcgcagtag gcggtggacc tggcggattt    180
attagtgccg gaatcagtgc tgttcttggt tgtatgtaa                           219
```

<210> SEQ ID NO 84
<211> LENGTH: 220
<212> TYPE: PRT
<213> ORGANISM: Streptococcus dysgalactiae subsp. equisimilis

<400> SEQUENCE: 84

```
Met Lys Lys Leu Lys Arg Leu Val Ile Ser Leu Val Thr Ser Leu Leu
1               5                   10                  15

Val Ile Ser Ser Thr Val Pro Ala Leu Val Tyr Ala Asn Glu Thr Asn
            20                  25                  30

Asn Phe Ala Glu Thr Gln Lys Glu Ile Thr Thr Asn Ser Glu Ala Thr
        35                  40                  45

Leu Thr Asn Glu Asp Tyr Thr Lys Leu Thr Ser Glu Val Lys Thr Ile
    50                  55                  60

Tyr Thr Asn Leu Ile Gln Tyr Asp Gln Thr Lys Asn Lys Phe Tyr Val
65                  70                  75                  80

Asp Glu Asp Lys Thr Glu Gln Tyr Tyr Asn Tyr Asp Asp Glu Ser Ile
                85                  90                  95

Lys Gly Val Tyr Leu Met Lys Asp Ser Leu Asn Asp Glu Leu Asn Asn
            100                 105                 110

Asn Asn Ser Ser Asn Tyr Ser Glu Ile Ile Asn Gln Lys Ile Ser Glu
        115                 120                 125

Ile Asp Tyr Val Leu Gln Gly Asn Asp Ile Asn Asn Leu Ile Pro Ser
    130                 135                 140

Asn Thr Arg Val Lys Arg Ser Ala Asp Phe Ser Trp Ile Gln Arg Cys
145                 150                 155                 160

Leu Glu Glu Ala Trp Gly Tyr Ala Ile Ser Leu Val Thr Leu Lys Gly
                165                 170                 175

Ile Ile Asn Leu Phe Lys Ala Gly Lys Phe Glu Ala Ala Ala Ala Lys
            180                 185                 190

Leu Ala Ser Ala Thr Ala Gly Arg Ile Ala Gly Met Ala Ala Leu Phe
        195                 200                 205

Ala Phe Val Ala Thr Cys Gly Ala Thr Thr Val Ser
    210                 215                 220
```

<210> SEQ ID NO 85
<211> LENGTH: 663
<212> TYPE: DNA
<213> ORGANISM: Streptococcus dysgalactiae subsp. equisimilis

<400> SEQUENCE: 85

```
atgaaaaaat taaacgtctc tgttatctct cttgttactt cattactagt aatttcaagt     60
acagttccag cacttgttta cgctaatgaa acaaataact tgcagaaaac tcaaaagaa    120 attacaacaa attcagaagc aacattaacc aatgaagact acactaaatt aacttccgaa    180
gtaaaaacaa tttatacaaa tctgattcaa tacgaccaaa caaaaaacaa attttacgtc    240
gatgaagaca aaactgaaca atattataac tacgatgatg aaagtataaa aggggtttat    300
ctcatgaaag atagtttgaa cgatgagtta acaataata actcttcaaa ctattctgaa    360
ataattaatc aaaaaatctc tgaaattgac tatgtccttc aaggaaacga tataaataat    420
```

```
ttaattccta gcaataccag agtaaaaaga tcagcagatt tttcttggat tcaaagatgt    480
ctagaagaag catggggata tgctattagt ctagttactc taaaaggaat aatcaatcta    540
tttaaagcag gaaaatttga agctgctgct gctaaattag cttctgctac agcaggtaga    600
atcgctggaa tggctgcctt atttgctttc gtagcaactt gcggtgcgac aactgtatca    660
taa                                                                  663
```

<210> SEQ ID NO 86
<211> LENGTH: 57
<212> TYPE: PRT
<213> ORGANISM: Enterococcus faecalis

<400> SEQUENCE: 86

```
Met Lys Gln Tyr Lys Val Leu Asn Glu Lys Glu Met Lys Lys Pro Ile
1               5                   10                  15

Gly Gly Glu Ser Val Phe Ser Lys Ile Gly Asn Ala Val Gly Pro Ala
            20                  25                  30

Ala Tyr Trp Ile Leu Lys Gly Leu Gly Asn Met Ser Asp Val Asn Gln
        35                  40                  45

Ala Asp Arg Ile Asn Arg Lys Lys His
    50                  55
```

<210> SEQ ID NO 87
<211> LENGTH: 174
<212> TYPE: DNA
<213> ORGANISM: Enterococcus faecalis

<400> SEQUENCE: 87

```
atgaagcaat ataaagtatt gaatgaaaaa gaaatgaaaa aacctattgg gggagagtcg    60 gttttagta aataggtaa tgctgtaggt ccagctgctt attggatttt aaaaggatta    120
ggtaatatga gtgatgtaaa ccaagctgat agaattaata gaaagaaaca ttaa          174
```

<210> SEQ ID NO 88
<211> LENGTH: 44
<212> TYPE: PRT
<213> ORGANISM: Enterococcus faecalis

<400> SEQUENCE: 88

```
Met Gly Ala Ile Ala Lys Leu Val Ala Lys Phe Gly Trp Pro Ile Val
1               5                   10                  15

Lys Lys Tyr Tyr Lys Gln Ile Met Gln Phe Ile Gly Glu Gly Trp Ala
            20                  25                  30

Ile Asn Lys Ile Ile Asp Trp Ile Lys Lys His Ile
        35                  40
```

<210> SEQ ID NO 89
<211> LENGTH: 135
<212> TYPE: DNA
<213> ORGANISM: Enterococcus faecalis

<400> SEQUENCE: 89

```
atgggagcaa tcgcaaaatt agtagcaaag tttggatggc caattgttaa aaagtattac    60
aaacaaatta tgcaatttat tggagaagga tgggcaatta caaaaattat tgattggatc    120
aaaaaacata tttaa                                                     135
```

<210> SEQ ID NO 90
<211> LENGTH: 43
<212> TYPE: PRT

<213> ORGANISM: Enterococcus faecalis

<400> SEQUENCE: 90

| Met | Gly | Ala | Ile | Ala | Lys | Leu | Val | Ala | Lys | Phe | Gly | Trp | Pro | Phe | Ile |
|---|---|---|---|---|---|---|---|---|---|---|---|---|---|---|---|
| 1 | | | | 5 | | | | | 10 | | | | | 15 | |

| Lys | Lys | Phe | Tyr | Lys | Gln | Ile | Met | Gln | Phe | Ile | Gly | Gly | Trp | Thr |
|---|---|---|---|---|---|---|---|---|---|---|---|---|---|---|
| | | | 20 | | | | | 25 | | | | | 30 | |

| Ile | Asp | Gln | Ile | Glu | Lys | Trp | Leu | Lys | Arg | His |
|---|---|---|---|---|---|---|---|---|---|---|
| | | | 35 | | | | | 40 | | |

<210> SEQ ID NO 91
<211> LENGTH: 132
<212> TYPE: DNA
<213> ORGANISM: Enterococcus faecalis

<400> SEQUENCE: 91

```
atgggagcaa tcgcaaaatt agtagcaaag tttggatggc catttattaa aaaattctac    60
aaacaaatta tgcagtttat cggacaagga tggacaatag atcaaattga aaaatggtta   120
aaaagacatt ga                                                       132
```

<210> SEQ ID NO 92
<211> LENGTH: 74
<212> TYPE: PRT
<213> ORGANISM: Enterococcus faecalis

<400> SEQUENCE: 92

| Met | Leu | Asn | Lys | Lys | Leu | Leu | Glu | Asn | Gly | Val | Val | Asn | Ala | Val | Thr |
|---|---|---|---|---|---|---|---|---|---|---|---|---|---|---|---|
| 1 | | | | 5 | | | | | 10 | | | | | 15 | |

| Ile | Asp | Glu | Leu | Asp | Ala | Gln | Phe | Gly | Gly | Met | Ser | Lys | Arg | Asp | Cys |
|---|---|---|---|---|---|---|---|---|---|---|---|---|---|---|---|
| | | | 20 | | | | | 25 | | | | | 30 | | |

| Asn | Leu | Met | Lys | Ala | Cys | Cys | Ala | Gly | Gln | Ala | Val | Thr | Tyr | Ala | Ile |
|---|---|---|---|---|---|---|---|---|---|---|---|---|---|---|---|
| | | 35 | | | | | 40 | | | | | 45 | | | |

| His | Ser | Leu | Leu | Asn | Arg | Leu | Gly | Gly | Asp | Ser | Ser | Asp | Pro | Ala | Gly |
|---|---|---|---|---|---|---|---|---|---|---|---|---|---|---|---|
| | 50 | | | | | 55 | | | | | 60 | | | | |

| Cys | Asn | Asp | Ile | Val | Arg | Lys | Tyr | Cys | Lys |
|---|---|---|---|---|---|---|---|---|---|
| 65 | | | | | 70 | | | | |

<210> SEQ ID NO 93
<211> LENGTH: 225
<212> TYPE: DNA
<213> ORGANISM: Enterococcus faecalis

<400> SEQUENCE: 93

```
atgttaaata aaaaattatt agaaaatggt gtagtaaatg ctgtaacaat tgatgaactt    60
gatgctcaat tggtggaat gagcaaacgt gattgtaact tgatgaaggc gtgttgtgct   120
ggacaagcag taacatatgc tattcatagt ctttaaatc gattaggtgg agactctagt   180
gatccagctg gttgtaatga tattgtaaga aaatattgta aataa                   225
```

<210> SEQ ID NO 94
<211> LENGTH: 65
<212> TYPE: PRT
<213> ORGANISM: Enterococcus faecium

<400> SEQUENCE: 94

| Met | Lys | His | Leu | Lys | Ile | Leu | Ser | Ile | Lys | Glu | Thr | Gln | Leu | Ile | Tyr |
|---|---|---|---|---|---|---|---|---|---|---|---|---|---|---|---|
| 1 | | | | 5 | | | | | 10 | | | | | 15 | |

| Gly | Gly | Thr | Thr | His | Ser | Gly | Lys | Tyr | Tyr | Gly | Asn | Gly | Val | Tyr | Cys |
|---|---|---|---|---|---|---|---|---|---|---|---|---|---|---|---|
| | | | 20 | | | | | 25 | | | | | 30 | | |

Thr Lys Asn Lys Cys Thr Val Asp Trp Ala Lys Ala Thr Thr Cys Ile
        35                  40                  45

Ala Gly Met Ser Ile Gly Gly Phe Leu Gly Gly Ala Ile Pro Gly Lys
 50                  55                  60

Cys
 65

<210> SEQ ID NO 95
<211> LENGTH: 195
<212> TYPE: DNA
<213> ORGANISM: Enterococcus faecium

<400> SEQUENCE: 95
atgaaacatt taaaaatttt gtctattaaa gagacacaac ttatctatgg gggtaccact      60
catagtggaa aatattatgg aaatggagtg tattgcacta aaaataaatg tacggtcgat     120
tgggccaagg caactacttg tattgcagga atgtctatag gtggtttttt aggtggagca     180
attccaggga agtgc                                                     195

<210> SEQ ID NO 96
<211> LENGTH: 105
<212> TYPE: PRT
<213> ORGANISM: Enterococcus faecalis

<400> SEQUENCE: 96

Met Val Lys Glu Asn Lys Phe Ser Lys Ile Phe Ile Leu Met Ala Leu
 1               5                  10                  15

Ser Phe Leu Gly Leu Ala Leu Phe Ser Ala Ser Leu Gln Phe Leu Pro
            20                  25                  30

Ile Ala His Met Ala Lys Glu Phe Gly Ile Pro Ala Ala Val Ala Gly
        35                  40                  45

Thr Val Leu Asn Val Val Glu Ala Gly Gly Trp Val Thr Thr Ile Val
 50                  55                  60

Ser Ile Leu Thr Ala Val Gly Ser Gly Gly Leu Ser Leu Leu Ala Ala
 65                  70                  75                  80

Ala Gly Arg Glu Ser Ile Lys Ala Tyr Leu Lys Lys Glu Ile Lys Lys
                85                  90                  95

Lys Gly Lys Arg Ala Val Ile Ala Trp
            100                 105

<210> SEQ ID NO 97
<211> LENGTH: 318
<212> TYPE: DNA
<213> ORGANISM: Enterococcus faecalis

<400> SEQUENCE: 97
atggttaaag aaaataaatt ttctaagatt tttattttaa tggctttgag ttttttgggg      60
ttagccttgt ttagtgcaag tcttcagttt tgcccattg cacatatggc taaagagttc     120
ggtataccag cagcagttgc aggaactgtg cttaatgtag ttgaagctgg tggatgggtc     180
actactattg tatcaattct tactgctgta ggtagcggag gtctttcttt actcgctgca     240
gcaggaagag agtcaattaa agcataccct aagaagaaa ttaagaaaaa aggaaaaaga     300
gcagttattg cttggtaa                                                 318

<210> SEQ ID NO 98
<211> LENGTH: 71
<212> TYPE: PRT

<213> ORGANISM: Enterococcus faecium

<400> SEQUENCE: 98

Met Gln Asn Val Lys Glu Leu Ser Thr Lys Glu Met Lys Gln Ile Ile
1               5                   10                  15
Gly Gly Glu Asn Asp His Arg Met Pro Asn Glu Leu Asn Arg Pro Asn
            20                  25                  30
Asn Leu Ser Lys Gly Gly Ala Lys Cys Gly Ala Ala Ile Ala Gly Gly
        35                  40                  45
Leu Phe Gly Ile Pro Lys Gly Pro Leu Ala Trp Ala Ala Gly Leu Ala
    50                  55                  60
Asn Val Tyr Ser Lys Cys Asn
65                  70

<210> SEQ ID NO 99
<211> LENGTH: 216
<212> TYPE: DNA
<213> ORGANISM: Enterococcus faecium

<400> SEQUENCE: 99
atgcaaaatg taaagaatt aagtacgaaa gagatgaaac aaattatcgg tggagaaaat      60
gatcacagaa tgcctaatga gttaaataga cctaacaact tatctaaagg tggagcaaaa    120
tgtggtgctg caattgctgg gggattattt ggaatcccaa aaggaccact agcatgggct    180
gctgggttag caaatgtata ctctaaatgc aactaa                              216

<210> SEQ ID NO 100
<211> LENGTH: 58
<212> TYPE: PRT
<213> ORGANISM: Enterococcus mundtii

<400> SEQUENCE: 100

Met Lys Lys Leu Thr Ser Lys Glu Met Ala Gln Val Val Gly Gly Lys
1               5                   10                  15
Tyr Tyr Gly Asn Gly Val Ser Cys Asn Lys Lys Gly Cys Ser Val Asp
            20                  25                  30
Trp Gly Lys Ala Ile Gly Ile Ile Gly Asn Asn Ser Ala Ala Asn Leu
        35                  40                  45
Ala Thr Gly Gly Ala Ala Gly Trp Lys Ser
    50                  55

<210> SEQ ID NO 101
<211> LENGTH: 177
<212> TYPE: DNA
<213> ORGANISM: Enterococcus mundtii

<400> SEQUENCE: 101
ttgaagaaat taacatcaaa agaaatggca caagtagtag gtggaaaata ctacggtaat     60
ggagtctcat gtaataaaaa agggtgcagt gttgattggg gaaaagctat tggcattatt    120
ggaaataatt ctgctgcgaa tttagctact ggtggagcag ctggttggaa aagttaa       177

<210> SEQ ID NO 102
<211> LENGTH: 44
<212> TYPE: PRT
<213> ORGANISM: Enterococcus faecalis

<400> SEQUENCE: 102

Met Leu Ala Lys Ile Lys Ala Met Ile Lys Lys Phe Pro Asn Pro Tyr
1               5                   10                  15

```
Thr Leu Ala Ala Lys Leu Thr Thr Tyr Glu Ile Asn Trp Tyr Lys Gln
            20                  25                  30

Gln Tyr Gly Arg Tyr Pro Trp Glu Arg Pro Val Ala
        35                  40

<210> SEQ ID NO 103
<211> LENGTH: 135
<212> TYPE: DNA
<213> ORGANISM: Enterococcus faecalis

<400> SEQUENCE: 103
atgttagcaa aaattaaagc gatgattaag aagtttccga acccttatac tttagcagct      60
aagctaacga cttacgaaat taattggtat aaacaacaat acggtcgtta tccttgggag     120
cgccctgtag cataa                                                      135

<210> SEQ ID NO 104
<211> LENGTH: 71
<212> TYPE: PRT
<213> ORGANISM: Enterococcus faecium

<400> SEQUENCE: 104

Met Arg Lys Lys Leu Phe Ser Leu Ala Leu Ile Gly Ile Phe Gly Leu
1               5                   10                  15

Val Val Thr Asn Phe Gly Thr Lys Val Asp Ala Ala Thr Arg Ser Tyr
            20                  25                  30

Gly Asn Gly Val Tyr Cys Asn Asn Ser Lys Cys Trp Val Asn Trp Gly
        35                  40                  45

Glu Ala Lys Glu Asn Ile Ala Gly Ile Val Ile Ser Gly Trp Ala Ser
    50                  55                  60

Gly Leu Ala Gly Met Gly His
65                  70

<210> SEQ ID NO 105
<211> LENGTH: 216
<212> TYPE: DNA
<213> ORGANISM: Enterococcus faecium

<400> SEQUENCE: 105
atgagaaaaa aattatttag tttagctctt attggaatat ttgggttagt tgtgacaaat      60
tttggtacaa aagttgatgc agctacgcgt tcatatggta atggtgttta ttgtaataat     120
agtaaatgct gggttaactg gggagaagct aaagagaata ttgcaggaat cgttattagt     180
ggctgggctt ctggtttggc aggtatggga cattaa                               216

<210> SEQ ID NO 106
<211> LENGTH: 34
<212> TYPE: PRT
<213> ORGANISM: Enterococcus faecium

<400> SEQUENCE: 106

Met Asn Phe Leu Lys Asn Gly Ile Ala Lys Trp Met Thr Gly Ala Glu
1               5                   10                  15

Leu Gln Ala Tyr Lys Lys Lys Tyr Gly Cys Leu Pro Trp Glu Lys Ile
            20                  25                  30

Ser Cys

<210> SEQ ID NO 107
<211> LENGTH: 105
```

<212> TYPE: DNA
<213> ORGANISM: Enterococcus faecium

<400> SEQUENCE: 107

```
atgaattttc ttaaaaatgg tatcgcaaaa tggatgaccg gtgctgaatt gcaagcgtat      60
aaaaagaaat atggatgctt gccatgggaa aaaatttctt gttaa                    105
```

<210> SEQ ID NO 108
<211> LENGTH: 76
<212> TYPE: PRT
<213> ORGANISM: Enterococcus faecalis

<400> SEQUENCE: 108

```
Met Lys Lys Lys Leu Val Lys Gly Leu Val Ile Cys Gly Met Ile Gly
1               5                   10                  15

Ile Gly Phe Thr Ala Leu Gly Thr Asn Val Glu Ala Ala Thr Tyr Tyr
            20                  25                  30

Gly Asn Gly Val Tyr Cys Asn Lys Gln Lys Cys Trp Val Asp Trp Ser
        35                  40                  45

Arg Ala Arg Ser Glu Ile Ile Asp Arg Gly Val Lys Ala Tyr Val Asn
    50                  55                  60

Gly Phe Thr Lys Val Leu Gly Gly Ile Gly Arg
65                  70                  75
```

<210> SEQ ID NO 109
<211> LENGTH: 231
<212> TYPE: DNA
<213> ORGANISM: Enterococcus faecalis

<400> SEQUENCE: 109

```
atgaaaaaga aattagttaa aggcttagtt atttgtggca tgattgggat tggttttaca     60
gcattaggaa caaatgtaga agccgccacg tattacggaa atggtgtcta ttgcaataag    120
caaaaatgtt gggtagattg gagtagagca cgttctgaaa ttatagacag aggcgtaaaa    180
gcatacgtca atggatttac gaaagtgtta ggtggtatag gtggaagata a             231
```

<210> SEQ ID NO 110
<211> LENGTH: 60
<212> TYPE: PRT
<213> ORGANISM: Enterococcus faecalis

<400> SEQUENCE: 110

```
Met Lys Lys Glu Glu Leu Val Gly Met Ala Lys Glu Asp Phe Leu Asn
1               5                   10                  15

Val Ile Cys Glu Asn Asp Asn Lys Leu Glu Asn Ser Gly Ala Lys Cys
            20                  25                  30

Pro Trp Trp Asn Leu Ser Cys His Leu Gly Asn Asp Gly Lys Ile Cys
        35                  40                  45

Thr Tyr Ser His Glu Cys Thr Ala Gly Cys Asn Ala
    50                  55                  60
```

<210> SEQ ID NO 111
<211> LENGTH: 183
<212> TYPE: DNA
<213> ORGANISM: Enterococcus faecalis

<400> SEQUENCE: 111

```
atgaaaaaag aagaattagt aggaatggct aaggaagact ttttaaatgt tatttgtgaa     60
aatgacaaca aactagaaaa tagtggagca aaatgtcctt ggtggaatct ttcttgtcat    120
```

-continued

```
ttaggcaatg atggtaaaat ttgcacttat tcacatgaat gtaccgcagg ttgtaatgca      180
taa                                                                   183
```

<210> SEQ ID NO 112
<211> LENGTH: 61
<212> TYPE: PRT
<213> ORGANISM: Enterococcus faecalis

<400> SEQUENCE: 112

```
Met Thr Glu Leu Asn Lys Arg Leu Gln Leu Lys Arg Asp Val Ser Thr
1               5                   10                  15

Glu Asn Ser Leu Lys Lys Ile Ser Asn Thr Asp Glu Thr His Gly Gly
            20                  25                  30

Val Thr Thr Ser Ile Pro Cys Thr Val Met Val Ser Ala Ala Val Cys
        35                  40                  45

Pro Thr Leu Val Cys Ser Asn Lys Cys Gly Gly Arg Gly
    50                  55                  60
```

<210> SEQ ID NO 113
<211> LENGTH: 186
<212> TYPE: DNA
<213> ORGANISM: Enterococcus faecalis

<400> SEQUENCE: 113

```
atgactgaac ttacaaaag attacaatta aaaagagatg tttcaacaga aatagtttg       60 aaaaaattt ctaatactga tgaaacacat gggggagtta ctacatcaat tccatgtaca     120
gtaatggtta gtgcggcagt atgtcctacc cttgtttgct cgaataaatg tggcggtaga   180
ggctag                                                              186
```

<210> SEQ ID NO 114
<211> LENGTH: 58
<212> TYPE: PRT
<213> ORGANISM: Enterococcus faecium

<400> SEQUENCE: 114

```
Met Gln Asn Val Lys Glu Val Ser Val Lys Glu Met Lys Gln Ile Ile
1               5                   10                  15

Gly Gly Ser Asn Asp Ser Leu Trp Tyr Gly Val Gly Gln Phe Met Gly
            20                  25                  30

Lys Gln Ala Asn Cys Ile Thr Asn His Pro Val Lys His Met Ile Ile
        35                  40                  45

Pro Gly Tyr Cys Leu Ser Lys Ile Leu Gly
    50                  55
```

<210> SEQ ID NO 115
<211> LENGTH: 177
<212> TYPE: DNA
<213> ORGANISM: Enterococcus faecium

<400> SEQUENCE: 115

```
atgcaaaatg taaagaagt ttctgtaaaa gagatgaaac aaattatcgg tggttctaat       60
gatagtcttt ggtatggtgt aggacaattt atgggtaaac aagcaaactg tataacaaac    120
catcctgtta aacacatgat aattcctgga tattgtttat cgaaaatttt agggtaa       177
```

<210> SEQ ID NO 116
<211> LENGTH: 55
<212> TYPE: PRT

<213> ORGANISM: Enterococcus faecium

<400> SEQUENCE: 116

Met Lys Lys Tyr Asn Glu Leu Ser Lys Lys Glu Leu Leu Gln Ile Gln
1               5                   10                  15

Gly Gly Ile Ala Pro Ile Ile Val Ala Gly Leu Gly Tyr Leu Val Lys
            20                  25                  30

Asp Ala Trp Asp His Ser Asp Gln Ile Ile Ser Gly Phe Lys Lys Gly
        35                  40                  45

Trp Asn Gly Gly Arg Arg Lys
    50                  55

<210> SEQ ID NO 117
<211> LENGTH: 168
<212> TYPE: DNA
<213> ORGANISM: Enterococcus faecium

<400> SEQUENCE: 117
atgaaaaaat ataatgagtt atctaaaaaa gaacttctac agattcaagg aggaatagca    60
cctattatag ttgctggcct tggctattta gtaaaagatg catgggatca ctcagatcaa   120
ataatctcag gatttaaaaa aggttggaat ggtggacgta gaaaataa               168

<210> SEQ ID NO 118
<211> LENGTH: 343
<212> TYPE: PRT
<213> ORGANISM: Enterococcus faecalis

<400> SEQUENCE: 118

Met Lys Asn Ile Leu Leu Ser Ile Leu Gly Val Leu Ser Ile Val Val
1               5                   10                  15

Ser Leu Ala Phe Ser Ser Tyr Ser Val Asn Ala Ala Ser Asn Glu Trp
            20                  25                  30

Ser Trp Pro Leu Gly Lys Pro Tyr Ala Gly Arg Tyr Glu Glu Gly Gln
        35                  40                  45

Gln Phe Gly Asn Thr Ala Phe Asn Arg Gly Gly Thr Tyr Phe His Asp
    50                  55                  60

Gly Phe Asp Phe Gly Ser Ala Ile Tyr Gly Asn Gly Ser Val Tyr Ala
65                  70                  75                  80

Val His Asp Gly Lys Ile Leu Tyr Ala Gly Trp Asp Pro Val Gly Gly
                85                  90                  95

Gly Ser Leu Gly Ala Phe Ile Val Leu Gln Ala Gly Asn Thr Asn Val
            100                 105                 110

Ile Tyr Gln Glu Phe Ser Arg Asn Val Gly Asp Ile Lys Val Ser Thr
        115                 120                 125

Gly Gln Thr Val Lys Lys Gly Gln Leu Ile Gly Lys Phe Thr Ser Ser
    130                 135                 140

His Leu His Leu Gly Met Thr Lys Lys Glu Trp Arg Ser Ala His Ser
145                 150                 155                 160

Ser Trp Asn Lys Asp Asp Gly Thr Trp Phe Asn Pro Ile Pro Ile Leu
                165                 170                 175

Gln Gly Gly Ser Thr Pro Thr Pro Asn Pro Gly Pro Lys Asn Phe
            180                 185                 190

Thr Thr Asn Val Arg Tyr Gly Leu Arg Val Leu Gly Ser Trp Leu
        195                 200                 205

Pro Glu Val Thr Asn Phe Asn Asn Thr Asn Asp Gly Phe Ala Gly Tyr
    210                 215                 220

Pro Asn Arg Gln His Asp Met Leu Tyr Ile Lys Val Asp Lys Gly Gln
225                 230                 235                 240

Met Lys Tyr Arg Val His Thr Ala Gln Ser Gly Trp Leu Pro Trp Val
            245                 250                 255

Ser Lys Gly Asp Lys Ser Asp Thr Val Asn Gly Ala Ala Gly Met Pro
        260                 265                 270

Gly Gln Ala Ile Asp Gly Val Gln Leu Asn Tyr Ile Thr Pro Lys Gly
    275                 280                 285

Glu Lys Leu Ser Gln Ala Tyr Tyr Arg Ser Gln Thr Thr Lys Arg Ser
290                 295                 300

Gly Trp Leu Lys Val Ser Ala Asp Asn Gly Ser Ile Pro Gly Leu Asp
305                 310                 315                 320

Ser Tyr Ala Gly Ile Phe Gly Glu Pro Leu Asp Arg Leu Gln Ile Gly
                325                 330                 335

Ile Ser Gln Ser Asn Pro Phe
            340

<210> SEQ ID NO 119
<211> LENGTH: 1032
<212> TYPE: DNA
<213> ORGANISM: Enterococcus faecalis

<400> SEQUENCE: 119
atgaaaaata tttactttc tattctaggg gtattatcta tcgttgtttc tttggcgttt      60
tcttcttatt ctgtcaacgc agcttctaat gagtggtcgt ggccactggg caaaccatat    120
gcgggaagat atgaagaagg acaacaattc gggaacactg catttaaccg aggaggtact    180
tatttccatg atgggtttga ctttggttct gctatttatg aaatggcag tgtgtatgct     240 gtgcatgatg gtaaaatttt tatgctggt tgggatcctg taggtggagg ctcattaggt     300
gcatttattg tactacaagc gggaaacaca aatgtgattt atcaagaatt tagccgaaat    360
gttggagata ttaaagttag cactggacaa actgttaaaa aggacagct gataggaaag    420 tttacttcta gtcatttaca tttaggaatg acaaaaaaag aatggcgttc tgctcattct    480
tcttggaata aagatgatgg cacttggttt aacccaattc ctatacttca aggaggatct    540
acgcctacgc ctccaaatcc aggaccaaaa aatttcacaa caaatgttcg ttacggattg    600
cgggtcctcg gaggttcatg gttaccgaaa gtaaccaact ttaacaatac caatgatggt    660
ttcgcaggtt acctaatcg tcaacatgat atgctttata taaaggtaga taaagggcaa    720
atgaaatatc gtgttcacac ggctcaaagt ggatggttgc cttgggtaag taaaggggat    780
aagagcgata cagtaaatgg agcggcaggt atgcctggac aagcaattga tggtgttcag    840
ctaaactata taactcctaa gggagaaaaa ttatcacagg cttactatcg ttcacaaact    900
acgaaacgat caggctggtt aaaagtaagt gcagataatg gttctattcc tggactagac    960
agttatgcag gaatctttgg agaaccgttg gatcgcttgc aaataggtat ttcacagtca   1020
aatccatttt aa                                                        1032

<210> SEQ ID NO 120
<211> LENGTH: 56
<212> TYPE: PRT
<213> ORGANISM: Staphylococcus epidermidis

<400> SEQUENCE: 120

Met Glu Asn Lys Lys Asp Leu Phe Asp Leu Glu Ile Lys Lys Asp Asn
1               5                   10                  15

```
Met Glu Asn Asn Glu Leu Glu Ala Gln Ser Leu Gly Pro Ala Ile
                20                  25                  30

Lys Ala Thr Arg Gln Val Cys Pro Lys Ala Thr Arg Phe Val Thr Val
            35                  40                  45

Ser Cys Lys Lys Ser Asp Cys Gln
    50                  55

<210> SEQ ID NO 121
<211> LENGTH: 171
<212> TYPE: DNA
<213> ORGANISM: Staphylococcus epidermidis

<400> SEQUENCE: 121
atggaaaaca aaaagatttt atttgattta gaaatcaaaa aagataatat ggaaaataat     60
aatgaattag aagctcaatc tcttggtcct gcaattaagg caactagaca ggtatgtcct    120
aaagcaacac gttttgttac agtttcttgt aaaaaaagtg attgtcaata g              171

<210> SEQ ID NO 122
<211> LENGTH: 51
<212> TYPE: PRT
<213> ORGANISM: Staphylococcus epidermidis

<400> SEQUENCE: 122

Met Ala Ala Phe Met Lys Leu Ile Gln Phe Leu Ala Thr Lys Gly Gln
1               5                   10                  15

Lys Tyr Val Ser Leu Ala Trp Lys His Lys Gly Thr Ile Leu Lys Trp
            20                  25                  30

Ile Asn Ala Gly Gln Ser Phe Glu Trp Ile Tyr Lys Gln Ile Lys Lys
        35                  40                  45

Leu Trp Ala
    50

<210> SEQ ID NO 123
<211> LENGTH: 156
<212> TYPE: DNA
<213> ORGANISM: Staphylococcus epidermidis

<400> SEQUENCE: 123
atggcagcat ttatgaagtt aattcagttc ttagcaacta aaggtcaaaa gtatgtttca     60
cttgcatgga acataaagg tactatttta aaatggatta acgccggtca aagttttgaa    120
tggatttata acaaatcaa aaaattatgg gcataa                              156

<210> SEQ ID NO 124
<211> LENGTH: 52
<212> TYPE: PRT
<213> ORGANISM: Staphylococcus epidermidis

<400> SEQUENCE: 124

Met Glu Ala Val Lys Glu Lys Asn Asp Leu Phe Asn Leu Asp Val Lys
1               5                   10                  15

Val Asn Ala Lys Glu Ser Asn Asp Ser Gly Ala Glu Pro Arg Ile Ala
            20                  25                  30

Ser Lys Phe Ile Cys Thr Pro Gly Cys Ala Lys Thr Gly Ser Phe Asn
        35                  40                  45

Ser Tyr Cys Cys
    50
```

```
<210> SEQ ID NO 125
<211> LENGTH: 159
<212> TYPE: DNA
<213> ORGANISM: Staphylococcus epidermidis

<400> SEQUENCE: 125
atggaagcag taaaagaaaa aaatgatctt tttaatcttg atgttaaagt taatgcaaaa    60
gaatctaacg attcaggagc tgaaccaaga attgctagta aatttatatg tactcctgga   120
tgtgcaaaaa caggtagttt taacagttat tgttgttaa                          159

<210> SEQ ID NO 126
<211> LENGTH: 55
<212> TYPE: PRT
<213> ORGANISM: Staphylococcus epidermidis

<400> SEQUENCE: 126

Met Asn Asn Ser Leu Phe Asp Leu Asn Leu Asn Lys Gly Val Glu Thr
1               5                   10                  15

Gln Lys Ser Asp Leu Ser Pro Gln Ser Ala Ser Val Leu Lys Thr Ser
            20                  25                  30

Ile Lys Val Ser Lys Lys Tyr Cys Lys Gly Val Thr Leu Thr Cys Gly
        35                  40                  45

Cys Asn Ile Thr Gly Gly Lys
    50                  55

<210> SEQ ID NO 127
<211> LENGTH: 168
<212> TYPE: DNA
<213> ORGANISM: Staphylococcus epidermidis

<400> SEQUENCE: 127
atgaataact cattattcga tttaaaccta aacaaaggtg tagaaactca aaagagtgat    60
ttaagtccgc aatctgctag tgtcttgaag acttctatta agtatctaaa aaatattgt   120 aaaggtgtta ctttaacatg cggttgcaat attactggtg gtaaataa               168

<210> SEQ ID NO 128
<211> LENGTH: 52
<212> TYPE: PRT
<213> ORGANISM: Staphylococcus gallinarum

<400> SEQUENCE: 128

Met Glu Ala Val Lys Glu Lys Asn Glu Leu Phe Asp Leu Asp Val Lys
1               5                   10                  15

Val Asn Ala Lys Glu Ser Asn Asp Ser Gly Ala Glu Pro Arg Ile Ala
            20                  25                  30

Ser Lys Phe Leu Cys Thr Pro Gly Cys Ala Lys Thr Gly Ser Phe Asn
        35                  40                  45

Ser Tyr Cys Cys
    50

<210> SEQ ID NO 129
<211> LENGTH: 159
<212> TYPE: DNA
<213> ORGANISM: Staphylococcus gallinarum

<400> SEQUENCE: 129
atggaagcag taaaagagaa aaatgaactt tttgatcttg acgttaaagt aaatgcaaaa    60
gagtctaatg attcaggcgc agaaccacga attgctagta aatttttatg tactcctgga   120
```

-continued

```
tgtgccaaaa caggtagctt caatagctac tgttgttaa                            159
```

<210> SEQ ID NO 130
<211> LENGTH: 63
<212> TYPE: PRT
<213> ORGANISM: Lactococcus garvieae

<400> SEQUENCE: 130

```
Met Glu Asn Asn Tyr Thr Val Leu Ser Asp Glu Glu Leu Gln Lys
1               5                   10                  15

Ile Asp Gly Gly Ile Gly Gly Ala Leu Gly Asn Ala Leu Asn Gly Leu
            20                  25                  30

Gly Thr Trp Ala Asn Met Met Asn Gly Gly Phe Val Asn Gln Trp
        35                  40                      45

Gln Val Tyr Ala Asn Lys Gly Lys Ile Asn Gln Tyr Arg Pro Tyr
    50                  55                  60
```

<210> SEQ ID NO 131
<211> LENGTH: 192
<212> TYPE: DNA
<213> ORGANISM: Lactococcus garvieae

<400> SEQUENCE: 131

```
atggaaaaca acaattacac agtactttca gatgaagaac tacaaaaaat tgatggtgga      60
atcggcgggg ctcttggtaa tgctctcaac ggattaggta cctgggcaaa catgatgaac     120
ggtggaggat tgttaatca gtggcaagtt tatgctaata aaggaaaaat aaatcaatac     180
cgtccgtatt aa                                                        192
```

<210> SEQ ID NO 132
<211> LENGTH: 63
<212> TYPE: PRT
<213> ORGANISM: Lactococcus garvieae

<400> SEQUENCE: 132

```
Met Phe Asp Leu Val Ala Thr Gly Met Ala Ala Gly Val Ala Lys Thr
1               5                   10                  15

Ile Val Asn Ala Val Ser Ala Gly Met Asp Ile Ala Thr Ala Leu Ser
            20                  25                  30

Leu Phe Ser Gly Ala Phe Thr Ala Ala Gly Gly Ile Met Ala Leu Ile
        35                  40                  45

Lys Lys Tyr Ala Gln Lys Lys Leu Trp Lys Gln Leu Ile Ala Ala
    50                  55                  60
```

<210> SEQ ID NO 133
<211> LENGTH: 192
<212> TYPE: DNA
<213> ORGANISM: Lactococcus garvieae

<400> SEQUENCE: 133

```
atgtttgatt tagtcgcgac tggaatggct gcaggtgtag caaaaactat tgttaatgcc      60
gttagtgctg gtatggatat tgccactgct ttatcattgt tctcaggagc ttttactgca     120
gctgggggaa ttatggcact cattaaaaaa tatgctcaaa agaaattatg gaaacagctt     180
attgctgcat aa                                                        192
```

<210> SEQ ID NO 134
<211> LENGTH: 91
<212> TYPE: PRT
<213> ORGANISM: Lactobacillus gasseri

<400> SEQUENCE: 134

Met Val Thr Lys Tyr Gly Arg Asn Leu Gly Leu Asn Lys Val Glu Leu
1               5                   10                  15

Phe Ala Ile Trp Ala Val Leu Val Val Ala Leu Leu Leu Thr Thr Ala
            20                  25                  30

Asn Ile Tyr Trp Ile Ala Asp Gln Phe Gly Ile His Leu Ala Thr Gly
        35                  40                  45

Thr Ala Arg Lys Leu Leu Asp Ala Met Ala Ser Gly Ala Ser Leu Gly
    50                  55                  60

Thr Ala Phe Ala Ala Ile Leu Gly Val Thr Leu Pro Ala Trp Ala Leu
65                  70                  75                  80

Ala Ala Ala Gly Ala Leu Gly Ala Thr Ala Ala
                85                  90

<210> SEQ ID NO 135
<211> LENGTH: 276
<212> TYPE: DNA
<213> ORGANISM: Lactobacillus gasseri

<400> SEQUENCE: 135
atggttacta agtacggacg taatttaggt ttgaacaagg tagagttgtt tgcaatttgg      60
gcggttttag tagttgctct tttattgacc acagcgaaca tttattggat tgctgatcaa     120
ttcgggattc atttagcgac tggaacagcc cgtaagttat tagatgcaat ggcttctggt     180
gcctcattgg gaactgcctt tgctgctatt ttgggcgtga cattacctgc atgggctttg     240
gcagctgcag gagcattggg agcgactgca gcctag                              276

<210> SEQ ID NO 136
<211> LENGTH: 75
<212> TYPE: PRT
<213> ORGANISM: Lactobacillus gasseri

<400> SEQUENCE: 136

Met Lys Asn Phe Asn Thr Leu Ser Phe Glu Thr Leu Ala Asn Ile Val
1               5                   10                  15

Gly Gly Arg Asn Asn Trp Ala Ala Asn Ile Gly Gly Val Gly Gly Ala
            20                  25                  30

Thr Val Ala Gly Trp Ala Leu Gly Asn Ala Val Cys Gly Pro Ala Cys
        35                  40                  45

Gly Phe Val Gly Ala His Tyr Val Pro Ile Ala Trp Ala Gly Val Thr
    50                  55                  60

Ala Ala Thr Gly Gly Phe Gly Lys Ile Arg Lys
65                  70                  75

<210> SEQ ID NO 137
<211> LENGTH: 228
<212> TYPE: DNA
<213> ORGANISM: Lactobacillus gasseri

<400> SEQUENCE: 137
atgaaaaatt ttaatacatt atcatttgaa acattggcta acatagttgg tgggagaaat      60
aattgggctg ctaatatagg tggagtaggt ggagcgacag tcgctggatg ggctcttgga     120
aatgcagttt gcggtcctgc ttgtggcttt gttggagcac actatgttcc aatagcatgg     180
gctggcgtaa cggcagctac tggtggattc ggaaagataa gaaagtag                  228

<210> SEQ ID NO 138
<211> LENGTH: 64
<212> TYPE: PRT
<213> ORGANISM: Lactobacillus plantarum

<400> SEQUENCE: 138

```
Met Ser Lys Leu Val Lys Thr Leu Thr Ile Ser Glu Ile Ser Lys Ala
1               5                   10                  15

Gln Asn Asn Gly Gly Lys Pro Ala Trp Cys Trp Tyr Thr Leu Ala Met
            20                  25                  30

Cys Gly Ala Gly Tyr Asp Ser Gly Thr Cys Asp Tyr Met Tyr Ser His
        35                  40                  45

Cys Phe Gly Ile Lys His His Ser Ser Gly Ser Ser Tyr His Cys
    50                  55                  60
```

<210> SEQ ID NO 139
<211> LENGTH: 195
<212> TYPE: DNA
<213> ORGANISM: Lactobacillus plantarum

<400> SEQUENCE: 139

```
atgagtaaat tggttaagac acttactata agtgaaattt ctaaggctca aaacaacggt    60
ggaaaacctg catggtgttg gtatacttta gcaatgtgtg gtgctggtta tgattcggga   120
acctgtgatt atatgtattc gcattgtttt ggtataaagc atcatagtag tggtagtagc   180
agttatcatt gttag                                                    195
```

<210> SEQ ID NO 140
<211> LENGTH: 359
<212> TYPE: PRT
<213> ORGANISM: Haloferax mediterranei

<400> SEQUENCE: 140

```
Met Ser Lys Asp Arg Asp Gly Arg Arg Thr Ser Arg Gly Thr Leu
1               5                   10                  15

Lys Lys Ile Gly Gly Phe Ser Leu Gly Ala Leu Ser Phe Gly Ala Val
            20                  25                  30

Gly Arg Thr Gln Ala Ala Thr Gly Ser Ser Val Thr Thr Ala Asp Ile
        35                  40                  45

Ala Pro Pro Gly Pro Asn Gly Asp Pro Lys Ser Val Gln Ile Asp Asp
    50                  55                  60

Lys Tyr Thr Gly Ala Glu Met Tyr Gly Glu Gly Asp Phe Arg Val Gly
65                  70                  75                  80

Leu Gly Thr Asp Leu Thr Met Tyr Pro Pro Val Tyr Arg Glu Ser Leu
                85                  90                  95

Gly Asn Gly Ser Gly Gly Trp Glu Phe Asp Phe Thr Val Cys Gly Ser
            100                 105                 110

Thr Ala Cys Arg Phe Val Asp Ser Asn Gly Asp Val Lys Glu Asp Asp
        115                 120                 125

Lys Ala Lys Glu Met Trp Trp Gln Glu Ile Asn Phe Asn Asp Ile Asn
    130                 135                 140

Gln Asp Leu Tyr Ser Arg Asn Asp Ser Asp Trp Val Gly Ser Thr Pro
145                 150                 155                 160

Ala Asp Thr Gln Pro Glu Phe Asp Tyr Thr Glu Phe Ala Leu Ala Arg
                165                 170                 175

Asp Gly Val Thr Leu Ala Leu Thr Ala Leu Asn Pro Ala Met Gly Ser
            180                 185                 190
```

Leu Ala Leu Gly Ala Thr Tyr Phe Leu Ser Asp Met Val Asn Trp Ile
            195                 200                 205

Ala Ser Gln His Glu Asp Asp Ser Ser Leu Lys Arg Lys Trp Asp Tyr
        210                 215                 220

Asp Gly Leu Ser Gly Pro Leu Tyr Ala Asp Ser Ser Thr Tyr Leu Leu
225                 230                 235                 240

Ala Arg Asp Glu Met Thr Ser Asn Ser Tyr Glu Ser Phe Thr Ile Asp
                245                 250                 255

Asn Ile Ala Val Ala Phe Pro Glu Phe Pro Val Arg Thr Lys Tyr Tyr
            260                 265                 270

Val Thr Phe Thr Ala Pro Asp Asp Pro Ser Thr Gln Ser Ile Ser Thr
        275                 280                 285

Leu Glu Glu Glu Gly Ile Tyr Arg Val Pro Ala Thr Glu Val Ala Ala
    290                 295                 300

Ala Arg Pro Pro Gly Ser Arg Arg Ser Lys Ser Ala Ala Asp Glu Met
305                 310                 315                 320

Val Tyr Val Ala Asp Pro Lys Lys Phe Ile Glu Val Glu Pro Val Lys
                325                 330                 335

Asn Pro Ser Ile Pro Asp Arg Ile Tyr Glu Glu Ile Glu Gln Lys Lys
            340                 345                 350

Lys Gln Arg Ser Arg Lys Gln
        355

<210> SEQ ID NO 141
<211> LENGTH: 1080
<212> TYPE: DNA
<213> ORGANISM: Haloferax mediterranei

<400> SEQUENCE: 141
atgtcgaaag acagagatgg gagaaggaca agtcggcgag gcacgttaaa gaaaatcggc      60
ggtttcagtc tcggagcgct tagtttcggg gcagtcggac gaactcaagc ggcgaccggc     120
tcatcggtta cgaccgctga tatcgcacct cccggaccga acggagaccc gaagagtgtt     180
cagatagatg ataaatacac cggagccgag atgtacggcg aggtgacttc agagtcggt     240 ctcggaactg acctgacgat gtatccgccc gtgtaccgtg agagtcttgg aaatggaagc     300
gggggttggg aattcgactt caccgttgt gggtccactg cctgtcgatt tgtggacagt      360
aacggtgacg tcaaagagga cgacaaggcg aaagaaatgt ggtggcagga aattaacttc     420
aacgacataa atcaggattt atacagtcgg aacgattccg actgggtcgg gtcgaccct      480 gccgataccc aaccggagtt cgattacacc gactttgcgc tcgctcggga cggagtgacg     540
ctcgctctca cggcactcaa ccccgcaatg gggagtcttg cactcggtgc cacgtacttc     600
ctcagcgaca tggtgaactg gattgcgagc cagcacgaag acgacagttc gctcaagaga     660
aaatgggatt acgacgggct aagtgggccg ttgtacgccg attcgtcgac gtacctactg     720
gcacgcgacg agatgacttc gaactcgtac gaatcattca cgatcgataa catcgccgtt     780
gccttcccag agttccccgt ccggaccaag tactacgtca cattcactgc gccggatgac     840
ccgtcaacgc agtcgatatc tacgctcgaa gaggagggaa tctaccgagt gcccgctacg     900
gaagtggctg cggccagacc accggggtcc cgacgttcca atcggcagc cgacgagatg     960 gtgtacgttg ccgatccgaa gaagttcata gaggtcgagc cggtgaagaa cccaagtatc    1020
ccggaccgaa tctacgagga gatagagcaa aaaagaaac aacggagtag gaaacagtag    1080

<210> SEQ ID NO 142

```
<211> LENGTH: 311
<212> TYPE: PRT
<213> ORGANISM: Haloarchaeon S8a

<400> SEQUENCE: 142

Met Ser Asp Lys Asp Ser Ile Asn Arg Arg Asn Val Leu Arg Lys Ile
1               5                   10                  15

Gly Gly Ile Gly Val Ala Ser Ala Val Gly Phe Ser Gly Leu Ala Ser
            20                  25                  30

Gly Glu Ser Leu Ser Asp Asp Glu Lys Gln Asp Val Ile Asp Thr Ile
        35                  40                  45

Tyr Lys Ser Gln Arg Val Glu Gln Ile Lys Lys Phe Gly Gly Val
50                  55                  60

Asn Ile Glu Pro Lys Lys Val Gln Ser Val Thr Thr Asn Gln Ser Gly
65                  70                  75                  80

Asp Leu Val Thr Ala Lys Leu Ser Val Ser Asp Gly Asp Leu Val Tyr
                85                  90                  95

Ser Ser Val Lys Asp Thr Thr Val Ile Val Gln Phe Arg Ser Ala
                100                 105                 110

Ser Glu Ile Gly Glu Ser Trp Pro Lys Asn Thr Glu Ala Phe Ile Lys
            115                 120                 125

Ser Thr Ser Ser Gly Val Asp Leu Leu Arg Thr Ala Thr Asp Glu Glu
130                 135                 140

Ile Lys Asp Val Thr Glu Gly Val Asn Thr Ser Glu Ile Glu Ser Ala
145                 150                 155                 160

Asp Ala Val Asn Ile Phe Ile Asp Pro Glu Ser Gln Thr Tyr Tyr Met
                165                 170                 175

Glu Lys Tyr Asp Phe Asn Asn Lys Val Leu Glu Met Phe Glu Leu Ala
            180                 185                 190

Thr Gly Gly Thr Ser Ser Gly Lys Ile Ser Pro Thr Arg Glu Asp Gln
        195                 200                 205

Asn His Glu Tyr Asn Val Arg Glu His Lys Val Phe Asn Ser Glu Lys
    210                 215                 220

Gln Asn Ile Gln Leu Gln Ser Asp Cys Asn Ile Asn Ser Asn Thr Ala
225                 230                 235                 240

Ala Asp Val Ile Leu Cys Phe Asn Gln Val Gly Ser Cys Ala Leu Cys
                245                 250                 255

Ser Pro Thr Leu Val Gly Gly Pro Val Pro Thr Val Ala Cys Leu Leu
            260                 265                 270

Val Val Cys Phe Gly Thr Pro Asn Ala Val Ser Ala Ile Leu Glu Glu
        275                 280                 285

Val Asp Asn Ser Cys Phe Asn Leu Ile Lys Asp Val Ile Ser Cys Trp
    290                 295                 300

Asp Glu Trp Thr Ser Phe Trp
305                 310

<210> SEQ ID NO 143
<211> LENGTH: 936
<212> TYPE: DNA
<213> ORGANISM: Haloarchaeon S8a

<400> SEQUENCE: 143
atgtcggata aagacagcat taacagaaga aatgtattaa gaaaaattgg cggtatcggt    60
gtggcttcag ctgtcggatt ttctggtttg gcaagcgggg aaagtcttag cgatgatgag   120
aaacaagatg ttattgacac aatttacaaa tcacaaagag ttgaacagat aaagaaaaag   180
```

-continued

```
ttcggaggag tgaatattga gccgaaaaag gttcaatctg taacgaccaa tcagagcgga      240
gatcttgtta cggcgaagct gtcggttagt gatggggatt tggtatattc gagtgtcaaa      300
gatacaactg taatagttca gttcgataga tcggcttctg aaattggtga agttggccc       360 aagaatactg aggcattcat caaatcgacg tcctctgggg tcgatcttct acgtacagca      420
actgatgaag aaataaagga cgttactgag ggagtcaaca catctgaaat tgaatctgcg      480
gatgctgtta acatatttat tgatcctgaa tcacagacat actatatgga aaatatgac      540 tttaataata aggtacttga gatgtttgaa ttagcgacag gtgggacaag tagtggtaaa      600
atctccccca cacgtgaaga ccagaatcac gaatataatg ttagggaaca taaagtattt      660
aactcagaaa aacagaatat acaacttcag agtgactgta atataaacag taacaccgct      720
gctgatgtta ttctatgctt caaccaggtt ggttcttgtg cactctgctc cccgacttta      780
gtcggaggtc cagtccctac agttgcatgt ctcttagtcg tctgtttcgg cactccaaat      840
gctgtgtccg cgatacttga agaagtcgat aattcttgct ttaacttgat caaggatgta      900
atttcgtgtt gggatgaatg gactagcttc tggtga                                936
```

<210> SEQ ID NO 144
<211> LENGTH: 333
<212> TYPE: PRT
<213> ORGANISM: Lactobacillus helveticus

<400> SEQUENCE: 144

```
Met Lys His Leu Asn Glu Thr Thr Asn Val Arg Ile Leu Ser Gln Phe
1               5                   10                  15

Asp Met Asp Thr Gly Tyr Gln Ala Val Val Gln Lys Gly Asn Val Gly
                20                  25                  30

Ser Lys Tyr Val Tyr Gly Leu Gln Leu Arg Lys Gly Ala Thr Thr Ile
            35                  40                  45

Leu Arg Gly Tyr Arg Gly Ser Lys Ile Asn Asn Pro Ile Leu Glu Leu
        50                  55                  60

Ser Gly Gln Ala Gly Gly His Thr Gln Thr Trp Glu Phe Ala Gly Asp
65                  70                  75                  80

Arg Lys Asp Ile Asn Gly Glu Glu Arg Ala Gly Gln Trp Phe Ile Gly
                85                  90                  95

Val Lys Pro Ser Lys Ile Glu Gly Ser Lys Ile Ile Trp Ala Lys Gln
            100                 105                 110

Ile Ala Arg Val Asp Leu Arg Asn Gln Met Gly Pro His Tyr Ser Asn
        115                 120                 125

Thr Asp Phe Pro Arg Leu Ser Tyr Leu Asn Arg Ala Gly Ser Asn Pro
    130                 135                 140

Phe Ala Gly Asn Lys Met Thr His Ala Glu Ala Val Ser Pro Asp
145                 150                 155                 160

Tyr Thr Lys Phe Leu Ile Ala Thr Val Glu Asn Asn Cys Ile Gly His
                165                 170                 175

Phe Thr Ile Tyr Asn Leu Asp Thr Ile Asn Glu Lys Leu Asp Glu Lys
            180                 185                 190

Gly Asn Ser Glu Asp Val Asn Leu Glu Thr Val Lys Tyr Glu Asp Ser
        195                 200                 205

Phe Ile Ile Asp Asn Leu Tyr Gly Asp Asp Asn Ser Ile Val Asn
    210                 215                 220

Ser Ile Gln Gly Tyr Asp Leu Asp Asn Asp Gly Asn Ile Tyr Ile Ser
225                 230                 235                 240
```

```
Ser Gln Lys Ala Pro Asp Phe Asp Gly Ser Tyr Tyr Ala His His Lys
                245                 250                 255

Gln Ile Val Lys Ile Pro Tyr Tyr Ala Arg Ser Lys Glu Ser Glu Asp
            260                 265                 270

Gln Trp Arg Ala Val Asn Leu Ser Glu Phe Gly Gly Leu Asp Ile Pro
        275                 280                 285

Gly Lys His Ser Glu Val Glu Ser Ile Gln Ile Ile Gly Glu Asn His
    290                 295                 300

Cys Tyr Leu Thr Val Ala Tyr His Ser Lys Asn Lys Ala Gly Glu Asn
305                 310                 315                 320

Lys Thr Thr Leu Asn Glu Ile Tyr Glu Leu Ser Trp Asn
                325                 330
```

<210> SEQ ID NO 145
<211> LENGTH: 1002
<212> TYPE: DNA
<213> ORGANISM: Lactobacillus helveticus

<400> SEQUENCE: 145

```
atgaagcatt taaatgaaac aactaatgtt agaattttaa gtcaatttga tatggatact    60
ggctatcaag cagtagttca aaaaggcaat gtaggttcaa aatatgtata tggattacaa   120
cttcgcaaag gtgctactac tatcttgcgt ggttaccgtg aagtaaaat taataaccct   180
attcttgaat tatctggtca agcaggtggt cacacacaga catgggaatt tgctggtgat   240
cgtaaagaca ttaatggtga agaaagagca ggtcaatggt ttataggtgt taaaccatcg   300
aaaattgaag gaagcaaaat tatttgggca agcaaattg caagagttga tcttagaaat   360
caaatgggac ctcattattc aaatactgac tttcctcgat tatcctactt gaatcgcgcc   420
ggttctaatc catttgctgg taataagatg acgcatgccg aagccgcagt atcacctgat   480
tatactaagt tttaattgc tactgttgaa ataactgta ttggtcattt tactatatac   540
aatttagata caattaatga aaaacttgat gaaaagggaa atagtgaaga tgttaatctc   600
gaaactgtta aatacgaaga tagttttatc attgataatt tatatggtga tgataataat   660
tctattgtaa attcaattca agggtatgat ttggataatg atggaaatat ttatatttcc   720
agtcaaaaag cgccagattt tgatggctct tattatgcac atcataagca gattgttaag   780
attccatatt atgctcggtc taagaaagc gaagaccaat ggagagctgt aaatttaagc   840
gaattcggtg gcttggatat tccaggtaaa catagtgaag ttgaaagcat ccaaattatt   900
ggtgagaatc attgttactt aactgttgca tatcattcta aaaataaagc gggtgaaaat   960
aaaactactt tgaatgagat ttatgaatta tcttggaatt ag                    1002
```

<210> SEQ ID NO 146
<211> LENGTH: 74
<212> TYPE: PRT
<213> ORGANISM: Enterococcus hirae

<400> SEQUENCE: 146

```
Met Lys Lys Val Leu Lys His Cys Val Ile Leu Gly Ile Leu Gly
1               5                   10                  15

Thr Cys Leu Ala Gly Ile Gly Thr Gly Ile Lys Val Asp Ala Ala Thr
                20                  25                  30

Tyr Tyr Gly Asn Gly Leu Tyr Cys Asn Lys Glu Lys Cys Trp Val Asp
            35                  40                  45

Trp Asn Gln Ala Lys Gly Glu Ile Gly Lys Ile Ile Val Asn Gly Trp
```

-continued

```
                50                  55                  60
Val Asn His Gly Pro Trp Ala Pro Arg Arg
 65                  70

<210> SEQ ID NO 147
<211> LENGTH: 225
<212> TYPE: DNA
<213> ORGANISM: Enterococcus hirae

<400> SEQUENCE: 147
atgaaaaaga aagtattaaa acattgtgtt attctaggaa tattaggaac ttgtctagct     60
ggcatcggta caggaataaa agttgatgca gctacttact atggaaatgg tctttattgt    120
aacaaagaaa atgttgggt agattggaat caagctaaag agaaattgg aaaaattatt     180 gttaatggtt gggttaatca tggtccatgg gcacctagaa ggtag                    225

<210> SEQ ID NO 148
<211> LENGTH: 75
<212> TYPE: PRT
<213> ORGANISM: Lactobacillus johnsonii

<400> SEQUENCE: 148

Met Lys Gln Phe Asn Tyr Leu Ser His Lys Asp Leu Ala Val Val Val
 1               5                  10                  15

Gly Gly Arg Asn Asn Trp Gln Thr Asn Val Gly Gly Ala Val Gly Ser
                20                  25                  30

Ala Met Ile Gly Ala Thr Val Gly Gly Thr Ile Cys Gly Pro Ala Cys
            35                  40                  45

Ala Val Ala Gly Ala His Tyr Leu Pro Ile Leu Trp Thr Ala Val Thr
        50                  55                  60

Ala Ala Thr Gly Gly Phe Gly Lys Ile Arg Lys
 65                  70                  75

<210> SEQ ID NO 149
<211> LENGTH: 228
<212> TYPE: DNA
<213> ORGANISM: Lactobacillus johnsonii

<400> SEQUENCE: 149
atgaaacaat ttaattattt atcacataaa gatttagcag tcgttgttgg tggaagaaat     60
aattggcaaa caaatgtggg aggagcagtg ggatcagcta tgattggggc tacagttggt    120
ggtacaattt gtggacctgc atgtgctgta gctggtgccc attatcttcc tattttatgg    180
acagcggtta cagctgcaac aggtggtttt ggcaagataa gaaagtag                 228

<210> SEQ ID NO 150
<211> LENGTH: 62
<212> TYPE: PRT
<213> ORGANISM: Lactobacillus johnsonii

<400> SEQUENCE: 150

Met Lys Leu Asn Asp Lys Glu Leu Ser Lys Ile Val Gly Gly Asn Arg
 1               5                  10                  15

Trp Gly Asp Thr Val Leu Ser Ala Ala Ser Gly Ala Gly Thr Gly Ile
                20                  25                  30

Lys Ala Cys Lys Ser Phe Gly Pro Trp Gly Met Ala Ile Cys Gly Val
            35                  40                  45

Gly Gly Ala Ala Ile Gly Gly Tyr Phe Gly Tyr Thr His Asn
        50                  55                  60
```

<210> SEQ ID NO 151
<211> LENGTH: 189
<212> TYPE: DNA
<213> ORGANISM: Lactobacillus johnsonii

<400> SEQUENCE: 151
atgaaattaa atgacaaaga attatcaaag attgttggtg gaaatcgatg gggagatact      60
gttttatcag ctgctagtgg cgcaggaact ggtattaaag catgtaaaag ttttggccca     120
tggggaatgg caatttgtgg tgtaggaggt gcagcaatag gaggttattt tggctatact     180
cataattaa                                                             189

<210> SEQ ID NO 152
<211> LENGTH: 59
<212> TYPE: PRT
<213> ORGANISM: Lactococcus lactis subsp. lactis

<400> SEQUENCE: 152

Met Asn Lys Asn Glu Ile Glu Thr Gln Pro Val Thr Trp Leu Glu Glu
1               5                   10                  15

Val Ser Asp Gln Asn Phe Asp Glu Asp Val Phe Gly Ala Cys Ser Thr
            20                  25                  30

Asn Thr Phe Ser Leu Ser Asp Tyr Trp Gly Asn Asn Gly Ala Trp Cys
        35                  40                  45

Thr Leu Thr His Glu Cys Met Ala Trp Cys Lys
    50                  55

<210> SEQ ID NO 153
<211> LENGTH: 180
<212> TYPE: DNA
<213> ORGANISM: Lactococcus lactis subsp. lactis

<400> SEQUENCE: 153
atgaacaaaa atgaaattga aacacaacca gttacatggt tggaagaagt atctgatcaa      60
aattttgatg aagatgtatt tggtgcgtgt agtactaaca cattctcgct cagtgattac     120
tggggaaata acgggcttg gtgtacactc actcatgaat gtatggcttg gtgtaaataa      180

<210> SEQ ID NO 154
<211> LENGTH: 65
<212> TYPE: PRT
<213> ORGANISM: Lactococcus lactis subsp. lactis

<400> SEQUENCE: 154

Met Lys Glu Lys Asn Met Lys Lys Asn Asp Thr Ile Glu Leu Gln Leu
1               5                   10                  15

Gly Lys Tyr Leu Glu Asp Asp Met Ile Glu Leu Ala Glu Gly Asp Glu
            20                  25                  30

Ser His Gly Gly Thr Thr Pro Ala Thr Pro Ala Ile Ser Ile Leu Ser
        35                  40                  45

Ala Tyr Ile Ser Thr Asn Thr Cys Pro Thr Thr Lys Cys Thr Arg Ala
    50                  55                  60

Cys
65

<210> SEQ ID NO 155
<211> LENGTH: 198
<212> TYPE: DNA
<213> ORGANISM: Lactococcus lactis subsp. lactis

<400> SEQUENCE: 155

```
atgaaagaaa aaaatatgaa aaagaatgac actattgaat tacaattggg aaaatacctt      60
gaagatgata tgattgaatt agctgaaggg gatgagtctc atggaggaac aacaccagca     120
actcctgcaa tctctattct cagtgcatat attagtacca atacttgtcc aacaacaaaa     180
tgtacacgtg cttgttaa                                                   198
```

<210> SEQ ID NO 156
<211> LENGTH: 51
<212> TYPE: PRT
<213> ORGANISM: Lactococcus lactis subsp. lactis

<400> SEQUENCE: 156

```
Met Lys Glu Gln Asn Ser Phe Asn Leu Leu Gln Glu Val Thr Glu Ser
1               5                   10                  15
Glu Leu Asp Leu Ile Leu Gly Ala Lys Gly Gly Ser Gly Val Ile His
            20                  25                  30
Thr Ile Ser His Glu Cys Asn Met Asn Ser Trp Gln Phe Val Phe Thr
        35                  40                  45
Cys Cys Ser
    50
```

<210> SEQ ID NO 157
<211> LENGTH: 156
<212> TYPE: DNA
<213> ORGANISM: Lactococcus lactis subsp. lactis

<400> SEQUENCE: 157

```
atgaaagaac aaaactcttt taatcttctt caagaagtga cagaaagtga attggacctt      60
attttaggtg caaaaggcgg cagtggagtt attcatacaa tttctcatga atgtaatatg     120
aatagctggc aatttgtatt tacttgctgc tcttaa                               156
```

<210> SEQ ID NO 158
<211> LENGTH: 53
<212> TYPE: PRT
<213> ORGANISM: Lactococcus lactis

<400> SEQUENCE: 158

```
Met Ala Gly Phe Leu Lys Val Val Gln Leu Leu Ala Lys Tyr Gly Ser
1               5                   10                  15
Lys Ala Val Gln Trp Ala Trp Ala Asn Lys Gly Lys Ile Leu Asp Trp
            20                  25                  30
Leu Asn Ala Gly Gln Ala Ile Asp Trp Val Val Ser Lys Ile Lys Gln
        35                  40                  45
Ile Leu Gly Ile Lys
    50
```

<210> SEQ ID NO 159
<211> LENGTH: 162
<212> TYPE: DNA
<213> ORGANISM: Lactococcus lactis

<400> SEQUENCE: 159

```
atggcagggt ttttaaaagt agttcaatta ctagctaaat atggttctaa agctgtacaa      60
tgggcttggg caaacaaggg taagatttta gattggctta atgcaggtca ggctattgat     120
tgggtagttt cgaaaattaa gcaaatttta ggtattaagt aa                        162
```

<210> SEQ ID NO 160
<211> LENGTH: 53
<212> TYPE: PRT
<213> ORGANISM: Lactococcus lactis

<400> SEQUENCE: 160

Met Ala Gly Phe Leu Lys Val Val Gln Ile Leu Ala Lys Tyr Gly Ser
1               5                   10                  15

Lys Ala Val Gln Trp Ala Trp Ala Asn Lys Gly Lys Ile Leu Asp Trp
            20                  25                  30

Ile Asn Ala Gly Gln Ala Ile Asp Trp Val Val Glu Lys Ile Lys Gln
        35                  40                  45

Ile Leu Gly Ile Lys
        50

<210> SEQ ID NO 161
<211> LENGTH: 162
<212> TYPE: DNA
<213> ORGANISM: Lactococcus lactis

<400> SEQUENCE: 161
atggcagggt ttttaaaagt agtccaaatt ttggctaagt atggttctaa agccgtacaa      60
tgggcatggg caaataaagg aaaaatctta gattggatta atgcaggtca agctattgac     120
tgggtagttg aaaagattaa gcaaattttg ggtattaaat aa                         162

<210> SEQ ID NO 162
<211> LENGTH: 65
<212> TYPE: PRT
<213> ORGANISM: Lactobacillus amylovorus

<400> SEQUENCE: 162

Met Lys Gln Leu Asn Ser Glu Gln Leu Gln Asn Ile Ile Gly Gly Asn
1               5                   10                  15

Arg Trp Thr Asn Ala Tyr Ser Ala Ala Leu Gly Cys Ala Val Pro Gly
            20                  25                  30

Val Lys Tyr Gly Lys Lys Leu Gly Gly Val Trp Gly Ala Val Ile Gly
        35                  40                  45

Gly Val Gly Gly Ala Ala Val Cys Gly Leu Ala Gly Tyr Val Arg Lys
    50                  55                  60

Gly
65

<210> SEQ ID NO 163
<211> LENGTH: 198
<212> TYPE: DNA
<213> ORGANISM: Lactobacillus amylovorus

<400> SEQUENCE: 163
atgaaacaat tgaattcaga acaattacaa aatattatcg gtggaaatag atggactaat      60
gcatacagcg cagctttggg atgcgctgtc cctggagtta aatatggaaa aaaacttggt     120
ggcgtatggg gtgctgtaat tggtggcgta ggcggtgcag cagtctgtgg cttggcgggt     180
tatgttcgta aaggctaa                                                   198

<210> SEQ ID NO 164
<211> LENGTH: 68
<212> TYPE: PRT
<213> ORGANISM: Lactobacillus sakei L45

<400> SEQUENCE: 164

Met Lys Thr Glu Lys Lys Val Leu Asp Glu Leu Ser Leu His Ala Ser
1               5                   10                  15

Ala Lys Met Gly Ala Arg Asp Val Glu Ser Ser Met Asn Ala Asp Ser
            20                  25                  30

Thr Pro Val Leu Ala Ser Val Ala Val Ser Met Glu Leu Leu Pro Thr
        35                  40                  45

Ala Ser Val Leu Tyr Ser Asp Val Ala Gly Cys Phe Lys Tyr Ser Ala
50                  55                  60

Lys His His Cys
65

<210> SEQ ID NO 165
<211> LENGTH: 207
<212> TYPE: DNA
<213> ORGANISM: Lactobacillus sakei L45

<400> SEQUENCE: 165
atgaaaacag aaaaaaaggt tttagatgaa ctgagcttac acgcttctgc aaaaatggga      60
gcacgtgatg ttgaatccag catgaatgca gactcaacac cagttttagc atcagtcgct     120
gtatccatgg aattattgcc aactgcgtct gttctttatt cggatgttgc aggttgcttc     180
aaatattctg caaacatca ttgttag                                         207

<210> SEQ ID NO 166
<211> LENGTH: 91
<212> TYPE: PRT
<213> ORGANISM: Lactococcus lactis subsp. lactis

<400> SEQUENCE: 166

Met Lys Thr Lys Ser Leu Val Leu Ala Leu Ser Ala Val Thr Leu Phe
1               5                   10                  15

Ser Ala Gly Gly Ile Val Ala Gln Ala Glu Gly Thr Trp Gln His Gly
            20                  25                  30

Tyr Gly Val Ser Ser Ala Tyr Ser Asn Tyr His His Gly Ser Lys Thr
        35                  40                  45

His Ser Ala Thr Val Val Asn Asn Thr Gly Arg Gln Gly Lys Asp
50                  55                  60

Thr Gln Arg Ala Gly Val Trp Ala Lys Ala Thr Val Gly Arg Asn Leu
65                  70                  75                  80

Thr Glu Lys Ala Ser Phe Tyr Tyr Asn Phe Trp
                85                  90

<210> SEQ ID NO 167
<211> LENGTH: 276
<212> TYPE: DNA
<213> ORGANISM: Lactococcus lactis subsp. lactis

<400> SEQUENCE: 167
atgaaaacca agtctctcgt attggcatta tctgcggtta cgttattctc tgccggagga      60
attgtagctc aagctgaagg aacatggcaa catggatatg gtgttagttc ggcatattca     120
aattatcatc atggtagcaa aactcattca gccacagttg taaataataa tactggccga     180
caaggtaagg atacacaacg tgccggtgtt tgggcaaaag ctactgttgg acgtaactta     240
actgaaaaag cttcatttta ttataacttt tggtaa                               276

<210> SEQ ID NO 168

```
<211> LENGTH: 75
<212> TYPE: PRT
<213> ORGANISM: Lactococcus lactis subsp. cremoris

<400> SEQUENCE: 168

Met Lys Asn Gln Leu Asn Phe Asn Ile Val Ser Asp Glu Glu Leu Ser
1               5                   10                  15

Glu Ala Asn Gly Gly Lys Leu Thr Phe Ile Gln Ser Thr Ala Ala Gly
            20                  25                  30

Asp Leu Tyr Tyr Asn Thr Asn Thr His Lys Tyr Val Tyr Gln Gln Thr
        35                  40                  45

Gln Asn Ala Phe Gly Ala Ala Ala Asn Thr Ile Val Asn Gly Trp Met
    50                  55                  60

Gly Gly Ala Ala Gly Gly Phe Gly Leu His His
65                  70                  75

<210> SEQ ID NO 169
<211> LENGTH: 228
<212> TYPE: DNA
<213> ORGANISM: Lactococcus lactis subsp. cremoris

<400> SEQUENCE: 169
atgaaaaatc aattaaattt taatattgtt tcagatgaag aactttcaga agctaacgga     60
ggaaaattaa catttattca atcgacagcg gctggagatt tatattacaa tactaataca    120
cacaaatatg tttaccaaca aactcaaaac gcttttgggg ctgctgctaa taccattgtt    180
aatggatgga tgggtggcgc tgctggaggt ttcgggttgc accattga                 228

<210> SEQ ID NO 170
<211> LENGTH: 68
<212> TYPE: PRT
<213> ORGANISM: Lactococcus lactis subsp. cremoris

<400> SEQUENCE: 170

Met Lys Asn Gln Leu Asn Phe Asn Ile Val Ser Asp Glu Glu Leu Ala
1               5                   10                  15

Glu Val Asn Gly Gly Ser Leu Gln Tyr Val Met Ser Ala Gly Pro Tyr
            20                  25                  30

Thr Trp Tyr Lys Asp Thr Arg Thr Gly Lys Thr Ile Cys Lys Gln Thr
        35                  40                  45

Ile Asp Thr Ala Ser Tyr Thr Phe Gly Val Met Ala Glu Gly Trp Gly
    50                  55                  60

Lys Thr Phe His
65

<210> SEQ ID NO 171
<211> LENGTH: 207
<212> TYPE: DNA
<213> ORGANISM: Lactococcus lactis subsp. cremoris

<400> SEQUENCE: 171
atgaaaaatc aattaaattt taatattgtt tctgatgaag aacttgcaga agttaatgga     60
ggaagcttgc agtatgttat gagtgctgga ccatatactt ggtataaaga tactagaaca    120
ggaaaaacaa tatgtaaaca gacaattgac acagcaagtt atacatttgg tgtaatggca    180
gaaggatggg gaaaaacatt ccactaa                                        207

<210> SEQ ID NO 172
<211> LENGTH: 63
```

```
<212> TYPE: PRT
<213> ORGANISM: Lactococcus sp. QU 12

<400> SEQUENCE: 172

Met Lys Leu Ile Asp His Leu Gly Ala Pro Arg Trp Ala Val Asp Thr
1               5                   10                  15

Ile Leu Gly Ala Ile Ala Val Gly Asn Leu Ala Ser Trp Val Leu Ala
            20                  25                  30

Leu Val Pro Gly Pro Gly Trp Ala Val Lys Ala Gly Leu Ala Thr Ala
        35                  40                  45

Ala Ala Ile Val Lys His Gln Gly Lys Ala Ala Ala Ala Trp
    50                  55                  60

<210> SEQ ID NO 173
<211> LENGTH: 192
<212> TYPE: DNA
<213> ORGANISM: Lactococcus sp. QU 12

<400> SEQUENCE: 173
atgaaattaa ttgatcattt aggtgctcca agatgggccg ttgatactat tttaggtgca      60
atcgcagttg ggaacttagc aagttgggtt ctagcgcttg tccctggtcc agggtgggca     120
gtaaaagctg gtttagcaac tgctgctgcc atcgttaaac atcaaggtaa agctgccgct     180
gctgcttggt aa                                                         192

<210> SEQ ID NO 174
<211> LENGTH: 50
<212> TYPE: PRT
<213> ORGANISM: Brevibacillus sp. GI-9

<400> SEQUENCE: 174

Met Ala Cys Gln Cys Pro Asp Ala Ile Ser Gly Trp Thr His Thr Asp
1               5                   10                  15

Tyr Gln Cys His Gly Leu Glu Asn Lys Met Tyr Arg His Val Tyr Ala
            20                  25                  30

Ile Cys Met Asn Gly Thr Gln Val Tyr Cys Arg Thr Glu Trp Gly Ser
        35                  40                  45

Ser Cys
    50

<210> SEQ ID NO 175
<211> LENGTH: 153
<212> TYPE: DNA
<213> ORGANISM: Brevibacillus sp. GI-9

<400> SEQUENCE: 175
atggcttgcc aatgtccaga tgcgatctca ggttggacgc atacagatta ccagtgtcac      60
ggtttggaga ataaaatgta tagacatgtt tatgcaattt gcatgaacgg tactcaagta     120
tattgcagaa cagagtgggg tagcagctgc tag                                  153

<210> SEQ ID NO 176
<211> LENGTH: 57
<212> TYPE: PRT
<213> ORGANISM: Leuconostoc pseudomesenteroides

<400> SEQUENCE: 176

Met Asn Lys Glu Tyr Asn Ser Ile Ser Asn Phe Lys Lys Ile Thr Asn
1               5                   10                  15

Lys Asp Leu Gln Asn Ile Asn Gly Gly Phe Ile Gly Arg Ala Ile Gly
```

```
                20                  25                  30
Asp Phe Val Tyr Phe Gly Ala Lys Gly Leu Arg Glu Ser Gly Lys Leu
            35                  40                  45

Leu Asn Tyr Tyr Tyr Lys His Lys His
        50                  55

<210> SEQ ID NO 177
<211> LENGTH: 174
<212> TYPE: DNA
<213> ORGANISM: Leuconostoc pseudomesenteroides

<400> SEQUENCE: 177
atgaataaag aatataatag cattagcaat tttaaaaaaa ttactaataa agacttgcaa      60
aacataaatg gtggatttat tggtagggca ataggtgact tgtgtacttt tggagcgaag     120
ggactaagag aatctggtaa actacttaat tattactata agcataagca ttga           174

<210> SEQ ID NO 178
<211> LENGTH: 53
<212> TYPE: PRT
<213> ORGANISM: Leuconostoc pseudomesenteroides

<400> SEQUENCE: 178

Met Lys Asn Gln Leu Met Ser Phe Glu Val Ile Ser Glu Lys Glu Leu
1               5                   10                  15

Ser Thr Val Gln Gly Gly Lys Gly Leu Gly Lys Leu Ile Gly Ile Asp
            20                  25                  30

Trp Leu Leu Gly Gln Ala Lys Asp Ala Val Lys Gln Tyr Lys Lys Asp
        35                  40                  45

Tyr Lys Arg Trp His
    50

<210> SEQ ID NO 179
<211> LENGTH: 162
<212> TYPE: DNA
<213> ORGANISM: Leuconostoc pseudomesenteroides

<400> SEQUENCE: 179
atgaaaaatc agttaatgtc tttcgaagtg atatcagaaa aagaattgtc cacggtacaa      60
ggtggcaaag gcttaggtaa actcatagga attgattggc ttttgggtca agctaaggac     120
gctgttaaac agtacaagaa ggattacaaa cgttggcact aa                         162

<210> SEQ ID NO 180
<211> LENGTH: 61
<212> TYPE: PRT
<213> ORGANISM: Leuconostoc gelidum

<400> SEQUENCE: 180

Met Met Asn Met Lys Pro Thr Glu Ser Tyr Glu Gln Leu Asp Asn Ser
1               5                   10                  15

Ala Leu Glu Gln Val Val Gly Gly Lys Tyr Tyr Gly Asn Gly Val His
            20                  25                  30

Cys Thr Lys Ser Gly Cys Ser Val Asn Trp Gly Glu Ala Phe Ser Ala
        35                  40                  45

Gly Val His Arg Leu Ala Asn Gly Gly Asn Gly Phe Trp
    50                  55                  60

<210> SEQ ID NO 181
<211> LENGTH: 186
```

<212> TYPE: DNA
<213> ORGANISM: Leuconostoc gelidum

<400> SEQUENCE: 181

```
atgatgaaca tgaaacctac ggaaagctat gagcaattgg ataatagtgc tctcgaacaa    60
gtcgtaggag gtaagtatta tggtaacgga gttcattgca caaaaagtgg ttgttctgta   120
aactggggag aagccttttc agctggagta catcgtttag caaatggtgg aaatggtttc   180
tggtaa                                                              186
```

<210> SEQ ID NO 182
<211> LENGTH: 61
<212> TYPE: PRT
<213> ORGANISM: Leuconostoc carnosum

<400> SEQUENCE: 182

```
Met Asn Asn Met Lys Ser Ala Asp Asn Tyr Gln Gln Leu Asp Asn Asn
1               5                   10                  15
Ala Leu Glu Gln Val Val Gly Gly Lys Tyr Tyr Gly Asn Gly Val His
            20                  25                  30
Cys Thr Lys Ser Gly Cys Ser Val Asn Trp Gly Glu Ala Phe Ser Ala
        35                  40                  45
Gly Val His Arg Leu Ala Asn Gly Gly Asn Gly Phe Trp
    50                  55                  60
```

<210> SEQ ID NO 183
<211> LENGTH: 186
<212> TYPE: DNA
<213> ORGANISM: Leuconostoc carnosum

<400> SEQUENCE: 183

```
atgaataaca tgaaatctgc ggataattat cagcaattgg ataataatgc tctcgaacaa    60
gtcgtaggag gtaagtatta tggtaacgga gttcattgca caaaaagtgg ttgttctgta   120
aactggggag aagccttttc agctggagta catcgtttag caaatggtgg aaatggtttc   180
tggtaa                                                              186
```

<210> SEQ ID NO 184
<211> LENGTH: 63
<212> TYPE: PRT
<213> ORGANISM: Leuconostoc mesenteroides

<400> SEQUENCE: 184

```
Met Phe Leu Val Asn Gln Leu Gly Ile Ser Lys Ser Leu Ala Asn Thr
1               5                   10                  15
Ile Leu Gly Ala Ile Ala Val Gly Asn Leu Ala Ser Trp Leu Leu Ala
            20                  25                  30
Leu Val Pro Gly Pro Gly Trp Ala Thr Lys Ala Ala Leu Ala Thr Ala
        35                  40                  45
Glu Thr Ile Val Lys His Glu Gly Lys Ala Ala Ile Ala Trp
    50                  55                  60
```

<210> SEQ ID NO 185
<211> LENGTH: 192
<212> TYPE: DNA
<213> ORGANISM: Leuconostoc mesenteroides

<400> SEQUENCE: 185

```
atgttcttgg taaatcagtt agggatttca aaatcgttag ctaatactat tcttggtgca    60
```

```
attgctgttg gtaatttggc cagttggtta ttagctttgg ttcctggtcc gggttgggca      120
acaaaagcag cacttgcgac agctgaaaca attgtgaagc atgaaggaaa agcagctgct      180
attgcgtggt aa                                                          192
```

<210> SEQ ID NO 186
<211> LENGTH: 74
<212> TYPE: PRT
<213> ORGANISM: Bacillus licheniformis

<400> SEQUENCE: 186

```
Met Ser Lys Lys Glu Met Ile Leu Ser Trp Lys Asn Pro Met Tyr Arg
1               5                   10                  15

Thr Glu Ser Ser Tyr His Pro Ala Gly Asn Ile Leu Lys Glu Leu Gln
            20                  25                  30

Glu Glu Glu Gln His Ser Ile Ala Gly Gly Thr Ile Thr Leu Ser Thr
        35                  40                  45

Cys Ala Ile Leu Ser Lys Pro Leu Gly Asn Asn Gly Tyr Leu Cys Thr
    50                  55                  60

Val Thr Lys Glu Cys Met Pro Ser Cys Asn
65                  70
```

<210> SEQ ID NO 187
<211> LENGTH: 225
<212> TYPE: DNA
<213> ORGANISM: Bacillus licheniformis

<400> SEQUENCE: 187

```
atgtcaaaaa aggaaatgat tctttcatgg aaaaatccta tgtatcgcac tgaatcttct       60
tatcatccag cagggaacat ccttaaagaa ctccaggaag aggaacagca cagcatcgcc      120
ggaggcacaa tcacgctcag cacttgtgcc atcttgagca agccgttagg aaataacgga      180
tacctgtgta cagtgacaaa agaatgcatg ccaagctgta actaa                     225
```

<210> SEQ ID NO 188
<211> LENGTH: 266
<212> TYPE: PRT
<213> ORGANISM: Brevibacterium linens

<400> SEQUENCE: 188

```
Met Asn Asn Leu Tyr Arg Glu Leu Ala Pro Ile Pro Gly Pro Ala Trp
1               5                   10                  15

Ala Glu Ile Glu Glu Glu Ala Arg Arg Thr Phe Lys Arg Asn Ile Ala
            20                  25                  30

Gly Arg Arg Ile Val Asp Val Ala Gly Pro Thr Gly Phe Glu Thr Ser
        35                  40                  45

Ala Val Thr Thr Gly His Ile Arg Asp Val Gln Ser Glu Thr Ser Gly
    50                  55                  60

Leu Gln Val Lys Gln Arg Ile Val Gln Glu Tyr Ile Glu Leu Arg Thr
65                  70                  75                  80

Pro Phe Thr Val Thr Arg Gln Ala Ile Asp Asp Val Ala Arg Gly Ser
            85                  90                  95

Gly Asp Ser Asp Trp Gln Pro Val Lys Asp Ala Ala Thr Thr Ile Ala
        100                 105                 110

Met Ala Glu Asp Arg Ala Ile Leu His Gly Leu Asp Ala Ala Gly Ile
    115                 120                 125

Gly Gly Ile Val Pro Gly Ser Ser Asn Ala Ala Val Ala Ile Pro Asp
        130                 135                 140
```

```
Ala Val Glu Asp Phe Ala Asp Ala Val Ala Gln Ala Leu Ser Val Leu
145                 150                 155                 160

Arg Thr Val Gly Val Asp Gly Pro Tyr Ser Leu Leu Leu Ser Ser Ala
                165                 170                 175

Glu Tyr Thr Lys Val Ser Glu Ser Thr Asp His Gly Tyr Pro Ile Arg
            180                 185                 190

Glu His Leu Ser Arg Gln Leu Gly Ala Gly Glu Ile Ile Trp Ala Pro
        195                 200                 205

Ala Leu Glu Gly Ala Leu Leu Val Ser Thr Arg Gly Gly Asp Tyr Glu
    210                 215                 220

Leu His Leu Gly Gln Asp Leu Ser Ile Gly Tyr Tyr Ser His Asp Ser
225                 230                 235                 240

Glu Thr Val Glu Leu Tyr Leu Gln Glu Thr Phe Gly Phe Leu Ala Leu
                245                 250                 255

Thr Asp Glu Ser Ser Val Pro Leu Ser Leu
            260                 265
```

<210> SEQ ID NO 189
<211> LENGTH: 801
<212> TYPE: DNA
<213> ORGANISM: Brevibacterium linens

<400> SEQUENCE: 189

```
gtgaataacc tctatcgcga gcttgccccc atccccggcc cggcctgggc ggagatcgag      60
gaggaggctc gacggacatt caaacgcaat atcgccggcc gccggatcgt cgatgtcgca     120
gggcccacgg gcttcgagac ctccgcggtg accactggcc acatccgaga cgtccagtcg     180
gagacgagcg gactgcaggt taagcagcgc atcgtgcagg aatacatcga gctgcggacc     240
ccattcaccg tgactcggca ggccatcgat gacgtggccc gcgggtccgg tgactcggac     300
tggcagcccg tcaaggatgc ggccacgacg atcgcgatgg ctgaagatcg gccattctc     360
cacgggctcg atgcggccgg gatcggcgga atcgttcccg gcagctcgaa tgccgcagtg     420
gccatccccg acgccgtcga ggacttcgcg gacgccgtcg cccaggcgct gagtgtgctg     480
cgcacggtgg gagtcgacgg gccctacagc ctgttgctct cctccgcgga gtacaccaag     540
gtctccgagt ccaccgacca cggctacccg atccgcgagc acctctcccg gcagctcggc     600
gccgagaga tcatctgggc gcccgcgctc gaagggcgc tgctcgtctc cacgcgcggg     660
ggtgactacg agctccacct cggccaggac ctgtcgatcg gttactacag ccacgacagc     720
gagaccgtcg aactctatct gcaggagacc ttcggattcc tcgcgctgac cgacgaatcc     780
agtgtgcctt tgagcctctg a                                             801
```

<210> SEQ ID NO 190
<211> LENGTH: 71
<212> TYPE: PRT
<213> ORGANISM: Listeria innocua

<400> SEQUENCE: 190

```
Met Lys Lys Ala Ala Leu Lys Phe Ile Ile Val Ile Ala Ile Leu Gly
1               5                   10                  15

Phe Ser Phe Ser Phe Phe Ser Ile Gln Ser Glu Ala Lys Ser Tyr Gly
            20                  25                  30

Asn Gly Val Gln Cys Asn Lys Lys Cys Trp Val Asp Trp Gly Ser
        35                  40                  45

Ala Ile Ser Thr Ile Gly Asn Asn Ser Ala Ala Asn Trp Ala Thr Gly
```

```
                50                  55                  60

Gly Ala Ala Gly Trp Lys Ser
65                  70

<210> SEQ ID NO 191
<211> LENGTH: 216
<212> TYPE: DNA
<213> ORGANISM: Listeria innocua

<400> SEQUENCE: 191
ttgaagaagg cagcgttaaa atttattatt gttattgcta ttctaggttt cagttttcct      60
ttctttagca tacaatctga agctaaatct tatggaaatg gagttcagtg taataagaaa     120
aaatgttggg tagattgggg tagtgctata agtactattg gaataattc tgcagcgaat     180 tgggctacag gtggagcagc tggttggaaa agctga                              216

<210> SEQ ID NO 192
<211> LENGTH: 68
<212> TYPE: PRT
<213> ORGANISM: Bacillus sp.

<400> SEQUENCE: 192

Met Ser Gln Glu Ala Ile Ile Arg Ser Trp Lys Asp Pro Phe Ser Arg
1               5                   10                  15

Glu Asn Ser Thr Gln Asn Pro Ala Gly Asn Pro Phe Ser Glu Leu Lys
            20                  25                  30

Glu Ala Gln Met Asp Lys Leu Val Gly Ala Gly Asp Met Glu Ala Ala
        35                  40                  45

Cys Thr Phe Thr Leu Pro Gly Gly Gly Gly Val Cys Thr Leu Thr Ser
    50                  55                  60

Glu Cys Ile Cys
65

<210> SEQ ID NO 193
<211> LENGTH: 207
<212> TYPE: DNA
<213> ORGANISM: Bacillus sp.

<400> SEQUENCE: 193
atgagtcaag aagctatcat tcgttcatgg aaagatcctt tttcccgtga aaattctaca      60
caaaatccag ctggtaaccc attcagtgag ctgaaagaag cacaaatgga taagttagta    120
ggtgcgggag acatggaagc agcatgtact tttacattgc ctggtggcgg cggtgtttgt    180
actctaactt ctgaatgtat tgttaa                                         207

<210> SEQ ID NO 194
<211> LENGTH: 61
<212> TYPE: PRT
<213> ORGANISM: Leuconostoc mesenteroides

<400> SEQUENCE: 194

Met Thr Asn Met Lys Ser Val Glu Ala Tyr Gln Gln Leu Asp Asn Gln
1               5                   10                  15

Asn Leu Lys Lys Val Val Gly Gly Lys Tyr Tyr Gly Asn Gly Val His
            20                  25                  30

Cys Thr Lys Ser Gly Cys Ser Val Asn Trp Gly Glu Ala Ala Ser Ala
        35                  40                  45

Gly Ile His Arg Leu Ala Asn Gly Gly Asn Gly Phe Trp
    50                  55                  60
```

<210> SEQ ID NO 195
<211> LENGTH: 186
<212> TYPE: DNA
<213> ORGANISM: Leuconostoc mesenteroides

<400> SEQUENCE: 195

```
atgacgaata tgaagtctgt ggaagcatat cagcaattag ataaccagaa tctcaagaaa      60
gttgttggtg gaaagtatta tgggaatggt gttcactgta caaaaagtgg atgctctgtt     120
aactggggag aagctgcctc agctggcata catcgtttgg ccaatggtgg aaatggattt     180
tggtaa                                                                 186
```

<210> SEQ ID NO 196
<211> LENGTH: 68
<212> TYPE: PRT
<213> ORGANISM: Clavibacter michiganensis subsp. michiganensis

<400> SEQUENCE: 196

```
Met Asn Asp Ile Leu Glu Thr Glu Thr Pro Val Met Val Ser Pro Arg
1               5                   10                  15

Trp Asp Met Leu Leu Asp Ala Gly Glu Asp Thr Ser Pro Ser Val Gln
            20                  25                  30

Thr Gln Ile Asp Ala Glu Phe Arg Arg Val Val Ser Pro Tyr Met Ser
        35                  40                  45

Ser Ser Gly Trp Leu Cys Thr Leu Thr Ile Glu Cys Gly Thr Ile Ile
    50                  55                  60

Cys Ala Cys Arg
65
```

<210> SEQ ID NO 197
<211> LENGTH: 207
<212> TYPE: DNA
<213> ORGANISM: Clavibacter michiganensis subsp. michiganensis

<400> SEQUENCE: 197

```
atgaacgaca tcctcgagac ggagaccccc gtcatggtca gccccggtg ggacatgctg       60 ctcgacgcgg gcgaggacac cagcccgtcc gtccagaccc agatcgacgc ggagttccgt    120
cgcgtcgtga gcccgtacat gtccagcagc ggctggctct gcacgctcac catcgaatgt    180
ggcaccatca tctgcgcgtg tcgctga                                         207
```

<210> SEQ ID NO 198
<211> LENGTH: 69
<212> TYPE: PRT
<213> ORGANISM: Escherichia coli

<400> SEQUENCE: 198

```
Met Glu Leu Lys Ala Ser Glu Phe Gly Val Val Leu Ser Val Asp Ala
1               5                   10                  15

Leu Lys Leu Ser Arg Gln Ser Pro Leu Gly Val Gly Ile Gly Gly Gly
            20                  25                  30

Gly Gly Gly Gly Gly Gly Gly Ser Cys Gly Gly Gln Gly Gly Gly Cys
        35                  40                  45

Gly Gly Cys Ser Asn Gly Cys Ser Gly Gly Asn Gly Gly Ser Gly Gly
    50                  55                  60

Ser Gly Ser His Ile
65
```

<210> SEQ ID NO 199
<211> LENGTH: 207
<212> TYPE: DNA
<213> ORGANISM: Escherichia coli

<400> SEQUENCE: 199

```
atggaattaa aagcgagtga atttggtgta gttttgtccg ttgatgctct taaattatca      60
cgccagtctc cattaggtgt tggcattggt ggtggtggcg gcggcggcgg cggcggtagc     120
tgcggtggtc aaggtggcgg ttgtggtggt tgcagcaacg gttgtagtgg tggaaacggt     180
ggcagcggcg gaagtggttc acatatc                                        207
```

<210> SEQ ID NO 200
<211> LENGTH: 7
<212> TYPE: PRT
<213> ORGANISM: Escherichia coli

<400> SEQUENCE: 200

Met Arg Thr Gly Asn Ala Asn
1               5

<210> SEQ ID NO 201
<211> LENGTH: 24
<212> TYPE: DNA
<213> ORGANISM: Escherichia coli

<400> SEQUENCE: 201

```
atgcgtactg gtaatgcaaa ctaa                                            24
```

<210> SEQ ID NO 202
<211> LENGTH: 99
<212> TYPE: PRT
<213> ORGANISM: Klebsiella pneumoniae

<400> SEQUENCE: 202

Met Arg Glu Ile Ser Gln Lys Asp Leu Asn Leu Ala Phe Gly Ala Gly
1               5                   10                  15

Glu Thr Asp Pro Asn Thr Gln Leu Leu Asn Asp Leu Gly Asn Asn Met
            20                  25                  30

Ala Trp Gly Ala Ala Leu Gly Ala Pro Gly Gly Leu Gly Ser Ala Ala
        35                  40                  45

Leu Gly Ala Ala Gly Gly Ala Leu Gln Thr Val Gly Gln Gly Leu Ile
    50                  55                  60

Asp His Gly Pro Val Asn Val Pro Ile Pro Val Leu Ile Gly Pro Ser
65                  70                  75                  80

Trp Asn Gly Ser Gly Ser Gly Tyr Asn Ser Ala Thr Ser Ser Ser Gly
                85                  90                  95

Ser Gly Ser

<210> SEQ ID NO 203
<211> LENGTH: 300
<212> TYPE: DNA
<213> ORGANISM: Klebsiella pneumoniae

<400> SEQUENCE: 203

```
atgagagaaa ttagtcaaaa ggacttaaat cttgcttttg gtgcaggaga gaccgatcca      60
aatactcaac ttctaaacga ccttggaaat aatatggcat ggggtgctgc tcttggcgct     120
cctggcggat taggatcagc agctttgggg gccgcgggag gtgcattaca aactgtaggg     180
```

```
caaggattaa ttgaccatgg tcctgtaaat gtccccatcc ctgtactcat cgggccaagc    240
tggaatggta gcggtagtgg ttataacagc gcaacatcca gttccggtag tggtagttaa    300
```

<210> SEQ ID NO 204
<211> LENGTH: 75
<212> TYPE: PRT
<213> ORGANISM: Escherichia coli

<400> SEQUENCE: 204

Met Arg Glu Ile Thr Glu Ser Gln Leu Arg Tyr Ile Ser Gly Ala Gly
1               5                   10                  15

Gly Ala Pro Ala Thr Ser Ala Asn Ala Ala Gly Ala Ala Ile Val
            20                  25                  30

Gly Ala Leu Ala Gly Ile Pro Gly Gly Pro Leu Gly Val Val Val Gly
        35                  40                  45

Ala Val Ser Ala Gly Leu Thr Thr Ala Ile Gly Ser Thr Val Gly Ser
    50                  55                  60

Gly Ser Ala Ser Ser Ala Gly Gly Gly Ser
65                  70                  75

<210> SEQ ID NO 205
<211> LENGTH: 228
<212> TYPE: DNA
<213> ORGANISM: Escherichia coli

<400> SEQUENCE: 205

```
atgcgagaaa taacagaatc acagttaaga tatatttccg gggcgggagg tgcgccagcg    60
acttcagcta atgccgcagg tgctgcagct attgttggag ctctcgccgg aatacctggt   120
ggtccacttg gggttgtagt tggagccgta tctgccggtt tgacaacagc aattggctcg   180
accgtgggaa gtggtagtgc cagttcttct gctggtggcg gtagctaa                228
```

<210> SEQ ID NO 206
<211> LENGTH: 58
<212> TYPE: PRT
<213> ORGANISM: Escherichia coli

<400> SEQUENCE: 206

Met Ile Lys His Phe His Phe Asn Lys Leu Ser Ser Gly Lys Lys Asn
1               5                   10                  15

Asn Val Pro Ser Pro Ala Lys Gly Val Ile Gln Ile Lys Lys Ser Ala
            20                  25                  30

Ser Gln Leu Thr Lys Gly Gly Ala Gly His Val Pro Glu Tyr Phe Val
        35                  40                  45

Gly Ile Gly Thr Pro Ile Ser Phe Tyr Gly
    50                  55

<210> SEQ ID NO 207
<211> LENGTH: 177
<212> TYPE: DNA
<213> ORGANISM: Escherichia coli

<400> SEQUENCE: 207

```
atgattaagc attttcattt taataaactg tcttctggta aaaaaaataa tgttccatct    60
cctgcaaagg gggttataca aataaaaaaa tcagcatcgc aactcacaaa aggtggtgca   120
ggacatgtgc ctgagtattt tgtggggatt ggtacaccta tctttcta tggctga       177
```

<210> SEQ ID NO 208

```
<211> LENGTH: 90
<212> TYPE: PRT
<213> ORGANISM: Escherichia coli

<400> SEQUENCE: 208

Met Tyr Met Arg Glu Leu Asp Arg Glu Glu Leu Asn Cys Val Gly Gly
1               5                   10                  15
Ala Gly Asp Pro Leu Ala Asp Pro Asn Ser Gln Ile Val Arg Gln Ile
            20                  25                  30
Met Ser Asn Ala Ala Trp Gly Pro Pro Leu Val Pro Glu Arg Phe Arg
        35                  40                  45
Gly Met Ala Val Gly Ala Ala Gly Val Thr Gln Thr Val Leu Gln
    50                  55                  60
Gly Ala Ala Ala His Met Pro Val Asn Val Pro Ile Pro Lys Val Pro
65                  70                  75                  80
Met Gly Pro Ser Trp Asn Gly Ser Lys Gly
                85                  90

<210> SEQ ID NO 209
<211> LENGTH: 273
<212> TYPE: DNA
<213> ORGANISM: Escherichia coli

<400> SEQUENCE: 209
atgtatatga gagagttaga tagagaggaa ttaaattgcg ttggtggggc tggagatccg     60
cttgcagatc ctaattccca aattgtaaga cagataatgt ctaatgcggc atggggcccg    120
cctttggtgc cagagcggtt taggggaatg gctgttggag ccgcaggtgg ggttacgcag    180
acagttcttc aaggagcagc agctcatatg ccggttaatg tccctatacc taaagttccg    240
atgggaccct catggaacgg aagtaaagga taa                                 273

<210> SEQ ID NO 210
<211> LENGTH: 50
<212> TYPE: PRT
<213> ORGANISM: Enterococcus mundtii

<400> SEQUENCE: 210

Met Ser Gln Val Val Gly Gly Lys Tyr Tyr Gly Asn Gly Val Ser Cys
1               5                   10                  15
Asn Lys Lys Gly Cys Ser Val Asp Trp Gly Lys Ala Ile Gly Ile Ile
            20                  25                  30
Gly Asn Asn Ser Ala Ala Asn Leu Ala Thr Gly Gly Ala Ala Gly Trp
        35                  40                  45
Lys Ser
    50

<210> SEQ ID NO 211
<211> LENGTH: 153
<212> TYPE: DNA
<213> ORGANISM: Enterococcus mundtii

<400> SEQUENCE: 211
atgtcacagg tagtaggtgg aaaatactac ggtaatggag tctcatgtaa taaaaaaggg     60
tgcagtgttg attggggaaa agcgattggc attattggaa ataattctgc tgcgaattta    120
gctactggtg gagcagctgg ttggaaaagt taa                                 153

<210> SEQ ID NO 212
<211> LENGTH: 58
```

```
<212> TYPE: PRT
<213> ORGANISM: Enterococcus mundtii

<400> SEQUENCE: 212

Met Lys Lys Leu Thr Ser Lys Glu Met Ala Gln Val Val Gly Gly Lys
1               5                   10                  15

Tyr Tyr Gly Asn Gly Leu Ser Cys Asn Lys Lys Gly Cys Ser Val Asp
            20                  25                  30

Trp Gly Lys Ala Ile Gly Ile Ile Gly Asn Asn Ser Ala Ala Asn Leu
        35                  40                  45

Ala Thr Gly Gly Ala Ala Gly Trp Lys Ser
    50                  55

<210> SEQ ID NO 213
<211> LENGTH: 177
<212> TYPE: DNA
<213> ORGANISM: Enterococcus mundtii

<400> SEQUENCE: 213
ttgaagaaat taacatcaaa agaaatggca caagtagtag gtgggaaata ctacggtaat      60
ggattatcat gtaataaaaa agggtgcagt gttgattggg gaaaagctat tggcattatt    120
ggaaataatt ctgctgcgaa tttagctact ggtggagcag ctggttggaa aagttaa       177

<210> SEQ ID NO 214
<211> LENGTH: 63
<212> TYPE: PRT
<213> ORGANISM: Streptococcus mutans

<400> SEQUENCE: 214

Met Ser Asn Thr Gln Leu Leu Glu Val Leu Gly Thr Glu Thr Phe Asp
1               5                   10                  15

Val Gln Glu Asp Leu Phe Ala Phe Asp Thr Thr Asp Thr Thr Ile Val
            20                  25                  30

Ala Ser Asn Asp Asp Pro Asp Thr Arg Phe Lys Ser Trp Ser Leu Cys
        35                  40                  45

Thr Pro Gly Cys Ala Arg Thr Gly Ser Phe Asn Ser Tyr Cys Cys
    50                  55                  60

<210> SEQ ID NO 215
<211> LENGTH: 192
<212> TYPE: DNA
<213> ORGANISM: Streptococcus mutans

<400> SEQUENCE: 215
atgtcaaaca cacaattatt agaagtcctt ggtactgaaa cttttgatgt tcaagaagat      60
ctctttgctt ttgatacaac agatactact attgtggcaa gcaacgacga tccagatact    120
cgtttcaaaa gttggagcct tgtacgcct ggttgtgcaa ggacaggtag tttcaatagt     180
tactgttgct ga                                                        192

<210> SEQ ID NO 216
<211> LENGTH: 53
<212> TYPE: PRT
<213> ORGANISM: Streptococcus mutans

<400> SEQUENCE: 216

Met Asn Lys Leu Asn Ser Asn Ala Val Val Ser Leu Asn Glu Val Ser
1               5                   10                  15

Asp Ser Glu Leu Asp Thr Ile Leu Gly Gly Asn Arg Trp Trp Gln Gly
```

20                  25                  30

Val Val Pro Thr Val Ser Tyr Glu Cys Arg Met Asn Ser Trp Gln His
            35                  40                  45

Val Phe Thr Cys Cys
    50

<210> SEQ ID NO 217
<211> LENGTH: 162
<212> TYPE: DNA
<213> ORGANISM: Streptococcus mutans

<400> SEQUENCE: 217
atgaacaagt taaacagtaa cgcagtagtt tctttgaatg aagtttcaga ttctgaattg      60
gatactattt tgggtggtaa tcgttggtgg caaggtgttg tgccaacggt ctcatatgag     120
tgtcgcatga attcatggca acatgttttc acttgctgtt aa                       162

<210> SEQ ID NO 218
<211> LENGTH: 57
<212> TYPE: PRT
<213> ORGANISM: Lactococcus lactis subsp. lactis

<400> SEQUENCE: 218

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
        35                  40                  45

Cys His Cys Ser Ile His Val Ser Lys
    50                  55

<210> SEQ ID NO 219
<211> LENGTH: 174
<212> TYPE: DNA
<213> ORGANISM: Lactococcus lactis subsp. lactis

<400> SEQUENCE: 219
atgagtacaa aagattttaa cttggatttg gtatctgttt cgaagaaaga ttcaggtgca      60
tcaccacgca ttacaagtat ttcgctatgt acacccggtt gtaaacagg agctctgatg     120 ggttgtaaca tgaaaacagc aacttgtcat tgtagtattc acgtaagcaa ataa          174

<210> SEQ ID NO 220
<211> LENGTH: 57
<212> TYPE: PRT
<213> ORGANISM: Lactococcus lactis

<400> SEQUENCE: 220

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
        35                  40                  45

Cys Asn Cys Ser Val His Val Ser Lys
    50                  55

<210> SEQ ID NO 221
<211> LENGTH: 171

<212> TYPE: DNA
<213> ORGANISM: Lactococcus lactis

<400> SEQUENCE: 221

```
atgagtacaa aagatttcaa cttggatttg gtatctgttt cgaagaaaga ttcaggtgca    60
tcaccacgca ttacaagtat ttcgctatgt acacccggtt gtaaaacagg agctctgatg   120
ggttgtaaca tgaaaacagc aacttgtaat tgtagcgttc acgtaagcaa a            171
```

<210> SEQ ID NO 222
<211> LENGTH: 57
<212> TYPE: PRT
<213> ORGANISM: Lactococcus lactis

<400> SEQUENCE: 222

Met Ser Thr Lys Asp Phe Asn Leu Asp Leu Val Ser Val Ser Lys Thr
1               5                   10                  15

Asp Ser Gly Ala Ser Thr Arg Ile Thr Ser Ile Ser Leu Cys Thr Pro
            20                  25                  30

Gly Cys Lys Thr Gly Val Leu Met Gly Cys Asn Leu Lys Thr Ala Thr
        35                  40                  45

Cys Asn Cys Ser Val His Val Ser Lys
    50                  55

<210> SEQ ID NO 223
<211> LENGTH: 174
<212> TYPE: DNA
<213> ORGANISM: Lactococcus lactis

<400> SEQUENCE: 223

```
atgagtacaa aagatttcaa cttagatttg gtatctgttt caaaaacaga ttctggcgct    60
tcaacacgta ttaccagcat ttcgctttgt acaccaggtt gtaaaacagg tgttctgatg   120
ggatgtaacc tgaaaacagc aacttgtaat tgtagcgttc acgtaagcaa ataa         174
```

<210> SEQ ID NO 224
<211> LENGTH: 55
<212> TYPE: PRT
<213> ORGANISM: Streptococcus uberis

<400> SEQUENCE: 224

Met Asn Asn Glu Asp Phe Asn Leu Asp Leu Ile Lys Ile Ser Lys Glu
1               5                   10                  15

Asn Asn Ser Gly Ala Ser Pro Arg Ile Thr Ser Lys Ser Leu Cys Thr
            20                  25                  30

Pro Gly Cys Lys Thr Gly Ile Leu Met Thr Cys Pro Leu Lys Thr Ala
        35                  40                  45

Thr Cys Gly Cys His Phe Gly
    50                  55

<210> SEQ ID NO 225
<211> LENGTH: 168
<212> TYPE: DNA
<213> ORGANISM: Streptococcus uberis

<400> SEQUENCE: 225

```
atgaacaatg aagattttaa tttggatctc atcaaaatct caaaggaaaa caactcagga    60
gcttcacctc gaataactag taaatcatta tgtactcctg gatgtaagac gggtattttg   120
atgacttgtc cactaaaaac tgcaacctgt ggttgtcatt ttggataa                168
```

<210> SEQ ID NO 226
<211> LENGTH: 57
<212> TYPE: PRT
<213> ORGANISM: Lactococcus lactis subsp. lactis

<400> SEQUENCE: 226

Met Ser Thr Lys Asp Phe Asn Leu Asp Leu Val Ser Val Ser Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
        35                  40                  45

Cys Asn Cys Ser Ile His Val Ser Lys
    50                  55

<210> SEQ ID NO 227
<211> LENGTH: 174
<212> TYPE: DNA
<213> ORGANISM: Lactococcus lactis subsp. lactis

<400> SEQUENCE: 227
atgagtacaa aagatttaa cttggatttg gtatctgttt cgaagaaaga ttcaggtgca      60
tcaccacgca ttacaagtat ttcgctatgt acaccggtt gtaaaacagg agctctgatg     120
ggttgtaaca tgaaaacagc aacttgtaat tgtagtattc acgtaagcaa ataa           174

<210> SEQ ID NO 228
<211> LENGTH: 57
<212> TYPE: PRT
<213> ORGANISM: Staphylococcus warneri

<400> SEQUENCE: 228

Met Glu Asn Ser Lys Val Met Lys Asp Ile Glu Val Ala Asn Leu Leu
1               5                   10                  15

Glu Glu Val Gln Glu Asp Glu Leu Asn Glu Val Leu Gly Ala Lys Lys
            20                  25                  30

Lys Ser Gly Val Ile Pro Thr Val Ser His Asp Cys His Met Asn Ser
        35                  40                  45

Phe Gln Phe Val Phe Thr Cys Cys Ser
    50                  55

<210> SEQ ID NO 229
<211> LENGTH: 174
<212> TYPE: DNA
<213> ORGANISM: Staphylococcus warneri

<400> SEQUENCE: 229
atggaaaatt ctaaagttat gaaggacatt gaagtagcaa atttattaga agaggttcaa      60
gaagatgaat tgaatgaagt cttaggagct aagaaaaagt caggagtaat cccaactgtg     120
tcacacgatt gccatatgaa ttctttccaa tttgtattta cttgttgttc ataa            174

<210> SEQ ID NO 230
<211> LENGTH: 58
<212> TYPE: PRT
<213> ORGANISM: Paenibacillus polymyxa

<400> SEQUENCE: 230

Met Ala Glu Asn Leu Phe Asp Leu Asp Ile Gln Val Asn Lys Ser Gln
1               5                   10                  15

Gly Ser Val Glu Pro Gln Val Leu Ser Ile Val Ala Cys Ser Ser Gly
                20                  25                  30

Cys Gly Ser Gly Lys Thr Ala Ala Ser Cys Val Glu Thr Cys Gly Asn
            35                  40                  45

Arg Cys Phe Thr Asn Val Gly Ser Leu Cys
        50                  55

<210> SEQ ID NO 231
<211> LENGTH: 177
<212> TYPE: DNA
<213> ORGANISM: Paenibacillus polymyxa

<400> SEQUENCE: 231
atggctgaaa acttatttga tctggacatt caagtaaaca aatctcaagg ttctgtagag     60
cctcaggttc tgagcattgt tgcatgttct agcggatgtg gtagcggtaa aacagctgcc    120
agttgtgttg aaacttgtgg caaccggtgc tttactaacg ttggttcact ctgctaa      177

<210> SEQ ID NO 232
<211> LENGTH: 62
<212> TYPE: PRT
<213> ORGANISM: Pediococcus acidilactici

<400> SEQUENCE: 232

Met Lys Lys Ile Glu Lys Leu Thr Glu Lys Glu Met Ala Asn Ile Ile
1               5                   10                  15

Gly Gly Lys Tyr Tyr Gly Asn Gly Val Thr Cys Gly Lys His Ser Cys
                20                  25                  30

Ser Val Asp Trp Gly Lys Ala Thr Thr Cys Ile Ile Asn Asn Gly Ala
            35                  40                  45

Met Ala Trp Ala Thr Gly Gly His Gln Gly Asn His Lys Cys
        50                  55                  60

<210> SEQ ID NO 233
<211> LENGTH: 189
<212> TYPE: DNA
<213> ORGANISM: Pediococcus acidilactici

<400> SEQUENCE: 233
atgaaaaaaa ttgaaaaatt aactgaaaaa gaaatggcca atatcattgg tggtaaatac     60
tacggtaatg gggttacttg tggcaaacat tcctgctctg ttgactgggg taaggctacc    120
acttgcataa tcaataatgg agctatggca tgggctactg gtggacatca aggtaatcat    180
aaatgctag                                                            189

<210> SEQ ID NO 234
<211> LENGTH: 60
<212> TYPE: PRT
<213> ORGANISM: Pediococcus pentosaceus

<400> SEQUENCE: 234

Met Thr Glu Ile Lys Val Leu Asn Asp Lys Glu Leu Lys Asn Val Val
1               5                   10                  15

Gly Gly Lys Tyr Tyr Gly Asn Gly Val His Cys Gly Lys Lys Thr Cys
                20                  25                  30

Tyr Val Asp Trp Gly Gln Ala Thr Ala Ser Ile Gly Lys Ile Ile Val
            35                  40                  45

Asn Gly Trp Thr Gln His Gly Pro Trp Ala His Arg
        50                  55                  60

<210> SEQ ID NO 235
<211> LENGTH: 183
<212> TYPE: DNA
<213> ORGANISM: Pediococcus pentosaceus

<400> SEQUENCE: 235
atgactgaaa ttaaagtact aaacgataag gaactaaaaa atgtcgtagg aggaaagtat      60
tacggtaacg gagtgcattg tggtaaaaag acttgctatg tggactgggg acaagctaca     120
gctagcattg gaaaaattat agtgaacgga tggacacaac acgggccttg gcacataga     180 taa                                                                   183

<210> SEQ ID NO 236
<211> LENGTH: 60
<212> TYPE: PRT
<213> ORGANISM: Staphylococcus epidermidis

<400> SEQUENCE: 236

Met Lys Asn Asn Lys Asn Leu Phe Asp Leu Glu Ile Lys Lys Glu Thr
1               5                   10                  15

Ser Gln Asn Thr Asp Glu Leu Glu Pro Gln Thr Ala Gly Pro Ala Ile
            20                  25                  30

Arg Ala Ser Val Lys Gln Cys Gln Lys Thr Leu Lys Ala Thr Arg Leu
        35                  40                  45

Phe Thr Val Ser Cys Lys Gly Lys Asn Gly Cys Lys
    50                  55                  60

<210> SEQ ID NO 237
<211> LENGTH: 183
<212> TYPE: DNA
<213> ORGANISM: Staphylococcus epidermidis

<400> SEQUENCE: 237
atgaaaaata caaaaattt atttgattta gaaattaaaa aagaaacaag tcaaaacact        60
gatgaacttg aacctcaaac tgctggacca gcgattagag cttctgtgaa acaatgtcag     120
aaaactttga agctacgcg tttatttaca gtgtcttgca aggaaaaaaa cggatgtaaa     180
tag                                                                  183

<210> SEQ ID NO 238
<211> LENGTH: 62
<212> TYPE: PRT
<213> ORGANISM: Carnobacterium maltaromaticum

<400> SEQUENCE: 238

Met Lys Thr Val Lys Glu Leu Ser Val Lys Glu Met Gln Leu Thr Thr
1               5                   10                  15

Gly Gly Lys Tyr Tyr Gly Asn Gly Val Ser Cys Asn Lys Asn Gly Cys
            20                  25                  30

Thr Val Asp Trp Ser Lys Ala Ile Gly Ile Ile Gly Asn Asn Ala Ala
        35                  40                  45

Ala Asn Leu Thr Thr Gly Gly Ala Ala Gly Trp Asn Lys Gly
    50                  55                  60

<210> SEQ ID NO 239
<211> LENGTH: 189
<212> TYPE: DNA
<213> ORGANISM: Carnobacterium maltaromaticum

<400> SEQUENCE: 239

-continued

```
atgaaaactg ttaaagaact tagcgttaaa gaaatgcaac taactacagg aggtaagtat    60
tacggaaatg gcgtttcctg taataaaaat ggttgtactg tagattggag caaagctatt   120
gggattatag gaaacaatgc agcagcaaat ttgactacag gtggagccgc tggttggaac   180
aaaggataa                                                            189
```

<210> SEQ ID NO 240
<211> LENGTH: 69
<212> TYPE: PRT
<213> ORGANISM: Lactobacillus plantarum
<220> FEATURE:
<221> NAME/KEY: VARIANT
<222> LOCATION: 40
<223> OTHER INFORMATION: Xaa = any amino acid

<400> SEQUENCE: 240

Met Tyr Lys Glu Leu Thr Val Asp Glu Leu Ala Leu Ile Asp Gly Gly
1               5                   10                  15

Lys Lys Lys Lys Lys Val Ala Cys Thr Trp Gly Asn Ala Ala Thr
            20                  25                  30

Ala Ala Ala Ser Gly Ala Val Xaa Gly Ile Leu Gly Pro Thr Gly
        35                  40                  45

Ala Leu Ala Gly Ala Ile Trp Gly Val Ser Gln Cys Ala Ser Asn Asn
    50                  55                  60

Leu His Gly Met His
65

<210> SEQ ID NO 241
<211> LENGTH: 210
<212> TYPE: DNA
<213> ORGANISM: Lactobacillus plantarum
<220> FEATURE:
<221> NAME/KEY: misc_feature
<222> LOCATION: 119
<223> OTHER INFORMATION: n = a, c, t or g

<400> SEQUENCE: 241

```
atgtataaag aattaacagt tgatgaatta gcattgattg atggaggaaa aaagaagaag    60
aaaaaagtag cttgtacttg gggaaatgca gcaacagccg ctgcttctgg tgcagttang   120
ggtattcttg gtgggcctac tggtgcactg gctggagcta tctggggcgt ttcacaatgc   180
gcgtctaaca acttacacgg catgcactaa                                    210
```

<210> SEQ ID NO 242
<211> LENGTH: 56
<212> TYPE: PRT
<213> ORGANISM: Lactobacillus plantarum

<400> SEQUENCE: 242

Met Met Lys Lys Ile Glu Lys Leu Thr Glu Lys Glu Met Ala Asn Ile
1               5                   10                  15

Ile Gly Gly Lys Tyr Tyr Gly Asn Gly Val Thr Cys Gly Lys His Ser
            20                  25                  30

Cys Ser Val Asn Trp Gly Gln Ala Phe Ser Cys Ser Val Ser His Leu
        35                  40                  45

Ala Asn Phe Gly His Gly Lys Cys
    50                  55

<210> SEQ ID NO 243
<211> LENGTH: 171

```
<212> TYPE: DNA
<213> ORGANISM: Lactobacillus plantarum

<400> SEQUENCE: 243
atgatgaaaa aaattgaaaa attaactgaa aagaaatgg ccaatatcat tggtggtaaa      60
tactatggta atggggttac ttgtggtaaa cattcctgct ctgttaactg gggccaagca     120
ttttcttgta gtgtgtcaca tttagctaac ttcggtcatg gaaagtgcta a              171

<210> SEQ ID NO 244
<211> LENGTH: 64
<212> TYPE: PRT
<213> ORGANISM: Lactobacillus plantarum

<400> SEQUENCE: 244
```

Met Ser Lys Leu Val Lys Thr Leu Thr Val Asp Glu Ile Ser Lys Ile
1               5                   10                  15

Gln Thr Asn Gly Gly Lys Pro Ala Trp Cys Trp Tyr Thr Leu Ala Met
            20                  25                  30

Cys Gly Ala Gly Tyr Asp Ser Gly Thr Cys Asp Tyr Met Tyr Ser His
        35                  40                  45

Cys Phe Gly Val Lys His Ser Ser Gly Gly Gly Ser Tyr His Cys
    50                  55                  60

```
<210> SEQ ID NO 245
<211> LENGTH: 195
<212> TYPE: DNA
<213> ORGANISM: Lactobacillus plantarum

<400> SEQUENCE: 245
atgagtaaac tagttaaaac attaactgtc gatgaaatct ctaagattca aaccatggt      60 ggaaaacctg catggtgttg gtacacattg gcaatgtgcg gtgctggtta tgattcaggc    120
acttgtgatt atatgtattc acactgcttt ggtgtaaaac actctagcgg tggtggcggt    180
agctaccatt gttag                                                      195

<210> SEQ ID NO 246
<211> LENGTH: 56
<212> TYPE: PRT
<213> ORGANISM: Lactobacillus plantarum

<400> SEQUENCE: 246
```

Met Leu Gln Phe Glu Lys Leu Gln Tyr Ser Arg Leu Pro Gln Lys Lys
1               5                   10                  15

Leu Ala Lys Ile Ser Gly Gly Phe Asn Arg Gly Gly Tyr Asn Phe Gly
            20                  25                  30

Lys Ser Val Arg His Val Val Asp Ala Ile Gly Ser Val Ala Gly Ile
        35                  40                  45

Arg Gly Ile Leu Lys Ser Ile Arg
    50                  55

```
<210> SEQ ID NO 247
<211> LENGTH: 171
<212> TYPE: DNA
<213> ORGANISM: Lactobacillus plantarum

<400> SEQUENCE: 247
atgctacagt ttgagaaatt acaatattcc aggttgccgc aaaaaaagct tgccaaaata     60
tctggtggtt ttaatcgggg cggttataac tttggtaaaa gtgttcgaca tgttgttgat    120
```

```
gcaattggtt cagttgcagg cattcgtggt attttgaaaa gtattcgtta a          171
```

<210> SEQ ID NO 248
<211> LENGTH: 52
<212> TYPE: PRT
<213> ORGANISM: Lactobacillus plantarum

<400> SEQUENCE: 248

```
Met Lys Lys Phe Leu Val Leu Arg Asp Arg Glu Leu Asn Ala Ile Ser
1               5                   10                  15
Gly Gly Val Phe His Ala Tyr Ser Ala Arg Gly Val Arg Asn Asn Tyr
            20                  25                  30
Lys Ser Ala Val Gly Pro Ala Asp Trp Val Ile Ser Ala Val Arg Gly
        35                  40                  45
Phe Ile His Gly
    50
```

<210> SEQ ID NO 249
<211> LENGTH: 159
<212> TYPE: DNA
<213> ORGANISM: Lactobacillus plantarum

<400> SEQUENCE: 249

```
atgaaaaaat ttctagtttt gcgtgaccgt gaattaaatg ctatttcagg tggcgttttc    60
catgcctata gcgcgcgtgg cgttcggaat aattataaaa gtgctgttgg gcctgccgat   120
tgggtcatta gcgctgtccg aggattcatc cacggatag                          159
```

<210> SEQ ID NO 250
<211> LENGTH: 55
<212> TYPE: PRT
<213> ORGANISM: Lactobacillus plantarum

<400> SEQUENCE: 250

```
Met Thr Val Asn Lys Met Ile Lys Asp Leu Asp Val Val Asp Ala Phe
1               5                   10                  15
Ala Pro Ile Ser Asn Asn Lys Leu Asn Gly Val Val Gly Gly Gly Ala
            20                  25                  30
Trp Lys Asn Phe Trp Ser Ser Leu Arg Lys Gly Phe Tyr Asp Gly Glu
        35                  40                  45
Ala Gly Arg Ala Ile Arg Arg
    50                  55
```

<210> SEQ ID NO 251
<211> LENGTH: 168
<212> TYPE: DNA
<213> ORGANISM: Lactobacillus plantarum

<400> SEQUENCE: 251

```
atgactgtga acaaaatgat taaggatttg gatgtagtag atgcatttgc acctatttct    60
aataataagt tgaacggggt tgttggggga ggcgcttgga aaaatttctg gtctagttta   120
agaaaaggat tttatgatgg cgaagctggc agagcaatcc gtcgttaa                168
```

<210> SEQ ID NO 252
<211> LENGTH: 57
<212> TYPE: PRT
<213> ORGANISM: Lactobacillus plantarum

<400> SEQUENCE: 252

```
Met Lys Ile Lys Leu Thr Val Leu Asn Glu Phe Glu Glu Leu Thr Ala
```

```
              1               5                  10                 15
Asp Ala Glu Lys Asn Ile Ser Gly Gly Arg Arg Ser Arg Lys Asn Gly
                      20                  25                  30

Ile Gly Tyr Ala Ile Gly Tyr Ala Phe Gly Ala Val Glu Arg Ala Val
            35                  40                  45

Leu Gly Gly Ser Arg Asp Tyr Asn Lys
        50                  55
```

<210> SEQ ID NO 253
<211> LENGTH: 174
<212> TYPE: DNA
<213> ORGANISM: Lactobacillus plantarum

<400> SEQUENCE: 253

```
atgaaaatta aattaactgt tttaaatgaa tttgaagaat taactgctga cgctgaaaag    60
aatatttctg gtggccgtcg gagtcgtaaa aatggaattg gatacgctat tggttatgcg   120
tttggcgcgg ttgaacgggc cgtgcttggt ggttcaaggg attataataa gtga         174
```

<210> SEQ ID NO 254
<211> LENGTH: 47
<212> TYPE: PRT
<213> ORGANISM: Lactobacillus plantarum

<400> SEQUENCE: 254

```
Met Asp Lys Phe Glu Lys Ile Ser Thr Ser Asn Leu Glu Lys Ile Ser
1               5                  10                  15

Gly Gly Asp Leu Thr Thr Lys Leu Trp Ser Ser Trp Gly Tyr Tyr Leu
            20                  25                  30

Gly Lys Lys Ala Arg Trp Asn Leu Lys His Pro Tyr Val Gln Phe
        35                  40                  45
```

<210> SEQ ID NO 255
<211> LENGTH: 141
<212> TYPE: DNA
<213> ORGANISM: Lactobacillus plantarum

<400> SEQUENCE: 255

```
atggataaat ttgaaaaaat tagtacatct aacctagaaa agatctctgg cggtgattta    60
acaaccaagt tatggagctc ttggggatat tatcttggca agaaagcacg ttggaattta   120
aagcacccat atgttcaatt t                                             141
```

<210> SEQ ID NO 256
<211> LENGTH: 55
<212> TYPE: PRT
<213> ORGANISM: Lactobacillus plantarum

<400> SEQUENCE: 256

```
Met Asn Asn Leu Asn Lys Phe Ser Thr Leu Gly Lys Ser Ser Leu Ser
1               5                  10                  15

Gln Ile Glu Gly Gly Ser Val Pro Thr Ser Val Tyr Thr Leu Gly Ile
            20                  25                  30

Lys Ile Leu Trp Ser Ala Tyr Lys His Arg Lys Thr Ile Glu Lys Ser
        35                  40                  45

Phe Asn Lys Gly Phe Tyr His
    50                  55
```

<210> SEQ ID NO 257
<211> LENGTH: 168

<212> TYPE: DNA
<213> ORGANISM: Lactobacillus plantarum

<400> SEQUENCE: 257
atgaataact tgaataaatt ttctactcta ggcaagagta gcttgtctca aattgagggc    60
ggatcagtcc caacttcagt atatacgctt ggaattaaaa ttctatggtc tgcgtataag   120
catcgcaaaa cgattgaaaa aagtttaat aaaggctttt atcattaa                 168

<210> SEQ ID NO 258
<211> LENGTH: 55
<212> TYPE: PRT
<213> ORGANISM: Lactobacillus plantarum

<400> SEQUENCE: 258

Met Asn Asn Ala Leu Ser Phe Glu Gln Gln Phe Thr Asp Phe Ser Thr
1               5                   10                  15

Leu Ser Asp Ser Glu Leu Glu Ser Val Glu Gly Gly Arg Asn Lys Leu
            20                  25                  30

Ala Tyr Asn Met Gly His Tyr Ala Gly Lys Ala Thr Ile Phe Gly Leu
        35                  40                  45

Ala Ala Trp Ala Leu Leu Ala
    50                  55

<210> SEQ ID NO 259
<211> LENGTH: 168
<212> TYPE: DNA
<213> ORGANISM: Lactobacillus plantarum

<400> SEQUENCE: 259
atgaataacg cattaagttt tgaacaacaa tttacagact tcagcacctt atcggactct    60
gaattagaat ccgttgaggg tggccgaaat aagcttgcat ataatatggg cattacgct   120
ggtaaggcaa ccatttttgg acttgcagca tgggcactcc ttgcatga                168

<210> SEQ ID NO 260
<211> LENGTH: 47
<212> TYPE: PRT
<213> ORGANISM: Lactobacillus plantarum

<400> SEQUENCE: 260

Met Asp Lys Ile Ile Lys Phe Gln Gly Ile Ser Asp Asp Gln Leu Asn
1               5                   10                  15

Ala Val Ile Gly Gly Lys Lys Lys Gln Ser Trp Tyr Ala Ala Ala
            20                  25                  30

Gly Asp Ala Ile Val Ser Phe Gly Glu Gly Phe Leu Asn Ala Trp
        35                  40                  45

<210> SEQ ID NO 261
<211> LENGTH: 144
<212> TYPE: DNA
<213> ORGANISM: Lactobacillus plantarum

<400> SEQUENCE: 261
atggataaga ttattaagtt tcaagggatt tctgatgatc aattaaatgc tgttatcggt    60
gggaaaaaga aaaacaatc ttggtacgca gcagctggtg atgcaatcgt tagttttggt   120
gaaggatttt taaatgcttg gtaa                                          144

<210> SEQ ID NO 262
<211> LENGTH: 59

```
<212> TYPE: PRT
<213> ORGANISM: Lactobacillus plantarum

<400> SEQUENCE: 262

Met Lys Ile Ser Lys Ile Glu Ala Gln Ala Arg Lys Asp Phe Phe Lys
1               5                   10                  15

Lys Ile Asp Thr Asn Ser Asn Leu Leu Asn Val Asn Gly Ala Lys Cys
            20                  25                  30

Lys Trp Trp Asn Ile Ser Cys Asp Leu Gly Asn Gly His Val Cys
        35                  40                  45

Thr Leu Ser His Glu Cys Gln Val Ser Cys Asn
    50                  55

<210> SEQ ID NO 263
<211> LENGTH: 180
<212> TYPE: DNA
<213> ORGANISM: Lactobacillus plantarum

<400> SEQUENCE: 263
atgaaaattt ctaagattga agctcaggct cgtaaagatt tttttaaaaa aatcgatact      60
aactcgaact tattaaatgt aaatggtgcc aaatgcaagt ggtggaatat ttcgtgtgat     120
ttaggaaata atggccatgt ttgtaccttg tcacatgaat gccaagtatc ttgtaactaa     180

<210> SEQ ID NO 264
<211> LENGTH: 67
<212> TYPE: PRT
<213> ORGANISM: Lactobacillus plantarum

<400> SEQUENCE: 264

Met Thr Lys Thr Ser Arg Arg Lys Asn Ala Ile Ala Asn Tyr Leu Glu
1               5                   10                  15

Pro Val Asp Glu Lys Ser Ile Asn Glu Ser Phe Gly Ala Gly Asp Pro
            20                  25                  30

Glu Ala Arg Ser Gly Ile Pro Cys Thr Ile Gly Ala Ala Val Ala Ala
        35                  40                  45

Ser Ile Ala Val Cys Pro Thr Thr Lys Cys Ser Lys Arg Cys Gly Lys
    50                  55                  60

Arg Lys Lys
65

<210> SEQ ID NO 265
<211> LENGTH: 204
<212> TYPE: DNA
<213> ORGANISM: Lactobacillus plantarum

<400> SEQUENCE: 265
atgactaaaa ctagtcgtcg taagaatgct attgctaatt atttagaacc agtcgacgaa      60
aaaagtatta tgaatctttt tggggctggg gatccggaag caagatccgg aattccatgt     120
acaatcggcg cagctgtcgc agcatcaatt gcagtttgtc caactactaa gtgtagtaaa     180
cgttgtggca agcgtaagaa ataa                                             204

<210> SEQ ID NO 266
<211> LENGTH: 48
<212> TYPE: PRT
<213> ORGANISM: Lactobacillus plantarum

<400> SEQUENCE: 266

Met Lys Ile Gln Ile Lys Gly Met Lys Gln Leu Ser Asn Lys Glu Met
```

```
                1               5                   10                  15
            Gln Lys Ile Val Gly Gly Lys Ser Ser Ala Tyr Ser Leu Gln Met Gly
                                20                  25                  30
            Ala Thr Ala Ile Lys Gln Val Lys Lys Leu Phe Lys Lys Trp Gly Trp
                    35                  40                  45
```

<210> SEQ ID NO 267
<211> LENGTH: 147
<212> TYPE: DNA
<213> ORGANISM: Lactobacillus plantarum

<400> SEQUENCE: 267

```
atgaaaattc aaattaaagg tatgaagcaa cttagtaata aggaaatgca aaaaatagta      60
ggtggaaaga gtagtgcgta ttctttgcag atggggcaa ctgcaattaa acaggtaaag     120
aaactgttta aaaaatgggg atggtaa                                         147
```

<210> SEQ ID NO 268
<211> LENGTH: 207
<212> TYPE: PRT
<213> ORGANISM: Propionibacterium jensenii

<400> SEQUENCE: 268

```
Met Asn Lys Thr His Lys Met Ala Thr Leu Val Ile Ala Ala Ile Leu
 1               5                  10                  15

Ala Ala Gly Met Thr Ala Pro Thr Ala Tyr Ala Asp Ser Pro Gly Asn
                20                  25                  30

Thr Arg Ile Thr Ala Ser Glu Gln Ser Val Leu Thr Gln Ile Leu Gly
            35                  40                  45

His Lys Pro Thr Gln Thr Glu Tyr Asn Arg Tyr Val Glu Thr Tyr Gly
        50                  55                  60

Ser Val Pro Thr Glu Ala Asp Ile Asn Ala Tyr Ile Glu Ala Ser Glu
 65                  70                  75                  80

Ser Glu Gly Ser Ser Ser Gln Thr Ala Ala His Asp Asp Ser Thr Ser
                85                  90                  95

Pro Gly Thr Ser Thr Glu Ile Tyr Thr Gln Ala Ala Pro Ala Arg Phe
            100                 105                 110

Ser Met Phe Phe Leu Ser Gly Thr Trp Ile Thr Arg Ser Gly Val Val
        115                 120                 125

Ser Leu Ser Leu Lys Pro Arg Lys Gly Gly Ile Gly Asn Glu Gly Asp
    130                 135                 140

Glu Arg Thr Trp Lys Thr Val Tyr Asp Lys Phe His Asn Ala Gly Gln
145                 150                 155                 160

Trp Thr Arg Tyr Lys Asn Asn Gly Val Asp Ala Ser Met Lys Lys Gln
                165                 170                 175

Tyr Met Cys His Phe Lys Tyr Gly Met Val Lys Thr Pro Trp Asn Leu
            180                 185                 190

Glu Pro His Lys Lys Ala Ala Asp Val Ser Pro Val Lys Cys Asn
        195                 200                 205
```

<210> SEQ ID NO 269
<211> LENGTH: 624
<212> TYPE: DNA
<213> ORGANISM: Propionibacterium jensenii

<400> SEQUENCE: 269

```
atgaacaaaa cacacaaaat ggcgacgctg gtaattgccg cgatcttggc cgccggaatg      60
```

```
accgcaccaa ctgcctatgc agattctcct ggaaacacca gaattacagc cagcgagcaa    120
agcgtcctta cccagatact cggccacaaa cctacacaaa ctgaatataa ccgatacgtt    180
gagacttacg gaagcgtacc gaccgaagca gacatcaacg catatataga agcgtctgaa    240
tctgagggat catcaagtca aacggctgct cacgatgact cgacatcacc cggcacgagt    300
accgaaatct acacgcaggc agcccctgcc aggttctcaa tgttttcct gtccggaact    360 tggatcacta ggagtggtgt agtatcgctc tccttgaagc caaggaaggg tggtattggc    420
aacgaggggg acgagcgtac ctggaagact gtatacgaca aattccataa cgctgggcaa    480
tggacacgat acaagaacaa cggcgtagac gccagcatga aaaagcagta catgtgccac    540
ttcaagtacg ggatggtgaa gacgccatgg aatctggagc cccacaagaa ggctgcagac    600
gtcagtccag tcaagtgcaa ctag                                          624
```

<210> SEQ ID NO 270
<211> LENGTH: 96
<212> TYPE: PRT
<213> ORGANISM: Propionibacterium thoenii

<400> SEQUENCE: 270

Met Lys Lys Thr Leu Leu Arg Ser Gly Thr Ile Ala Leu Ala Thr Ala
1               5                   10                  15

Ala Ala Phe Gly Ala Ser Leu Ala Ala Ala Pro Ser Ala Met Ala Val
            20                  25                  30

Pro Gly Gly Cys Thr Tyr Thr Arg Ser Asn Arg Asp Val Ile Gly Thr
        35                  40                  45

Cys Lys Thr Gly Ser Gly Gln Phe Arg Ile Arg Leu Asp Cys Asn Asn
    50                  55                  60

Ala Pro Asp Lys Thr Ser Val Trp Ala Lys Pro Lys Val Met Val Ser
65                  70                  75                  80

Val His Cys Leu Val Gly Gln Pro Arg Ser Ile Ser Phe Glu Thr Lys
                85                  90                  95

<210> SEQ ID NO 271
<211> LENGTH: 291
<212> TYPE: DNA
<213> ORGANISM: Propionibacterium thoenii

<400> SEQUENCE: 271

```
atgaagaaga ccctcctgcg aagtggaacg atcgcactgg cgaccgcggc tgcatttggc     60
gcatcattgg cagccgcccc atctgccatg gccgttcctg gtggttgcac gtacacaaga   120
agcaatcgcg acgtcatcgg tacctgcaag actggaagcg gccagttccg aatccgactt   180
gactgcaaca acgctccaga caaaacttca gtctgggcca agcccaaggt aatggtgtcg   240 ttcactgtc ttgttggtca accgaggtcc atctcgttcg agaccaagtg a             291
```

<210> SEQ ID NO 272
<211> LENGTH: 255
<212> TYPE: PRT
<213> ORGANISM: Propionibacterium freudenreichii subsp freudenreii

<400> SEQUENCE: 272

Met Asn Thr Lys Ala Val Asn Leu Lys Ser Glu Asn Thr Thr Lys Leu
1               5                   10                  15

Val Ser Tyr Leu Thr Glu Asn Gln Leu Asp Glu Phe Ile Arg Arg Ile
            20                  25                  30

Arg Ile Asp Gly Ala Leu Val Glu Glu Val Ser Gln Asn Ala Lys Gln

```
                35                  40                  45
Ala Leu Asp Asn Thr Gly Leu Asn Gly Trp Ile Asn Thr Asp Cys Asp
     50                  55                  60

Glu Gly Leu Leu Ser Asp Phe Ile Ser Lys Ile Ala Ser Ala Arg Trp
 65                  70                  75                  80

Ile Pro Leu Ala Glu Ser Ile Arg Pro Ala Val Thr Asp Arg Asp Lys
                 85                  90                  95

Tyr Arg Val Ser Cys Trp Phe Tyr Gln Gly Met Asn Ile Ala Ile Tyr
                100                 105                 110

Ala Asn Ile Gly Gly Val Ala Asn Ile Ile Gly Tyr Thr Glu Ala Ala
            115                 120                 125

Val Ala Thr Leu Leu Gly Ala Val Ala Val Ala Pro Val Val Pro
    130                 135                 140

Gly Thr Pro Thr Pro Pro Lys Asp Lys Ser Ser Gln Tyr Lys Glu Val
145                 150                 155                 160

Pro Leu Ala Val Arg Leu Ser Glu Thr Tyr His Glu Glu Gly Val Arg
                165                 170                 175

Gly Leu Phe Asp Glu Leu Asn Tyr Ser Glu Ser Arg Met Ile Ser Thr
            180                 185                 190

Leu Arg Arg Ala Ser Thr Asp Gly Val Leu Ile Asn Ser Trp Asn Asp
        195                 200                 205

Gly Gln Asp Thr Ile Leu Leu Lys Lys Tyr Asn Phe Gln Asp Leu Gln
    210                 215                 220

Leu Thr Val Arg Ser Arg Ile Val Gly Asn Gln Thr Ile Ile Glu Glu
225                 230                 235                 240

Cys Lys Ile Thr Asp Gly Arg Lys Thr Leu Ser Asp Glu Thr Val
                245                 250                 255

<210> SEQ ID NO 273
<211> LENGTH: 768
<212> TYPE: DNA
<213> ORGANISM: Propionibacterium freudenreichii subsp freudenreii

<400> SEQUENCE: 273
atgaatacca aagctgtaaa tctgaagtca gaaaacacga ctaagttggt gagctacctt    60
acggaaaatc aattggatga gtttattaga aggattcgca ttgatggcgc tcttgtggaa   120
gaggtcagtc aaaatgctaa gcaggcctta gataatactg gctcaatgg ctggataaat    180 actgattgcg atgaaggcct tctctctgat ttcatttcaa agatagcaag tgctagatgg   240
attccattag ctgagtcaat tcgacctgcg gtgactgaca gggataagta tcgagtaagt   300
tgctggttct accaggggat gaatatagca atttacgcaa atatcggtgg cgtggccaat   360
attatcggct atacggaggc cgcagtcgca cactccttg tgcagttgt ggcggtagct    420 cctgtggtcc ctggaactcc aaccctcca aggacaaga gttcgcaata taaggaggtt    480
ccccttgccg ttcgtctttc cgaaacatac cacgaagagg gagtacgagg tctattcgac   540
gagctgaact actccgagag ccgtatgatc tctactctaa ggcgagcatc aaccgatgga   600
gtcctaatta ttcttggaa cgatgggcag gatacaattc tgcttaagaa gtacaatttc    660
caagacttgc aactgactgt caggagccgc attgttggga atcaaacaat aattgaagaa   720
tgcaaaatca ctgatggtag aaaaactctt tcagacgaga ctgtgtag             768

<210> SEQ ID NO 274
<211> LENGTH: 618
<212> TYPE: PRT
```

<213> ORGANISM: Pseudomonas aeruginosa

<400> SEQUENCE: 274

```
Met Ala Arg Pro Ile Ala Asp Leu Ile His Phe Asn Ser Thr Thr Val
1               5                   10                  15

Thr Ala Ser Gly Asp Val Tyr Tyr Gly Pro Gly Gly Thr Gly Ile
            20                  25                  30

Gly Pro Ile Ala Arg Pro Ile Glu His Gly Leu Asp Ser Ser Thr Glu
        35                  40                  45

Asn Gly Trp Gln Glu Phe Glu Ser Tyr Ala Asp Val Gly Val Asp Pro
    50                  55                  60

Arg Arg Tyr Val Pro Leu Gln Val Lys Glu Lys Arg Arg Glu Ile Glu
65                  70                  75                  80

Leu Gln Phe Arg Asp Ala Glu Lys Lys Leu Glu Ala Ser Val Gln Ala
                85                  90                  95

Glu Leu Asp Lys Ala Asp Ala Ala Leu Gly Pro Ala Lys Asn Leu Ala
            100                 105                 110

Pro Leu Asp Val Ile Asn Arg Ser Leu Thr Ile Val Gly Asn Ala Leu
        115                 120                 125

Gln Gln Lys Asn Gln Lys Leu Leu Leu Asn Gln Lys Lys Ile Thr Ser
    130                 135                 140

Leu Gly Ala Lys Asn Phe Leu Thr Arg Thr Ala Glu Glu Ile Gly Glu
145                 150                 155                 160

Gln Ala Val Arg Glu Gly Asn Ile Asn Gly Pro Glu Ala Tyr Met Arg
                165                 170                 175

Phe Leu Asp Arg Glu Met Glu Gly Leu Thr Ala Ala Tyr Asn Val Lys
            180                 185                 190

Leu Phe Thr Glu Ala Ile Ser Ser Leu Gln Ile Arg Met Asn Thr Leu
        195                 200                 205

Thr Ala Ala Lys Ala Ser Ile Glu Ala Ala Ala Asn Lys Ala Arg
    210                 215                 220

Glu Gln Ala Ala Ala Glu Ala Lys Arg Lys Ala Glu Glu Gln Ala Arg
225                 230                 235                 240

Gln Gln Ala Ala Ile Arg Ala Ala Asn Thr Tyr Ala Met Pro Ala Asn
                245                 250                 255

Gly Ser Val Val Ala Thr Ala Ala Gly Arg Gly Leu Ile Gln Val Ala
            260                 265                 270

Gln Gly Ala Ala Ser Leu Ala Gln Ala Ile Ser Asp Ala Ile Ala Val
        275                 280                 285

Leu Gly Arg Val Leu Ala Ser Ala Pro Ser Val Met Ala Val Gly Phe
    290                 295                 300

Ala Ser Leu Thr Tyr Ser Ser Arg Thr Ala Glu Gln Trp Gln Asp Gln
305                 310                 315                 320

Thr Pro Asp Ser Val Arg Tyr Ala Leu Gly Met Asp Ala Ala Lys Leu
                325                 330                 335

Gly Leu Pro Pro Ser Val Asn Leu Asn Ala Val Ala Lys Ala Ser Gly
            340                 345                 350

Thr Val Asp Leu Pro Met Arg Leu Thr Asn Glu Ala Arg Gly Asn Thr
        355                 360                 365

Thr Thr Leu Ser Val Val Ser Thr Asp Gly Val Ser Val Pro Lys Ala
    370                 375                 380

Val Pro Val Arg Met Ala Ala Tyr Asn Ala Thr Thr Gly Leu Tyr Glu
385                 390                 395                 400
```

```
Val Thr Val Pro Ser Thr Thr Ala Glu Ala Pro Pro Leu Ile Leu Thr
            405                 410                 415

Trp Thr Pro Ala Ser Pro Pro Gly Asn Gln Asn Pro Ser Ser Thr Thr
            420                 425                 430

Pro Val Val Pro Lys Pro Val Pro Val Tyr Glu Gly Ala Thr Leu Thr
            435                 440                 445

Pro Val Lys Ala Thr Pro Glu Thr Tyr Pro Gly Val Ile Thr Leu Pro
            450                 455                 460

Glu Asp Leu Ile Ile Gly Phe Pro Ala Asp Ser Gly Ile Lys Pro Ile
465                 470                 475                 480

Tyr Val Met Phe Arg Asp Pro Arg Asp Val Pro Gly Ala Ala Thr Gly
                485                 490                 495

Lys Gly Gln Pro Val Ser Gly Asn Trp Leu Gly Ala Ala Ser Gln Gly
                500                 505                 510

Glu Gly Ala Pro Ile Pro Ser Gln Ile Ala Asp Lys Leu Arg Gly Lys
                515                 520                 525

Thr Phe Lys Asn Trp Arg Asp Phe Arg Glu Gln Phe Trp Ile Ala Val
            530                 535                 540

Ala Asn Asp Pro Glu Leu Ser Lys Gln Phe Asn Pro Gly Ser Leu Ala
545                 550                 555                 560

Val Met Arg Asp Gly Ala Pro Tyr Val Arg Glu Ser Glu Gln Ala
                565                 570                 575

Gly Gly Arg Ile Lys Ile Glu Ile His His Lys Val Arg Val Ala Asp
                580                 585                 590

Gly Gly Gly Val Tyr Asn Met Gly Asn Leu Val Ala Val Thr Pro Lys
                595                 600                 605

Arg His Ile Glu Ile His Lys Gly Gly Lys
        610                 615
```

<210> SEQ ID NO 275
<211> LENGTH: 1857
<212> TYPE: DNA
<213> ORGANISM: Pseudomonas aeruginosa

<400> SEQUENCE: 275

```
atggcacgac ccattgctga ccttatccac ttcaactcta caactgtcac ggcaagcgga     60
gacgtttatt acggccctgg gggaggtacc ggcattggcc ccattgccag acctatagag    120
cacggcttgg attcgtccac tgaaaatggc tggcaagagt ttgaaagtta tgctgatgtg    180
ggcgttgacc ccagacgcta tgttcctctt caggttaaag aaaaacgcag ggagatcgag    240
cttcagttcc gagatgccga gaaaaaactt gaggcgtcgg tacaagccga gctggataag    300
gctgatgccg ctcttggtcc ggcaaagaat cttgcaccat ggacgtcat caaccgcagt    360 ctgaccatcg ttggaaacgc cctccagcaa aagaatcaaa actactgct gaatcagaag    420 aagattacca gcctgggtgc aaagaatttc cttacccgta cggcggaaga gatcggtgaa    480
caagcggtgc gagaaggcaa tattaacggg cctgaagcct atatgcgctt cctcgacagg    540
gaaatggaag gtctcacggc agcttataac gtaaaactct tcaccgaagc gatcagtagt    600
ctccagatcc gcatgaatac gttgaccgcc gccaaagcaa gtattgaggc ggccgcagca    660
aacaaggcgc gtgaacaagc agcggctgag gccaaacgca aagccgaaga gcaggcccgc    720
cagcaagcgg cgataagagc tgccaatacc tatgccatgc cggccaatgg cagcgttgtc    780
gccaccgccg caggccgggg tctgatccag gtcgcacaag gcgccgcatc ccttgctcaa    840
gcgatctccg atgcgattgc cgtcctgggc cgggtcctgg cttcagcacc ctcggtgatg    900
```

-continued

```
gccgtgggct tgccagtct gacctactcc tcccggactg ccgagcaatg gcaggaccaa      960
acgcccgata gcgttcgtta cgccctgggc atggatgccg ctaaattggg gcttcccca     1020 agcgtaaacc tgaacgcggt tgcaaaagcc agcggtaccg tcgatctgcc gatgcgcctg    1080
accaacgagg cacgaggcaa cacgacgacc ctttcggtgg tcagcaccga tggtgtgagc    1140
gttccgaaag ccgttccggt ccggatggcg gcctacaatg ccacgacagg cctgtacgag    1200
gttacggttc cctctacgac cgcagaagcg ccgccactga tcctgacctg gacgccggcg    1260
agtcctccag gaaaccagaa cccttcgagt accactccgg tcgtaccgaa gccggtgccg    1320
gtatatgagg gagcgaccct acaccggtg aaggctaccc cggaaaccta tcctggggtg     1380
attacactac cggaagacct gatcatcggc ttcccggccg actcggggat caagccgatc    1440
tatgtgatgt tcagggatcc gcgggatgta cctggtgctg cgactggcaa gggacagccc    1500
gtcagcggta attggctcgg cgccgcctct caaggtgagg gggctccaat tccaagccag    1560
attgcggata aactacgtgg taagacattc aaaaactggc gggactttcg ggaacaattc    1620
tggatagctg tggctaatga tcctgagtta agtaaacagt ttaatcctgg tagtttagct    1680
gtaatgagag atggagggc tccttatgtc agagagtcag aacaggctgg cgggagaata    1740
aagatcgaaa tccaccacaa ggttcgagta gcagatgag gcggcgttta caatatgggg     1800
aaccttgttg cagtaacgcc aaaacgtcat atagaaatcc acaagggagg gaagtga      1857
```

<210> SEQ ID NO 276
<211> LENGTH: 689
<212> TYPE: PRT
<213> ORGANISM: Pseudomonas aeruginosa

<400> SEQUENCE: 276

```
Met Ala Val Asn Asp Tyr Glu Pro Gly Ser Met Val Ile Thr His Val
  1               5                  10                  15

Gln Gly Gly Arg Asp Ile Ile Gln Tyr Ile Pro Ala Arg Ser Ser
             20                  25                  30

Tyr Gly Thr Pro Pro Phe Val Pro Gly Pro Ser Pro Tyr Val Gly
         35                  40                  45

Thr Gly Met Gln Glu Tyr Arg Lys Leu Arg Ser Thr Leu Asp Lys Ser
     50                  55                  60

His Ser Glu Leu Lys Lys Asn Leu Lys Asn Glu Thr Leu Lys Glu Val
 65                  70                  75                  80

Asp Glu Leu Lys Ser Glu Ala Gly Leu Pro Gly Lys Ala Val Ser Ala
                 85                  90                  95

Asn Asp Ile Arg Asp Glu Lys Ser Ile Val Asp Ala Leu Met Asp Ala
            100                 105                 110

Lys Ala Lys Ser Leu Lys Ala Ile Glu Asp Arg Pro Ala Asn Leu Tyr
        115                 120                 125

Thr Ala Ser Asp Phe Pro Gln Lys Ser Glu Ser Met Tyr Gln Ser Gln
    130                 135                 140

Leu Leu Ala Ser Arg Lys Phe Tyr Gly Glu Phe Leu Asp Arg His Met
145                 150                 155                 160

Ser Glu Leu Ala Lys Ala Tyr Ser Ala Asp Ile Tyr Lys Ala Gln Ile
                165                 170                 175

Ala Ile Leu Lys Gln Thr Ser Gln Glu Leu Glu Asn Lys Ala Arg Ser
            180                 185                 190

Leu Glu Ala Glu Ala Gln Arg Ala Ala Ala Glu Val Glu Ala Asp Tyr
        195                 200                 205
```

```
Lys Ala Arg Lys Ala Asn Val Glu Lys Lys Val Gln Ser Glu Leu Asp
        210                 215                 220

Gln Ala Gly Asn Ala Leu Pro Gln Leu Thr Asn Pro Thr Pro Glu Gln
225                 230                 235                 240

Trp Leu Glu Arg Ala Thr Gln Leu Val Thr Gln Ala Ile Ala Asn Lys
            245                 250                 255

Lys Lys Leu Gln Thr Ala Asn Asn Ala Leu Ile Ala Lys Ala Pro Asn
                260                 265                 270

Ala Leu Glu Lys Gln Lys Ala Thr Tyr Asn Ala Asp Leu Leu Val Asp
        275                 280                 285

Glu Ile Ala Ser Leu Gln Ala Arg Leu Asp Lys Leu Asn Ala Glu Thr
        290                 295                 300

Ala Arg Arg Lys Glu Ile Ala Arg Gln Ala Ala Ile Arg Ala Ala Asn
305                 310                 315                 320

Thr Tyr Ala Met Pro Ala Asn Gly Ser Val Ala Thr Ala Ala Gly
            325                 330                 335

Arg Gly Leu Ile Gln Val Ala Gln Gly Ala Ala Ser Leu Ala Gln Ala
                340                 345                 350

Ile Ser Asp Ala Ile Ala Val Leu Gly Arg Val Leu Ala Ser Ala Pro
        355                 360                 365

Ser Val Met Ala Val Gly Phe Ala Ser Leu Thr Tyr Ser Ser Arg Thr
370                 375                 380

Ala Glu Gln Trp Gln Asp Gln Thr Pro Asp Ser Val Arg Tyr Ala Leu
385                 390                 395                 400

Gly Met Asp Ala Ala Lys Leu Gly Leu Pro Pro Ser Val Asn Leu Asn
            405                 410                 415

Ala Val Ala Lys Ala Ser Gly Thr Val Asp Leu Pro Met Arg Leu Thr
                420                 425                 430

Asn Glu Ala Arg Gly Asn Thr Thr Leu Ser Val Val Ser Thr Asp
        435                 440                 445

Gly Val Ser Val Pro Lys Ala Val Pro Val Arg Met Ala Ala Tyr Asn
        450                 455                 460

Ala Thr Thr Gly Leu Tyr Glu Val Thr Val Pro Ser Thr Thr Ala Glu
465                 470                 475                 480

Ala Pro Pro Leu Ile Leu Thr Trp Thr Pro Ala Ser Pro Gly Asn
            485                 490                 495

Gln Asn Pro Ser Ser Thr Thr Pro Val Val Pro Lys Pro Val Pro Val
                500                 505                 510

Tyr Glu Gly Ala Thr Leu Thr Pro Val Lys Ala Thr Pro Glu Thr Tyr
        515                 520                 525

Pro Gly Val Ile Thr Leu Pro Glu Asp Leu Ile Gly Phe Pro Ala
530                 535                 540

Asp Ser Gly Ile Lys Pro Ile Tyr Val Met Phe Arg Asp Pro Arg Asp
545                 550                 555                 560

Val Pro Gly Ala Ala Thr Gly Lys Gly Gln Pro Val Ser Gly Asn Trp
            565                 570                 575

Leu Gly Ala Ala Ser Gln Gly Glu Gly Ala Pro Ile Pro Ser Gln Ile
                580                 585                 590

Ala Asp Lys Leu Arg Gly Lys Thr Phe Lys Asn Trp Arg Asp Phe Arg
        595                 600                 605

Glu Gln Phe Trp Ile Ala Val Ala Asn Asp Pro Glu Leu Ser Lys Gln
610                 615                 620
```

```
Phe Asn Pro Gly Ser Leu Ala Val Met Arg Asp Gly Gly Ala Pro Tyr
625                 630                 635                 640

Val Arg Glu Ser Glu Gln Ala Gly Gly Arg Ile Lys Ile Glu Ile His
            645                 650                 655

His Lys Val Arg Ile Ala Asp Gly Gly Gly Val Tyr Asn Met Gly Asn
        660                 665                 670

Leu Val Ala Val Thr Pro Lys Arg His Ile Glu Ile His Lys Gly Gly
    675                 680                 685

Lys

<210> SEQ ID NO 277
<211> LENGTH: 2070
<212> TYPE: DNA
<213> ORGANISM: Pseudomonas aeruginosa

<400> SEQUENCE: 277
```

| | |
|---|---:|
| atggctgtca atgattacga acctggttcg atggttatta cacatgtgca gggtggtggg | 60 |
| cgtgacataa tccagtatat tcctgctcga tcaagctacg gtactccacc atttgtccca | 120 |
| ccaggaccaa gtccgtatgt cggtactgga atgcaggagt acaggaagct aagaagtacg | 180 |
| cttgataagt cccattcaga actcaagaaa acctgaaaa atgaaccct gaaggaggtt | 240 |
| gatgaactca gagtgaagc ggggttgcca ggtaaagcgg tcagtgccaa tgacatccgc | 300 |
| gatgaaaaga gtatcgttga tgcactcatg gatgccaaag caaaatcgct aaaggccatt | 360 |
| gaggatcgcc cggccaatct ttatacggct tcagactttc ctcagaagtc agagtcgatg | 420 |
| taccagagtc agttgctggc cagccgaaaa ttctatggag agttcctgga tcgccatatg | 480 |
| agtgagctgg ccaaagcgta cagcgccgat atctataagg cgcaaatcgc tatcttgaaa | 540 |
| caaacgtctc aagagctgga gaataaagcc cggtcattgg aagcagaagc ccagcgagcc | 600 |
| gctgctgagg tggaggcgga ctacaaggcc aggaaggcaa atgtcgagaa aaaagtgcag | 660 |
| tccgagcttg accaggctgg gaatgctttg cctcaactga ccaatccaac gccagagcag | 720 |
| tggcttgaac gcgctactca actggttacg caggcgatcg ccaataagaa gaaattgcag | 780 |
| actgcaaaca atgccttgat tgccaaggca cccaatgcac tggagaaaca aaaggcaacc | 840 |
| tacaacgccg atctcctagt ggatgaaatc gccagcctgc aagcacggct ggacaagctg | 900 |
| aacgccgaaa cggcaaggcg caaggaaatc gctcgtcaag cggcgatcag gctgccaat | 960 |
| acttatgcca tgccagccaa tggcagcgtt gtcgccaccg ccgcaggccg ggtctgatc | 1020 |
| caggtcgcac aaggcgccgc atcccttgct caagcgatct ccgatgcgat tgccgtcctg | 1080 |
| ggccgggtcc tggcttcagc accctcggtg atggccgtgg gctttgccag tctgacctac | 1140 |
| tcctcccgga ctgccgagca atggcaggac caaacgcccg atagcgttcg ttacgccctg | 1200 |
| ggcatggatg ccgctaaatt ggggcttccc ccaagcgtaa acctgaacgc ggttgcaaaa | 1260 |
| gccagcggta ccgtcgatct gccgatcgc ctgaccaacg aggcacgagg caacacgacg | 1320 |
| acccctttcgg tggtcagcac cgatggtgtg agcgttccga agccgttcc ggtccggatg | 1380 |
| gcggcctaca tgccacgac aggcctgtac gaggttacgg ttccctctac gaccgcagaa | 1440 |
| gcgccgccac tgatcctgac ctggacgccg gcgagtcctc caggaaacca gaaccccttcg | 1500 |
| agtaccactc cggtcgtacc gaagccggtg ccggtatatg agggagcgac ccttacaccg | 1560 |
| gtgaaggcta ccccggaaac ctatcctggg gtgattacac taccggaaga cctgatcatc | 1620 |
| ggcttccccgg ccgactcggg gatcaagccg atctatgtga tgttcaggga tccgcgggat | 1680 |
| gtacctggtg ctgcgactgg caagggacag cccgtcagcg gtaattggct cggcgccgcc | 1740 |

```
tctcaaggtg aggggctcc aattccaagc cagattgcgg ataaactacg tggtaagaca   1800
ttcaaaaact ggcgggactt tcgggaacaa ttctggatag ctgtggctaa tgatcctgag   1860
ttaagtaaac agtttaatcc tggtagttta gctgtaatga gagatggagg ggctccttat   1920
gtcagagagt cagaacaggc tggcgggaga ataaagatcg aaatccacca caaggttcga   1980
atagcagatg gaggcggcgt ttacaatatg gggaaccttg ttgcagtaac gccaaaacgt   2040
catatagaaa tccacaaggg agggaagtga                                     2070
```

<210> SEQ ID NO 278
<211> LENGTH: 47
<212> TYPE: PRT
<213> ORGANISM: Ruminococcus gnavus

<400> SEQUENCE: 278

Met Arg Asn Asp Val Leu Thr Leu Thr Asn Pro Met Glu Glu Lys Glu
1               5                   10                  15

Leu Glu Gln Ile Leu Gly Gly Gly Asn Gly Val Leu Lys Thr Ile Ser
            20                  25                  30

His Glu Cys Asn Met Asn Thr Trp Gln Phe Leu Phe Thr Cys Cys
        35                  40                  45

<210> SEQ ID NO 279
<211> LENGTH: 144
<212> TYPE: DNA
<213> ORGANISM: Ruminococcus gnavus

<400> SEQUENCE: 279

```
atgagaaatg acgtattaac attaacaaac ccaatggaag agaacgaact ggagcagatc   60
ttaggtggtg gcaatggtgt gttaaaaacg attagccacg aatgcaatat gaacacatgg   120
cagttcctgt ttacttgttg ctaa                                            144
```

<210> SEQ ID NO 280
<211> LENGTH: 55
<212> TYPE: PRT
<213> ORGANISM: Lactobacillus sakei

<400> SEQUENCE: 280

Met Lys Asn Ala Lys Ser Leu Thr Ile Gln Glu Met Lys Ser Ile Thr
1               5                   10                  15

Gly Gly Lys Tyr Tyr Gly Asn Gly Val Ser Cys Asn Ser His Gly Cys
            20                  25                  30

Ser Val Asn Trp Gly Gln Ala Trp Thr Cys Gly Val Asn His Leu Ala
        35                  40                  45

Asn Gly Gly His Gly Val Cys
    50                  55

<210> SEQ ID NO 281
<211> LENGTH: 168
<212> TYPE: DNA
<213> ORGANISM: Lactobacillus sakei

<400> SEQUENCE: 281

```
atgaaaaacg caaaaagcct aacaattcaa gaaatgaaat ctattacagg tggtaaatac   60
tatggtaatg gcgttagctg taactctcac ggctgttcag taaattgggg gcaagcatgg   120
acttgtggag taaaccatct agctaatggc ggtcatggag tttgttaa                 168
```

```
<210> SEQ ID NO 282
<211> LENGTH: 59
<212> TYPE: PRT
<213> ORGANISM: Lactobacillus sakei

<400> SEQUENCE: 282
```

Met Asn Asn Val Lys Glu Leu Ser Met Thr Glu Leu Gln Thr Ile Thr
1               5                   10                  15

Gly Gly Ala Arg Ser Tyr Gly Asn Gly Val Tyr Cys Asn Asn Lys Lys
            20                  25                  30

Cys Trp Val Asn Arg Gly Glu Ala Thr Gln Ser Ile Ile Gly Gly Met
        35                  40                  45

Ile Ser Gly Trp Ala Ser Gly Leu Ala Gly Met
    50                  55

```
<210> SEQ ID NO 283
<211> LENGTH: 180
<212> TYPE: DNA
<213> ORGANISM: Lactobacillus sakei

<400> SEQUENCE: 283
atgaataatg taaaagaatt aagtatgaca gaattacaaa caattaccgg cggtgctaga      60
tcatatggca acggtgttta ctgtaataat aaaaaatgtt gggtaaatcg gggtgaagca     120
acgcaaagta ttattggtgg tatgattagc ggctgggcta gtggtttagc tggaatgtaa     180

<210> SEQ ID NO 284
<211> LENGTH: 61
<212> TYPE: PRT
<213> ORGANISM: Lactobacillus sakei

<400> SEQUENCE: 284
```

Met Glu Lys Phe Ile Glu Leu Ser Leu Lys Glu Val Thr Ala Ile Thr
1               5                   10                  15

Gly Gly Lys Tyr Tyr Gly Asn Gly Val His Cys Gly Lys His Ser Cys
            20                  25                  30

Thr Val Asp Trp Gly Thr Ala Ile Gly Asn Ile Gly Asn Asn Ala Ala
        35                  40                  45

Ala Asn Trp Ala Thr Gly Gly Asn Ala Gly Trp Asn Lys
    50                  55                  60

```
<210> SEQ ID NO 285
<211> LENGTH: 186
<212> TYPE: DNA
<213> ORGANISM: Lactobacillus sakei

<400> SEQUENCE: 285
atggaaaagt ttattgaatt atctttaaaa gaagtaacag caattacagg tggaaaatat      60
tatggtaacg gtgtacactg tggaaaacat tcatgtaccg tagactgggg aacagctatt     120
ggaaatatcg aaataatgc agctgcaaac tgggccacag gcggaaacgc tggctggaat     180
aaataa                                                                186

<210> SEQ ID NO 286
<211> LENGTH: 56
<212> TYPE: PRT
<213> ORGANISM: Streptococcus salivarius

<400> SEQUENCE: 286
```

Met Lys Ser Thr Asn Asn Gln Ser Ile Ala Glu Ile Ala Ala Val Asn
1               5                   10                  15

Ser Leu Gln Glu Val Ser Met Glu Glu Leu Asp Gln Ile Ile Gly Ala
            20                  25                  30

Gly Asn Gly Val Val Leu Thr Leu Thr His Glu Cys Asn Leu Ala Thr
        35                  40                  45

Trp Thr Lys Lys Leu Lys Cys Cys
    50                  55

<210> SEQ ID NO 287
<211> LENGTH: 171
<212> TYPE: DNA
<213> ORGANISM: Streptococcus salivarius

<400> SEQUENCE: 287
atgaaatcaa caaataatca agtatcgca gaaattgcag cagtaaactc actacaagaa      60
gtaagtatgg aggaactaga ccaaattatt ggtgccggaa acggagtggt tcttactctt    120
actcatgaat gtaacctagc aacttggaca aaaaaactaa aatgttgcta a              171

<210> SEQ ID NO 288
<211> LENGTH: 51
<212> TYPE: PRT
<213> ORGANISM: Streptococcus pyogenes serotype M28

<400> SEQUENCE: 288

Met Ser Phe Met Lys Asn Ser Lys Asp Ile Leu Thr Asn Ala Ile Glu
1               5                   10                  15

Glu Val Ser Glu Lys Glu Leu Met Glu Val Ala Gly Gly Lys Lys Gly
            20                  25                  30

Ser Gly Trp Phe Ala Thr Ile Thr Asp Asp Cys Pro Asn Ser Val Phe
        35                  40                  45

Val Cys Cys
    50

<210> SEQ ID NO 289
<211> LENGTH: 156
<212> TYPE: DNA
<213> ORGANISM: Streptococcus pyogenes serotype M28

<400> SEQUENCE: 289
atgagtttta tgaaaaattc aaaggatatt ttgactaatg ctatcgaaga agtttctgaa      60
aaagaactta tggaagtagc tggtggtaaa aaaggttccg gttggtttgc aactattact    120
gatgactgtc cgaactcagt attcgtttgt tgttaa                              156

<210> SEQ ID NO 290
<211> LENGTH: 48
<212> TYPE: PRT
<213> ORGANISM: Streptococcus salivarius

<400> SEQUENCE: 290

Met Lys Asn Ser Lys Asp Val Leu Asn Asn Ala Ile Glu Glu Val Ser
1               5                   10                  15

Glu Lys Glu Leu Met Glu Val Ala Gly Gly Lys Lys Gly Pro Gly Trp
            20                  25                  30

Ile Ala Thr Ile Thr Asp Asp Cys Pro Asn Ser Ile Phe Val Cys Cys
        35                  40                  45

<210> SEQ ID NO 291
<211> LENGTH: 147
<212> TYPE: DNA

<213> ORGANISM: Streptococcus salivarius

<400> SEQUENCE: 291

```
atgaaaaact caaagatgt tttgaacaat gctatcgaag aggtttctga aaagaactt    60
atggaagtag ctggtggtaa aaaaggtcca ggttggattg caactattac tgatgactgt  120
ccaaactcaa tattcgtttg ttgttaa                                      147
```

<210> SEQ ID NO 292
<211> LENGTH: 48
<212> TYPE: PRT
<213> ORGANISM: Streptococcus salivarius

<400> SEQUENCE: 292

```
Met Lys Asn Ser Lys Asp Ile Leu Asn Asn Ala Ile Glu Glu Val Ser
1               5                   10                  15
Glu Lys Glu Leu Met Glu Val Ala Gly Gly Lys Arg Gly Ser Gly Trp
                20                  25                  30
Ile Ala Thr Ile Thr Asp Asp Cys Pro Asn Ser Val Phe Val Cys Cys
            35                  40                  45
```

<210> SEQ ID NO 293
<211> LENGTH: 147
<212> TYPE: DNA
<213> ORGANISM: Streptococcus salivarius

<400> SEQUENCE: 293

```
atgaaaaact caaagatat tttgaacaat gctatcgaag aagtttctga aaagaactt    60
atggaagtag ctggtggtaa aagaggttca ggttggattg caactattac tgatgactgt  120
ccaaactcag tattcgtttg ttgttaa                                      147
```

<210> SEQ ID NO 294
<211> LENGTH: 62
<212> TYPE: PRT
<213> ORGANISM: Staphylococcus aureus

<400> SEQUENCE: 294

```
Met Lys Ser Ser Phe Leu Glu Lys Asp Ile Glu Glu Gln Val Thr Trp
1               5                   10                  15
Phe Glu Glu Val Ser Glu Gln Glu Phe Asp Asp Asp Ile Phe Gly Ala
                20                  25                  30
Cys Ser Thr Asn Thr Phe Ser Leu Ser Asp Tyr Trp Gly Asn Lys Gly
            35                  40                  45
Asn Trp Cys Thr Ala Thr His Glu Cys Met Ser Trp Cys Lys
        50                  55                  60
```

<210> SEQ ID NO 295
<211> LENGTH: 189
<212> TYPE: DNA
<213> ORGANISM: Staphylococcus aureus

<400> SEQUENCE: 295

```
atgaaaagtt cttttttaga aaagatata gaagaacaag tgacatggtt cgaggaagtt    60
tcagaacaag aatttgacga tgatatttt ggagcttgta gtacaaacac tttttctttg   120
agtgactatt ggggtaataa aggaaattgg tgtactgcta ctcacgaatg tatgtcttgg   180
tgtaaataa                                                          189
```

<210> SEQ ID NO 296

```
<211> LENGTH: 67
<212> TYPE: PRT
<213> ORGANISM: Staphylococcus aureus

<400> SEQUENCE: 296
```

Met Lys Asn Glu Leu Gly Lys Phe Leu Glu Glu Asn Glu Leu Glu Leu
1               5                   10                  15

Gly Lys Phe Ser Glu Ser Asp Met Leu Glu Ile Thr Asp Asp Glu Val
                20                  25                  30

Tyr Ala Gly Thr Pro Leu Ala Leu Leu Gly Gly Ala Ala Thr Gly
            35                  40                  45

Val Ile Gly Tyr Ile Ser Asn Gln Thr Cys Pro Thr Thr Ala Cys Thr
    50                  55                  60

Arg Ala Cys
65

```
<210> SEQ ID NO 297
<211> LENGTH: 204
<212> TYPE: DNA
<213> ORGANISM: Staphylococcus aureus

<400> SEQUENCE: 297
```
atgaaaaatg aattaggtaa gttttagaa gaaaacgaat tagagttagg taaattttca      60
gaatcagaca tgctagaaat tactgatgat gaagtatatg cagctggaac acctttagcc    120
ttattgggtg gagctgccac cggggtgata ggttatattt ctaaccaaac atgtccaaca    180
actgcttgta cacgcgcttg ctag                                            204

```
<210> SEQ ID NO 298
<211> LENGTH: 46
<212> TYPE: PRT
<213> ORGANISM: Streptococcus pyogenes

<400> SEQUENCE: 298
```

Met Asn Asn Thr Ile Lys Asp Phe Asp Leu Asp Leu Lys Thr Asn Lys
1               5                   10                  15

Lys Asp Thr Ala Thr Pro Tyr Val Gly Ser Arg Tyr Leu Cys Thr Pro
                20                  25                  30

Gly Ser Cys Trp Lys Leu Val Cys Phe Thr Thr Thr Val Lys
            35                  40                  45

```
<210> SEQ ID NO 299
<211> LENGTH: 141
<212> TYPE: DNA
<213> ORGANISM: Streptococcus pyogenes

<400> SEQUENCE: 299
```
atgaataaca caattaaaga ctttgatctc gatttgaaaa caaataaaaa agacactgct      60
acaccttatg ttggtagccg ttacctatgt acccctggtt cttgttggaa attagtttgc    120
tttacaacaa ctgttaaata a                                               141

```
<210> SEQ ID NO 300
<211> LENGTH: 51
<212> TYPE: PRT
<213> ORGANISM: Streptococcus pyogenes

<400> SEQUENCE: 300
```

Met Glu Lys Asn Asn Glu Val Ile Asn Ser Ile Gln Glu Val Ser Leu
1               5                   10                  15

Glu Glu Leu Asp Gln Ile Ile Gly Ala Gly Lys Asn Gly Val Phe Lys
            20                  25                  30

Thr Ile Ser His Glu Cys His Leu Asn Thr Trp Ala Phe Leu Ala Thr
        35                  40                  45

Cys Cys Ser
    50

<210> SEQ ID NO 301
<211> LENGTH: 156
<212> TYPE: DNA
<213> ORGANISM: Streptococcus pyogenes

<400> SEQUENCE: 301
atggaaaaaa ataatgaagt aatcaactct attcaagaag ttagtcttga agaactcgat    60
caaattatcg gtgctggaaa aaatggtgtg tttaaaacaa tttctcatga gtgtcatttg   120
aatacatggg cattccttgc tacttgttgt tcataa                             156

<210> SEQ ID NO 302
<211> LENGTH: 51
<212> TYPE: PRT
<213> ORGANISM: Streptococcus pyogenes serotype M49

<400> SEQUENCE: 302

Met Thr Lys Glu His Glu Ile Ile Asn Ser Ile Gln Glu Val Ser Leu
1               5                  10                  15

Glu Glu Leu Asp Gln Ile Ile Gly Ala Gly Lys Asn Gly Val Phe Lys
            20                  25                  30

Thr Ile Ser His Glu Cys His Leu Asn Thr Trp Ala Phe Leu Ala Thr
        35                  40                  45

Cys Cys Ser
    50

<210> SEQ ID NO 303
<211> LENGTH: 156
<212> TYPE: DNA
<213> ORGANISM: Streptococcus pyogenes serotype M49

<400> SEQUENCE: 303
atggaaaaaa ataatgaagt aatcaactct attcaagaag ttagtcttga agaactcgat    60
caaattatcg gtgctggaaa aaatggtgtg tttaaaacaa tttctcatga gtgtcatttg   120
aatacatggg cattccttgc tacttgttgc tcataa                             156

<210> SEQ ID NO 304
<211> LENGTH: 56
<212> TYPE: PRT
<213> ORGANISM: Bacillus subtilis

<400> SEQUENCE: 304

Met Glu Lys Leu Phe Lys Glu Val Lys Leu Glu Glu Leu Glu Asn Gln
1               5                  10                  15

Lys Gly Ser Gly Leu Gly Lys Ala Gln Cys Ala Ala Leu Trp Leu Gln
            20                  25                  30

Cys Ala Ser Gly Gly Thr Ile Gly Cys Gly Gly Gly Ala Val Ala Cys
        35                  40                  45

Gln Asn Tyr Arg Gln Phe Cys Arg
    50                  55

<210> SEQ ID NO 305

```
<211> LENGTH: 171
<212> TYPE: DNA
<213> ORGANISM: Bacillus subtilis

<400> SEQUENCE: 305
atggaaaagc tatttaaaga agttaaacta gaggaactcg aaaaccaaaa aggtagtgga      60
ttaggaaaag ctcagtgtgc tgcgttgtgg ctacaatgtg ctagtggcgg tacaattggt     120
tgtggtggcg gagctgttgc ttgtcaaaac tatcgtcaat tctgcagata a              171

<210> SEQ ID NO 306
<211> LENGTH: 56
<212> TYPE: PRT
<213> ORGANISM: Bacillus subtilis

<400> SEQUENCE: 306

Met Ser Lys Phe Asp Asp Phe Asp Leu Asp Val Val Lys Val Ser Lys
1               5                   10                  15

Gln Asp Ser Lys Ile Thr Pro Gln Trp Lys Ser Glu Ser Leu Cys Thr
            20                  25                  30

Pro Gly Cys Val Thr Gly Ala Leu Gln Thr Cys Phe Leu Gln Thr Leu
        35                  40                  45

Thr Cys Asn Cys Lys Ile Ser Lys
    50                  55

<210> SEQ ID NO 307
<211> LENGTH: 171
<212> TYPE: DNA
<213> ORGANISM: Bacillus subtilis

<400> SEQUENCE: 307
atgtcaaagt tcgatgattt cgatttggat gttgtgaaag tctctaaaca agactcaaaa      60
atcactccgc aatggaaaag tgaatcactt tgtacaccag gatgtgtaac tggtgcattg     120
caaacttgct tccttcaaac actaacttgt aactgcaaaa tctctaaata a              171

<210> SEQ ID NO 308
<211> LENGTH: 50
<212> TYPE: PRT
<213> ORGANISM: Bacillus subtilis

<400> SEQUENCE: 308

Met Lys Leu Pro Val Gln Gln Val Tyr Ser Val Tyr Gly Gly Lys Asp
1               5                   10                  15

Leu Pro Lys Gly His Ser His Ser Thr Met Pro Phe Leu Ser Lys Leu
            20                  25                  30

Gln Phe Leu Thr Lys Ile Tyr Leu Leu Asp Ile His Thr Gln Pro Phe
        35                  40                  45

Phe Ile
    50

<210> SEQ ID NO 309
<211> LENGTH: 153
<212> TYPE: DNA
<213> ORGANISM: Bacillus subtilis

<400> SEQUENCE: 309
ttgaaattgc cggtgcaaca ggtctattcg gtctatgggg gtaaggatct cccaaaaggg      60
catagtcatt ctactatgcc cttttttaagt aaattacaat ttttaactaa aatctacctc    120
ttggatatac atacacaacc gttttttcatt tga                                 153
```

<210> SEQ ID NO 310
<211> LENGTH: 43
<212> TYPE: PRT
<213> ORGANISM: Bacillus subtilis

<400> SEQUENCE: 310

Met Lys Lys Ala Val Ile Val Glu Asn Lys Gly Cys Ala Thr Cys Ser
1               5                   10                  15

Ile Gly Ala Ala Cys Leu Val Asp Gly Pro Ile Pro Asp Phe Glu Ile
            20                  25                  30

Ala Gly Ala Thr Gly Leu Phe Gly Leu Trp Gly
        35                  40

<210> SEQ ID NO 311
<211> LENGTH: 132
<212> TYPE: DNA
<213> ORGANISM: Bacillus subtilis

<400> SEQUENCE: 311
atgaaaaaag ctgtcattgt agaaaacaaa ggttgtgcaa catgctcgat cggagccgct    60
tgtctagtgg acggtcctat ccctgatttt gaaattgccg gtgcaacagg tctattcggt   120 ctatggggt aa                                                        132

<210> SEQ ID NO 312
<211> LENGTH: 58
<212> TYPE: PRT
<213> ORGANISM: Streptococcus thermophilus

<400> SEQUENCE: 312

Met Met Asn Ala Thr Glu Asn Gln Ile Phe Val Glu Thr Val Ser Asp
1               5                   10                  15

Gln Glu Leu Glu Met Leu Ile Gly Gly Ala Asp Arg Gly Trp Ile Lys
            20                  25                  30

Thr Leu Thr Lys Asp Cys Pro Asn Val Ile Ser Ser Ile Cys Ala Gly
        35                  40                  45

Thr Ile Ile Thr Ala Cys Lys Asn Cys Ala
    50                  55

<210> SEQ ID NO 313
<211> LENGTH: 177
<212> TYPE: DNA
<213> ORGANISM: Streptococcus thermophilus

<400> SEQUENCE: 313
atgatgaatg ctactgaaaa ccaaattttt gttgagactg tgagtgacca agaattagaa    60
atgttaattg gtggtgcaga tcgtggatgg attaagactt taacaaaaga ttgtccaaat   120
gtaatttctt caatttgtgc aggtacaatt attacagcct gtaaaaattg tgcttaa      177

<210> SEQ ID NO 314
<211> LENGTH: 64
<212> TYPE: PRT
<213> ORGANISM: Streptococcus thermophilus

<400> SEQUENCE: 314

Met Lys Gln Tyr Asn Gly Phe Glu Val Leu His Glu Leu Asp Leu Ala
1               5                   10                  15

Asn Val Thr Gly Gly Gln Ile Asn Trp Gly Ser Val Val Gly His Cys
            20                  25                  30

Ile Gly Gly Ala Ile Ile Gly Gly Ala Phe Ser Gly Gly Ala Ala Ala
        35                  40                  45

Gly Val Gly Cys Leu Val Gly Ser Gly Lys Ala Ile Ile Asn Gly Leu
    50                  55                  60

<210> SEQ ID NO 315
<211> LENGTH: 195
<212> TYPE: DNA
<213> ORGANISM: Streptococcus thermophilus

<400> SEQUENCE: 315
atgaagcagt ataatggttt tgaggttcta catgaacttg acttagcaaa tgtaactggc    60
ggtcaaatta attggggatc agttgtagga cactgtatag gtggagctat tatcggaggt   120
gcattttcag gaggtgcagc ggctggagta ggatgccttg ttgggagcgg aaaggcaatc   180
ataaatggat ataa                                                    195

<210> SEQ ID NO 316
<211> LENGTH: 85
<212> TYPE: PRT
<213> ORGANISM: Streptococcus thermophilus

<400> SEQUENCE: 316

Met Asn Thr Ile Thr Ile Cys Lys Phe Asp Val Leu Asp Ala Glu Leu
1               5                   10                  15

Leu Ser Thr Val Glu Gly Gly Tyr Ser Gly Lys Asp Cys Leu Lys Asp
            20                  25                  30

Met Gly Gly Tyr Ala Leu Ala Gly Ala Gly Ser Gly Ala Leu Trp Gly
        35                  40                  45

Ala Pro Ala Gly Gly Val Gly Ala Leu Pro Gly Ala Phe Val Gly Ala
    50                  55                  60

His Val Gly Ala Ile Ala Gly Gly Phe Ala Cys Met Gly Gly Met Ile
65                  70                  75                  80

Gly Asn Lys Phe Asn
                85

<210> SEQ ID NO 317
<211> LENGTH: 258
<212> TYPE: DNA
<213> ORGANISM: Streptococcus thermophilus

<400> SEQUENCE: 317
atgaatacaa taactatttg taaatttgat gttttagatg ctgaacttct ttcgacagtt    60
gagggtggat actctggtaa ggattgttta aaagacatgg aggatatgc attggcagga   120 gctggaagtg gagctctgtg gggagctcca gcaggaggtg ttggagcact tccaggtgca   180
tttgtcggag ctcatgttgg ggcaattgca ggaggctttg catgtatggg tggaatgatt   240
ggtaataagt ttaactaa                                                258

<210> SEQ ID NO 318
<211> LENGTH: 52
<212> TYPE: PRT
<213> ORGANISM: Bacillus cereus

<400> SEQUENCE: 318

Met Ser Glu Ile Lys Lys Ala Leu Asn Thr Leu Glu Ile Glu Asp Phe
1               5                   10                  15

Asp Ala Ile Glu Met Val Asp Val Asp Ala Met Pro Glu Asn Glu Ala

```
            20                  25                  30

Leu Glu Ile Met Gly Ala Ser Cys Thr Thr Cys Val Cys Thr Cys Ser
        35                  40                  45

Cys Cys Thr Thr
    50

<210> SEQ ID NO 319
<211> LENGTH: 159
<212> TYPE: DNA
<213> ORGANISM: Bacillus cereus

<400> SEQUENCE: 319
atgagtgaaa ttaaaaaagc attaaatacg cttgaaattg aagattttga tgcaattgaa      60
atggttgatg ttgatgctat gccagaaaac gaagcgcttg aaattatggg agcgtcatgt     120
acgacatgcg tatgtacatg cagttgttgt acaacttga                            159

<210> SEQ ID NO 320
<211> LENGTH: 47
<212> TYPE: PRT
<213> ORGANISM: Bacillus cereus

<400> SEQUENCE: 320

Met Glu Val Met Asn Asn Ala Leu Ile Thr Lys Val Asp Glu Glu Ile
1               5                   10                  15

Gly Gly Asn Ala Ala Cys Val Ile Gly Cys Ile Gly Ser Cys Val Ile
            20                  25                  30

Ser Glu Gly Ile Gly Ser Leu Val Gly Thr Ala Phe Thr Leu Gly
        35                  40                  45

<210> SEQ ID NO 321
<211> LENGTH: 144
<212> TYPE: DNA
<213> ORGANISM: Bacillus cereus

<400> SEQUENCE: 321
atggaagtta tgaacaatgc tttaattaca aaagtagatg aggagattgg aggaaacgct      60
gcttgtgtaa ttggttgtat tggcagttgc gtaattagtg aaggaattgg ttcacttgta     120
ggaacagcat ttactttagg ttaa                                            144

<210> SEQ ID NO 322
<211> LENGTH: 49
<212> TYPE: PRT
<213> ORGANISM: Bacillus cereus

<400> SEQUENCE: 322

Met Glu Val Leu Asn Lys Gln Asn Val Asn Ile Ile Pro Glu Ser Glu
1               5                   10                  15

Glu Val Gly Gly Trp Val Ala Cys Val Gly Ala Cys Gly Thr Val Cys
            20                  25                  30

Leu Ala Ser Gly Gly Val Gly Thr Glu Phe Ala Ala Ala Ser Tyr Phe
        35                  40                  45

Leu

<210> SEQ ID NO 323
<211> LENGTH: 150
<212> TYPE: DNA
<213> ORGANISM: Bacillus cereus

<400> SEQUENCE: 323
```

```
atggaagttt taaacaaaca aaatgtaaat attattccag aatctgaaga agtaggtgga    60
tgggtagcat gtgttggagc atgtggtaca gtatgtcttg ctagtggtgg tgttggaaca   120
gagtttgcag ctgcatctta tttcctataa                                    150
```

<210> SEQ ID NO 324
<211> LENGTH: 40
<212> TYPE: PRT
<213> ORGANISM: Bacillus thuringiensis

<400> SEQUENCE: 324

Met Glu Thr Pro Val Val Gln Pro Arg Asp Trp Thr Cys Trp Ser Cys
1 5 10 15

Leu Val Cys Ala Ala Cys Ser Val Glu Leu Leu Asn Leu Val Thr Ala
20 25 30

Ala Thr Gly Ala Ser Thr Ala Ser
35 40

<210> SEQ ID NO 325
<211> LENGTH: 123
<212> TYPE: DNA
<213> ORGANISM: Bacillus thuringiensis

<400> SEQUENCE: 325
atggaaacac cagtagtaca accaagggat tggacttgtt ggagttgctt agtatgtgca 60
gcatgttctg tggaattatt aaatttagtt actgcggcaa caggggctag tactgcaagc 120
taa 123

<210> SEQ ID NO 326
<211> LENGTH: 42
<212> TYPE: PRT
<213> ORGANISM: Rhizobium leguminosarum bv. trifolii

<400> SEQUENCE: 326

Met Asp Asn Lys Val Ala Lys Asn Val Glu Val Lys Lys Gly Ser Ile
1 5 10 15

Lys Ala Thr Phe Lys Ala Ala Val Leu Lys Ser Lys Thr Lys Val Asp
20 25 30

Ile Gly Gly Ser Arg Gln Gly Cys Val Ala
35 40

<210> SEQ ID NO 327
<211> LENGTH: 129
<212> TYPE: DNA
<213> ORGANISM: Rhizobium leguminosarum bv. trifolii

<400> SEQUENCE: 327
atggataaca aggttgcgaa gaatgtcgaa gtgaagaagg gctccatcaa ggcgaccttc 60
aaggctgctg ttctgaagtc gaagacgaag gtcgacatcg gaggtagccg tcagggctgc 120
gtcgcttaa 129

<210> SEQ ID NO 328
<211> LENGTH: 70
<212> TYPE: PRT
<213> ORGANISM: Streptococcus uberis

<400> SEQUENCE: 328

Met Asn Thr Ile Glu Lys Phe Glu Asn Ile Lys Leu Phe Ser Leu Lys
1 5 10 15

Lys Ile Ile Gly Gly Lys Thr Val Asn Tyr Gly Asn Gly Leu Tyr Cys
            20                  25                  30

Asn Gln Lys Lys Cys Trp Val Asn Trp Ser Glu Thr Ala Thr Thr Ile
            35                  40                  45

Val Asn Asn Ser Ile Met Asn Gly Leu Thr Gly Gly Asn Ala Gly Trp
50                      55                  60

His Ser Gly Gly Arg Ala
65                  70

<210> SEQ ID NO 329
<211> LENGTH: 213
<212> TYPE: DNA
<213> ORGANISM: Streptococcus uberis

<400> SEQUENCE: 329
atgaatacaa ttgaaaaatt tgaaaatatt aaactttttt cactaaagaa aattatcggt     60
ggcaaaactg taaattatgg taatggcctt tattgtaacc aaaaaaaatg ctgggtaaac    120
tggtcagaaa ctgctacaac aatagtaaat aattccatca tgaacgggct cacaggtggt    180
aatgcgggtt ggcactcagg cgggagagca taa                                 213

<210> SEQ ID NO 330
<211> LENGTH: 76
<212> TYPE: PRT
<213> ORGANISM: Streptococcus uberis

<400> SEQUENCE: 330

Met Asp Ile Leu Leu Glu Leu Ala Gly Tyr Thr Gly Ile Ala Ser Gly
1               5                   10                  15

Thr Ala Lys Lys Val Val Asp Ala Ile Asp Lys Gly Ala Ala Ala Phe
            20                  25                  30

Val Ile Ile Ser Ile Ile Ser Thr Val Ile Ser Ala Gly Ala Leu Gly
            35                  40                  45

Ala Val Ser Ala Ser Ala Asp Phe Ile Ile Leu Thr Val Lys Asn Tyr
50                      55                  60

Ile Ser Arg Asn Leu Lys Ala Gln Ala Val Ile Trp
65                  70                  75

<210> SEQ ID NO 331
<211> LENGTH: 231
<212> TYPE: DNA
<213> ORGANISM: Streptococcus uberis

<400> SEQUENCE: 331
atggacattt tattagaact cgcaggatat actgggatag cctcaggtac tgcaaaaaaa     60
gttgttgatg ccattgataa aggagctgca gcctttgtta tatttcaat tatctcaaca    120 gtaattagtg cgggagcatt gggagcagtt tcagcctcag ctgattttat tattttaact    180
gtaaaaaatt acattagtag aaatttaaaa gcacaagctg tcatttggta a             231

<210> SEQ ID NO 332
<211> LENGTH: 64
<212> TYPE: PRT
<213> ORGANISM: Clostridium perfringens

<400> SEQUENCE: 332

Met Asp Ser Glu Leu Phe Lys Leu Met Ala Thr Gln Gly Ala Phe Ala
1               5                   10                  15

-continued

```
Ile Leu Phe Ser Tyr Leu Leu Phe Tyr Val Leu Lys Glu Asn Ser Lys
            20                  25                  30

Arg Glu Asp Lys Tyr Gln Asn Ile Ile Glu Glu Leu Thr Glu Leu Leu
        35                  40                  45

Pro Lys Ile Lys Glu Asp Val Glu Asp Ile Lys Glu Lys Leu Asn Lys
    50                  55                  60
```

<210> SEQ ID NO 333
<211> LENGTH: 195
<212> TYPE: DNA
<213> ORGANISM: Clostridium perfringens

<400> SEQUENCE: 333

```
atggatagtg aattatttaa gttaatggca acacaaggag cctttgcaat attattttcg     60
tatttattgt tttatgtttt aaaagagaat agtaaaagag aagataagta tcaaaatata    120
atagaggagc ttacagaatt attgccaaaa ataaaagaag atgtagaaga tataaaagaa    180
aaacttaata aatag                                                     195
```

<210> SEQ ID NO 334
<211> LENGTH: 47
<212> TYPE: PRT
<213> ORGANISM: Micrococcus varians

<400> SEQUENCE: 334

```
Met Thr Asn Ala Phe Gln Ala Leu Asp Glu Val Thr Asp Ala Glu Leu
1               5                   10                  15

Asp Ala Ile Leu Gly Gly Gly Ser Gly Val Ile Pro Thr Ile Ser His
            20                  25                  30

Glu Cys His Met Asn Ser Phe Gln Phe Val Phe Thr Cys Cys Ser
        35                  40                  45
```

<210> SEQ ID NO 335
<211> LENGTH: 144
<212> TYPE: DNA
<213> ORGANISM: Micrococcus varians

<400> SEQUENCE: 335

```
atgacgaacg catttcaggc actggacgaa gtcacggacg ccgagctcga cgccatcctt     60
ggcgggggca gtggtgttat tcccacgatc agccacgagt gccacatgaa ctccttccag    120
ttcgtgttca cctgctgctc ctga                                           144
```

<210> SEQ ID NO 336
<211> LENGTH: 285
<212> TYPE: PRT
<213> ORGANISM: Streptococcus equi subsp. zooepidemicus

<400> SEQUENCE: 336

```
Met Lys Arg Ile Phe Phe Ala Phe Leu Ser Leu Cys Leu Phe Ile Phe
1               5                   10                  15

Gly Thr Gln Thr Val Ser Ala Ala Thr Tyr Thr Arg Pro Leu Asp Thr
            20                  25                  30

Gly Asn Ile Thr Thr Gly Phe Asn Gly Tyr Pro Gly His Val Gly Val
        35                  40                  45

Asp Tyr Ala Val Pro Val Gly Thr Pro Val Arg Ala Val Ala Asn Gly
    50                  55                  60

Thr Val Lys Phe Ala Gly Asn Gly Ala Asn His Pro Trp Met Leu Trp
65                  70                  75                  80
```

Met Ala Gly Asn Cys Val Leu Ile Gln His Ala Asp Gly Met His Thr
            85                  90                  95

Gly Tyr Ala His Leu Ser Lys Ile Ser Val Ser Thr Asp Ser Thr Val
        100                 105                 110

Lys Gln Gly Gln Ile Ile Gly Tyr Thr Gly Ala Thr Gly Gln Val Thr
        115                 120                 125

Gly Pro His Leu His Phe Glu Met Leu Pro Ala Asn Pro Asn Trp Gln
        130                 135                 140

Asn Gly Phe Ser Gly Arg Ile Asp Pro Thr Gly Tyr Ile Ala Asn Ala
145                 150                 155                 160

Pro Val Phe Asn Gly Thr Thr Pro Thr Glu Pro Thr Thr Pro Thr Thr
                165                 170                 175

Asn Leu Lys Ile Tyr Lys Val Asp Asp Leu Gln Lys Ile Asn Gly Ile
            180                 185                 190

Trp Gln Val Arg Asn Asn Ile Leu Val Pro Thr Asp Phe Thr Trp Val
        195                 200                 205

Asp Asn Gly Ile Ala Ala Asp Asp Val Ile Glu Val Thr Ser Asn Gly
210                 215                 220

Thr Arg Thr Ser Asp Gln Val Leu Gln Lys Gly Gly Tyr Phe Val Ile
225                 230                 235                 240

Asn Pro Asn Asn Val Lys Ser Val Gly Thr Pro Met Lys Gly Ser Gly
                245                 250                 255

Gly Leu Ser Trp Ala Gln Val Asn Phe Thr Thr Gly Gly Asn Val Trp
            260                 265                 270

Leu Asn Thr Thr Ser Lys Asp Asn Leu Leu Tyr Gly Lys
            275                 280                 285

<210> SEQ ID NO 337
<211> LENGTH: 858
<212> TYPE: DNA
<213> ORGANISM: Streptococcus equi subsp. zooepidemicus

<400> SEQUENCE: 337
atgaaacgta tatttttgc tttcttaagt ttatgcttat ttatattcgg aacacaaacg      60
gtatctgcag ctacttatac tcggccatta gatacgggaa atatcactac agggtttaac    120 ggatacc ctg tcatgttgg agtcgattat gcagtacccg ttggaactcc ggttagagca    180
gttgcaaatg gtacagtcaa atttgcaggt aatgggcta atcacccatg gatgctttgg      240
atggctggaa actgtgttct aattcaacat gctgacggga tgcatactgg atatgcacac    300
ttatcaaaaa tttcagttag cacagatagt acagttaaac aaggacaaat cataggttat    360
actggtgcca ccggccaagt taccggtcca catttgcatt ttgaaatgtt gccagcaaat    420
cctaactggc aaaatggttt ttctggaaga atagatccaa ccggatacat cgctaatgcc    480
cctgtattta atggaacaac acctacagaa cctactactc ctacaacaaa tttaaaaatc    540
tataaagttg atgatttaca aaaaattaat ggtatttggc aagtaagaaa taacatactt    600
gtaccaactg atttcacatg ggttgataat ggaattgcag cagatgatgt aattgaagta    660
actagcaatg gaacaagaac ctctgaccaa gttcttcaaa aaggtggtta ttttgtcatc    720
aatcctaata atgttaaaag tgttggaact ccgatgaaag gtagtggtgg tctatcttgg    780
gctcaagtaa actttacaac aggtggaaat gtctggttaa atactactag caaagacaac    840
ttactttacg gaaaataa                                                  858

<210> SEQ ID NO 338

```
<211> LENGTH: 45
<212> TYPE: PRT
<213> ORGANISM: Myxococcus fulvus

<400> SEQUENCE: 338

Ala Asn Cys Ser Cys Ser Thr Ala Ser Asp Tyr Cys Pro Ile Leu Thr
1               5                   10                  15

Phe Cys Thr Thr Gly Thr Ala Cys Ser Tyr Thr Pro Thr Gly Cys Gly
            20                  25                  30

Thr Gly Trp Val Tyr Cys Ala Cys Asn Gly Asn Phe Tyr
        35                  40                  45

<210> SEQ ID NO 339
<211> LENGTH: 135
<212> TYPE: DNA
<213> ORGANISM: Artificial Sequence
<220> FEATURE:
<223> OTHER INFORMATION: Polynucleotide encoding the polypeptide of SEQ
      ID NO: 338

<400> SEQUENCE: 339
gcgaactgca gctgcagcac cgcgagcgat tattgcccga ttctgacctt ttgcaccacc      60
ggcaccgcgt gcagctatac cccgaccggc tgcggcaccg ctgggtgta ttgcgcgtgc      120 aacggcaact tttat                                                      135

<210> SEQ ID NO 340
<211> LENGTH: 19
<212> TYPE: PRT
<213> ORGANISM: Streptomyces griseoluteus

<400> SEQUENCE: 340

Cys Ala Asn Ser Cys Ser Tyr Gly Pro Leu Thr Trp Ser Cys Asp Gly
1               5                   10                  15

Asn Thr Lys

<210> SEQ ID NO 341
<211> LENGTH: 57
<212> TYPE: DNA
<213> ORGANISM: Artificial Sequence
<220> FEATURE:
<223> OTHER INFORMATION: Polynucleotide encoding the polypeptide of SEQ
      ID NO: 340

<400> SEQUENCE: 341
tgcgcgaaca gctgcagcta tggcccgctg acctggagct gcgatggcaa caccaaa       57

<210> SEQ ID NO 342
<211> LENGTH: 19
<212> TYPE: PRT
<213> ORGANISM: Streptoverticillium griseoverticillatum

<400> SEQUENCE: 342

Cys Lys Gln Ser Cys Ser Phe Gly Pro Phe Thr Phe Val Cys Asp Gly
1               5                   10                  15

Asn Thr Lys

<210> SEQ ID NO 343
<211> LENGTH: 57
<212> TYPE: DNA
<213> ORGANISM: Artificial Sequence
<220> FEATURE:
<223> OTHER INFORMATION: Polynucleotide encoding the polypeptide of SEQ
      ID NO: 342
```

<400> SEQUENCE: 343
tgcaaacaga gctgcagctt tggcccgttt acctttgtgt gcgatggcaa caccaaa      57

<210> SEQ ID NO 344
<211> LENGTH: 7
<212> TYPE: PRT
<213> ORGANISM: Carnobacterium sp.

<400> SEQUENCE: 344

Gly Ser Glu Ile Gln Pro Arg
1               5

<210> SEQ ID NO 345
<211> LENGTH: 21
<212> TYPE: DNA
<213> ORGANISM: Artificial Sequence
<220> FEATURE:
<223> OTHER INFORMATION: Polynucleotide encoding the polypeptide of SEQ
      ID NO: 344

<400> SEQUENCE: 345
ggcagcgaaa ttcagccgcg c                                              21

<210> SEQ ID NO 346
<211> LENGTH: 39
<212> TYPE: PRT
<213> ORGANISM: Lactococcus lactis subsp. lactis

<400> SEQUENCE: 346

Gly Thr Trp Asp Asp Ile Gly Gln Gly Ile Gly Arg Val Ala Tyr Trp
1               5                   10                  15

Val Gly Lys Ala Met Gly Asn Met Ser Asp Val Asn Gln Ala Ser Arg
            20                  25                  30

Ile Asn Arg Lys Lys Lys His
        35

<210> SEQ ID NO 347
<211> LENGTH: 117
<212> TYPE: DNA
<213> ORGANISM: Artificial Sequence
<220> FEATURE:
<223> OTHER INFORMATION: Polynucleotide encoding the polypeptide of SEQ
      ID NO: 346

<400> SEQUENCE: 347
ggcacctggg atgatattgg ccagggcatt ggccgcgtgg cgtattgggt gggcaaagcg    60
atgggcaaca tgagcgatgt gaaccaggcg agccgcatta accgcaaaaa aaaacat     117

<210> SEQ ID NO 348
<211> LENGTH: 35
<212> TYPE: PRT
<213> ORGANISM: Lactococcus lactis subsp. lactis

<400> SEQUENCE: 348

Lys Lys Trp Gly Trp Leu Ala Trp Val Asp Pro Ala Tyr Glu Phe Ile
1               5                   10                  15

Lys Gly Phe Gly Lys Gly Ala Ile Lys Glu Gly Asn Lys Asp Lys Trp
            20                  25                  30

Lys Asn Ile
        35

```
<210> SEQ ID NO 349
<211> LENGTH: 105
<212> TYPE: DNA
<213> ORGANISM: Artificial Sequence
<220> FEATURE:
<223> OTHER INFORMATION: Polynucleotide encoding the polypeptide of SEQ
      ID NO: 348

<400> SEQUENCE: 349
aaaaaatggg gctggctggc gtgggtggat ccggcgtatg aatttattaa aggctttggc      60
aaaggcgcga ttaaagaagg caacaaagat aaatggaaaa acatt                    105

<210> SEQ ID NO 350
<211> LENGTH: 19
<212> TYPE: PRT
<213> ORGANISM: Streptomyces sp.

<400> SEQUENCE: 350

Cys Val Gln Ser Cys Ser Phe Gly Pro Leu Thr Trp Ser Cys Asp Gly
1               5                   10                  15

Asn Thr Lys

<210> SEQ ID NO 351
<211> LENGTH: 57
<212> TYPE: DNA
<213> ORGANISM: Artificial Sequence
<220> FEATURE:
<223> OTHER INFORMATION: Polynucleotide encoding the polypeptide of SEQ
      ID NO: 350

<400> SEQUENCE: 351
tgcgtgcaga gctgcagctt tggcccgctg acctggagct gcgatggcaa caccaaa        57

<210> SEQ ID NO 352
<211> LENGTH: 19
<212> TYPE: PRT
<213> ORGANISM: Actinoplanes liguriae

<400> SEQUENCE: 352

Ser Ser Gly Trp Val Cys Thr Leu Thr Ile Glu Cys Gly Thr Val Ile
1               5                   10                  15

Cys Ala Cys

<210> SEQ ID NO 353
<211> LENGTH: 57
<212> TYPE: DNA
<213> ORGANISM: Artificial Sequence
<220> FEATURE:
<223> OTHER INFORMATION: Polynucleotide encoding the polypeptide of SEQ
      ID NO: 352

<400> SEQUENCE: 353
agcagcggct gggtgtgcac cctgaccatt gaatgcggca ccgtgatttg cgcgtgc        57

<210> SEQ ID NO 354
<211> LENGTH: 38
<212> TYPE: PRT
<213> ORGANISM: Lactobacillus curvatus
<220> FEATURE:
<221> NAME/KEY: VARIANT
<222> LOCATION: 34
<223> OTHER INFORMATION: Xaa = any amino acid
<220> FEATURE:
<221> NAME/KEY: VARIANT
<222> LOCATION: 37
<223> OTHER INFORMATION: Xaa = any amino acid
```

<400> SEQUENCE: 354

Tyr Thr Ala Lys Gln Cys Leu Gln Ala Ile Gly Ser Cys Gly Ile Ala
1               5                   10                  15

Gly Thr Gly Ala Gly Ala Ala Gly Gly Pro Ala Gly Ala Phe Val Gly
            20                  25                  30

Ala Xaa Val Val Xaa Ile
        35

<210> SEQ ID NO 355
<211> LENGTH: 114
<212> TYPE: DNA
<213> ORGANISM: Artificial Sequence
<220> FEATURE:
<223> OTHER INFORMATION: Polynucleotide encoding the polypeptide of SEQ
      ID NO: 354
<220> FEATURE:
<221> NAME/KEY: misc_feature
<222> LOCATION: 100, 101, 102, 109, 110, 111
<223> OTHER INFORMATION: n = A,T,C or G
<220> FEATURE:
<221> NAME/KEY: misc_feature
<222> LOCATION: (100)...(102)
<223> OTHER INFORMATION: nnn = a codon other than a stop codon
<220> FEATURE:
<221> NAME/KEY: misc_feature
<222> LOCATION: (109)...(111)
<223> OTHER INFORMATION: nnn = a codon other than a stop codon

<400> SEQUENCE: 355
tataccgcga acagtgcct gcaggcgatt ggcagctgcg gcattgcggg caccggcgcg      60
ggcgcggcgg gcggcccggc gggcgcgttt gtgggcgcgn nngtggtgnn natt         114

<210> SEQ ID NO 356
<211> LENGTH: 42
<212> TYPE: PRT
<213> ORGANISM: Lactobacillus sakei
<220> FEATURE:
<221> NAME/KEY: VARIANT
<222> LOCATION: 32
<223> OTHER INFORMATION: Xaa = any amino acid

<400> SEQUENCE: 356

Thr Lys Tyr Tyr Gly Asn Gly Val Tyr Cys Asn Ser Lys Lys Cys Trp
1               5                   10                  15

Val Asp Trp Gly Gln Ala Ala Gly Gly Ile Gly Gln Thr Val Val Xaa
            20                  25                  30

Gly Trp Leu Gly Gly Ala Ile Pro Gly Lys
        35                  40

<210> SEQ ID NO 357
<211> LENGTH: 126
<212> TYPE: DNA
<213> ORGANISM: Artificial Sequence
<220> FEATURE:
<223> OTHER INFORMATION: Polynucleotide encoding the polypeptide of SEQ
      ID NO: 356
<220> FEATURE:
<221> NAME/KEY: misc_feature
<222> LOCATION: (94)...(96)
<223> OTHER INFORMATION: nnn = any amino acid-coding triplet

<400> SEQUENCE: 357
accaaatatt atggcaacgg cgtgtattgc aacagcaaaa aatgctgggt ggattggggc      60
caggcggcgg gcggcattgg ccagaccgtg gtgnnnggct ggctgggcgg cgcgattccg    120

```
<210> SEQ ID NO 358
<211> LENGTH: 22
<212> TYPE: PRT
<213> ORGANISM: Streptococcus mutans

<400> SEQUENCE: 358

Phe Lys Ser Trp Ser Phe Cys Thr Pro Gly Cys Ala Lys Thr Gly Ser
1               5                   10                  15

Phe Asn Ser Tyr Cys Cys
            20

<210> SEQ ID NO 359
<211> LENGTH: 132
<212> TYPE: DNA
<213> ORGANISM: Artificial Sequence
<220> FEATURE:
<223> OTHER INFORMATION: Polynucleotide encoding the polypeptide of SEQ
      ID NO: 358

<400> SEQUENCE: 359
tttaaaagct ggagcttttg cacccccgggc tgcgcgaaaa ccggcagctt taacagctat      60
tgctgcttta aaagctggag cttttgcacc ccgggctgcg cgaaaaccgg cagctttaac     120
agctattgct gc                                                         132

<210> SEQ ID NO 360
<211> LENGTH: 43
<212> TYPE: PRT
<213> ORGANISM: Enterococcus mundtii

<400> SEQUENCE: 360

Lys Tyr Tyr Gly Asn Gly Val Ser Cys Asn Lys Gly Cys Ser Val
1               5                   10                  15

Asp Trp Gly Lys Ala Ile Gly Ile Ile Gly Asn Asn Ser Ala Ala Asn
            20                  25                  30

Leu Ala Thr Gly Gly Ala Ala Gly Trp Ser Lys
        35                  40

<210> SEQ ID NO 361
<211> LENGTH: 129
<212> TYPE: DNA
<213> ORGANISM: Artificial Sequence
<220> FEATURE:
<223> OTHER INFORMATION: Polynucleotide encoding the polypeptide of SEQ
      ID NO: 360

<400> SEQUENCE: 361
aaatattatg caacggcgt gagctgcaac aaaaaaggct gcagcgtgga ttggggcaaa       60
gcgattggca ttattggcaa caacagcgcg gcgaacctgg cgaccggcgg cgcggcgggc    120
tggagcaaa                                                            129

<210> SEQ ID NO 362
<211> LENGTH: 41
<212> TYPE: PRT
<213> ORGANISM: Lactobacillus sakei
<220> FEATURE:
<221> NAME/KEY: VARIANT
<222> LOCATION: 9, 14, 33, 37
<223> OTHER INFORMATION: Xaa = any amino acid

<400> SEQUENCE: 362
```

```
Lys Tyr Tyr Gly Asn Gly Val His Xaa Gly Lys His Ser Xaa Thr Val
1               5                   10                  15

Asp Trp Gly Thr Ala Ile Gly Asn Ile Gly Asn Asn Ala Ala Ala Asn
            20                  25                  30

Xaa Ala Thr Gly Xaa Asn Ala Gly Gly
        35              40
```

<210> SEQ ID NO 363
<211> LENGTH: 123
<212> TYPE: DNA
<213> ORGANISM: Artificial Sequence
<220> FEATURE:
<223> OTHER INFORMATION: Polynucleotide encoding the polypeptide of SEQ
      ID NO: 362
<220> FEATURE:
<221> NAME/KEY: misc_feature
<222> LOCATION: (25)...(27)
<223> OTHER INFORMATION: nnn = any amino acid-coding triplet
<220> FEATURE:
<221> NAME/KEY: misc_feature
<222> LOCATION: (40)...(42)
<223> OTHER INFORMATION: nnn = any amino acid-coding triplet
<220> FEATURE:
<221> NAME/KEY: misc_feature
<222> LOCATION: (97)...(99)
<223> OTHER INFORMATION: nnn = any amino acid-coding triplet
<220> FEATURE:
<221> NAME/KEY: misc_feature
<222> LOCATION: (109)...(111)
<223> OTHER INFORMATION: nnn = any amino acid-coding triplet

<400> SEQUENCE: 363
aaatattatg caacggcgt gcatnnnggc aaacatagcn nnaccgtgga ttggggcacc    60
gcgattggca acattggcaa caacgcggcg gcgaacnnng cgaccggcnn naacgcgggc   120
ggc                                                                123

<210> SEQ ID NO 364
<211> LENGTH: 31
<212> TYPE: PRT
<213> ORGANISM: Lactobacillus paracasei

<400> SEQUENCE: 364

```
Gly Met Ser Gly Tyr Ile Gln Gly Ile Pro Asp Phe Leu Lys Gly Tyr
1               5                   10                  15

Leu His Gly Ile Ser Ala Ala Asn Lys His Lys Lys Gly Arg Leu
            20                  25                  30
```

<210> SEQ ID NO 365
<211> LENGTH: 93
<212> TYPE: DNA
<213> ORGANISM: Artificial Sequence
<220> FEATURE:
<223> OTHER INFORMATION: Polynucleotide encoding the polypeptide of SEQ
      ID NO: 364

<400> SEQUENCE: 365
ggcatgagcg gctatattca gggcattccg gatttctga aaggctatct gcatggcatt    60
agcgcggcga acaaacataa aaaaggccgc ctg                               93

<210> SEQ ID NO 366
<211> LENGTH: 31
<212> TYPE: PRT
<213> ORGANISM: Leuconostoc mesenteroides

<400> SEQUENCE: 366

-continued

Lys Gly Lys Gly Phe Trp Ser Trp Ala Ser Lys Ala Thr Ser Trp Leu
1               5                   10                  15

Thr Gly Pro Gln Gln Pro Gly Ser Pro Leu Leu Lys Lys His Arg
            20                  25                  30

<210> SEQ ID NO 367
<211> LENGTH: 93
<212> TYPE: DNA
<213> ORGANISM: Artificial Sequence
<220> FEATURE:
<223> OTHER INFORMATION: Polynucleotide encoding the polypeptide of SEQ
      ID NO: 366

<400> SEQUENCE: 367
aaaggcaaag gcttttggag ctgggcgagc aaagcgacca gctggctgac cggcccgcag      60
cagccgggca gcccgctgct gaaaaaacat cgc                                  93

<210> SEQ ID NO 368
<211> LENGTH: 43
<212> TYPE: PRT
<213> ORGANISM: Leuconostoc mesenteroides

<400> SEQUENCE: 368

Lys Asn Tyr Gly Asn Gly Val His Cys Thr Lys Lys Gly Cys Ser Val
1               5                   10                  15

Asp Trp Gly Tyr Ala Trp Thr Asn Ile Ala Asn Asn Ser Val Met Asn
            20                  25                  30

Gly Leu Thr Gly Gly Asn Ala Gly Trp His Asn
        35                  40

<210> SEQ ID NO 369
<211> LENGTH: 129
<212> TYPE: DNA
<213> ORGANISM: Artificial Sequence
<220> FEATURE:
<223> OTHER INFORMATION: Polynucleotide encoding the polypeptide of SEQ
      ID NO: 368

<400> SEQUENCE: 369
aaaaactatg gcaacggcgt gcattgcacc aaaaaaggct gcagcgtgga ttggggctat      60
gcgtggacca acattgcgaa caacagcgtg atgaacggcc tgaccggcgg caacgcgggc     120
tggcataac                                                            129

<210> SEQ ID NO 370
<211> LENGTH: 47
<212> TYPE: PRT
<213> ORGANISM: Bacillus subtilis

<400> SEQUENCE: 370

Ala Ile Lys Leu Val Gln Ser Pro Asn Gly Asn Phe Ala Ala Ser Phe
1               5                   10                  15

Val Leu Asp Gly Thr Lys Trp Ile Phe Lys Ser Lys Tyr Tyr Asp Ser
            20                  25                  30

Ser Lys Gly Tyr Trp Val Gly Ile Tyr Glu Val Trp Asp Arg Lys
        35                  40                  45

<210> SEQ ID NO 371
<211> LENGTH: 141
<212> TYPE: DNA
<213> ORGANISM: Artificial Sequence
<220> FEATURE:
<223> OTHER INFORMATION: Polynucleotide encoding the polypeptide of SEQ

ID NO: 370

<400> SEQUENCE: 371
gcgattaaac tggtgcagag cccgaacggc aactttgcgg cgagctttgt gctggatggc    60
accaaatgga tttttaaaag caaatattat gatagcagca aaggctattg ggtgggcatt   120
tatgaagtgt gggatcgcaa a                                             141

<210> SEQ ID NO 372
<211> LENGTH: 12
<212> TYPE: PRT
<213> ORGANISM: Bacillus licheniformis
<220> FEATURE:
<221> NAME/KEY: VARIANT
<222> LOCATION: 7
<223> OTHER INFORMATION: Xaa = any amino acid

<400> SEQUENCE: 372

Ile Ser Leu Glu Ile Cys Xaa Ile Phe His Asp Asn
1               5                   10

<210> SEQ ID NO 373
<211> LENGTH: 36
<212> TYPE: DNA
<213> ORGANISM: Artificial Sequence
<220> FEATURE:
<223> OTHER INFORMATION: Polynucleotide encoding the polypeptide of SEQ
      ID NO: 372
<220> FEATURE:
<221> NAME/KEY: misc_feature
<222> LOCATION: (19)...(21)
<223> OTHER INFORMATION: nnn = any amino acid-coding triplet

<400> SEQUENCE: 373
attagcctgg aaatttgcnn nattttcat gataac                               36

<210> SEQ ID NO 374
<211> LENGTH: 37
<212> TYPE: PRT
<213> ORGANISM: Lactococcus lactis subsp. lactis

<400> SEQUENCE: 374

Thr Ser Tyr Gly Asn Gly Val His Cys Asn Lys Ser Lys Cys Trp Ile
1               5                   10                  15

Asp Val Ser Glu Leu Glu Thr Tyr Lys Ala Gly Thr Val Ser Asn Pro
            20                  25                  30

Lys Asp Ile Leu Trp
        35

<210> SEQ ID NO 375
<211> LENGTH: 111
<212> TYPE: DNA
<213> ORGANISM: Artificial Sequence
<220> FEATURE:
<223> OTHER INFORMATION: Polynucleotide encoding the polypeptide of SEQ
      ID NO: 374

<400> SEQUENCE: 375
accagctatg gcaacggcgt gcattgcaac aaaagcaaat gctggattga tgtgagcgaa    60
ctggaaacct ataaagcggg caccgtgagc aacccgaaag atattctgtg g            111

<210> SEQ ID NO 376
<211> LENGTH: 9
<212> TYPE: PRT
<213> ORGANISM: Serratia plymuthica -continued

<400> SEQUENCE: 376

Asp Tyr His His Gly Val Arg Val Leu
1               5

<210> SEQ ID NO 377
<211> LENGTH: 27
<212> TYPE: DNA
<213> ORGANISM: Artificial Sequence
<220> FEATURE:
<223> OTHER INFORMATION: Polynucleotide encoding the polypeptide of SEQ
      ID NO: 376

<400> SEQUENCE: 377
gattatcatc atggcgtgcg cgtgctg                                           27

<210> SEQ ID NO 378
<211> LENGTH: 15
<212> TYPE: PRT
<213> ORGANISM: Halobacterium sp.

<400> SEQUENCE: 378

Asp Ile Asp Ile Thr Gly Cys Ser Ala Cys Lys Tyr Ala Ala Gly
1               5                   10                  15

<210> SEQ ID NO 379
<211> LENGTH: 45
<212> TYPE: DNA
<213> ORGANISM: Artificial Sequence
<220> FEATURE:
<223> OTHER INFORMATION: Polynucleotide encoding the polypeptide of SEQ
      ID NO: 378

<400> SEQUENCE: 379
gatattgata ttaccggctg cagcgcgtgc aaatatgcgg cgggc                       45

<210> SEQ ID NO 380
<211> LENGTH: 12
<212> TYPE: PRT
<213> ORGANISM: Bacillus subtilis
<220> FEATURE:
<221> NAME/KEY: VARIANT
<222> LOCATION: 1, 2, 6
<223> OTHER INFORMATION: Xaa = any amino acid

<400> SEQUENCE: 380

Xaa Xaa Lys Glu Ile Xaa His Ile Phe His Asp Asn
1               5                   10

<210> SEQ ID NO 381
<211> LENGTH: 36
<212> TYPE: DNA
<213> ORGANISM: Artificial Sequence
<220> FEATURE:
<223> OTHER INFORMATION: Polynucleotide encoding the polypeptide of SEQ
      ID NO: 380
<220> FEATURE:
<221> NAME/KEY: misc_feature
<222> LOCATION: (1)...(3)
<223> OTHER INFORMATION: nnn = any amino acid-coding triplet
<220> FEATURE:
<221> NAME/KEY: misc_feature
<222> LOCATION: (4)...(6)
<223> OTHER INFORMATION: nnn = any amino acid-coding triplet
<220> FEATURE:
<221> NAME/KEY: misc_feature
<222> LOCATION: (16)...(18)
<223> OTHER INFORMATION: nnn = any amino acid-coding triplet

<400> SEQUENCE: 381
nnnnnnaaag aaattnnnca tatttttcat gataac          36

<210> SEQ ID NO 382
<211> LENGTH: 12
<212> TYPE: PRT
<213> ORGANISM: Lactobacillus curvatus

<400> SEQUENCE: 382

Thr Pro Val Val Asn Pro Pro Phe Leu Gln Gln Thr
1               5                   10

<210> SEQ ID NO 383
<211> LENGTH: 36
<212> TYPE: DNA
<213> ORGANISM: Artificial Sequence
<220> FEATURE:
<223> OTHER INFORMATION: Polynucleotide encoding the polypeptide of SEQ
      ID NO: 382

<400> SEQUENCE: 383
accccggtgg tgaacccgcc gtttctgcag cagacc          36

<210> SEQ ID NO 384
<211> LENGTH: 10
<212> TYPE: PRT
<213> ORGANISM: Lactobacillus curvatus
<220> FEATURE:
<221> NAME/KEY: VARIANT
<222> LOCATION: 10
<223> OTHER INFORMATION: Xaa = any amino acid

<400> SEQUENCE: 384

Val Ala Pro Phe Pro Glu Gln Phe Leu Xaa
1               5                   10

<210> SEQ ID NO 385
<211> LENGTH: 30
<212> TYPE: DNA
<213> ORGANISM: Artificial Sequence
<220> FEATURE:
<223> OTHER INFORMATION: Polynucleotide encoding the polypeptide of SEQ
      ID NO: 384
<220> FEATURE:
<221> NAME/KEY: misc_feature
<222> LOCATION: (28)...(30)
<223> OTHER INFORMATION: nnn = any amino acid-coding triplet

<400> SEQUENCE: 385
gtggcgccgt ttccggaaca gtttctgnnn          30

<210> SEQ ID NO 386
<211> LENGTH: 9
<212> TYPE: PRT
<213> ORGANISM: Lactobacillus curvatus

<400> SEQUENCE: 386

Asn Ile Pro Gln Leu Thr Pro Thr Pro
1               5

<210> SEQ ID NO 387
<211> LENGTH: 27
<212> TYPE: DNA
<213> ORGANISM: Artificial Sequence
<220> FEATURE:
<223> OTHER INFORMATION: Polynucleotide encoding the polypeptide of SEQ
      ID NO: 386

<400> SEQUENCE: 387
aacattccgc agctgacccc gaccccg                                              27

<210> SEQ ID NO 388
<211> LENGTH: 18
<212> TYPE: PRT
<213> ORGANISM: Bacillus thuringiensis subsp. entomocidus
<220> FEATURE:
<221> NAME/KEY: VARIANT
<222> LOCATION: 4, 7, 10
<223> OTHER INFORMATION: Xaa = any amino acid

<400> SEQUENCE: 388

Asp Trp Thr Xaa Trp Ser Xaa Leu Val Xaa Ala Ala Cys Ser Val Glu
1               5                   10                  15

Leu Leu

<210> SEQ ID NO 389
<211> LENGTH: 54
<212> TYPE: DNA
<213> ORGANISM: Artificial Sequence
<220> FEATURE:
<223> OTHER INFORMATION: Polynucleotide encoding the polypeptide of SEQ
      ID NO: 388
<220> FEATURE:
<221> NAME/KEY: misc_feature
<222> LOCATION: (10)...(12)
<223> OTHER INFORMATION: nnn = any amino acid-coding triplet
<220> FEATURE:
<221> NAME/KEY: misc_feature
<222> LOCATION: (19)...(21)
<223> OTHER INFORMATION: nnn = any amino acid-coding triplet
<220> FEATURE:
<221> NAME/KEY: misc_feature
<222> LOCATION: (28)...(30)
<223> OTHER INFORMATION: nnn = any amino acid-coding triplet

<400> SEQUENCE: 389
gattggaccn nntggagcnn nctggtgnnn gcggcgtgca gcgtggaact gctg          54

<210> SEQ ID NO 390
<211> LENGTH: 30
<212> TYPE: PRT
<213> ORGANISM: Lactobacillus curvatus

<400> SEQUENCE: 390

Ala Tyr Pro Gly Asn Gly Val His Cys Gly Lys Tyr Ser Cys Thr Val
1               5                   10                  15

Asp Lys Gln Thr Ala Ile Gly Asn Ile Gly Asn Asn Ala Ala
            20                  25                  30

<210> SEQ ID NO 391
<211> LENGTH: 90
<212> TYPE: DNA
<213> ORGANISM: Artificial Sequence
<220> FEATURE:
<223> OTHER INFORMATION: Polynucleotide encoding the polypeptide of SEQ
      ID NO: 390

<400> SEQUENCE: 391
gcgtatccgg gcaacggcgt gcattgcggc aaatatagct gcaccgtgga taaacagacc    60
gcgattggca acattggcaa caacgcggcg                                      90

<210> SEQ ID NO 392
<211> LENGTH: 43

```
<212> TYPE: PRT
<213> ORGANISM: Carnobacterium divergens

<400> SEQUENCE: 392

Thr Lys Tyr Tyr Gly Asn Gly Val Tyr Cys Asn Ser Lys Lys Cys Trp
1               5                   10                  15

Val Asp Trp Gly Thr Ala Gln Gly Cys Ile Asp Val Val Ile Gly Gln
            20                  25                  30

Leu Gly Gly Gly Ile Pro Gly Lys Gly Lys Cys
        35                  40

<210> SEQ ID NO 393
<211> LENGTH: 129
<212> TYPE: DNA
<213> ORGANISM: Artificial Sequence
<220> FEATURE:
<223> OTHER INFORMATION: Polynucleotide encoding the polypeptide of SEQ
      ID NO: 392

<400> SEQUENCE: 393
accaaatatt atggcaacgg cgtgtattgc aacagcaaaa aatgctgggt ggattggggc    60
accgcgcagg gctgcattga tgtggtgatt ggccagctgg cggcggcat tccgggcaaa    120 ggcaaatgc                                                           129

<210> SEQ ID NO 394
<211> LENGTH: 62
<212> TYPE: PRT
<213> ORGANISM: Enterococcus sp.

<400> SEQUENCE: 394

Asn Arg Trp Tyr Cys Asn Ser Ala Ala Gly Gly Val Gly Gly Ala Ala
1               5                   10                  15

Val Cys Gly Leu Ala Gly Tyr Val Gly Glu Ala Lys Glu Asn Ile Ala
            20                  25                  30

Gly Glu Val Arg Lys Gly Trp Gly Met Ala Gly Gly Phe Thr His Asn
        35                  40                  45

Lys Ala Cys Lys Ser Phe Pro Gly Ser Gly Trp Ala Ser Gly
    50                  55                  60

<210> SEQ ID NO 395
<211> LENGTH: 186
<212> TYPE: DNA
<213> ORGANISM: Artificial Sequence
<220> FEATURE:
<223> OTHER INFORMATION: Polynucleotide encoding the polypeptide of SEQ
      ID NO: 394

<400> SEQUENCE: 395
aaccgctggt attgcaacag cgcggcgggc ggcgtgggcg gcgcggcggt gtgcggcctg    60
gcgggctatg tgggcgaagc gaaagaaaac attgcgggcg aagtgcgcaa aggctggggc    120
atggcgggcg gctttaccca taacaaagcg tgcaaaagct tccgggcag cggctgggcg    180 agcggc                                                              186

<210> SEQ ID NO 396
<211> LENGTH: 39
<212> TYPE: PRT
<213> ORGANISM: Enterococcus faecium

<400> SEQUENCE: 396

Thr Thr Lys Asn Tyr Gly Asn Gly Val Cys Asn Ser Val Asn Trp Cys
```

```
                1               5                  10                 15
Gln Cys Gly Asn Val Trp Ala Ser Cys Asn Leu Ala Thr Gly Cys Ala
                20                 25                 30

Ala Trp Leu Cys Lys Leu Ala
                35

<210> SEQ ID NO 397
<211> LENGTH: 117
<212> TYPE: DNA
<213> ORGANISM: Artificial Sequence
<220> FEATURE:
<223> OTHER INFORMATION: Polynucleotide encoding the polypeptide of SEQ
      ID NO: 396

<400> SEQUENCE: 397
accaccaaaa actatggcaa cggcgtgtgc aacagcgtga actggtgcca gtgcggcaac         60
gtgtgggcga gctgcaacct ggcgaccggc tgcgcggcgt ggctgtgcaa actggcg          117

<210> SEQ ID NO 398
<211> LENGTH: 30
<212> TYPE: PRT
<213> ORGANISM: Paenibacillus polymyxa

<400> SEQUENCE: 398

Ala Ser Ile Ile Lys Thr Thr Ile Lys Val Ser Lys Ala Val Cys Lys
1               5                  10                 15

Thr Leu Thr Cys Ile Cys Thr Gly Ser Cys Ser Asn Cys Lys
                20                 25                 30

<210> SEQ ID NO 399
<211> LENGTH: 90
<212> TYPE: DNA
<213> ORGANISM: Artificial Sequence
<220> FEATURE:
<223> OTHER INFORMATION: Polynucleotide encoding the polypeptide of SEQ
      ID NO: 398

<400> SEQUENCE: 399
gcgagcatta ttaaaaccac cattaaagtg agcaaagcgg tgtgcaaaac cctgacctgc         60
atttgcaccg gcagctgcag caactgcaaa                                          90

<210> SEQ ID NO 400
<211> LENGTH: 31
<212> TYPE: PRT
<213> ORGANISM: Staphylococcus epidermidis

<400> SEQUENCE: 400

Ser Ala Ser Ile Val Lys Thr Thr Ile Lys Ala Ser Lys Lys Leu Cys
1               5                  10                 15

Arg Gly Phe Thr Leu Thr Cys Gly Cys His Phe Thr Gly Lys Lys
                20                 25                 30

<210> SEQ ID NO 401
<211> LENGTH: 93
<212> TYPE: DNA
<213> ORGANISM: Artificial Sequence
<220> FEATURE:
<223> OTHER INFORMATION: Polynucleotide encoding the polypeptide of SEQ
      ID NO: 400

<400> SEQUENCE: 401
agcgcgagca ttgtgaaaac caccattaaa gcgagcaaaa aactgtgccg cggctttacc         60
```

```
ctgacctgcg gctgccattt taccggcaaa aaa                           93
```

<210> SEQ ID NO 402
<211> LENGTH: 43
<212> TYPE: PRT
<213> ORGANISM: Enterococcus faecium

<400> SEQUENCE: 402

```
Lys Tyr Tyr Gly Asn Gly Val Ser Cys Asn Lys Lys Gly Cys Ser Val
1               5                   10                  15

Asp Trp Gly Lys Ala Ile Gly Ile Ile Gly Asn Asn Ala Ala Ala Asn
            20                  25                  30

Leu Thr Thr Gly Gly Lys Ala Ala Trp Ala Cys
        35                  40
```

<210> SEQ ID NO 403
<211> LENGTH: 129
<212> TYPE: DNA
<213> ORGANISM: Artificial Sequence
<220> FEATURE:
<223> OTHER INFORMATION: Polynucleotide encoding the polypeptide of SEQ
      ID NO: 402

<400> SEQUENCE: 403

```
aaatattatg gcaacggcgt gagctgcaac aaaaaaggct gcagcgtgga ttggggcaaa    60
gcgattggca ttattggcaa caacgcggcg gcgaacctga ccaccggcgg caaagcggcg   120
tgggcgtgc                                                          129
```

<210> SEQ ID NO 404
<211> LENGTH: 39
<212> TYPE: PRT
<213> ORGANISM: Paenibacillus polymyxa

<400> SEQUENCE: 404

```
Ala Thr Tyr Tyr Gly Asn Gly Leu Tyr Cys Asn Lys Gln Lys His Tyr
1               5                   10                  15

Thr Trp Val Asp Trp Asn Lys Ala Ser Arg Glu Ile Gly Lys Ile Thr
            20                  25                  30

Val Asn Gly Trp Val Gln His
        35
```

<210> SEQ ID NO 405
<211> LENGTH: 117
<212> TYPE: DNA
<213> ORGANISM: Artificial Sequence
<220> FEATURE:
<223> OTHER INFORMATION: Polynucleotide encoding the polypeptide of SEQ
      ID NO: 404

<400> SEQUENCE: 405

```
gcgacctatt atggcaacgg cctgtattgc aacaaacaga acattatac ctgggtggat    60 tggaacaaag cgagccgcga aattggcaaa attaccgtga acggctgggt gcagcat    117
```

<210> SEQ ID NO 406
<211> LENGTH: 35
<212> TYPE: PRT
<213> ORGANISM: Bacillus circulans

<400> SEQUENCE: 406

```
Val Asn Tyr Gly Asn Gly Val Ser Cys Ser Lys Thr Lys Cys Ser Val
1               5                   10                  15
```

```
Asn Trp Gly Ile Ile Thr His Gln Ala Phe Arg Val Thr Ser Gly Val
            20                  25                  30

Ala Ser Gly
        35

<210> SEQ ID NO 407
<211> LENGTH: 105
<212> TYPE: DNA
<213> ORGANISM: Artificial Sequence
<220> FEATURE:
<223> OTHER INFORMATION: Polynucleotide encoding the polypeptide of SEQ
      ID NO: 406

<400> SEQUENCE: 407
gtgaactatg gcaacggcgt gagctgcagc aaaaccaaat gcagcgtgaa ctggggcatt    60 attcccatc aggcgtttcg cgtgaccagc ggcgtggcga gcggc                    105

<210> SEQ ID NO 408
<211> LENGTH: 30
<212> TYPE: PRT
<213> ORGANISM: Paenibacillus polymyxa

<400> SEQUENCE: 408

Phe Val Tyr Gly Asn Gly Val Thr Ser Ile Leu Val Gln Ala Gln Phe
1               5                   10                  15

Leu Val Asn Gly Gln Arg Arg Phe Phe Tyr Thr Pro Asp Lys
            20                  25                  30

<210> SEQ ID NO 409
<211> LENGTH: 90
<212> TYPE: DNA
<213> ORGANISM: Artificial Sequence
<220> FEATURE:
<223> OTHER INFORMATION: Polynucleotide encoding the polypeptide of SEQ
      ID NO: 408

<400> SEQUENCE: 409
tttgtgtatg gcaacggcgt gaccagcatt ctggtgcagg cgcagtttct ggtgaacggc    60
cagcgccgct ttttttatac cccggataaa                                    90

<210> SEQ ID NO 410
<211> LENGTH: 13
<212> TYPE: PRT
<213> ORGANISM: Lactobacillus rhamnosus

<400> SEQUENCE: 410

Ala Val Pro Ala Val Arg Lys Thr Asn Glu Thr Leu Asp
1               5                   10

<210> SEQ ID NO 411
<211> LENGTH: 39
<212> TYPE: DNA
<213> ORGANISM: Artificial Sequence
<220> FEATURE:
<223> OTHER INFORMATION: Polynucleotide encoding the polypeptide of SEQ
      ID NO: 410

<400> SEQUENCE: 411
gcggtgccgg cggtgcgcaa aaccaacgaa accctggat                          39

<210> SEQ ID NO 412
<211> LENGTH: 69
<212> TYPE: PRT
<213> ORGANISM: Bacillus licheniformis
```

-continued

<400> SEQUENCE: 412

Met Lys Asn Ser Ala Ala Arg Glu Ala Phe Lys Gly Ala Asn His Pro
1               5                   10                  15

Ala Gly Met Val Ser Glu Glu Glu Leu Lys Ala Leu Val Gly Gly Asn
            20                  25                  30

Asp Val Asn Pro Glu Thr Thr Pro Ala Thr Thr Ser Ser Trp Thr Cys
        35                  40                  45

Ile Thr Ala Gly Val Thr Val Ser Ala Ser Leu Cys Pro Thr Thr Lys
    50                  55                  60

Cys Thr Ser Arg Cys
65

<210> SEQ ID NO 413
<211> LENGTH: 207
<212> TYPE: DNA
<213> ORGANISM: Artificial Sequence
<220> FEATURE:
<223> OTHER INFORMATION: Polynucleotide encoding the polypeptide of SEQ
      ID NO: 412

<400> SEQUENCE: 413
atgaaaaaca gcgcggcgcg cgaagcgttt aaaggcgcga accatccggc gggcatggtg      60
agcgaagaag aactgaaagc gctggtgggc ggcaacgatg tgaacccgga accaccccg     120 gcgaccacca gcagctggac ctgcattacc gcgggcgtga ccgtgagcgc gagcctgtgc    180
ccgaccacca aatgcaccag ccgctgc                                         207

<210> SEQ ID NO 414
<211> LENGTH: 36
<212> TYPE: PRT
<213> ORGANISM: Lactobacillus plantarum

<400> SEQUENCE: 414

Lys Tyr Tyr Gly Asn Gly Leu Ser Cys Ser Lys Lys Gly Cys Thr Val
1               5                   10                  15

Asn Trp Gly Gln Ala Phe Ser Cys Gly Val Asn Arg Val Ala Thr Ala
            20                  25                  30

Gly His Gly Lys
        35

<210> SEQ ID NO 415
<211> LENGTH: 108
<212> TYPE: DNA
<213> ORGANISM: Artificial Sequence
<220> FEATURE:
<223> OTHER INFORMATION: Polynucleotide encoding the polypeptide of SEQ
      ID NO: 414

<400> SEQUENCE: 415
aaatattatg gcaacggcct gagctgcagc aaaaaaggct gcaccgtgaa ctggggccag      60
gcgtttagct gcggcgtgaa ccgcgtggcg accgcgggcc atggcaaa                 108

<210> SEQ ID NO 416
<211> LENGTH: 24
<212> TYPE: PRT
<213> ORGANISM: Lactobacillus acidophilus

<400> SEQUENCE: 416

Gly Asn Pro Lys Val Ala His Cys Ala Ser Gln Ile Gly Arg Ser Thr
1               5                   10                  15

```
Ala Trp Gly Ala Val Ser Gly Ala
            20
```

<210> SEQ ID NO 417
<211> LENGTH: 72
<212> TYPE: DNA
<213> ORGANISM: Artificial Sequence
<220> FEATURE:
<223> OTHER INFORMATION: Polynucleotide encoding the polypeptide of SEQ
      ID NO: 416

<400> SEQUENCE: 417

```
ggcaacccga aagtggcgca ttgcgcgagc cagattggcc gcagcaccgc gtggggcgcg      60
gtgagcggcg cg                                                         72
```

<210> SEQ ID NO 418
<211> LENGTH: 40
<212> TYPE: PRT
<213> ORGANISM: Enterococcus faecalis

<400> SEQUENCE: 418

```
Trp Leu Pro Pro Ala Gly Leu Leu Gly Arg Cys Gly Arg Trp Phe Arg
1               5                   10                  15

Pro Trp Leu Leu Trp Leu Gln Ser Gly Ala Gln Tyr Lys Trp Leu Gly
            20                  25                  30

Asn Leu Phe Gly Leu Gly Pro Lys
        35                  40
```

<210> SEQ ID NO 419
<211> LENGTH: 120
<212> TYPE: DNA
<213> ORGANISM: Artificial Sequence
<220> FEATURE:
<223> OTHER INFORMATION: Polynucleotide encoding the polypeptide of SEQ
      ID NO: 418

<400> SEQUENCE: 419

```
tggctgccgc cggcgggcct gctgggccgc tgcggccgct ggtttcgccc gtggctgctg      60
tggctgcaga gcggcgcgca gtataaatgg ctgggcaacc tgtttggcct gggcccgaaa     120
```

<210> SEQ ID NO 420
<211> LENGTH: 40
<212> TYPE: PRT
<213> ORGANISM: Anabaena variabilis

<400> SEQUENCE: 420

```
Asn Leu Asp Gln Trp Leu Thr Glu Gln Val His Glu Phe Gln Asp Met
1               5                   10                  15

Tyr Leu Glu Pro Gln Ala Ile Ser Asn Gln Asp Ile Thr Phe Lys Leu
            20                  25                  30

Ser Asp Leu Asp Phe Ile His Asn
        35                  40
```

<210> SEQ ID NO 421
<211> LENGTH: 124
<212> TYPE: DNA
<213> ORGANISM: Anabaena variabilis

<400> SEQUENCE: 421

```
taatttagat cagtggttaa cagaacaagt tcatgagttt caagatatgt acttggaacc      60
acaagcaata tccaatcaag acattacctt caaactatct gacctagatt ttattcataa     120
```

```
ttga                                                              124
```

<210> SEQ ID NO 422
<211> LENGTH: 40
<212> TYPE: PRT
<213> ORGANISM: Nostoc sp

<400> SEQUENCE: 422

Asn Leu Asp Gln Trp Leu Thr Glu Gln Val His Glu Phe Gln Asp Met
1               5                   10                  15

Tyr Leu Glu Pro Gln Ala Ile Ser Asn Gln Asp Ile Thr Phe Lys Leu
            20                  25                  30

Ser Asp Leu Asp Phe Ile His Asn
        35                  40

<210> SEQ ID NO 423
<211> LENGTH: 123
<212> TYPE: DNA
<213> ORGANISM: Nostoc sp

<400> SEQUENCE: 423

```
aatttagatc aatggttaac agaacaagtt catgagtttc aagatatgta cttggaacca    60
caagcaatat ccaatcaaga cattaccttc aaactgtcag acctagattt tattcataat   120
tga                                                                123
```

<210> SEQ ID NO 424
<211> LENGTH: 7
<212> TYPE: PRT
<213> ORGANISM: Nostoc azollae

<400> SEQUENCE: 424

His Arg Glu Lys Lys Ser Ala
1               5

<210> SEQ ID NO 425
<211> LENGTH: 24
<212> TYPE: DNA
<213> ORGANISM: Nostoc azollae

<400> SEQUENCE: 425

```
cacagagaga aaaaatcagc atag                                          24
```

<210> SEQ ID NO 426
<211> LENGTH: 23
<212> TYPE: PRT
<213> ORGANISM: Acaryochloris marina

<400> SEQUENCE: 426

Thr Ser Asn Asn Trp Leu Ala Lys Asn Tyr Leu Ser Met Trp Asn Lys
1               5                   10                  15

Lys Ser Ser Asn Pro Asn Leu
            20

<210> SEQ ID NO 427
<211> LENGTH: 72
<212> TYPE: DNA
<213> ORGANISM: Acaryochloris marina

<400> SEQUENCE: 427

```
acaagcaata actggctagc caaaaactat ctttctatgt ggaataaaaa gagcagtaat    60
```
ccaaaccttt ag                                                           72

<210> SEQ ID NO 428
<211> LENGTH: 6
<212> TYPE: PRT
<213> ORGANISM: Cyanothece

<400> SEQUENCE: 428

Phe Arg Tyr Phe Trp Trp
1               5

<210> SEQ ID NO 429
<211> LENGTH: 21
<212> TYPE: DNA
<213> ORGANISM: Cyanothece

<400> SEQUENCE: 429
tttagatatt tttggtggta a                                                 21

<210> SEQ ID NO 430
<211> LENGTH: 6
<212> TYPE: PRT
<213> ORGANISM: Cyanothece

<400> SEQUENCE: 430

Phe Arg Tyr Phe Trp Trp
1               5

<210> SEQ ID NO 431
<211> LENGTH: 21
<212> TYPE: DNA
<213> ORGANISM: Cyanothece

<400> SEQUENCE: 431
tttagatatt tttggtggta a                                                 21

<210> SEQ ID NO 432
<211> LENGTH: 9
<212> TYPE: PRT
<213> ORGANISM: Cyanothece

<400> SEQUENCE: 432

Cys Gly Glu Lys Trp Arg Ile Phe Ser
1               5

<210> SEQ ID NO 433
<211> LENGTH: 27
<212> TYPE: DNA
<213> ORGANISM: Cyanothece

<400> SEQUENCE: 433
tgtggagaaa aatggagaat ttttagc                                           27

<210> SEQ ID NO 434
<211> LENGTH: 8
<212> TYPE: PRT
<213> ORGANISM: Cyanothece

<400> SEQUENCE: 434

Phe Arg Leu Gln Leu Trp Gln Phe
1               5

<210> SEQ ID NO 435
<211> LENGTH: 24

```
<212> TYPE: DNA
<213> ORGANISM: Cyanothece

<400> SEQUENCE: 435
tttcgcttac aactgtggca attt                                              24

<210> SEQ ID NO 436
<211> LENGTH: 16
<212> TYPE: PRT
<213> ORGANISM: Cyanothece

<400> SEQUENCE: 436

Leu Gly Cys Asn Gln Ser Ser Ile Trp Ser Ile Phe Phe Trp Asn His
1               5                   10                  15

<210> SEQ ID NO 437
<211> LENGTH: 51
<212> TYPE: DNA
<213> ORGANISM: Cyanothece

<400> SEQUENCE: 437
ctaggatgta accagagcag tatctggtca attttttttct ggaatcatta a               51

<210> SEQ ID NO 438
<211> LENGTH: 40
<212> TYPE: PRT
<213> ORGANISM: Microcoleus chthonoplastes

<400> SEQUENCE: 438

Tyr Asn Leu Gln Gly Leu Pro Ala Ile Glu Ser Glu Asp Cys Ile Pro
1               5                   10                  15

Asp Ser Val Ala Pro Ser Asp Asp Trp Phe Ser Gly Val Ser Ser Leu
            20                  25                  30

Phe Asn Arg Leu Thr Gly Leu Gly
        35                  40

<210> SEQ ID NO 439
<211> LENGTH: 123
<212> TYPE: DNA
<213> ORGANISM: Microcoleus chthonoplastes

<400> SEQUENCE: 439
tataacctac aggggttgcc agcaattgag tcagaagact gtatcccaga ttctgtagcg      60
ccttcggatg attggttttc aggcgtatcg tctctgttta accgcttgac tgggttgggt     120
tag                                                                    123

<210> SEQ ID NO 440
<211> LENGTH: 37
<212> TYPE: PRT
<213> ORGANISM: Nostoc sp

<400> SEQUENCE: 440

Trp Met Ala Ile Arg Arg Ile Leu Arg Cys His Pro Phe His Pro Gly
1               5                   10                  15

Gly Tyr Asp Pro Val Pro Glu Leu Gly Glu His Cys Cys His His Asp
            20                  25                  30

Ser Gly Asn Lys Gly
        35

<210> SEQ ID NO 441
<211> LENGTH: 114
```

```
<212> TYPE: DNA
<213> ORGANISM: Nostoc sp

<400> SEQUENCE: 441
tggatggcga ttcgccgcat tttgcgttgt catccattcc acccagggg ttatgatcct    60
gtaccagagt tgggtgagca ttgttgtcat catgatagcg ggaataaggg gtga         114

<210> SEQ ID NO 442
<211> LENGTH: 35
<212> TYPE: PRT
<213> ORGANISM: Anabaena variabilis

<400> SEQUENCE: 442
```

Trp Met Gly Ile Arg Arg Ile Leu Arg Cys His Pro Phe His Pro Gly
1               5                   10                  15

Gly Tyr Asp Pro Val Pro Glu Val Gly Glu His Cys Cys His His Asp
            20                  25                  30

Ser Gly Lys
        35

```
<210> SEQ ID NO 443
<211> LENGTH: 108
<212> TYPE: DNA
<213> ORGANISM: Anabaena variabilis

<400> SEQUENCE: 443
tggatgggga ttcgccgcat tttgcgttgt catccattcc acccaggcgg ttatgatcct    60
gtaccagagg tgggtgagca ttgttgtcat catgatagcg ggaagtag                108

<210> SEQ ID NO 444
<211> LENGTH: 48
<212> TYPE: PRT
<213> ORGANISM: Nodularia spumigena

<400> SEQUENCE: 444
```

Trp Met Ala Thr Arg Arg Ile Leu Arg Cys His Pro Phe His Pro Gly
1               5                   10                  15

Gly Tyr Asp Pro Val Pro Glu Val Lys His Asn Cys Cys Asp Gln His
            20                  25                  30

Leu Ser Asp Ser Gly Lys Gln Thr Thr Glu Asp His His Lys Gly Ser
        35                  40                  45

```
<210> SEQ ID NO 445
<211> LENGTH: 147
<212> TYPE: DNA
<213> ORGANISM: Nodularia spumigena

<400> SEQUENCE: 445
tggatggcga ctcggcggat tttgcgttgt catcccttcc atcctggtgg atatgatcca    60
gttccagagg taaaacacaa ttgctgcgat cagcatctgt ccgattctgg gaaacagacc   120
acagaagacc atcacaaagg ctcgtag                                       147

<210> SEQ ID NO 446
<211> LENGTH: 34
<212> TYPE: PRT
<213> ORGANISM: Nostoc azollae

<400> SEQUENCE: 446
```

Trp Met Ala Thr Leu Arg Ile Leu Arg Cys His Pro Phe His Pro Gly
1               5                   10                  15

Gly Tyr Asp Pro Val Pro Gly Leu Ala Glu Lys Ser Cys Cys Asp His
            20                  25                  30

His Asp

<210> SEQ ID NO 447
<211> LENGTH: 105
<212> TYPE: DNA
<213> ORGANISM: Nostoc azollae

<400> SEQUENCE: 447
tggatggcaa ctttgcggat ttacgctgt catcctttcc atcctggtgg ttatgatcct        60
gtaccaggac tagcggaaaa atcctgttgt gaccatcatg attga                      105

<210> SEQ ID NO 448
<211> LENGTH: 28
<212> TYPE: PRT
<213> ORGANISM: Synechococcus

<400> SEQUENCE: 448

Trp Leu Thr Ala Lys Arg Phe Cys Arg Cys His Pro Leu His Pro Gly
1               5                   10                  15

Gly Tyr Asp Pro Val Pro Glu Lys Lys Ser Val Leu
            20                  25

<210> SEQ ID NO 449
<211> LENGTH: 87
<212> TYPE: DNA
<213> ORGANISM: Synechococcus

<400> SEQUENCE: 449
tggctaacag ccaagcgctt ttgtcgctgt catccgcttc atcctggcgg gtatgatccg        60
gtaccggaga agaaatcggt actctaa                                           87

<210> SEQ ID NO 450
<211> LENGTH: 23
<212> TYPE: PRT
<213> ORGANISM: Prochlorococcus marinus

<400> SEQUENCE: 450

Trp Leu Thr Leu Arg Arg Leu Ser Arg Cys His Pro Phe Thr Pro Cys
1               5                   10                  15

Gly Cys Asp Pro Val Pro Asp
            20

<210> SEQ ID NO 451
<211> LENGTH: 72
<212> TYPE: DNA
<213> ORGANISM: Prochlorococcus marinus

<400> SEQUENCE: 451
tggctcaccc tgcggcgcct gtctcgttgc catccttta ccccctgtgg ttgcgacccg        60
gtgcctgatt aa                                                           72

<210> SEQ ID NO 452
<211> LENGTH: 69
<212> TYPE: PRT
<213> ORGANISM: Escherichia coli

<400> SEQUENCE: 452

Met Ser Tyr Lys Lys Leu Tyr Gln Leu Thr Ala Ile Phe Ser Leu Pro

```
  1               5                  10                 15
Leu Thr Ile Leu Leu Val Ser Leu Ser Ser Leu Arg Ile Val Gly Glu
                 20                  25                 30
Gly Asn Ser Tyr Val Asp Val Phe Leu Ser Phe Ile Ile Phe Leu Gly
                 35                  40                 45
Phe Ile Glu Leu Ile His Gly Ile Arg Lys Ile Leu Val Trp Ser Gly
 50                  55                  60
Trp Lys Asn Gly Ser
 65
```

<210> SEQ ID NO 453
<211> LENGTH: 210
<212> TYPE: DNA
<213> ORGANISM: Escherichia coli

<400> SEQUENCE: 453

```
atgagttata aaaaactgta ccaattgacg gctatattta gtttacctct tactatctta      60
ttggtttcac tttcatccct tcggattgtt ggcgaaggga attcttatgt tgacgttttt    120
ctaagcttta taatatttct tggttttatt gagctgattc atggattcg aaagattttg     180
gtctggtcag gctggaaaaa cggaagttaa                                     210
```

<210> SEQ ID NO 454
<211> LENGTH: 85
<212> TYPE: PRT
<213> ORGANISM: Escherichia coli

<400> SEQUENCE: 454

```
Met Gly Leu Lys Leu Asp Leu Thr Trp Phe Asp Lys Ser Thr Glu Asp
 1               5                  10                  15
Phe Lys Gly Glu Glu Tyr Ser Lys Asp Phe Gly Asp Asp Gly Ser Val
                 20                  25                  30
Met Glu Ser Leu Gly Val Pro Phe Lys Asp Asn Val Asn Asn Gly Cys
                 35                  40                  45
Phe Asp Val Ile Ala Glu Trp Val Pro Leu Leu Gln Pro Tyr Phe Asn
 50                  55                  60
His Gln Ile Asp Ile Ser Asp Asn Glu Tyr Phe Val Ser Phe Asp Tyr
 65                  70                  75                  80
Arg Asp Gly Asp Trp
                 85
```

<210> SEQ ID NO 455
<211> LENGTH: 258
<212> TYPE: DNA
<213> ORGANISM: Escherichia coli

<400> SEQUENCE: 455

```
atgggactta aattggattt aacttggttt gataaaagta cagaagattt taagggtgag     60
gagtattcaa aagattttgg agatgacggt tcagttatgg aaagtctagg tgtgcctttt    120
aaggataatg ttaataacgg ttgctttgat gttatagctg aatgggtacc tttgctacaa    180
ccatacttta tcatcaaat tgatatttcc gataatgagt attttgtttc gtttgattat     240
cgtgatggtg attggtga                                                  258
```

<210> SEQ ID NO 456
<211> LENGTH: 113
<212> TYPE: PRT
<213> ORGANISM: Escherichia coli

<400> SEQUENCE: 456

Met Ser Leu Arg Tyr Tyr Ile Lys Asn Ile Leu Phe Gly Leu Tyr Cys
1               5                   10                  15

Thr Leu Ile Tyr Ile Tyr Leu Ile Thr Lys Asn Ser Glu Gly Tyr Tyr
            20                  25                  30

Phe Leu Val Ser Asp Lys Met Leu Tyr Ala Ile Val Ile Ser Thr Ile
        35                  40                  45

Leu Cys Pro Tyr Ser Lys Tyr Ala Ile Glu Tyr Ile Ala Phe Asn Phe
    50                  55                  60

Ile Lys Lys Asp Phe Phe Glu Arg Arg Lys Asn Leu Asn Asn Ala Pro
65              70                  75                  80

Val Ala Lys Leu Asn Leu Phe Met Leu Tyr Asn Leu Leu Cys Leu Val
                85                  90                  95

Leu Ala Ile Pro Phe Gly Leu Gly Leu Phe Ile Ser Ile Lys Asn
            100                 105                 110

Asn

<210> SEQ ID NO 457
<211> LENGTH: 342
<212> TYPE: DNA
<213> ORGANISM: Escherichia coli

<400> SEQUENCE: 457
atgagcttaa gatactacat aaaaaatatt ttatttggcc tgtactgcac acttatatat      60 atataccta taacaaaaaa cagcgaaggg tattatttcc ttgtgtcaga taagatgcta     120
tatgcaatag tgataagcac tattctatgt ccatattcaa aatatgctat tgaatacata     180
gcttttaact tcataaagaa agattttttc gaaagaagaa aaaacctaaa taacgccccc     240
gtagcaaaat taaacctatt tatgctatat aatctacttt gtttggtcct agcaatccca     300
tttggattgc taggactttt tatatcaata agaataatt aa                         342

<210> SEQ ID NO 458
<211> LENGTH: 85
<212> TYPE: PRT
<213> ORGANISM: Escherichia coli

<400> SEQUENCE: 458

Met Gly Leu Lys Leu His Ile His Trp Phe Asp Lys Lys Thr Glu Glu
1               5                   10                  15

Phe Lys Gly Gly Glu Tyr Ser Lys Asp Phe Gly Asp Asp Gly Ser Val
            20                  25                  30

Ile Glu Ser Leu Gly Met Pro Leu Lys Asp Asn Ile Asn Asn Gly Trp
        35                  40                  45

Phe Asp Val Glu Lys Pro Trp Val Ser Ile Leu Gln Pro His Phe Lys
    50                  55                  60

Asn Val Ile Asp Ile Ser Lys Asp Tyr Phe Val Ser Phe Val Tyr
65              70                  75                  80

Arg Asp Gly Asn Trp
                85

<210> SEQ ID NO 459
<211> LENGTH: 258
<212> TYPE: DNA
<213> ORGANISM: Escherichia coli

<400> SEQUENCE: 459

```
atgggctta aattacatat tcattggttt gataagaaaa ccgaagagtt taaaggcggt      60
gaatactcaa aagacttcgg tgatgatggt tctgtcattg aaagtctggg gatgccttta    120
aaggataata ttaataatgg ttggtttgat gttgaaaaac catgggtttc gatattacag    180
ccacacttta aaaatgtaat cgatattagt aaatttgatt actttgtatc ctttgtttac    240
cgggatggta actggtaa                                                  258
```

<210> SEQ ID NO 460
<211> LENGTH: 86
<212> TYPE: PRT
<213> ORGANISM: Escherichia coli

<400> SEQUENCE: 460

```
Met Glu Leu Lys His Ser Ile Ser Asp Tyr Thr Glu Ala Glu Phe Leu
1               5                   10                  15
Glu Phe Val Lys Lys Ile Cys Arg Ala Glu Gly Ala Thr Glu Glu Asp
                20                  25                  30
Asp Asn Lys Leu Val Arg Glu Phe Glu Arg Leu Thr Glu His Pro Asp
            35                  40                  45
Gly Ser Asp Leu Ile Tyr Tyr Pro Arg Asp Asp Arg Glu Asp Ser Pro
        50                  55                  60
Glu Gly Ile Val Lys Glu Ile Lys Glu Trp Arg Ala Ala Asn Gly Lys
65                  70                  75                  80
Ser Gly Phe Lys Gln Gly
                85
```

<210> SEQ ID NO 461
<211> LENGTH: 261
<212> TYPE: DNA
<213> ORGANISM: Escherichia coli

<400> SEQUENCE: 461

```
atggaactga acatagtat tagtgattat accgaggctg aatttctgga gtttgtaaaa      60
aaaatatgta gagctgaagg tgctactgaa gaggatgaca taaaattagt gagagagttt    120
gagcgattaa ctgagcaccc agatggttca gatctgattt attatcctcg cgatgacagg    180
gaagatagtc ctgaagggat tgtcaaggaa attaaagaat ggcgagctgc taacggtaag    240
tcaggattta acagggctg a                                               261
```

<210> SEQ ID NO 462
<211> LENGTH: 178
<212> TYPE: PRT
<213> ORGANISM: Citrobacter freundii

<400> SEQUENCE: 462

```
Met Met Asn Glu His Ser Ile Asp Thr Asp Asn Arg Lys Ala Asn Asn
1               5                   10                  15
Ala Leu Tyr Leu Phe Ile Ile Ile Gly Leu Ile Pro Leu Leu Cys Ile
                20                  25                  30
Phe Val Val Tyr Tyr Lys Thr Pro Asp Ala Leu Leu Leu Arg Lys Ile
            35                  40                  45
Ala Thr Ser Thr Glu Asn Leu Pro Ser Ile Thr Ser Ser Tyr Asn Pro
        50                  55                  60
Leu Met Thr Lys Val Met Asp Ile Tyr Cys Lys Thr Ala Pro Phe Leu
65                  70                  75                  80
Ala Leu Ile Leu Tyr Ile Leu Thr Phe Lys Ile Arg Lys Leu Ile Asn
```

85                  90                  95
Asn Thr Asp Arg Asn Thr Val Leu Arg Ser Cys Leu Leu Ser Pro Leu
                100                 105                 110

Val Tyr Ala Ala Ile Val Tyr Leu Phe Cys Phe Arg Asn Phe Glu Leu
            115                 120                 125

Thr Thr Ala Gly Arg Pro Val Arg Leu Met Ala Thr Asn Asp Ala Thr
        130                 135                 140

Leu Leu Leu Phe Tyr Ile Gly Leu Tyr Ser Ile Ile Phe Phe Thr Thr
145                 150                 155                 160

Tyr Ile Thr Leu Phe Thr Pro Val Thr Ala Phe Lys Leu Leu Lys Lys
                165                 170                 175

Arg Gln

<210> SEQ ID NO 463
<211> LENGTH: 537
<212> TYPE: DNA
<213> ORGANISM: Citrobacter freundii

<400> SEQUENCE: 463
atgatgaatg aacactcaat agatacggac aacagaaagg ccaataacgc attgtattta      60
tttataataa tcggattaat accattattg tgcattttg ttgtttacta caaaacgcca      120
gacgctttac ttttacgtaa aattgctaca agcactgaga atctcccgtc aataacatcc     180
tcctacaacc cattaatgac aaaggttatg gatatttatt gtaaaacagc gcctttcctt     240
gccttaatac tatacatcct aacctttaaa atcagaaaat taatcaacaa caccgacagg     300
aacactgtac ttagatcttg tttattaagt ccattggtct atgcagcaat tgtttatcta     360
ttctgcttcc gaatttttga gttaacaaca gccggaaggc ctgtcagatt aatggccacc     420
aatgacgcaa cactattgtt attttatatt ggtctgtact caataatttt ctttacaacc     480
tatatcacgc tattcacacc agtcactgca tttaaattat taaaaaaaag gcagtaa       537

<210> SEQ ID NO 464
<211> LENGTH: 111
<212> TYPE: PRT
<213> ORGANISM: Escherichia coli

<400> SEQUENCE: 464

Met Asn Arg Lys Tyr Tyr Phe Asn Asn Met Trp Trp Gly Trp Val Thr
1               5                   10                  15

Gly Gly Tyr Met Leu Tyr Met Ser Trp Asp Tyr Glu Phe Lys Tyr Arg
            20                  25                  30

Leu Leu Phe Trp Cys Ile Ser Leu Cys Gly Met Val Leu Tyr Pro Val
        35                  40                  45

Ala Lys Trp Tyr Ile Glu Asp Thr Ala Leu Lys Phe Thr Arg Pro Asp
    50                  55                  60

Phe Trp Asn Ser Gly Phe Phe Ala Asp Thr Pro Gly Lys Met Gly Leu
65                  70                  75                  80

Leu Ala Val Tyr Thr Gly Thr Val Phe Ile Leu Ser Leu Pro Leu Ser
                85                  90                  95

Met Ile Tyr Ile Leu Ser Val Ile Ile Lys Arg Leu Ser Val Arg
            100                 105                 110

<210> SEQ ID NO 465
<211> LENGTH: 336
<212> TYPE: DNA
<213> ORGANISM: Escherichia coli

<400> SEQUENCE: 465

```
atgaacagaa aatattattt taataatatg tggtggggat gggtgacggg gggatatatg      60
ctgtatatgt catgggatta tgagtttaaa tacagattac tgttctggtg tatttctctc     120
tgcggaatgg ttttgtatcc ggttgcaaaa tggtatattg aagatacagc tctaaaattt     180
acccggcctg atttctggaa cagcggtttt tttgctgata cacctggaaa aatgggggttg    240
cttgcggttt atacgggtac tgttttcata ttatctcttc cgttaagtat gatatatatt     300
ctttctgtta ttataaaaag gctgtctgta agatag                                336
```

<210> SEQ ID NO 466
<211> LENGTH: 115
<212> TYPE: PRT
<213> ORGANISM: Escherichia coli

<400> SEQUENCE: 466

```
Met Lys Leu Asp Ile Ser Val Lys Tyr Leu Leu Lys Ser Leu Ile Pro
1               5                   10                  15
Ile Leu Ile Ile Leu Thr Val Phe Tyr Leu Gly Trp Lys Asp Asn Gln
            20                  25                  30
Glu Asn Ala Arg Met Phe Tyr Ala Phe Ile Gly Cys Ile Ile Ser Ala
        35                  40                  45
Ile Thr Phe Pro Phe Ser Met Arg Ile Ile Gln Lys Met Val Ile Arg
    50                  55                  60
Phe Thr Gly Lys Glu Phe Trp Gln Lys Asp Phe Phe Thr Asn Pro Val
65                  70                  75                  80
Gly Gly Ser Leu Thr Ala Ile Phe Glu Leu Phe Cys Phe Val Ile Ser
                85                  90                  95
Val Pro Val Val Ala Ile Tyr Leu Ile Phe Ile Leu Cys Lys Ala Leu
            100                 105                 110
Ser Gly Lys
        115
```

<210> SEQ ID NO 467
<211> LENGTH: 348
<212> TYPE: DNA
<213> ORGANISM: Escherichia coli

<400> SEQUENCE: 467

```
atgaaactgg atatatctgt aaagtattta ctgaaaagcc tgataccaat cctcattatt     60
cttacagttt ttatctggga tggaaagat aaccaggaaa atgcaagaat gttttatgcg    120
ttcatcggat gcattatcag tgccattact tttccttttt caatgaggat aatacagaaa    180
atggtaataa ggtttacagg gaagaattc tggcaaaaag acttctttac aaatccagtt    240
ggcggaagct taactgcaat atttgaatta ttctgtttcg ttatatcagt tcctgtggtt    300
gccatttact aattttttat actctgcaaa gccctttcag gaaaatga                 348
```

<210> SEQ ID NO 468
<211> LENGTH: 131
<212> TYPE: PRT
<213> ORGANISM: Escherichia coli

<400> SEQUENCE: 468

```
Met His Asn Thr Leu Leu Glu Lys Ile Ile Ala Tyr Leu Ser Leu Pro
1               5                   10                  15
Gly Phe His Ser Leu Asn Asn Pro Pro Leu Ser Glu Ala Phe Asn Leu
```

```
            20                  25                  30
Tyr Val His Thr Ala Pro Leu Ala Ala Thr Ser Leu Phe Ile Phe Thr
            35                  40                  45

His Lys Glu Leu Glu Leu Lys Pro Lys Ser Ser Pro Leu Arg Ala Leu
 50                  55                  60

Lys Ile Leu Thr Pro Phe Thr Ile Leu Tyr Ile Ser Met Ile Tyr Cys
 65                  70                  75                  80

Phe Leu Leu Thr Asp Thr Glu Leu Thr Leu Ser Ser Lys Thr Phe Val
                 85                  90                  95

Leu Ile Val Lys Lys Arg Ser Val Phe Val Phe Leu Tyr Asn Thr
                100                 105                 110

Ile Tyr Trp Asp Ile Tyr Ile His Ile Phe Val Leu Leu Val Pro Tyr
                115                 120                 125

Arg Asn Ile
    130

<210> SEQ ID NO 469
<211> LENGTH: 396
<212> TYPE: DNA
<213> ORGANISM: Escherichia coli

<400> SEQUENCE: 469
atgcacaata cactcctcga aaaaatcatc gcatacctat ccctaccagg atttcattca      60
ttaaacaacc cgcccctaag cgaagcattc aatctctatg ttcatacagc ccctttagct     120
gcaaccagct tattcatatt cacacacaaa gaattagagt taaaaccaaa gtcgtcacct     180
ctgcgggcac taagatatat aactcctttc actattcttt atatatccat gatatactgt     240
ttcttgctaa ctgacacaga actaaccttg tcatcaaaaa catttgtatt aatagtcaaa     300
aaacgatctg ttttgtctt ttttctatat aacactatat attgggatat atatattcac     360
atatttgtac ttttggttcc ttataggaac atataa                              396

<210> SEQ ID NO 470
<211> LENGTH: 85
<212> TYPE: PRT
<213> ORGANISM: Escherichia coli

<400> SEQUENCE: 470

Met Glu Leu Lys Asn Ser Ile Ser Asp Tyr Thr Glu Thr Glu Phe Lys
  1               5                  10                  15

Lys Ile Ile Glu Asp Ile Ile Asn Cys Glu Gly Asp Glu Lys Lys Gln
                 20                  25                  30

Asp Asp Asn Leu Glu His Phe Ile Ser Val Thr Glu His Pro Ser Gly
                 35                  40                  45

Ser Asp Leu Ile Tyr Tyr Pro Glu Gly Asn Asn Asp Gly Ser Pro Glu
     50                  55                  60

Ala Val Ile Lys Glu Ile Lys Glu Trp Arg Ala Ala Asn Gly Lys Ser
 65                  70                  75                  80

Gly Phe Lys Gln Gly
             85

<210> SEQ ID NO 471
<211> LENGTH: 258
<212> TYPE: DNA
<213> ORGANISM: Escherichia coli

<400> SEQUENCE: 471
```

```
atggaactga aaacagcat tagtgattac actgaaactg aattcaaaaa aattattgaa      60
gacatcatca attgtgaagg tgatgaaaaa aaacaggatg ataacctcga gcattttata    120
agtgttactg agcatcctag tggttctgat ctgatttatt acccagaagg taataatgat    180
ggtagccctg aagctgttat taaagagatt aaagaatggc gagctgctaa cggtaagtca    240
ggatttaaac agggctga                                                   258
```

<210> SEQ ID NO 472
<211> LENGTH: 98
<212> TYPE: PRT
<213> ORGANISM: Lactococcus lactis subsp. lactis

<400> SEQUENCE: 472

```
Met Lys Lys Lys Gln Ile Glu Phe Glu Asn Glu Leu Arg Ser Met Leu
1               5                   10                  15

Ala Thr Ala Leu Glu Lys Asp Ile Ser Gln Glu Glu Arg Asn Ala Leu
            20                  25                  30

Asn Ile Ala Glu Lys Ala Leu Asp Asn Ser Glu Tyr Leu Pro Lys Ile
        35                  40                  45

Ile Leu Asn Leu Arg Lys Ala Leu Thr Pro Leu Ala Ile Asn Arg Thr
    50                  55                  60

Leu Asn His Asp Leu Ser Glu Leu Tyr Lys Phe Ile Thr Ser Ser Lys
65                  70                  75                  80

Ala Ser Asn Lys Asn Leu Gly Gly Gly Leu Ile Met Ser Trp Gly Arg
                85                  90                  95

Leu Phe
```

<210> SEQ ID NO 473
<211> LENGTH: 297
<212> TYPE: DNA
<213> ORGANISM: Lactococcus lactis subsp. lactis

<400> SEQUENCE: 473

```
atgaaaaaaa aacaaataga atttgaaaac gagctaagaa gtatgttggc taccgcccttt     60 gaaaaagaca ttagtcaaga ggaaagaaat gctctgaata ttgcagaaaa ggcgcttgac    120
aattctgaat atttaccaaa aattattta aacctcagaa aagccctaac tccattagct    180
ataaatcgaa cacttaacca tgatttatct gaactgtata aattcattac aagttccaaa    240
gcatcaaaca aaaatttagg tggtggttta attatgtcgt ggggacgact attctaa      297
```

<210> SEQ ID NO 474
<211> LENGTH: 98
<212> TYPE: PRT
<213> ORGANISM: Lactococcus lactis subsp. cremoris

<400> SEQUENCE: 474

```
Met Lys Lys Lys Gln Ile Glu Phe Glu Asn Glu Leu Arg Ser Met Leu
1               5                   10                  15

Ala Thr Ala Leu Glu Lys Asp Ile Ser Gln Glu Glu Arg Asn Ala Leu
            20                  25                  30

Asn Ile Ala Glu Lys Ala Leu Asp Asn Ser Glu Tyr Leu Pro Lys Ile
        35                  40                  45

Ile Leu Asn Leu Arg Lys Ala Leu Thr Pro Leu Ala Ile Asn Arg Thr
    50                  55                  60

Leu Asn His Asp Leu Ser Glu Leu Tyr Lys Phe Ile Thr Ser Ser Lys
65                  70                  75                  80
```

Ala Ser Asn Lys Asn Leu Gly Gly Gly Leu Ile Met Ser Trp Gly Arg
            85                  90                  95

Leu Phe

<210> SEQ ID NO 475
<211> LENGTH: 297
<212> TYPE: DNA
<213> ORGANISM: Lactococcus lactis subsp. cremoris

<400> SEQUENCE: 475
atgaaaaaaa aacaaataga atttgaaaac gagctaagaa gtatgttggc taccgcccTt      60 gaaaagaca ttagtcaaga ggaaagaaat gctctgaata ttgcagaaaa ggcgcttgac     120
aattctgaat atttaccaaa aattattta aacctcagaa aagccctaac tccattagct    180
ataaatcgaa cacttaacca tgatttatct gaactgtata aattcattac aagttccaaa   240
gcatcaaaca aaaatttagg tggtggttta attatgtcgt ggggacgact attctaa      297

<210> SEQ ID NO 476
<211> LENGTH: 87
<212> TYPE: PRT
<213> ORGANISM: Escherichia coli

<400> SEQUENCE: 476

Met Asn Lys Met Ala Met Ile Asp Leu Ala Lys Leu Phe Leu Ala Ser
1               5                   10                  15

Lys Ile Thr Ala Ile Glu Phe Ser Glu Arg Ile Cys Val Glu Arg Arg
            20                  25                  30

Arg Leu Tyr Gly Val Lys Asp Leu Ser Pro Asn Ile Leu Asn Cys Gly
        35                  40                  45

Glu Glu Leu Phe Met Ala Ala Glu Arg Phe Glu Pro Asp Ala Asp Arg
    50                  55                  60

Ala Asn Tyr Glu Ile Asp Asp Asn Gly Leu Lys Val Glu Val Arg Ser
65                  70                  75                  80

Ile Leu Glu Lys Phe Lys Leu
                85

<210> SEQ ID NO 477
<211> LENGTH: 249
<212> TYPE: DNA
<213> ORGANISM: Escherichia coli

<400> SEQUENCE: 477
atgatcgatt tggcgaaatt attttagct tcgaaaatta cagtgattga gttttcagag      60
cgaatttgtg ttgaacggag aagattgtat ggtgttaagg atttgtctcc gaatatatta    120
aattgtgggg aagagttgtc tatggctgct gagcgatttg agcctgatgc agatagggct    180
aattatgaaa ttgatgataa tggacttaag gtcgaggtcc gatctatctt ggaaaaactt    240
aaatcataa                                                            249

<210> SEQ ID NO 478
<211> LENGTH: 83
<212> TYPE: PRT
<213> ORGANISM: Escherichia coli

<400> SEQUENCE: 478

Met Lys Leu Ser Pro Lys Ala Ile Glu Val Cys Asn Glu Ala Ala
1               5                   10                  15

Lys Lys Gly Leu Trp Ile Leu Gly Ile Asp Gly Gly His Trp Leu Asn 20     25     30

Pro Gly Phe Arg Ile Asp Ser Ser Ala Ser Trp Thr Tyr Asp Met Pro
    35     40     45

Glu Glu Tyr Lys Ser Lys Ile Pro Glu Asn Asn Arg Leu Ala Ile Glu
  50     55     60

Asn Ile Lys Asp Asp Ile Glu Asn Gly Tyr Thr Ala Phe Ile Ile Thr
65     70     75     80

Leu Lys Met

<210> SEQ ID NO 479
<211> LENGTH: 243
<212> TYPE: DNA
<213> ORGANISM: Escherichia coli

<400> SEQUENCE: 479

```
atgaagttat caccaaaagc tgcaatagaa gtttgtaatg aagcagcgaa aaaaggctta      60
tggatttttgg gcattgatgg tgggcattgg ctgaatcctg gattcaggat agatagttca     120
gcatcatgga catatgatat gccggagaat acaaatcaaa atccctgaa ataatagat       180
tggctattga aaatattaaa gatgatattg agaatggata cactgctttc attatcacgt    240
taa                                                                   243
```

<210> SEQ ID NO 480
<211> LENGTH: 85
<212> TYPE: PRT
<213> ORGANISM: Escherichia coli

<400> SEQUENCE: 480

Met Gly Leu Lys Leu His Ile Asn Trp Phe Asp Lys Arg Thr Glu Glu
1     5     10     15

Phe Lys Gly Gly Glu Tyr Ser Lys Asp Phe Gly Asp Asp Gly Ser Val
    20     25     30

Ile Glu Arg Leu Gly Met Pro Phe Lys Asp Asn Ile Asn Asn Gly Trp
    35     40     45

Phe Asp Val Ile Ala Glu Trp Val Pro Leu Leu Gln Pro Tyr Phe Asn
  50     55     60

His Gln Ile Asp Ile Ser Asp Asn Glu Tyr Phe Val Ser Phe Asp Tyr
65     70     75     80

Arg Asp Gly Asp Trp
    85

<210> SEQ ID NO 481
<211> LENGTH: 258
<212> TYPE: DNA
<213> ORGANISM: Escherichia coli

<400> SEQUENCE: 481

```
atggggctta aattacatat taattggttt gataagacga ccgaggaatt taaaggtggt      60
gagtattcaa aagattttgg agatgatggc tcggtcattg aacgtcttgg aatgcctta     120
aaagataata tcaataatgg ttggtttgat gttatagctg aatgggtacc tttgctacaa    180
ccatacttta tcatcaaat tgatatttcc gataatgagt attttgtttc gtttgattat    240
cgtgatggtg attggtga                                                   258
```

<210> SEQ ID NO 482
<211> LENGTH: 85
<212> TYPE: PRT

<213> ORGANISM: Escherichia coli

<400> SEQUENCE: 482

Met Glu Leu Lys Lys Ser Ile Gly Asp Tyr Thr Glu Thr Glu Phe Lys
1               5                   10                  15

Lys Ile Ile Glu Asn Ile Ile Asn Cys Glu Gly Asp Glu Lys Lys Gln
            20                  25                  30

Asp Asp Asn Leu Glu His Phe Ile Ser Val Thr Glu His Pro Ser Gly
        35                  40                  45

Ser Asp Leu Ile Tyr Tyr Pro Glu Gly Asn Asn Asp Gly Ser Pro Glu
    50                  55                  60

Ala Val Ile Lys Glu Ile Lys Glu Trp Arg Ala Ala Asn Gly Lys Ser
65                  70                  75                  80

Gly Phe Lys Gln Gly
            85

<210> SEQ ID NO 483
<211> LENGTH: 258
<212> TYPE: DNA
<213> ORGANISM: Escherichia coli

<400> SEQUENCE: 483
gtggagctaa agaaaagtat tggtgattac actgaaaccg aattcaaaaa aattattgaa       60
aacatcatca attgtgaagg tgatgaaaaa aaacaggatg ataacctcga gcattttata      120
agtgttactg agcatcctag tggttctgat ctgatttatt acccagaagg taataatgat      180
ggtagccctg aagctgttat taaagagatt aaagaatggc gagctgctaa cggtaagtca      240
ggatttaaac agggctga                                                    258

<210> SEQ ID NO 484
<211> LENGTH: 86
<212> TYPE: PRT
<213> ORGANISM: Escherichia coli

<400> SEQUENCE: 484

Met Glu Leu Lys His Ser Ile Ser Asp Tyr Thr Glu Ala Glu Phe Leu
1               5                   10                  15

Gln Leu Val Thr Thr Ile Cys Asn Ala Asp Thr Ser Ser Glu Glu Glu
            20                  25                  30

Leu Val Lys Leu Val Thr His Phe Glu Glu Met Thr Glu His Pro Ser
        35                  40                  45

Gly Ser Asp Leu Ile Tyr Tyr Pro Lys Glu Gly Asp Asp Asp Ser Pro
    50                  55                  60

Ser Gly Ile Val Asn Thr Val Lys Gln Trp Arg Ala Ala Asn Gly Lys
65                  70                  75                  80

Ser Gly Phe Lys Gln Gly
            85

<210> SEQ ID NO 485
<211> LENGTH: 261
<212> TYPE: DNA
<213> ORGANISM: Escherichia coli

<400> SEQUENCE: 485
atggaactga agcatagcat tagtgattat acagaagctg aattttttaca acttgtaaca       60 acaatttgta atgcgaacac ttccagtgaa gaagaactgg ttaaattggt tacacacttt      120
gaggaaatga ctgagcaccc tagtggtagt gatttaatat attcccaaa agaaggtgat       180

```
gatgactcac cttcaggtat tgtaaacaca gtaaaacaat ggcgagccgc taacggtaag    240
tcaggattta aacagggcta a                                              261
```

<210> SEQ ID NO 486
<211> LENGTH: 141
<212> TYPE: PRT
<213> ORGANISM: Escherichia coli

<400> SEQUENCE: 486

```
Met Leu Thr Leu Tyr Gly Tyr Ile Arg Asn Val Phe Leu Tyr Arg Met
1               5                   10                  15

Asn Asp Arg Ser Cys Gly Asp Phe Met Lys Val Ile Ser Met Lys Phe
            20                  25                  30

Ile Phe Ile Leu Thr Ile Ile Ala Leu Ala Ala Val Phe Phe Trp Ser
        35                  40                  45

Glu Asp Lys Gly Pro Ala Cys Tyr Gln Val Ser Asp Glu Gln Ala Arg
    50                  55                  60

Thr Phe Val Lys Asn Asp Tyr Leu Gln Arg Met Lys Arg Trp Asp Asn
65                  70                  75                  80

Asp Val Gln Leu Leu Gly Thr Glu Ile Pro Lys Ile Thr Trp Glu Lys
                85                  90                  95

Ile Glu Arg Ser Leu Thr Asp Val Glu Asp Glu Lys Thr Leu Leu Val
            100                 105                 110

Pro Phe Lys Ala Glu Gly Pro Asp Gly Lys Arg Met Tyr Tyr Gly Met
        115                 120                 125

Tyr His Cys Glu Glu Gly Tyr Val Glu Tyr Ala Asn Asp
    130                 135                 140
```

<210> SEQ ID NO 487
<211> LENGTH: 354
<212> TYPE: DNA
<213> ORGANISM: Escherichia coli

<400> SEQUENCE: 487

```
atgaaagtaa ttagcatgaa atttattttt attttaacga ttattgctct tgctgctgtt    60 ttttctggt ctgaagataa aggtccggca tgctatcagg tcagcgatga acaggccaga   120
acgtttgtaa aaaatgatta cctgcaaaga atgaaacgct gggacaacga tgtacaactt   180
cttggtacag aaatcccgaa aattacatgg gaaaagattg agagaagttt aacagatgtt   240
gaagatgaaa aaacacttct tgtcccattt aaagctgaag cccggacgg taagagaatg    300 tattatggca tgtaccattg tgaggaggga tatgttgaat atgcgaatga ctaa          354
```

<210> SEQ ID NO 488
<211> LENGTH: 175
<212> TYPE: PRT
<213> ORGANISM: Escherichia coli

<400> SEQUENCE: 488

```
Met Thr Ser Asn Lys Asp Lys Asn Lys Lys Ala Asn Glu Ile Leu Tyr
1               5                   10                  15

Ala Phe Ser Ile Ile Gly Ile Ile Pro Leu Met Ala Ile Leu Ile Leu
            20                  25                  30

Arg Ile Asn Asp Pro Tyr Ser Gln Val Leu Tyr Tyr Leu Tyr Asn Lys
        35                  40                  45

Val Ala Phe Leu Pro Ser Ile Thr Ser Leu His Asp Pro Val Met Thr
    50                  55                  60
```

```
Thr Leu Met Ser Asn Tyr Asn Lys Thr Ala Pro Val Met Gly Ile Leu
 65                  70                  75                  80

Val Phe Leu Cys Thr Tyr Lys Thr Arg Glu Ile Ile Lys Pro Val Thr
                 85                  90                  95

Arg Lys Leu Val Val Gln Ser Cys Phe Trp Gly Pro Phe Tyr Ala
            100                 105                 110

Ile Leu Ile Tyr Ile Thr Leu Phe Tyr Asn Leu Glu Leu Thr Thr Ala
            115                 120                 125

Gly Gly Phe Phe Lys Leu Leu Ser His Asn Val Ile Thr Leu Phe Ile
            130                 135             140

Leu Tyr Cys Ser Ile Tyr Phe Thr Val Leu Thr Met Thr Tyr Ala Ile
145                 150                 155                 160

Leu Leu Met Pro Leu Leu Val Ile Lys Tyr Phe Lys Gly Arg Gln
                165                 170                 175
```

<210> SEQ ID NO 489
<211> LENGTH: 528
<212> TYPE: DNA
<213> ORGANISM: Escherichia coli

<400> SEQUENCE: 489

```
atgaccagca ataaagataa gaacaagaaa gcaaacgaaa tattatatgc attttccata    60
atcgggatta ttccattaat ggctatatta atacttcgaa taaatgatcc atattctcaa   120
gtgctgtact acttatataa taaggtggca tttctcccctt ctattacatc attgcatgat   180
cccgtcatga caaacttat gtcaaactac aacaagacag cgccagttat gggtattctc    240
gtttttcttt gcacatataa gacaagagaa atcataaagc cagtaacaag aaaacttgtt   300
gtgcaatcct gttctggggg gcccgttttt tatgccattc tgatttatat cacactgttc   360
tataatctgg aactaacaac agcaggtggt tttttttaaat tattatctca taatgtcatc   420
actctgttta ttttatattg ctccatttac tttactgttt taaccatgac atatgcgatt   480
ttactgatgc cattacttgt cattaaatat tttaaaggga ggcagtaa                528
```

<210> SEQ ID NO 490
<211> LENGTH: 78
<212> TYPE: PRT
<213> ORGANISM: Escherichia coli

<400> SEQUENCE: 490

```
Met Asp Arg Lys Arg Thr Lys Leu Glu Leu Leu Phe Ala Phe Ile Ile
  1               5                  10                  15

Asn Ala Thr Ala Ile Tyr Ile Ala Leu Ala Ile Tyr Asp Cys Val Phe
                 20                  25                  30

Arg Gly Lys Asp Phe Leu Ser Met His Thr Phe Cys Phe Ser Ala Leu
             35                  40                  45

Met Ser Ala Ile Cys Tyr Phe Val Gly Asp Asn Tyr Tyr Ser Ile Ser
         50                  55                  60

Asp Lys Ile Lys Arg Arg Ser Tyr Glu Asn Ser Asp Ser Lys
 65                  70                  75
```

<210> SEQ ID NO 491
<211> LENGTH: 237
<212> TYPE: DNA
<213> ORGANISM: Escherichia coli

<400> SEQUENCE: 491

```
atggatagaa aaagaacaaa attagagttg ttatttgcat ttataataaa tgccaccgca      60
atatatattg cattagctat atatgattgt gttttagag gaaaggactt tttatccatg      120
catacatttt gcttctctgc attaatgtct gcaatatgtt actttgttgg tgataattat    180
tattcaatat ccgataagat aaaaaggaga tcatatgaga actctgactc taaatga       237
```

<210> SEQ ID NO 492
<211> LENGTH: 113
<212> TYPE: PRT
<213> ORGANISM: Shigella sonnei

<400> SEQUENCE: 492

```
Met Ser Leu Arg Tyr Tyr Ile Lys Asn Ile Leu Phe Gly Leu Tyr Cys
1               5                   10                  15

Ala Leu Ile Tyr Ile Tyr Leu Ile Thr Lys Asn Asn Glu Gly Tyr Tyr
            20                  25                  30

Phe Leu Ala Ser Asp Lys Met Leu Tyr Ala Ile Val Ile Ser Thr Ile
        35                  40                  45

Leu Cys Pro Tyr Ser Lys Tyr Ala Ile Glu His Ile Phe Phe Lys Phe
    50                  55                  60

Ile Lys Lys Asp Phe Phe Arg Lys Arg Lys Asn Leu Asn Lys Cys Pro
65                  70                  75                  80

Arg Gly Lys Ile Lys Pro Tyr Leu Cys Val Tyr Asn Leu Leu Cys Leu
                85                  90                  95

Val Leu Ala Ile Pro Phe Gly Leu Leu Gly Leu Val Tyr Ile Asn Lys
            100                 105                 110

Glu
```

<210> SEQ ID NO 493
<211> LENGTH: 342
<212> TYPE: DNA
<213> ORGANISM: Shigella sonnei

<400> SEQUENCE: 493

```
atgagtttaa gatactacat aaaaaatatt ttgtttggcc tatactgcgc acttatatat    60 atataccta taacaaaaaa caacgaaggg tattatttcc tagcgtcaga taagatgcta    120
tacgcaatag tgataagcac tattctatgc ccatattcaa aatatgctat tgaacacata    180 tttttaagt tcataaagaa agattttttc agaaaaagaa aaaacctaaa taatgccccc    240
cgtggcaaaa ttaaaccgta tttatgcgta tacaatctac tttgtttggt cctagcaatc    300
ccatttggat tgctaggact tgtttatatc aataagaat aa                        342
```

<210> SEQ ID NO 494
<211> LENGTH: 113
<212> TYPE: PRT
<213> ORGANISM: Escherichia coli

<400> SEQUENCE: 494

```
Met Ser Leu Arg Tyr Tyr Ile Lys Asn Ile Leu Phe Gly Leu Tyr Cys
1               5                   10                  15

Thr Leu Ile Tyr Ile Tyr Leu Ile Thr Lys Asn Ser Glu Gly Tyr Tyr
            20                  25                  30

Phe Leu Val Thr Asp Lys Met Leu Tyr Ala Ile Val Ile Ser Thr Ile
        35                  40                  45

Leu Cys Pro Tyr Ser Lys Tyr Ala Ile Glu His Ile Ala Phe Asn Phe
    50                  55                  60
```

```
Ile Lys Lys His Phe Phe Glu Arg Arg Lys Asn Leu Asn Asn Ala Pro
 65                  70                  75                  80

Val Ala Lys Leu Asn Leu Phe Met Leu Tyr Asn Leu Leu Cys Leu Val
                 85                  90                  95

Leu Ala Ile Pro Phe Gly Leu Leu Gly Leu Phe Ile Ser Ile Lys Asn
            100                 105                 110

Asn

<210> SEQ ID NO 495
<211> LENGTH: 342
<212> TYPE: DNA
<213> ORGANISM: Escherichia coli

<400> SEQUENCE: 495
atgagcttaa gatactacat aaaaaatatt ttatttggcc tgtactgcac acttatatat     60
atatacctta taacaaaaaa cagcgaagag tattatttcc ttgtgacaga taagatgcta    120
tatgcaatag tgataagcac tattctatgt ccatattcaa atatgctat tgaacacata     180 gcttttaact tcataaagaa acattttttc gaaagaagaa aaaacctaaa taacgccccc    240
gtagcaaaat taaacctatt tatgctatat aatctacttt gtttggtcct agcaatccca    300
tttggattgc taggactttt tatatcaata aagaataatt aa                       342

<210> SEQ ID NO 496
<211> LENGTH: 113
<212> TYPE: PRT
<213> ORGANISM: Leuconostoc gelidum

<400> SEQUENCE: 496

Met Arg Lys Asn Asn Ile Leu Leu Asp Asp Ala Lys Ile Tyr Thr Asn
  1               5                  10                  15

Lys Leu Tyr Leu Leu Ile Asp Arg Lys Asp Asp Ala Gly Tyr Gly
                 20                  25                  30

Asp Ile Cys Asp Val Leu Phe Gln Val Ser Lys Lys Leu Asp Ser Thr
             35                  40                  45

Lys Asn Val Glu Ala Leu Ile Asn Arg Leu Val Asn Tyr Ile Arg Ile
 50                  55                  60

Thr Ala Ser Thr Asn Arg Ile Lys Phe Ser Lys Asp Glu Glu Ala Val
 65                  70                  75                  80

Ile Ile Glu Leu Gly Val Ile Gly Gln Lys Ala Gly Leu Asn Gly Gln
                 85                  90                  95

Tyr Met Ala Asp Phe Ser Asp Lys Ser Gln Tyr Ser Ile Phe Glu
            100                 105                 110

Arg

<210> SEQ ID NO 497
<211> LENGTH: 342
<212> TYPE: DNA
<213> ORGANISM: Leuconostoc gelidum

<400> SEQUENCE: 497
ttgagaaaaa ataacatttt attggacgat gctaaaatat acacgaacaa actctatttg     60
ctattaatcg atagaaaaga tgacgctggg tatggagata tttgtgatgt tttgtttcag    120
gtatccaaaa aattagatag cacaaaaaat gtagaagcat tgattaaccg attggtcaat    180
tatatacgaa ttaccgcttc aacaaacaga attaagtttt caaaagatga agaggctgta    240
attatagaac ttggtgtaat tggtcagaag gctggattaa acggccaata catggctgat    300
```

```
ttttctgaca aatctcagtt ttatagtatc tttgaaagat aa                              342
```

<210> SEQ ID NO 498
<211> LENGTH: 91
<212> TYPE: PRT
<213> ORGANISM: Lactococcus lactis subsp. cremoris

<400> SEQUENCE: 498

Met Lys Lys Val Asp Thr Glu Lys Gln Ile Thr Ser Trp Ala Ser
1               5                   10                  15

Asp Leu Ala Ser Lys Asn Glu Thr Lys Val Gln Glu Lys Leu Ile Leu
            20                  25                  30

Ser Ser Tyr Ile Gln Asp Ile Glu Asn His Val Tyr Phe Pro Lys Ala
        35                  40                  45

Met Ile Ser Leu Glu Lys Lys Leu Arg Asp Gln Asn Asn Ile Cys Ala
    50                  55                  60

Leu Ser Lys Glu Val Asn Gln Phe Tyr Phe Lys Val Val Glu Val Asn
65                  70                  75                  80

Gln Arg Lys Ser Trp Met Val Gly Leu Ile Val
                85                  90

<210> SEQ ID NO 499
<211> LENGTH: 276
<212> TYPE: DNA
<213> ORGANISM: Lactococcus lactis subsp. cremoris

<400> SEQUENCE: 499

```
atgaaaaaaa aagttgatac agaaaaacaa attacttctt gggcatctga cttagcttcc        60
aaaaatgaaa caaaggttca agaaaaatta atactgtctt cttatattca ggacatcgaa       120
aaccatgttt actttccaaa agcaatgatt tctttagaaa aaaaattacg agaccaaaat       180
aatatttgcg ctttatcaaa agaagtcaat cagtttttatt ttaaagttgt tgaagtaaat      240
caaagaaaat cctggatggt aggtttgata gtttaa                                 276
```

<210> SEQ ID NO 500
<211> LENGTH: 112
<212> TYPE: PRT
<213> ORGANISM: Pediococcus acidilactici

<400> SEQUENCE: 500

Met Asn Lys Thr Lys Ser Glu His Ile Lys Gln Gln Ala Leu Asp Leu
1               5                   10                  15

Phe Thr Arg Leu Gln Phe Leu Leu Gln Lys His Asp Thr Ile Glu Pro
            20                  25                  30

Tyr Gln Tyr Val Leu Asp Ile Leu Glu Thr Gly Ile Ser Lys Thr Lys
        35                  40                  45

His Asn Gln Gln Thr Pro Glu Arg Gln Ala Arg Val Val Tyr Asn Lys
    50                  55                  60

Ile Ala Ser Gln Ala Leu Val Asp Lys Leu His Phe Thr Ala Glu Glu
65                  70                  75                  80

Asn Lys Val Leu Ala Ala Ile Asn Glu Leu Ala His Ser Gln Lys Gly
                85                  90                  95

Trp Gly Glu Phe Asn Met Leu Asp Thr Thr Asn Thr Trp Pro Ser Gln
                100                 105                 110

<210> SEQ ID NO 501
<211> LENGTH: 339

<212> TYPE: DNA
<213> ORGANISM: Pediococcus acidilactici

<400> SEQUENCE: 501

```
atgaataaga ctaagtcgga acatattaaa caacaagctt tggacttatt tactaggcta    60
cagtttttac tacagaagca cgatactatc gaaccttacc agtacgtttt agatattctg   120
gagactggta tcagtaaaac taaacataac cagcaaacgc ctgaacgaca agctcgtgta   180
gtctacaaca agattgccag ccaagcgtta gtagataagt tacattttac tgccgaagaa   240
aacaaagttc tagcagccat caatgaattg gcgcattctc aaaaagggtg gggcgagttt   300
aacatgctag atactaccaa tacgtggcct agccaatag                          339
```

<210> SEQ ID NO 502
<211> LENGTH: 88
<212> TYPE: PRT
<213> ORGANISM: Carnobacterium maltaromaticum

<400> SEQUENCE: 502

```
Met Ile Lys Asp Glu Lys Ile Asn Lys Ile Tyr Ala Leu Val Lys Ser
  1               5                  10                  15
Ala Leu Asp Asn Thr Asp Val Lys Asn Asp Lys Lys Leu Ser Leu Leu
                 20                  25                  30
Leu Met Arg Ile Gln Glu Thr Ser Ile Asn Gly Glu Leu Phe Tyr Asp
             35                  40                  45
Tyr Lys Lys Glu Leu Gln Pro Ala Ile Ser Met Tyr Ser Ile Gln His
         50                  55                  60
Asn Phe Arg Val Pro Asp Leu Val Lys Leu Leu Ala Leu Val Gln
 65                  70                  75                  80
Thr Pro Lys Ala Trp Ser Gly Phe
                 85
```

<210> SEQ ID NO 503
<211> LENGTH: 267
<212> TYPE: DNA
<213> ORGANISM: Carnobacterium maltaromaticum

<400> SEQUENCE: 503

```
atgataaaag atgaaaaaat aaataaaatc tatgctttag ttaagagcgc acttgataat    60
acggatgtta agaatgataa aaactttct ttacttctta tgagaataca agaaacatca   120
attaatggag aactatttta cgattataaa aagaattac agccagctat tagtatgtac   180
tctattcaac ataactttcg ggttcctgac gatctagtaa aactgttagc attagttcaa   240
acacctaaag cttggtcagg gttttaa                                       267
```

<210> SEQ ID NO 504
<211> LENGTH: 111
<212> TYPE: PRT
<213> ORGANISM: Carnobacterium maltaromaticum

<400> SEQUENCE: 504

```
Met Asp Ile Lys Ser Gln Thr Leu Tyr Leu Asn Leu Ser Glu Ala Tyr
  1               5                  10                  15
Lys Asp Pro Glu Val Lys Ala Asn Glu Phe Leu Ser Lys Leu Val Val
                 20                  25                  30
Gln Cys Ala Gly Lys Leu Thr Ala Ser Asn Ser Glu Asn Ser Tyr Ile
             35                  40                  45
Glu Val Ile Ser Leu Leu Ser Arg Gly Ile Ser Ser Tyr Tyr Leu Ser
```

```
                50                    55                     60
His Lys Arg Ile Ile Pro Ser Ser Met Leu Thr Ile Tyr Thr Gln Ile
 65                      70                   75                 80

Gln Lys Asp Ile Lys Asn Gly Asn Ile Asp Thr Glu Lys Leu Arg Lys
                     85                  90                  95

Tyr Glu Ile Ala Lys Gly Leu Met Ser Val Pro Tyr Ile Tyr Phe
                100                 105                 110
```

<210> SEQ ID NO 505
<211> LENGTH: 336
<212> TYPE: DNA
<213> ORGANISM: Carnobacterium maltaromaticum

<400> SEQUENCE: 505

```
atggatataa agtctcaaac attatatttg aatctaagcg aggcatataa agaccctgaa      60
gtaaaagcta atgaattctt atcaaaatta gttgtacaat gtgctgggaa attaacagct     120
tcaaacagtg agaacagtta tattgaagta atatcattgc tatctagggg tatttctagt     180
tattatttat cccataaacg tataattcct tcaagtatgt taactatata tactcaaata     240
caaaaggata taaaaaacgg gaatattgac accgaaaaat taggaaaata tgagatagca     300
aaaggattaa tgtccgttcc ttatatatat ttctaa                               336
```

<210> SEQ ID NO 506
<211> LENGTH: 245
<212> TYPE: PRT
<213> ORGANISM: Lactococcus lactis subsp. lactis

<400> SEQUENCE: 506

```
Met Arg Arg Tyr Leu Ile Leu Ile Val Ala Leu Ile Gly Ile Thr Gly
 1                5                  10                  15

Leu Ser Gly Cys Tyr Gln Thr Ser His Lys Lys Val Arg Phe Asp Glu
                 20                  25                  30

Gly Ser Tyr Thr Asn Phe Ile Tyr Asp Asn Lys Ser Tyr Phe Val Thr
             35                  40                  45

Asp Lys Glu Ile Pro Gln Glu Asn Val Asn Asn Ser Lys Val Lys Phe
         50                  55                  60

Tyr Lys Leu Leu Ile Val Asp Met Lys Ser Glu Lys Leu Leu Ser Ser
 65                  70                  75                  80

Ser Asn Lys Asn Ser Val Thr Leu Val Leu Asn Asn Ile Tyr Glu Ala
                 85                  90                  95

Ser Asp Lys Ser Leu Cys Met Gly Ile Asn Asp Arg Tyr Tyr Lys Ile
            100                 105                 110

Leu Pro Glu Ser Asp Lys Gly Ala Val Lys Ala Leu Arg Leu Gln Asn
        115                 120                 125

Phe Asp Val Thr Ser Asp Ile Ser Asp Asp Asn Phe Val Ile Asp Lys
    130                 135                 140

Asn Asp Ser Arg Lys Ile Asp Tyr Met Gly Asn Ile Tyr Ser Ile Ser
145                 150                 155                 160

Asp Thr Thr Val Ser Asp Glu Glu Leu Gly Glu Tyr Gln Asp Val Leu
                165                 170                 175

Ala Glu Val Arg Val Phe Asp Ser Ser Gly Lys Ser Ile Pro Arg
            180                 185                 190

Ser Glu Trp Gly Arg Ile Asp Lys Asp Gly Ser Asn Ser Lys Gln Ser
        195                 200                 205

Arg Thr Glu Trp Asp Tyr Gly Glu Ile His Ser Ile Arg Gly Lys Ser
```

```
            210                 215                 220
Leu Thr Glu Ala Phe Ala Val Glu Ile Asn Asp Asp Phe Lys Leu Ala
225                 230                 235                 240

Thr Lys Val Gly Asn
            245

<210> SEQ ID NO 507
<211> LENGTH: 738
<212> TYPE: DNA
<213> ORGANISM: Lactococcus lactis subsp. lactis

<400> SEQUENCE: 507
atgagaagat atttaatact tattgtggcc ttaataggga taacaggttt atcagggtgt      60
tatcaaacaa gtcataaaaa ggtgaggttt gacgaaggaa gttatactaa ttttatttat     120
gataataaat cgtatttcgt aactgataag gagattcctc aggagaacgt taacaattcc     180
aaagtaaaat tttataagct gttgattgtt gacatgaaaa gtgagaaact tttatcaagt     240
agcaacaaaa atagtgtgac tttggtctta ataatatttt atgaggcttc tgacaagtcg     300
ctatgtatgg gtattaacga cagatactat aagatacttc cagaaagtga taaggggcg      360 gtcaaagctt tgagattaca aactttgat gtgacaagcg atatttctga tgataatttt      420
gttattgata aaaatgattc acgaaaaatt gactatatgg aaatatttta cagtatatcg     480
gacaccaccg tatctgatga agaattggga gaatatcagg atgttttagc tgaagtacgt     540
gtgtttgatt cagttagtgg caaaagtatc ccgaggtctg aatgggggag aattgataag     600
gatggttcaa attccaaaca gagtaggacg gaatgggatt atggcgaaat ccattctatt     660
agaggaaaat ctcttactga agcatttgcc gttgagataa atgatgattt taagcttgca     720
acgaaggtag gaaactag                                                    738

<210> SEQ ID NO 508
<211> LENGTH: 261
<212> TYPE: PRT
<213> ORGANISM: Rhizobium leguminosarum bv. trifolii

<400> SEQUENCE: 508

Met Asn Asp Glu Ile Cys Leu Thr Gly Gly Gly Arg Thr Thr Val Thr
1               5                   10                  15

Arg Arg Gly Gly Val Val Tyr Arg Glu Gly Gly Pro Trp Ser Ser Thr
            20                  25                  30

Val Ile Ser Leu Leu Arg His Leu Glu Ala Ser Gly Phe Ala Glu Ala
        35                  40                  45

Pro Ser Val Val Gly Thr Gly Phe Asp Glu Arg Gly Arg Glu Thr Leu
    50                  55                  60

Ser Phe Ile Glu Gly Glu Phe Val His Pro Pro Trp Ser Glu Glu
65                  70                  75                  80

Ala Phe Pro Gln Phe Gly Met Met Leu Arg Arg Leu His Asp Ala Thr
                85                  90                  95

Ala Ser Phe Lys Pro Pro Glu Asn Ser Met Trp Arg Asp Trp Phe Gly
            100                 105                 110

Arg Asn Leu Gly Glu Gly Gln His Val Ile Gly His Cys Asp Thr Gly
        115                 120                 125

Pro Trp Asn Ile Val Cys Arg Ser Gly Leu Pro Val Gly Leu Ile Asp
    130                 135                 140

Trp Glu Val Ala Gly Pro Val Arg Ala Asp Ile Glu Leu Ala Gln Ala
145                 150                 155                 160
```

-continued

```
Cys Trp Leu Asn Ala Gln Leu Tyr Asp Asp Asp Ile Ala Glu Arg Val
                165                 170                 175
Gly Leu Gly Ser Val Thr Met Arg Ala His Gln Val Arg Leu Leu Leu
        180                 185                 190
Asp Gly Tyr Gly Leu Ser Arg Lys Gln Arg Gly Gly Phe Val Asp Lys
    195                 200                 205
Leu Ile Thr Phe Ala Val His Asp Ala Ala Glu Gln Ala Lys Glu Ala
210                 215                 220
Ala Val Thr Pro Glu Ser Asn Asp Ala Glu Pro Leu Trp Ala Ile Ala
225                 230                 235                 240
Trp Arg Thr Arg Ser Ala Ser Trp Met Leu His His Arg Gln Thr Leu
                245                 250                 255
Glu Ala Ala Leu Ala
            260

<210> SEQ ID NO 509
<211> LENGTH: 786
<212> TYPE: DNA
<213> ORGANISM: Rhizobium leguminosarum bv. trifolii

<400> SEQUENCE: 509
atgaatgatg agatttgcct gacaggtggc ggacgaacga ctgtcacgcg gcgcggcgga      60
gtcgtgtatc gcgaaggcgg cccgtggtca tcaaccgtca tttcgctcct gcggcatctg    120
gaagcctctg gcttcgctga agctccttcc gttgtcggca ccggtttcga tgagcgcggc    180
cgggagacat tatcgtttat cgagggtgag tttgttcacc caggcccttg gtcggaggag    240
gcttttccgc aatttggaat gatgttgcgg cgactgcacg atgccaccgc ctcgttcaaa    300
cctcccgaaa actcgatgtg gcgcgattgg ttcgggcgta acctcggtga gggtcaacac    360
gtaataggac actgcgacac aggcccatgg aacattgttt gccggtcagg attgcctgtc    420
gggttgatag attgggaggt ggctgggcct gtcaggccgg atatcgaatt ggcccaggct    480
tgttggctga atgcccagct ctacgatgac gacattgcgg agagggtcgg attaggctct    540
gtgaccatga gcgcatca agttcgcctg ctgcttgacg gctatggtct gtctcggaag    600
caacgcggcg gcttcgtcga caagctaatc acgttcgcag ttcacgatgc ggccgagcag    660
gcgaaagagg cggctgtcac gccagagtcg aacgatgcgg aaccgctatg ggcaattgcc    720
tggcgcacta gaagtgcctc ctggatgctc catcatcggc aaacactgga agcagcgctg    780
gcatag                                                                786
```

<210> SEQ ID NO 510
<211> LENGTH: 436
<212> TYPE: PRT
<213> ORGANISM: Bacillus subtilis

<400> SEQUENCE: 510

```
Met Asn Asn Ile Ile Pro Ile Met Ser Leu Leu Phe Lys Gln Leu Tyr
1               5                   10                  15
Ser Arg Gln Gly Lys Lys Asp Ala Ile Arg Ile Ala Ala Gly Leu Val
            20                  25                  30
Ile Leu Ala Val Phe Glu Ile Gly Leu Ile Arg Gln Ala Gly Ile Asp
        35                  40                  45
Glu Ser Val Leu Arg Lys Thr Tyr Ile Ile Leu Ala Leu Leu Leu Met
    50                  55                  60
Asn Thr Tyr Met Val Phe Leu Ser Val Thr Ser Gln Trp Lys Glu Ser
```

```
                65                  70                  75                  80
Tyr Met Lys Leu Ser Cys Leu Leu Pro Ile Ser Ser Arg Ser Phe Trp
                    85                  90                  95

Leu Ala Gln Ser Val Val Leu Phe Val Asp Thr Cys Leu Arg Arg Thr
                100                 105                 110

Leu Phe Phe Phe Ile Leu Pro Leu Phe Leu Phe Gly Asn Gly Thr Leu
                115                 120                 125

Ser Gly Ala Gln Thr Leu Phe Trp Leu Gly Arg Phe Ser Phe Phe Thr
                130                 135                 140

Val Tyr Ser Ile Ile Phe Gly Val Val Leu Ser Asn His Phe Val Lys
145                 150                 155                 160

Lys Lys Asn Leu Met Phe Leu Leu His Ala Ala Ile Phe Ala Cys Val
                165                 170                 175

Cys Ile Ser Ala Ala Leu Met Pro Ala Ala Thr Ile Pro Leu Cys Ala
                180                 185                 190

Val His Ile Leu Trp Ala Val Val Ile Asp Phe Pro Val Phe Leu Gln
                195                 200                 205

Ala Pro Pro Gln Gln Gly Lys Met His Ser Phe Met Arg Arg Ser Glu
                210                 215                 220

Phe Ser Phe Tyr Lys Arg Glu Trp Asn Arg Phe Ile Ser Ser Lys Ala
225                 230                 235                 240

Met Leu Leu Asn Tyr Ala Val Met Ala Val Phe Ser Gly Phe Phe Ser
                245                 250                 255

Phe Gln Met Met Asn Thr Gly Ile Phe Asn Gln Gln Val Ile Tyr Ile
                260                 265                 270

Val Ile Ser Ala Leu Leu Leu Ile Cys Ser Pro Ile Ala Leu Leu Tyr
                275                 280                 285

Ser Ile Glu Lys Asn Asp Arg Met Leu Leu Ile Thr Leu Pro Ile Lys
                290                 295                 300

Arg Lys Thr Met Phe Trp Ala Lys Tyr Arg Phe Tyr Ser Gly Leu Leu
305                 310                 315                 320

Ala Gly Gly Phe Leu Leu Val Val Met Ile Val Gly Phe Ile Ser Gly
                325                 330                 335

Arg Ser Ile Ser Val Leu Thr Phe Leu Gln Cys Ile Glu Leu Leu Leu
                340                 345                 350

Ala Gly Ala Tyr Ile Arg Leu Thr Ala Asp Glu Lys Arg Pro Ser Phe
                355                 360                 365

Ser Trp Gln Thr Glu Gln Gln Leu Trp Ser Gly Phe Ser Lys Tyr Arg
                370                 375                 380

Ser Tyr Leu Phe Cys Leu Pro Leu Phe Leu Ala Ile Leu Ala Gly Thr
385                 390                 395                 400

Ala Val Ser Leu Ala Val Ile Pro Ile Ala Gly Leu Val Ile Val Tyr
                405                 410                 415

Tyr Leu Gln Lys Gln Asp Gly Gly Phe Phe Asp Thr Ser Lys Arg Glu
                420                 425                 430

Arg Leu Gly Ser
            435

<210> SEQ ID NO 511
<211> LENGTH: 1000
<212> TYPE: DNA
<213> ORGANISM: Bacillus subtilis

<400> SEQUENCE: 511
```

```
atgaataaca taatccctat catgtctttg ctgttcaaac agctttacag ccggcaaggg      60
aaaaaggacg ccatccgcat tgccgcaggc cttgtcattc tggccgtgtt tgaaatcggg     120
ctgatccgcc aggccggcat tgatgaatcg gtgttgcgca aaacgtatat catactcgcg     180
cttcttttga tgaacacata tatggtgttt ctttccgtga catcacaatg gaaggaatct     240
tatatgaagc tgagctgcct gctgccgatt cttcacggag cttttggct cgcccagagt      300
gtcgttttgt ttgtcgatac ctgtttgaga agaactttat tcttttttat tttaccgctg     360
ttcttatttg gaaacggaac gctgtcaggg gcgcaaacat tgttttggct cggcaggttt     420
tcgttttta ccgtttactc cattattttc ggagttgtgc taagcaacca cttcgtcaaa      480
aagaagaact tgatgtttct gctgcatgcg gcgatattcg cctgtgtatg tatcagcgcc     540
gctttgatgc cggccgccac gattccgctt gcgcggttc atatcctgtg gcggtggtc       600
attgactttc ctgtctttct gcaggcgcct ccgcagcagg gcaagatgca ttcatttatg     660
cggcgatctg aattttcgtt ttacaaaaga gaatggaacc gatttatctc ttctaaagcg     720
atgctgttaa attacgcggt aatggcggta ttcagcggct tcttttcgtt ccagatgatg     780
aacaccggca tcttcaatca gcaagtgatt tatatcgtga tttccgcgct tttgctcatc     840
tgctcgccga tcgcccttt gtattcgatt gaaaaaaatg accggatgct gctcatcacg     900
cttccgatca agcgaaaaac gatgttttgg gcgaaatatc gcttttattc aggcctattg     960
gcaggcggat ttctccttgt cgtgatgatt gtgggtttca                         1000
```

<210> SEQ ID NO 512
<211> LENGTH: 239
<212> TYPE: PRT
<213> ORGANISM: Bacillus subtilis

<400> SEQUENCE: 512

```
Met Ser Ile Leu Asp Ile His Asp Val Ser Val Trp Tyr Glu Arg Asp
1               5                   10                  15

Asn Val Ile Leu Glu Gln Val Asp Leu His Leu Glu Lys Gly Ala Val
            20                  25                  30

Tyr Gly Leu Leu Gly Val Asn Gly Ala Gly Lys Thr Thr Leu Ile Asn
        35                  40                  45

Thr Leu Thr Gly Val Asn Arg Asn Phe Ser Gly Arg Phe Thr Leu Cys
    50                  55                  60

Gly Ile Glu Ala Glu Ala Gly Met Pro Gln Lys Thr Ser Asp Gln Leu
65                  70                  75                  80

Lys Thr His Arg Tyr Phe Ala Ala Asp Tyr Pro Leu Leu Phe Thr Glu
                85                  90                  95

Ile Thr Ala Lys Asp Tyr Val Ser Phe Val His Ser Leu Tyr Gln Lys
            100                 105                 110

Asp Phe Ser Glu Gln Gln Phe Ala Ser Leu Ala Glu Ala Phe His Phe
        115                 120                 125

Ser Lys Tyr Ile Asn Arg Arg Ile Ser Glu Leu Ser Leu Gly Asn Arg
    130                 135                 140

Gln Lys Val Val Leu Met Thr Gly Leu Leu Arg Ala Pro Leu Phe
145                 150                 155                 160

Ile Leu Asp Glu Pro Leu Val Gly Leu Asp Val Glu Ser Ile Glu Val
                165                 170                 175

Phe Tyr Gln Lys Met Arg Glu Tyr Cys Glu Ala Gly Gly Thr Ile Leu
            180                 185                 190

Phe Ser Ser His Leu Leu Asp Val Val Gln Arg Phe Cys Asp Tyr Ala
```

```
                195                 200                 205
Ala Ile Leu His Asn Lys Gln Ile Gln Lys Val Ile Pro Ile Gly Glu
    210                 215                 220

Glu Thr Asp Leu Arg Arg Glu Phe Phe Glu Val Ile Gly His Glu
225                 230                 235
```

<210> SEQ ID NO 513
<211> LENGTH: 716
<212> TYPE: DNA
<213> ORGANISM: Bacillus subtilis

<400> SEQUENCE: 513

```
gcattttgga tatacacgat gtatccgttt ggtatgaacg ggacaacgtc atcttagagc    60
acgtggactt acacttagaa aaaggcgccg tttacggatt gcttggggta acggtgccg    120
gcaaaacaac actgatcaat acgctgacag gagtgaaccg caattacagc gggggcttta   180
cgctgtgcgg cattgaagct gaggccggca tgccgcagaa acatcagat caactgaaga    240
ttcaccgtta cttcgccgct gattatccgc tgctgtttac agaaattacg gcgaaggact   300
atgtgtcttt cgtccattcg ctttatcaaa aggattttc agagcgacag tttgccagtt    360
tggctgaggc cttttcatttt tcaaaataca tcaacaggaa atctcggag ctgtccttgg    420
ggaacaggca aaggttgtg ttgatgacag gattattgct gcgggctccc ctgtttattt     480
tggatgagcc gctcgtcggt ttggatgtgg aatcaataga ggtctttat cagaaaatgc    540
gggagtactg tgaggaaggc ggaaccattt tgttttcttc ccatctgctc gatgtcgtgc    600
agagattttg tgatttttgcg gccattctgc acaacaaaca gatccaaaag gtcattccga   660
ttggggagga gaccgatctg cggcgggaat ttttgaggt tatcggccat gaataa         716
```

<210> SEQ ID NO 514
<211> LENGTH: 53
<212> TYPE: PRT
<213> ORGANISM: Bacillus subtilis

<400> SEQUENCE: 514

```
Met Ser Pro Ala Gln Arg Arg Ile Leu Leu Tyr Ile Leu Ser Phe Ile
1               5                   10                  15

Phe Val Ile Gly Ala Val Val Tyr Phe Val Lys Ser Asp Tyr Leu Phe
            20                  25                  30

Thr Leu Ile Phe Ile Ala Ile Ala Ile Leu Phe Gly Met Arg Ala Arg
        35                  40                  45

Lys Ala Asp Ser Arg
    50
```

<210> SEQ ID NO 515
<211> LENGTH: 162
<212> TYPE: DNA
<213> ORGANISM: Bacillus subtilis

<400> SEQUENCE: 515

```
ttgtcaccag cacaaagaag aatttttactg tatatccttt catttatctt tgtcatcggc    60
gcagtcgtct attttgtcaa aagcgattat ctgtttacgc tgattttcat tgccattgcc   120
attctgttcg ggatgcgcgc gcggaaggct gactcgcgat ga                      162
```

<210> SEQ ID NO 516
<211> LENGTH: 87
<212> TYPE: PRT
<213> ORGANISM: Escherichia coli

<400> SEQUENCE: 516

Met Glu Leu Lys Asn Ser Ile Ser Asp Tyr Thr Glu Ala Glu Phe Val
1               5                   10                  15

Gln Leu Leu Lys Glu Ile Glu Lys Glu Asn Val Ala Ala Thr Asp Asp
            20                  25                  30

Val Leu Asp Val Leu Leu Glu His Phe Val Lys Ile Thr Glu His Pro
        35                  40                  45

Asp Gly Thr Asp Leu Ile Tyr Tyr Pro Ser Asp Asn Arg Asp Asp Ser
    50                  55                  60

Pro Glu Gly Ile Val Lys Glu Ile Lys Glu Trp Arg Ala Ala Asn Gly
65                  70                  75                  80

Lys Pro Gly Phe Lys Gln Gly
                85

<210> SEQ ID NO 517
<211> LENGTH: 264
<212> TYPE: DNA
<213> ORGANISM: Escherichia coli

<400> SEQUENCE: 517
atggaactga aaatagtat tagtgattac acagaggctg agtttgttca acttcttaag      60
gaaattgaaa agagaatgt tgctgcaact gatgatgtgt tagatgtgtt actcgaacac    120
tttgtaaaaa ttactgagca tccagatgga acggatctga tttattatcc tagtgataat    180
agagacgata gccccgaagg gattgtcaag gaaattaaag aatggcgagc tgctaacggt    240
aagccaggat ttaaacaggg ctga                                           264

<210> SEQ ID NO 518
<211> LENGTH: 87
<212> TYPE: PRT
<213> ORGANISM: Pseudomonas aeruginosa

<400> SEQUENCE: 518

Met Lys Ser Lys Ile Ser Glu Tyr Thr Glu Lys Glu Phe Leu Glu Phe
1               5                   10                  15

Val Glu Asp Ile Tyr Thr Asn Asn Lys Lys Phe Pro Thr Glu Glu
            20                  25                  30

Ser His Ile Gln Ala Val Leu Glu Phe Lys Lys Leu Thr Glu His Pro
        35                  40                  45

Ser Gly Ser Asp Leu Leu Tyr Tyr Pro Asn Glu Asn Arg Glu Asp Ser
    50                  55                  60

Pro Ala Gly Val Val Lys Glu Val Lys Glu Trp Arg Ala Ser Lys Gly
65                  70                  75                  80

Leu Pro Gly Phe Lys Ala Gly
                85

<210> SEQ ID NO 519
<211> LENGTH: 264
<212> TYPE: DNA
<213> ORGANISM: Pseudomonas aeruginosa

<400> SEQUENCE: 519
atgaagtcca agatttccga atatacggaa aaagagtttc ttgagtttgt tgaagacata     60
tacacaaaca ataagaaaaa gttccctacc gaggagtctc atattcaagc cgtgcttgaa    120
tttaaaaaac taacggaaca cccaagcggc tcagaccttc tttactaccc caacgaaaat    180
agagaagata gcccagctgg agttgtaaag gaagttaaag aatggcgtgc ttccaagggg    240
cttcctggct ttaaggccgg ttag                                           264

<210> SEQ ID NO 520
<211> LENGTH: 87
<212> TYPE: PRT
<213> ORGANISM: Pseudomonas aeruginosa

<400> SEQUENCE: 520

Met Lys Ser Lys Ile Ser Glu Tyr Thr Glu Lys Glu Phe Leu Glu Phe
1               5                   10                  15

Val Lys Asp Ile Tyr Thr Asn Asn Lys Lys Phe Pro Thr Glu Glu
            20                  25                  30

Ser His Ile Gln Ala Val Leu Glu Phe Lys Lys Leu Thr Glu His Pro
        35                  40                  45

Ser Gly Ser Asp Leu Leu Tyr Tyr Pro Asn Glu Asn Arg Glu Asp Ser
    50                  55                  60

Pro Ala Gly Val Val Lys Glu Val Lys Glu Trp Arg Ala Ser Lys Gly
65                  70                  75                  80

Leu Pro Gly Phe Lys Ala Gly
                85

<210> SEQ ID NO 521
<211> LENGTH: 264
<212> TYPE: DNA
<213> ORGANISM: Pseudomonas aeruginosa

<400> SEQUENCE: 521
atgaagtcca agatttccga atatacggaa aaagagtttc ttgagtttgt taaagacata    60
tacacaaaca ataagaaaaa gttccctacc gaggagtctc atattcaagc cgtgcttgaa    120
tttaaaaaac taacggaaca cccaagcggc tcagaccttc tttactaccc caacgaaaat    180
agagaagata gcccagctgg agttgtaaag gaagttaaag aatggcgtgc ttccaagggg    240
cttcctggct ttaaggccgg ttag                                           264

<210> SEQ ID NO 522
<211> LENGTH: 95
<212> TYPE: PRT
<213> ORGANISM: Enterococcus hirae

<400> SEQUENCE: 522

Met Asp Phe Thr Lys Glu Glu Lys Leu Leu Asn Ala Ile Ser Lys Val
1               5                   10                  15

Tyr Asn Glu Ala Thr Ile Asp Asp Tyr Pro Asp Leu Lys Glu Lys Leu
            20                  25                  30

Phe Leu Tyr Ser Lys Glu Ile Ser Glu Gly Lys Ser Val Gly Glu Val
        35                  40                  45

Ser Met Lys Leu Ser Ser Phe Leu Gly Arg Tyr Ile Leu Lys His Lys
    50                  55                  60

Phe Gly Leu Pro Lys Ser Leu Ile Glu Leu Gln Glu Ile Val Ser Lys
65                  70                  75                  80

Glu Ser Gln Val Tyr Arg Gly Trp Ala Ser Ile Gly Ile Trp Ser
                85                  90                  95

<210> SEQ ID NO 523
<211> LENGTH: 288
<212> TYPE: DNA
<213> ORGANISM: Enterococcus hirae

<400> SEQUENCE: 523

```
atggatttta ctaaagaaga aaaacttta aatgcaatta gtaaagtata caatgaagca    60
actatagatg actatcctga cttaaaagaa aagctctttc tttattctaa agaaatcagt   120
gagggaaaaa gtgttggtga agttagtatg aaattagta gttttcttgg aagatatatt   180
ttaaaacata aatttggatt acctaaatct taatagaat tacaagaaat tgttagtaag   240
gaatctcaag tatatagagg atgggcttct attggtattt ggagttaa               288
```

<210> SEQ ID NO 524
<211> LENGTH: 113
<212> TYPE: PRT
<213> ORGANISM: Leuconostoc mesenteroides

<400> SEQUENCE: 524

```
Met Lys Lys Lys Tyr Arg Tyr Leu Glu Asp Ser Lys Asn Tyr Thr Ser
1               5                   10                  15
Thr Leu Tyr Ser Leu Leu Val Asp Asn Val Asp Lys Pro Gly Tyr Ser
            20                  25                  30
Asp Ile Cys Asp Val Leu Leu Gln Val Ser Lys Lys Leu Asp Asn Thr
        35                  40                  45
Gln Ser Val Glu Ala Leu Ile Asn Arg Leu Val Asn Tyr Ile Arg Ile
    50                  55                  60
Thr Ala Ser Thr Tyr Lys Ile Ile Phe Ser Lys Lys Glu Glu Glu Leu
65                  70                  75                  80
Ile Ile Lys Leu Gly Val Ile Gly Gln Lys Ala Gly Leu Asn Gly Gln
                85                  90                  95
Tyr Met Ala Asp Phe Ser Asp Lys Ser Gln Phe Tyr Ser Val Phe Asp
            100                 105                 110
Gln
```

<210> SEQ ID NO 525
<211> LENGTH: 342
<212> TYPE: DNA
<213> ORGANISM: Leuconostoc mesenteroides

<400> SEQUENCE: 525

```
ttgaaaaaaa agtatcggta tttagaagat agcaaaaatt acactagtac actctattct    60
ctgttagttg ataatgttga caaacctgga tactcagata tttgcgatgt tttgcttcaa   120
gtttctaaga agttggataa tactcaaagt gttgaagcgc taattaatcg attggttaat   180
tatattcgta ttactgcttc aacatacaaa attatttttt caaaaaaaga agaggaattg   240
attataaaac ttggtgttat tggacaaaaa gctggactta atggtcagta tatggctgat   300
ttttcagaca agtctcagtt ttacagcgtt ttcgatcagt aa                     342
```

<210> SEQ ID NO 526
<211> LENGTH: 93
<212> TYPE: PRT
<213> ORGANISM: Escherichia coli

<400> SEQUENCE: 526

```
Met Ser Phe Leu Asn Phe Ala Phe Ser Pro Val Phe Phe Ser Ile Met
1               5                   10                  15
Ala Cys Tyr Phe Ile Val Trp Arg Asn Lys Arg Asn Glu Phe Val Cys
            20                  25                  30
Asn Arg Leu Leu Ser Ile Ile Ile Ile Ser Phe Leu Ile Cys Phe Ile
```

```
            35                  40                  45

Tyr Pro Trp Leu Asn Tyr Lys Ile Glu Val Lys Tyr Tyr Ile Phe Glu
     50                  55                  60

Gln Phe Tyr Leu Phe Cys Phe Leu Ser Ser Leu Val Ala Val Val Ile
 65                  70                  75                  80

Asn Leu Ile Val Tyr Phe Ile Leu Tyr Arg Arg Cys Ile
                 85                  90

<210> SEQ ID NO 527
<211> LENGTH: 282
<212> TYPE: DNA
<213> ORGANISM: Escherichia coli

<400> SEQUENCE: 527
atgagttttc ttaattttgc attttctcct gtattcttct ccattatggc gtgttatttc      60
attgtatgga gaaataaacg aaacgaattt gtctgcaata gattgctatc aattataata     120
atatcttttt tgatatgctt catatatcca tggctaaatt acaaaatcga agttaaatat     180
tatatatttg aacagtttta tcttttttgt tttttatcgt cactcgtggc tgttgtaata     240
aacctaattg tatactttat attatacagg agatgtatat ga                        282

<210> SEQ ID NO 528
<211> LENGTH: 96
<212> TYPE: PRT
<213> ORGANISM: Escherichia coli

<400> SEQUENCE: 528

Met His Leu Lys Tyr Tyr Leu His Asn Leu Pro Glu Ser Leu Ile Pro
 1               5                  10                  15

Trp Ile Leu Ile Leu Ile Phe Asn Asp Asn Asp Asn Thr Pro Leu Leu
             20                  25                  30

Phe Ile Phe Ile Ser Ser Ile His Val Leu Leu Tyr Pro Tyr Ser Lys
         35                  40                  45

Leu Thr Ile Ser Arg Tyr Ile Lys Glu Asn Thr Lys Leu Lys Lys Glu
     50                  55                  60

Pro Trp Tyr Leu Cys Lys Leu Ser Ala Leu Phe Tyr Leu Leu Met Ala
 65                  70                  75                  80

Ile Pro Val Gly Leu Pro Ser Phe Ile Tyr Tyr Thr Leu Lys Arg Asn
                 85                  90                  95

<210> SEQ ID NO 529
<211> LENGTH: 291
<212> TYPE: DNA
<213> ORGANISM: Escherichia coli

<400> SEQUENCE: 529
atgcatttaa aatactacct acataattta cctgaatcac ttataccatg gattcttatt      60
ttaatattta cgacaatga taacactcct ttgttattta tatttatatc atcaatacat     120
gtattgctat atccatactc taaattaacc atatctagat atatcaaaga aaatacaaag     180
ttaaaaaaag aaccctggta cttatgcaag ttatctgcat tgttttattt attaatggca     240
atcccagtag gattgccaag tttcatatat tacactctaa agagaaatta a             291

<210> SEQ ID NO 530
<211> LENGTH: 344
<212> TYPE: PRT
<213> ORGANISM: Escherichia coli
```

<400> SEQUENCE: 530

```
Met Met Ile Gln Ser His Pro Leu Leu Ala Ala Pro Leu Ala Val Gly
1               5                   10                  15
Asp Thr Ile Gly Phe Phe Ser Ser Ala Pro Ala Thr Val Thr Ala
            20                  25                  30
Lys Asn Arg Phe Phe Arg Gly Val Glu Phe Leu Gln Arg Lys Gly Phe
                35                  40                  45
Lys Leu Val Ser Gly Lys Leu Thr Gly Lys Thr Asp Phe Tyr Arg Ser
    50                  55                  60
Gly Thr Ile Lys Glu Arg Ala Gln Glu Phe Asn Glu Leu Val Tyr Asn
65                  70                  75                  80
Pro Asp Ile Thr Cys Ile Met Ser Thr Ile Gly Gly Asp Asn Ser Asn
                85                  90                  95
Ser Leu Leu Pro Phe Leu Asp Tyr Asp Ala Ile Ile Ala Asn Pro Lys
                100                 105                 110
Ile Ile Ile Gly Tyr Ser Asp Thr Thr Ala Leu Leu Ala Gly Ile Tyr
            115                 120                 125
Ala Lys Thr Gly Leu Ile Thr Phe Tyr Gly Pro Ala Leu Ile Pro Ser
130                 135                 140
Phe Gly Glu His Pro Pro Leu Val Asp Ile Thr Tyr Glu Ser Phe Ile
145                 150                 155                 160
Lys Ile Leu Thr Arg Lys Gln Ser Gly Ile Tyr Thr Tyr Thr Leu Pro
                165                 170                 175
Glu Lys Trp Ser Asp Glu Ser Ile Asn Trp Asn Glu Asn Lys Ile Leu
            180                 185                 190
Arg Pro Lys Lys Leu Tyr Lys Asn Asn Cys Ala Phe Tyr Gly Ser Gly
        195                 200                 205
Lys Val Glu Gly Arg Val Ile Gly Gly Asn Leu Asn Thr Leu Thr Gly
210                 215                 220
Ile Trp Gly Ser Glu Trp Met Pro Glu Ile Leu Asn Gly Asp Ile Leu
225                 230                 235                 240
Phe Ile Glu Asp Ser Arg Lys Ser Ile Ala Thr Ile Glu Arg Leu Phe
                245                 250                 255
Ser Met Leu Lys Leu Asn Arg Val Phe Asp Lys Val Ser Ala Ile Ile
            260                 265                 270
Leu Gly Lys His Glu Leu Phe Asp Cys Ala Gly Ser Lys Arg Arg Pro
        275                 280                 285
Tyr Glu Val Leu Thr Glu Val Leu Asp Gly Lys Gln Ile Pro Val Leu
290                 295                 300
Asp Gly Phe Asp Cys Ser His Thr His Pro Met Leu Thr Leu Pro Leu
305                 310                 315                 320
Gly Val Lys Leu Ala Ile Asp Phe Asp Asn Lys Asn Ile Ser Ile Thr
                325                 330                 335
Glu Gln Tyr Leu Ser Thr Glu Lys
            340
```

<210> SEQ ID NO 531
<211> LENGTH: 1000
<212> TYPE: DNA
<213> ORGANISM: Escherichia coli

<400> SEQUENCE: 531

```
atgatgatac aatctcatcc actactggcc gctcccctgg cagtaggaga tacaattggt    60
ttcttttcat catctgctcc ggcaacagtt actgcaaaaa atcgttttt tcggggagtt    120
```

-continued

```
gagtttcttc agagaaaggg atttaagctg gtatcaggga agcttaccgg taaaacagat      180
ttttatcgtt caggtactat taaagaaaga gctcaagaat ttaatgagtt agtctacaat      240
cctgatatta cctgtataat gtcaacgatc ggtggagata acagtaattc actactaccg      300
tttctggact atgatgctat cattgcaaac cccaaaatta tcataggtta ctcagataca      360
actgctttat tagcaggaat atatgcaaaa acagggttaa taacattcta tggaccagct      420
cttattcctt cgtttggtga acatccacct cttgtggata acatatga atcatttatt       480 aaaatactaa caagaaaaca atcaggaata tatacctaca cattacctga aaagtggagt      540
gatgagagca taaactggaa tgaaaacaag atattaaggc ctaagaagct atataaaaac      600
aactgtgcct tttatggttc cggaaaagtt gagggggcgtg taattggagg aaatctaaat     660
actttgacag gtatatgggg gagtgaatgg atgcctgaaa ttcttaatgg agatatattg      720
tttattgagg acagtcggaa aagcattgca acaattgaac gattattctc tatgctaaag      780
cttaatcgcg tgtttgataa agttagtgca ataatactcg ggaaacatga gcttttttgat     840 tgtgcaggaa gtaaacgcag accatatgaa gtattaacag aggtattaga tgggaaacag      900
attcctgtac tggatggatt tgattgttca catacacatc caatgctaac tcttccactt      960
ggtgtaaaat tagctattga ctttgacaac aaaaatatat                           1000
```

<210> SEQ ID NO 532
<211> LENGTH: 90
<212> TYPE: PRT
<213> ORGANISM: Lactobacillus sakei

<400> SEQUENCE: 532

```
Met Lys Ala Asp Tyr Lys Lys Ile Asn Ser Ile Leu Thr Tyr Thr Ser
1               5                   10                  15

Thr Ala Leu Lys Asn Pro Lys Ile Ile Lys Asp Lys Asp Leu Val Val
            20                  25                  30

Leu Leu Thr Ile Ile Gln Glu Glu Ala Lys Gln Asn Arg Ile Phe Tyr
        35                  40                  45

Asp Tyr Lys Arg Lys Phe Arg Pro Ala Val Thr Arg Phe Thr Ile Asp
    50                  55                  60

Asn Asn Phe Glu Ile Pro Asp Cys Leu Val Lys Leu Leu Ser Ala Val
65                  70                  75                  80

Glu Thr Pro Lys Ala Trp Ser Gly Phe Ser
            85                  90
```

<210> SEQ ID NO 533
<211> LENGTH: 268
<212> TYPE: DNA
<213> ORGANISM: Lactobacillus sakei

<400> SEQUENCE: 533

```
ggcagattat aaaaaaataa attcaatact aacttacaca tctactgctt taaaaaaccc      60
taaaattata aaagataaag atttagtagt ccttctaact attattcaag aagaagccaa     120
acaaaataga atctttttatg attataaaag aaaatttcgt ccagcggtta ctcgctttac     180
aattgataat aattttgaga ttcctgattg tttggttaaa ctactgtcag ctgttgaaac     240
acctaaggcg tggtctggat ttagttag                                        268
```

<210> SEQ ID NO 534
<211> LENGTH: 83
<212> TYPE: PRT

<213> ORGANISM: Escherichia coli

<400> SEQUENCE: 534

Met Lys Leu Ser Pro Lys Ala Ala Ile Glu Val Cys Asn Glu Ala Ala
1               5                   10                  15

Lys Lys Gly Leu Trp Ile Leu Gly Ile Asp Gly Gly His Trp Leu Asn
            20                  25                  30

Pro Gly Phe Arg Ile Asp Ser Ser Ala Ser Trp Thr Tyr Asp Met Pro
        35                  40                  45

Glu Glu Tyr Lys Ser Lys Thr Pro Glu Asn Asn Arg Leu Ala Ile Glu
    50                  55                  60

Asn Ile Lys Asp Asp Ile Glu Asn Gly Tyr Thr Ala Phe Ile Ile Thr
65                  70                  75                  80

Leu Lys Met

<210> SEQ ID NO 535
<211> LENGTH: 251
<212> TYPE: DNA
<213> ORGANISM: Escherichia coli

<400> SEQUENCE: 535
tgaagttatc accaaaagct gcaatagaag tttgtaatga agcagcgaaa aaaggcttat      60
ggattttggg cattgatggt gggcattggc tgaatcctgg attcaggata gatagttcag     120
catcatggac atatgatatg ccggaggaat acaaatcaaa aacccctgaa ataatagat      180 tggctattga aaatattaaa gatgatattg agaatggata cactgctttc attatcacgt     240
taaagatgta a                                                          251

<210> SEQ ID NO 536
<211> LENGTH: 436
<212> TYPE: PRT
<213> ORGANISM: Bacillus subtilis

<400> SEQUENCE: 536

Met Asn Asn Ile Phe Pro Ile Met Ser Leu Leu Phe Lys Gln Leu Tyr
1               5                   10                  15

Ser Arg Gln Gly Lys Lys Asp Ala Ile Arg Ile Ala Ala Gly Leu Val
            20                  25                  30

Ile Leu Ala Val Phe Glu Ile Gly Leu Ile Arg Gln Ala Gly Ile Asp
        35                  40                  45

Glu Ser Val Leu Gly Lys Thr Tyr Ile Ile Leu Ala Leu Leu Leu Met
    50                  55                  60

Asn Thr Tyr Met Val Phe Leu Ser Val Thr Ser Gln Trp Lys Glu Ser
65                  70                  75                  80

Tyr Met Lys Leu Ser Cys Leu Leu Pro Ile Ser Ser Arg Ser Phe Trp
                85                  90                  95

Leu Ala Gln Ser Val Val Leu Phe Val Asp Thr Cys Leu Arg Arg Thr
            100                 105                 110

Leu Phe Phe Phe Ile Leu Pro Leu Phe Leu Phe Gly Asn Gly Thr Leu
        115                 120                 125

Ser Gly Ala Gln Thr Leu Phe Trp Leu Gly Arg Phe Ser Phe Phe Thr
    130                 135                 140

Val Tyr Ser Ile Leu Phe Gly Val Met Leu Ser Asn His Phe Val Lys
145                 150                 155                 160

Lys Lys Asn Ser Met Phe Leu Leu His Ala Ala Val Phe Ala Phe Val
                165                 170                 175

```
Cys Leu Ser Ala Ala Phe Met Pro Ala Val Thr Ile Pro Leu Cys Ala
                180                 185                 190

Val His Met Leu Trp Ala Val Ile Ile Asp Phe Pro Val Phe Leu Gln
            195                 200                 205

Ala Pro Pro His Gln Ser Lys Met His Phe Phe Met Arg Arg Ser Glu
210                 215                 220

Phe Ser Phe Tyr Lys Arg Glu Trp Asn Arg Phe Ile Ser Ser Lys Ala
225                 230                 235                 240

Met Leu Leu Asn Tyr Val Val Met Ala Ala Phe Ser Gly Phe Phe Ser
                245                 250                 255

Phe Gln Met Met Asn Thr Gly Ile Phe Asn Gln Gln Val Ile Tyr Ile
            260                 265                 270

Val Ile Ser Ala Leu Leu Leu Ile Cys Ser Pro Ile Ala Leu Leu Tyr
        275                 280                 285

Ser Ile Glu Lys Asn Asp Arg Met Leu Leu Ile Thr Leu Pro Ile Lys
    290                 295                 300

Arg Arg Thr Met Phe Trp Ala Lys Tyr Arg Phe Tyr Ser Gly Leu Leu
305                 310                 315                 320

Ala Gly Gly Phe Leu Leu Val Ala Ile Ile Val Gly Phe Ile Ser Gly
                325                 330                 335

Arg Pro Ile Ser Ala Leu Thr Phe Val Gln Cys Met Glu Leu Leu Leu
            340                 345                 350

Ala Gly Ala Phe Ile Arg Leu Thr Ala Asp Glu Lys Arg Pro Ser Phe
        355                 360                 365

Gly Trp Gln Thr Glu Gln Gln Leu Trp Ser Gly Phe Ser Lys Tyr Arg
    370                 375                 380

Ser Tyr Leu Phe Cys Leu Pro Leu Phe Leu Ala Thr Leu Ala Gly Thr
385                 390                 395                 400

Ala Val Ser Leu Ala Val Ile Pro Ile Ala Ala Leu Ile Ile Val Tyr
                405                 410                 415

Tyr Leu Gln Lys Gln Asp Gly Gly Phe Phe Asp Thr Ser Lys Arg Glu
            420                 425                 430

Arg Ile Gly Ser
        435

<210> SEQ ID NO 537
<211> LENGTH: 1000
<212> TYPE: DNA
<213> ORGANISM: Bacillus subtilis

<400> SEQUENCE: 537
ttggggagga gaccgatctg cggcgggaat tttttgaggt tatcggccat gaataacata      60
ttccccatca tgtcgttgct gttcaaacag ctgtacagcc ggcaagggaa aaaggacgct     120
atccgcattg ctgcagggct tgtgattctc gccgtgtttg aaatcgggct gatccgacaa     180
gccggcattg acgaatcggt gttgggaaaa acgtatatca tattggcgct tctcttaatg     240
aacacgtata tggtgtttct ttccgtgaca tcacaatgga aggaatctta tatgaagctg     300
agctgtctgc tgccgatttc atcacggagc ttttggctcg cccagagtgt cgttctgttt     360
gtcgataccT gtttgagaag aacgttattc tttttttatt taccgctgtt cttatttgga     420
aacggaacgc tgtcagggc gcaaacattg ttttggcttg cagatttttc gttttttacc     480
gtttactcga ttctattcgg agttatgcta agcaaccatt tcgtcaaaaa gaagaactcg     540
atgtttctgc tgcatgcggc ggtattcgcc tttgtatgcc tcagtgccgc ttttatgccg     600
```

```
gccgtcacga tcccgctatg cgcggttcac atgctatggg cggtgatcat tgactttccg    660
gtctttctgc aggcgcctcc gcatcagagc aagatgcatt ttttatgcg gcgatctgaa     720 ttttcgtttt acaaaagaga atggaaccga tttatttctt ctaaagcgat gctgttaaat    780
tacgtggtga tggcggcgtt cagcggattc ttttcgttcc agatgatgaa cactggcatc    840
ttcaatcagc aagtgattta tattgtgatt ccgctctat tgctgatttg ctcgccgatc     900 gccctttttgt actctattga aaaaaacgat cgcatgctgc tcatcacgct tccaattaaa   960
agaagaacga tgttttgggc gaaatatcgc ttttattcag                         1000
```

<210> SEQ ID NO 538
<211> LENGTH: 580
<212> TYPE: PRT
<213> ORGANISM: Escherichia coli

<400> SEQUENCE: 538

```
Met Glu Arg Lys Gln Lys Asn Ser Leu Phe Asn Tyr Ile Tyr Ser Leu
1               5                   10                  15

Met Asp Val Arg Gly Lys Phe Leu Phe Phe Ser Met Leu Phe Ile Thr
                20                  25                  30

Ser Leu Ser Ser Ile Ile Ile Ser Ile Ser Pro Leu Ile Leu Ala Lys
            35                  40                  45

Ile Thr Asp Leu Leu Ser Gly Ser Leu Ser Asn Phe Ser Tyr Glu Tyr
        50                  55                  60

Leu Val Leu Leu Ala Cys Leu Tyr Met Phe Cys Val Ile Ser Asn Lys
65                  70                  75                  80

Ala Ser Val Phe Leu Phe Met Ile Leu Gln Ser Ser Leu Arg Ile Asn
                85                  90                  95

Met Gln Lys Lys Met Ser Leu Lys Tyr Leu Arg Glu Leu Tyr Asn Glu
            100                 105                 110

Asn Ile Thr Asn Leu Ser Lys Asn Asn Ala Gly Tyr Thr Thr Gln Ser
        115                 120                 125

Leu Asn Gln Ala Ser Asn Asp Ile Tyr Ile Leu Val Arg Asn Val Ser
    130                 135                 140

Gln Asn Ile Leu Ser Pro Val Ile Gln Leu Ile Ser Thr Ile Val Val
145                 150                 155                 160

Val Leu Ser Thr Lys Asp Trp Phe Ser Ala Gly Val Phe Phe Leu Tyr
                165                 170                 175

Ile Leu Val Phe Val Ile Phe Asn Thr Arg Leu Thr Gly Ser Leu Ala
            180                 185                 190

Ser Leu Arg Lys His Ser Met Asp Ile Thr Leu Asn Ser Tyr Ser Leu
        195                 200                 205

Leu Ser Asp Thr Val Asp Asn Met Ile Ala Ala Lys Lys Asn Asn Ala
    210                 215                 220

Leu Arg Leu Ile Ser Glu Arg Tyr Glu Asp Ala Leu Thr Gln Glu Asn
225                 230                 235                 240

Asn Ala Gln Lys Lys Tyr Trp Leu Leu Ser Ser Lys Val Leu Leu Leu
                245                 250                 255

Asn Ser Leu Leu Ala Val Ile Leu Phe Gly Ser Val Phe Ile Tyr Asn
            260                 265                 270

Ile Leu Gly Val Leu Asn Gly Val Val Ser Ile Gly His Phe Ile Met
        275                 280                 285

Ile Thr Ser Tyr Ile Ile Leu Leu Ser Thr Pro Val Glu Asn Ile Gly
    290                 295                 300
```

Ala Leu Leu Ser Glu Ile Arg Gln Ser Met Ser Ser Leu Ala Gly Phe
305                 310                 315                 320

Ile Gln Arg His Ala Glu Asn Lys Ala Thr Ser Pro Ser Ile Pro Phe
            325                 330                 335

Leu Asn Met Glu Arg Lys Leu Asn Leu Ser Ile Arg Glu Leu Ser Phe
        340                 345                 350

Ser Tyr Ser Asp Asp Lys Lys Ile Leu Asn Ser Val Ser Leu Asp Leu
    355                 360                 365

Phe Thr Gly Lys Met Tyr Ser Leu Thr Gly Pro Ser Gly Ser Gly Lys
370                 375                 380

Ser Thr Leu Val Lys Ile Ile Ser Gly Tyr Tyr Lys Asn Tyr Phe Gly
385                 390                 395                 400

Asp Ile Tyr Leu Asn Asp Ile Ser Leu Arg Asn Ile Ser Asp Glu Asp
                405                 410                 415

Leu Asn Asp Ala Ile Tyr Tyr Leu Thr Gln Asp Asp Tyr Ile Phe Met
            420                 425                 430

Asp Thr Leu Arg Phe Asn Leu Arg Leu Ala Asn Tyr Asp Ala Ser Glu
        435                 440                 445

Asn Glu Ile Phe Lys Val Leu Lys Leu Ala Asn Leu Ser Val Val Asn
    450                 455                 460

Asn Glu Pro Val Ser Leu Asp Thr His Leu Ile Asn Arg Gly Asn Asn
465                 470                 475                 480

Tyr Ser Gly Gly Gln Lys Gln Arg Ile Ser Leu Ala Arg Leu Phe Leu
                485                 490                 495

Arg Lys Pro Ala Ile Ile Ile Asp Glu Ala Thr Ser Ala Leu Asp
            500                 505                 510

Tyr Ile Asn Glu Ser Glu Ile Leu Ser Ser Ile Arg Thr His Phe Pro
        515                 520                 525

Asp Ala Leu Ile Ile Asn Ile Ser His Arg Ile Asn Leu Leu Glu Cys
    530                 535                 540

Ser Asp Cys Val Tyr Val Leu Asn Glu Gly Asn Ile Val Ala Ser Gly
545                 550                 555                 560

His Phe Arg Asp Leu Met Val Ser Asn Glu Tyr Ile Ser Gly Leu Ala
                565                 570                 575

Ser Val Thr Glu
            580

<210> SEQ ID NO 539
<211> LENGTH: 1000
<212> TYPE: DNA
<213> ORGANISM: Escherichia coli

<400> SEQUENCE: 539
atggaaagaa aacagaaaaa ctcattattt aattatattt attcattaat ggatgtaaga        60
ggtaaatttt tattcttttc catgttattc attacatcat tatcatcgat aatcatatct       120
atttcaccat tgattcttgc aaagattaca gatttactgt ctggctcatt gtcaaatttt       180
agttatgaat atctggtttt acttgcctgt ttatacatgt tttgcgttat atctaataaa       240
gcaagtgttt ttttatttat gatactgcaa agtagtctac gtattaacat gcagaaaaaa       300
atgtcgctaa agtatttgag agaattgtat aacgaaaata taactaactt gagtaaaaat       360
aatgctggat atacaacgca aagtcttaac caggcttcaa atgacattta tattcttgtg       420
agaaatgttt cccagaatat cctgtcacct gttatacaac ttatttccac tattgttgtt       480

```
gttttatcta cgaaggactg gttttctgcc ggtgtgtttt ttctctatat tctggtattt    540 gtaatttta ataccagact gactggcagt ttagcgtctc tcagaaaaca cagcatggat    600
atcactctta actcttatag tctgttatct gatactgttg ataacatgat agcagctaaa    660
aagaataatg cattaagact tatttctgaa cgttatgaag atgctctcac tcaggaaaac    720
aatgctcaga aaaatactg gttactcagt tctaaagttc ttttattgaa ctctttactt    780
gctgtaatat tatttggttc tgtattcata tataatattt taggtgtgct gaatggtgta    840
gttagtatcg gccacttcat tatgattaca tcatatatca ttcttctttc aacgccagtg    900
gaaaatatag gggcattgct aagtgagatc aggcagtcaa tgtctagcct ggcaggtttt    960
attcaacgtc atgccgagaa taaagccaca tctccttcaa                         1000

<210> SEQ ID NO 540
<211> LENGTH: 95
<212> TYPE: PRT
<213> ORGANISM: Klebsiella pneumoniae

<400> SEQUENCE: 540

Met Thr Leu Leu Ser Phe Gly Phe Ser Pro Val Phe Ser Val Met
1               5                   10                  15

Ala Phe Cys Ile Ile Ser Arg Ser Lys Phe Tyr Pro Gln Arg Thr Arg
            20                  25                  30

Asn Lys Val Ile Val Leu Ile Leu Leu Thr Phe Phe Ile Cys Phe Leu
        35                  40                  45

Tyr Pro Leu Thr Lys Val Tyr Leu Val Gly Ser Tyr Gly Ile Phe Asp
    50                  55                  60

Lys Phe Tyr Leu Phe Cys Phe Ile Ser Thr Leu Ile Ala Ile Ala Ile
65              70                  75                  80

Asn Val Val Ile Leu Thr Ile Asn Gly Ala Lys Asn Glu Arg Asn
            85                  90                  95

<210> SEQ ID NO 541
<211> LENGTH: 288
<212> TYPE: DNA
<213> ORGANISM: Klebsiella pneumoniae

<400> SEQUENCE: 541
atgacattac tttcatttgg attttctcct gttttctttt cagtcatggc gttctgtatc    60
atttcacgta gtaaattcta tccgcagaga acgcgaaaca aagttattgt tctgatttta   120 ctaactttt ttatttgttt tttatatcca ttaacaaaag tgtatctggt gggaagttac    180
ggtatatttg acaaattcta cctcttttgc tttatttcta cgttaattgc aatagcaatt    240
aacgtagtga tacttacaat aaatggagct aagaatgaga gaaattag                288

<210> SEQ ID NO 542
<211> LENGTH: 13
<212> TYPE: RNA
<213> ORGANISM: Artificial Sequence
<220> FEATURE:
<223> OTHER INFORMATION: Kozak sequence

<400> SEQUENCE: 542
gccgccrcca ugg                                                       13

<210> SEQ ID NO 543
<211> LENGTH: 6
<212> TYPE: RNA
<213> ORGANISM: Artificial Sequence
```

```
<220> FEATURE:
<223> OTHER INFORMATION: Shine-Delgarno sequence

<400> SEQUENCE: 543 ggaggu                                                                        6

<210> SEQ ID NO 544
<211> LENGTH: 30
<212> TYPE: DNA
<213> ORGANISM: Artificial Sequence
<220> FEATURE:
<223> OTHER INFORMATION: Lead promoter

<400> SEQUENCE: 544
gaaaaccttg tcaatgaaga gcgatctatg                                             30

<210> SEQ ID NO 545
<211> LENGTH: 30
<212> TYPE: DNA
<213> ORGANISM: Artificial Sequence
<220> FEATURE:
<223> OTHER INFORMATION: FecA promoter

<400> SEQUENCE: 545
ttctcgttcg actcatagct gaacacaaca                                             30

<210> SEQ ID NO 546
<211> LENGTH: 16
<212> TYPE: DNA
<213> ORGANISM: Artificial Sequence
<220> FEATURE:
<223> OTHER INFORMATION: Cu-sensitive promoter

<400> SEQUENCE: 546
atgacaaaat tgtcat                                                            16

<210> SEQ ID NO 547
<211> LENGTH: 30
<212> TYPE: DNA
<213> ORGANISM: Artificial Sequence
<220> FEATURE:
<223> OTHER INFORMATION: Fe promoter

<400> SEQUENCE: 547
accaatgctg ggaacggcca gggcacctaa                                             30

<210> SEQ ID NO 548
<211> LENGTH: 30
<212> TYPE: DNA
<213> ORGANISM: Artificial Sequence
<220> FEATURE:
<223> OTHER INFORMATION: Fe and UV promoters

<400> SEQUENCE: 548
ctgaaagcgc ataccgctat ggaggggtt                                              30

<210> SEQ ID NO 549
<211> LENGTH: 30
<212> TYPE: DNA
<213> ORGANISM: Artificial Sequence
<220> FEATURE:
<223> OTHER INFORMATION: PrFe (PI + PII rus operon)

<400> SEQUENCE: 549
tagatatgcc tgaaagcgca taccgctatg                                             30
```

<210> SEQ ID NO 550
<211> LENGTH: 30
<212> TYPE: DNA
<213> ORGANISM: Artificial Sequence
<220> FEATURE:
<223> OTHER INFORMATION: Lux cassette right promoter

<400> SEQUENCE: 550
tgttatagtc gaatacctct ggcggtgata                              30

<210> SEQ ID NO 551
<211> LENGTH: 30
<212> TYPE: DNA
<213> ORGANISM: Artificial Sequence
<220> FEATURE:
<223> OTHER INFORMATION: P(Las) TetO

<400> SEQUENCE: 551
ttttggtaca ctccctatca gtgatagaga                              30

<210> SEQ ID NO 552
<211> LENGTH: 30
<212> TYPE: DNA
<213> ORGANISM: Artificial Sequence
<220> FEATURE:
<223> OTHER INFORMATION: P(Las) CIO

<400> SEQUENCE: 552 cttttggta cactacctct ggcggtgata                               30

<210> SEQ ID NO 553
<211> LENGTH: 30
<212> TYPE: DNA
<213> ORGANISM: Artificial Sequence
<220> FEATURE:
<223> OTHER INFORMATION: P(Rhl)

<400> SEQUENCE: 553
tacgcaagaa aatggtttgt tatagtcgaa                              30

<210> SEQ ID NO 554
<211> LENGTH: 30
<212> TYPE: DNA
<213> ORGANISM: Artificial Sequence
<220> FEATURE:
<223> OTHER INFORMATION: Double Promoter (LuxR/HSL, positive / cI,
      negative)

<400> SEQUENCE: 554
cgtgcgtgtt gataacaccg tgcgtgttga                              30

<210> SEQ ID NO 555
<211> LENGTH: 30
<212> TYPE: DNA
<213> ORGANISM: Artificial Sequence
<220> FEATURE:
<223> OTHER INFORMATION: P2 promoter in agr operon from S. aureus

<400> SEQUENCE: 555
agattgtact aaatcgtata atgacagtga                              30

<210> SEQ ID NO 556
<211> LENGTH: 30
<212> TYPE: DNA
<213> ORGANISM: Artificial Sequence
<220> FEATURE:

<223> OTHER INFORMATION: plux-cI hybrid promoter

<400> SEQUENCE: 556
gtgttgatgc ttttatcacc gccagtggta         30

<210> SEQ ID NO 557
<211> LENGTH: 30
<212> TYPE: DNA
<213> ORGANISM: Artificial Sequence
<220> FEATURE:
<223> OTHER INFORMATION: plux-lac hybrid promoter

<400> SEQUENCE: 557
agtgtgtgga attgtgagcg gataacaatt         30

<210> SEQ ID NO 558
<211> LENGTH: 30
<212> TYPE: DNA
<213> ORGANISM: Artificial Sequence
<220> FEATURE:
<223> OTHER INFORMATION: CinR, CinL and glucose controlled promotor

<400> SEQUENCE: 558
acatcttaaa agttttagta tcatattcgt         30

<210> SEQ ID NO 559
<211> LENGTH: 30
<212> TYPE: DNA
<213> ORGANISM: Artificial Sequence
<220> FEATURE:
<223> OTHER INFORMATION: RhIR promoter repressible by CI

<400> SEQUENCE: 559
tacgcaagaa aatggtttgt tatagtcgaa         30

<210> SEQ ID NO 560
<211> LENGTH: 30
<212> TYPE: DNA
<213> ORGANISM: Artificial Sequence
<220> FEATURE:
<223> OTHER INFORMATION: Reverse Lux Promoter

<400> SEQUENCE: 560
tcttgcgtaa acctgtacga tcctacaggt         30

<210> SEQ ID NO 561
<211> LENGTH: 30
<212> TYPE: DNA
<213> ORGANISM: Artificial Sequence
<220> FEATURE:
<223> OTHER INFORMATION: rhlI promoter

<400> SEQUENCE: 561
atcctccttt agtcttcccc ctcatgtgtg         30

<210> SEQ ID NO 562
<211> LENGTH: 30
<212> TYPE: DNA
<213> ORGANISM: Artificial Sequence
<220> FEATURE:
<223> OTHER INFORMATION: lasI promoter

<400> SEQUENCE: 562
taaaattatg aaatttgcat aaattcttca         30

```
<210> SEQ ID NO 563
<211> LENGTH: 30
<212> TYPE: DNA
<213> ORGANISM: Artificial Sequence
<220> FEATURE:
<223> OTHER INFORMATION: LuxR+3OC6HSL independent R0065

<400> SEQUENCE: 563
gtgttgacta ttttacctct ggcggtgata                                30

<210> SEQ ID NO 564
<211> LENGTH: 30
<212> TYPE: DNA
<213> ORGANISM: Artificial Sequence
<220> FEATURE:
<223> OTHER INFORMATION: LasR/LasI Inducible & RHLR/RHLI repressible
      Promoter

<400> SEQUENCE: 564
gaaatctggc agttttggt acacgaaagc                                 30

<210> SEQ ID NO 565
<211> LENGTH: 30
<212> TYPE: DNA
<213> ORGANISM: Artificial Sequence
<220> FEATURE:
<223> OTHER INFORMATION: pLux/cI Hybrid Promoter

<400> SEQUENCE: 565
acaccgtgcg tgttgatata gtcgaataaa                                30

<210> SEQ ID NO 566
<211> LENGTH: 30
<212> TYPE: DNA
<213> ORGANISM: Artificial Sequence
<220> FEATURE:
<223> OTHER INFORMATION: pLas promoter

<400> SEQUENCE: 566
aaaattatga aatttgtata aattcttcag                                30

<210> SEQ ID NO 567
<211> LENGTH: 30
<212> TYPE: DNA
<213> ORGANISM: Artificial Sequence
<220> FEATURE:
<223> OTHER INFORMATION: pLas/cI Hybrid Promoter

<400> SEQUENCE: 567
ggttcttttt ggtacctctg gcggtgataa                                30

<210> SEQ ID NO 568
<211> LENGTH: 30
<212> TYPE: DNA
<213> ORGANISM: Artificial Sequence
<220> FEATURE:
<223> OTHER INFORMATION: pLas/Lux Hybrid Promoter

<400> SEQUENCE: 568
tgtaggatcg tacaggtata aattcttcag                                30

<210> SEQ ID NO 569
<211> LENGTH: 30
<212> TYPE: DNA
<213> ORGANISM: Artificial Sequence
<220> FEATURE:
<223> OTHER INFORMATION: pLux
```

<400> SEQUENCE: 569
caagaaaatg gtttgttata gtcgaataaa                                            30

<210> SEQ ID NO 570
<211> LENGTH: 30
<212> TYPE: DNA
<213> ORGANISM: Artificial Sequence
<220> FEATURE:
<223> OTHER INFORMATION: pLux/Las Hybrid Promoter

<400> SEQUENCE: 570
ctatctcatt tgctagtata gtcgaataaa                                            30

<210> SEQ ID NO 571
<211> LENGTH: 30
<212> TYPE: DNA
<213> ORGANISM: Artificial Sequence
<220> FEATURE:
<223> OTHER INFORMATION: Hybrid promoter: HSL-LuxR activated, P22 C2
      repressed

<400> SEQUENCE: 571
tagtttataa tttaagtgtt ctttaatttc                                            30

<210> SEQ ID NO 572
<211> LENGTH: 30
<212> TYPE: DNA
<213> ORGANISM: Artificial Sequence
<220> FEATURE:
<223> OTHER INFORMATION: PAI+LasR -> LuxI (AI)

<400> SEQUENCE: 572
caccttcggg tgggcctttc tgcgtttata                                            30

<210> SEQ ID NO 573
<211> LENGTH: 30
<212> TYPE: DNA
<213> ORGANISM: Artificial Sequence
<220> FEATURE:
<223> OTHER INFORMATION: PAI+LasR -> LasI & AI+LuxR --[\m]LasI

<400> SEQUENCE: 573
aataactctg atagtgctag tgtagatctc                                            30

<210> SEQ ID NO 574
<211> LENGTH: 30
<212> TYPE: DNA
<213> ORGANISM: Artificial Sequence
<220> FEATURE:
<223> OTHER INFORMATION: PAI+LasR -> LasI+GFP & AI+LuxR --[\m]LasI+GFP

<400> SEQUENCE: 574
caccttcggg tgggcctttc tgcgtttata                                            30

<210> SEQ ID NO 575
<211> LENGTH: 30
<212> TYPE: DNA
<213> ORGANISM: Artificial Sequence
<220> FEATURE:
<223> OTHER INFORMATION: Complex QS -> LuxI & LasI circuit

<400> SEQUENCE: 575
caccttcggg tgggcctttc tgcgtttata                                            30

```
<210> SEQ ID NO 576
<211> LENGTH: 30
<212> TYPE: DNA
<213> ORGANISM: Artificial Sequence
<220> FEATURE:
<223> OTHER INFORMATION: position 3 mutated promoter lux pR-3 (luxR &
      HSL regulated)

<400> SEQUENCE: 576
caagaaaatg gtttgttata gtcgaataaa                                          30

<210> SEQ ID NO 577
<211> LENGTH: 30
<212> TYPE: DNA
<213> ORGANISM: Artificial Sequence
<220> FEATURE:
<223> OTHER INFORMATION: position 5 mutated promoter lux pR-5 (luxR &
      HSL regulated)

<400> SEQUENCE: 577
caagaaaatg gtttgttata gtcgaataaa                                          30

<210> SEQ ID NO 578
<211> LENGTH: 30
<212> TYPE: DNA
<213> ORGANISM: Artificial Sequence
<220> FEATURE:
<223> OTHER INFORMATION: position 3&5 mutated promoter lux pR-3/5
      (luxR & HSL regulated)

<400> SEQUENCE: 578
caagaaaatg gtttgttata gtcgaataaa                                          30

<210> SEQ ID NO 579
<211> LENGTH: 30
<212> TYPE: DNA
<213> ORGANISM: Artificial Sequence
<220> FEATURE:
<223> OTHER INFORMATION: Promoter (HSL-mediated luxR repressor)

<400> SEQUENCE: 579
ttgacacctg taggatcgta caggtataat                                          30

<210> SEQ ID NO 580
<211> LENGTH: 30
<212> TYPE: DNA
<213> ORGANISM: Artificial Sequence
<220> FEATURE:
<223> OTHER INFORMATION: Promoter (luxR & HSL regulated -- lux pR)

<400> SEQUENCE: 580
caagaaaatg gtttgttata gtcgaataaa                                          30

<210> SEQ ID NO 581
<211> LENGTH: 30
<212> TYPE: DNA
<213> ORGANISM: Artificial Sequence
<220> FEATURE:
<223> OTHER INFORMATION: Promoter (luxR & HSL regulated -- lux pL)

<400> SEQUENCE: 581
cacgcaaaac ttgcgacaaa caataggtaa                                          30

<210> SEQ ID NO 582
<211> LENGTH: 30
<212> TYPE: DNA
<213> ORGANISM: Artificial Sequence
```

<220> FEATURE:
<223> OTHER INFORMATION: Promoter (RhlR & C4-HSL regulated)

<400> SEQUENCE: 582
gttagctttc gaattggcta aaaagtgttc        30

<210> SEQ ID NO 583
<211> LENGTH: 30
<212> TYPE: DNA
<213> ORGANISM: Artificial Sequence
<220> FEATURE:
<223> OTHER INFORMATION: Promoter (cinR and HSL regulated)

<400> SEQUENCE: 583
ccattctgct ttccacgaac ttgaaaacgc        30

<210> SEQ ID NO 584
<211> LENGTH: 30
<212> TYPE: DNA
<213> ORGANISM: Artificial Sequence
<220> FEATURE:
<223> OTHER INFORMATION: Promoter (LasR & PAI regulated)

<400> SEQUENCE: 584
ggccgcgggt tcttttttggt acacgaaagc        30

<210> SEQ ID NO 585
<211> LENGTH: 30
<212> TYPE: DNA
<213> ORGANISM: Artificial Sequence
<220> FEATURE:
<223> OTHER INFORMATION: Promoter, Standard (luxR and HSL regulated --
      lux pR)

<400> SEQUENCE: 585
aagaaaatgg tttgttgata ctcgaataaa        30

<210> SEQ ID NO 586
<211> LENGTH: 30
<212> TYPE: DNA
<213> ORGANISM: Artificial Sequence
<220> FEATURE:
<223> OTHER INFORMATION: P(Bla)

<400> SEQUENCE: 586
gtttatacat aggcgagtac tctgttatgg        30

<210> SEQ ID NO 587
<211> LENGTH: 30
<212> TYPE: DNA
<213> ORGANISM: Artificial Sequence
<220> FEATURE:
<223> OTHER INFORMATION: P(Cat)

<400> SEQUENCE: 587
agaggttcca actttcacca taatgaaaca        30

<210> SEQ ID NO 588
<211> LENGTH: 30
<212> TYPE: DNA
<213> ORGANISM: Artificial Sequence
<220> FEATURE:
<223> OTHER INFORMATION: P(Kat)

<400> SEQUENCE: 588
taaacaacta acggacaatt ctacctaaca        30

<210> SEQ ID NO 589
<211> LENGTH: 30
<212> TYPE: DNA
<213> ORGANISM: Artificial Sequence
<220> FEATURE:
<223> OTHER INFORMATION: Template for Building Primer Family Member

<400> SEQUENCE: 589
acatcaagcc aaattaaaca ggattaacac                                     30

<210> SEQ ID NO 590
<211> LENGTH: 30
<212> TYPE: DNA
<213> ORGANISM: Artificial Sequence
<220> FEATURE:
<223> OTHER INFORMATION: Reverse lambda cI-regulated promoter

<400> SEQUENCE: 590
gaggtaaaat agtcaacacg cacggtgtta                                     30

<210> SEQ ID NO 591
<211> LENGTH: 30
<212> TYPE: DNA
<213> ORGANISM: Artificial Sequence
<220> FEATURE:
<223> OTHER INFORMATION: Key Promoter absorbs 3

<400> SEQUENCE: 591
caggccggaa taactcccta taatgcgcca                                     30

<210> SEQ ID NO 592
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 592
ggctagctca gtcctaggta cagtgctagc                                     30

<210> SEQ ID NO 593
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 593
agctagctca gtcctaggta ttatgctagc                                     30

<210> SEQ ID NO 594
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 594
agctagctca gtcctaggta ctgtgctagc                                     30

<210> SEQ ID NO 595
<211> LENGTH: 30
<212> TYPE: DNA
<213> ORGANISM: Artificial Sequence
<220> FEATURE:

<223> OTHER INFORMATION: constitutive promoter family member

<400> SEQUENCE: 595
agctagctca gtcctaggga ttatgctagc                                              30

<210> SEQ ID NO 596
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 596
agctagctca gtcctaggta ttgtgctagc                                              30

<210> SEQ ID NO 597
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 597
ggctagctca gtcctaggta ctatgctagc                                              30

<210> SEQ ID NO 598
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 598
ggctagctca gtcctaggta tagtgctagc                                              30

<210> SEQ ID NO 599
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 599
ggctagctca gccctaggta ttatgctagc                                              30

<210> SEQ ID NO 600
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 600
agctagctca gtcctaggta taatgctagc                                              30

<210> SEQ ID NO 601
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 601
agctagctca gtcctaggga ctgtgctagc                                              30

```
<210> SEQ ID NO 602
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 602
ggctagctca gtcctaggta caatgctagc                                          30

<210> SEQ ID NO 603
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 603
ggctagctca gtcctaggta tagtgctagc                                          30

<210> SEQ ID NO 604
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 604
agctagctca gtcctaggga ttatgctagc                                          30

<210> SEQ ID NO 605
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 605
ggctagctca gtcctaggga ttatgctagc                                          30

<210> SEQ ID NO 606
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 606
ggctagctca gtcctaggta caatgctagc                                          30

<210> SEQ ID NO 607
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 607
agctagctca gcccttggta caatgctagc                                          30

<210> SEQ ID NO 608
<211> LENGTH: 30
<212> TYPE: DNA
<213> ORGANISM: Artificial Sequence
<220> FEATURE:
<223> OTHER INFORMATION: constitutive promoter family member
```

```
<400> SEQUENCE: 608
agctagctca gtcctaggga ctatgctagc                                             30

<210> SEQ ID NO 609
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 609
agctagctca gtcctaggga ttgtgctagc                                             30

<210> SEQ ID NO 610
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 610
ggctagctca gtcctaggta ttgtgctagc                                             30

<210> SEQ ID NO 611
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 611
agctagctca gtcctaggta taatgctagc                                             30

<210> SEQ ID NO 612
<211> LENGTH: 30
<212> TYPE: DNA
<213> ORGANISM: Artificial Sequence
<220> FEATURE:
<223> OTHER INFORMATION: 1bp mutant from J23107

<400> SEQUENCE: 612
ggctagctca gtcctaggta ttatgctagc                                             30

<210> SEQ ID NO 613
<211> LENGTH: 30
<212> TYPE: DNA
<213> ORGANISM: Artificial Sequence
<220> FEATURE:
<223> OTHER INFORMATION: 1bp mutant from J23114

<400> SEQUENCE: 613
ggctagctca gtcctaggta caatgctagc                                             30

<210> SEQ ID NO 614
<211> LENGTH: 30
<212> TYPE: DNA
<213> ORGANISM: Artificial Sequence
<220> FEATURE:
<223> OTHER INFORMATION: pBAD reverse

<400> SEQUENCE: 614
aaagtgtgac gccgtgcaaa taatcaatgt                                             30

<210> SEQ ID NO 615
<211> LENGTH: 30
```

```
<212> TYPE: DNA
<213> ORGANISM: Artificial Sequence
<220> FEATURE:
<223> OTHER INFORMATION: NikR promoter, a protein of the ribbon helix-
      helix family of trancription factors that repress expre

<400> SEQUENCE: 615
gacgaatact taaaatcgtc atacttattt                                         30

<210> SEQ ID NO 616
<211> LENGTH: 30
<212> TYPE: DNA
<213> ORGANISM: Artificial Sequence
<220> FEATURE:
<223> OTHER INFORMATION: lacq_Promoter

<400> SEQUENCE: 616
aaacctttcg cggtatggca tgatagcgcc                                         30

<210> SEQ ID NO 617
<211> LENGTH: 30
<212> TYPE: DNA
<213> ORGANISM: Artificial Sequence
<220> FEATURE:
<223> OTHER INFORMATION: lacIQ - promoter sequence

<400> SEQUENCE: 617
tgatagcgcc cggaagagag tcaattcagg                                         30

<210> SEQ ID NO 618
<211> LENGTH: 30
<212> TYPE: DNA
<213> ORGANISM: Artificial Sequence
<220> FEATURE:
<223> OTHER INFORMATION: E. Coli CreABCD phosphate sensing operon
      promoter

<400> SEQUENCE: 618
ttatttaccg tgacgaacta attgctcgtg                                         30

<210> SEQ ID NO 619
<211> LENGTH: 30
<212> TYPE: DNA
<213> ORGANISM: Artificial Sequence
<220> FEATURE:
<223> OTHER INFORMATION: GlnRS promoter

<400> SEQUENCE: 619
catacgccgt tatacgttgt ttacgctttg                                         30

<210> SEQ ID NO 620
<211> LENGTH: 30
<212> TYPE: DNA
<213> ORGANISM: Artificial Sequence
<220> FEATURE:
<223> OTHER INFORMATION: Constitutive weak promoter of lacZ

<400> SEQUENCE: 620
ttatgcttcc ggctcgtatg ttgtgtggac                                         30

<210> SEQ ID NO 621
<211> LENGTH: 30
<212> TYPE: DNA
<213> ORGANISM: Artificial Sequence
<220> FEATURE:
<223> OTHER INFORMATION: Mutated LacZ promoter
```

<400> SEQUENCE: 621
ttatgcttcc ggctcgtatg gtgtgtggac                                30

<210> SEQ ID NO 622
<211> LENGTH: 30
<212> TYPE: DNA
<213> ORGANISM: Artificial Sequence
<220> FEATURE:
<223> OTHER INFORMATION: constitutive promoter with (TA)10 between -10
      and -35 elements

<400> SEQUENCE: 622
atatatatat atatataatg gaagcgtttt                                30

<210> SEQ ID NO 623
<211> LENGTH: 30
<212> TYPE: DNA
<213> ORGANISM: Artificial Sequence
<220> FEATURE:
<223> OTHER INFORMATION: constitutive promoter with (TA)9 between -10
      and -35 elements

<400> SEQUENCE: 623
atatatatat atatataatg gaagcgtttt                                30

<210> SEQ ID NO 624
<211> LENGTH: 30
<212> TYPE: DNA
<213> ORGANISM: Artificial Sequence
<220> FEATURE:
<223> OTHER INFORMATION: constitutive promoter with (C)10 between -10
      and -35 elements

<400> SEQUENCE: 624
ccccgaaagc ttaagaatat aattgtaagc                                30

<210> SEQ ID NO 625
<211> LENGTH: 30
<212> TYPE: DNA
<213> ORGANISM: Artificial Sequence
<220> FEATURE:
<223> OTHER INFORMATION: constitutive promoter with (C)12 between -10
      and -35 elements

<400> SEQUENCE: 625
ccccgaaagc ttaagaatat aattgtaagc                                30

<210> SEQ ID NO 626
<211> LENGTH: 30
<212> TYPE: DNA
<213> ORGANISM: Artificial Sequence
<220> FEATURE:
<223> OTHER INFORMATION: optimized (TA) repeat constitutive promoter
      with 13 bp between -10 and -35 elements

<400> SEQUENCE: 626
tgacaatata tatatatata taatgctagc                                30

<210> SEQ ID NO 627
<211> LENGTH: 30
<212> TYPE: DNA
<213> ORGANISM: Artificial Sequence
<220> FEATURE:
<223> OTHER INFORMATION: optimized (TA) repeat constitutive promoter
      with 15 bp between -10 and -35 elements

<400> SEQUENCE: 627
acaatatata tatatatata taatgctagc                                    30

<210> SEQ ID NO 628
<211> LENGTH: 30
<212> TYPE: DNA
<213> ORGANISM: Artificial Sequence
<220> FEATURE:
<223> OTHER INFORMATION: optimized (TA) repeat constitutive promoter
      with 17 bp between -10 and -35 elements

<400> SEQUENCE: 628
aatatatata tatatatata taatgctagc                                    30

<210> SEQ ID NO 629
<211> LENGTH: 30
<212> TYPE: DNA
<213> ORGANISM: Artificial Sequence
<220> FEATURE:
<223> OTHER INFORMATION: optimized (TA) repeat constitutive promoter
      with 19 bp between -10 and -35 elements

<400> SEQUENCE: 629
tatatatata tatatatata taatgctagc                                    30

<210> SEQ ID NO 630
<211> LENGTH: 30
<212> TYPE: DNA
<213> ORGANISM: Artificial Sequence
<220> FEATURE:
<223> OTHER INFORMATION: optimized (TA) repeat constitutive promoter
      with 21 bp between -10 and -35 elements

<400> SEQUENCE: 630
tatatatata tatatatata taatgctagc                                    30

<210> SEQ ID NO 631
<211> LENGTH: 30
<212> TYPE: DNA
<213> ORGANISM: Artificial Sequence
<220> FEATURE:
<223> OTHER INFORMATION: optimized (A) repeat constitutive promoter with
      17 bp between -10 and -35 elements

<400> SEQUENCE: 631
aaaaaaaaaa aaaaaaaata taatgctagc                                    30

<210> SEQ ID NO 632
<211> LENGTH: 30
<212> TYPE: DNA
<213> ORGANISM: Artificial Sequence
<220> FEATURE:
<223> OTHER INFORMATION: optimized (A) repeat constitutive promoter with
      18 bp between -10 and -35 elements

<400> SEQUENCE: 632
aaaaaaaaaa aaaaaaaata taatgctagc                                    30

<210> SEQ ID NO 633
<211> LENGTH: 30
<212> TYPE: DNA
<213> ORGANISM: Artificial Sequence
<220> FEATURE:
<223> OTHER INFORMATION: J23101:GFP

<400> SEQUENCE: 633
caccttcggg tgggcctttc tgcgtttata                                    30

<210> SEQ ID NO 634
<211> LENGTH: 30
<212> TYPE: DNA
<213> ORGANISM: Artificial Sequence
<220> FEATURE:
<223> OTHER INFORMATION: J23119:IFP

<400> SEQUENCE: 634
caccttcggg tgggcctttc tgcgtttata                               30

<210> SEQ ID NO 635
<211> LENGTH: 30
<212> TYPE: DNA
<213> ORGANISM: Artificial Sequence
<220> FEATURE:
<223> OTHER INFORMATION: J23119:HO1

<400> SEQUENCE: 635
caccttcggg tgggcctttc tgcgtttata                               30

<210> SEQ ID NO 636
<211> LENGTH: 30
<212> TYPE: DNA
<213> ORGANISM: Artificial Sequence
<220> FEATURE:
<223> OTHER INFORMATION: Infrared signal reporter (J23119:IFP:J23119:
      HO1)

<400> SEQUENCE: 636
caccttcggg tgggcctttc tgcgtttata                               30

<210> SEQ ID NO 637
<211> LENGTH: 30
<212> TYPE: DNA
<213> ORGANISM: Artificial Sequence
<220> FEATURE:
<223> OTHER INFORMATION: Double terminator + constitutive promoter

<400> SEQUENCE: 637
ggctagctca gtcctaggta cagtgctagc                               30

<210> SEQ ID NO 638
<211> LENGTH: 30
<212> TYPE: DNA
<213> ORGANISM: Artificial Sequence
<220> FEATURE:
<223> OTHER INFORMATION: Double terminator + Constitutive promoter +
      Strong RBS

<400> SEQUENCE: 638
tgctagctac tagagattaa agaggagaaa                               30

<210> SEQ ID NO 639
<211> LENGTH: 30
<212> TYPE: DNA
<213> ORGANISM: Artificial Sequence
<220> FEATURE:
<223> OTHER INFORMATION: IPTG inducible Lac promoter cassette

<400> SEQUENCE: 639
ttgtgagcgg ataacaagat actgagcaca                               30

<210> SEQ ID NO 640
<211> LENGTH: 30
<212> TYPE: DNA

```
<213> ORGANISM: Artificial Sequence
<220> FEATURE:
<223> OTHER INFORMATION: IPTG inducible Lac promoter cassette

<400> SEQUENCE: 640
ttgtgagcgg ataacaagat actgagcaca                                    30

<210> SEQ ID NO 641
<211> LENGTH: 30
<212> TYPE: DNA
<213> ORGANISM: Artificial Sequence
<220> FEATURE:
<223> OTHER INFORMATION: IPTG inducible Lac promoter cassette

<400> SEQUENCE: 641
ttgtgagcgg ataacaagat actgagcaca                                    30

<210> SEQ ID NO 642
<211> LENGTH: 30
<212> TYPE: DNA
<213> ORGANISM: Artificial Sequence
<220> FEATURE:
<223> OTHER INFORMATION: M13K07 gene I promoter

<400> SEQUENCE: 642
cctgttttta tgttattctc tctgtaaagg                                    30

<210> SEQ ID NO 643
<211> LENGTH: 30
<212> TYPE: DNA
<213> ORGANISM: Artificial Sequence
<220> FEATURE:
<223> OTHER INFORMATION: M13K07 gene II promoter

<400> SEQUENCE: 643
aaatatttgc ttatacaatc ttcctgtttt                                    30

<210> SEQ ID NO 644
<211> LENGTH: 30
<212> TYPE: DNA
<213> ORGANISM: Artificial Sequence
<220> FEATURE:
<223> OTHER INFORMATION: M13K07 gene III promoter

<400> SEQUENCE: 644
gctgataaac cgatacaatt aaaggctcct                                    30

<210> SEQ ID NO 645
<211> LENGTH: 30
<212> TYPE: DNA
<213> ORGANISM: Artificial Sequence
<220> FEATURE:
<223> OTHER INFORMATION: M13K07 gene IV promoter

<400> SEQUENCE: 645
ctcttctcag cgtcttaatc taagctatcg                                    30

<210> SEQ ID NO 646
<211> LENGTH: 30
<212> TYPE: DNA
<213> ORGANISM: Artificial Sequence
<220> FEATURE:
<223> OTHER INFORMATION: M13K07 gene V promoter

<400> SEQUENCE: 646
atgagccagt tcttaaaatc gcataaggta                                    30
```

<210> SEQ ID NO 647
<211> LENGTH: 30
<212> TYPE: DNA
<213> ORGANISM: Artificial Sequence
<220> FEATURE:
<223> OTHER INFORMATION: M13K07 gene VI promoter

<400> SEQUENCE: 647
ctattgattg tgacaaaata aacttattcc                               30

<210> SEQ ID NO 648
<211> LENGTH: 30
<212> TYPE: DNA
<213> ORGANISM: Artificial Sequence
<220> FEATURE:
<223> OTHER INFORMATION: M13K07 gene VIII promoter

<400> SEQUENCE: 648
gtttcgcgct tggtataatc gctggggtc                                30

<210> SEQ ID NO 649
<211> LENGTH: 30
<212> TYPE: DNA
<213> ORGANISM: Artificial Sequence
<220> FEATURE:
<223> OTHER INFORMATION: M13110

<400> SEQUENCE: 649
ctttgcttct gactataata gtcagggtaa                               30

<210> SEQ ID NO 650
<211> LENGTH: 30
<212> TYPE: DNA
<213> ORGANISM: Artificial Sequence
<220> FEATURE:
<223> OTHER INFORMATION: Modified promoter sequence of g3.

<400> SEQUENCE: 650
aaaccgatac aattaaaggc tcctgctagc                               30

<210> SEQ ID NO 651
<211> LENGTH: 30
<212> TYPE: DNA
<213> ORGANISM: Artificial Sequence
<220> FEATURE:
<223> OTHER INFORMATION: Constitutive Promoter I

<400> SEQUENCE: 651
caccacactg atagtgctag tgtagatcac                               30

<210> SEQ ID NO 652
<211> LENGTH: 30
<212> TYPE: DNA
<213> ORGANISM: Artificial Sequence
<220> FEATURE:
<223> OTHER INFORMATION: Constitutive Promoter II

<400> SEQUENCE: 652
gccggaataa ctccctataa tgcgccacca                               30

<210> SEQ ID NO 653
<211> LENGTH: 30
<212> TYPE: DNA
<213> ORGANISM: Artificial Sequence
<220> FEATURE:

<223> OTHER INFORMATION: --Specify Parts List--

<400> SEQUENCE: 653
ttgacaagct tttcctcagc tccgtaaact        30

<210> SEQ ID NO 654
<211> LENGTH: 30
<212> TYPE: DNA
<213> ORGANISM: Artificial Sequence
<220> FEATURE:
<223> OTHER INFORMATION: Full-length stationary phase osmY promoter

<400> SEQUENCE: 654
ggtttcaaaa ttgtgatcta tatttaacaa        30

<210> SEQ ID NO 655
<211> LENGTH: 30
<212> TYPE: DNA
<213> ORGANISM: Artificial Sequence
<220> FEATURE:
<223> OTHER INFORMATION: Minimal stationary phase osmY promoter

<400> SEQUENCE: 655
ggtttcaaaa ttgtgatcta tatttaacaa        30

<210> SEQ ID NO 656
<211> LENGTH: 30
<212> TYPE: DNA
<213> ORGANISM: Artificial Sequence
<220> FEATURE:
<223> OTHER INFORMATION: htpG Heat Shock Promoter

<400> SEQUENCE: 656
tctattccaa taagaaatc ttcctgcgtg        30

<210> SEQ ID NO 657
<211> LENGTH: 30
<212> TYPE: DNA
<213> ORGANISM: Artificial Sequence
<220> FEATURE:
<223> OTHER INFORMATION: Promoter veg a constitutive promoter for B.
      subtilis

<400> SEQUENCE: 657
aaaaatgggc tcgtgttgta caataaatgt        30

<210> SEQ ID NO 658
<211> LENGTH: 30
<212> TYPE: DNA
<213> ORGANISM: Artificial Sequence
<220> FEATURE:
<223> OTHER INFORMATION: Promoter 43 a constitutive promoter for B.
      subtilis

<400> SEQUENCE: 658
aaaaaaagcg cgcgattatg taaaatataa        30

<210> SEQ ID NO 659
<211> LENGTH: 30
<212> TYPE: DNA
<213> ORGANISM: Artificial Sequence
<220> FEATURE:
<223> OTHER INFORMATION: Strong constitutive promoter for Bacillus
      subtilis

<400> SEQUENCE: 659
aattgcagta ggcatgacaa aatggactca                                30

<210> SEQ ID NO 660
<211> LENGTH: 30
<212> TYPE: DNA
<213> ORGANISM: Artificial Sequence
<220> FEATURE:
<223> OTHER INFORMATION: PliaG

<400> SEQUENCE: 660
caagcttttc ctttataata gaatgaatga                                30

<210> SEQ ID NO 661
<211> LENGTH: 30
<212> TYPE: DNA
<213> ORGANISM: Artificial Sequence
<220> FEATURE:
<223> OTHER INFORMATION: PlepA

<400> SEQUENCE: 661
tctaagctag tgtatttttgc gtttaatagt                               30

<210> SEQ ID NO 662
<211> LENGTH: 30
<212> TYPE: DNA
<213> ORGANISM: Artificial Sequence
<220> FEATURE:
<223> OTHER INFORMATION: Pveg

<400> SEQUENCE: 662
aatgggctcg tgttgtacaa taaatgtagt                                30

<210> SEQ ID NO 663
<211> LENGTH: 30
<212> TYPE: DNA
<213> ORGANISM: Artificial Sequence
<220> FEATURE:
<223> OTHER INFORMATION: Promoter ctc for B. subtilis

<400> SEQUENCE: 663
atccttatcg ttatgggtat tgtttgtaat                                30

<210> SEQ ID NO 664
<211> LENGTH: 30
<212> TYPE: DNA
<213> ORGANISM: Artificial Sequence
<220> FEATURE:
<223> OTHER INFORMATION: Promoter gsiB for B. subtilis

<400> SEQUENCE: 664
taaaagaatt gtgagcggga atacaacaac                                30

<210> SEQ ID NO 665
<211> LENGTH: 30
<212> TYPE: DNA
<213> ORGANISM: Artificial Sequence
<220> FEATURE:
<223> OTHER INFORMATION: Promoter 43 a constitutive promoter for B.
      subtilis

<400> SEQUENCE: 665
aaaaaaagcg cgcgattatg taaaatataa                                30

<210> SEQ ID NO 666
<211> LENGTH: 30
<212> TYPE: DNA

```
<213> ORGANISM: Artificial Sequence
<220> FEATURE:
<223> OTHER INFORMATION: Pspv2 from Salmonella

<400> SEQUENCE: 666
tacaaaataa ttcccctgca aacattatca                                    30

<210> SEQ ID NO 667
<211> LENGTH: 30
<212> TYPE: DNA
<213> ORGANISM: Artificial Sequence
<220> FEATURE:
<223> OTHER INFORMATION: Pspv from Salmonella

<400> SEQUENCE: 667
tacaaaataa ttcccctgca aacattatcg                                    30

<210> SEQ ID NO 668
<211> LENGTH: 30
<212> TYPE: DNA
<213> ORGANISM: Artificial Sequence
<220> FEATURE:
<223> OTHER INFORMATION: T7 promoter (strong promoter from T7
      bacteriophage)

<400> SEQUENCE: 668
agggaataca agctacttgt tcttttttgca                                   30

<210> SEQ ID NO 669
<211> LENGTH: 23
<212> TYPE: DNA
<213> ORGANISM: Artificial Sequence
<220> FEATURE:
<223> OTHER INFORMATION: T7 Promoter

<400> SEQUENCE: 669
taatacgact cactataggg aga                                           23

<210> SEQ ID NO 670
<211> LENGTH: 28
<212> TYPE: DNA
<213> ORGANISM: Artificial Sequence
<220> FEATURE:
<223> OTHER INFORMATION: T7 Promoter

<400> SEQUENCE: 670
gaatttaata cgactcacta tagggaga                                      28

<210> SEQ ID NO 671
<211> LENGTH: 19
<212> TYPE: DNA
<213> ORGANISM: Artificial Sequence
<220> FEATURE:
<223> OTHER INFORMATION: T7 consensus -10 and rest

<400> SEQUENCE: 671
taatacgact cactatagg                                                19

<210> SEQ ID NO 672
<211> LENGTH: 30
<212> TYPE: DNA
<213> ORGANISM: Artificial Sequence
<220> FEATURE:
<223> OTHER INFORMATION: overlapping T7 promoter

<400> SEQUENCE: 672
```

```
gagtcgtatt aatacgactc actataggg                                30
```

<210> SEQ ID NO 673
<211> LENGTH: 30
<212> TYPE: DNA
<213> ORGANISM: Artificial Sequence
<220> FEATURE:
<223> OTHER INFORMATION: more overlapping T7 promoter

<400> SEQUENCE: 673

```
agtgagtcgt actacgactc actataggg                                30
```

<210> SEQ ID NO 674
<211> LENGTH: 30
<212> TYPE: DNA
<213> ORGANISM: Artificial Sequence
<220> FEATURE:
<223> OTHER INFORMATION: weaken overlapping T7 promoter

<400> SEQUENCE: 674

```
gagtcgtatt aatacgactc tctataggg                                30
```

<210> SEQ ID NO 675
<211> LENGTH: 23
<212> TYPE: DNA
<213> ORGANISM: Artificial Sequence
<220> FEATURE:
<223> OTHER INFORMATION: T7 Consensus Promoter Sequence

<400> SEQUENCE: 675

```
taatacgact cactataggg aga                                      23
```

<210> SEQ ID NO 676
<211> LENGTH: 23
<212> TYPE: DNA
<213> ORGANISM: Artificial Sequence
<220> FEATURE:
<223> OTHER INFORMATION: T7 RNAP promoter

<400> SEQUENCE: 676

```
ttatacgact cactataggg aga                                      23
```

<210> SEQ ID NO 677
<211> LENGTH: 23
<212> TYPE: DNA
<213> ORGANISM: Artificial Sequence
<220> FEATURE:
<223> OTHER INFORMATION: T7 RNAP promoter

<400> SEQUENCE: 677

```
gaatacgact cactataggg aga                                      23
```

<210> SEQ ID NO 678
<211> LENGTH: 23
<212> TYPE: DNA
<213> ORGANISM: Artificial Sequence
<220> FEATURE:
<223> OTHER INFORMATION: T7 RNAP promoter

<400> SEQUENCE: 678

```
taatacgtct cactataggg aga                                      23
```

<210> SEQ ID NO 679
<211> LENGTH: 23
<212> TYPE: DNA
<213> ORGANISM: Artificial Sequence

```
<220> FEATURE:
<223> OTHER INFORMATION: T7 RNAP promoter

<400> SEQUENCE: 679
tcatacgact cactataggg aga                                              23

<210> SEQ ID NO 680
<211> LENGTH: 30
<212> TYPE: DNA
<213> ORGANISM: Artificial Sequence
<220> FEATURE:
<223> OTHER INFORMATION: T7 strong promoter

<400> SEQUENCE: 680
taatacgact cactataggg agaccacaac                                       30

<210> SEQ ID NO 681
<211> LENGTH: 30
<212> TYPE: DNA
<213> ORGANISM: Artificial Sequence
<220> FEATURE:
<223> OTHER INFORMATION: T7 weak binding and processivity

<400> SEQUENCE: 681
taattgaact cactaaaggg agaccacagc                                       30

<210> SEQ ID NO 682
<211> LENGTH: 30
<212> TYPE: DNA
<213> ORGANISM: Artificial Sequence
<220> FEATURE:
<223> OTHER INFORMATION: T7 weak binding promoter

<400> SEQUENCE: 682
cgaagtaata cgactcacta ttagggaaga                                       30

<210> SEQ ID NO 683
<211> LENGTH: 30
<212> TYPE: DNA
<213> ORGANISM: Artificial Sequence
<220> FEATURE:
<223> OTHER INFORMATION: pCyc (Medium) Promoter

<400> SEQUENCE: 683
acaaacacaa atacacacac taaattaata                                       30

<210> SEQ ID NO 684
<211> LENGTH: 30
<212> TYPE: DNA
<213> ORGANISM: Artificial Sequence
<220> FEATURE:
<223> OTHER INFORMATION: pAdh (Strong) Promoter

<400> SEQUENCE: 684
ccaagcatac aatcaactat ctcatataca                                       30

<210> SEQ ID NO 685
<211> LENGTH: 30
<212> TYPE: DNA
<213> ORGANISM: Artificial Sequence
<220> FEATURE:
<223> OTHER INFORMATION: pSte5 (Weak) Promoter

<400> SEQUENCE: 685
gatacaggat acagcggaaa caacttttaa                                       30
```

```
<210> SEQ ID NO 686
<211> LENGTH: 30
<212> TYPE: DNA
<213> ORGANISM: Artificial Sequence
<220> FEATURE:
<223> OTHER INFORMATION: yeast ADH1 promoter

<400> SEQUENCE: 686
tttcaagcta taccaagcat acaatcaact                                30

<210> SEQ ID NO 687
<211> LENGTH: 30
<212> TYPE: DNA
<213> ORGANISM: Artificial Sequence
<220> FEATURE:
<223> OTHER INFORMATION: cyc100 minimal promoter

<400> SEQUENCE: 687
cctttgcagc ataaattact atacttctat                                30

<210> SEQ ID NO 688
<211> LENGTH: 30
<212> TYPE: DNA
<213> ORGANISM: Artificial Sequence
<220> FEATURE:
<223> OTHER INFORMATION: cyc70 minimal promoter

<400> SEQUENCE: 688
cctttgcagc ataaattact atacttctat                                30

<210> SEQ ID NO 689
<211> LENGTH: 30
<212> TYPE: DNA
<213> ORGANISM: Artificial Sequence
<220> FEATURE:
<223> OTHER INFORMATION: cyc43 minimal promoter

<400> SEQUENCE: 689
cctttgcagc ataaattact atacttctat                                30

<210> SEQ ID NO 690
<211> LENGTH: 30
<212> TYPE: DNA
<213> ORGANISM: Artificial Sequence
<220> FEATURE:
<223> OTHER INFORMATION: cyc28 minimal promoter

<400> SEQUENCE: 690
cctttgcagc ataaattact atacttctat                                30

<210> SEQ ID NO 691
<211> LENGTH: 30
<212> TYPE: DNA
<213> ORGANISM: Artificial Sequence
<220> FEATURE:
<223> OTHER INFORMATION: cyc16 minimal promoter

<400> SEQUENCE: 691
cctttgcagc ataaattact atacttctat                                30

<210> SEQ ID NO 692
<211> LENGTH: 30
<212> TYPE: DNA
<213> ORGANISM: Artificial Sequence
<220> FEATURE:
<223> OTHER INFORMATION: pPGK1
```

<400> SEQUENCE: 692
ttatctactt tttacaacaa atataaaaca                                    30

<210> SEQ ID NO 693
<211> LENGTH: 30
<212> TYPE: DNA
<213> ORGANISM: Artificial Sequence
<220> FEATURE:
<223> OTHER INFORMATION: pCYC Yeast Promoter

<400> SEQUENCE: 693
acaaacacaa atacacacac taaattaata                                    30

<210> SEQ ID NO 694
<211> LENGTH: 30
<212> TYPE: DNA
<213> ORGANISM: Artificial Sequence
<220> FEATURE:
<223> OTHER INFORMATION: Yeast GPD (TDH3) Promoter

<400> SEQUENCE: 694
gtttcgaata aacacacata aacaaacaaa                                    30

<210> SEQ ID NO 695
<211> LENGTH: 30
<212> TYPE: DNA
<213> ORGANISM: Artificial Sequence
<220> FEATURE:
<223> OTHER INFORMATION: yeast mid-length ADH1 promoter

<400> SEQUENCE: 695
ccaagcatac aatcaactat ctcatataca                                    30

<210> SEQ ID NO 696
<211> LENGTH: 30
<212> TYPE: DNA
<213> ORGANISM: Artificial Sequence
<220> FEATURE:
<223> OTHER INFORMATION: Yeast CLB1 promoter region, G2/M cell cycle
      specific

<400> SEQUENCE: 696
accatcaaag gaagctttaa tcttctcata                                    30

<210> SEQ ID NO 697
<211> LENGTH: 30
<212> TYPE: DNA
<213> ORGANISM: Artificial Sequence
<220> FEATURE:
<223> OTHER INFORMATION: CMV promoter

<400> SEQUENCE: 697
agaacccact gcttactggc ttatcgaaat                                    30

<210> SEQ ID NO 698
<211> LENGTH: 30
<212> TYPE: DNA
<213> ORGANISM: Artificial Sequence
<220> FEATURE:
<223> OTHER INFORMATION: Ubc Promoter

<400> SEQUENCE: 698
ggccgttttt ggcttttttg ttagacgaag                                    30

<210> SEQ ID NO 699
<211> LENGTH: 9
<212> TYPE: PRT
<213> ORGANISM: Lactobacillus curvatus

<400> SEQUENCE: 699

Asn Ile Pro Gln Leu Thr Pro Thr Pro
1               5

<210> SEQ ID NO 700
<211> LENGTH: 27
<212> TYPE: DNA
<213> ORGANISM: Lactobacillus curvatus

<400> SEQUENCE: 700
aacattccgc agctgacccc gaccccg                                          27

<210> SEQ ID NO 701
<211> LENGTH: 18
<212> TYPE: PRT
<213> ORGANISM: Bacillus thuringiensis
<220> FEATURE:
<221> NAME/KEY: VARIANT
<222> LOCATION: 4, 7, 10
<223> OTHER INFORMATION: Xaa = any amino acid

<400> SEQUENCE: 701

Asp Trp Thr Xaa Trp Ser Xaa Leu Val Xaa Ala Ala Cys Ser Val Glu
1               5                   10                  15

Leu Leu

<210> SEQ ID NO 702
<211> LENGTH: 54
<212> TYPE: DNA
<213> ORGANISM: Bacillus thuringiensis
<220> FEATURE:
<221> NAME/KEY: misc_feature
<222> LOCATION: 10, 11, 12, 19, 20, 21, 28, 29, 30
<223> OTHER INFORMATION: n = A,T,C or G

<400> SEQUENCE: 702
gattggaccn nntggagcnn nctggtgnnn gcggcgtgca gcgtggaact gctg            54

<210> SEQ ID NO 703
<211> LENGTH: 30
<212> TYPE: PRT
<213> ORGANISM: Lactobacillus curvatus L442

<400> SEQUENCE: 703

Ala Tyr Pro Gly Asn Gly Val His Cys Gly Lys Tyr Ser Cys Thr Val
1               5                   10                  15

Asp Lys Gln Thr Ala Ile Gly Asn Ile Gly Asn Asn Ala Ala
            20                  25                  30

<210> SEQ ID NO 704
<211> LENGTH: 90
<212> TYPE: DNA
<213> ORGANISM: Lactobacillus curvatus L442

<400> SEQUENCE: 704
gcgtatccgg gcaacggcgt gcattgcggc aaatatagct gcaccgtgga taaacagacc      60
gcgattggca acattggcaa caacgcggcg                                       90

<210> SEQ ID NO 705

<211> LENGTH: 43
<212> TYPE: PRT
<213> ORGANISM: Carnobacterium divergens

<400> SEQUENCE: 705

Thr Lys Tyr Tyr Gly Asn Gly Val Tyr Cys Asn Ser Lys Lys Cys Trp
1               5                   10                  15

Val Asp Trp Gly Thr Ala Gln Gly Cys Ile Asp Val Val Ile Gly Gln
            20                  25                  30

Leu Gly Gly Gly Ile Pro Gly Lys Gly Lys Cys
        35                  40

<210> SEQ ID NO 706
<211> LENGTH: 129
<212> TYPE: DNA
<213> ORGANISM: Carnobacterium divergens

<400> SEQUENCE: 706
accaaatatt atggcaacgg cgtgtattgc aacagcaaaa aatgctgggt ggattggggc    60
accgcgcagg gctgcattga tgtggtgatt ggccagctgg cggcggcat tccgggcaaa   120 ggcaaatgc                                                          129

<210> SEQ ID NO 707
<211> LENGTH: 24
<212> TYPE: PRT
<213> ORGANISM: Microbispora sp. (strain 107891)

<400> SEQUENCE: 707

Val Thr Ser Trp Ser Leu Cys Thr Pro Gly Cys Thr Ser Pro Gly Gly
1               5                   10                  15

Gly Ser Asn Cys Ser Phe Cys Cys
            20

<210> SEQ ID NO 708
<211> LENGTH: 72
<212> TYPE: DNA
<213> ORGANISM: Microbispora sp. (strain 107891)

<400> SEQUENCE: 708
gtgaccagct ggagcctgtg caccccgggc tgcaccagcc cgggcggcgg cagcaactgc    60
agcttttgct gc                                                        72

<210> SEQ ID NO 709
<211> LENGTH: 62
<212> TYPE: PRT
<213> ORGANISM: Enterococcus sp.

<400> SEQUENCE: 709

Asn Arg Trp Tyr Cys Asn Ser Ala Ala Gly Gly Val Gly Gly Ala Ala
1               5                   10                  15

Val Cys Gly Leu Ala Gly Tyr Val Gly Glu Ala Lys Glu Asn Ile Ala
            20                  25                  30

Gly Glu Val Arg Lys Gly Trp Gly Met Ala Gly Gly Phe Thr His Asn
        35                  40                  45

Lys Ala Cys Lys Ser Phe Pro Gly Ser Gly Trp Ala Ser Gly
    50                  55                  60

<210> SEQ ID NO 710
<211> LENGTH: 186
<212> TYPE: DNA

<213> ORGANISM: Enterococcus sp.

<400> SEQUENCE: 710

```
aaccgctggt attgcaacag cgcggcgggc ggcgtgggcg gcgcggcggt gtgcggcctg     60
gcgggctatg tgggcgaagc gaaagaaaac attgcgggcg aagtgcgcaa aggctggggc    120
atggcgggcg gctttaccca taacaaagcg tgcaaaagct ttccgggcag cggctgggcg    180
agcggc                                                              186
```

<210> SEQ ID NO 711
<211> LENGTH: 39
<212> TYPE: PRT
<213> ORGANISM: Enterococcus faecium

<400> SEQUENCE: 711

Thr Thr Lys Asn Tyr Gly Asn Gly Val Cys Asn Ser Val Asn Trp Cys
1               5                   10                  15

Gln Cys Gly Asn Val Trp Ala Ser Cys Asn Leu Ala Thr Gly Cys Ala
            20                  25                  30

Ala Trp Leu Cys Lys Leu Ala
        35

<210> SEQ ID NO 712
<211> LENGTH: 117
<212> TYPE: DNA
<213> ORGANISM: Enterococcus faecium

<400> SEQUENCE: 712

```
accaccaaaa actatggcaa cggcgtgtgc aacagcgtga actggtgcca gtgcggcaac     60
gtgtgggcga gctgcaacct ggcgaccggc tgcgcggcgt ggctgtgcaa actggcg       117
```

<210> SEQ ID NO 713
<211> LENGTH: 30
<212> TYPE: PRT
<213> ORGANISM: Paenibacillus polymyxa

<400> SEQUENCE: 713

Ala Ser Ile Ile Lys Thr Thr Ile Lys Val Ser Lys Ala Val Cys Lys
1               5                   10                  15

Thr Leu Thr Cys Ile Cys Thr Gly Ser Cys Ser Asn Cys Lys
            20                  25                  30

<210> SEQ ID NO 714
<211> LENGTH: 90
<212> TYPE: DNA
<213> ORGANISM: Paenibacillus polymyxa

<400> SEQUENCE: 714

```
gcgagcatta ttaaaaccac cattaaagtg agcaaagcgg tgtgcaaaac cctgacctgc     60
atttgcaccg gcagctgcag caactgcaaa                                     90
```

<210> SEQ ID NO 715
<211> LENGTH: 31
<212> TYPE: PRT
<213> ORGANISM: Staphylococcus epidermidis

<400> SEQUENCE: 715

Ser Ala Ser Ile Val Lys Thr Thr Ile Lys Ala Ser Lys Lys Leu Cys
1               5                   10                  15

Arg Gly Phe Thr Leu Thr Cys Gly Cys His Phe Thr Gly Lys Lys

<210> SEQ ID NO 716
<211> LENGTH: 93
<212> TYPE: DNA
<213> ORGANISM: Staphylococcus epidermidis

<400> SEQUENCE: 716
agcgcgagca ttgtgaaaac caccattaaa gcgagcaaaa aactgtgccg cggctttacc    60
ctgacctgcg gctgccattt taccggcaaa aaa                                 93

<210> SEQ ID NO 717
<211> LENGTH: 58
<212> TYPE: PRT
<213> ORGANISM: Enterococcus faecium

<400> SEQUENCE: 717

Met Glu Lys Leu Thr Val Lys Glu Met Ser Gln Val Val Gly Gly Lys
1               5                   10                  15

Tyr Tyr Gly Asn Gly Val Ser Cys Asn Lys Lys Gly Cys Ser Val Asp
            20                  25                  30

Trp Gly Lys Ala Ile Gly Ile Ile Gly Asn Asn Ala Ala Ala Asn Leu
        35                  40                  45

Thr Thr Gly Gly Lys Ala Gly Trp Lys Gly
    50                  55

<210> SEQ ID NO 718
<211> LENGTH: 178
<212> TYPE: DNA
<213> ORGANISM: Enterococcus faecium

<400> SEQUENCE: 718
atggaaaaat taactgtgaa agaaatgtcg caagtagttg gcggaaagta ctatggtaac    60
ggagtatcat gtaataaaaa gggatgtagt gttgattggg gaaaagctat tggtattatt   120
ggaaataatg ctgctgctaa tttaactact ggcggaaaag cagggtggaa aggttaac     178

<210> SEQ ID NO 719
<211> LENGTH: 39
<212> TYPE: PRT
<213> ORGANISM: Paenibacillus polymyxa

<400> SEQUENCE: 719

Ala Thr Tyr Tyr Gly Asn Gly Leu Tyr Cys Asn Lys Gln Lys His Tyr
1               5                   10                  15

Thr Trp Val Asp Trp Asn Lys Ala Ser Arg Glu Ile Gly Lys Ile Thr
            20                  25                  30

Val Asn Gly Trp Val Gln His
        35

<210> SEQ ID NO 720
<211> LENGTH: 93
<212> TYPE: DNA
<213> ORGANISM: Paenibacillus polymyxa

<400> SEQUENCE: 720
agcgcgagca ttgtgaaaac caccattaaa gcgagcaaaa aactgtgccg cggctttacc    60
ctgacctgcg gctgccattt taccggcaaa aaa                                 93

<210> SEQ ID NO 721

```
<211> LENGTH: 35
<212> TYPE: PRT
<213> ORGANISM: Bacillus circulans

<400> SEQUENCE: 721

Val Asn Tyr Gly Asn Gly Val Ser Cys Ser Lys Thr Lys Cys Ser Val
1               5                   10                  15

Asn Trp Gly Ile Ile Thr His Gln Ala Phe Arg Val Thr Ser Gly Val
            20                  25                  30

Ala Ser Gly
        35

<210> SEQ ID NO 722
<211> LENGTH: 105
<212> TYPE: DNA
<213> ORGANISM: Bacillus circulans

<400> SEQUENCE: 722
gtgaactatg gcaacggcgt gagctgcagc aaaaccaaat gcagcgtgaa ctggggcatt      60
attacccatc aggcgtttcg cgtgaccagc ggcgtggcga gcggc                     105

<210> SEQ ID NO 723
<211> LENGTH: 30
<212> TYPE: PRT
<213> ORGANISM: Paenibacillus polymyxa

<400> SEQUENCE: 723

Phe Val Tyr Gly Asn Gly Val Thr Ser Ile Leu Val Gln Ala Gln Phe
1               5                   10                  15

Leu Val Asn Gly Gln Arg Arg Phe Phe Tyr Thr Pro Asp Lys
            20                  25                  30

<210> SEQ ID NO 724
<211> LENGTH: 90
<212> TYPE: DNA
<213> ORGANISM: Paenibacillus polymyxa

<400> SEQUENCE: 724
tttgtgtatg gcaacggcgt gaccagcatt ctggtgcagg cgcagtttct ggtgaacggc      60
cagcgccgct ttttttatac cccggataaa                                       90

<210> SEQ ID NO 725
<211> LENGTH: 13
<212> TYPE: PRT
<213> ORGANISM: Lactobacillus rhamnosus

<400> SEQUENCE: 725

Ala Val Pro Ala Val Arg Lys Thr Asn Glu Thr Leu Asp
1               5                   10

<210> SEQ ID NO 726
<211> LENGTH: 39
<212> TYPE: DNA
<213> ORGANISM: Lactobacillus rhamnosus

<400> SEQUENCE: 726
gcggtgccgg cggtgcgcaa aaccaacgaa accctggat                             39

<210> SEQ ID NO 727
<211> LENGTH: 60
<212> TYPE: PRT
<213> ORGANISM: Bacillus licheniformis
```

-continued

<400> SEQUENCE: 727

Met Lys Asn Ser Ala Ala Arg Glu Ala Phe Lys Gly Ala Asn His Pro
1               5                   10                  15

Ala Gly Met Val Ser Glu Glu Leu Lys Ala Leu Val Gly Gly Asn
            20                  25                  30

Asp Val Asn Pro Glu Thr Thr Pro Ala Thr Thr Ser Ser Trp Thr Cys
        35                  40                  45

Ile Thr Ala Gly Val Thr Val Ser Ala Ser Leu Cys
    50                  55                  60

<210> SEQ ID NO 728
<211> LENGTH: 180
<212> TYPE: DNA
<213> ORGANISM: Bacillus licheniformis

<400> SEQUENCE: 728
atgaaaaaca gcgcggcgcg cgaagcgttt aaaggcgcga accatccggc gggcatggtg     60
agcgaagaag aactgaaagc gctggtgggc ggcaacgatg tgaacccgga aaccaccccg    120
gcgaccacca gcagctggac ctgcattacc gcgggcgtga ccgtgagcgc gagcctgtgc    180

<210> SEQ ID NO 729
<211> LENGTH: 689
<212> TYPE: PRT
<213> ORGANISM: Pseudomonas aeruginosa

<400> SEQUENCE: 729

Met Ala Val Asn Asp Tyr Glu Pro Gly Ser Met Val Ile Thr His Val
1               5                   10                  15

Gln Gly Gly Gly Arg Asp Ile Ile Gln Tyr Ile Pro Ala Arg Ser Ser
            20                  25                  30

Tyr Gly Thr Pro Pro Phe Val Pro Pro Gly Pro Ser Pro Tyr Val Gly
        35                  40                  45

Thr Gly Met Gln Glu Tyr Arg Lys Leu Arg Ser Thr Leu Asp Lys Ser
    50                  55                  60

His Ser Glu Leu Lys Lys Asn Leu Lys Asn Glu Thr Leu Lys Glu Val
65                  70                  75                  80

Asp Glu Leu Lys Ser Glu Ala Gly Leu Pro Gly Lys Ala Val Ser Ala
                85                  90                  95

Asn Asp Ile Arg Asp Glu Lys Ser Ile Val Asp Ala Leu Met Asp Ala
            100                 105                 110

Lys Ala Lys Ser Leu Lys Ala Ile Glu Asp Arg Pro Ala Asn Leu Tyr
        115                 120                 125

Thr Ala Ser Asp Phe Pro Gln Lys Ser Glu Ser Met Tyr Gln Ser Gln
    130                 135                 140

Leu Leu Ala Ser Arg Lys Phe Tyr Gly Glu Phe Leu Asp Arg His Met
145                 150                 155                 160

Ser Glu Leu Ala Lys Ala Tyr Ser Ala Asp Ile Tyr Lys Ala Gln Ile
                165                 170                 175

Ala Ile Leu Lys Gln Thr Ser Gln Glu Leu Glu Asn Lys Ala Arg Ser
            180                 185                 190

Leu Glu Ala Glu Ala Gln Arg Ala Ala Ala Glu Val Glu Ala Asp Tyr
        195                 200                 205

Lys Ala Arg Lys Ala Asn Val Gly Lys Lys Val Gln Ser Glu Leu Asp
    210                 215                 220

```
Gln Ala Gly Asn Ala Leu Pro Gln Leu Thr Asn Pro Thr Pro Glu Gln
225                 230                 235                 240

Trp Leu Glu Arg Ala Thr Gln Leu Val Thr Gln Ala Ile Ala Asn Lys
            245                 250                 255

Lys Lys Leu Gln Thr Ala Asn Asn Ala Leu Ile Ala Lys Ala Pro Asn
                260                 265                 270

Ala Leu Glu Lys Gln Lys Ala Thr Tyr Asn Ala Asp Leu Leu Val Asp
            275                 280                 285

Glu Ile Ala Ser Leu Gln Ala Arg Leu Asp Lys Leu Asn Ala Glu Thr
290                 295                 300

Ala Arg Lys Glu Ile Ala Arg Gln Ala Ala Ile Arg Ala Ala Asn
305                 310                 315                 320

Thr Tyr Ala Met Pro Ala Asn Gly Ser Val Ala Thr Ala Ala Gly
                325                 330                 335

Arg Gly Leu Ile Gln Val Ala Gln Gly Ala Ala Ser Leu Ala Gln Ala
                340                 345                 350

Ile Ser Asp Ala Ile Ala Val Leu Gly Arg Val Leu Ala Ser Ala Pro
                355                 360                 365

Ser Val Met Ala Val Gly Phe Ala Ser Leu Thr Tyr Ser Ser Arg Thr
370                 375                 380

Ala Glu Gln Trp Gln Asp Gln Thr Pro Asp Ser Val Arg Tyr Ala Leu
385                 390                 395                 400

Gly Met Asp Ala Ala Lys Leu Gly Leu Pro Pro Ser Val Asn Leu Asn
                405                 410                 415

Ala Val Ala Lys Ala Ser Gly Thr Val Asp Leu Pro Met Arg Leu Thr
                420                 425                 430

Asn Glu Ala Arg Gly Asn Thr Thr Thr Leu Ser Val Val Ser Thr Asp
                435                 440                 445

Gly Val Ser Val Pro Lys Ala Val Pro Val Arg Met Ala Ala Tyr Asn
450                 455                 460

Ala Thr Thr Gly Leu Tyr Glu Val Thr Val Pro Ser Thr Thr Ala Glu
465                 470                 475                 480

Ala Pro Pro Leu Ile Leu Thr Trp Thr Pro Ala Ser Pro Pro Gly Asn
                485                 490                 495

Gln Asn Pro Ser Ser Thr Thr Pro Val Val Pro Lys Pro Val Pro Val
                500                 505                 510

Tyr Glu Gly Ala Thr Leu Thr Pro Val Lys Ala Thr Pro Glu Thr Tyr
                515                 520                 525

Pro Gly Val Ile Thr Leu Pro Glu Asp Leu Ile Gly Phe Pro Ala
                530                 535                 540

Asp Ser Gly Ile Lys Pro Ile Tyr Val Met Phe Arg Asp Pro Arg Asp
545                 550                 555                 560

Val Pro Gly Ala Ala Thr Gly Lys Gly Gln Pro Val Ser Gly Asn Trp
                565                 570                 575

Leu Gly Ala Ala Ser Gln Gly Glu Gly Ala Pro Ile Pro Ser Gln Ile
                580                 585                 590

Ala Asp Lys Leu Arg Gly Lys Thr Phe Lys Asn Trp Arg Asp Phe Arg
                595                 600                 605

Glu Gln Phe Trp Ile Ala Val Ala Asn Asp Pro Glu Leu Ser Lys Gln
                610                 615                 620

Phe Asn Pro Gly Ser Leu Ala Val Met Arg Asp Gly Gly Ala Pro Tyr
625                 630                 635                 640

Val Arg Glu Ser Glu Gln Ala Gly Gly Arg Ile Lys Ile Glu Ile His
```

645                 650                 655
His Lys Val Arg Ile Ala Asp Gly Gly Gly Val Tyr Asn Met Gly Asn
            660                 665                 670

Leu Val Ala Val Thr Pro Lys Arg His Ile Glu Ile His Lys Gly Gly
        675                 680                 685

Lys

<210> SEQ ID NO 730
<211> LENGTH: 2070
<212> TYPE: DNA
<213> ORGANISM: Pseudomonas aeruginosa

<400> SEQUENCE: 730

| | | | | | |
|---|---|---|---|---|---|
| atggctgtca | atgattacga | acctggttcg | atggttatta | cacatgtgca | gggtggtggg | 60 |
| cgtgacataa | tccagtatat | tcctgctcga | tcaagctacg | gtactccacc | atttgtccca | 120 |
| ccaggaccaa | gtccgtatgt | cggtactgga | atgcaggagt | acaggaagct | aagaagtacg | 180 |
| cttgataagt | cccattcaga | actcaagaaa | aacctgaaaa | atgaacccct | gaaggaggtt | 240 |
| gatgaactca | agagtgaagc | ggggttgcca | ggtaaagcgg | tcagtgccaa | tgacatccgc | 300 |
| gatgaaaaga | gtatcgttga | tgcactcatg | gatgccaaag | caaaatcgct | aaaggccatt | 360 |
| gaggatcgcc | cggccaatct | ttatacggct | tcagactttc | ctcagaagtc | agagtcgatg | 420 |
| taccagagtc | agttgctggc | cagccgaaaa | ttctatggag | agttcctgga | tcgccatatg | 480 |
| agtgagctgg | ccaaagcgta | cagcgccgat | atctataagg | cgcaaatcgc | tatcttgaaa | 540 |
| caaacgtctc | aagagctgga | gaataaagcc | cggtcattgg | aagcagaagc | ccagcgagcc | 600 |
| gctgctgagg | tggaggcgga | ctacaaggcc | aggaaggcaa | atgtcgagaa | aaaagtgcag | 660 |
| tccgagcttg | accaggctgg | gaatgctttg | cctcaactga | ccaatccaac | gccagagcag | 720 |
| tggcttgaac | gcgctactca | actggttacg | caggcgatcg | ccaataagaa | gaaattgcag | 780 |
| actgcaaaca | atgccttgat | tgccaaggca | cccaatgcac | tggagaaaca | aaaggcaacc | 840 |
| tacaacgccg | atctcctagt | ggatgaaatc | gccagcctgc | aagcacggct | ggacaagctg | 900 |
| aacgccgaaa | cggcaaggcg | caaggaaatc | gctcgtcaag | cggcgatcag | ggctgccaat | 960 |
| acttatgcca | tgccagccaa | tggcagcgtt | gtcgccaccg | ccgcaggccg | gggtctgatc | 1020 |
| caggtcgcac | aaggcgccgc | atcccttgct | caagcgatct | ccgatgcgat | tgccgtcctg | 1080 |
| ggccgggtcc | tggcttcagc | accctcggtg | atggccgtgg | gctttgccag | tctgacctac | 1140 |
| tcctcccgga | ctgccgagca | atggcaggac | caaacgcccg | atagcgttcg | ttacgccctg | 1200 |
| ggcatggatg | ccgctaaatt | ggggcttccc | ccaagcgtaa | acctgaacgc | ggttgcaaaa | 1260 |
| gccagcggta | ccgtcgatct | gccgatgcgc | ctgaccaacg | aggcacgagg | caacacgacg | 1320 |
| acccttttcgg | tggtcagcac | cgatggtgtg | agcgttccga | aagccgttcc | ggtccggatg | 1380 |
| gcggcctaca | atgccacgac | aggcctgtac | gaggttacgg | ttccctctac | gaccgcagaa | 1440 |
| gcgccgccac | tgatcctgac | ctggacgccg | gcgagtcctc | caggaaaacca | gaacccttcg | 1500 |
| agtaccactc | cggtcgtacc | gaagccggtg | ccggtatatg | agggagcgac | ccttacaccg | 1560 |
| gtgaaggcta | ccccggaaac | ctatcctggg | gtgattacac | taccggaaga | cctgatcatc | 1620 |
| ggcttcccgg | ccgactcggg | gatcaagccg | atctatgtga | tgttcaggga | tccgcgggat | 1680 |
| gtacctggtg | ctgcgactgg | caagggacag | cccgtcagcg | gtaattggct | cggcgccgcc | 1740 |
| tctcaaggtg | aggggctcc | aattccaagc | cagattgcgg | ataaactacg | tggtaagaca | 1800 |
| ttcaaaaact | ggcgggactt | tcgggaacaa | ttctggatag | ctgtggctaa | tgatcctgag | 1860 |

```
ttaagtaaac agtttaatcc tggtagttta gctgtaatga gagatggagg ggctccttat   1920
gtcagagagt cagaacaggc tggcgggaga ataaagatcg aaatccacca caaggttcga   1980
atagcagatg gaggcggcgt ttacaatatg gggaaccttg ttgcagtaac gccaaaacgt   2040
catatagaaa tccacaaggg agggaagtga                                    2070
```

<210> SEQ ID NO 731
<211> LENGTH: 36
<212> TYPE: PRT
<213> ORGANISM: Lactobacillus plantarum

<400> SEQUENCE: 731

```
Lys Tyr Tyr Gly Asn Gly Leu Ser Cys Ser Lys Lys Gly Cys Thr Val
1               5                   10                  15

Asn Trp Gly Gln Ala Phe Ser Cys Gly Val Asn Arg Val Ala Thr Ala
            20                  25                  30

Gly His Gly Lys
        35
```

<210> SEQ ID NO 732
<211> LENGTH: 108
<212> TYPE: DNA
<213> ORGANISM: Lactobacillus plantarum

<400> SEQUENCE: 732

```
aaatattatg gcaacggcct gagctgcagc aaaaaaggct gcaccgtgaa ctggggccag    60
gcgtttagct gcggcgtgaa ccgcgtggcg accgcgggcc atggcaaa               108
```

<210> SEQ ID NO 733
<211> LENGTH: 30
<212> TYPE: PRT
<213> ORGANISM: Lactococcus lactis

<400> SEQUENCE: 733

```
Met Lys Thr Ile Leu Arg Phe Val Ala Gly Tyr Asp Ile Ala Ser His
1               5                   10                  15

Lys Lys Lys Thr Gly Gly Tyr Pro Trp Glu Arg Gly Lys Ala
            20                  25                  30
```

<210> SEQ ID NO 734
<211> LENGTH: 93
<212> TYPE: DNA
<213> ORGANISM: Lactococcus lactis

<400> SEQUENCE: 734

```
atgaaaacaa tcctacgttt tgttgctggc tacgatattg ctagtcataa aaagaaaact    60
ggcggctatc catgggaacg tggaaaagct taa                                93
```

<210> SEQ ID NO 735
<211> LENGTH: 24
<212> TYPE: PRT
<213> ORGANISM: Lactobacillus acidophilus

<400> SEQUENCE: 735

```
Gly Asn Pro Lys Val Ala His Cys Ala Ser Gln Ile Gly Arg Ser Thr
1               5                   10                  15

Ala Trp Gly Ala Val Ser Gly Ala
            20
```

```
<210> SEQ ID NO 736
<211> LENGTH: 72
<212> TYPE: DNA
<213> ORGANISM: Lactobacillus acidophilus

<400> SEQUENCE: 736
ggcaacccga aagtggcgca ttgcgcgagc cagattggcc gcagcaccgc gtggggcgcg      60
gtgagcggcg cg                                                         72

<210> SEQ ID NO 737
<211> LENGTH: 53
<212> TYPE: PRT
<213> ORGANISM: Lactobacillus salivarius cp400

<400> SEQUENCE: 737

Met Phe Phe Asn Phe Met Lys Lys Val Asp Val Lys Lys Asn Phe Gly
1               5                   10                  15

Tyr Lys Glu Val Ser Arg Lys Asp Leu Ala Lys Val Asn Gly Gly Lys
            20                  25                  30

Arg Lys Lys His Arg Cys Arg Val Tyr Asn Asn Gly Met Pro Thr Gly
        35                  40                  45

Met Tyr Arg Trp Cys
    50

<210> SEQ ID NO 738
<211> LENGTH: 162
<212> TYPE: DNA
<213> ORGANISM: Lactobacillus salivarius cp400

<400> SEQUENCE: 738 atgttttta atttatgaa aaagtagat gtgaagaaga attttggata taaagaagtt        60
tctagaaaag atctagctaa agtaaatggt ggaaagagaa agaaacatcg ttgcagagtt     120
tataataatg gaatgcctac aggaatgtat cgttggtgct aa                        162

<210> SEQ ID NO 739
<211> LENGTH: 5
<212> TYPE: PRT
<213> ORGANISM: Artificial Sequence
<220> FEATURE:
<223> OTHER INFORMATION: Caspase 2 consensus sequence

<400> SEQUENCE: 739

Asp Val Ala Asp Leu
1               5

<210> SEQ ID NO 740
<211> LENGTH: 5
<212> TYPE: PRT
<213> ORGANISM: Artificial Sequence
<220> FEATURE:
<223> OTHER INFORMATION: Caspase 2 consensus sequence

<400> SEQUENCE: 740

Asp Val Ala Asp Ile
1               5

<210> SEQ ID NO 741
<211> LENGTH: 12
<212> TYPE: PRT
<213> ORGANISM: Artificial Sequence
<220> FEATURE:
<223> OTHER INFORMATION: Synthetic RAP-binding peptide, RBP
```

```
<400> SEQUENCE: 741

Phe His Trp Trp Gln Thr Ser Pro Ala His Phe Ser
1               5                   10

<210> SEQ ID NO 742
<211> LENGTH: 12
<212> TYPE: PRT
<213> ORGANISM: Artificial Sequence
<220> FEATURE:
<223> OTHER INFORMATION: Synthetic RAP-binding peptide, RBP

<400> SEQUENCE: 742

Trp Pro Phe Ala His Trp Pro Trp Gln Tyr Pro Arg
1               5                   10

<210> SEQ ID NO 743
<211> LENGTH: 9
<212> TYPE: PRT
<213> ORGANISM: Artificial Sequence
<220> FEATURE:
<223> OTHER INFORMATION: Synthetic AgrC ligand
<220> FEATURE:
<221> NAME/KEY: VARIANT
<222> LOCATION: 5, 9
<223> OTHER INFORMATION: Thiolacton linkage between C5 and F9

<400> SEQUENCE: 743

Gly Asp Ser Val Cys Ala Ser Tyr Phe
1               5

<210> SEQ ID NO 744
<211> LENGTH: 7
<212> TYPE: PRT
<213> ORGANISM: Artificial Sequence
<220> FEATURE:
<223> OTHER INFORMATION: Synthetic AgrC ligand
<220> FEATURE:
<221> NAME/KEY: VARIANT
<222> LOCATION: 3, 7
<223> OTHER INFORMATION: Thiolacton linkage between C3 and F7

<400> SEQUENCE: 744

Ser Val Cys Ala Ser Tyr Phe
1               5

<210> SEQ ID NO 745
<211> LENGTH: 5
<212> TYPE: PRT
<213> ORGANISM: Artificial Sequence
<220> FEATURE:
<223> OTHER INFORMATION: Synthetic Cry1Aa ligand

<400> SEQUENCE: 745

Ser Lys Ala Asp Thr
1               5

<210> SEQ ID NO 746
<211> LENGTH: 5
<212> TYPE: PRT
<213> ORGANISM: Artificial Sequence
<220> FEATURE:
<223> OTHER INFORMATION: Synthetic Cry1Aa ligand

<400> SEQUENCE: 746

Ser Lys Pro Ala Asp
1               5
```

```
<210> SEQ ID NO 747
<211> LENGTH: 11
<212> TYPE: PRT
<213> ORGANISM: Artificial Sequence
<220> FEATURE:
<223> OTHER INFORMATION: Synthetic Fsr ligand
<220> FEATURE:
<221> NAME/KEY: VARIANT
<222> LOCATION: 3, 11
<223> OTHER INFORMATION: Lacton linkage between S3 and A11

<400> SEQUENCE: 747

Gln Asn Ser Ala Ala Ala Phe Ala Ala Trp Ala
 1               5                  10

<210> SEQ ID NO 748
<211> LENGTH: 11
<212> TYPE: PRT
<213> ORGANISM: Artificial Sequence
<220> FEATURE:
<223> OTHER INFORMATION: Synthetic Fsr ligand
<220> FEATURE:
<221> NAME/KEY: VARIANT
<222> LOCATION: 3, 11
<223> OTHER INFORMATION: Lacton linkage between S3 and A11

<400> SEQUENCE: 748

Gln Asn Ser Ala Ala Ala Phe Gly Gln Trp Ala
 1               5                  10

<210> SEQ ID NO 749
<211> LENGTH: 7
<212> TYPE: PRT
<213> ORGANISM: Artificial Sequence
<220> FEATURE:
<223> OTHER INFORMATION: Synthetic AgrC1, AgrC2
<220> FEATURE:
<221> NAME/KEY: VARIANT
<222> LOCATION: 4, 7
<223> OTHER INFORMATION: Thiolacton linkage between C4 and M7)

<400> SEQUENCE: 749

Tyr Ser Thr Cys Phe Ile Met
 1               5

<210> SEQ ID NO 750
<211> LENGTH: 7
<212> TYPE: PRT
<213> ORGANISM: Artificial Sequence
<220> FEATURE:
<223> OTHER INFORMATION: Synthetic AgrC1, AgrC2
<220> FEATURE:
<221> NAME/KEY: VARIANT
<222> LOCATION: 3, 7
<223> OTHER INFORMATION: Thiolacton linkage between C3 and M7

<400> SEQUENCE: 750

Ser Thr Cys Ala Phe Ile Met
 1               5
```

METHODS AND COMPOSITIONS FOR MAKING BACTERIOCINS AND ANTIMICROBIAL PEPTIDES

RELATED APPLICATIONS

This application is a U.S. national phase application under 35 U.S.C. § 371 of International Application No. PCT/US2018/048846, filed on Aug. 30, 2018, which claims the benefit of U.S. Provisional Application No. 62/720,804, filed Aug. 21, 2018, and U.S. Provisional Application No. 62/552,835, Filed Aug. 31, 2017. The contents of the aforementioned applications are expressly incorporated herein by reference in their entirety.

REFERENCE TO SEQUENCE LISTING, TABLE, OR COMPUTER PROGRAM LISTING

The present application is being filed along with a Sequence Listing in electronic format. The Sequence Listing is provided as a file entitled SYNG003WO SEQUENCE.TXT, created and last saved on Aug. 29, 2018, which is 402,916 bytes in size. The information in the electronic format of the Sequence Listing is incorporated herein by reference in its entirety.

BACKGROUND

Microbial organism-mediated processes can be used in a variety of industrial processes for the manufacture of products of interest, for example for fermentation in a feedstock. Additionally, microbial organisms can be used to manufacture products in sterile environments, such as in the manufacture of pharmaceuticals, biologics, and cosmetics. Additionally, populations of microbial organisms are involved in maintaining the health and metabolic functions of multicellular organisms, for example as cultures of microbial flora in the gut and skin of humans, or the roots of the plants. The efficiency and efficacy of these processes can be affected by culture conditions, as well as the phenotypic characteristics of microbial organisms present in the culture.

Tuning populations of microbial organisms, for example to reduce or eliminate undesired microbial organisms can be useful for maintaining the industrial processes and maintaining the health of tissues that comprise microbial organisms.

FIELD

Embodiments herein relate generally to producing gene products for the control of growth of microorganisms. More particularly, some embodiments relate to methods, reagents, and microfluidic devices for making bacteriocins. The bacteriocins can be produced in a composition, such as a specified mixture of bacteriocins, which can be useful for controlling the growth of populations of microbial organisms. In some embodiments antimicrobial peptides and/or bacteriocins are produced in desired ratios in a composition.

SUMMARY

Some embodiments include a method of making bacteriocins. The method can comprise expressing a nucleic acid comprising a bacteriocin coding sequence and a second polypeptide coding sequence in a single reading frame, in which the second polypeptide comprises, consists essentially of, or consists of a bacteriocin or signal molecule. The nucleic acid can further comprise cleavage site coding sequences disposed between the bacteriocin coding sequence and the second polypeptide coding sequence in the single reading frame. Thus, a pro-polypeptide comprising the bacteriocin, second polypeptide, and cleavage sites disposed between the bacteriocin and second polypeptide can be generated. In some embodiments, the method further comprises cleaving the cleavage site, thus separating the bacteriocin and second polypeptide from each other. The method can thus produce a composition comprising the bacteriocin and the second polypeptide. In some embodiments, the second polypeptide comprises, consists essentially of, or consists of a bacteriocin. In some embodiments, the second polypeptide comprises, consists essentially of, or consists of an antimicrobial peptide. In some embodiments, the second polypeptide comprises, consists essentially of, or consists of the signal molecule. In some embodiments, the expressing is performed by a microbial cell that does not produce a functional immunity modulator for at least one of the bacteriocins. In some embodiments, the microbial cell does not produce a functional immunity modulator for any of the bacteriocins. In some embodiments, the expressing is performed in vitro. In some embodiments, at least one of the bacteriocins is inactive when it is part of the pro-polypeptide. In some embodiments, the method further comprises isolating the pro-polypeptide prior to the cleaving. In some embodiments, the isolating comprises affinity purifying the pro-polypeptide, in which the affinity purification comprises binding an affinity tag encoded by the nucleic acid. In some embodiments, the nucleic acid comprises three bacteriocin coding sequences in the single reading frame. In some embodiments, at least two of the bacteriocins are different from each other. In some embodiments, the composition comprises a desired ratio of bacteriocins, or a desired ratio of signal molecules and bacteriocins. In some embodiments, at least a portion the desired ratio is achieved by a ratio of bacteriocin coding sequences, or bacteriocin and signal molecule coding sequences in the single reading frame of the nucleic acid. In some embodiments, the desired ratio is further achieved by a second nucleic acid comprising a ratio of bacteriocins coding sequences and further comprising cleavage sites between the bacteriocin coding sequences. In some embodiments, desired ratio is achieved by a ratio of bacteriocin coding sequences in the single reading frame of the nucleic acid. In some embodiments, the desired ratio of bacteriocins is selected to target an undesired microbial organism or population of undesired microbial organisms, and/or the desired ratio of bacteriocins is selected to balance a population of a microbiome of an animal, a human organ, a plant, a plant root, and/or soil (e.g. in the context of a plant root and soil). In some embodiments, the desired ratio of bacteriocins and signal molecules is selected to control genetic drift of a target microbial cell, and stimulate growth or production of a producing cell. In some embodiments, the desired ratio comprises a ratio of a first bacteriocin to a second bacteriocin of 1:2, 1:3, 1:4, 1:5, 1:6, 1:7, 1:8, 1:9, 1:10, 2:3, 2:5, 2:7, 2:9, 3:4, 3:5, 3:7, 3:8, 3:10, 4:5, 4:7, 4:9, 5:6, 5:7, 5:8, 5:9, 6:7, 7:8, 7:9, 7:10, 8:9, or 9:10, in which the first bacteriocin is different from the second bacteriocin. In some embodiments, the cleavage sites are for a wild-type, variant, or synthetic cleavage enzyme, such as an endopeptidase. In some embodiments, the cleavage sites are for a cleavage enzyme selected from the group consisting of: Arg-C proteinase, Asp-N endopeptidase, BNPS-Skatole, Caspase 1, Caspase 2, Caspase 3, Caspase 4, Caspase 5, Caspase 6, Caspase 7, Caspase 8, Caspase 9, Caspase 10, Chymotrypsin-high specificity, Clostripain (Clostridiopeptidase B), CNBr, Enterokinase, Factor Xa, Formic acid, Glutamyl endopeptidase, GranzymeB, Hydroxylamine, Iodosobenzoic acid, LysC, Neutrophil elastase, NTCB (2-nitro-5-thiocyanobenzoic acid), Pepsin (pH1.3), Pepsin (pH>2), Proline-endopeptidase, Proteinase K, Staphylococcal peptidase I, Thermolysin, Thrombin, or Trypsin. In some embodiments, the cleavage sites are for a single cleavage enzyme, and wherein the cleavage enzyme does not cleave within the bacteriocins. In some embodiments, at least one cleavage site is for a first cleavage enzyme, and another cleavage site is for a second cleavage enzyme, and neither the first nor the second cleavage enzyme cleaves within the bacteriocins. In some embodiments, the composition produced by the method further comprises a signal molecule (in which the nucleotide further comprises: a coding sequence for a signal molecule in the single reading frame), and a cleavage site sequence disposed between the signal molecule and a bacteriocin coding sequence. In some embodiments, the signal molecule is selected from the group consisting of: quorum sensing molecules, signal transduction receptor ligands, growth factors, hormones, and cytokines, and wherein the signal molecule can be wild-type, mutant, or synthetic. In some embodiments, the signal molecule comprises, consists of, or consists essentially of a quorum sensing peptide. In some embodiments, the pro-polypeptide has a length of no more than about 2000 amino acids. In some embodiments, the method further comprises expressing a second nucleic acid encoding a second pro-polypeptide comprising two bacteriocins and cleavage sites disposed therebetween, wherein the second pro-polypeptide is different from the first pro-polypeptide. In some embodiments, cleaving the pro-polypeptide comprises physical treatment of a peptide linker comprised by the cleavage site, wherein the peptide linker is chemical-sensitive or pH sensitive. In some embodiments, the method further comprises chemically modifying the bacteriocins. In some embodiments, the bacteriocins are chemically modified co-translationally. In some embodiments, the bacteriocins are chemically modified following the cleaving. In some embodiments, a pro-polypeptide as described herein comprises two or more antimicrobial peptides instead of bacteriocins, and upon cleavage, a composition comprising antimicrobial peptides is produced. In some embodiments, a pro-polypeptide as described herein comprises one or more antimicrobial peptides and one or more bacteriocins, and upon cleavage, a composition comprising a mixture of antimicrobial peptides and bacteriocins is produced.

Some embodiments include an isolated nucleic acid comprising a bacteriocin coding sequence and a second polypeptide coding sequence in a single reading frame, in which the second polypeptide comprises, consists essentially of, or consists of a bacteriocin or a signal molecule. The isolated nucleic acid can comprise cleavage site coding sequences disposed between the bacteriocin coding sequences and in the single reading frame. In some embodiments, the second polypeptide comprises, consists essentially of, or consists of the bacteriocin. In some embodiments, the second polypeptide comprises, consists essentially of, or consists of an antimicrobial peptide. In some embodiments, the second polypeptide comprises, consists essentially of, or consists of the signal molecule. In some embodiments, the cleavage site coding sequences encode cleavage sites for a cleavage enzyme, and in which the bacteriocin coding sequences do not comprise cleavage sites for the cleavage enzyme. In some embodiments, the nucleic acid comprises three bacteriocin coding sequences in the single reading frame. In some embodiments, the nucleic acid comprises at least 5, 10, 15, or 20 bacteriocin sequences in the single reading frame. In some embodiments, a cleavage site coding sequence is disposed in frame between any two adjacent bacteriocin and/or signal molecule coding sequences. In some embodiments, at least two of the bacteriocin sequences encode different bacteriocins from each other. In some embodiments, the three bacteriocin sequences are present in a desired ratio or portion of a desired ratio. In some embodiments, the desired ratio is selected to target an undesired microbial organism or population of undesired microbial organisms. In some embodiments, the desired ratio of bacteriocins is selected to balance a population of a microbiome of an animal, a human organ, a plant, a plant root, and/or soil (e.g., in the context of a plant root and soil). In some embodiments, the cleavage sites are for a wild-type, variant, or synthetic cleavage enzyme, such as an endopeptidase. In some embodiments, the cleavage sites are for a cleavage enzyme selected from the group consisting of: Arg-C proteinase, Asp-N endopeptidase, BNPS-Skatole, Caspase 1, Caspase 2, Caspase 3, Caspase 4, Caspase 5, Caspase 6, Caspase 7, Caspase 8, Caspase 9, Caspase 10, Chymotrypsin-high specificity, Clostripain (Clostridiopeptidase B), CNBr, Enterokinase, Factor Xa, Formic acid, Glutamyl endopeptidase, GranzymeB, Hydroxylamine, Iodosobenzoic acid, LysC, Neutrophil elastase, NTCB (2-nitro-5-thiocyanobenzoic acid), Pepsin (pH1.3), Pepsin (pH>2), Proline-endopeptidase, Proteinase K, Staphylococcal peptidase I, Thermolysin, Thrombin, or Trypsin. In some embodiments, a first cleavage site coding sequence encodes a first cleavage site is for a first cleavage enzyme, and wherein a second cleavage site coding sequence encodes a cleavage site for a second cleavage enzyme that is different from the first cleavage enzyme, and wherein the bacteriocins do not comprise a cleavage site for any of the first or second cleavage enzyme. In some embodiments, the cleavage sites comprise a pH- or chemically-sensitive linker. In some embodiments, the isolated nucleic acid further comprises a coding sequence for a signal molecule in the single reading frame, in which a cleavage site coding sequences is disposed between the coding sequence for signal molecule and an adjacent bacteriocin coding sequence. In some embodiments, the signal molecule is selected from the group consisting of: quorum sensing molecules, signal transduction receptor ligands, growth factors, hormones, and cytokines, and in which the signal molecule can be wild-type, mutant, or synthetic. In some embodiments, an isolated nucleic acid as described herein comprises two or more antimicrobial peptide coding sequences instead of bacteriocin coding sequences, and encodes a pro-polypeptide comprising the antimicrobial peptides. In some embodiments, an isolated nucleic acid as described herein comprises one or more antimicrobial peptide coding sequences and one or more bacteriocin coding sequences, and encodes a pro-polypeptide comprising one or more antimicrobial peptides and one or more bacteriocins.

Some embodiments include a microbial cell, comprising a promoter operably linked to the isolated nucleic acid of any of the embodiments described herein, in which the isolated microbial cell does not produce a functional immunity modulator for a bacteriocin encoded by the isolated nucleic acid. In some embodiments, the cell does not produce a functional immunity modulator for any of the bacteriocins encoded by the isolated nucleic acid.

Some embodiments include an isolated pro-polypeptide comprising two bacteriocins, and/or a bacteriocin and a signal molecule, cleavage sites disposed between the bacteriocins and/or the bacteriocin and the signal molecule; and an affinity tag. In some embodiments, the pro-polypeptide comprises the two bacteriocins. In some embodiments, the pro-polypeptide comprises the bacteriocin and the signal molecule. In some embodiments, the pro-polypeptide comprises three bacteriocins. In some embodiments, the pro-polypeptide comprises at least 5, 10, 15, or 20 bacteriocins. In some embodiments, the pro-polypeptide comprises a signal molecule. In some embodiments, the cleavage sites are for a cleavage enzyme, and wherein the bacteriocin coding sequences do not comprise cleavage sites for the cleavage enzyme. In some embodiments, a cleavage site is for a first cleavage enzyme, in which another cleavage site is for a second cleavage enzyme different from the first cleavage enzyme, and in which the bacteriocins do not comprise a cleavage site for any of the first or second cleavage enzymes. In some embodiments, the isolated pro-polypeptide further comprises a co-translational or post-translational modification. In some embodiments, an isolated pro-polypeptide as described herein comprises two or more antimicrobial peptides instead of bacteriocins. In some embodiments, an isolated pro-polypeptide as described herein comprises one or more antimicrobial peptides and one or more bacteriocins.

In some embodiments, a composition comprising two more bacteriocins in a ratio selected to target a microbial cell or populations of microbial cells is described. Each of the bacteriocins of the composition can comprise, at its N-terminus, C-terminus, or N-terminus and C-terminus, a portion of a cleavage sequence that has been cleaved, in which the portions of cleavage sequences at the N-, C-, or N- and C-termini of the bacteriocins are for cleavage sites of the same or different cleavage enzyme. In some embodiments, at least some of the bacteriocins further comprise a tag. In some embodiments, the tag is selected from the group consisting of affinity tags, a signal sequence, or a stability tag. In some embodiments, the composition further comprises a signal molecule in a desired ratio with the bacteriocins, wherein the signal molecule comprises, at its N-terminus, C-terminus, or N-terminus and C-terminus, a portion of a cleavage sequence that has been cleaved, wherein the portions of cleavage sequences at the N-, C-, or N- and C-termini of the signal molecule are for cleavage sites of the same or different cleavage enzymes. In some embodiments, the ratio of bacteriocins is selected to target an undesired microbial organism or population of undesired microbial organisms. In some embodiments, the ratio of bacteriocins is selected to balance a population of a microbiome of an animal, a human organ, a plant, a plant root, and/or soil (e.g., in the context of a plant root and soil). In some embodiments, the composition is formulated for topical or oral administration to a human subject. In some embodiments, the composition is for use in balancing a population of a microbiome, for example, that of an animal, a human organ (such as a gut or skin), a plant, a plant root, and/or soil. In some embodiments, the isolated pro-polypeptide as described herein comprises one or more antimicrobial peptides. The pro-polypeptide can be cleaved, and the composition can comprise one or more antimicrobial peptides that comprise portions of cleavage sequences at the N-, C-, or N- and C-termini.

Some embodiments include a method for producing a specified mixture of bacteriocins and/or antimicrobial proteins, for example. The method can comprise selecting the mixture to comprise two or more different bacteriocins and/or antimicrobial proteins. The method can comprise, in a microfluidic device comprising discrete coding substrates that each encode an antimicrobial peptide or bacteriocin: placing discrete coding substrates that encode the antimicrobial peptides and/or bacteriocins of the specified mixture in fluid communication with an in vitro transcription/translation solution; incubating the discrete coding substrates with the in vitro transcription/translation solution, thus generating antimicrobial peptides and/or bacteriocins encoded by the discrete coding substrates; and mixing the antimicrobial peptides and/or bacteriocins in the microfluidic device, thus producing the specified mixture of antimicrobial peptides and/or bacteriocins. In some embodiments, the method further comprises producing two or more submixtures each comprising a subset of the specified mixture of antimicrobial peptides and/or bacteriocins and combining the submixtures to produce the specified mixture of antimicrobial peptides and/or bacteriocins. In some embodiments, selecting further comprises selecting a stoichiometry of the two or more different antimicrobial peptides and/or bacteriocins of the specified mixture. In some embodiments, the specified mixture of antimicrobial peptides and/or bacteriocins comprises a specified stoichiometry, and combining the submixtures results in the specified stoichiometry. In some embodiments, the discrete coding substrates are comprised within separate chambers. In some embodiments, the discrete coding substrates comprise nucleic acids immobilized thereon. In some embodiments, discrete coding substrates encoding antimicrobial peptides and/or bacteriocins of the specified mixture, but not other discrete coding substrates, are placed in fludic communication with the in vitro transcription/translation solution. In some embodiments, incubating the discrete coding substrates with the in vitro transcription/translation solution comprises flowing the in vitro transcription/translation solution into each chamber. In some embodiments, the in vitro transcription/translation solution comprises an in vitro transcription reagent and/or an in vitro translation reagent. In some embodiments, placing the discrete coding substrates that encode the antimicrobial peptides and/or bacteriocins of the specified mixture in fluid communication with an in vitro transcription/translation solution comprises (i) opening valves so as to place a source of the in vitro transcription/translation solution in fluid communication with the discrete coding substrates; (ii) closing valves so as to inhibit fluid communication between the source of the in vitro transcription/translation solution and the other discrete coding substrates, or a combination of (i) and (ii). In some embodiments, mixing the antimicrobial peptides and/or bacteriocins in the microfluidic device comprises opening a valve to place the discrete coding substrates in fluid communication with a fluidic reservoir, in which the antimicrobial peptides and/or bacteriocins are mixed in the fluidic reservoir. In some embodiments, the method further comprises screening the mixture of antimicrobial peptides and/or bacteriocins in situ for a desired effect. In some embodiments, the screening is for inhibition of the growth or reproduction of a pathogenic microbial organism in a microbiome of a subject, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract. In some embodiments, the screening is for an absence of deleterious effects of the mixture of antimicrobial peptides and/or bacteriocins on a microbiome of a subject, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract. In some embodiments, the screening is performed in real time. For example, the screening can be performed withing 120 minutes, 60 minutes, 30 minutes, 15 minutes, 10 minutes, 5 minute, or 1 minute of the specified mixture of antimicrobial peptides and/or bacteriocins being generated. In some embodiments, the screening is for stabilization of an antimicrobial peptide and/or bacteriocin or for destruction of a microbial biofilm. In some embodiments, one or more of the discrete coding substrates encodes an auxiliary protein with anti-protease activity. In some embodiments, the screening is for enhancement of growth or reproduction of a non-pathogenic microbial organism in a microbiome of a subject, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract. In some embodiments, one or more of the discrete coding substrates encodes an auxiliary protein that attracts the non-pathogenic microbial organism, or that enhances growth or reproduction of the non-pathogenic microbial organism in the microbiome of a subject. In some embodiments, the method further comprises delivering the specified mixture of antimicrobial peptides and/or bacteriocins to a wound via a tubing or membrane, thereby cleaning or dressing the wound. In some embodiments, the desired effect comprises antimicrobial activity. In some embodiments, the method further comprises screening 1, 2, 3, 4, 5, 6, 7, 8, 9, or 10 different mixtures against a microbial infection. In some embodiments, the method further comprises delivering the mixture of specified antimicrobial peptides and/or bacteriocins, in combination with a chemical antibiotic and/or a phage antibiotic, to a subject. In some embodiments, the in vitro transcription/translation solution is lyophyilized, and further comprising adding water to the in vitro transcription/translation solution. In some embodiments, the method comprises making a specified mixture of bacteriocins. As such the method can comprise, in a microfluidic device comprising discrete coding substrates that each encode a bacteriocin: placing discrete coding substrates that encode the bacteriocins of the specified mixture in fluid communication with an in vitro transcription/translation solution; incubating the discrete coding substrates with the in vitro transcription/translation solution, thus generating bacteriocins encoded by the discrete coding substrates; and mixing the bacteriocins in the microfluidic device, thus producing the specified mixture of bacteriocins. In some embodiments, the method comprises making a specified mixture of bacteriocins that does not comprise antimicrobial peptides. In some embodiments, the method comprises making a specified mixture of antimicrobial peptides. In some embodiments, the method comprises making a specified mixture of antimicrobial peptides that does not comprise bacteriocins. In some embodiments, the method comprises making a specified mixture of bacteriocins and antimicrobial peptides. It will be understood that if a method, microfluidic device or system as described herein is for making a specified mixture of bacteriocins that does not comprise antimicrobial peptides, such a method, microfluidic device or system need not comprise selecting antimicrobial peptides as part of a specified mixture, need not comprise discrete coding substrates encoding antimicrobial peptides, and need not produce or flow any antimicrobial peptides. It will be understood that if a method, microfluidic device or system as described herein is for making a specified mixture of antimicrobial peptides that does not comprise bacteriocins, such a method, microfluidic device or system need not comprise selecting bacteriocins as part of a specified mixture, need not comprise discrete coding substrates encoding bacteriocins, and need not produce or flow any bacteriocins.

Some embodiments include a microfluidic device for producing a specified mixture of antimicrobial peptides and/or bacteriocins. The device can comprise discrete coding substrates that each encode an antimicrobial peptide and/or bacteriocin; an in vitro transcription/translation solution; a fluidic reservoir; and valves each disposed on a fluidic path between a discrete coding substrate and the fluidic reservoir, each valve configured to regulate flow between the discrete coding substrate and the fluidic reservoir. The device can be configured to be placed in data communication with a processor configured to: based on the specified mixture of antimicrobial peptides and/or bacteriocins, configure the valves to place the discrete coding substrates that encode the antimicrobial peptides and/or bacteriocins of the mixture, but not other discrete coding substrates, in fluidic communication with the fluidic reservoir; permit incubation of the in vitro transcription/translation solution with the discrete coding substrates that encode the antimicrobial peptides and/or bacteriocins of the specified mixture, so that the antimicrobial peptides and/or bacteriocins of the specified mixture are produced; permit flow of the antimicrobial peptides and/or bacteriocins through the valves into the fluidic reservoir; and control flow of fluid in the fluidic reservoir, in which the flow comprises movement of the antimicrobial peptides and/or bacteriocins in the fluidic reservoir, thereby producing the specified mixture of antimicrobial peptides and/or bacteriocins in the fluidic reservoir. In some embodiments, the specified mixture of antimicrobial peptides and/or bacteriocins comprises two or more submixtures each comprising, consisting essentially of, or consisting of a subset of antimicrobial peptides and/or bacteriocins; and the processor is configured to permit flow of each submixture into the fluidic reservoir, thereby producing the specified mixture of antimicrobial peptides and/or bacteriocins. In some embodiments, the specified mixture of antimicrobial peptides and/or bacteriocins comprises a sum of the subsets of antimicrobial peptides and/or bacteriocins in a specified stoichiometry, and wherein combination of the submixtures yields the specified stoichiometry. In some embodiments, the discrete coding substrates are comprised within separate chambers. In some embodiments, the discrete coding substrates comprise nucleic acids immobilized thereon. In some embodiments, the discrete coding substrates comprise a material or product selected from the group consisting of a chip, bead, nanoparticle, well, membrane, matrix, plastic, metal, glass, polymer, polysaccharide, and paramagnetic compound. In some embodiments, the in vitro transcription/translation solution comprises an in vitro transcription reagent and/or an in vitro translation reagent. In some embodiments, the device is portable. In some embodiments, one or more of the discrete coding substrates encodes an auxiliary protein comprising, consisting essentially of, or consisting of a protein for stabilization of antimicrobial peptides and/or bacteriocins, a protein with anti-protease activity, or a protein for destruction of a microbial biofilm. In some embodiments, one or more of the discrete coding substrates encodes an auxiliary protein that attracts a non-pathogenic microbial organism, or that enhances growth or reproduction of the non-pathogenic microbial organism in a microbiome of a subject, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract. In some embodiments, the fluidic reservoir is configured to be placed in fluid communication with a tissue of a subject. In some embodiments, the tissue comprises a microbiome, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract. In some embodiments, the fluidic reservoir is configured to be placed in fluid communication with a wound of a subject. In some embodiments, the microfluidic device further comprises a fluidic passage such as a tube or membrane through which the fluidic reservoir is capable of being placed in fluid communication with the microbiome or wound, through which the specified mixture of antimicrobial peptides and/or bacteriocins is capable of being delivered to the microbiome or wound. In some embodiments, wherein each discrete coding substrate encodes a different bacteriocin. In some embodiments, a discrete coding substrate comprises the isolated nucleic acid comprising, consisting essentially of, or consisting of an antimicrobial peptide and/or bacteriocin coding sequence and a second polypeptide coding sequence in a single reading frame, as described herein. In some embodiments, a discrete coding substrate encodes an isolated pro-polypeptide as described herein. In embodiments, the microfluidic device further comprises the processor. In some embodiments, the microfluidic device further comprises a reservoir of chemical or phage antibiotics configured to mix with the mixture of specified antimicrobial peptides and/or bacteriocins. In some embodiments, the microfluidic device further comprise an antibiotic comprising, consisting essentially of, or consisting of chemical antibiotic and/or a phage antibiotic. In some embodiments, the in vitro transcription/translation solution is lyophyilized. In some embodiments, the microfluidic device is for producing a specified mixture of bacteriocins. As such, the device can comprise discrete coding substrates that each encode a bacteriocin; an in vitro transcription/translation solution; a fluidic reservoir; and valves each disposed on a fluidic path between a discrete coding substrate and the fluidic reservoir, each valve configured to regulate flow between the discrete coding substrate and the fluidic reservoir. In some embodiments, the microfluidic device is for producing a specified mixture of bacteriocins that does not comprise antimicrobial peptides. In some embodiments, the microfluidic device is for producing a specified mixture of antimicrobial peptides. In some embodiments, the microfluidic device is for producing a specified mixture of antimicrobial peptides that does not comprise bacteriocins. In some embodiments, the microfluidic device is for producing a specified mixture of bacteriocins and antimicrobial peptides.

Some embodiments include a system. The system can comprise a microfluidic device described herein, and a processor configured to: based on a specified mixture of antimicrobial peptides and/or bacteriocins (as described herein), configure the valves to place the discrete coding substrates that encode the antimicrobial peptides and/or bacteriocins of the mixture, but not other discrete coding substrates, in fluidic communication with the fluidic reservoir; permit incubation of the in vitro transcription/translation solution with the discrete coding substrates that encode the antimicrobial peptides and/or bacteriocins of the specified mixture, so that the antimicrobial peptides and/or bacteriocins of the specified mixture are produced; permit flow of the antimicrobial peptides and/or bacteriocins through the valves into the fluidic reservoir; and control flow of fluid in the fluidic reservoir, wherein the flow comprises movement of the antimicrobial peptides and/or bacteriocins in the fluidic reservoir, thus producing the specified mixture of antimicrobial peptides and/or bacteriocins in the fluidic reservoir. In some embodiments, the microfluidic device is comprised by a cartridge, and the system comprises a coupling for placing the cartridge in data communication with the processor. In some embodiments, the system further comprises a reservoir of in vitro transcription/translation solution. In some embodiments, the system further comprise a reservoir of chemical and/or phage antibiotics configured to mix with the mixture of specified antimicrobial peptides and/or bacteriocins. In some embodiments, the system further comprise an antibiotic comprising, consisting essentially of, or consisting of a chemical antibiotic and/or a phage. In some embodiments, the in vitro transcription/translation solution is lyophyilized. In some embodiments, the system is for producing a specified mixture of bacteriocins. As such, the processor can be configured to, based on a specified mixture of antimicrobial peptides and/or bacteriocins (as described herein), configure the valves to place the discrete coding substrates that encode the bacteriocins of the mixture, but not other discrete coding substrates, in fluidic communication with the fluidic reservoir; permit incubation of the in vitro transcription/translation solution with the discrete coding substrates that encode the antimicrobial peptides and/or bacteriocins of the specified mixture, so that the bacteriocins of the specified mixture are produced. In some embodiments, the system is for producing a specified mixture of bacteriocins that does not comprise antimicrobial peptides. In some embodiments, the system is for producing a specified mixture of antimicrobial peptides. In some embodiments, the system is for producing a specified mixture of antimicrobial peptides. In some embodiments, the system is for producing a specified mixture of antimicrobial peptides that does not comprise bacteriocins. In some embodiments, the system is for producing a specified mixture of bacteriocins and antimicrobial peptides.

Some embodiments include a microfluidic device for producing a specified mixture of antimicrobial peptides and/or bacteriocins. The device can comprises discrete coding substrates that each encode an antimicrobial peptide and/or bacteriocin, and valves each disposed on a fluidic path connected to a discrete coding substrate. Each valve can be configured to regulate flow to or from the discrete coding substrate. The device can be configured to be placed in fluid communication with a fluidic reservoir and/or an in vitro transcription/translation solution. In some embodiments, the device further comprises a fluidic reservoir or an in vitro transcription/translation solution. Some embodiments include a microfluidic device for producing a specified mixture of bacteriocins. The device can comprise discrete coding substrates that each encode a bacteriocin, and valves each disposed on a fluidic path to or from a discrete coding substrate, configured to place the discrete coding substrate in fluid communication with a fluidic reservoir and/or an in vitro transcription/translation solution.

DETAILED DESCRIPTION

Figure 1:
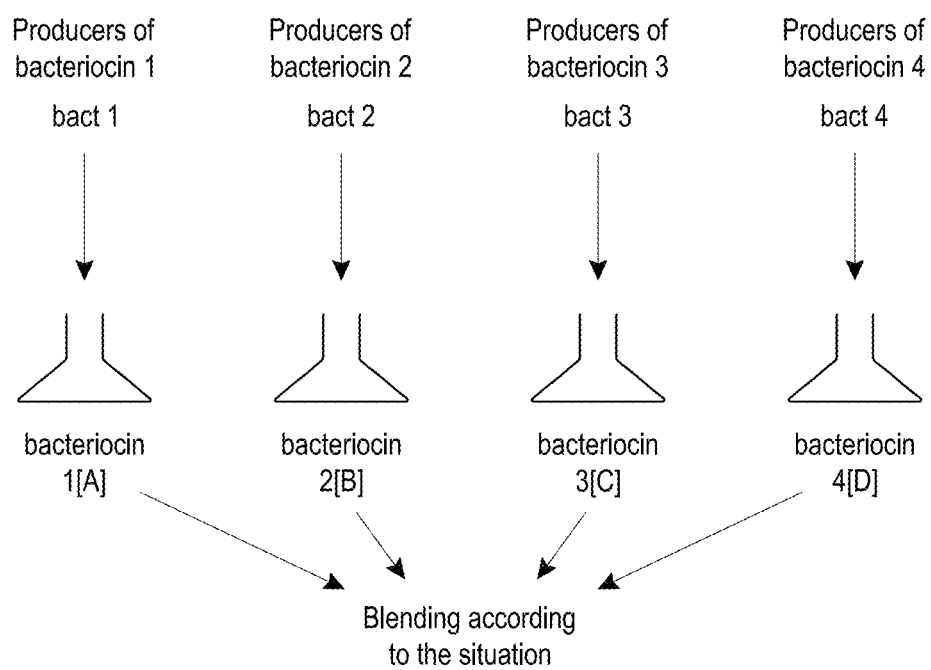
FIG. 1 is a schematic diagram of a conventional method for making a composition comprising bacteriocins. As shown, there are multiple strains for the production of a bacteriocin mixture. However, it is contemplated that there is a very high likelihood that the different bacteriocins will be of different concentrations ([A]≠[B]≠[C]≠[D]). Additionally, it is contemplated that the bacteriocins produced may be toxic to the host so as to cause production problems

Described in accordance with some embodiments herein are methods and compositions for making bacteriocins in a desired ratio. Some embodiments include compositions comprising bacteriocins in precise ratios or stoichiometries, which can be useful for tuning the population of microbial organisms in a number of applications, for example in industrial biotechnology manufacturing processes, pharmaceutical, biologic, and cosmetic manufacturing, and medical applications. In some embodiments, a single pro-polypeptide containing multiple bacteriocins separated by cleavage sites is encoded by a nucleic acid, and produced (see, for example, FIG. 2) by a genetically-engineered microbial cell containing the nucleic acid. In some embodiments, the pro-polypeptide can further comprise signal molecules that can modulate the growth of microbial cells and/or cells of a multicellular host. The bacteriocins in the pro-polypeptide can be in an inactive form, and thus the microbial cell does not require immunity against these bacteriocins. The pro-polypeptide can be isolated, for example by affinity purification. The cleavage sites of the pro-polypeptide can be cleaved (see, for example, FIG. 3), thus producing a mixture of active bacteriocins. Conceptually, the pro-polypeptide can be envisioned as a strand of "spaghetti," containing multiple component bacteriocins, which can then be cleaved into the individual bacteriocins. It is noted that in this Application, for brevity, a pro-polypeptide may also be referred to as "spaghetti." Some embodiments include microfluidic devices and methods for making specified mixtures of bacteriocins. The "specified mixtures" of bacteriocins of methods and microfluidic devices of some embodiments herein can be specified according to parameters that include, but are not limited to, the composition of bacteriocins (so that the comprise specified bacteriocins and/or do not comprise other bacteriocins), the stoichiometry of the bacteriocins of the mixture, and optionally, the presence of auxiliary proteins. The microfluidic device can comprise discrete coding substrates that each encode a bacteriocin (See, for example, FIG. 5). Discrete coding substrates encoding the bacteriocins of the specified mixture can be placed in fluid communication with an in vitro transcription/translation solution, so that the discrete coding substrates encoding the bacteriocins of the specified mixture are incubated with the in vitro transcription/translation solution, thus producing the bacteriocins of the specified mixture. The bacteriocins of the specified mixture can then be placed in fluid communication with a fluidic reservoir of the microfluidic device, and the bacteriocins fluidically move to the fluidic reservoir, thus producing the specified mixture of antimicrobial peptides and/or bacteriocins in the fluidic reservoir. In some embodiments, each discrete coding substrate encodes a different bacteriocin. In some embodiments, a discrete coding substrate encodes two or more different bacteriocins. In some embodiments, at least one or all of the discrete coding substrates encode a "spaghetti" pro-polypeptide as described herein. Optionally, the discrete coding substrate can comprise or encode a protease as described herein, which can cleave the cleavage sites of the pro-polypeptide so that the discrete coding substrate can produce two or more bacteriocins in a specified stoichiometry. The microfluidic device can comprise an outlet, configured to place the specified mixture of antimicrobial peptides and/or bacteriocins in fludic communication with a tissue, a wound, a host microbiome, or a vessel. The specified mixture of bactericins can be used, for example, as a point-of-care antimicrobial composition, and/or to test the effects of the specified mixture on a host tissue and/or host microbiome, for example one comprising an undesired microbial organism.

Advantageously, the relative quantities of different bacteriocins in the pro-polypeptide will precisely determine the ratio of bacteriocins in the mixture after cleavage, and this ratio will be maintained regardless of the rate of expression of the polypeptide within or among different microbial cells. In contrast, conventional methods in which bacteriocins are translated as separate peptides or produced by different cells (see FIG. 1) can be subject to variations in transformation efficiency, genetic engineering efficiency, and/or gene expression efficiency (for example if some bacteriocin-encoding plasmids replicate and/or initiate transcription more efficiently than others), so that the final ratios of bacteriocins will be less precise than embodiments herein. As another advantage, since each nucleic acid can encode many bacteriocins, some embodiments herein provide for a much more efficient genetic modification of a host cell than conventional approaches that would involve introducing multiple constructs each encoding a particular bacteriocin. As another advantage, since the bacteriocins can be produced in their inactive form in the pro-polypeptide, the "workhorse" microbial organism that produces the bacteriocins does not need to be configured with immunity to all, some, or any of these bacteriocins, and thus can readily be used to produce mixtures of any of a number of different bacteriocins. Although in some embodiments, the producing microbial organism can naturally or artificially be configured with immunity to one or more or all of the bacteriocins included in the pro-polypeptide.

Populations of microbial organisms targeted by bacteriocin compositions of some embodiments herein can exist in a number in commercially useful environments such as industrial cultures, fermenters, pharmaceutical, biological, and cosmetic manufacturing, in microbiomes, such as human organs, animals, and plants (e.g. on the roots or soil in which the plant grows), and in products, such as foods (for human and/or animals), drug products, and cosmetic products. Without being limited by theory, it is contemplated that populations of microbial organisms in any of these environments do not necessarily co-exist at a steady state. For example, as reviewed in Jaramillo et al., Nature Microbiology 2: 17119 (2017), as populations of microbial organisms interact with each other (directly or indirectly), they can affect each other in positive or negative ways, but are not expected to exist at steady state, which conventionally lead to challenges in maintaining a co-culture. In some embodiments, when certain populations of microbial organisms reach a quantity or density above a certain threshold, a mixture of bacteriocins produced according to methods, and/or through the use or pro-polypeptides and/or nucleic acids and/or microbial cells of some embodiments herein can be added to the environment so as to target the microbial cells of this population. For example, if a population contains a large excess of microbial organism #1, and a smaller excess of microbial organism #2, in accordance with some embodiments, a mixture comprising a relatively high ratio of bacteriocin #1 (targeting microbial organism #1) to bacteriocin #2 (targeting microbial organism #2) can be administered to the population, so as to reduce the growth of microbial organisms #1 and #2, with a greater reduction targeted to microbial organism #1.

Bacteriocins and Antimicrobial Peptides

As used herein, "bacteriocin," and variations of this root term, has its customary and ordinary meaning as understood by one of skill in the art in view of this disclosure. It refers to a polypeptide that is secreted by a host cell and can neutralize at least one cell other than the individual host cell in which the polypeptide is made, including cells clonally related to the host cell and other microbial cells. "Bacteriocin" also encompasses a cell-free or chemically synthesized version of such a polypeptide. A cell that expresses a particular "immunity modulator" (discussed in more detail herein) is immune to the neutralizing effects of a particular bacteriocin or group of bacteriocins. As such, bacteriocins can neutralize a cell producing the bacteriocin and/or other microbial cells, so long as these cells do not produce an appropriate immunity modulator. As such, a host cell can exert cytotoxic or growth-inhibiting effects on a plurality of other microbial organisms by secreting bacteriocins. Detailed descriptions of bacteriocins, including methods and compositions for using bacteriocins to control the growth of microbial cells can be found, for example, in U.S. Pat. No. 9,333,227, which is hereby incorporated by reference in its entirety. "Bacteriocin" is not limited by the origin of the polypeptide, and by way of example is contemplated to encompass any bacteriocin, such as naturally-occurring bacteriocins, synthetic bacteriocins, and variants and combinations thereof.

The bacteriocins of some embodiments are initially produced in a pro-polypeptide, which can then be cleaved as described herein to produce the individual bacteriocins. In some embodiments, the pro-polypeptide is produced by the translational machinery (e.g. a ribosome, etc.) of a microbial cell. In some embodiments, the pro-polypeptide is produced by an in vitro expression system. The pro-polypeptide can undergo cleavage (for example processing by a cleavage enzyme such as a naturally-occurring or synthetic protease) to yield the polypeptide of the bacteriocin itself. As such, in some embodiments, a bacteriocin is produced from a precursor polypeptide. In some embodiments, a bacteriocin comprises a polypeptide that has undergone post-translational modifications, for example cleavage, or the addition of one or more functional groups. In some embodiments, a pro-polypeptide comprising, consisting essentially of, or consisting of bacteriocins and cleavage sites as described herein is chemically synthesized.

"Antibiotic," and variations of this root term, has its customary and ordinary meaning as understood by one of skill in the art in view of this disclosure. It refers to a metabolite, or an intermediate of a metabolic pathway which can kill or arrest the growth of at least one microbial cell. Some antibiotics can be produced by microbial cells, for example bacteria. Some antibiotics can be synthesized chemically. It is understood that bacteriocins are distinct from antibiotics, at least in that bacteriocins refer to gene products (which, in some embodiments, undergo additional post-translational processing) or synthetic analogs of the same, while antibiotics refer to intermediates or products of metabolic pathways or synthetic analogs of the same.

Neutralizing activity of bacteriocins can include, for example, arrest of microbial reproduction, or cytotoxicity. Some bacteriocins have cytotoxic activity (e.g. "bacteriocide" effects), and thus can kill microbial organisms, for example bacteria, yeast, algae, synthetic microorganisms, and the like. Some bacteriocins can inhibit the reproduction of microbial organisms (e.g. "bacteriostatic" effects), for example bacteria, yeast, algae, synthetic microorganisms, and the like, for example by arresting the cell cycle. In some neutralizing comprises, consists of, or consists essentially of arrest of microbial reproduction, inhibition of reproduction of microbial organisms, and/or cytotoxicity.

In some embodiments, a particular neutralizing activity or ranges of activities (e.g. cytotoxicity or arrest of microbial reproduction) is selected based on the type of microbial regulation that is desired and the particular strains or species of microbial organisms being targeted. As such, in some embodiments, particular bacteriocins or combinations of bacteriocins are selected. For example, in some embodiments, microbial cells are engineered to express particular bacteriocins based on the cells being regulated. In some embodiments, for example if contaminating cells are to be killed, at least one cytotoxic bacteriocin is provided. In some embodiments, a bacteriocin or combination of bacteriocins which is effective against contaminants which commonly occur in a particular culture, or a particular geographic location, or a particular type of culture grown in a particular geographic location are selected. In some embodiments, for example embodiments in which reversible regulation of microbial cell ratios is desired, a bacteriocin that inhibits microbial reproduction is provided. Without being limited by any particular theory, many bacteriocins can have neutralizing activity against microbial organisms that typically occupy the same ecological niche as the species that produces the bacteriocin. As such, in some embodiments, when a particular spectrum of bacteriocin activity is desired, a bacteriocin is selected from a host species that occupies the same (or similar) ecological niche as the microbial organism or organisms targeted by the bacteriocin. In some embodiments, a particular mixture and/or ratio is selected to target a single microbial organism (which can include targeting one or more than one microbial organisms of that type, for example clonally related microbial organisms). For example a particular type of microbial organism may be targeted more efficiently by a predetermined mixture and/or ratio of bacteriocins than by a single bacteriocin.

In some embodiments, one or more bacteriocin activities are selected in advance of culture growth, and a pro-polypeptide comprising the bacteriocins in a desired stoichiometry is prepared. A polynucleotide encoding the pro-polypeptide can be prepared, for example using nucleic acid synthesis and/or molecular cloning, and can be used to produce the pro-polypeptide. The polynucleotide can be transcribed (if a DNA) and translated using a number of suitable systems, for example in a microbial cell, or in an in vitro expression system. In some embodiments, bacteriocins (and ratios thereof) may be selected based on their ability to neutralize one or more invading organisms which are likely to attempt to grow in a particular culture. In some embodiments, bacteriocins (and ratios thereof) may be selected based on their ability to limit the growth of particular useful microbial strains in an environment, for example in an industrial feedstock, or in a fermenter, or in a food, pharmaceutical, or cosmetic manufacturing environment, or in a tissue environment such as a gut or skin microbiome, or in maintaining or tuning a microbial population in a plant, a plant root, and/or soil, or in preserving or maintaining the quality of a food, drug or cosmetic product. In some embodiments, one or more bacteriocin activities (and/or ratios) are selected based on one or more microbial strains or a population of microbial strains an existing environment. For example, in some embodiments, if particular invaders are identified in an environment, a panel of neutralizing bacteriocins (and ratios thereof) can be selected to neutralize the identified invaders. In some embodiments, the bacteriocins are selected to neutralize all or substantially all of the microbial cells in an environment, for example to eliminate an industrial culture in a culture environment so that a new industrial culture can be introduced to the culture environment, or to prevent or inhibit contamination of a pharmaceutical or cosmetic manufacturing environment, or to prevent or minimize contamination or spoilage of a food, drug, or cosmetic product.

For example, in some embodiments, an anti-fungal activity (such as anti-yeast activity) is desired. A number of bacteriocins with anti-fungal activity have been identified. For example, bacteriocins from *Bacillus* have been shown to have neutralizing activity against yeast strains (see Adetunji and Olaoye (2013) Malaysian Journal of Microbiology 9: 130-13, hereby incorporated by reference in its entirety), an *Enterococcus faecalis* peptide (WLPPAGLL-GRCGRWFRPWLLWLQ SGAQY KWLGNLFGLGPK, SEQ ID NO: 1) has been shown to have neutralizing activity against *Candida* species (see Shekh and Roy (2012) BMC Microbiology 12: 132, hereby incorporated by reference in its entirety), and bacteriocins from *Pseudomonas* have been shown to have neutralizing activity against fungi such as *Curvularia lunata, Fusarium* species, *Helminthosporium* species, and Biopolaris species (Shalani and Srivastava (2008) The Internet Journal of Microbiology. Volume 5 Number 2. DOI: 10.5580/27dd—accessible on the world-wide web at archive.ispub.com/journal/the-internet-journal-of-microbiology/volume-5-number-2/screening-for-antifungal-activity-of-*pseudomonas-fluorescens*-against-phytopathogenic-fungi.html#sthash.d0Ys03UO.1DKuT1US.dpuf, hereby incorporated by reference in its entirety). By way of example, botrycidin AJ1316 (see Zuber, P et al. (1993) Peptide Antibiotics. In *Bacillus subtilis* and Other Gram-Positive Bacteria: Biochemistry, Physiology, and Molecular Genetics ed Sonenshein et al., pp. 897-916, American Society for Microbiology, hereby incorporated by reference in its entirety) and alirin B1 (see Shenin et al. (1995) Antibiot Khimioter 50: 3-7, hereby incorporated by reference in its entirety) from *B. subtilis* have been shown to have antifungal activities. As such, in some embodiments, for example embodiments in which neutralization of a fungal microbial organism is desired, a bacteriocin comprises at least one of botrycidin AJ1316 or alirin B1.

For example, in some embodiments, bacteriocin activity in a culture of a particular microorganism (or collection of different microorganisms) is desirable, and bacteriocins are selected in predetermined ratios in order to neutralize microorganisms other than the desired microorganism(s). Bacteriocins typically produced by the desired microorganisms can be selected, as the desired microbial organisms can already produce the relevant immunity modulators against these bacteriocins, or can readily be engineered to produce the immunity modulators. As such, the selected bacteriocins can target undesired microbial cells, while causing little or no neutralization of the desired microbial organisms. For example, in some embodiments, bacteriocins are selected in particular ratios in order to neutralize invading microbial organisms typically found in a cyanobacteria culture environment, while preserving the cyanobacteria. Clusters of conserved bacteriocin polypeptides have been identified in a wide variety of cyanobacteria species. For example, at least 145 putative bacteriocin gene clusters have been identified in at least 43 cyanobacteria species, as reported in Wang et al. (2011), Genome Mining Demonstrates the Widespread Occurrence of Gene Clusters Encoding Bacteriocins in Cyanobacteria. PLoS ONE 6(7): e22384, hereby incorporated by reference in its entirety. Exemplary cyanobacteria bacteriocins are shown in Table 1.2, as SEQ ID NO's 420, 422, 424, 426, 428, 430, 432, 434, 436, 438, 440, 442, 444, 446, 448, and 450.

In some embodiments, a microbial cell produces bacteriocins. In some embodiments, bacteriocins neutralize cells of a different species or strain from the microbial cell that produced bacteriocins. In some embodiments, bacteriocins neutralize cells of the same species or strain as the host cell if these cells lack an appropriate immunity modulator. As bacteriocins can mediate neutralization of both host and non-host microbial organisms, the skilled artisan will readily appreciate that a bacteriocin is distinct from poison-antidote systems, which involve an endogenous mechanism by which a host microorganism can neutralize only itself. In other words, bacteriocins can neutralize cells other than the cell in which they are produced (for example, bacteriocins can be selected and/or engineered to act as an ecological niche protector), while poison molecules kill only the individual cell in which they are produced (for example, to act as suicidal systems).

A number of bacteriocins have been identified and characterized. Without being limited by theory, exemplary bacteriocins can be classified as "class I" bacteriocins, which typically undergo post-translational modification, and "class II" bacteriocins, which are typically unmodified. Additionally, exemplary bacteriocins in each class can be categorized into various subgroups, as summarized in Table 1.1, which is adapted from Cotter, P. D. et al. "Bacteriocins—a viable alternative to antibiotics" Nature Reviews Microbiology (2013) 11: 95-105, hereby incorporated by reference in its entirety.

Without being limited by theory, bacteriocins can effect neutralization of a target microbial cell in a variety of ways. For example, a bacteriocin can permeabilize a cell wall, thus depolarizing the cell wall and interfering with respiration.

TABLE 1.1

Classification of Exemplary Bacteriocins

| Group | Distinctive feature | Examples |
|---|---|---|
| Class I (typically modified) | | |
| MccC7-C51-type bacteriocins | Is covalently attached to a carboxy-terminal aspartic acid | MccC7-051 |
| Lasso peptides | Have a lasso structure | MccJ25 |
| Linear azole- or azoline-containing peptides | Possess heterocycles but not other modifications | MccB17 |
| Lantibiotics | Possess lanthionine bridges | Nisin, planosporicin, mersacidin, actagardine, mutacin 1140 |
| Linaridins | Have a linear structure and contain dehydrated amino acids | Cypemycin |
| Proteusins | Contain multiple hydroxylations, epimerizations and methylations | Polytheonamide A |
| Sactibiotics | Contain sulphur-α-carbon linkages | Subtilosin A, thuricin CD |
| Patellamide-like cyanobactins | Possess heterocycles and undergo macrocyclization | Patellamide A |
| Anacyclamide-like cyanobactins | Cyclic peptides consisting of proteinogenic amino acids with prenyl attachments | Anacyclamide A10 |
| Thiopeptides | Contain a central pyridine, dihydropyridine or piperidine ring as well as heterocycles | Thiostrepton, nocathiacin I, GE2270 A, philipimycin |
| Bottromycins | Contain macrocyclic amidine, a decarboxylated carboxy-terminal thiazole and carbon-methylated amino acids | Bottromycin A2 |
| Glycocins | Contain S-linked glycopeptides | Sublancin 168 |
| Class II (typically unmodified or cyclic) | | |
| IIa peptides (pediocin PA-1-like bacteriocins) | Possess a conserved YGNGV motif (in which N represents any amino acid) | Pediocin PA-1, enterocin CRL35, carnobacteriocin BM1 |
| IIb peptides | Two unmodified peptides are required for activity | ABP118, lactacin F |
| IIc peptides | Cyclic peptides | Enterocin AS-48 |
| IId peptides | Unmodified, linear, non-pediocin-like, single-peptide bacteriocins | MccV, MccS, epidermicin NI01, lactococcin A |
| IIe peptides | Contain a serine-rich carboxy-terminal region with a non-ribosomal siderophore-type modification | MccE492, MccM |

A number of bacteriocins can be used in accordance with embodiments herein. Exemplary bacteriocins are shown in Table 1.2. In some embodiments, at least one bacteriocin comprising, consisting essentially of, or consisting of a polypeptide sequence of Table 1.2 is provided. As shown in Table 1.2, some bacteriocins function as pairs of molecules. As such, it will be understood that unless explicitly stated otherwise, when a functional "bacteriocin" or "providing a bacteriocin," or the like is discussed herein, functional bacteriocin pairs are included along with bacteriocins that function individually. With reference to Table 1.2, "organisms of origin" listed in parentheses indicate alternative names and/or strain information for organisms known the produce the indicated bacteriocin. However, in some embodiments herein, bacteriocins are produced by a desired microbial organisms, and thus are not limited to the examples of organisms known to produce the bacteriocins shown in Table 1.2

Embodiments herein also include peptides and proteins with identity to bacteriocins described in Table 1.2. The term "identity" has its customary and ordinary meaning as understood by one of skill in the art in view of this disclosure. It is meant to include nucleic acid or protein sequence homology or three-dimensional homology. As used herein, a "variant" of a polypeptide, such as a bacteriocin, signal molecule, immunity modulator, tag (or any other component peptide of a pro-polypeptide as described herein) has its customary and ordinary meaning as understood by one of skill in the art in view of this disclosure. It will be understood to include identity as described herein to the reference sequence of at least about 70%, for example, at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity, including ranges between any two of the listed values, for example 70%-100%, 75%-100%, 80%-100%, 85%-100%, 90%-100%, 95%-100%, 97%-100%, 99%-100%, 70%-99%, 75%-99%, 80%-99%, 85%-99%, 90%-99%, 95%-99%, 97%-99%, 70%-95%, 75%-95%, 80%-95%, 85%-95%, 90%-95%, 70%-90%, 75%-90%, 80%-90%, and 85%-90%. Several techniques exist to determine nucleic acid or polypeptide sequence homology and/or three-dimensional homology to polypeptides. These methods are routinely employed to discover the extent of identity that one sequence, domain, or model has to a target sequence, domain, or model. Percent identity may be determined using the BLAST software (Altschul, S. F., et al. (1990) "Basic local alignment search tool." J. Mol. Biol. 215:403-410, accessible on the world wide web at blast.ncbi.nlm.nih.gov) with the default parameters.

A vast range of functional bacteriocins can incorporate features of bacteriocins disclosed herein, thus providing for a vast degree of identity to the bacteriocins in Table 1.2. In some embodiments, a bacteriocin has at least about 50% identity, for example, at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any one of the polypeptides of Table 1.2, including ranges between any two of the listed values, for example 70%-100%, 75%-100%, 80%-100%, 85%-100%, 90%-100%, 95%-100%, 97%-100%, 99%-100%, 70%-99%, 75%-99%, 80%-99%, 85%-99%, 90%-99%, 95%-99%, 97%-99%, 70%-95%, 75%-95%, 80%-95%, 85%-95%, 90%-95%, 70%-90%, 75%-90%, 80%-90%, and 85%-90%.

In some embodiments, a bacteriocin with identity to a bacteriocin in Table 1.2 is provided, in which the bacteriocin has been modified to remove one or more cleavage sites that are being used in a pro-polypeptide as described herein. Without being limited by theory, it is contemplated that modifying bacteriocins to remove cleavage sites (for example by making conservative substitutions, such as small non-polar to small non-polar amino acid, e.g. Leu→Ile, or small polar to small polar amino acid, e.g., Ser→Thr) can prevent the bacteriocin itself from being cleaved when the pro-polypeptide is cleaved as described herein. As such, in some embodiments a bacteriocin in a pro-polypeptide as described herein (e.g., a bacteriocin of Table 1.2, or a variant thereof) does not contain any cleavage sites that are used to separate the bacteriocins (or other elements) of the pro-polypeptide.

TABLE 1.2

Exemplary Bacteriocins

| Polypeptide SEQ ID NO: | Name | Class | Organism of origin | Polynucleotide SEQ ID NO: |
|---|---|---|---|---|
| 4 | Acidocin 8912 | Unclassified | *Lactobacillus acidophilus* | 5 |
| 6 | Acidocin A | class IIA/YGNGV | *Lactobacillus acidophilus* | 7 |
| 8 | Acidocin B (AcdB) | Unclassified | *Lactobacillus acidophilus* | 9 |
| 10 | Acidocin LF221B (Gassericin K7 B) | Unclassified | *Lactobacillus gasseri* | 11 |
| 12 | Aureocin A53 | Unclassified | *Staphylococcus aureus* | 13 |
| 14 | Avicin A | class IIA/YGNGV | *Enterococcus avium* (*Streptococcus avium*) | 15 |
| 16 | Bacteriocin 31 | Unclassified | *Enterococcus faecalis* (*Streptococcus faecalis*) | 17 |
| 18 | Bacteriocin J46 | Unclassified | *Lactococcus lactis* | 19 |
| 20 | Bacteriocin T8 | class IIa | *Enterococcus faecium* (*Streptococcus faecium*) | 21 |
| 22 | Boticin B | Unclassified | *Clostridium botulinum* | 23 |
| 24 | Bovicin HJ50 | Lantibiotic | *Streptococcus equinus* (*Streptococcus bovis*) | 25 |
| 26 | Brochocin-c | Unclassified | *Brochothrix campestris* | 27 |
| 28 | Butyrivibriocin AR10 | Unclassified | *Butyrivibrio fibrisolvens* | 29 |
| 30 | Butyrivibriocin OR79 | Lantibiotic | *Butyrivibrio fibrisolvens* | 31 |
| 32 | Carnobacteriocin B2 (Carnocin CP52) | class IIA/YGNGV | *Carnobacterium maltaromaticum* (*Carnobacterium piscicola*) | 33 |
| 34 | Carnobacteriocin BM1 (Carnobacteriocin B1) | class IIA/YGNGV | *Carnobacterium maltaromaticum* (*Carnobacterium piscicola*) | 35 |
| 36 | Carnobacteriocin-A (Piscicolin-61) | class IIc, non subgrouped bacteriocins (problematic) | *Carnobacterium maltaromaticum* (*Carnobacterium piscicola*) | 37 |
| 38 | Carnocyclin-A | Unclassified | *Carnobacterium maltaromaticum* (*Carnobacterium piscicola*) | 39 |
| 40 | Carocin D | Unclassified | *Pectobacterium carotovorum* subsp. *carotovorum* (*Erwinia carotovora* subsp. *carotovora*) | 41 |
| 42 | Cerein 7B | Unclassified | *Bacillus cereus* | 43 |
| 44 | Cinnamycin (Lanthiopeptin) | Lantibiotic | *Streptoverticillium griseoverticillatum* | 45 |
| 46 | Circularin A | Unclassified | *Geobacillus kaustophilus* (strain HTA426) | 47 |
| 48 | Closticin 574 | Unclassified | *Clostridium tyrobutyricum* | 49 |
| 50 | Coagulin A | Unclassified | *Bacillus coagulans* | 51 |
| 52 | Colicin-10 | Unclassified | *Escherichia coli* | 53 |
| 54 | Colicin-E1 | Unclassified | *Escherichia coli* | 55 |
| 56 | Colicin-Ia | Unclassified | *Escherichia coli* | 57 |
| 58 | Colicin-Ib | Unclassified | *Escherichia coli* | 59 |
| 60 | Colicin-M | Unclassified | *Escherichia coli* | 61 |
| 62 | Colicin-N | Unclassified | *Escherichia coli* | 63 |
| 64 | Colicin-V (Microcin-V) | Unclassified | *Escherichia coli* | 65 |
| 66 | Columbicin A | Lantibiotic | *Enterococcus columbae* | 67 |
| 68 | Curvacin-A | class IIA/YGNGV | *Lactobacillus curvatus* | 69 |
| 70 | Cypemycin | Unclassified | *Streptomyces* sp. | 71 |
| 72 | Cytolysin | Lantibiotic | *Bacillus halodurans* (strain ATCC BAA-125/ DSM 18197/FERM 7344/ JCM 9153/C-125) | 73 |
| 74 | Divercin V41 | class IIa/YGNGV | *Carnobacterium divergens* (*Lactobacillus divergens*) | 75 |
| 76 | Divergicin 750 | Unclassified | *Carnobacterium divergens* (*Lactobacillus divergens*) | 77 |
| 78 | Divergicin A | Class IIc | *Carnobacterium divergens* (*Lactobacillus divergens*) | 79 |
| 80 | Durancin Q | Unclassified | *Enterococcus durans* | 81 |

TABLE 1.2-continued

Exemplary Bacteriocins

| Polypeptide SEQ ID NO: | Name | Class | Organism of origin | Polynucleotide SEQ ID NO: |
|---|---|---|---|---|
| 82 | Durancin TW-49M | Unclassified | *Enterococcus durans* | 83 |
| 84 | Dysgalacticin | Unclassified | *Streptococcus dysgalactiae* subsp. *equisimilis* (*Streptococcus equisimilis*) | 85 |
| 86 | Enterocin 1071A | Unclassified | *Enterococcus faecalis* (*Streptococcus faecalis*) | 87 |
| 88 | Enterocin 7A (Enterocin L50A) | bacteriocins without sequence leader | *Enterococcus faecalis* (*Streptococcus faecalis*) | 89 |
| 90 | Enterocin 7B | Unclassified | *Enterococcus faecalis* (*Streptococcus faecalis*) | 91 |
| 92 | Enterocin 96 | Class II | *Enterococcus faecalis* (strain ATCC 700802/ V583) | 93 |
| 94 | Enterocin A | Class IIa, IIc (problematic) | *Enterococcus faecium* (*Streptococcus faecium*) | 95 |
| 96 | Enterocin AS-48 (BACTERIOCIN AS-48) | Unclassified | *Enterococcus faecalis* (*Streptococcus faecalis*) | 97 |
| 98 | Enterocin B | class IIc, non subgrouped bacteriocins (problematic) | *Enterococcus faecium* (*Streptococcus faecium*) | 99 |
| 100 | Enterocin CRL35 (Mundticin KS) | Class IIa | *Enterococcus mundtii* | 101 |
| 102 | Enterocin EJ97 | Unclassified | *Enterococcus faecalis* (*Streptococcus faecalis*) | 103 |
| 104 | Enterocin P | Class IIa, IIb and IIc (problematic) | *Enterococcus faecium* (*Streptococcus faecium*) | 105 |
| 106 | Enterocin Q | Class IIc | *Enterococcus faecium* (*Streptococcus faecium*) | 107 |
| 108 | Enterocin SE-K4 | Class IIa | *Enterococcus faecalis* (Streptococcus faecalis) | 109 |
| 110 | Enterocin W alfa | Class IIb | *Enterococcus faecalis* (Streptococcus faecalis) | 111 |
| 112 | Enterocin W beta | Class IIb | *Enterococcus faecalis* (Streptococcus faecalis) | 113 |
| 114 | Enterocin Xalpha | Class IIb | *Enterococcus faecium* (Streptococcus faecium) | 115 |
| 116 | Enterocin Xbeta | Class IIb | *Enterococcus faecium* (Streptococcus faecium) | 117 |
| 118 | Enterolysin A | class III | *Enterococcus faecalis* (Streptococcus faecalis) | 119 |
| 120 | Epicidin 280 | Lantibiotic | *Staphylococcus epidermidis* | 121 |
| 122 | Epidermicin NI01 | Unclassified | *Staphylococcus epidermidis* | 123 |
| 124 | Epidermin | Lantibiotic | *Staphylococcus epidermidis* | 125 |
| 126 | Epilancin K7 | Lantibiotic | *Staphylococcus epidermidis* | 127 |
| 128 | Gallidermin | Lantibiotic | *Staphylococcus gallinarum* | 129 |
| 130 | Garvicin A | IId | *Lactococcus garvieae* | 131 |
| 132 | Garvicin ML | Unclassified | *Lactococcus garvieae* | 133 |
| 134 | Gassericin A | Unclassified | *Lactobacillus gasseri* | 135 |
| 136 | Gassericin T (gassericin K7 B) | Unclassified | *Lactobacillus gasseri* | 137 |
| 138 | Glycocin F | Unclassified | *Lactobacillus plantarum* | 139 |
| 140 | Halocin H4 | Unclassified | *Haloferax mediterranei* (strain ATCC 33500/ DSM 1411/JCM 8866/ NBRC 14739/NCIMB 2177/R-4) (*Halobacterium mediterranei*) | 141 |
| 142 | Halocin-58 | Unclassified | *Haloarchaeon* S8a | 143 |
| 144 | Helveticin-J | Unclassified | *Lactobacillus helveticus* (*Lactobacillus suntoryeus*) | 145 |

TABLE 1.2-continued

Exemplary Bacteriocins

| Polypeptide SEQ ID NO: | Name | Class | Organism of origin | Polynucleotide SEQ ID NO: |
|---|---|---|---|---|
| 146 | Hiracin JM79 | Class II sec-dependent | *Enterococcus hirae* | 147 |
| 148 | Lactacin-F (lafA) | class IIB | *Lactobacillus johnsonii* (strain CNCM I-12250/ La1/NCC 533) | 149 |
| 150 | Lactacin-F (lafX) | class IIB | *Lactobacillus johnsonii* (strain CNCM I-12250/ La1/NCC 533) | 151 |
| 152 | Lacticin 3147 A1 | Lantibiotic | *Lactococcus lactis* subsp. *lactis* (*Streptococcus lactis*) | 153 |
| 154 | Lacticin 3147 A2 | Lantibiotic | *Lactococcus lactis* subsp. *lactis* (*Streptococcus lactis*) | 155 |
| 156 | Lacticin 481 (Lactococcin DR) | Lantibiotic | *Lactococcus lactis* subsp. *lactis* (*Streptococcus lactis*) | 157 |
| 158 | Lacticin Q | Unclassified | *Lactococcus lactis* | 159 |
| 160 | Lacticin Z | Unclassified | *Lactococcus lactis* | 161 |
| 162 | Lactobin-A (Amylovorin-L471) | class IIB | *Lactobacillus amylovorus* | 163 |
| 164 | Lactocin-S | Lantibiotic | *Lactobacillus sakei* L45 | 165 |
| 166 | Lactococcin 972 | Unclassified | *Lactococcus lactis* subsp. *lactis* (*Streptococcus lactis*) | 167 |
| 168 | Lactococcin-A | Unclassified | *Lactococcus lactis* subsp. *cremoris* (*Streptococcus cremoris*) | 169 |
| 170 | Lactococcin-B | Unclassified | *Lactococcus lactis* subsp. *cremoris* (*Streptococcus cremoris*) | 171 |
| 172 | Lactocyclicin Q | Unclassified | *Lactococcus* sp. QU 12 | 173 |
| 174 | Laterosporulin | Unclassified | *Brevibacillus* sp. GI-9 | 175 |
| 176 | Leucocin N | Class IId | *Leuconostoc pseudomesenteroides* | 177 |
| 178 | Leucocin Q | Class IId | *Leuconostoc pseudomesenteroides* | 179 |
| 180 | Leucocin-A (Leucocin A-UAL 187) | class IIA/YGNGV | *Leuconostoc gelidum* | 181 |
| 182 | Leucocin-B (Leucocin B-Ta11a) | class IIA/YGNGV | *Leuconostoc carnosum* | 183 |
| 184 | Leucocyclicin Q | Unclassified | *Leuconostoc mesenteroides* | 185 |
| 186 | Lichenicidin A1 | Lantibiotic (two-peptide) | *Bacillus licheniformis* (strain DSM 13/ATCC 14580) | 187 |
| 188 | Linocin M18 | Unclassified | *Brevibacterium linens* | 189 |
| 190 | Listeriocin 743A | Class IIa | *Listeria innocua* | 191 |
| 192 | Mersacidin | Lantibiotic, type B | *Bacillus* sp. (strain HIL-Y85/54728) | 193 |
| 194 | Mesentericin Y105 | class IIA/YGNGV | *Leuconostoc mesenteroides* | 195 |
| 196 | Michiganin-A | Lantibiotic | *Clavibacter michiganensis* subsp. *michiganensis* | 197 |
| 198 | Microcin B17 (MccB17) | Unclassified | *Escherichia coli* | 199 |
| 200 | Microcin C7 | Unclassified | *Escherichia coli* | 201 |
| 202 | Microcin E492 | Unclassified | *Klebsiella pneumoniae* | 203 |
| 204 | Microcin H47 | Unclassified | *Escherichia coli* | 205 |
| 206 | Microcin J25 | Unclassified | *Escherichia coli* | 207 |
| 208 | Microcin-24 | Unclassified | *Escherichia coli* | 209 |
| 210 | Mundticin KS | Unclassified | *Enterococcus mundtii* | 211 |
| 212 | Mundticin L | class IIA/YGNGV | *Enterococcus mundtii* | 213 |
| 214 | Mutacin 1140 (Mutacin III) | Lantibiotic | *Streptococcus mutans* | 215 |
| 216 | Mutacin-2 | Lantibiotic | *Streptococcus mutans* | 217 |
| 218 | Nisin A | Lantibiotic | *Lactococcus lactis* subsp. *lactis* (*Streptococcus lactis*) | 219 |
| 220 | Nisin F | Lantibiotic | *Lactococcus lactis* | 221 |
| 222 | Nisin Q | Lantibiotic | *Lactococcus lactis* | 223 |
| 224 | Nisin U | Lantibiotic | *Streptococcus uberis* | 225 |

TABLE 1.2-continued

Exemplary Bacteriocins

| Polypeptide SEQ ID NO: | Name | Class | Organism of origin | Polynucleotide SEQ ID NO: |
|---|---|---|---|---|
| 226 | Nisin Z | Lantibiotic | *Lactococcus lactis* subsp. *lactis* (*Streptococcus lactis*) | 227 |
| 228 | Nukacin ISK-1 | Lantibiotic | *Staphylococcus warneri* | 229 |
| 230 | Paenicidin A | Lantibiotic | *Paenibacillus polymyxa* (*Bacillus polymyxa*) | 231 |
| 232 | Pediocin PA-1 (Pediocin ACH) | class IIA/YGNGV | *Pediococcus acidilactici* | 233 |
| 234 | Penocin A | class IIA/YGNGV | *Pediococcus pentosaceus* (strain ATCC 25745/183-1w) | 235 |
| 236 | Pep5 | Lantibiotic | *Staphylococcus epidermidis* | 237 |
| 238 | Piscicolin 126 | class IIA/YGNGV | *Carnobacterium maltaromaticum* (*Carnobacterium piscicola*) | 239 |
| 240 | Plantaricin 1.25 β | Unclassified | *Lactobacillus plantarum* | 241 |
| 242 | Plantaricin 423 | class IIa | *Lactobacillus plantarum* | 243 |
| 244 | Plantaricin ASM1 | Unclassified | *Lactobacillus plantarum* | 245 |
| 246 | Plantaricin E | Unclassified | *Lactobacillus plantarum* | 247 |
| 248 | Plantaricin F | Class IIb | *Lactobacillus plantarum* | 249 |
| 250 | Plantaricin J | Class IIb | *Lactobacillus plantarum* | 251 |
| 252 | Plantaricin K | Unclassified | *Lactobacillus plantarum* | 253 |
| 254 | Plantaricin NC8 α | Unclassified | *Lactobacillus plantarum* | 255 |
| 256 | Plantaricin NC8 β | Unclassified | *Lactobacillus plantarum* | 257 |
| 258 | Plantaricin S α | Unclassified | *Lactobacillus plantarum* | 259 |
| 260 | Plantaricin S β | Unclassified | *Lactobacillus plantarum* | 261 |
| 262 | Plantaricin W α | Lantibiotic (two-peptide) | *Lactobacillus plantarum* | 263 |
| 264 | Plantaricin W β | Lantibiotic (two-peptide) | *Lactobacillus plantarum* | 265 |
| 266 | Plantaricin-A | Unclassified | *Lactobacillus plantarum* (strain ATCC BAA-793/NCIMB 8826/WCFS1) | 267 |
| 268 | Propionicin SM1 | Unclassified | *Propionibacterium jensenii* | 269 |
| 270 | Propionicin T1 | Unclassified | *Propionibacterium thoenii* | 271 |
| 272 | Propionicin-F | Unclassified | *Propionibacterium freudenreichii* subsp. *freudenreichii* | 273 |
| 274 | Pyocin S1 | Unclassified | *Pseudomonas aeruginosa* | 275 |
| 276 | Pyocin S2 | colicin/pyosin nuclease family | *Pseudomonas aeruginosa* (strain ATCC 15692/PAO1/1C/PRS 101/LMG 12228) | 277 |
| 278 | Ruminococcin-A | Lantibiotic | *Ruminococcus gnavus* | 279 |
| 280 | Sakacin G | Class IIa | *Lactobacillus sakei* | 281 |
| 282 | Sakacin-A | class IIA/YGNGV | *Lactobacillus sakei* | 283 |
| 284 | Sakacin-P (Sakacin 674) | class IIA/YGNGV | *Lactobacillus sakei* | 285 |
| 286 | Salivaricin 9 | lantibiotic | *Streptococcus salivarius* | 287 |
| 288 | Salivaricin A | Lantibiotic | *Streptococcus pyogenes* serotype M28 (strain MGAS6180) | 289 |
| 290 | Salivaricin A3 | Lantibiotic | *Streptococcus salivarius* | 291 |
| 292 | Salivaricin-A sa | Lantibiotic | *Streptococcus salivarius* | 293 |
| 294 | Staphylococcin C55 alpha | Lantibiotic (two-peptide) | *Staphylococcus aureus* | 295 |
| 296 | Staphylococcin C55 beta | Lantibiotic (two-peptide) | *Staphylococcus aureus* | 297 |
| 298 | Streptin | lantibiotic | *Streptococcus pyogenes* | 299 |
| 300 | Streptococcin A-FF22 | Lantibiotic | *Streptococcus pyogenes* | 301 |
| 302 | Streptococcin A-M49 | Lantibiotic | *Streptococcus pyogenes* serotype M49 | 303 |
| 304 | Sublancin 168 | Lantibiotic | *Bacillus subtilis* (strain 168) | 305 |
| 306 | Subtilin | Lantibiotic | *Bacillus subtilis* | 307 |
| 308 | Subtilosin | Unclassified | *Bacillus subtilis* (strain 168) | 309 |
| 310 | Subtilosin-A | Unclassified | *Bacillus subtilis* (strain 168) | 311 |

TABLE 1.2-continued

| Exemplary Bacteriocins | | | | |
|---|---|---|---|---|
| Polypeptide SEQ ID NO: | Name | Class | Organism of origin | Polynucleotide SEQ ID NO: |
| 312 | Thermophilin 1277 | Lantibiotic | *Streptococcus thermophilus* | 313 |
| 314 | Thermophilin 13 | Unclassified | *Streptococcus thermophilus* | 315 |
| 316 | Thermophilin A | Unclassified | *Streptococcus thermophilus* | 317 |
| 318 | Thiocillin (Micrococcin P1) (Micrococcin P2) (Thiocillin I) (Thiocillin II) (Thiocillin III) (Thiocillin IV) (Antibiotic YM-266183) (Antibiotic YM-266184) | Unclassified | *Bacillus cereus* (strain ATCC 14579/DSM 31) | 319 |
| 320 | Thuricin CD alpha | two-peptide lantibiotic | *Bacillus cereus* 95/8201 | 321 |
| 322 | Thuricin CD beta | two-peptide lantibiotic | *Bacillus cereus* 95/8201 | 323 |
| 324 | Thuricin-17 | Class IId | *Bacillus thuringiensis* | 325 |
| 326 | Trifolitoxin | Unclassified | *Rhizobium leguminosarum* bv. *trifolii* | 327 |
| 328 | Ubericin A | Class IIa | *Streptococcus uberis* | 329 |
| 330 | Uberolysin | Unclassified | *Streptococcus uberis* | 331 |
| 332 | UviB | Unclassified | *Clostridium perfringens* | 333 |
| 334 | Variacin | Lantibiotic, Type A | *Micrococcus varians* | 335 |
| 336 | Zoocin A | Unclassified | *Streptococcus equi* subsp. *zooepidemicus* | 337 |
| 338 | Fulvocin-C | Unclassified | *Myxococcus fulvus* | 339 |
| 340 | Duramycin-C | Lantibiotic | *Streptomyces griseoluteus* | 341 |
| 342 | Duramycin (duramycin-B) (Leucopeptin) | Lantibiotic B | *Streptoverticillium griseoverticillatum* | 343 |
| 344 | Carnocin UI49 | lantibiotic | *Carnobacterium* sp. (strain UI49) | 345 |
| 346 | Lactococcin-G α | Unclassified | *Lactococcus lactis* subsp. *lactis* (*Streptococcus lactis*) | 347 |
| 348 | Lactococcin-G β | Unclassified | *Lactococcus lactis* subsp. *lactis* (*Streptococcus lactis*) | 349 |
| 350 | Ancovenin | Lantibiotic | *Streptomyces* sp. (strain A647P-2) | 351 |
| 352 | Actagardine (Gardimycin) | Lantibiotic | *Actinoplanes liguriae* | 353 |
| 354 | Curvaticin FS47 | Unclassified | *Lactobacillus curvatus* | 355 |
| 356 | Bavaricin-MN | class IIA/YGNGV | *Lactobacillus sakei* | 357 |
| 358 | Mutacin B-Ny266 | Lantibiotic | *Streptococcus mutans* | 359 |
| 360 | Mundticin | class IIA/YGNGV | *Enterococcus mundtii* | 361 |
| 362 | Bavaricin-A | class IIA/YGNGV | *Lactobacillus sakei* | 363 |
| 364 | Lactocin-705 | Class IIb | *Lactobacillus paracasei* | 365 |
| 366 | Leucocin-B | Unclassified | *Leuconostoc mesenteroides* | 367 |
| 368 | Leucocin C | class IIA/YGNGV | *Leuconostoc mesenteroides* | 369 |
| 370 | LCI | Unclassified | *Bacillus subtilis* | 371 |
| 372 | Lichenin | Unclassified | *Bacillus licheniformis* | 373 |
| 374 | Lactococcin MMFII | class IIA/YGNGV | *Lactococcus lactis* subsp. *lactis* (*Streptococcus lactis*) | 375 |
| 376 | Serracin-P | Phage-Tail-Like | *Serratia plymuthica* | 377 |
| 378 | Halocin-C8 | Unclassified | *Halobacterium* sp. (strain AS7092) | 379 |
| 380 | Subpeptin JM4-B | Unclassified | *Bacillus subtilis* | 381 |
| 382 | Curvalicin-28a | Unclassified | *Lactobacillus curvatus* | 383 |
| 384 | Curvalicin-28b | Unclassified | *Lactobacillus curvatus* | 385 |
| 386 | Curvalicin-28c | Unclassified | *Lactobacillus curvatus* | 387 |
| 388 | Thuricin-S | Unclassified | *Bacillus thuringiensis* subsp. *entomocidus* | 389 |

TABLE 1.2-continued

Exemplary Bacteriocins

| Polypeptide SEQ ID NO: | Name | Class | Organism of origin | Polynucleotide SEQ ID NO: |
|---|---|---|---|---|
| 390 | Curvaticin L442 | Unclassified | *Lactobacillus curvatus* | 391 |
| 392 | Divergicin M35 | class IIa/YGNGV | *Carnobacterium divergens* (*Lactobacillus divergens*) | 393 |
| 394 | Enterocin E-760 | class IIb | *Enterococcus* sp. | 395 |
| 396 | Bacteriocin E50-52 | Unclassified | *Enterococcus faecium* (*Streptococcus faecium*) | 397 |
| 398 | Paenibacillin | Unclassified | *Paenibacillus polymyxa* (*Bacillus polymyxa*) | 399 |
| 400 | Epilancin 15x | Unclassified | *Staphylococcus epidermidis* | 401 |
| 402 | Enterocin-HF | class IIa | *Enterococcus faecium* (*Streptococcus faecium*) | 403 |
| 404 | Bacillocin 602 | Class IIa | *Paenibacillus polymyxa* (*Bacillus polymyxa*) | 405 |
| 406 | Bacillocin 1580 | Class IIa | *Bacillus circulans* | 407 |
| 408 | Bacillocin B37 | Unclassified | *Paenibacillus polymyxa* (*Bacillus polymyxa*) | 409 |
| 410 | Rhamnosin A | Unclassified | *Lactobacillus rhamnosus* | 411 |
| 412 | Lichenicidin A2 | Lantibiotic (two-peptide) | *Bacillus licheniformis* (strain DSM 13/ATCC 14580) | 413 |
| 414 | Plantaricin C19 | Class IIa | *Lactobacillus plantarum* | 415 |
| 416 | Acidocin J1132 β | Class IIb | *Lactobacillus acidophilus* | 417 |
| 418 | factor with anti-*Candida* activity | Unclassified | *Enterococcus faecalis* | 419 |
| 420 | Ava_1098 (putative heterocyst differentiation protein) | Unclassified | *Anabaena variabilis* ATCC 29413 | 421 |
| 422 | alr2818 (putative heterocyst differentiation protein) | Unclassified | *Nostoc* sp 7120 | 423 |
| 424 | Aazo_0724 (putative heterocyst differentiation protein) | Unclassified | *Nostoc azollae* 0708 | 425 |
| 426 | AM1_4010 (putative heterocyst differentiation protein) | Unclassified | *Acaryochloris marina* MBIC11017 | 427 |
| 428 | PCC8801_3266 (putative heterocyst differentiation protein) | Unclassified | *Cyanothece* PCC 8801 | 429 |
| 430 | Cyan8802_2855 (putative heterocyst differentiation protein) | Unclassified | *Cyanothece* PCC 8802 | 431 |
| 432 | PCC7424_3517 | Unclassified | *Cyanothece* PCC 7424 | 433 |
| 434 | cce_2677(putative HetP protein) | Unclassified | *Cyanothece* ATCC 51142 | 435 |
| 436 | CY0110_11572 (putative heterocyst differentiation protein) | Unclassified | *Cyanothece* CCY0110 | 437 |
| 438 | MC7420_4637 | Unclassified | *Microcoleus chthonoplastes* PCC 7420 | 439 |
| 440 | asr1611 (putative DUF37 family protein) | Unclassified | *Nostoc* sp 7120 | 441 |
| 442 | Ava_4222 (putative DUF37 family protein) | Unclassified | *Anabaena variabilis* ATCC 29413 | 443 |
| 444 | N9414_07129 (putative DUF37 family protein) | Unclassified | *Nodularia spumigena* CCY9414 | 445 |
| 446 | Aazo_0083 (putative DUF37 family protein) | Unclassified | *Nostoc azollae* 0708 | 447 |
| 448 | S7335_3409 (putative DUF37 family protein) | Unclassified | *Synechococcus* PCC 7335 | 449 |
| 450 | P9303_21151 (putative DUF37 family protein) | Unclassified | *Prochlorococcus marinus* MIT 9303 | 451 |
| 699 | Curvalicin-28c | Unclassified | *Lactobacillus curvatus* | 700 |
| 701 | thruicin-S | Unclassified | *Bacillus thuringiensis* | 702 |
| 703 | curvaticin L442 | Unclassified | *Lactobacillus curvatus* L442 | 704 |
| 705 | Bacteriocin divergicin M35 | P84962 | *Carnobacterium divergens* (*Lactobacillus divergens*) | 706 |

TABLE 1.2-continued

Exemplary Bacteriocins

| Polypeptide SEQ ID NO: | Name | Class | Organism of origin | Polynucleotide SEQ ID NO: |
|---|---|---|---|---|
| 707 | Lantibiotic 107891 | P85065 | *Microbispora* sp. (strain 107891) | 708 |
| 709 | Enterocin E-760 (Bacteriocin E-760) | P85147 | *Enterococcus* sp. | 710 |
| 711 | Bacteriocin E50-52 | P85148 | *Enterococcus faecium* (*Streptococcus faecium*) | 712 |
| 713 | Lantibiotic paenibacillin | P86013 | *Paenibacillus polymyxa* (*Bacillus polymyxa*) | 714 |
| 715 | Lantibiotic epilancin 15X | P86047 | *Staphylococcus epidermidis* | 716 |
| 717 | Enterocin-HF | P86183 | *Enterococcus faecium* (*Streptococcus faecium*) | 718 |
| 719 | Bacteriocin SRCAM 602 | P86393 | *Paenibacillus polymyxa* (*Bacillus polymyxa*) | 720 |
| 721 | Bacteriocin SRCAM 1580 | P86394 | *Bacillus circulans* | 722 |
| 723 | Bacteriocin SRCAM 37 | P86395 | *Paenibacillus polymyxa* (*Bacillus polymyxa*) | 724 |
| 725 | Bacteriocin rhamnosin A (Fragment) | P86526 | *Lactobacillus rhamnosus* | 726 |
| 727 | Lantibiotic lichenicidin A2 (LchA2) (BliA2) | P86720 | *Bacillus licheniformis* (strain ATCC 14580/ DSM 13/JCM 2505/ NBRC 12200/NCIMB 9375/NRRL NRS-1264/ Gibson 46) | 728 |
| 729 | Pyocin-S2 (EC 3.1.-.-) (Killer protein) | | *Pseudomonas aeruginosa* (strain ATCC 15692/ DSM 22644/CIP 104116/ JCM 14847/LMG 12228/1C/PRS 101/ PAO1) | 730 |
| 731 | Plantaricin C19 (Fragment) | | *Lactobacillus plantarum* | 732 |
| 733 | LsbB | | *Lactococcus lactis* subsp. *lactis* (*Streptococcus lactis*) | 734 |
| 735 | ACIDOCIN J1132 beta peptide (Fragment) | | *Lactobacillus acidophilus* | 736 |
| 737 | Uncharacterized protein | | *Lactobacillus salivarius* cp400 | 738 |

As used herein, "bacteriocin polynucleotide" has its customary and ordinary meaning as understood by one of skill in the art in view of this disclosure. It refers to a polynucleotide encoding a bacteriocin. As used herein, "bacteriocin coding sequence" has its customary and ordinary meaning as understood by one of skill in the art in view of this disclosure. It refers to nucleic acid coding sequence (e.g., RNA or DNA) that encodes the polypeptide sequence of a bacteriocin. In some embodiments, the host cell comprises at least one bacteriocin.

Antimicrobial peptides are a class of peptides that confer innate immune activity to kill or arrest the growth of microbial organisms. As used herein "antimicrobial peptide" (including variations of this root term) has its customary and ordinary meaning as would be understood by one of ordinary skill in the art in view of this disclosure. Clasically, antimicrobial peptides have been described as peptides produced by the innate immune systems of invertebrates and vertebrates. Thus, while bactericins have classically been referred to a class of microbial gene products that target microbial organisms, antimicrobial peptides have classically been referred to as a class of invertebrate and vertebrate gene products that target microbial organisms. Examples of antimicrobial peptides suitable for methods, microfluidic devices, and systems of some embodiments herein are known in the art, and can be founds, for example, at The Antimicrobial Peptide Database accessible on the world wide web at aps.unmc.edu/AP/, which is incorporated herein by reference in its entirerty. Over 1000 anitmicrobial peptides and variants thereof have been identified and cataloged. The Antimicrobial Peptide Database is described in Wang et al. (2016), Nucleic Acids Res. 44(Database issue): D1087-D1093, which is incorporated herein by reference in its entirety. Examples of antimicrobial peptides include bacteriocins, antibacterial, antiviral, anti-HIV, antifungal, antiparasitic and anticancer peptides, such as Dermaseptin-B2, Abaecin, Ct-AMP1, Andropin, Aurein 1.1, Lactoferricin B, and Heliomicin. Methods, compositions, systems, and microfluidic devices of some embodiments comprise naturally-occuring antimicrobial peptides, or a nucleic acid encoding the same. Methods, compositions, systems, and microfluidic devices of some embodiments comprise non-naturally occurring antimicrobial peptides, or nucleic acids encoding the same. Methods, compositions, systems, and microfluidic devices of some embodiments include antimicrobial peptides that comprise a mutation or variation in a naturally-occuring antimicrobial peptides, or a nucleic acid encoding the same. Methods, compositions, systems, and microfluidic devices of some embodiments comprise antimicrobial peptides comprising, consisting essentially of, or consisting of non-naturally occuring peptide sequences, or nucleic acids encoding the same.

It is further contemplated that methods, systems, and microfluidic devices of some embodiments herein can be in conjunction with naturally occurring antimicrobial peptides, variants of naturally occurring antimicrobial peptides, and/or synthetic antimicrobial peptides. As such, antimicrobial peptides of methods, systems, and device of some embodiments can comprise, consist essentially of, or consist of naturally occurring antimicrobial peptides, variants of naturally occurring antimicrobial peptides, and/or synthetic antimicrobial peptides. In some embodiments, a variant antimicrobial peptide has at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to a reference antimicrobial peptide (for example Dermaseptin-B2, Abaecin, Ct-AMP1, Andropin, Aurein 1.1, Lactoferricin B, or Heliomicin), including ranges between any two of the listed values, for example 70%-100%, 75%-100%, 80%-100%, 85%-100%, 90%-100%, 95%-100%, 97%-100%, 99%-100%, 70%-99%, 75%-99%, 80%-99%, 85%-99%, 90%-99%, 95%-99%, 97%-99%, 70%-95%, 75%-95%, 80%-95%, 85%-95%, 90%-95%, 70%-90%, 75%-90%, 80%-90%, and 85%-90%. Wherever bacteriocins are mentioned herein, it is expressly contemplated that any antimicrobial peptide as described herein may be substituted for one, two or more, or all of the noted bacteriocins (although it will be appreciated that in some contexts, such as a bacteriocin-immunity modulator pair, the antimicrobial peptide will have different properties and interact differently than a bactericoin). Accordingly, some embodiments of the methods and microfluidic devices described herein include bacteriocins only, some embodiments of the methods and microfluidic devices described herein include antimicrobial peptides only, and some embodiments of the methods and microfluidic devices described herein include a combination of bacteriocins and antimicrobial peptides. Accordingly, in the methods and compositions of some embodiments, a pro-polypeptide comprises an antimicrobial peptide instead of a bacteriocin. Accordingly, in the methods and compositions of some embodiments, a pro-polypeptide comprises one or more antimicrobial peptides and one or more bacteriocins.

Bacteriocin Immunity Modulators

Exemplary bacteriocin immunity modulators are shown in Table 2. While the immunity modulators in Table 2 are naturally-occurring, the skilled artisan will appreciate that variants of the immunity modulators of Table 2, naturally-occurring immunity modulators other than the immunity modulators of Table 2, or synthetic immunity modulators can be used according to some embodiments herein. In some embodiments, a microbial cell that produced a pro-polypeptide comprising bacteriocins does not produce an immunity modulator for at least one of the bacteriocins. Without being limited by theory, it is contemplated that in some embodiments, the bacteriocins in the pro-polypeptide are inactive, and thus have little to no ability to neutralize the cell that produced them (or a cell clonally related to the cell that produced them), so that the cell does not require immunity against these bacteriocins of the pro-polypeptide.

In some embodiments, a particular immunity modulator or particular combination of immunity modulators confers immunity to a particular bacteriocin, particular class or category of bacteriocins, or particular combination of bacteriocins. Exemplary bacteriocins to which immunity modulators can confer immunity are identified in Table 2. While Table 2 identifies an "organism of origin" for exemplary immunity modulators, these immunity modulators can readily be expressed in other naturally-occurring, genetically modified, or synthetic microorganisms to provide a desired bacteriocin immunity activity in accordance with some embodiments herein. As such, as used herein "immunity modulator" has its customary and ordinary meaning as understood by one of skill in the art in view of this disclosure, and refers not only to structures expressly provided herein, but also to structure that have substantially the same effect as the "immunity modulator" structures described herein, including fully synthetic immunity modulators, and immunity modulators that provide immunity to bacteriocins that are functionally equivalent to the bacteriocins disclosed herein.

Exemplary polynucleotide sequences encoding the polypeptides of Table 2 are indicated in Table 2. The skilled artisan will readily understand that the genetic code is degenerate, and moreover, codon usage can vary based on the particular organism in which the gene product is being expressed, and as such, a particular polypeptide can be encoded by more than one polynucleotide. In some embodiments, a polynucleotide encoding a bacteriocin immunity modulator is selected based on the codon usage of the organism expressing the bacteriocin immunity modulator. In some embodiments, a polynucleotide encoding a bacteriocin immunity modulator is codon optimized based on the particular organism expressing the bacteriocin immunity modulator. A vast range of functional immunity modulators can incorporate features of immunity modulators disclosed herein, thus providing for a vast degree of identity to the immunity modulators in Table 2. In some embodiments, an immunity modulator has at least about 50% identity, for example, at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any one of the polypeptides of Table 2, or a range of identity defined by any two of the preceding values.

TABLE 2

Exemplary bacteriocin immunity modulators

| Polypeptide SEQ ID NO: | Name | Organism of origin | Polynucleotide SEQ ID NO: |
| --- | --- | --- | --- |
| 452 | Microcin H47 immunity modulator MchI | *Escherichia coli* | 453 |

TABLE 2-continued

Exemplary bacteriocin immunity modulators

| Polypeptide SEQ ID NO: | Name | Organism of origin | Polynucleotide SEQ ID NO: |
|---|---|---|---|
| 454 | Colicin-E3 immunity modulator (Colicin-E3 chain B) (ImmE3) (Microcin-E3 immunity modulator) | Escherichia coli | 455 |
| 456 | Colicin-E1 immunity modulator (ImmE1) (Microcin-E1 immunity modulator) | Escherichia coli | 457 |
| 458 | Cloacin immunity modulator | Escherichia coli | 459 |
| 460 | Colicin-E2 immunity modulator (ImmE2) (Microcin-E2 immunity modulator) | Escherichia coli | 461 |
| 462 | Colicin-A immunity modulator (Microcin-A immunity modulator) | Citrobacter freundii | 463 |
| 464 | Colicin-Ia immunity modulator | Escherichia coli | 465 |
| 466 | Colicin-Ib immunity modulator | Escherichia coli | 467 |
| 468 | Colicin-N immunity modulator (Microcin-N immunity modulator) | Escherichia coli | 469 |
| 470 | Colicin-E8 immunity modulator (ImmE8) (Microcin-E8 immunity modulator) | Escherichia coli | 471 |
| 472 | Lactococcin-A immunity modulator | Lactococcus lactis subsp. lactis (Streptococcus lactis) | 473 |
| 474 | Lactococcin-A immunity modulator | Lactococcus lactis subsp. cremoris (Streptococcus cremoris) | 475 |
| 476 | Colicin-D immunity modulator (Microcin-D immunity modulator) | Escherichia coli | 477 |
| 478 | Colicin-E5 immunity modulator (ImmE5) (Microcin-E5 immunity modulator) | Escherichia coli | 479 |
| 480 | Colicin-E6 immunity modulator (ImmE6) (Microcin-E6 immunity modulator) | Escherichia coli | 481 |
| 482 | Colicin-E8 immunity modulator in ColE6 (E8Imm[E6]) | Escherichia coli | 483 |
| 484 | Colicin-E9 immunity modulator (ImmE9) (Microcin-E9 immunity modulator) | Escherichia coli | 485 |
| 486 | Colicin-M immunity modulator (Microcin-M immunity modulator) | Escherichia coli | 487 |
| 488 | Colicin-B immunity modulator (Microcin-B immunity modulator) | Escherichia coli | 489 |
| 490 | Colicin-V immunity modulator (Microcin-V immunity modulator) | Escherichia coli | 491 |
| 492 | Colicin-E1 * immunity modulator (ImmE1) (Microcin-E1* immunity modulator) | Shigella sonnei | 493 |
| 494 | Colicin-E1 immunity modulator (ImmE1) (Microcin-E1 immunity modulator) | Escherichia coli | 495 |
| 496 | Probable leucocin-A immunity modulator | Leuconostoc gelidum | 497 |
| 498 | Lactococcin-B immunity modulator | Lactococcus lactis subsp. cremoris (Streptococcus cremoris) | 499 |
| 500 | Pediocin PA-1 immunity modulator (Pediocin ACH immunity modulator) | Pediococcus acidilactici | 501 |
| 502 | Putative carnobacteriocin-BM1 immunity modulator | Carnobacterium maltaromaticum (Carnobacterium piscicola) | 503 |
| 504 | Putative carnobacteriocin-B2 immunity modulator (Carnocin-CP52 immunity modulator) | Carnobacterium maltaromaticum (Carnobacterium piscicola) | 505 |

TABLE 2-continued

Exemplary bacteriocin immunity modulators

| Polypeptide SEQ ID NO: | Name | Organism of origin | Polynucleotide SEQ ID NO: |
|---|---|---|---|
| 506 | Nisin immunity modulator | *Lactococcus lactis* subsp. *lactis* (*Streptococcus lactis*) | 507 |
| 508 | Trifolitoxin immunity modulator | *Rhizobium leguminosarum* bv. *trifolii* | 509 |
| 510 | Antilisterial bacteriocin subtilosin biosynthesis protein AlbD | *Bacillus subtilis* (strain 168) | 511 |
| 512 | Putative ABC transporter ATP-binding protein AlbC (Antilisterial bacteriocin subtilosin biosynthesis protein AlbC) | *Bacillus subtilis* (strain 168) | 513 |
| 514 | Antilisterial bacteriocin subtilosin biosynthesis protein AlbB | *Bacillus subtilis* (strain 168) | 515 |
| 516 | Colicin-E7 immunity modulator (ImmE7) (Microcin-E7 immunity modulator) | *Escherichia coli* | 517 |
| 518 | Pyocin-S1 immunity modulator | *Pseudomonas aeruginosa* | 519 |
| 520 | Pyocin-S2 immunity modulator | *Pseudomonas aeruginosa* (strain ATCC 15692/ PAO1/1C/PRS 101/LMG 12228) | 521 |
| 522 | Hiracin-JM79 immunity factor | *Enterococcus hirae* | 523 |
| 524 | Probable mesentericin-Y105 immunity modulator | *Leuconostoc mesenteroides* | 525 |
| 526 | Microcin-24 immunity modulator | *Escherichia coli* | 527 |
| 528 | Colicin-K immunity modulator | *Escherichia coli* | 529 |
| 530 | Microcin C7 self-immunity modulator MccF | *Escherichia coli* | 531 |
| 532 | Sakacin-A immunity factor | *Lactobacillus sakei* | 533 |
| 534 | Colicin-E5 immunity modulator in ColE9 (E5Imm[E9]) | *Escherichia coli* | 535 |
| 536 | Antilisterial bacteriocin subtilosin biosynthesis protein AlbD | *Bacillus subtilis* | 537 |
| 538 | Microcin-J25 export ATP-binding/permease protein McjD (Microcin-J25 immunity modulator) (Microcin-J25 secretion ATP-binding protein McjD) | *Escherichia coli* | 539 |
| 540 | Microcin E492 immunity modulator | *Klebsiella pneumoniae* | 541 |

Promoters

Promoters are well known in the art. A promoter can be used to drive the transcription of one or more genes. In some embodiments, a promoter drives expression of polynucleotide encoding a desired gene product as described herein. In some embodiments, a promoter drives expression of a polynucleotide encoding a pro-polypeptide comprising two or more bacteriocins as described herein. In some embodiments, a promoter drives expression of an immunity modulator polynucleotide as described herein. In some embodiments, a promoter drives expression of a polynucleotide encoding a pro-polypeptide comprising two or more bacteriocins in a microbial cell, but the microbial cell does not express immunity modulators for one or more of these bacteriocins (for example, the cell can lack a promoter driving transcription of the immunity modulator, or can lack nucleic acid encoding the immunity modulator). Some promoters can drive transcription at all times ("constitutive promoters"). Some promoters can drive transcription under only select circumstances ("conditional promoters"), for example depending on the presence or absence of an environmental condition, chemical compound, gene product, stage of the cell cycle, or the like.

The skilled artisan will appreciate that depending on the desired expression activity, an appropriate promoter can be selected, and placed in cis with a nucleic acid sequence to be expressed. Exemplary promoters with exemplary activities, and useful in some embodiments herein are provided in Tables 3.1-3.11 herein. The skilled artisan will appreciate that some promoters are compatible with particular transcriptional machinery (e.g. RNA polymerases, general transcription factors, and the like). As such, while compatible "species" are identified for some promoters described herein, it is contemplated that in some embodiments, these promoters can readily function in microorganisms other than the identified species, for example in species with compatible endogenous transcriptional machinery, genetically modified species comprising compatible transcriptional machinery, or fully synthetic microbial organisms comprising compatible transcriptional machinery.

The promoters of Tables 3.1-3.11 herein are publicly available from the Biobricks foundation. It is noted that the Biobricks foundation encourages use of these promoters in accordance with BioBrick™ Public Agreement (BPA).

It should be appreciated that any of the "coding" polynucleotides described herein (for example a bacteriocin polynucleotide, immunity polynucleotide, or nucleotide encoding a pro-polypeptide comprising two or more bacteriocins) is generally amenable to being expressed under the control of a desired promoter. In some embodiments, a single "coding" polynucleotide is under the control of a single promoter. In some embodiments, two or more "coding" polynucleotides are under the control of a single promoter, for example two, three, four, five, six, seven, eight, nine, or ten polynucleotides.

Generally, translation initiation for a particular transcript is regulated by particular sequences at or 5' of the 5' end of the coding sequence of a transcript. For example, a coding sequence can begin with a start codon configured to pair with an initiator tRNA. While naturally-occurring translation systems typically use Met (AUG) as a start codon, it will be readily appreciated that an initiator tRNA can be engineered to bind to any desired triplet or triplets, and accordingly, triplets other than AUG can also function as start codons in certain embodiments. Additionally, sequences near the start codon can facilitate ribosomal assembly, for example a Kozak sequence ((gcc)gccRccAUGG, SEQ ID NO: 542, in which R represents "A" or "G") or Internal Ribosome Entry Site (IRES) in typical eukaryotic translational systems, or a Shine-Delgarno sequence (GGAGGU, SEQ ID NO: 543) in typical prokaryotic translation systems. As such in some embodiments, a transcript comprising a "coding" polynucleotide sequence, for example a bacteriocin polynucleotide or immunity polynucleotide, or nucleotide encoding a pro-polypeptide comprising two or more bacteriocins, comprises an appropriate start codon and translational initiation sequence. In some embodiments, for example if two or more "coding" polynucleotide sequences are positioned in cis on a transcript, each polynucleotide sequence comprises an appropriate start codon and translational initiation sequence(s). In some embodiments, for example if two or more "coding" polynucleotide sequences are positioned in cis on a transcript, the two sequences are under control of a single translation initiation sequence, and either provide a single polypeptide that can function with both encoded polypeptides in cis.

TABLE 3.1

Exemplary Metal-Sensitive Promoters

| SEQ ID NO: | Name | Description |
|---|---|---|
| 544 | BBa_I721001 | Lead Promoter |
| 545 | BBa_I731004 | FecA promoter |
| 546 | BBa_I760005 | Cu-sensitive promoter |
| 547 | BBa_I765000 | Fe promoter |
| 548 | BBa_I765007 | Fe and UV promoters |
| 549 | BBa_J3902 | PrFe (PI + PII rus operon) |

TABLE 3.2

Exemplary Cell Signaling-Responsive Promoters

| SEQ ID NO: | Name | Description |
|---|---|---|
| 550 | BBa_I1051 | Lux cassette right promoter |
| 551 | BBa_I14015 | P(Las) TetO |
| 552 | BBa_I14016 | P(Las) CIO |
| 553 | BBa_I14017 | P(Rh1) |
| 554 | BBa_I739105 | Double Promoter (LuxR/HSL, positive/cI, negative) |
| 555 | BBa_I746104 | P2 promoter in agr operon from S. aureus |
| 556 | BBa_I751501 | plux-cI hybrid promoter |
| 557 | BBa_I751502 | plux-lac hybrid promoter |
| 558 | BBa_I761011 | CinR, CinL and glucose controlled promotor |
| 559 | BBa_J06403 | RhlR promoter repressible by CI |
| 560 | BBa_J102001 | Reverse Lux Promoter |
| 561 | BBa_J64000 | rhlI promoter |
| 562 | BBa_J64010 | lasI promoter |
| 563 | BBa_J64067 | LuxR + 3OC6HSL independent R0065 |
| 564 | BBa_J64712 | LasR/LasI Inducible & RHLR/RHLI repressible Promoter |
| 565 | BBa_K091107 | pLux/cI Hybrid Promoter |
| 566 | BBa_K091117 | pLas promoter |
| 567 | BBa_K091143 | pLas/cI Hybrid Promoter |
| 568 | BBa_K091146 | pLas/Lux Hybrid Promoter |
| 569 | BBa_K091156 | pLux |
| 570 | BBa_K091157 | pLux/Las Hybrid Promoter |
| 571 | BBa_K145150 | Hybrid promoter: HSL-LuxR activated, P22 C2 repressed |
| 572 | BBa_K266000 | PAI + LasR -> LuxI (AI) |
| 573 | BBa_K266005 | PAI + LasR -> LasI & AI + LuxR --| LasI |
| 574 | BBa_K266006 | PAI + LasR -> LasI + GFP & AI + LuxR --| LasI + GFP |
| 575 | BBa_K266007 | Complex QS -> LuxI & LasI circuit |
| 576 | BBa_K658006 | position 3 mutated promoter lux pR-3 (luxR & HSL regulated) |
| 577 | BBa_K658007 | position 5 mutated promoter lux pR-5 (luxR & HSL regulated) |
| 578 | BBa_K658008 | position 3&5 mutated promoter lux pR-3/5 (luxR & HSL regulated) |
| 579 | BBa_R0061 | Promoter (HSL-mediated luxR repressor) |
| 580 | BBa_R0062 | Promoter (luxR & HSL regulated -- lux pR) |
| 581 | BBa_R0063 | Promoter (luxR & HSL regulated -- lux pL) |
| 582 | BBa_R0071 | Promoter (RhlR & C4-HSL regulated) |

TABLE 3.2-continued

Exemplary Cell Signaling-Responsive Promoters

| SEQ ID NO: | Name | Description |
|---|---|---|
| 583 | BBa_R0078 | Promoter (cinR and HSL regulated) |
| 584 | BBa_R0079 | Promoter (LasR & PAI regulated) |
| 585 | BBa_R1062 | Promoter, Standard (luxR and HSL regulated -- lux pR) |

TABLE 3.3

Exemplary Constitutive *E. coli* $\sigma^{70}$ Promoters

| SEQ ID NO: | Name | Description |
|---|---|---|
| 586 | BBa_I14018 | P(Bla) |
| 587 | BBa_I14033 | P(Cat) |
| 588 | BBa_I14034 | P(Kat) |
| 589 | BBa_I732021 | Template for Building Primer Family Member |
| 590 | BBa_I742126 | Reverse lambda cI-regulated promoter |
| 591 | BBa_J01006 | Key Promoter absorbs 3 |
| 592 | BBa_J23100 | constitutive promoter family member |
| 593 | BBa_J23101 | constitutive promoter family member |
| 594 | BBa_J23102 | constitutive promoter family member |
| 595 | BBa_J23103 | constitutive promoter family member |
| 596 | BBa_J23104 | constitutive promoter family member |
| 597 | BBa_J23105 | constitutive promoter family member |
| 598 | BBa_J23106 | constitutive promoter family member |
| 599 | BBa_J23107 | constitutive promoter family member |
| 600 | BBa_J23108 | constitutive promoter family member |
| 601 | BBa_J23109 | constitutive promoter family member |
| 602 | BBa_J23110 | constitutive promoter family member |
| 603 | BBa_J23111 | constitutive promoter family member |
| 604 | BBa_J23112 | constitutive promoter family member |
| 605 | BBa_J23113 | constitutive promoter family member |
| 606 | BBa_J23114 | constitutive promoter family member |
| 607 | BBa_J23115 | constitutive promoter family member |
| 608 | BBa_J23116 | constitutive promoter family member |
| 609 | BBa_J23117 | constitutive promoter family member |
| 610 | BBa_J23118 | constitutive promoter family member |
| 611 | BBa_J23119 | constitutive promoter family member |
| 612 | BBa_J23150 | 1 bp mutant from J23107 |
| 613 | BBa_J23151 | 1 bp mutant from J23114 |
| 614 | BBa_J44002 | pBAD reverse |
| 615 | BBa_J48104 | NikR promoter, a protein of the ribbon helix-helix family of trancription factors that repress expre |
| 616 | BBa_J54200 | lacq_Promoter |
| 617 | BBa_J56015 | lacIQ-promoter sequence |
| 618 | BBa_J64951 | *E. Coli* CreABCD phosphate sensing operon promoter |
| 619 | BBa_K088007 | GlnRS promoter |
| 620 | BBa_K119000 | Constitutive weak promoter of lacZ |
| 621 | BBa_K119001 | Mutated LacZ promoter |
| 622 | BBa_K137029 | constitutive promoter with (TA)10 between −10 and −35 elements |
| 623 | BBa_K137030 | constitutive promoter with (TA)9 between −10 and −35 elements |
| 624 | BBa_K137031 | constitutive promoter with (C)10 between −10 and −35 elements |
| 625 | BBa_K137032 | constitutive promoter with (C)12 between −10 and −35 elements |
| 626 | BBa_K137085 | optimized (TA) repeat constitutive promoter with 13 bp between −10 and −35 elements |
| 627 | BBa_K137086 | optimized (TA) repeat constitutive promoter with 15 bp between −10 and −35 elements |
| 628 | BBa_K137087 | optimized (TA) repeat constitutive promoter with 17 bp between −10 and −35 elements |
| 629 | BBa_K137088 | optimized (TA) repeat constitutive promoter with 19 bp between −10 and −35 elements |
| 630 | BBa_K137089 | optimized (TA) repeat constitutive promoter with 21 bp between −10 and −35 elements |
| 631 | BBa_K137090 | optimized (A) repeat constitutive promoter with 17 bp between −10 and −35 elements |
| 632 | BBa_K137091 | optimized (A) repeat constitutive promoter with 18 bp between −10 and −35 elements |

TABLE 3.3-continued

Exemplary Constitutive E. coli σ⁷⁰ Promoters

| SEQ ID NO: | Name | Description |
|---|---|---|
| 633 | BBa_K256002 | J23101: GFP |
| 634 | BBa_K256018 | J23119: IFP |
| 635 | BBa_K256020 | J23119: HO1 |
| 636 | BBa_K256033 | Infrared signal reporter (J23119: IFP: J23119: HO1) |
| 637 | BBa_K292000 | Double terminator + constitutive promoter |
| 638 | BBa_K292001 | Double terminator + Constitutive promoter + Strong RBS |
| 639 | BBa_K418000 | IPTG inducible Lac promoter cassette |
| 640 | BBa_K418002 | IPTG inducible Lac promoter cassette |
| 641 | BBa_K418003 | IPTG inducible Lac promoter cassette |
| 642 | BBa_M13101 | M13K07 gene I promoter |
| 643 | BBa_M13102 | M13K07 gene II promoter |
| 644 | BBa_M13103 | M13K07 gene III promoter |
| 645 | BBa_M13104 | M13K07 gene IV promoter |
| 646 | BBa_M13105 | M13K07 gene V promoter |
| 647 | BBa_M13106 | M13K07 gene VI promoter |
| 648 | BBa_M13108 | M13K07 gene VIII promoter |
| 649 | BBa_M13110 | M13110 |
| 650 | BBa_M31519 | Modified promoter sequence of g3. |
| 651 | BBa_R1074 | Constitutive Promoter I |
| 652 | BBa_R1075 | Constitutive Promoter II |
| 653 | BBa_S03331 | --Specify Parts List-- |

TABLE 3.4

Exemplary Constitutive E. coli σ$^s$ Promoters

| SEQ ID NO: | Name | Description |
|---|---|---|
| 654 | BBa_J45992 | Full-length stationary phase osmY promoter |
| 655 | BBa_J45993 | Minimal stationary phase osmY promoter |

TABLE 3.5

Exemplary Constitutive E. coli σ³² Promoters

| SEQ ID NO: | Name | Description |
|---|---|---|
| 656 | BBa_J45504 | htpG Heat Shock Promoter |

TABLE 3.6

Exemplary Constitutive B. subtilis σ$^A$ Promoters

| SEQ ID NO: | Name | Description |
|---|---|---|
| 657 | BBa_K143012 | Promoter veg a constitutive promoter for B. subtilis |
| 658 | BBa_K143013 | Promoter 43 a constitutive promoter for B. subtilis |
| 659 | BBa_K780003 | Strong constitutive promoter for Bacillus subtilis |
| 660 | BBa_K823000 | PliaG |
| 661 | BBa_K823002 | PlepA |
| 662 | BBa_K823003 | Pveg |

TABLE 3.7

Exemplary Constitutive B. subtilis σ$^B$ Promoters

| SEQ ID NO: | Name | Description |
|---|---|---|
| 663 | BBa_K143010 | Promoter ctc for B. subtilis |
| 664 | BBa_K143011 | Promoter gsiB for B. subtilis |
| 665 | BBa_K143013 | Promoter 43 a constitutive promoter for B. subtilis |

TABLE 3.8

Exemplary Constitutive Promoters from miscellaneous prokaryotes

| SEQ ID NO: | Name | Description |
|---|---|---|
| 666 | a_K112706 | Pspv2 from Salmonella |
| 667 | BBa_K112707 | Pspv from Salmonella |

TABLE 3.9

Exemplary Constitutive Promoters from bacteriophage T7

| SEQ ID NO: | Name | Description |
|---|---|---|
| 668 | BBa_I712074 | T7 promoter (strong promoter from T7 bacteriophage) |
| 669 | BBa_I719005 | T7 Promoter |
| 670 | BBa_J34814 | T7 Promoter |
| 671 | BBa_J64997 | T7 consensus −10 and rest |
| 672 | BBa_K113010 | overlapping T7 promoter |
| 673 | BBa_K113011 | more overlapping T7 promoter |
| 674 | BBa_K113012 | weaken overlapping T7 promoter |
| 675 | BBa_R0085 | T7 Consensus Promoter Sequence |
| 676 | BBa_R0180 | T7 RNAP promoter |
| 677 | BBa_R0181 | T7 RNAP promoter |
| 678 | BBa_R0182 | T7 RNAP promoter |
| 679 | BBa_R0183 | T7 RNAP promoter |
| 680 | BBa_Z0251 | T7 strong promoter |

TABLE 3.9-continued

Exemplary Constitutive Promoters from bacteriophage T7

| SEQ ID NO: | Name | Description |
|---|---|---|
| 681 | BBa_Z0252 | T7 weak binding and processivity |
| 682 | BBa_Z0253 | T7 weak binding promoter |

TABLE 3.10

Exemplary Constitutive Promoters from yeast

| SEQ ID NO: | Name | Description |
|---|---|---|
| 683 | BBa_I766555 | pCyc (Medium) Promoter |
| 684 | BBa_I766556 | pAdh (Strong) Promoter |
| 685 | BBa_I766557 | pSte5 (Weak) Promoter |
| 686 | BBa_J63005 | yeast ADH1 promoter |
| 687 | BBa_K105027 | cyc100 minimal promoter |
| 688 | BBa_K105028 | cyc70 minimal promoter |
| 689 | BBa_K105029 | cyc43 minimal promoter |
| 690 | BBa_K105030 | cyc28 minimal promoter |
| 691 | BBa_K105031 | cyc16 minimal promoter |
| 692 | BBa_K122000 | pPGK1 |
| 693 | BBa_K124000 | pCYC Yeast Promoter |
| 694 | BBa_K124002 | Yeast GPD (TDH3) Promoter |
| 695 | BBa_K319005 | yeast mid-length ADH1 promoter |
| 696 | BBa_M31201 | Yeast CLB1 promoter region, G2/M cell cycle specific |

TABLE 3.11

Exemplary Constitutive Promoters from miscellaneous eukaryotes

| SEQ ID NO: | Name | Description |
|---|---|---|
| 697 | BBa_I712004 | CMV promoter |
| 698 | BBa_K076017 | Ubc Promoter |

The above-referenced promoters are provided by way of non-limiting example only. The skilled artisan will readily recognize that many variants of the above-referenced promoters, and many other promoters (including promoters isolated from naturally existing organisms, variations thereof, and fully synthetic promoters) can readily be used in accordance with some embodiments herein.

Cleavage Sites

As used herein, "cleavage site" has its customary and ordinary meaning as understood by one of skill in the art in view of this disclosure. It refers to a polypeptide sequence that mediates the cleavage of a polypeptide (for example by hydrolysis of a peptide bond) to separate a single polypeptide into two or more discrete polypeptides. In some embodiments, a cleavage site comprises, consists of, or consists essentially of a consensus polypeptide sequence for cleavage by a "cleavage enzyme," such as a peptidase. In some embodiments, the cleavage enzyme is a wild-type, a variant, or a synthetic cleavage enzyme, for example a wild-type, variant, or synthetic endopeptidase. A number of example cleavage enzymes and their corresponding cleavage sites are described herein. For reference, the cleavage sites are described with reference to formula (I), below:

$$Pn\text{-}P4\text{-}P3\text{-}P2\text{-}P1\text{-}\|Cleavage\|\text{-}P1'\text{-}P2'\text{-}P3'\text{-}P4'\text{-}Pm' \quad (I)$$

in which amino acid residues in a substrate undergoing cleavage are designated P1, P2, P3, P4 etc. in the N-terminal (or "upstream") direction from the cleaved bond. Likewise, the residues in C-terminal (or "downstream") direction of the cleavage site are designated P1', P2', P3', P4'. etc.

Example cleavage enzymes and their cleavage sites useful in accordance with some embodiments herein are described in Table 4, below.

It is noted that a number of cleavage enzymes cleave at consensus sequences, and thus, a particular cleavage enzyme can cut at two or more particular polypeptide sequences that fall within the scope of a consensus sequence (or consensus sequences) for that cleavage enzyme. As such, for convenience herein, unless explicitly stated otherwise, two cleavage sites may be referred to as the "same" when they are both cut by the same cleavage enzyme under the same conditions, even if they are two different sequences (which may fall within the scope of that cleavage enzyme's consensus sequence(s)). For example, the sequences DVADL (SEQ ID NO: 739) and DVADI (SEQ ID NO: 740) may both be referred to as the "same" cleavage site for the purposes of cleavage by Caspase 2 because they both fall within the scope of consensus sequence for Caspase 2, even though these cleavage sites are not identical. On the other hand, also for convenience herein, unless explicitly stated otherwise, two cleavage sites may be referred to as "different" when they are each cut by different cleavage enzymes, but would not be cut by the same cleavage enzyme.

TABLE 4

Example Cleavage Enzymes and Cleavage Sites

| Cleavage Enzyme Name | Cleavage Site (with reference to Formula (1)) | | | | | |
|---|---|---|---|---|---|---|
| | P4 | P3 | P2 | P1 | P1' | P2' |
| Arg-C proteinase | — | — | — | R | — | — |
| Asp-N endopeptidase | — | — | — | — | D | — |
| BNPS-Skatole | — | — | — | W | — | — |
| Caspase 1 | F, W, Y, or L | — | H, A or T | D | not P, E, D, Q, K or R | — |
| Caspase 2 | D | V | A | D | not P, E, D, Q, K or R | — |
| Caspase 3 | D | M | Q | D | not P, E, D, Q, K or R | — |
| Caspase 4 | L | E | V | D | not P, E, D, Q, K or R | — |
| Caspase 5 | L or W | E | H | D | — | — |
| Caspase 6 | V | E | H or I | D | not P, E, D, Q, K or R | — |

TABLE 4-continued

Example Cleavage Enzymes and Cleavage Sites

| Cleavage Enzyme Name | Cleavage Site (with reference to Formula (1)) | | | | | |
|---|---|---|---|---|---|---|
| | P4 | P3 | P2 | P1 | P1' | P2' |
| Caspase 7 | D | E | V | D | not P, E, D, Q, K or R | — |
| Caspase 8 | I or L | E | T | D | not P, E, D, Q, K or R | — |
| Caspase 9 | L | E | H | D | — | — |
| Caspase 10 | I | E | A | D | — | — |
| Chymotrypsin-high specificity (C-term to [FYW], not before P) | — | — | — | F or Y | not P | — |
| | — | — | — | W | not M or P | — |
| | — | — | — | F, L or Y | not P | — |
| | — | — | — | W | not M or P | — |
| Chymotrypsin-low specificity (C-term to [FYWML], not before P | — | — | — | M | Not P or Y | — |
| | — | — | — | H | not D, M, P, or W | — |
| Clostripain (Clostridiopeptidase B) | — | — | — | R | — | — |
| CNBr | — | — | — | M | — | — |
| Enterokinase | D or E | D or E | D or E | K | — | — |
| Factor Xa | A, F, G, I, L, T, V or M | D or E | G | R | — | — |
| Formic acid | — | — | — | D | — | — |
| Glutamyl endopeptidase | — | — | — | E | — | — |
| GranzymeB | I | E | P | D | — | — |
| Hydroxylamine | — | — | — | N | G | — |
| Iodosobenzoic acid | — | — | — | W | — | — |
| LysC | — | — | — | K | — | — |
| Neutrophil elastase | — | — | — | A or V | — | — |
| NTCB (2-nitro-5-thiocyanobenzoic acid) | — | — | — | — | C | — |
| Pepsin (pH 1.3) | — | not H, K, or R | not P | not R | F or L | not P |
| | — | not H, K, or R | not P | F or L | — | not P |
| Pepsin (pH > 2) | — | not H, K, or R | not P | not R | F, L, W, or Y | not P |
| | — | not H, K, or R | not P | F, L, W, or Y | — | not P |
| Proline-endopeptidase | — | — | H, K or R | P | not P | — |
| Proteinase K | — | — | — | A, E, F, I, L, T, V, W or Y | — | — |
| Staphylococcal peptidase I | — | — | not E | E | — | — |
| Thermolysin | — | — | — | not D or E | A, F, I, L, M or V | — |
| Thrombin | A, F, G, I, L, T, V or M | A, F, G, I, L, T, V, W or A | P | R | not D or E | Not DE |
| Trypsin (please note the exceptions in the following rows) | — | — | — | K or R | not P | — |
| | — | — | W | K | P | — |
| | — | — | M | R | P | — |
| Exceptions to the Trypsin Consensus Site Noted in the rows above | — | — | C or D | K | D | — |
| | — | — | C | K | H or Y | — |
| | — | — | C | R | K | — |
| | — | — | R | R | H or R | — |

Additional information about cleavage sites can be found on the world wide web at web.expasy.org/peptide_cutter/peptidecutter_enzymes.html, which is herein incorporated by reference in its entirety.

In some embodiments the cleavage site comprises, consists essentially of, or consists of a cleavage site of Table 4. As such, in some embodiments, the cleavage site comprises, consists essentially of, or consists of a cleavage site for Arg-C proteinase, Asp-N endopeptidase, BNPS-Skatole, Caspase 1, Caspase 2, Caspase 3, Caspase 4, Caspase 5, Caspase 6, Caspase 7, Caspase 8, Caspase 9, Caspase 10, Chymotrypsin-high specificity, Clostripain (Clostridiopeptidase B), CNBr, Enterokinase, Factor Xa, Formic acid, Glutamyl endopeptidase, GranzymeB, Hydroxylamine, Iodosobenzoic acid, LysC, Neutrophil elastase, NTCB (2-nitro-5-thiocyanobenzoic acid), Pepsin (pH1.3), Pepsin (pH>2), Proline-endopeptidase, Proteinase K, Staphylococcal peptidase I, Thermolysin, Thrombin, or Trypsin. As such, in the methods of some embodiments herein, one or more of the listed enzymes is used to cleave the cleavage sites.

In some embodiments the cleavage site comprises, consists essentially of, or consists of a chemical- or pH-sensitive linker. Such linkers can undergo cleavage in the presence of a suitable chemical (in the case of chemical-sensitive linkers), or at a suitable pH (in the case of pH linkers). In some embodiments, the pH-sensitive linker undergoes enzyme-mediated cleavage when the pH is in a suitable range. For example, the pH-sensitive linkers such as the valine-citrulline (vc) dipeptide is cleaved in a pH-sensitive manner by cathepsin B at acidic pH's (e.g., in the 4.8-6 range) (See, e.g., Jain et al. Pharmaceutical Research, 32: 3526-3540, (2015)), which is hereby incorporated by reference in its entirety). In some embodiments, the pH-sensitive linker undergoes a cleavage event when the pH is in a particular range. For example, tunable pH sensitive linkers based on a phosphoraamidate backbone have also been described, which can undergo hydrolysis at a pH of less than 7.4 are described in PCT Pub. No. WO 2016028700, which is hereby incorporated by reference it its entirety). In some embodiments, the chemical-sensitive linker undergoes a cleavage event in the present of a chemical. For example, linkers comprising, consisting essentially or, consisting of disulfide bridges can be released upon the introduction of glutathione (See, e.g., Jain et al. Pharmaceutical Research, 32: 3526-3540, (2015)).

Signal Molecules

In some embodiments, pro-polypeptides comprise one or more signal molecules. As used herein, a "signal molecule" has its customary and ordinary meaning as understood by one of skill in the art in view of this disclosure. It refers to a secreted molecule that is capable of modulating, inducing, or inhibiting an activity or process in the cell that produced it, or in a different cell (a subject cell can be a microbial cell or a non-microbial cell, for example a cell of a multicellular organism such as an animal or plant). Example signal molecules include, but are not limited to, signaling peptides, quorum sensing molecules (for example, quorum sensing peptides), signal transduction receptor ligands, growth factors, hormones, and cytokines. In some embodiments, a signal molecule comprises, consists essentially of, or consists of a signaling peptides, quorum sensing molecules (for example, quorum sensing peptides), signal transduction receptor ligands, growth factors, hormones, or cytokine. In some embodiments, a signal molecule comprises, consists essentially of, or consists of a combination of two or more of signaling peptides, quorum sensing molecules (for example, quorum sensing peptides), signal transduction receptor ligands, growth factors, hormones, and cytokines, which can include combinations of two or more of the same type of molecule (for example a combination of two signaling peptides or a combination of two receptor ligands), as well as combinations of two different kinds of molecules (e.g., a combination of a cytokine and a hormone). In some embodiments, the signal molecule is for microbe-host dialog, and as such, the signal molecule is selected to target one or more cells of a host organism, for example a plant or animal. In some embodiments, the signal molecule stimulates, inhibits, increases, or decreases the production of bacteriocins and/or the growth rate of a subpopulation of a flora. In some embodiments, the signal molecule comprises, consists of, or consists essentially of a quorum sensing peptide, or a variant thereof as described herein.

Example quorum sensing peptides suitable for pro-polypeptides, methods, and/or encoded by nucleic acids of some embodiments include, but are not limited to, quorum sensing peptides such as the peptides shown in Table 5 below, including variants of these peptides, and combinations of two or more of any of these peptides. Without being limited by theory, it is contemplated that microbial cells, such as gram-positive bacteria use quorum sensing peptides to orchestrate cell-to-cell communication. A review of quorum sensing peptides can be found in Rajput et al., PLoS One DOI:10.1371/journal.pone.0120066 Mar. 17, 2015, pp. 1-16, which is hereby incorporated by reference in its entirety. The quorum sensing peptides can induce activation of downstream response regulators and/or transcription factors in a target microbial cell. It is noted that in some embodiments, the downstream response regulators or transcription factors can be configured to activate or repress transcription of a target nucleic acid of interest. Accordingly, in some embodiments, a target microbial cell is genetically engineered to express or repress transcription (and subsequent expression) of a gene product of interest upon stimulation by a signal peptide of a pro-polypeptide.

In some embodiments, the signal molecule of the pro-polypeptide comprises, consists essentially of, or consists of a signal molecule (e.g., a quorum sensing molecule such as a quorum sensing peptide), which stimulates transcription of one or more bacteriocin polynucleotides in the target microbial cell. The target microbial cell can be genetically engineered to place one or more bacteriocin polynucleotides under the control of a transcription factor that responds to the quorum sensing molecule. In some embodiments, transcription of one or more bacteriocin polynucleotides is configured to be induced by a transcription factor (e.g., a transcriptional activator) that responds to the quorum sensing molecule. As such, signaling by the signal molecule (e.g. quorum sensing molecule) of the pro-polypeptide can stimulate the production of one or more additional bacteriocins by the target microbial cell.

In some embodiments, the target microbial cell is genetically modified to place one or more molecules of a poison-antidote system under the control of a transcription factor or response regulator that responds to a signal molecule (e.g., a quorum sensing molecule such as a quorum sensing peptide) so as to induce a suicidal response in target cell upon signaling by the signal molecule. Poison-antidote systems, which are distinct from bacteriocins, can be useful for accomplishing such a suicidal response, which in turn can be useful for containment and/or selective growth of microbial cells. Exemplary poison antidote systems are described in U.S. Pat. Nos. 5,910,438, 6,180,407, 7,176,029, and 7,183,097, each of which is hereby incorporated by reference in its entirety. In some embodiments, a poison-antidote system comprises a cytotoxic (poison) polypeptide, and a corresponding antitoxin (antidote) polypeptide in a single cell. As used herein, a "poison polynucleotide" has its customary and ordinary meaning as understood by one of skill in the art in view of this disclosure, and can refer to a polynucleotide encoding a poison polypeptide. An "antidote polynucleotide" has its customary and ordinary meaning as understood by one of skill in the art in view of this disclosure, and can refer to a polynucleotide encoding an antidote polypeptide. As such, in some embodiments, the target microbial cell is configured to induce transcription of a poison polynucleotide in response to a signal molecule such as a quorum sensing molecule, so as to induce a suicidal response in the target microbial cell. In some embodiments, the target microbial cell is configured to transcriptionally repress an antibody polynucleotide (while continuing to express a corresponding poison polypeptide) in response to a signal molecule such as a quorum sensing molecule, so as to induce a suicidal response in the target microbial cell.

In some embodiments, the quorum sensing peptides are naturally-occurring. In some embodiments, the quorum sensing peptide comprises, consists essentially of, or consists of a variant of a naturally-occurring quorum sensing peptide. In some embodiments, the quorum sensing peptide comprises, consists essentially of, or consists of a synthetic peptide. Information on quorum sensing peptides, including example sequences, can be found on the quorumpeps database, accessible on the world wide web at quorumpeps.ugent.be., which is hereby incorporated by reference in its entirety.

TABLE 5

| Name | Species | SEQ ID NO: (if peptide shown) |
|---|---|---|
| phrANTH3 | *Bacillus anthracis* | — |
| phrANTH1 | *Bacillus anthracis* | — |
| phrANTH2 | *Bacillus anthracis* | — |
| PapR5I | *Bacillus cereus* | — |
| PapR5IV | *Bacillus cereus* | — |
| PapR5II | *Bacillus cereus* | — |
| PapR7III | *Bacillus cereus* | — |
| PapR7IV | *Bacillus cereus* | — |
| PapR7II | *Bacillus cereus* | — |
| PapR5III | *Bacillus cereus* | — |
| PapR7I | *Bacillus cereus, Bacillus thuringiensis* | — |
| Phr0662 | *Bacillus halodurans* | — |
| phr1988 | *Bacillus halodurans* | — |
| ComX RO-B-2 | *Bacillus mojavensis* | — |
| ComX RO-H-1 | *Bacillus mojavensis* | — |
| ComX RO-C-2 | *Bacillus mojavensis* | — |
| Phr-pPL10-1, PhrPUM | *Bacillus pumilus* | — |
| PHRBST1 | *Bacillus stearothermophilus* | — |
| PhrA | *Bacillus subtilis* | — |
| ComX 168 | *Bacillus subtilis* | — |
| Mersacidin | *Bacillus subtilis* | — |
| PhrI | *Bacillus subtilis* | — |
| PhrG | *Bacillus subtilis* | — |
| PhrK | *Bacillus subtilis* | — |
| ComX RO-E-2 | *Bacillus subtilis* | — |
| Subtilin | *Bacillus subtilis* | — |
| ComX RS-B-1 | *Bacillus subtilis* | — |
| Phr-pLS20 | *Bacillus subtilis* | — |
| PhrF | *Bacillus subtilis* | — |
| Phr-pTA1040 | *Bacillus subtilis* | — |
| Phr-pPOD2000, Phr-pTA1060 | *Bacillus subtilis* | — |
| PhrE | *Bacillus subtilis* | — |
| BsEDF | *Bacillus subtilis* | — |
| ComX natto | *Bacillus subtilis* | — |
| Entianin | *Bacillus subtilis* | — |
| Competence and Sporulation Factor, CSF, PhrC | *Bacillus subtilis, Bacillus mojavensis* | — |
| NprRB | *Bacillus thuringiensis* | — |
| PisN | *Carnobacterium maltaromaticum* | — |
| CbaX | *Carnobacterium maltaromaticum* | — |
| Carnobacteriocin B2, CB2, CbnB2 | *Carnobacterium piscicola* | — |
| CbnS, CS | *Carnobacterium piscicola, Carnobacterium maltaromaticum* | — |
| AIP, Autoinducing peptide | *Clostridium acetobutylicum* | — |
| PHRCACET4 | *Clostridium acetobutylicum* | — |
| PHRCACET1 | *Clostridium acetobutylicum* | — |
| AgrD2, AIP, Autoinducing peptide | *Clostridium botulinum* | — |
| AgrD2, AIP, Autoinducing peptide | *Clostridium botulinum* | — |
| AgrD2, AIP, Autoinducing peptide | *Clostridium botulinum* | — |
| AgrD2, AIP, Autoinducing peptide | *Clostridium botulinum* | — |

TABLE 5-continued

| Name | Species | SEQ ID NO: (if peptide shown) |
|---|---|---|
| AgrD1, AIP, Autoinducing peptide | *Clostridium botulinum* | — |
| AgrDCp | *Clostridium perfringens* | — |
| WS9326A | *Clostridium perfringens* | — |
| WS9326B | *Clostridium perfringens* | — |
| Cochinmicin II/III | *Clostridium perfringens* | — |
| AgrD2, AIP, Autoinducing peptide | *Clostridium sporogenes* | — |
| AgrD1, AIP, Autoinducing peptide | *Clostridium sporogenes* | — |
| AgrD | *Clostridium thermocellum* | — |
| QSP1 | *Cryptococcus neoformans* | — |
| QSP24 | *Cryptococcus neoformans* | — |
| QSP2 | *Cryptococcus neoformans* | — |
| — | *Eikenella corodens* | — |
| cAM373 | *Enterococcus faecalis* | — |
| iCF10 | *Enterococcus faecalis* | — |
| iPD1 | *Enterococcus faecalis* | — |
| cPD1 | *Enterococcus faecalis* | — |
| GBAP, Gelatinase Biosynthesis-Activating Pheromone | *Enterococcus faecalis* | — |
| cAD1 | *Enterococcus faecalis* | — |
| iAD1 | *Enterococcus faecalis* | — |
| cCF10 | *Enterococcus faecalis* | — |
| iAM373 | *Enterococcus faecalis* | — |
| cOB1 | *Enterococcus faecalis* | — |
| EntF | *Enterococcus faecium* | — |
| EDF, Extracellular death factor | *Escherichia coli* | — |
| LamD | *Lactobacillus plantarum* | — |
| PltA | *Lactobacillus plantarum* | — |
| Plantaricin A, PlnA | *Lactobacillus plantarum* | — |
| IP-TX | *Lactobacillus sakei* | — |
| IP-673 | *Lactobacillus sakei* | — |
| Orf4 | *Lactobacillus sakei* | — |
| Nisin A | *Lactococcus lactis* | — |
| AIP | *Listeria monocytogenes* | — |
| PaEDF-1 | *Pseudomonas aeruginosa* | — |
| PaEDF-2 | *Pseudomonas aeruginosa* | — |
| PaEDF-3 | *Pseudomonas aeruginosa* | — |
| AIP, Autoinducing peptide | *Staphylococcus arlettae* | — |
| AIP2, Autoinducing peptide 2 | *Staphylococcus aureus* | — |
| AIP3, Autoinducing peptide 3 | *Staphylococcus aureus* | — |
| AIP1, Autoinducing peptide 1 | *Staphylococcus aureus* | — |
| AIP4, Autoinducing peptide 4 | *Staphylococcus aureus* | — |
| AIP, Autoinducing peptide | *Staphylococcus auricularis* | — |
| AIP, Autoinducing peptide | *Staphylococcus auricularis* | — |
| AIP, Autoinducing peptide | *Staphylococcus capitis* | — |
| AIP, Autoinducing peptide | *Staphylococcus capitis* | — |
| AIP, Autoinducing peptide | *Staphylococcus caprae* | — |
| AIP, Autoinducing peptide | *Staphylococcus caprae* | — |
| AIP, Autoinducing peptide | *Staphylococcus caprae* | — |
| AIP, Autoinducing peptide | *Staphylococcus carnosus* | — |
| AIP, Autoinducing peptide | *Staphylococcus cochnii* subsp. *cochnii* | — |
| AIP, Autoinducing peptide | *Staphylococcus cochnii* subsp. *urealyticum* | — |
| AIP2, Autoinducing peptide 2 | *Staphylococcus epidermidis* | — |
| AIP, Autoinducing peptide | *Staphylococcus epidermidis* | — |
| AIP, Autoinducing peptide | *Staphylococcus epidermidis* | — |
| AIP, Autoinducing peptide | *Staphylococcus epidermidis* | — |
| Pep5 | *Staphylococcus epidermidis* | — |
| AIP4, Autoinducing peptide 4 | *Staphylococcus epidermidis* | — |
| AIP1, Autoinducing peptide 1 | *Staphylococcus epidermidis* | — |
| AIP3, Autoinducing peptide 3 | *Staphylococcus epidermidis* | — |
| AIP-II | *Staphylococcus epidermidis* | — |
| AIP-III | *Staphylococcus epidermidis* | — |

TABLE 5-continued

| Name | Species | SEQ ID NO: (if peptide shown) |
|---|---|---|
| AIP, Autoinducing peptide | Staphylococcus gallinarum | — |
| AIP, Autoinducing peptide | Staphylococcus lugdunensis | — |
| AIP, Autoinducing peptide | Staphylococcus lugdunensis | — |
| AIP, Autoinducing peptide | Staphylococcus simulans | — |
| AIP, Autoinducing peptide | Staphylococcus simulans | — |
| AIP, Autoinducing peptide | Staphylococcus simulans | — |
| AIP, Autoinducing peptide | Staphylococcus warneri | — |
| AIP, Autoinducing peptide | Staphylococcus xylosus | — |
| Short Hydrophobic Peptide 3, SHP3 | Streptococcus agalactiae | — |
| Competence Stimulating Peptide, CSP | Streptococcus crista | — |
| SilCR | Streptococcus dysgalactiae | — |
| Competence Stimulating Peptide, CSP | Streptococcus gordonii | — |
| Competence Stimulating Peptide, CSP | Streptococcus gordonii | — |
| Competence Stimulating Peptide, CSP | Streptococcus milleri | — |
| Competence Stimulating Peptide, CSP | Streptococcus mitis | — |
| Competence Stimulating Peptide, CSP | Streptococcus mitis | — |
| Competence Stimulating Peptide, CSP | Streptococcus mitis | — |
| Competence Stimulating Peptide, CSP | Streptococcus mitis | — |
| Competence Stimulating Peptide, CSP | Streptococcus mitis | — |
| Competence Stimulating Peptide, CSP | Streptococcus mitis | — |
| Competence Stimulating Peptide, CSP | Streptococcus mitis, Streptococcus pneumoniae, Streptococcus oralis | — |
| 18-CSP, Competence Stimulating Peptide | Streptococcus mutans | — |
| 21-CSP, Competence Stimulating Peptide | Streptococcus mutans | — |
| Short Hydrophobic Peptide, SHP1509 | Streptococcus mutans | — |
| ComS | Streptococcus mutans | — |
| Competence Stimulating Peptide, CSP | Streptococcus oralis | — |
| Competence Stimulating Peptide, CSP | Streptococcus oralis | — |
| Competence Stimulating Peptide, CSP | Streptococcus pneumoniae | — |
| Competence Stimulating Peptide, CSP | Streptococcus pneumoniae | — |
| Bacteriocin Inducing Peptide, BIP | Streptococcus pneumoniae | — |
| Bacteriocin Inducing Peptide, BIP, BIP-2, BIpC | Streptococcus pneumoniae | — |
| Bacteriocin Inducing Peptide, BIP-1, BIpC | Streptococcus pneumoniae | — |
| Streptin 1 | Streptococcus pyogenes | — |
| XIP | Streptococcus pyogenes | — |
| XIP | Streptococcus pyogenes | — |
| SHP2-C10 | Streptococcus pyogenes | — |
| SHP2-C9 | Streptococcus pyogenes | — |
| SHP2-C7 | Streptococcus pyogenes | — |
| SHP3-C10 | Streptococcus pyogenes | — |
| SHP3-C9 | Streptococcus pyogenes | — |
| SHP3-C7 | Streptococcus pyogenes | — |
| Competence Stimulating Peptide, CSP | Streptococcus pyogenes, Streptococcus pneumoniae | — |
| Competence Stimulating Peptide, CSP | Streptococcus sanguis | — |
| STP | Streptococcus thermophilus | — |
| SHP1358(15-23) | Streptococcus thermophilus | — |
| ComS, SHP0316(18-24) | Streptococcus thermophilus | — |
| Short Hydrophobic Peptide; SHP1299 | Streptococcus thermophilus | — |
| Competence Stimulating Peptide, CSP | Streptococcus thermophilus, Streptococcus constellatus, Streptococcus anginosus | — |
| Siamycin I | Streptomyces species | — |
| TM0504 | Thermotoga maritima | — |
| Synthetic RAP-binding peptide, RBP | Synthetic (FHWWQTSPAHFS) | 741 |
| Synthetic RAP-binding peptide, RBP | Synthetic (WPFAHWPWQYPR) | 742 |
| Synthetic AgrC ligand | Synthetic (GDSVCASYF, thiolacton linkage between C5 and F9) | 743 |
| Synthetic AgrC ligand | Synthetic (SVCASYF, thiolacton linkage between C3 and F7) | 744 |
| Synthetic Cry1Aa ligand | Synthetic (SKADT) | 745 |
| Synthetic Cry1Aa ligand | Synthetic (SKPAD) | 746 |
| Synthetic Fsr ligand | Synthetic (benzyloxycarbonyl-QNSAAAFAAWA, lacton linkage between S3 and A11) | 747 |
| Synthetic Fsr ligand | Synthetic (benzyloxycarbonyl-QNSAAAFGQWA, lacton linkage between S3 and A11) | 748 |
| Synthetic AgrC1, AgrC2 | Synthetic (YSTC(alpha-aminobutyric acid)FIM, thiolacton linkage between C4 and M7) | 749 |
| Synthetic AgrC1, AgrC2 | Synthetic (N-4-(4-benzoylphenoxy)butyryl-STCAFIM, thiolacton linkage between C3 and M7) | 750 |

Cytokines are a class of signal molecules that are typically produced by cells, such as cells of the immune system, and capable of inducing a response in other cells. A number of different cytokines can be used in pro-polypeptides, methods, and/or encoded by nucleic acids of some embodiments herein. It is contemplated that a pro-polypeptide comprising a bacteriocin and a cytokine in accordance with some embodiments can be useful to induce antimicrobial activity (by the bacteriocin(s)), and a host response, for example immune cell suppression or immune cell stimulation (by the cytokine(s)). In some embodiments, the cytokine comprises, consists essentially of, or consists of a naturally-occurring cytokine, variant of a naturally occurring, or synthetic cytokine. A number of suitable cytokines can be used in pro-polypeptides, methods, compositions, cells, or encoded by nucleic acids in accordance with some embodiments herein, including, but not limited to IL-1, IL-2, IL-3, IL-4, IL-5, IL-6, IL-7, IL-8, IL-9, IL-10, IL-11, IL-12, IL-13, IL-15, IL-16, IL-17, IL-18, IL-19, IL-20, IL-21, IL-22, IL-23, IFN-α, IFN-β, IFN-γ, TNF-α, TNF-β, TGF-β1, M-CSF, G-CSF, and GM-CSF, variants of any of these, or any combination of two or more of these.

Hormones are a class of signal molecules that are typically produced by cells of multicellular organisms, and signal to other cells, frequently circulating through different tissues and/or organs of a multicellular organism. A number of different hormones can be used in pro-polypeptides, methods, and/or be encoded by nucleic acids of some embodiments herein. It is contemplated that a pro-polypeptide comprising a bacteriocin and a hormone in accordance with some embodiments can be useful to induce antimicrobial activity (by the bacteriocin(s)), along with a host response, for example cell growth or proliferation (by the hormone(s)). In some embodiments, the cytokine comprises, consists essentially of, or consists of a naturally-occurring hormone, variant of a naturally occurring hormone, or synthetic hormone. Example hormones suitable for pro-polypeptides, methods, and/or encoded by nucleic acids of some embodiments include, but are not limited to, protein and peptide hormones, for example activin and inhibit, adiponectin, adipose-derived hormones, adrenocorticotropic hormone, agouti gene, agouti signaling peptide, allatostatin, amylin, amylin family, angiotensin, ANGPTL8, asprosin, atrial natriuretic peptide, big gastrin, bovine somatotropin, bradykinin, brain-derived neurotrophic factor, calcitonin, ciliary neurotrophic factor, corticotropin-releasing hormone, crustacean neurohormone family, endothelin, enteroglucagon, erythroferrone, fellutamide, FGF15, FGF15/19, FGF19, FNDC5, follicle-stimulating hormone, gastrin, gastroinhibitory peptide, ghrelin, glucagon-like peptide-1, gonadotropin, gonadotropin release inhibitor, gonadotropin-releasing hormone, granulocyte colony-stimulating factor, growth hormone, growth hormone-releasing hormone, hepcidin, human chorionic gonadotropin, human placental lactogen, incretin, insulin, insulin analog, insulin aspart, insulin degludec, insulin glargine, insulin lispro, insulin-like growth factor, insulin-like growth factor 1, insulin-like growth factor 2, leptin, limostatin, liraglutide, little gastrin I, luteinizing hormone, melanocortin, melanocyte-stimulating hormone, alpha-melanocyte-stimulating hormone, beta-melanocyte-stimulating hormone, gamma-melanocyte-stimulating hormone, minigastrin, N-terminal prohormone of brain natriuretic peptide, nerve growth factor, neuropeptide VF precursor, neurotrophin-3, neurotrophin-4, NPH insulin, obestatin, osteocalcin, parathyroid hormone, peptide hormone, peptide YY, plasma renin activity, pramlintide, preprohormone, prolactin, relaxin, relaxin family peptide hormones, renin, salcatonin, sauvagine, secretin, secretin family, sincalide, stanniocalcin, teleost leptins, temporin, thyroid-stimulating hormone, thyrotropin-releasing hormone, urocortin, urocortin II, urocortin III, vasoactive intestinal peptide, vitellogenin, variants of any of these, or any combination of two or more of these.

Affinity Tags

In pro-polypeptides, methods, and nucleic acids encoding pro-polypeptides of some embodiments herein, a pro-polypeptide, or component peptide thereof (e.g. a bacteriocin or signal molecule) comprises an affinity tag. Optionally, one or more cleavage sites can be positioned between the affinity tag and the rest of the pro-polypeptide to facilitate removal of the affinity tag after affinity purification. Affinity tags can be used in purification, for example by contact with a molecule that binds the affinity tag immobilized on a solid phase, such as a bead. Example affinity tags suitable for pro-polypeptides, methods, and encoding by nucleic acids of some embodiments herein can comprise, consist essentially of, or consist of His-tags, glutathione-S-transferase (GST) tags, FLAG tags, strep tags, maltose binding protein (MBP), chitin binding protein (CBP), myc tags, HA tags, NE tags, and V5 tags, variants of any of these, or any combination of two or more of these.

Microbial Organisms

In some embodiments, genetically engineered microorganisms are provided. As used herein, genetically engineered "microbial organism," "microorganism," and variations of these root terms (such as pluralizations and the like), have their customary and ordinary meanings as understood by one of skill in the art in view of this disclosure. They encompass genetic modification of any naturally-occurring species or fully synthetic prokaryotic or eukaryotic unicellular organism, as well as Archae species. Thus, this expression can refer to cells of bacterial species, fungal species, and algae.

Exemplary microorganisms that can be used in accordance with embodiments herein include, but are not limited to, bacteria, yeast, and algae, for example photosynthetic microalgae. Furthermore, fully synthetic microorganism genomes can be synthesized and transplanted into single microbial cells, to produce synthetic microorganisms capable of continuous self-replication (see Gibson et al. (2010), "Creation of a Bacterial Cell Controlled by a Chemically Synthesized Genome," Science 329: 52-56, hereby incorporated by reference in its entirety). As such, in some embodiments, the microorganism is fully synthetic. A desired combination of genetic elements, including elements that regulate gene expression, and elements encoding gene products (for example bacteriocins, immunity modulators, poison, antidote, and industrially useful molecules) can be assembled on a desired chassis into a partially or fully synthetic microorganism. Description of genetically engineered microbial organisms for industrial applications can also be found in Wright, et al. (2013) "Building-in biosafety for synthetic biology" *Microbiology* 159: 1221-1235.

A variety of bacterial species and strains can be used in accordance with embodiments herein, and genetically modified variants, or synthetic bacteria based on a "chassis" of a known species can be provided. Exemplary bacteria with industrially applicable characteristics, which can be used in accordance with embodiments herein include, but are not limited to, *Bacillus* species (for example *Bacillus coagulans, Bacillus subtilis*, and *Bacillus licheniformis*), *Paenibacillus* species, *Streptomyces* species, *Micrococcus* species, *Corynebacterium* species, *Acetobacter* species, *Cyanobacteria* species, *Salmonella* species, *Rhodococcus* species, *Pseudomonas* species, *Lactobacillus* species, *Enterococcus* species, *Alcaligenes* species, *Klebsiella* species, *Paenibacillus* species, *Arthrobacter* species, *Corynebacterium* species, *Brevibacterium* species, *Thermus aquaticus, Pseudomonas stutzeri, Clostridium thermocellus*, and *Escherichia coli*.

A variety of yeast species and strains can be used in accordance with embodiments herein, and genetically modified variants, or synthetic yeast based on a "chassis" of a known species can be provided. Exemplary yeast with industrially applicable characteristics, which can be used in accordance with embodiments herein include, but are not limited to *Saccharomyces* species (for example, *Saccharomyces cerevisiae, Saccharomyces bayanus, Saccharomyces boulardii*), *Candida* species (for example, *Candida utilis, Candida krusei*), *Schizosaccharomyces* species (for example *Schizosaccharomyces pombe, Schizosaccharomyces japonicas*), *Pichia* or *Hansenula* species (for example, *Pichia pastoris* or *Hansenula polymorpha*) species, and *Brettanomyces* species (for example, *Brettanomyces claussenii*).

A variety of algae species and strains can be used in accordance with embodiments herein, and genetically modified variants, or synthetic algae based on a "chassis" of a known species can be created. In some embodiments, the algae comprises photosynthetic microalgae. Exemplary algae species that can be useful for biofuels, and can be used in accordance with embodiments herein, include *Botryococcus braunii, Chlorella species, Dunaliella tertiolecta, Gracilaria species, Pleurochrysis carterae*, and *Sargassum* species. Additionally, many algaes can be useful for food products, fertilizer products, waste neutralization, environmental remediation, and carbohydrate manufacturing (for example, biofuels).

Design of Pro-Polypeptides and Nucleic Acids Encoding Pro-Polypeptides

Pro-polypeptides comprising selected bacteriocins in desired ratios in accordance with some embodiments herein can be designed using a variety of approaches. For example, one option is to design a nucleic acid coding sequence comprising the bacteriocins, cleavage sites, and other features of the pro-polypeptide such as affinity tags and/or signal molecules in a single open reading frame. A polynucleotide having this sequence can then be sequenced. Additionally, computational tools are available to facilitate the design of pro-polypeptides (and nucleic acids encoding them) in accordance with some embodiments. For example, as described in Nielsen et al., "Genetic circuit design automation" Science (2016) 352: aac7341 (hereby incorporated by reference in its entirety), a computer-based design environment, Cello, permits a user to writes Verilog code that is automatically transformed into a DNA sequence. Accordingly, in some embodiments, text-based approach can readily be used to produce a nucleic acid encoding the desired elements of a pro-polypeptide, such as a particular combination and/or ratio of bacteriocins and cleavage sites separating the bacteriocins, and in a manner where bacteriocins are not cleaved by a cleavage enzyme that cleaves the cleavage sites. In some embodiments, the pro-polypeptide comprises selected bacteriocins and antimicrobial peptides in desired ratios. In some embodiments, the pro-polypeptide comprises selected antimicrobial peptides in desired ratios. In some embodiments, the pro-polypeptide comprises selected bacteriocins in desired ratios.

Genetic Modification of Microbial Organisms for Expression of Nucleic Acids

Techniques of genetically modifying microorganisms are well known in the art. In methods and compositions of some embodiments, a microorganism is genetically modified to comprise nucleic acid sequence regulating the expression of, and encoding, bacteriocins, for example pro-polypeptides comprising bacteriocins as described herein. In methods and compositions of some embodiments herein, polynucleotides encoding pro-polypeptides can be delivered to microorganisms, and can be stably integrated into the chromosomes of these microorganisms, or can exist free of the genome, for example in a plasmid, extrachromosomal array, episome, minichromosome, or the like.

Exemplary vectors for genetic modification of microbial cells include, but are not limited to, plasmids, viruses (including bacteriophage), and transposable elements. Additionally, it will be appreciated that entire microbial genomes comprising desired sequences can be synthesized and assembled in a cell (see, e.g. Gibson et al. (2010), Science 329: 52-56). As such, in some embodiments, a microbial genome (or portion thereof) is synthesized with desired features such as bacteriocin polynucleotide(s), and introduced into a microbial cell.

In some embodiments, a cassette for inserting one or more desired bacteriocin and/or immunity modulator polynucleotides into a polynucleotide sequence (for example inserting, into an expression vector, a cassette encoding a pro-polypeptide comprising bacteriocins) is provided. Exemplary cassettes include, but are not limited to, a Cre/lox cassette or FLP/FRT cassette. In some embodiments, the cassette is positioned on a plasmid, so that a plasmid with the desired polynucleotide encoding the desired pro-polypeptide can be readily introduced to the microbial cell. In some embodiments, the cassette is positioned in a desired position in the genome of the microbial cell.

In some embodiments, plasmid conjugation can be used to introduce a desired plasmid from a "donor" microbial cell to a recipient microbial cell. Goñi-Moreno, et al. (2013) Multicellular Computing Using Conjugation for Wiring. PLoS ONE 8(6): e65986, hereby incorporated by reference in its entirety. In some embodiments, plasmid conjugation can genetically modify a recipient microbial cell by introducing a conjugation plasmid from a donor microbial cell to a recipient microbial cell. Without being limited by any particular theory, conjugation plasmids that comprise the same or functionally same set of replication genes typically cannot coexist in the same microbial cell. As such, in some embodiments, plasmid conjugation "reprograms" a recipient microbial cell by introducing a new conjugation plasmid to supplant another conjugation plasmid that was present in the recipient cell. In some embodiments, plasmid conjugation is used to engineer (or reengineer) a microbial cell with a particular nucleic acid encoding a pro-polypeptide, or combination of different nucleic acids encoding different pro-polypeptide. According to some embodiments, a variety of conjugation plasmids comprising different nucleic acids comprising a variety of different pro-polypeptides is provided. The plasmids can comprise additional genetic elements as described herein, for example promoters, translational initiation sites, and the like. In some embodiments the variety of conjugation plasmids is provided in a collection of donor cells, so that a donor cell comprising the desired plasmid can be selected for plasmid conjugation. In some embodiments, a particular combination and/or ratio of bacteriocins is selected, and an appropriate donor cell (encoding the particular pro-polypeptide) is conjugated with a microbial cell of interest to introduce a conjugation plasmid comprising that combination into a recipient cell.

Pro-Polypeptides

Figure 2:
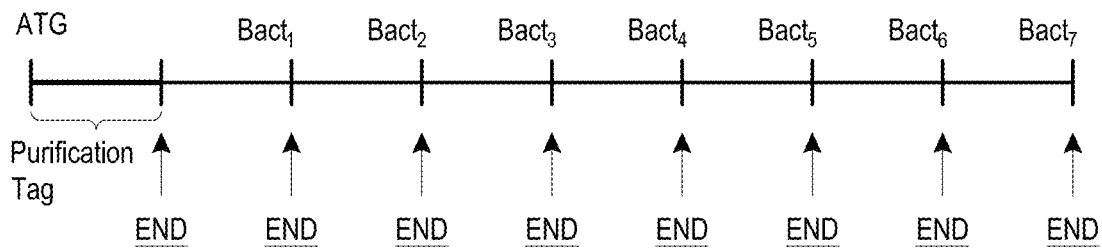
FIG. 2 is a schematic diagram of an embodiment of a nucleic acid encoding a pro-polypeptide comprising bacteriocins and cleavage sites in accordance with some embodiments herein. As shown, a single bacteria may produce a pro-polypeptide encoded by a synthetic gene. It is contemplated that the molecular ratio of one bacteriocin can be changed by putting multiple copies of it in the pro-polypeptide.
Figure 2:
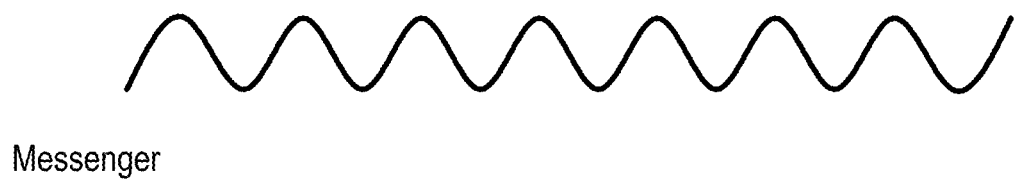
Figure 2:
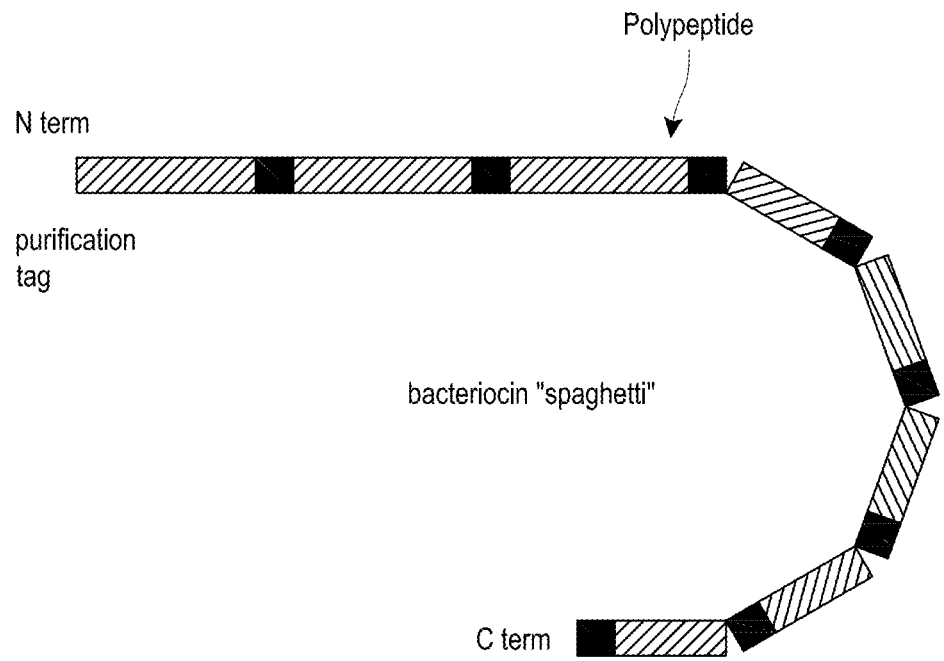

As used herein, "pro-polypeptide" has its customary and ordinary meaning as understood by one of skill in the art in view of this disclosure. It refers to a precursor polypeptide comprising, consisting essentially of, or consisting of at least two component peptides in a desired ratio (e.g., at least one bacteriocin and at least one signal molecule, or two or more bacteriocins, and optionally one or more other peptides disclosed herein (for example, a signaling peptide, a quorum sensing molecule such as a quorum sensing peptide, a signal transduction receptor ligand, a growth factor, a hormones, a cytokine, or a combination of two or more of any of the listed items), and at least one cleavage site separating the component peptides of the pro-polypeptide. An example pro-polypeptide in accordance with some embodiments is schematically illustrated in FIG. 2. The component peptides can be separated from each other by cleavage sites so that, upon cleavage, the component peptides are separated from each other and present in ratios that are determined by the number of copies of each component peptide in the pro-polypeptide (See FIG. 3). In some embodiments, one or more component peptides of the pro-polypeptide are in an inactive form, and become active upon cleavage from surrounding polypeptide sequences. Without being limited by theory, it is contemplated that in some embodiments, at least some, or in some embodiments all, of the bacteriocins are inactive when they are part of the pro-polypeptide so that, advantageously, the pro-polypeptide can be produced and/or modified by microbial cells that do not require immunity to those bacteriocins that are inactive. It is expressly contemplated that the pro-polypeptides described herein can be used in conjunction with any of the methods and kits as described herein. Furthermore, it will be appreciated that for any pro-polypeptide described herein, the polynucleotide or polynucleotides (to the extent that there are multiple possible codons) will be readily appreciated based on the skilled artisan's understanding of the genetic code.

Figure 4A:
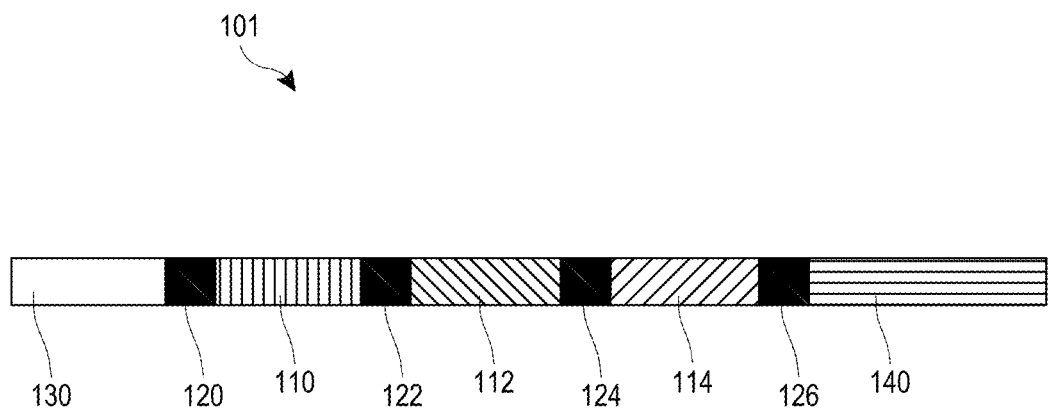
FIG. 4A is a schematic diagram of an embodiment of a pro-polypeptide comprising bacteriocins, cleavage sites, and a signal molecule in accordance with some embodiments herein.

FIG. 4A is a schematic diagram illustrating a pro-polypeptide 100 in accordance with some embodiments herein. The pro-polypeptide can comprise bacteriocins 110, 112, 114. The bacteriocins can be the same or different (e.g. all of the bacteriocins can be the same, or some bacteriocins can be the same while others are different, or all of the bacteriocins can be different from each other). The pro-polypeptide can further include one or more cleavage sites 120, 122, 124, and 126 disposed between the bacteriocins, and/or other polypeptides o the pro-polypeptide. In some embodiments, the pro-polypeptide further comprise a tag 130. In some embodiments, the pro-polypeptide further comprises a signal molecule 140 such as described herein, for example a quorum sensing molecule such as a quorum sensing peptide. In some embodiments, cleavage sites 120, 122, 124, and 126 are disposed between the bacteriocins, tag, and signal molecule. In some embodiments, the tag is useful for purifying the pro-polypeptide. In some embodiments, a cleavage site (e.g., 120, 122, 124, and 126) includes two or more consensus sites for an enzyme such as an endopeptidase. It is contemplated that in some embodiments, a cleavage site contains two or more cleavage consensus sequences (which can be the same or different), at least one of which is immediately downstream of the C-terminal of an upstream peptide and/or at least one of is immediately upstream of the N-terminal of a downstream polypeptide, so that the any vestiges can of the cleavage site can essentially eliminated or entirely eliminated of that peptide. In some embodiments, a "cleavage site" includes two or more consensus sequences, at least one of which is configured to be immediately upstream or downstream of a peptide (e.g., a bacteriocin) so as to remove any vestiges of that cleavage site from the peptide upon cleavage. In some embodiments, a "cleavage site" includes two consensus sequences, one of which is configured to be immediately downstream of an upstream peptide (e.g., a bacteriocin), and the other of which is immediately upstream of a downstream peptide (e.g. a bacteriocin) so as to remove any vestiges of that cleavage site from the C-terminal portion of the upstream peptide and from the N-terminal portion of the downstream peptide upon cleavage of both cleavage sites. Optionally, additional cleavage sites are positioned between these two cleavage sites.

Figure 4B:
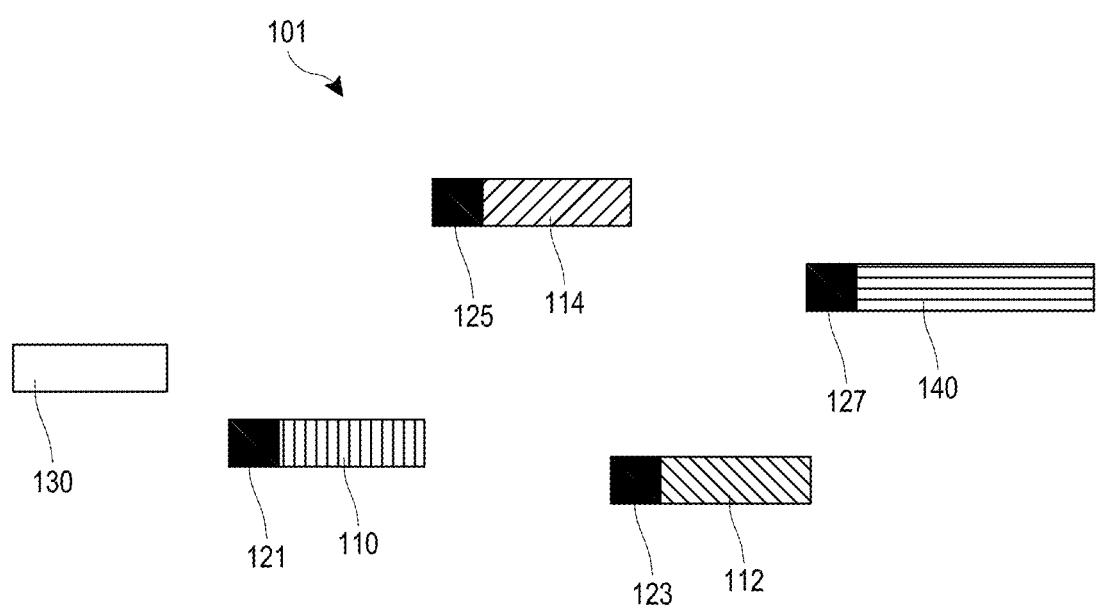
FIG. 4B is a schematic diagram of an embodiment of a composition comprising bacteriocins and a signal molecule following cleavage of a pro-polypeptide in accordance with some embodiments herein.

FIG. 4B is a schematic diagram illustrating a composition comprising bacteriocins 101 made from pro-polypeptide 100 in accordance with some embodiments herein. The composition can comprise bacteriocins 110, 112, 114. The bacteriocins can be the same or different (e.g. all of the bacteriocins can be the same, or some bacteriocins can be the same while others are different, or all of the bacteriocins can be different from each other). Optionally, some of the bacteriocins 110, 112, 114, can further comprise vestiges of cleavage sites, 121, 123, 125, 127. In some embodiments, the composition further comprises a tag 130, and/or a signal molecule 140 as described herein. Some of the bacteriocins 110, 112, 114, and/or the tag 130, and/or the signal molecule 140 can further comprise vestiges of cleavage sites, 121, 123, 125, 127. In some embodiments, following cleavage, a bacteriocin comprises no more than 0, 1, 2, 3, 4, 5, 6, 7, 8, 9, or 10, amino acids as a vestige of a cleavage site, including ranges between any two of the listed values. In some embodiments, bacteriocin does not comprise any vestiges od cleavage sites. In some embodiments, a bacteriocin comprises a vestige of a cleavage site on its N-terminal, on its C-terminal, or on its N- and C-termini. It is contemplated that in some embodiments, a signal molecule and/or tag also comprises vestiges as described herein. In some embodiments, a signal molecule and/or tag does not comprise any vestiges as described herein.

In some embodiments, a pro-polypeptide comprises, consists essentially of, or consists of at least one bacteriocin, at least one signal molecule, and one or more cleavage sites disposed between the bacteriocins and signal molecules, so that each bacteriocin or signal molecule can be separated from the rest of the pro-polypeptide by cleavage of the cleavage sites. In some embodiments, the bacteriocin(s) and signal molecule(s) are in a desired ratio.

In some embodiments, a pro-polypeptide comprises first component peptide comprising, consisting essentially of, or consisting of a bacteriocin, at least one additional component peptide (bacteriocin or signal molecule), and cleavage sites disposed between the component peptides. The pro-polypeptide can further comprise an affinity tag. In some embodiments, the affinity tag is separated from the bacteriocins (and/or other component peptides) of the pro-polypeptide by a cleavage site, so that after affinity purification of the pro-polypeptide, the affinity tag can be cleaved so as to remove it from the pro-polypeptides. In some embodiments, the pro-polypeptide comprises, consists essentially of, or consists of at least two bacteriocins, and optionally at least one signal molecule. In some embodiments, the isolated pro-polypeptide comprises three or more bacteriocins, for example, at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 bacteriocins, including ranges between any two of the listed values, for example, 3-10, 3-20, 3-30, 3-50, 5-10, 5-20, 5-30, 5-50, 7-10, 7-20, 7-30, 7-50, 10-20, 10-30, or 10-50 bacteriocins. In some embodiments, the pro-polypeptide comprises at least five bacteriocins.

It is further contemplated that the pro-polypeptide can include a signal molecule, which can facilitate communication to microbial cells, or to a host organism. Accordingly, in pro-polypeptides, methods, and nucleic acids of some embodiments, the pro-polypeptide further comprises a signal molecule. The signal molecule can be separated from other component peptides of the pro-polypeptide by a cleavage site. In some embodiments, the signal molecule comprises, consists essentially of, or consists of a quorum sensing molecule (e.g., a quorum sensing peptide), a cytokine, or a hormone as described herein. In some embodiments, a target cell is configured to produce additional gene products, for example bacteriocins, in response to the quorum sensing molecule. The target cell can be genetically engineered so that one or more bacteriocin polynucleotides are under the control of a transcription factor that responds to the quorum sensing molecule, so that, upon signaling by the quorum sensing molecule, the bacteriocin polynucleotides are transcribed, and the target cell produces additional bacteriocins.

In some embodiments, one or more cleavage sites are disposed in frame between any two adjacent component peptides (e.g., bacteriocins, signal molecules) of the pro-polypeptide. In some embodiments, one or more cleavage sites are disposed in frame between any two adjacent bacteriocins of the pro-polypeptide. It is noted that in pro-polypeptides, methods, and nucleic acids of some embodiments, component peptides (e.g., bacteriocins and/or signal molecules) or affinity tags positioned at or near the N- or C-terminus of a pro-polypeptide may be positioned near a cleavage site to separate them from the rest of the pro-polypeptide, but they are not flanked by cleavage sites on both sides. For example, for a bacteriocin on the N-terminus of a bacteriocin, there may be a cleavage site in the C-terminal direction from the bacteriocin, but no cleavage site on the N-terminal side of the bacteriocin. In some embodiments, for example, if a component peptide or affinity tag is near the N- or C-terminus of the pro-polypeptide, but there is additional N- or C-terminal sequence beyond the component peptide or affinity tag, the component peptide may comprise cleavage sites on both sides so as to facilitate removal of the additional N- or C-terminal sequence. In some embodiments, some additional N- or C-terminal sequences can remain on the component polypeptide.

It is noted that in some embodiments, the cleavage sites can comprise sequences targeted by a cleavage enzyme. In order to minimize or avoid cleavage of the bacteriocins or other component peptides (e.g., signal molecules) of the pro-polypeptide, it is contemplated that in some embodiments, the component peptides themselves do not contain cleavage sites for the cleavage enzyme(s) that target cleavage sites between the component peptides. As such, in some embodiments, the bacteriocins do not comprise cleavage sites for the cleavage enzyme or enzymes that target the cleavage sites between the bacteriocins. In some embodiments, two or more cleavage enzymes are used to target all of the cleavage sites between the component peptides of the pro-polypeptide, but the bacteriocins do not contain cleavage sites targeted by any of these cleavage enzymes. In some embodiments, at least one cleavage site is for a first cleavage enzyme, and another cleavage site is for a second cleavage enzyme different from the first cleavage enzyme, and the bacteriocins do not comprise a cleavage site for any of the first or second cleavage enzymes In some embodiments, the signal molecule(s) do not comprise the cleavage sites for the cleavage enzyme or enzymes that target the cleavage sites between the bacteriocins and signal molecules. It is noted that as in some embodiments, cleavage is performed after affinity purifying the pro-polypeptide. Consequently, it can be acceptable for an affinity tag itself to comprise one or more cleavage sites, as the affinity tag may be dispensable by the time cleavage is performed.

In some embodiments, the cleavage sites separating the component peptides of the pro-polypeptide are all targeted by the same cleavage enzyme so that a single enzyme can be used to cleave the pro-polypeptide into separate bacteriocins (and optionally, other peptides) in the desired ratios. In some embodiments, the cleavage sites separating the component peptides of the pro-polypeptide are collectively targeted by a combination of cleavage enzyme so that the number of cleavage enzymes that is smaller than the number of cleavage sites in the pro-polypeptide. In some embodiments, the cleavage sites separating the component peptides of the pro-polypeptide are collectively targeted by one, two, three, four, five, six, seven, eight, nine, or ten cleavage enzymes. In some embodiments, the cleavage sites comprise a chemical or pH-sensitive linker. As such, in some of these embodiments, the cleavage sites separating the component peptides of the pro-polypeptide are collectively cleaved by the same chemical and/or same pH conditions.

In some embodiments, the bacteriocins themselves comprise tags, for example affinity tags, signal sequences (for secretion, internalization, nuclear localization, etc.), or stability tags. Optionally, the tags can be cleavable from the pro-polypeptides. As such, the bacteriocin can comprise a cleavage site between itself and the tag. It can be useful for the tag to remain affixed to the bacteriocin after the component peptides are cleaved from the pro-polypeptide. As such, in some embodiments, the cleavage site between the bacteriocin and the tag can be targeted by different cleavage enzymes (and/or cleaved under different chemical or pH conditions) than the cleavage sites separating the component peptides from each other.

In some embodiments, the pro-polypeptide further comprises a post-translational or co-translation modification, for example, glycosylation, acetylation, methylation, PEGYlation, SUMOylation, ubiquitination, or two or more of any of these.

In some embodiments, the pro-polypeptide comprises a quantity of two or more different component peptides (e.g., bacteriocins and/or signal molecules) in a desired ratio, or portion of a desired ratio. For example, the ratio of a first bacteriocin to a second (different) bacteriocin, or to a signal molecule can be about 1:2, 1:3, 1:4, 1:5, 1:6, 1:7, 1:8, 1:9, 1:10, 2:3, 2:5, 2:7, 2:9, 3:4, 3:5, 3:7, 3:8, 3:10, 4:5, 4:7, 4:9, 5:6, 5:7, 5:8, 5:9, 6:7, 7:8, 7:9, 7:10, 8:9, or 9:10. In some embodiments, the pro-polypeptide comprises a quantity of two or more different bacteriocins in a desired ratio, or portion of a desired ratio. In some embodiments, the desired ratio of bacteriocins is selected to target an undesired microbial organism or population of undesired microbial organisms. In some embodiments, the desired ratio of bacteriocins is selected to balance a population of a microbiome of an animal, a human organ, a plant root, and/or soil. In some embodiments, the bacteriocins and/or signal molecules are present in a portion of a desired ratio, and the desired ratio can be achieved by adding an additional bacteriocin and/or signal molecule in a suitable ratio (for example, if the products of two different pro-polypeptides are combined, together, they can yield the desired ratio of component polypeptides such as bacteriocins and/or signal molecules).

In some embodiments, the pro-polypeptide has a length of no more than 20,000 amino acids, for example, no more than 20,000, 15,000, 10,000, 9000, 8000, 7000, 6000, 5000, 4000, 3000, 2000, 1000, 900, 800, 700, 600, 500, 400, 300, 200, or 100 amino acids, including between any two of the listed values, for example 100-20,000; 100-10,000; 100-5000; 100-2000; 100-1000; 500-20,000; 500-10,000; 500-5000; 500-2000; 500-1000; 1000-20,000; 1000-10,000; 1000-5000; or 1000-2000 amino acids. In some embodiments, the pro-polypeptide has a length of no more than 5000 amino acids. In some embodiments, the pro-polypeptide has a length of no more than 2000 amino acids.

Nucleic Acids

Methods, kits, microbial cells, and/or nucleic acids of some embodiments herein include a nucleic acid encoding a pro-polypeptide. In some embodiments, the nucleic acid encodes a bacteriocin and a signal molecule in a single reading frame, and encodes a cleavage site coding sequences disposed between the bacteriocin and signal molecule coding sequences. In some embodiments, an isolated nucleic acid comprises two bacteriocin coding sequences in a single reading frame. The isolated nucleic acid can further comprise cleavage site coding sequences disposed between the bacteriocin coding sequences and in the single reading frame. In methods, nucleic acids, microbial cells, and/or kits of some embodiments herein, a nucleic acid encodes any pro-polypeptide described herein. In some embodiments, a kit comprises a nucleic acid composing one or more pro-polypeptides as described herein. In some embodiments, the kit further comprises a microbial cell capable of expression the pro-polypeptide.

As noted herein, for nucleic acids of some embodiments, it can be advantageous for the bacteriocins (or other polypeptides) encoded by the nucleic acids to remain intact after cleavage. As such, in some embodiments, the nucleic acid encodes cleavage sites for a cleavage enzyme, and its bacteriocin and/or signal molecule coding sequences encode bacteriocins and/or signal molecules (respectively) that do not comprise cleavage sites for the cleavage enzyme. In some embodiments, the cleavage site coding sequences of the nucleic acid encode cleavage sites for a cleavage enzyme, and the bacteriocin coding sequences encode bacteriocins that do not comprise cleavage sites for the cleavage enzyme.

In some embodiments, the nucleic acid comprises three or more bacteriocin coding sequences in the single reading frame, for example 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 bacteriocin coding sequences, including ranges between any two of the listed values, for example, 3-10, 3-20, 3-30, 3-50, 5-10, 5-20, 5-30, 5-50, 7-10, 7-20, 7-30, 7-50, 10-20, 10-30, or 10-50 bacteriocin coding sequences. In some embodiments, the nucleic acid comprises at least three bacteriocin sequences in the single reading frame. In some embodiments, the nucleic acid comprises at least five bacteriocin sequences in the single reading frame. In some embodiments, at least two of the bacteriocin coding sequences encode different bacteriocins from each other.

In some embodiments, one or more cleavage site coding sequences are disposed in frame between any two adjacent bacteriocin coding sequences of the isolated nucleic acid. As noted herein, it can be advantageous for a single cleavage enzyme to be able to separate multiple, or all, of the component peptides of a pro-polypeptide. Accordingly, in some embodiments, each of the bacteriocin coding sequences (and, if present, signal molecule coding sequence(s)) are separated from each other by in-frame cleavage site coding sequences for the same enzyme. As such, upon translation of the nucleic acid, the resultant pro-polypeptide can be cleaved into its component peptides by a single enzyme.

In some embodiments, a cleavage site coding sequence encodes a cleavage site for a first cleavage enzyme, and another cleavage site coding sequence encodes another cleavage site for a different cleavage enzyme. In some embodiment, the bacteriocins encoded by the bacteriocin coding sequences do not comprise a cleavage site for any of the first or second cleavage enzymes. In some embodiment, no bacteriocins encoded by the isolated nucleic acids comprises a cleavage site for any of the cleavage enzymes that cleave the interspersed cleavage sites.

In some embodiments, all of the bacteriocin coding sequences (and, if present, signal molecule coding sequence(s)) are separated from each other by in-frame cleavage site coding sequences, which are collective cleaved by a combination of two, three, four, five, six, seven, eight, nine, or ten cleavage enzymes. As such, upon translation of the nucleic acid, that combination of cleavage enzymes can be used to cleave the pro-polypeptide into its component peptides.

In some embodiments, the cleavage site coding sequence encodes a cleavage site for a cleavage enzyme as described herein, for example in Table 4. In some embodiments the cleavage site coding sequence encodes a cleavage site that is chemically and/or pH-sensitive as described herein.

In some embodiments, the component peptide (e.g., bacteriocin and/or signal molecule) coding sequences of the isolated nucleic acid are present in a desired ratio, or portion of a desired ratio. In some embodiments, three of more bacteriocin sequences are present in a desired ratio or portion of a desired ratio. In some embodiments, the desired ratio is selected to target an undesired microbial organism or population of undesired microbial organisms. In some embodiments, the desired ratio of bacteriocins is selected to balance a population of a microbiome of an animal, a human organ, or a plant root and/or soil.

In some embodiments, the isolated nucleic acid further comprises a coding sequence for a signal molecule in the single reading frame. A cleavage site coding sequences can be disposed between the coding sequence for signal molecule and an adjacent bacteriocin coding sequence or sequences. In some embodiments, the signal molecule comprises a quorum sensing molecule, a signal transduction receptor ligand, a growth factor, a hormone, or a cytokine. In some embodiments, the signal molecule can be wild-type, mutant, or synthetic.

Microbial Cells for Making Bacteriocins

Methods, kits, and microbial cells of some embodiments comprise a microbial cell comprising an isolated nucleic acid as described herein. Such microbial cells can be useful for producing pro-polypeptides comprising bacteriocins in desired ratios as described herein. The microbial cell can comprise a promoter as described herein. The promoter can be operably linked to the isolated nucleic acid. Thus, the microbial cell can be configured to transcribe the isolated nucleic acid and translate it into a pro-polypeptide comprising bacteriocins. As noted herein, the bacteriocins of the pro-polypeptide can be inactive while they are part of the pro-polypeptide. Accordingly in some embodiments, the isolated microbial cell does not produce a functional immunity modulator for a bacteriocin encoded by the isolated nucleic acid. For example, the microbial cell can lack a coding sequence for the immunity modulator, or if it does comprise coding sequence for the immunity modulator, the coding sequence can be transcriptionally silent (e.g. due to lack of a promoter), and/or the coding sequence can be mutated so that any immunity modulator produced by the coding sequence is nonfunctional. In some embodiments, the promoter operationally linked to the nucleic acid comprises, consists essentially of, or consists of any of the promoters of Tables 3.1-3.11.

Methods of Making Bacteriocins

Figure 8:
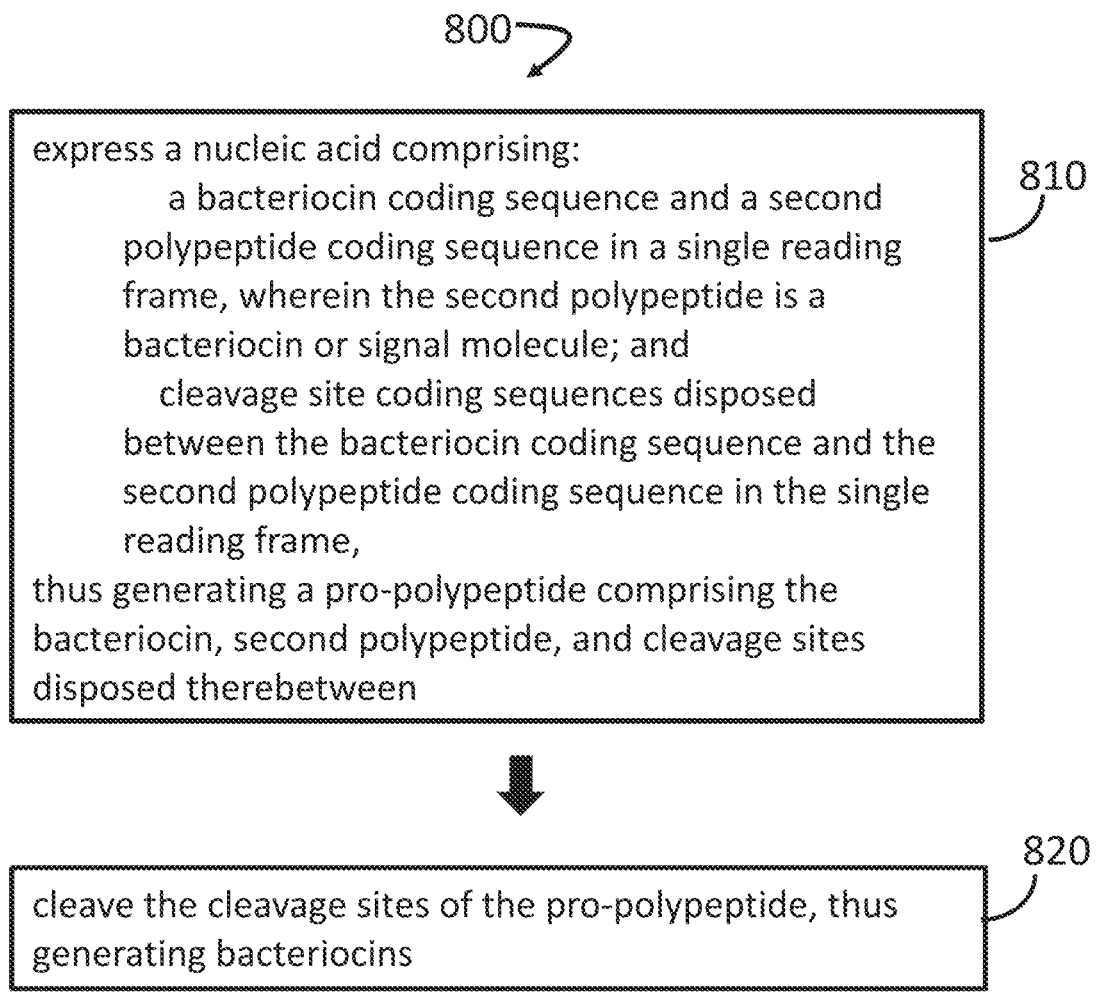
FIG. 8 is a flow diagram illustrating a method for making antimicrobial peptides and/or bacteriocins according to some embodiments herein.

Some embodiments include methods of making bacteriocins. The methods can be useful for making compositions comprising bacteriocins (and optionally, other molecules such as signal molecules) in a desired ratio. In some embodiments, a method of making bacteriocins comprises expressing a nucleic acid. The nucleic acid can comprise two bacteriocin coding sequences in a single reading frame, or a bacteriocin and a signal molecule coding sequence in a single reading frame (see, for example, FIG. 8). The nucleic acid can further comprise cleavage site coding sequences disposed between the bacteriocin coding sequences (or between the bacteriocin and signal molecule coding sequences) and in the single reading frame. The nucleic acid can be expressed to generate a pro-polypeptide comprising the bacteriocins and cleavage sites disposed therebetween. In some embodiments, nucleic acids encoding bacteriocins (and/or signal molecules) as described herein are expressed by a gene expression system to as to produce pro-polypeptides as described herein.

In some embodiments, for example, when producing bacteriocins for a semi-controlled environment as in biopharma production, the pro-polypeptide comprises a bacteriocin coding sequence, a signal molecule coding sequence, and a cleavage site disposed between the bacteriocin and signal molecule coding sequences. It is contemplated that such a pro-polypeptide can be used to produce a composition comprising the bacteriocin and signal molecule in a desired ratio, which can be useful for inhibiting genetically drifting microbial organisms (via the bacteriocin; for example if the immunity of the target organisms is tied to their maintenance of a certain genetic state; this approach is described in additional detail in U.S. Pat. No. 9,333,227). Additionally, the signal molecule can promote the growth, proliferation, or production of a desired product by producing cells in environment (for example, genetically engineered microbial cells, or mammalian cell culture such as CHO or BHK cells).

In some embodiments, the method further comprises cleaving the cleavage site, thus separating the bacteriocins (and/or signal molecules) from each other. Upon separation of the bacteriocins (and/or signal molecules), a composition comprising bacteriocins (or combination of bacteriocins and signal molecules) is thus produced. In some embodiments, the cleavage sites are cleaved by a cleavage enzyme or combination of cleavage enzymes as described herein, for example in Table 4. In some embodiments, the cleavage sites are cleaved by exposing a peptide comprising a pH-sensitive or chemically-sensitive linker to pH or chemical conditions that induce cleavage. In some embodiments, the pro-polypeptide is stored for period of time before cleaving, for example, at least 1 day, 2 days, 3 days, 4 days, 5 days, 6 days, 1 week, 2 weeks, 3 weeks, 4 weeks, 1 month, 2 months, or 3 three months, including ranges between any two of the listed values.

In some embodiments, bacteriocins are inactive when they are part of a pro-polypeptide. Accordingly, in some embodiments, the microbial cell does not produce a functional immunity modulator for at least one of the bacteriocins, for example, the microbial cell can lack a coding sequence for the immunity modulator, or if it does comprise coding sequence for the immunity modulator, the coding sequence can be transcriptionally silent (e.g. due to lack of a promoter), and/or the coding sequence can be mutated so that any immunity modulator produced by the coding sequence is nonfunctional. In some embodiments, the microbial cell comprises *E. coli* or *B. subtilis*.

In some embodiments, at least one of the bacteriocins is inactive when it is part of the pro-polypeptide.

In some embodiments, the nucleic acid is expressed in vitro. Cell-free expression systems can be used to transcribe and/or translate nucleic acids in vitro. In some embodiments, the in vitro expression system comprises, consists of, or consists essentially of cell extracts. In some embodiments, the in vitro expression system comprises an RNA polymerase, ribosomes, tRNAs (and the corresponding amino acids), an energy source, and enzymatic cofactors. The in vitro expression system can further comprise enzymes for co- or post-translational modification, and/or cellular components that mediate protein folding such as heat shock proteins.

In some embodiments, the method further comprises isolating the pro-polypeptide prior to the cleaving. The pro-polypeptide can be isolated from the microbial cell, or from the in vitro expression system as described herein. In some embodiments, isolation comprises purifying the pro-polypeptide. In some embodiments, isolating comprises affinity purifying the pro-polypeptide. The affinity purification can be performed using an affinity tag as described herein. The nucleic acid can encode an affinity tag on the pro-polypeptide. The affinity tag can be bound by a suitable binding agent specific for the affinity tag (e.g., an anti-myc antibody for a myc tag, or GSH-coated beads for the GST, or nickel or cobalt for a His tag). The binding agent can be immobilized on a solid phase, so that, upon binding of the affinity tag, the pro-polypeptide will be immobilized on the solid phase. The solid phase can be removed from the microbial cell and/or in vitro expression system. Optionally, the solid phase can be washed. The affinity tagged pro-polypeptide can then be released from the solid phase. For example, the pro-polypeptide can be isolated by immunoprecipitation, affinity chromatography, and the like.

In some embodiments, the nucleic acid comprises at least three bacteriocin coding sequences in a single reading frame, for example at least about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 bacteriocins, including ranges between any two of the listed values, for example, about 3-10, 3-20, 3-30, 3-50, 5-10, 5-20, 5-30, 5-50, 7-10, 7-20, 7-30, 7-50, 10-20, 10-30, or 10-50 bacteriocins. As such, the nucleic acid can produce a pro-polypeptide comprising the indicated number of bacteriocins.

In some embodiments, at least two of the bacteriocins are different from each other. In some embodiments, two or more of the bacteriocins are the same. In some embodiments, at least two of the bacteriocins are different from each other, and at least two of the bacteriocins are the same.

Upon cleavage of the pro-polypeptide, a composition comprising bacteriocins can be produced. In some embodiments, the composition comprises a desired ratio of bacteriocins. In some embodiments, at least a portion the desired ratio is achieved by a ratio of bacteriocin coding sequences in the single reading frame of the nucleic acid. Without being limited by theory, it is contemplated that in some embodiments, the nucleic acid encodes desired relative quantities of two or more different bacteriocins coding sequences in cis, the corresponding pro-polypeptide will also have these ratios of bacteriocins. For example, if the nucleic acid comprises two coding sequences for "bacteriocin A," and three coding sequences of "bacteriocin B," each separated by cleavage sites, the resultant pro-polypeptide will comprise a ratio of bacteriocin A to bacteriocin B of 2:3. Upon cleavage, the solution will comprise the bacteriocins in these ratios. It is noted that in some embodiments, additional proteins or polypeptides encoded by the nucleic acid are also produced in desired ratios, for example signal molecules. As such, a solution can be produced comprising bacteriocins and signal molecules in a predetermined ratio or range of ratios. In some embodiments, the predetermined ratio is achieved by a ratio of bacteriocin coding sequences in the single reading frame of the nucleic acid.

In some embodiments, the nucleic acid encodes bacteriocins (and optionally additional peptides such as signal molecules) in a portion of a desired ratio. Additional components can be added to achieve the final desired ratio. For example, a second, different pro-polypeptide can comprise bacteriocins and/or signal molecules in a second ratio. The two different polypeptides can together provide the final desired ratio of bacteriocins (and optionally other peptides, such as signal molecules) of interest. As such, in some embodiments, the desired ratio is further achieved by a second nucleic acid comprising a ratio of bacteriocin coding sequences and further comprising cleavage sites between the bacteriocin coding sequences.

A desired ratio can be selected for a number of applications. In some embodiments, a desired ratio of bacteriocins is selected to target an undesired microbial organism or population of undesired microbial organisms. For example, if an environment such as a culture medium, feedstock, fermenter, bioreactor, or microbiome contains, or is at risk of containing a population of undesired microbial organisms, a ratio of bacteriocins can be selected to target those undesired microbial organisms. In some embodiments, the desired ratio of bacteriocins is selected to balance a population of a microbiome of an animal (for example a horse, cow, sheep, pig, donkey, dog, cat, or non-human primate), a human organ (e.g., skin or a gut), or a plant root and/or soil microbiome, or to preserve a product such as a food product (human or non-human animal), pharmaceutical, or cosmetic product. In some embodiments, the desired ratio comprises a ratio between two bacteriocins in a pro-polypeptide (e.g., a first to second bacteriocin, first to third, second to third, or third to fourth, or fourth to fifth) of about 1:2, 1:3, 1:4, 1:5, 1:6, 1:7, 1:8, 1:9, 1:10, 2:3, 2:5, 2:7, 2:9, 3:4, 3:5, 3:7, 3:8, 3:10, 4:5, 4:7, 4:9, 5:6, 5:7, 5:8, 5:9, 6:7, 7:8, 7:9, 7:10, 8:9, or 9:10, in which the first (or second, or third, or fourth) bacteriocin is different from the second (or third, or fourth, or fifth) bacteriocin. It is noted that different pairs of bacteriocins in the pro-polypeptide can have different ratios to each other. Therefore, it is contemplated that the ratios three or more bacteriocins to each other can be ascertained by the individual (pair-wise) ratios of the bacteriocins to each other. For example, a first and second bacteriocin can have a ratio of 1:2, and a second and third bacteriocin can have a ratio of 2:5, so that the ratio of the first to the second to the third bacteriocin is 1:2:5, respectively. In some embodiments, the desired ratio comprises a ratio of a first bacteriocin to a second bacteriocin to a third bacteriocin of about 1:1:2, 1:2:2, 1:1:3, 1:2:3, 1:3:3, 2:2:3, or 2:3:3.

As noted herein, it can be advantageous for the bacteriocins to remain intact following cleavage of the pro-polypeptide. As such, in some embodiments, the bacteriocins of the pro-polypeptide do not contain any of the cleavage sites that separate the bacteriocins (or optional other polypeptides such as signal molecules). Upon cleavage of the cleavage sites, the bacteriocins can remain intact. In some embodiments, the cleavage sites are for a single cleavage enzyme, and the cleavage enzyme does not cleave within the bacteriocins. In some embodiments, at least one cleavage site is for a first cleavage enzyme, and another cleavage site is for a second cleavage enzyme, and neither the first nor the second cleavage enzyme cleaves within the bacteriocins.

In some embodiments, the composition produced by the method comprises a signal molecule as described herein. The nucleic acid can encode the signal molecule in the same reading frame as the other component(s) of the pro-polypeptide (e.g., the bacteriocins). A cleavage site sequence disposed between the signal molecule and the bacteriocin coding sequence or sequences. As such, upon cleavage of the cleavage sites, the signal molecule can be separate from the bacteriocin. In some embodiments, the signal molecule comprises, consists essentially of, or consists of a quorum sensing molecule, signal transduction receptor ligand, growth factor, hormones, or cytokine, or a combination of two or more of these. In some embodiments, the signal molecule is wild-type, mutant, or synthetic.

In some embodiments, the pro-polypeptide has a length of no more than 20,000 amino acids, for example, no more than 20,000, 15,000, 10,000, 9000, 8000, 7000, 6000, 5000, 4000, 3000, 2000, 1000, 900, 800, 700, 600, 500, 400, 300, 200, or 100 amino acids, including between any two of the listed values, for example 100-20,000; 100-10,000; 100-5000; 100-2000; 100-1000; 500-20,000; 500-10,000; 500-5000; 500-2000; 500-1000; 1000-20,000; 1000-10,000; 1000-5000; or 1000-2000 amino acids. In some embodiments, the pro-polypeptide has a length of no more than 5000 amino acids. In some embodiments, the pro-polypeptide has a length of no more than 2000 amino acids.

As noted herein, the ratios of bacteriocins (and other polypeptides such as signal molecules) can be further tuned by using two or more different pro-polypeptides to obtain particular ratios and/or combinations of molecules (e.g., bacteriocins, signal molecules). In some embodiments, the method comprises expressing a second nucleic acid encoding a second pro-polypeptide comprising two bacteriocins and cleavage sites disposed between the bacteriocins. The second pro-polypeptide can be different from the first pro-polypeptide, so cleavage of the second pro-polypeptide produces a different ratio of bacteriocins and/or signal molecules than the first pro-polypeptide once it has been cleaved.

In some embodiments, the method further comprises chemically modifying the bacteriocins. Example chemical modifications include, but are not limited to glycosylation, acetylation, methylation, PEGYlation, SUMOylation, ubiquitination, or two or more of any of these. In some embodiments, the bacteriocins are chemically modified co-translationally. In some embodiments, the bacteriocins are chemically modified post-translationally. For example, the microbial cell can comprise, or can be genetically engineered to comprise enzymes for co-translational modification or post-translational modification. For example, the in vitro expression system can comprise enzymes for co-translational or post-translational modification. For example, the in vitro expression system can comprise enzymes for post-translational modification, and/or, following isolation of the pro-polypeptide from the expression system (in vitro or microbial cell), the pro-polypeptide can be contacted with enzymes that produce the desired post-translational modification. In some embodiments, bacteriocins are chemically modified after the pro-polypeptide has been cleaved.

Figure 3:
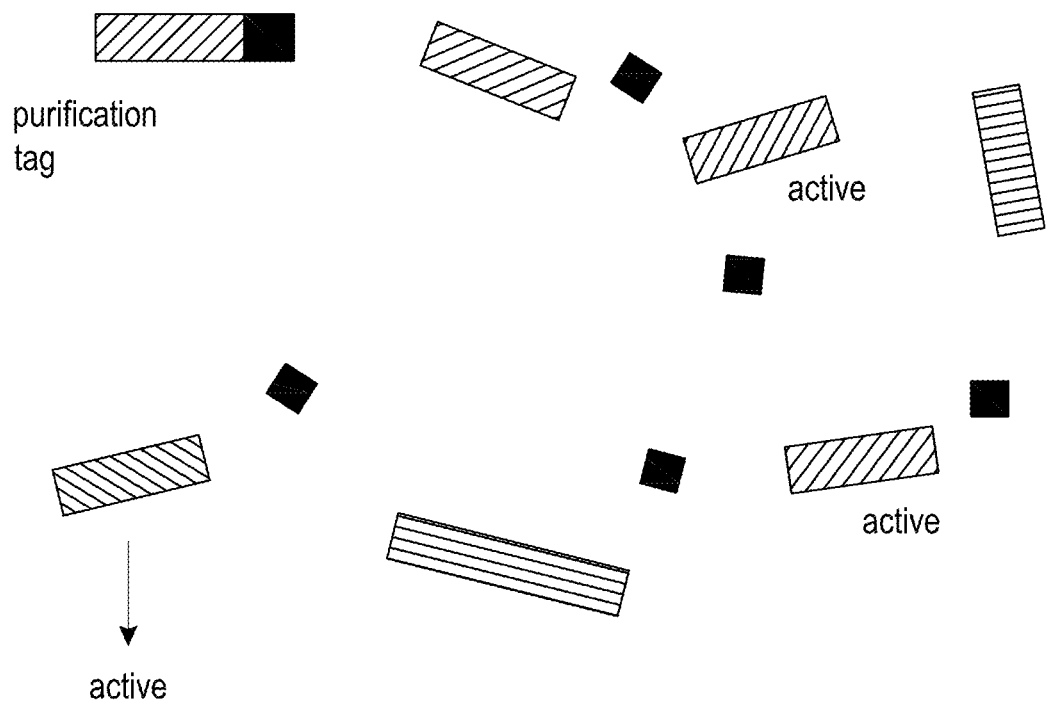
FIG. 3 is a schematic diagram of an embodiment of a composition comprising bacteriocins and cleavage sites in accordance with some embodiments herein.

Some embodiment include a composition comprising bacteriocins, which can be made according to methods of some embodiments herein is shown in FIG. 3. In some embodiments, the composition is produced by the cleavage of a pro-polypeptide as described herein. It is contemplated that the bacteriocins can be released by cleavage of the pro-polypeptide, for example via an endopeptidase. The result can be a mixture with the correct molecular blend according to a predetermined and/or desired result in terms of bacterial killing. In some embodiments, one strain of host cell can produce a multi-bacteriocin mixture in one fermentation. It is contemplated that there can be no toxic effect during production (and thus, no need of immunity in the host cell). Optionally, purification of the pro-polypeptide (and/or "cleaved" bacteriocins) can be performed purification via a tag. Optionally molecular adjustment between bacteriocins can be performed.

Compositions Comprising Bacteriocins

In some embodiments, compositions comprising bacteriocins in desired ratios are provided. Optionally, the composition can further comprise additional polypeptides, for example signal molecules, in desired ratios with the bacteriocins and/or each other.

In some embodiments, a composition comprises two or more bacteriocins in a ratio selected to target a microbial cell or populations of microbial cells. Each of the bacteriocins can comprise, at its N-terminus, C-terminus, or N-terminus and C-terminus, a portion of a cleavage sequence that has been cleaved. It is contemplated that when a pro-polypeptide comprising multiple bacteriocins as described herein is cleaved at its cleavage sites, at least some of the bacteriocins will comprise the vestiges of the cleavage site at their N- and/or C-termini, depending on the cleavage site. As such, it is contemplated that not only will the bacteriocins of the composition be in desired ratios with a very high degree of accuracy, but further, the bacteriocins will be structurally distinct in that many or all of the bacteriocins will comprise N- and/or C-terminal vestiges of cleavage sites, for example partial cleavage sites. In some embodiments, the portions of cleavage sequences at the N-, C-, or N- and C-termini of the bacteriocins are for cleavage sites of the same cleavage enzyme. In some embodiments, the portions of cleavage sequences at the N-, C-, or N- and C-termini of the bacteriocins are for cleavage sites of two or more different cleavage enzymes.

In some embodiments, some or all of the bacteriocins of the composition further comprise a tag. In some embodiments, the tag is selected from the group consisting of affinity tags, a signal sequence, or a stability tag. In some embodiments, a cleavage site is disposed between the tag and the bacteriocin.

In some embodiments, the composition further comprises a signal molecule as described herein. The signal molecule can also be in the desired ratio. The signal molecule can also comprise vestiges of cleavage sites at its N- and/or C-termini.

In some embodiments, the ratio of bacteriocins in the composition is selected to target an undesired microbial organism or population of undesired microbial organisms in an environment, such as an industrial manufacturing environment, a fermenter, a food, drug, or cosmetic manufacturing environment, or a product to be preserved (e.g., a food, drug, or cosmetic product). In some embodiments, the ratio of bacteriocins is selected to balance a population of a microbiome of an animal, a human organ, or a plant root and/or soil, or to preserve a product (such as a food, drug, or cosmetic product). In some embodiments, the composition is formulated for topical or oral administration to a human subject.

Coding Substrates

In accordance with methods and microfluidic devices and systems of some embodiments described herein, coding substrates are provided. A coding substrate can comprise a nucleic acid encoding a protein or peptide such as an antimicrobial peptide and/or bacteriocin (and, optionally, an auxiliary protein) as described herein. The coding substrates of methods and microfluidic devices of some embodiments encode antimicrobial peptides and/or bacteriocins, and can be used to produce a specified mixture of antimicrobial peptides and/or bacteriocins. The coding substrates can be discrete, and capable of being placed in fluidic isolation from each other (which may be referred to herein as "discrete" coding substrates). For example, in a method or microfluidic device of some embodiments, several discrete coding substrates may be used to produce a specified mixture of antimicrobial peptides and/or bacteriocins by way of in vitro transcription/translation, in which (i) only discrete coding substrates encoding the antimicrobial peptides and/or bacteriocins of the specified mixture are contacted and incubated with an in vitro transcription/translation solution, (ii) only coding substrates that have produced antimicrobial peptides and/or bacteriocins of the specified mixture are placed in fludic communication with a fluidic reservoir where the specified mixture is formed, or (i) and (ii). For example, valves as described herein can control the flow of in vitro transcription/translation solution to, and/or antimicrobial peptides and/or bacteriocins from discrete coding substrates (or chambers housing the discrete coding substrates). In methods and microfluidic devices of some embodiments, different coding substrates, encoding different antimicrobial peptides and/or bacteriocins from each other may be housed in separate chambers (of a microfluidic device as described herein), each of which may be placed in fluid communication with an in vitro transcription/translation solution by a valve. As such, in methods and microfluidic devices some embodiments, the discrete coding substrates of a microfluidic device are comprised within separate chambers. In some embodiments, the discrete coding substrates comprise, consist essentially of, or consist of beads. By way of example, beads encoding the antimicrobial peptides and/or bacteriocins of the specified mixture (but not beads encoding other antimicrobial peptides and/or bacteriocins) can be placed in fluid communication with an in vitro transcription/translation solution, either mechanically, or through the opening and/or closing of valve to direct fluids to the appropriate beads. In some embodiments, different discrete coding substrates encode different antimicrobial peptides and/or bacteriocins from each other. Some embodiments comprise a system comprising a processor. The system can be configured to be placed in fluid and/or data communication with a microfluidic device as described herein. Optionally, the system comprises a pump, and/or reservoirs of reagents (e.g., in vitro transcription/translation solution) which can be placed in fluid communication with the microfluidic device. In some embodiments, the microfluidic device is formatted as a cartridge for insertion into the system. In some embodiments, the coding substrates encode bacteriocins, but not antimicrobial peptides. In some embodiments, the coding substrates encode antimicrobial peptides, but not bacteriocins. In some embodiments, the coding substrates encode a combination of antimicrobial peptides and bacteriocins.

In accordance with the methods and microfluidic devices and systems of some embodiments described herein, the coding substrates are discrete coding substrates. In some embodiments, a discrete coding substrate is comprised within a chamber. Accordingly, in some embodiments, multiple discrete coding substrates are each comprised within a separate chamber. In some embodiments, two or more discrete coding substrates are comprised within the same chamber, so that a single chamber contains two or more discrete coding substrates, and thus can produce a mixture and/or stoichiometry of antimicrobial peptides and/or bacteriocins. In some embodiments, a chamber comprises at least 1, 2, 3, 4, 5, 6, 7, 8, 9, 10, 20, 30, 40, 50, 60, 70, 80, 90, 100, 100, 1000, 5000, 10,000, 500,000, 1,000,000, 10,000,000, or 100,000,000 discrete coding substrates, including ranges between any two of the listed values, for example 1-3, 1-5, 1-10, 1-50, 2-3, 2-5, 2-10, 2-20, 2-50, 2-100, 10-50, 50-100, 50-500, 50-1000, 100-500, 100-1000, 500-1000, 1000-5000, 5000-10,000, 10,000-50,000, 50,000-100,000, 100,000-500,000, 500,000-1,000,000, 1,000,000-10,000,000, 10,000,000-100,000,000, or 100,000,000-1,000,000,000 discrete coding substrates.

In accordance with the methods and microfluidic devices and systems of some embodiments described herein, the chambers of the microfluidic device comprising the discrete coding substrates are micro-scale chambers. For example, the chambers may each have a volume of no more than 1, 5, 10, 20, 50, 100, 250 or 500 microliters, including ranges between any two of the listed values, for example, 1-5 microliters, 1-10 microliters, 1-20 microliters, 1-50 microliters, 1-100 microliters, 1-500 microliters, 5-10 microliters, 5-20 microliters, 5-50 microliters, 5-100 microliters, 5-500 microliters, 10-20 microliters, 10-50 microliters, 10-100 microliters, 10-500 microliters, 50-100 microliters, or 50-500 microliters. In some embodiments, the chambers comprise, consist essentially of, or consist of a material or product selected from the group consisting of a well, nanowell, membrane, matrix, plastic, metal, glass, polymer, polysaccharide, and paramagnetic compound, or a combination of two or more of these. In accordance with the methods and microfluidic devices of some embodiments described herein, the coding substrates comprise, consist essentially of, or consist of a material or product selected from the group consisting of a chip, bead, nanoparticle, well, nanowell, membrane, matrix, plastic, metal, glass, polymer, polysaccharide, and paramagnetic compound, or a combination of two or more of these. Some embodiments include a microfluidic device comprising separate microchambers, each comprising one or more beads, each of which comprises, consstins essentially of, or consists of a coding substrate. The beads can each comprise nucleic acids encoding antimicrobial peptides and/or bacteriocins. In some embodiments, the device includes 1, 2, 3, 4, 5, 6, 7, 8, 9, 10, 10-50, 50-100, 100-500, 500-1000 or 1000-5000 chambers, or any number therebetween.

In accordance with the methods and microfluidic devices and systems of some embodiments described herein, the coding substrates comprise nucleic acids immobilized thereon. For example, the nucleic acids can be covalently bound to the coding substrate, hybridized to the coding substrate, and/or associated with the coding substrate via one or more force, such as an electrostatic force. In some embodiments, the nucleic acid comprises DNA. In some embodiments, the nucleic acid comprises RNA.

In some embodiments, a coding substrate further encodes or comprises an auxiliary protein, such as a protein for stabilization of antimicrobial peptides and/or bacteriocins, a protein with anti-protease activity (for example a serpentin), a protein for stabilization of antimicrobial peptides and/or bacteriocins, a protein for destruction of a microbial biofilm (for example a biofilm breaker such as Dispersin B), a pheromone protein, a protein that attracts a non-pathogenic microbial organism, or a protein that enhances growth or reproduction of the non-pathogenic microbial organism in a microbiome of a subject. Without being limited by theory it is contemplated that such an auxiliary protein can enhance expression and/or activity of an antimicrobial peptide and/or bacteriocin, for example, by stabilizing the antimicrobial peptide and/or bacteriocinin a particular environment, by inhibiting a protease from a particular environment that would degrade an antimicrobial peptide and/or bacteriocin, and/or by degrading fibrils of a microbial biofilm to enhance bacterial contact by the antimicrobial peptide and/or bacteriocin. In some embodiments, a discrete coding substrate encodes an antimicrobial peptide and/or bacteriocinin addition to an auxiliary protein. In some embodiments, a first coding substrate encodes an auxiliary protein and a second coding substrate encodes an antimicrobial peptide and/or bacteriocin. In some embodiments, the auxiliary proteins are selected with the antimicrobial peptides and/or bacteriocins. For example, if a mixture of antimicrobial peptides and/or bacteriocins is for an environment comprising a particular protease, for example trypsin, a coding substrate encoding an inhibitor of that protease can be selected along with coding substrates encoding the mixture of antimicrobial peptides and/or bacteriocins. In some embodiments, a coding substrate encodes an auxiliary protein with anti-protease activity. In some embodiments, the auxiliary protein with anti-protease is a protein for stabilization of antimicrobial peptides and/or bacteriocins. In some embodiments, one or more of the discrete coding substrates encodes an auxiliary protein that attracts a non-pathogenic microbial organism, or that enhances growth or reproduction of the non-pathogenic microbial organism in a microbiome of a subject, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract. In some embodiments, the auxiliary protein is a pheromone peptide that induces an antimicrobial peptide and/or bacteriocin of a desired microbial organism such as a non-pathogenic microbial organism (although in some embodiments, a pathogenic microbial organism is a desired microbial organism). Thus, for example, in some embodiments a discrete coding substrate encodes an auxiliary protein that induces or causes a bacteria to secrete an antimicrobial peptide and/or bacteriocin that inhibits growth or reproduction of another bacteria. In some embodiments, one or more of the discrete coding substrates encodes a protein that attracts the non-pathogenic microbial organism, or that enhances growth or reproduction of the non-pathogenic microbial organism in the microbiome of a subject. In some embodiments, bacteriocins, and not antimicrobial peptides are used.

Inhibition of growth or reproduction has its customary and ordinary meaning as understood by one of skill in the art in view of this disclosure. It refers to a decrease in or arrest of proliferation of microbial organisms (or a decrease in the rate of proliferation of microbial organisms), for example, arrest of the cell cycle and/or killing of microbial organisms. Similarly, enhancement of growth or reproduction refers to an increase in proliferation or the rate of proliferation of microbial organisms. Any method known in the art may be used to detect inhibition or enhancement of growth or reproduction.

In Vitro Transcription/Translation Solutions

In accordance with the methods, systems and microfluidic devices of some embodiments described herein, a transcription/translation solution can be used to produce an antimicrobial peptide and/or bacteriocin encoded by a coding substrate. As such, the transcription/translation solution may be useful for generating peptides, or antimicrobial peptides and/or bacteriocins, in a method or microfluidic device for producing a specified mixture of antimicrobial peptides and/or bacteriocins The term, "in vitro transcription/translation solution" encompasses an in vitro transcription solution and/or an in vitro translation solution sufficient to produce an antimicrobial peptide and/or bacteriocin from a coding substrate. By way of example, in embodiments in which the coding substrate comprises RNA transcripts encoding antimicrobial peptides and/or bacteriocins, it is contemplated that an "in vitro transcription/translation solution" comprising, consisting essentially of, or consisting of a translation solution is sufficient (since it will be understood that the RNA is already a transcript). By way of example, in embodiments in which the coding substrate comprises DNAs encoding antimicrobial peptides and/or bacteriocins, it is contemplated that an "in vitro transcription/translation solution" comprises a transcription solution (for transcribing the DNAs into RNAs) and a translation solution (for translating the RNAs into polypeptides). In some embodiments, the transcription and translation solution are together in a single solution. In some embodiments, the transcription and translation solution are in separate solutions, for example in vesicles suspended in a single solution, and/or in separate solutions that are applied sequentially. In some embodiments, components of the in vitro transcription/translation solution are lyophilized, and configured to be reconstituted into the in vitro transcription/translation solution upon the addition of water. In some embodiments, the in vitro transcription/translation solution is reconstituted by adding water to lyophilized components.

Translation solutions can be useful for translating nucleic acids in accordance with the methods, systems and/or microfluidic devices described herein. Suitable translation solutions can comprise, consist essentially of, or consist of reagents for in vitro translation (which, for convenience, may be referred to herein as "translation reagents"), and as such can be configured for in vitro translation of a transcript such as an RNA. Some embodiments include a transcription solution comprising reagents for transcription (which, for convenience, may be referred to herein as "transcription reagents"), and thus is configured for in vitro transcription and translation, for example to transcribe and translate a nucleic acid encoding an antimicrobial peptide and/or bacteriocin or other peptides as described herein. It is contemplated that in vitro transcription and translation in a single solution (such as a transcription solution further comprising a translation solution as described herein) can facilitate efficient in vitro production of antimicrobial peptides and/or bacteriocins or other peptides in accordance with methods and microfluidic devices of some embodiments. Thus, in accordance with the methods and microfluidic devices of some embodiments described herein, the in vitro transcription/translation solution comprises an in vitro transcription reagent and/or an in vitro translation reagent.

In accordance with the methods and microfluidic devices of some embodiments described herein, the translation solution comprises, consists essentially of, or consists of one or more translation reagents or in vitro translation reagents. Examples of translation reagents include, but are not limited to, a ribosome, a buffer, an amino acid, a tRNA (which may be conjugated to an amino acid), a lysate or extract such as an E. coli lysate or E. coli extract, and a cofactor or metallic ion such as $Mg^{2+}$, or a combination of two or more of any of the listed items. In accordance with the methods, systems and kits of some embodiments described herein the translation solution further comprises a transcription solution, and thus is configured for in vitro transcription and translation. As described herein, a transcription solution further comprising a translation solution contemplates a single solution that is suitable for in vitro transcription and translation. As such, a transcription solution further comprising a translation solution encompasses a single transcription/translation solution. It will be appreciated that some components of a transcription and/or translation solution, for example ribosomes, may not be liquids, and could potentially be isolated from the transcription and/or translation solution, for example by filtration and/or centrifugation. Translation solutions of methods and microfluidic devices of some embodiments described herein (and which can be comprised by translation solutions as described herein) can comprise, consist essentially or, or consist of one or more transcription reagents. Examples of transcription reagents include an RNA polymerase, a buffer, a nucleic acid mix (for example, NTPs including ATP, GTP, CTP, and UTP), a cofactor or metallic ion such as $Mg^{2+}$, a transcription inducer (such as a transcription factor, IPTG, or lactose), a polyadenylation enzyme, a capping enzyme, a lysate or extract such as a bacterial lysate or extract such as an E. coli lysate or E. coli extract, an SP6 polymerase, a T3 polymerase, a T7 RNA polymerase, or a mixture of two or more of any of the listed items. The transcription solution can be useful for transcribing a template, such as a candidate nucleic acid as described herein. Translation solutions of methods and microfluidic devices of some embodiments include one or more transcription reagents in combination with one or more translation reagents. In some embodiments, a microfluidic device and/or system comprises a reservoir comprising an in vitro transcription/translation solution as described herein. In some embodiments, the reservoir comprises an in vitro transcription solution and an in vitro translation solution which can be combined to produce the in vitro transcription/translation solution.

In some embodiments, the translation solution comprises a post-translational modification enzyme. Examples of post-translational modification enzymes include, but are not limited to a cleavage enzyme, a kinase, a phosphatase, a glycosyltransferase, or a mixture of any two of the listed items.

In accordance with the systems, methods and microfluidic devices of some embodiments described herein, the translation solution is provided to a coding substrate at a microliter-scale. For example, the translation solution may have a volume of 1 µl-1000 µl, 1 µl-50 µl, 1 µl-500 µl, 1 µl-900 µl, 50 µl-100 µl, 50 µl-500 µl, 50 µl-1000 µl, 100 µl-200 µl, 100 µl-500 µl, 100 µl-1000 µl, 200 µl-500 µl, 200 µl-1000 µl, 500 µl-900 µl, or 500 µl-1000 µl.

In accordance with the systems, methods and microfluidic devices of some embodiments described herein, the in vitro transcription/translation solution is lyophyilized. In some embodiments, the in vitro transcription/translation solution is configured be reconstituted in a solution such as water. As such, a microfluidic device of some embodiments can be stably stored for periods of time at ambient temperature, without substantial impact on the efficacty of the in vitro transcription/translation solution. Accordingly, it is contemplated that the microfluidic device of some embodiments is suitable for point-of-care treatment, and can be used to prepare specified mixtures of antimicrobial peptides and/or bacteriocins as needed (for example, in response to particular injuries, infections, and/or surgical procedures).

Microfluidic Devices and Systems

A fluidic system comprising a microfluidic device can be useful for producing specified mixtures of antimicrobial peptides and/or bacteriocins in accordance with the methods and microfluidic devices and systems of some embodiments described herein. In some embodiments, a system is configured to receive a microfluidic device comprising discrete coding substrates as described herein, so that the system can direct the microfluidic device to produce a specified mixture of antimicrobial peptides and/or bacteriocins via in vitro transcription/translation. In some embodiments, the system is configured to be in fluid and/or data communication with the device. For example, disposable cartridge can comprise, consist essentially of, or consist of a microfluidic device for use in conjunction with systems as described herein. As it is contemplated that specified mixtures of antimicrobial peptides and/or bacteriocins can be customized for particular applications, for example, to interact with a particular microbiome of a particular subject, or to target a particular infection, it is contemplated that single-use disposable microfluidic devices can minimize contamination (for example from residual bacteriocins) that may interfere with the stoichiometry and composition of the specified mixture of antimicrobial peptides and/or bacteriocins, and can be useful for maintaining sterility for medical use on a subject. As such, in some embodiments, the microfluidic device is sterile. In the methods and microfluidic devices of some embodiments, the fluidic device comprises a microfluidic device. As it will be understood that a "microfluidic device" is a kind of "fluidic device," a microfluidic device is expressly contemplated wherever a "fluidic device" is mentioned herein. Additionally, unless expressly stated otherwise, any disclosure of a fluidic device (such as a microfluidic device) herein is understood to be applicable to a microfluidic device of some embodiments, as well as methods comprising microfluidic devices as described herein.

In some embodiments, a microfluidic device for producing a specified mixture of antimicrobial peptides and/or bacteriocins is provided. In some embodiments, the device comprises discrete coding substrates, as described herein, that each encode an antimicrobial peptide and/or bacteriocin. The device can further comprise an in vitro transcription/translation solution as described herein. The device can further comprise a fluidic reservoir, one or more valves, and/or can be configured to be placed in data communication with a processor as described herein. The valves can regulate fluidic communication between the transcription/translation solution, the discrete coding substrates, and/or the fluidic reservoir. The processor can be configured to control the valves, so as to place coding substrates encoding the antimicrobial peptides and/or bacteriocins of the specified mixture in fluid communication with the in vitro transcription/translation solution so that the antimicrobial peptides and/or bacteriocins of the specified mixture are produced. The processor can be configured to control the valves (and, in some embodiments, fluidic flow) in the microfluidic device to place the antimicrobial peptides and/or bacteriocins of the mixture in fluid communication with the fluidic reservoir so that the antimicrobial peptides and/or bacteriocins of the specified mixture flow to the fluidic reservoir, thus providing the specified mixture of antimicrobial peptides and/or bacteriocins in the fluidic reservoir. Optionally, the antimicrobial peptides and/or bacteriocins of the specified mixture are actively mixed in the fluidic reservoir. In some embodiments, the antimicrobial peptides and/or bacteriocins of the specified mixture mix passively (but are not actively mixed) in the fluidic reservoir. In some embodiments, the microfluidic device comprises the processor. In some embodiments, the microfluidic device does not itself comprise the processor, but is configured to be placed in data communication with the processor. In some embodiments, the microfluidic device is for producing a specified mixture of bacteriocins, and not antimicrobial peptides. In some embodiments, the microfluidic device is for producing a specified mixture of antimicrobial peptides, and not bacteriocins. In some embodiments, the microfluidic device is for producing a specified mixture of bacteriocins and antimicrobial peptides.

Some embodiments of the methods and microfluidic devices described herein include a microfluidic device for producing a specified mixture of antimicrobial peptides and/or bacteriocins. The device can comprise: discrete coding substrates that each encode a bacteriocin and/or an antimicrobial peptide; an in vitro transcription/translation solution; a fluidic reservoir; valves each disposed on a fluidic path between a discrete coding substrate and the fluidic reservoir, each valve configured to regulate flow between the discrete coding substrate and the fluidic reservoir. The device can be configured to be placed in data communication with a processor configured to: based on the specified mixture of antimicrobial peptides and/or bacteriocins, configure the valves to place the discrete coding substrates that encode the antimicrobial peptides and/or bacteriocins of the mixture, but not other discrete coding substrates, in fluidic communication with the fluidic reservoir; permit incubation of the in vitro transcription/translation solution with the discrete coding substrates that encode the antimicrobial peptides and/or bacteriocins of the mixture, so that the antimicrobial peptides and/or bacteriocins of the specified mixture are produced; permit flow of the antimicrobial peptides and/or bacteriocins through the valves into the fluidic reservoir; and control flow of fluid in the fluidic reservoir, wherein the flow comprises movement of a fluid comprising the specified antimicrobial peptides and/or bacteriocins in the fluidic reservoir, thus producing the specified mixture of antimicrobial peptides and/or bacteriocins. In some embodiments, the microfluidic device comprises the processor. In some embodiments, the microfluidic device is for producing a specified mixture of bacteriocins, and not antimicrobial peptides. In some embodiments, the microfluidic device is for producing a specified mixture of antimicrobial peptides, and not bacteriocins. In some embodiments, the microfluidic device is for producing a specified mixture of bacteriocins and antimicrobial peptides.

In accordance with the methods and microfluidic devices of some embodiments described herein, the microfluidic device comprises discrete coding substrates but not a fluidic reservoir and/or an in vitro transcription/translation solution. As such, the microfluidic device can be placed in fluid and data communication with a system as described herein, and the system can provide the fluidic reservoir and/or the in vitro transcription/translation solution so that the specified mixture of antimicrobial peptides and/or bacteriocins can be produced. Accordingly, in some embodiments, the system comprises a fluidic reservoir and/or an in vitro transcription/translation solution as described herein. In some some embodiments, the microfluidic device does not comprise the fluidic reservoir, the in vitro transcription/translation solution, and/or any other components of the system, and is separate from these components of the system until it is placed in data and/or fluid communication with the system. In some embodiments, the microfluidic device is configured to be attached to the fluidic reservoir, the in vitro transcription/translation solution, and/or another component of the system. For example, the device may comprise a cartridge that is configured to be inserted into the system to place the discrete coding substrates of the cartridge in fluid communication with an external (to the cartridge) to the fluidic reservoir, in vitro transcription/translation solution, and/or other component of the system. In some embodiments, the cartridges are consumable. For example, a cartridge may comprise discrete coding substrates, be configured to be inserted into the system described herein to produce a mixture of specified antimicrobial peptides and/or bacteriocins, and then be discarded, after which another cartridge that includes other discrete coding substrates may be inserted into the system to produce a different mixture of specified antimicrobial peptides and/or bacteriocins. In some embodiments, a cartridge is configured to receive an in vitro transcription/translation solution from the system, so that the in vitro transcription/translation solution contacts the discrete coding substrates of the cartridge that encode the bacteriocins and/or antimicrobial peptides of the specified mixture. In some embodiments, the microfluidic device is for producing a specified mixture of bacteriocins, and not antimicrobial peptides. In some embodiments, the microfluidic device is for producing a specified mixture of antimicrobial peptides, and not bacteriocins. In some embodiments, the microfluidic device is for producing a specified mixture of bacteriocins and antimicrobial peptides.

Also contemplated are embodiments in which the system and/or microfluidic device is dry. In some embodiments, the system or microfluidic device comprises a lyophilized reagent configured to be dissolved in a fluid such as water.

Figure 5:
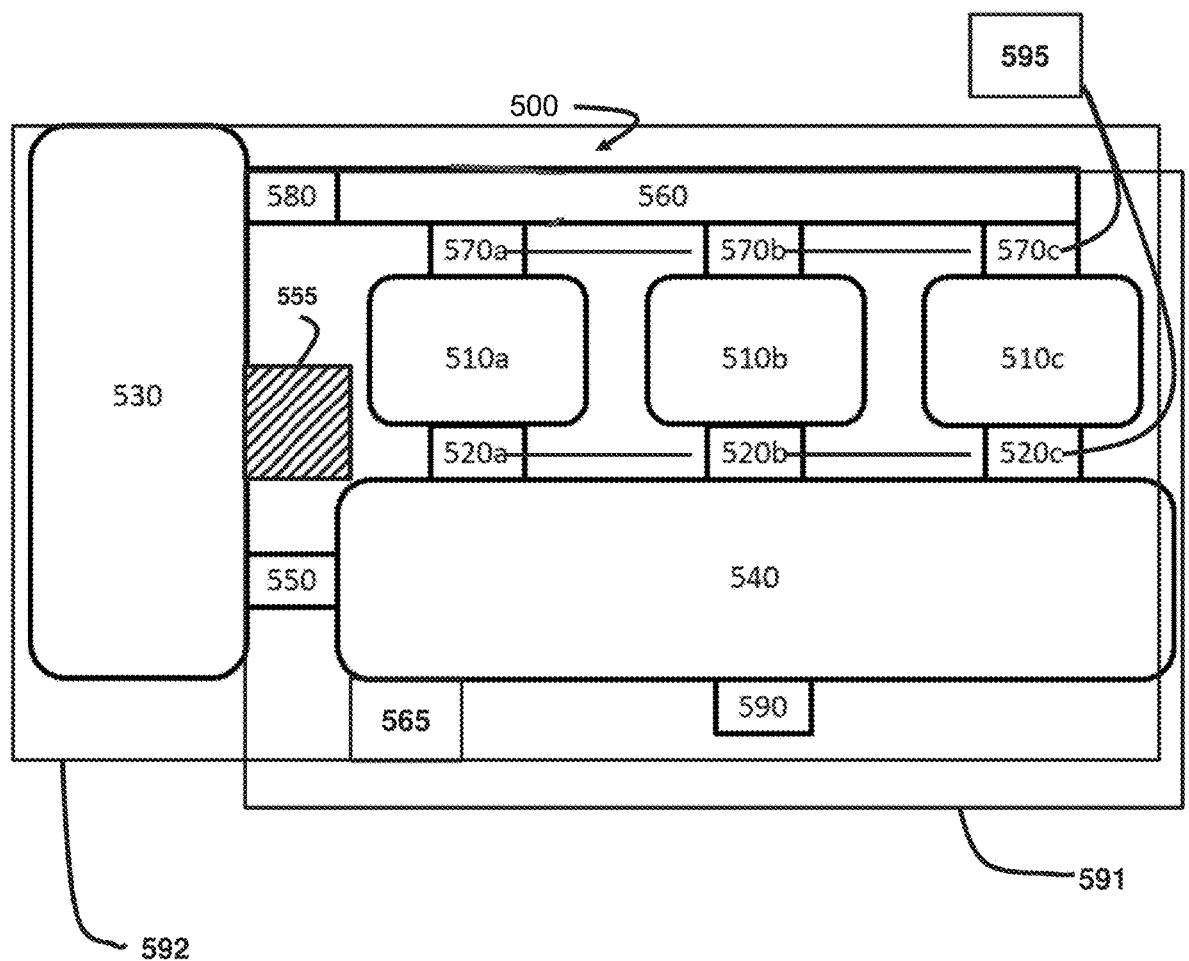
FIG. 5 is a schematic diagram depicting a microfluidic device in accordance with some embodiments herein.

FIG. 5 is a schematic diagram depicting a microfluidic device 500 of some embodiments herein. The microfluidic device 500 can comprise discrete coding substrates 510a, 510b, 510c (while three discrete coding substrates are shown by way of example, it is contemplated that microfluidic devices of embodiments herein can comprise other quantities of discrete coding substrates, as described herein). The device can comprise a fluidic reservoir 540, which, by way of example, can receive antimicrobial peptides and/or bacteriocins produced from the discrete coding substrates 510a, 510b, 510c, and thus can contain a specified mixture of antimicrobial peptides and/or bacteriocins as described herein. Valves 520a, 520b, 520c, and/or 570a, 570b, 570c can regulate fluidic flow to and from the discrete coding substrates 510a, 510b, 510c. In some embodiments, the microfluidic device further comprises an outlet 590, which can permit flow from the fluidic reservoir 540 out of the microfluidic device. For example, the specified mixture of antimicrobial peptides and/or bacteriocins can flow through the outlet 590 to a tissue, wound, microbiome of a subject, and/or vessel as described herein. In some embodiments, a processor 595 as described herein is in data communication with the device, and controls flow through valves 520a, 520b, 520c, and/or 570a, 570b, 570c and/or 550 and/or 580. In some embodiments, the device does not itself comprise a processor 595, and is configured to placed in data communication with a processor 595 as described herein so as to controls flow through valves 520a, 520b, 520c, and/or 570a, 570b, 570c and/or 550 and/or 580. It is contemplated that in accordance with microfluidic devices and methods of some embodiments herein, the production of antimicrobial peptides and/or bacteriocins of a specified mixture can be achieved by contacting only a subset of discrete coding substrates 510a, 510b, 510c with an in vitro transcription/translation solution in the first place (so that only some discrete coding substrates are used to produce an antimicrobial peptide and/or bacteriocin), and/or by only permitting a subset of antimicrobial peptides and/or bacteriocins produced from discrete coding substrates 510a, 510b, 510c to enter the fluidic reservoir 540. It is noted that contacting only a subset of the discrete coding substrates with in vitro transcription/translation solution can enhance efficiency by avoiding the use of in vitro transcription/translation solution on coding substrates that do not encode antimicrobial peptides and/or bacteriocins of the specified mixture. In some embodiments, the microfluidic device is part of a cartridge 591 that does not comprise a reservoir of in vitro transcription/translation solution. The cartridge 591 can be configured to place the microfluidic device in data communication with a system comprising a processor 595. Optionally the cartridge can also be placed in fluid communication with the system. In some embodiments, the microfluidic device is part of a cartridge 592 that comprises a reservoir of in vitro transcription/translation solution 530. The cartridge 592 can be configured to place the microfluidic device in data communication with a system comprising a processor 595. In some embodiments, the microfluidic device comprises, consists essentially of, or consists of the microfluidic device 600 shown in FIG. 6, which includes discrete coding substrates 610a, 610b, 610c, a channel 660, and valves 620a, 620b, 620c, 670a, 670b, 670c, and/or 680, similar to the microfluidic device 500 in FIG. 5. The microfluidic device optionally does not include In some embodiments, the microfluidic device 600 can be placed in fluid communication with a system comprising a reservoir of in vitro transcription/translation solution 530 or a fluidic reservoir 540, or in data communication with a heating element 555. For example, a disposable cartridge can comprise, consist essentially of, or consist of the microfluidic device 600, and can be configured to be placed in fluid communication with a system comprising in vitro transcription/translation solution 530 and a fluidic reservoir 540. The microfluidic device 600 can also be placed in data communication with a processor 595 and/or a heating element 555 of the system. In some embodiments, the microfluidic device is for producing a specified mixture of bacteriocins, and not antimicrobial peptides. In some embodiments, the microfluidic device is for producing a specified mixture of antimicrobial peptides, and not bacteriocins. In some embodiments, the microfluidic device is for producing a specified mixture of bacteriocins and antimicrobial peptides.

Figure 6:
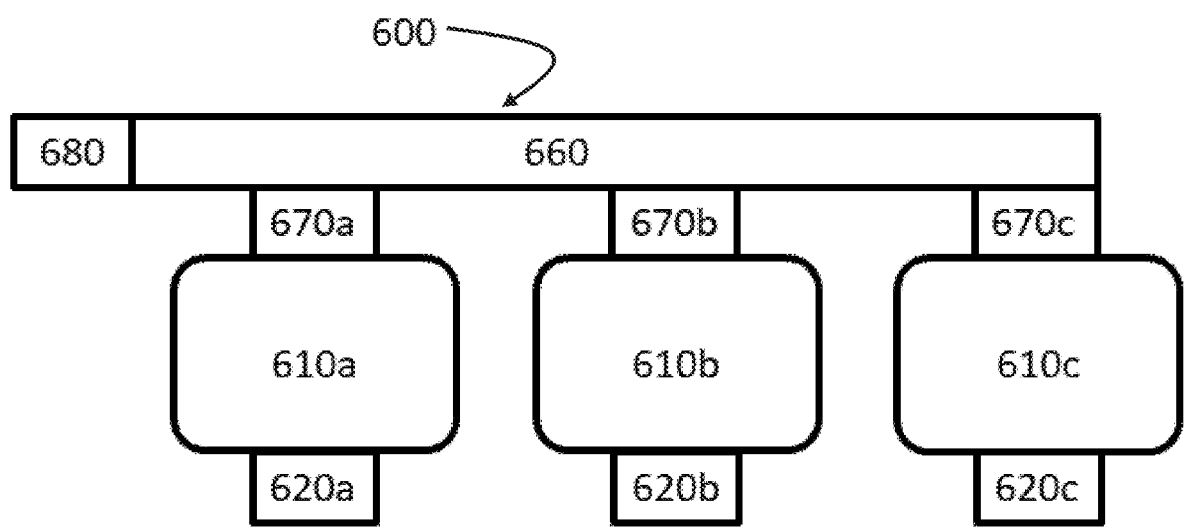
FIG. 6 is a schematic diagram depicting a microfluidic device in accordance with some embodiments herein.

In some embodiments, valves 520a, 520b, and 520c regulate flow between the discrete coding substrates 510a, 510b, 510c and the fluidic reservoir 540. Valves 570a, 570b, and 570c are optional, and/or valves 550 and 580 are optional, and/or the channel 560 is optional. In some embodiments, the reservoir of in vitro transcription/translation solution 530 can be in fluidic communication with the fluidic reservoir 540. Optionally, valve 550 is disposed between the reservoir of in vitro transcription/translation solution 530 and the fluidic reservoir 540, and regulates flow of in vitro transcription/translation solution to the fluidic reservoir 540. In some embodiments, the microfluidic device 600 of FIG. 6 is part of a cartridge.

In some embodiments, for example if only the antimicrobial peptides and/or bacteriocins of the specified mixture are permitted to enter the fluidic reservoir 540 from the coding substrates 510a, 510b, 510c, valves 570a, 570b, and 570c regulate flow between a reservoir of in vitro transcription/translation solution 530 and the discrete coding substrates 510a, 510b, 510c, and valves 520a, 520b, 520c are optional, and/or valve 550 is optional and/or valve 580 is optional. A channel 560 can connect the reservoir of in vitro transcription/translation solution 530 to the discrete coding substrates 510a, 510b, 510c, with optional intervening valve 580 between the reservoir 530 and the channel 560, and/or optional intervening valves 570a, 570b, 570c between the channel 560 and the discrete coding substrates 510a, 510b, 510c. In some embodiments, valves 570a, 570b, and 570c regulate flow between a reservoir of in vitro transcription/translation solution 530 and the discrete coding substrates 510a, 510b, 510c, and valves 520a, 520b, 520c regulate flow between the discrete coding substrates 510a, 510b, 510c and the fluidic reservoir 540. Optionally, channel 560 can connect the reservoir 530 to the discrete coding substrates 510a, 510b, 510c. Valve 580 is optional and/or valve 550 is optional.

The microfluidic device can further comprise an outlet 590. The outlet 590 can place the fluidic reservoir (and any mixture of antimicrobial peptides and/or bacteriocins therein) in fluidic communication with a tissue of a subject, a wound, and/or a microbiome of a subject as described herein. In some embodiments, the outlet 590 comprises a valve. In some embodiments, the outlet 590 can be placed in fluid communication with a vessel for storing a specified mixture of antimicrobial peptides and/or bacteriocins, for example a test tube, bag, or well.

In some embodiments, the in vitro transcription/translation solution reservoir 530 is in fluid communication with channel 560. Optional valve 580 controls from from the reservoir 530 to the channel 560. In some embodiments, valves 570a, 570b, and 570c regulate flow of transcription/translation solution from the channel 560 into discrete coding substrates 510a, 510b, 510c. By way of example, to produce a specified mixture of antimicrobial peptides and/or bacteriocins comprising antimicrobial peptides and/or bacteriocins encoded by discrete coding substrates 510a and 510b (but not 510c), valves 570a and 570b can be open, while valve 570c is closed, to permit flow of transcription/translation solution 530 into discrete coding substrates 510a and 510b, but not 510c. In some embodiments, discrete coding substrates 510a, 510b, and/or 510c are incubated with the in vitro transcription/translation solution to produce a specified mixture of antimicrobial peptides and/or bacteriocins that is released via valves 520a, 520b, and/or 520c into the fluidic reservoir 540.

In some embodiments, in vitro transcription/translation solution flows to the discrete coding substrates 510a, 510b, and/or 510c through the fluidic reservoir 540. The reservoir of in vitro transcription/translation solution 530 can be in fluid communication with the fluidic reservoir 540, optionally with flow regulated by intervening valve 550. Optionally, valves 520a, 520b, 520c regulate flow from the fluidic reservoir 540 to the discrete coding substrates 510a, 510b, and 510c. As such, the in vitro transcription/translation solution can be incubated with the appropriate discrete coding substrates to produce antimicrobial peptides and/or bacteriocins, and antimicrobial peptides and/or bacteriocins can then flow through valves 520a, 520b, and 520c to the fluidic reservoir 540. Valves 570a, 570b, 570c, the channel 560, and valve 580 can be optional. In some embodiments, discrete coding substrates 510a, 510b, and/or 510c are incubated with the in vitro transcription/translation solution to produce a specified mixture of antimicrobial peptides and/or bacteriocins that is released via valves 520a, 520b, and/or 520c into the fluidic reservoir 540. In some embodiments, the specified mixture of antimicrobial peptides and/or bacteriocins flows through the outlet 590 to a wound, tissue, microbiome of a subject, and/or vessel as described herein.

In some embodiments, valve 550 regulates flow from the in vitro transcription/translation solution reservoir 530 into fluidic reservoir 540, and valves 520a, 520b, and/or 520c regulate flow from discrete coding substrates 510a, 510b, and/or 510c to fluidic reservoir 540. Valves 570a, 570b, 570c, and 580, and channel 560 are optional. As such, in vitro transcription/translation solution can flow from the fluidic reservoir 540 to the discrete coding substrates 510a, 510b, and/or 510c, can be incubated with the discrete coding substrates 510a, 510b, and/or 510c to produce antimicrobial peptides and/or bacteriocins, and antimicrobial peptides and/or bacteriocins can flow to the fluidic reservoir 540. In some embodiments, the processor 595 regulates flow of in vitro transcription/translation solution through valves 520a, 520b, and 520c to the discrete coding substrates 510a, 510b, and/or 510c so that only discrete coding substrates encoding antimicrobial peptides and/or bacteriocins of the specified mixture receive in vitro transcription translation/solution. In some embodiments, the processor 595 permits flow of in vitro transcription translation/solution from the fluidic reservoir 540 to the discrete coding substrates 510a, 510b, and/or 510c encoding the antimicrobial peptides and/or bacteriocins of the specified mixture through valves 520a, 520b, and 520c, and after the antimicrobial peptides and/or bacteriocins have been produced by in vitro transcription translation, the processor 595 regulates valves 520a, 520b, 520c, so that only the antimicrobial peptides and/or bacteriocins of the specified mixture to enter the fluidic reservoir 540.

It can be appreciated that in some embodiments of the fluidic device 500 depicted in FIG. 5, valves 550, 570a, 570b, 570c, 580, and channel 560, are optional. For example, some embodiments of the fluidic device include valves 580, 570a, 570b and 570c, and flow means 560, but not valve 550. In some other embodiments, the fluidic device includes valve 550, but not valves 570a, 570b, 570c, or 580, or flow means 560. In some embodiments, the fluidic device includes valves 550, 570a, 570b, 570c, and 580, and flow means 560. In some embodiments, valve 580 is included, and valves 570a, 570b, and 570c are excluded. In some embodiments, valve 580 is excluded, and valves 570a, 570b, and 570c are included. It can also be appreciated that in some embodiments of the fluidic device 500, the outlet 590 does not comprise a valve.

In some embodiments, the outlet 590 permits a wash fluid into the fluidic reservoir 540, and any of the other valves may be opened to permit flow of the wash fluid into any other fluidically connected portion of the device. In some embodiments, the wash fluid comprises a buffer or a detergent. It can be appreciated that additional valves may be present in the microfluidic device to allow the inflow or outflow of fluids in any of the fluidic portions of the device.

In some embodiments, channel 560 comprises, consists essentially of, or consists of a microchannel, tube, pipe, and a hose, and as such, can contain and/or direct flow of a fluid. In some embodiments, the channel 560 comprises material such as rubber, plastic, metal.

In accordance with the methods and microfluidic devices of some embodiments described herein, the microfluidic device is portable. For example, some embodiments of the device may be removed from a laboratory and taken into a natural environment where a scientist performs tests with various mixtures of specified antimicrobial peptides and/or bacteriocins.

In accordance with the methods and microfluidic devices of some embodiments described herein, the microfluidic device comprises an outlet 590 through which the specified mixture of antimicrobial peptides and/or bacteriocins are delivered to a wound. For example, the outlet 590 can be connected to the wound via a membrane or tube. Thus, in some embodiments, the device comprises a wound dressing or wound cleaning device.

In some embodiments, fluid is passively transferred from one component of the device to another. The microfluidic devices of some embodiments include a pump 565 that actively pumps fluid from one component of the device to another.

In accordance with the methods and microfluidic devices of some embodiments described herein, the microfluidic device comprises a heating element 555 such as a heating block. In some embodiments, the heating element is configured to heat parts of the microfluidic device, such as the fluidic reservoir 540 and/or the discrete coding substrates 510a, 510b, and/or 510c to perform incubation step. In some embodiments, the incubation step is at at least about 0° C., 4° C., 25° C., 30° C., 37° C., 38° C., 40° C., including ranges between any two of the listed values, for example 0-40° C., or 36-38° C., or 4-40° C. In some embodiments, the incubation with the in vitro transcription/translation solution at least 1, 10, 30, 60 second, or at least 2, 3, 4, 5, 6, 7, 8, 9, 10, 15, 20, 25, or 30 minutes, including ranges between any two of the listed valued, for example 1-30 seconds, 30-60 seconds, 1-2 minutes, 2-5 minutes, 5-10 minutes, 10-15 minutes, 15-30 minutes, or 30-60 minutes, 1-2 hours, 2-5 hours, 5-10 hours, 10-15 hours, 15-24 hours, 24-48 hours, or 48-72 hours. In some embodiments, the incubation with the in vitro transcription/translation solution comprises more than one temperature at different times.

In accordance with the methods and microfluidic devices of some embodiments described herein, the microfluidic device comprises a reservoir of chemical and/or phage antibiotics configured to mix with the mixture of specified antimicrobial peptides and/or bacteriocins. In some embodiments, the microfluidic device comprises an antibiotic comprising a chemical antibiotic and/or a phage. In some embodiments, the system comprises a reservoir of chemical or phage antibiotics configured to mix with the mixture of specified antimicrobial peptides and/or bacteriocins. In accordance with the methods and microfluidic devices of some embodiments described herein, the microfluidic device comprises an antibiotic comprising a chemical antibiotic and/or a phage.

Fluidic Reservoirs

In methods and microfluidic devices of some embodiments herein, the microfluidic device comprise a fluidic reservoir 540. In some embodiments, the fluidic reservoir is or is configured to be in fluid communication with at least one discrete coding substrate (optionally, separated by a valve as described herein). In some embodiments, the fluidic reservoir is in fluid communication with discrete coding substrates or chambers housing the discrete coding substrates, as described herein. In some embodiments, the fluidic reservoir is placed in fluid communication with the discrete coding substrates (or chambers) by a channel, tubing, microfluidic tubing, membrane, mesh, opening, passageway, or two or more of these. By way of example, the channel, tubing, microfluidic tubing, membrane, mesh, opening, and/or passageway of some embodiments can comprise a material such as rubber, glass, plastic, metal, an organic compound, or two or more of these. In some embodiments, the fluidic reservoir is configured to receive antimicrobial peptides and/or bacteriocins of the specified mixture of antimicrobial peptides and/or bacteriocins. The specified antimicrobial peptides and/or bacteriocins can be mixed in the fluidic reservoir, forming the mixture, for example by passive mixing and/or by active mixing. In some embodiments, the microfluidic device comprises more than one fluidic reservoirs. In some embodiments, the fluidic reservoir has a volume of at least 1 μl, for example, at least 1, 5, 10, 100, 500, or 1000 μl, including ranges between any two of the listed values, for example, 1 μl-1000 μl, 1 μl-50 μl, 1 μl-500 μl, 1 μl-900 μl, 50 μl-100 μl, 50 μl-500 μl, 50 μl-1000 μl, 100 μl-200 μl, 100 μl-500 μl, 100 μl-1000 μl, 200 μl-500 μl, 200 μl-1000 μl, 500 μl-900 μl, 500 μl-1000 μl, 1 ml-1000 ml, 1 ml-50 ml, 1 ml-500 ml, 1 ml-900 ml, 50 ml-100 ml, 50 ml-500 ml, 50 ml-1000 ml, 100 ml-200 ml, 100 ml-500 ml, 100 ml-1000 ml, 200 ml-500 ml, 200 ml-1000 ml, 500 ml-900 ml, 500 ml-1000 ml.

Valves

In methods and microfluidic devices of some embodiments, the microfluidic device comprise one or more valves. As used herein, "valve" encompasses mechanical valves, as well as electromagnetic fields, conditional diffusion membranes, and other devices understood in the art to permit and restrict liquid flow. In some embodiments, a valve separates the fluidic reservoir from a discrete coding substrate, and controls the flow of fluids between the discrete coding substrate and fluidic reservoir. Each valve may be disposed on a fluidic path between a discrete coding substrate and the fluidic reservoir. Each valve may be configured to regulate flow between the discrete coding substrate and the fluidic reservoir. In some embodiments, each discrete coding substrate is separated from the fluidic reservoir by a valve configured to control the flow of fluid from the discrete coding substrate to the fluidic reservoir. In some embodiments, a valve as described herein comprises a hydraulic, pneumatic, manual, solenoid, motor valve, or socket ball valve, or a combination of two or more of these. In some embodiments, a valve as described herein comprises a two-port, three-port, or four-port valve. In some embodiments, a valve as described herein comprises a microfluidic valve or microvalve, such as a solenoid microvalve, screw microvalve, pneumatic microvalve, or a combination of two or more of these. In some embodiments, a valve is binary, so that flow through the valve is either "on" or "off." In some embodiments, a valve regulates the rate of flow though the valve.

In some embodiments, valves 520a, 520b, 520c are disposed between the fluidic reservoir 540 and the coding substrates 510a, 510b, 510c. For example, in some embodiments, valves are disposed between the fluidic reservoir and the coding substrates, and between the coding substrates and the fluidic reservoir. A single valve between the fluidic reservoir and the coding substrates may be opened to flush some or all of the coding substrates with a transcription/translation fluid, and then only valves between coding substrates of interest and the reservoir are opened after incubation, so that only antimicrobial peptides and/or bacteriocins of interest are included in a specified mixture of antimicrobial peptides and/or bacteriocins are permitted to flow into the fluidic reservoir.

In some embodiments, separate valves are disposed between the transcription/translation solution and the discrete coding substrates, so that separate valves can be opened and closed to place only discrete coding substrates of interest in contact with the transcription/translation solution, and thus produce a specified antimicrobial peptides and/or bacteriocins mixture upon incubation of the discrete coding substrates of interest with the transcription/translation solution. In view of this disclosure, the skilled artisan will appreciate that there are multiple ways for valves to regulate flow to and from the discrete coding substrates so that only antimicrobial peptides and/or bacteriocins of the specified mixture of antimicrobial peptides and/or bacteriocins are obtained in a mixture in the fluidic reservoir 540.

Smart bandages can comprise a processor, a sensor (such as a pH and/or temperature sensor), and a source of therapeutic agent, in which the processor is configured to control the administration of therapeutic agent. For example, the sensor can detect inflammation, and the processor can administer quantities of anti-inflammatory agent in response to the detected inflammation. Examples of suitable smart bandages may be found on the world wide web at www.cnet.com/news/this-smart-bandage-can-deliver-drugs-monitor-chronic-wounds, which is hereby incorporated by reference in its entirety. In some embodiments, the microfluidic device as described herein comprises a smart bandage. In some embodiments, the microfluidic device or system is configured to be placed in fluid communication with a smart bandage. For example, the port of the microfluidic device can be placed in fluid communication with a reservoir of a smart bandage, so that the smart bandage can control delivery of the specified mixture of antimicrobial peptides and/or bacteriocins to a subject. In some embodiments, the microfluidic device is comprised by a disposable cartridge that further comprises a smart bandage, and is in fluid communication with the fludic reservoir, so that a specified mixture of antimicrobial peptides and/or bacteriocins can be delivered to a subject via the smart bandage. Optionally, the disposable cartridge comprising the smart bandage and the microfluidic device comprises an adhesive for direct application to a tissue of a subject, for example skin. As such, the microfluidic device of some embodiments is for medical use. In some embodiments, the smart bandage monitors a wound or site of inflammation and delivers a specified mixture of antimicrobial peptides and/or bacteriocins as described herein to the skin or to a wound site.

Processors

A processor 595 can regulate valves in microfluidic devices and methods of some embodiments. The processor can be configured to, based on the specified mixture of antimicrobial peptides and/or bacteriocins, configure the valves to place the discrete coding substrates that encode the antimicrobial peptides and/or bacteriocins of the mixture, but not other discrete coding substrates, in fluidic communication with the fluidic reservoir. In some embodiments, the processor is configured to permit incubation of the in vitro transcription/translation solution with the discrete coding substrates that encode the antimicrobial peptides and/or bacteriocins of the mixture, so that the specified antimicrobial peptides and/or bacteriocins of the mixture are produced. In some embodiments, the processor is configured to permit flow of the specified antimicrobial peptides and/or bacteriocins through the valves into the fluidic reservoir. In some embodiments, the processor is configured to control flow of fluid in the fluidic reservoir. In some embodiments, the flow comprises movement of a fluid comprising the specified antimicrobial peptides and/or bacteriocins into and/or within the fluidic reservoir, thus producing the specified mixture of antimicrobial peptides and/or bacteriocins. For example, the flow can mix bacteriocins from different coding substrates once they are present in the fluidic reservoir, thus producing the specified mixture of antimicrobial peptides and/or bacteriocins. In some embodiments, the microfluidic device comprises a processor. In some embodiments, the microfluidic device does not itself comprise a processor, but is configured to be placed in data communication with the processor.

It is contemplated that a specified mixture of antimicrobial peptides and/or bacteriocins according to methods and microfluidic devices of some embodiments herein can be formed from two or more submixtures. For example, a first submixture of bacteriocins A and B in a ratio of 1:1 can be combined with the same quantity of a second submixture of bacteriocins B and C in a ratio of 1:1, thus producing a mixture of bacteriocins A, B, and C in ratios of 1:2:1. In accordance with the methods and microfluidic devices of some embodiments described herein, the specified mixture of antimicrobial peptides and/or bacteriocins comprises two or more submixtures each comprising a subset of antimicrobial peptides and/or bacteriocins, and the processor is configured to permit flow of each submixture into the fluidic reservoir, thereby producing the specified mixture of antimicrobial peptides and/or bacteriocins. In some embodiments, the specified mixture of antimicrobial peptides and/or bacteriocins comprises a sum of the submixtures of bacteriocins in a specified stoichiometry, and combination of the submixtures yields the mixture in the specified stoichiometry.

Methods for Producing a Specified Mixture of Antimicrobial Peptides and/or Bacteriocins In some embodiments, a method for producing a specified mixture of antimicrobial peptides and/or bacteriocins is provided. The method may include producing bacteriocins of the specified mixture, but not other bacteriocins, by in vitro transcription and translation of bacteriocins encoded by discrete coding substrates, and then mixing the selected bacteriocins from the in vitro transcription and translation to produce the specified mixture of antimicrobial peptides and/or bacteriocins. In some embodiments, the method includes producing bacteriocins by in vitro transcription and translation of bacteriocins encoded by discrete coding substrates, and then mixing bacteriocins of the specified mixture, but not other bacteriocins (if any) to produce the specified mixture of antimicrobial peptides and/or bacteriocins. In some embodiments, the method for producing a specified mixture of antimicrobial peptides and/or bacteriocins is performed on a microfluidic device as described herein. In some embodiments, the method is for producing a specified mixture of bacteriocins, and not antimicrobial peptides. In some embodiments, the method is for producing a specified mixture of antimicrobial peptides, and not bacteriocins. In some embodiments, the method is for producing a specified mixture of bacteriocins and antimicrobial peptides.

Figure 7:
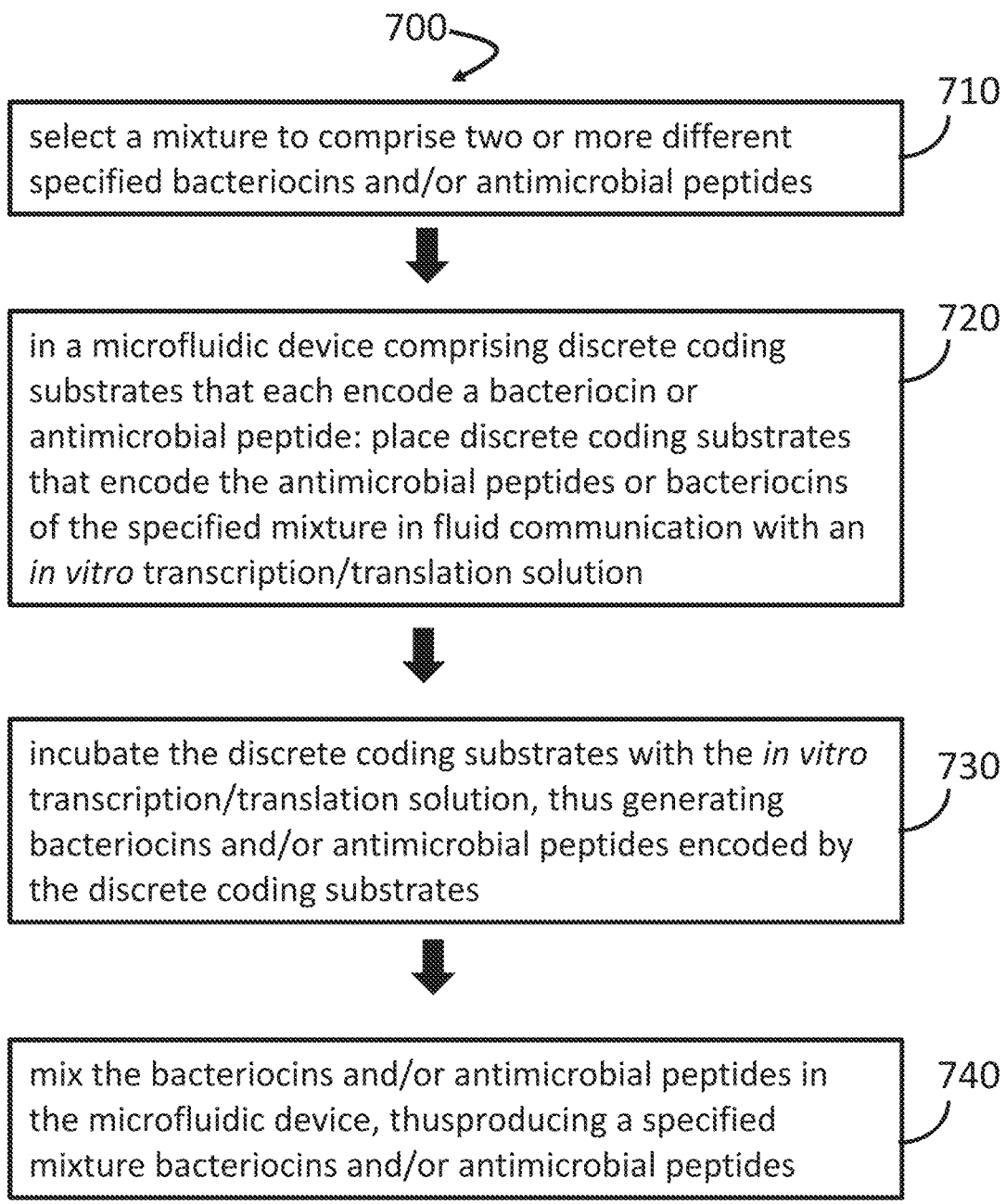
FIG. 7 is a flow diagram illustrating a method for producing a specified mixture of antimicrobial peptides and/or bacteriocins according to some embodiments herein.

FIG. 7 is a flow diagram illustrating a method for producing a specified mixture of antimicrobial peptides and/or bacteriocins 700 of some embodiments. The method can comprise selecting the specified mixture to comprise two or more different specified bacteriocins 710; in a microfluidic device comprising discrete coding substrates that each encode an antimicrobial peptide and/or bacteriocin: placing discrete coding substrates that encode the antimicrobial peptides and/or bacteriocins of the mixture, but not other discrete coding substrates, in fluid communication with an in vitro transcription/translation solution 720; incubating the discrete coding substrates with the in vitro transcription/translation solution, thus generating antimicrobial peptides and/or bacteriocins encoded by the discrete coding substrates 730; and mixing the bacteriocins in the microfluidic device, thus producing the specified mixture of antimicrobial peptides and/or bacteriocins 740.

In some embodiments, the method of producing a specified mixture of antimicrobial peptides and/or bacteriocins further comprises producing two or more submixtures each comprising a subset of the specified mixture of antimicrobial peptides and/or bacteriocins, and combining the submixtures to produce the specified mixture of antimicrobial peptides and/or bacteriocins. For example, the method can comprise performing (a) through (d) as follows to produce a first specified submixture of antimicrobial peptides and/or bacteriocins: (a) selecting a submixture to comprise two or more different specified antimicrobial peptides and/or bacteriocins; (b) in a microfluidic device comprising discrete coding substrates that each encode an antimicrobial peptide and/or bacteriocin: placing discrete coding substrates that encode the antimicrobial peptides and/or bacteriocins of the submixture, but not other discrete coding substrates, in fluid communication with an in vitro transcription/translation solution; (c) incubating the discrete coding substrates with the in vitro transcription/translation solution, thereby generating antimicrobial peptides and/or bacteriocins encoded by the discrete coding substrates; (d) mixing the antimicrobial peptides and/or bacteriocins in the microfluidic device, thereby producing the specified submixture of antimicrobial peptides and/or bacteriocins; repeating (a) through (d) to produce a second specified submixture of antimicrobial peptides and/or bacteriocins; and combining the first specified submixture of antimicrobial peptides and/or bacteriocins the second specified submixture of antimicrobial peptides and/or bacteriocins to produce the specified mixture of antimicrobial peptides and/or bacteriocins.

In some embodiments of the method of producing a specified mixture of antimicrobial peptides and/or bacteriocins, the selecting further comprises selecting a stoichiometry of the two or more different specified antimicrobial peptides and/or bacteriocins. In some embodiments, the specified mixture of antimicrobial peptides and/or bacteriocins comprises a specified stoichiometry, and combining the submixtures results in the specified stoichiometry. For example, a first submixture of bacteriocin "A" can be combined with a second submixture of bacteriocins "A" and "B" in a ratio of 1:1, to produce a specified mixture of antimicrobial peptides and/or bacteriocins "A" and "B" in a ratio of 2:1.

In some embodiments of the method of producing a specified mixture of antimicrobial peptides and/or bacteriocins, incubating the discrete coding substrates with the in vitro transcription/translation solution comprises flowing the in vitro transcription/translation solution to each discrete coding substrate encoding a bacteriocin of the mixture. In some embodiments, the method comprises placing the discrete coding substrates that encode the antimicrobial peptides and/or bacteriocins of the mixture, but not other discrete coding substrates, in fluid communication with an in vitro transcription/translation solution, comprising (i) opening valves so as to place a source of the in vitro transcription/translation solution in fluid communication with the discrete coding substrates; (ii) closing valves so as to inhibit fluid communication between the source of the in vitro transcription/translation solution and the other discrete coding substrates, or a combination of (i) and (ii). In some embodiments, mixing the antimicrobial peptides and/or bacteriocins in the microfluidic device comprises opening a valve to place the discrete coding substrates in fluid communication with a fluidic reservoir, wherein the antimicrobial peptides and/or bacteriocins are mixed in the fluidic reservoir.

In some embodiments, the method of producing a specified mixture of antimicrobial peptides and/or bacteriocins further comprises screening the mixture of antimicrobial peptides and/or bacteriocins in situ for a desired effect. In some embodiments, the screening is for inhibition of the growth or reproduction of a pathogenic microbial organism in a microbiome of a subject, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract. For example, the pathogenic bacteria can be a rapidly evolving bacteria or a bacteria exhibiting antibiotic resistance, for example MRSA. In some embodiments, the screening is for an absence of deleterious effects of the mixture of antimicrobial peptides and/or bacteriocins on a microbiome of a subject, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract. In some embodiments, the screening is performed in real time. For example, the screening can be performed withing 120 minutes, 60 minutes, 30 minutes, 15 minutes, 10 minutes, 5 minute, or 1 minute of the specified mixture of antimicrobial peptides and/or bacteriocins being generated. In some embodiments, the screening is for stabilization of a antimicrobial peptides and/or bacteriocins or for destruction of a microbial biofilm. In some embodiments, the screening is for enhancement of growth or reproduction of a non-pathogenic microbial organism in a microbiome of a subject, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract.

Some microbial organisms can evolve quickly. Advantageously, the methods, devices and systems described herein can be used to combat rapidly evolving microbial organisms by rapidly producing mixtures of specified bacteriocins that are tailored to an infection of a subject by the microbial organism. In some embodiments, the subject is infected with a *staphylococcus* such as MRSA, influenza virus, West Nile virus, or Zika virus. In some embodiments, the subject is diabetic and/or has an infection in an extremity such as a hand or foot.

Also envisioned is the use of antimicrobial peptides and/or bacteriocins in conjunction with conventional chemical antibiotics and/or phage antibiotics. In some embodiments, a method as described herein includes treatment of a microbial infection with a combination of a mixture of specified antimicrobial peptides and/or bacteriocins and a chemical antibiotic and/or a phage. Some embodiments comprise delivering the mixture of specified antimicrobial peptides and/or bacteriocins, in combination with a chemical antibiotic and/or a phage antibiotic, to a subject. Moreover, in some embodiments, a microfluidic device and/or system as described herein further comprises a conventional antibiotic, for example, an phage antibiotic or a small-molecule antibiotic such as a metabolite. In some embodiments, the microfluidic device and/or system further comprises a reservoir of antibiotic. The antibiotic can be selected from the group consisting of Amoxicillin, Amoxicillin/clavulanic acid (amoxicillin+clavulanic acid), Ampicillin, Benzathine benzylpenicillin, Benzylpenicillin, Cefalexin, Cefazolin, Cefixime, Cefotaxime, Ceftriaxone, Cloxacillin, Penicillin, Phenoxymethylpenicillin (penicillin V), Piperacillin/tazobactam, Procaine benzylpenicillin, Ceftazidimea, Meropenema, Aztreonama, Imipenem/cilastatin, Amikacin, Azithromycin[, Chloramphenicol, Ciprofloxacin, Clarithromycin, Clindamycin, Doxycycline, Erythromycin, Gentamicin, Metronidazole, Nitrofurantoin, Spectinomycin, Trimethoprim/sulfamethoxazole, Trimethoprim, Vancomycin, Clofazimine, Dapsone, Rifampicin, Ethambutol/isoniazid, Ethambutol/isoniazid/pyrazinamide/rifampicin, Ethambutol/isoniazid/rifampicin, Isoniazid, Isoniazid/pyrazinamide/rifampicin, Isoniazid/rifampicin, Pyrazinamide, Rifabutin, Rifampicin, Rifapentine, Amikacin, Bedaquiline, Capreomycin, Clofazimine, Cycloserine, Delamanid, Ethionamide, Kanamycin, Levofloxacin, Linezolid, Moxifloxacin, p-aminosalicylic acid, rifabutin, rifapentine, rifalazil, rifaximin. Streptomycin, a phage, or a combination of two or more of these antibiotics.

Some embodiments of the method of producing a specified mixture of antimicrobial peptides and/or bacteriocins further comprise delivering the specified mixture of antimicrobial peptides and/or bacteriocins to a wound via a tubing or membrane, thereby cleaning or dressing the wound. For example, the specified mixture of antimicrobial peptides and/or bacteriocins may be placed on a cut or open sore, and then the cut or sore may be closed and/or bandaged.

Some embodiments of the method of producing a specified mixture of antimicrobial peptides and/or bacteriocins include a wash of the microfluidic device. The wash can be with a wash fluid. For example, some embodiments include an incubation step with a transcription solution, followed by a wash step, followed by a separate incubation with a translation solution.

In some embodiments, the method further comprises administering the specified mixture of antimicrobial peptides and/or bacteriocins to a subject in need of treatment. For example, the subject can have an infection such as an infected wound, a surgical incision, and infection of the extremities associated with diabetes, and/or a biofilm. The specified mixture of antimicrobial peptides and/or bacteriocins can be selected to target the microbial organism(s) of the infection (or selected as a candidate to target the microbial organism(s) of the infection), and can be produced in a microfluidic device as described herein. The specified mixture of antimicrobial peptides and/or bacteriocins can be administered to the subject as described herein, for example at or near the site of infection. In some embodiments, the microfluidic device itself is directly applied to the infection (for example, as a smart bandage as described herein). In some embodiments, the method further comprises selecting the subject as having an infection in need of treatment. The method can further comprise selecting a specified mixture of antimicrobial peptides and/or bacteriocins to target the infection, and producing the specified mixture in a microfluidic device as described herein. Also contemplated are are medical uses of the microfluidic device for treating, inhibiting, preventing and/or reducing the risk of an infection. In some embodiments, the method (or medical use) comprises administering the specified mixture of antimicrobial peptides and/or bacteriocins and an antibiotic as described herein (for example a small molecule antibiotic and/or a phage) to the subject.

In some embodiments, the microfluidic device is for veterinary use, for example to produce a specified mixture of antimicrobial peptides and/or bacteriocins to treat an infection of a domestic animal or a farm animal, and/or to promote growth of the animal. Advantageously, uses of the specified mixture of antimicrobial peptides and/or bacteriocins in farm animals can avoid the use of antibiotics in food production. As noted in World Health Organization recommendations, doing so can reduce the development and proliferation of antibiotic-resistant microbial o.

In some embodiments, the microfluidic device is for use in a small fermenter (e.g., a fermenter less than or equal to 100 liters, 50 liters, 40 liters, 30 liters, 20 liters, 10 liters, 5 liters, 2 liters, or 1 liters in volume, including ranges between any two of the listed values), for example to produce specified mixtures of bacteriocins to target a contaminating organism in the small fermenter.

In some embodiments, the microfluidic device is for use in sterilizing medical devices. For example, the specified mixture of antimicrobial peptides and/or bacteriocins can be selected to target contaminants, such as MRSA on the medical device, and can be applied to the medical device on-site, for example at a hospital. In some embodiments, the microfluidic device is for use in pre-treating an implant with a specified mixture of antimicrobial peptides and/or bacteriocins, so as to inhibit or prevent infection and/or biofilm formation.

In some embodiments, the microfluidic device is for use in defense against a pathogen, for example in an epidemic, or in bioterrorism defense. Specified mixtures of bacteriocins directed against the pathogen (e.g., bioterrorism agent) can be distributed to systems as described herein manually or automatically, and the specified mixtures of bacteriocins targeting the pathogen (e.g., bioterrorism agent) can be produced in microfluidic devices at or near the site of the pathogen (e.g., bioterrorism agent).

In some embodiments, the method further comprises mixing the specified mixture of antimicrobial peptides and/ or bacteriocins with another reagent or antimicrobial compound to produce a final mixture. For example, the specified mixture of antimicrobial peptides and/or bacteriocins may be combined with a chemical or a natural fluid. In some embodiments, the specified mixture of antimicrobial peptides and/or bacteriocins is combined with an antibiotic drug or phage to produce the final mixture. In some embodiments, the final mixture is part of a formulation for a therapy such as, for example, an anti-pain therapy.

Example 1

A nucleic acid is provided encoding one copy of the coding sequence of the bacteriocin Subtilin, two copies of the coding sequence of the bacteriocin Bavaricin-MN, and one copy of the coding sequence for the quorum sensing factor BsEDF all in a single reading frame. The nucleic acid further encodes cleavage sites for Caspase 2 in the same reading frame, which flank each bacteriocin coding sequence and the BsEDF coding sequence. As such, the nucleic acid encodes a pro-polypeptide that comprises one copy of Subtilin, two copies of Bavaricin-MN, and one copy of BsEDF, each flanked by Caspase 2 cleavage sites. The nucleic acid is expressed in an $E.\ coli$ cell, which does not comprise coding sequence for the immunity modulators for either of Subtilosin-A or Bavaricin-MN, and thus does not produce functional immunity modulators for these bacteriocins. The pro-polypeptide is produced by the $E.\ coli$, and contains Subtilin and Bavaricin-MN in their inactive forms. The pro-polypeptide is purified by way of its His tag using a nickel-containing substrate. The purified pro-polypeptide is then cleaved using Caspase 2, producing a composition that comprises Subtilin, Bavaricin-MN, and BsEDF in a 1:2:1 ratio. The composition is added to an industrial feedstock to prevent the proliferation of undesired microbial organisms (via the bacteriocins), and to control the growth of genetically modified $B.\ subtilis$ (via the BsEDF).

Example 2

It is determined that a ratio of the bacteriocins Mundticin, Serracin-P, Thuricin-17, and Plantaricin J of 1:2:3:4 is useful for targeting a population of undesired microbial cells in animal food during storage. A nucleic acid encoding one copy of the coding sequence of Mundticin, two copies of the coding sequence of Serracin-P, three copies of the coding sequence of Thuricin-17, and four copies of the coding sequence Plantaricin J is synthesized. All of the bacteriocin coding sequences are in a single reading frame, and each bacteriocin coding sequence is separated from the other bacteriocin coding sequences by sequences encoding Granzyme B cleavage sites. The nucleic acid also encodes GST on the 3' end of the open reading frame, and immediately downstream of a Granzyme B cleavage site coding sequence. Thus, the nucleic acid encodes a pro-peptide comprising Mundticin, Serracin-P, Thuricin-17, Plantaricin J in a 4:3:2:1 ratio, respectively, along with a C-terminal GST tag. The nucleic acid is expressed in an in vitro translation system, so as to produce the pro-polypeptide. The pro-polypeptide is purified using GSH-coated beads. The pro-polypeptide is then cleaved by GranzymeB, producing a solution comprising active Mundticin, Serracin-P, Thuricin-17, and Plantaricin J in a ratio of 1:2:3:4, respectively. The cleavage site immediately adjacent to the GST tag is also cleaved, so that none of the bacteriocins comprises GST. The composition comprising the bacteriocins in the 1:2:3:4 ratio is added to the animal food, thus targeting the population of undesired microbial cells in the animal food.

Example 3

A microfluidic device is provided that comprises 244 chambers. Each chamber comprises a discrete coding substrate. Each discrete coding substrate is a chip, each chip comprising 10,000-20,000 DNAs. Molecules, each encoding a bacteriocin of Table 1.2. The DNA molecules in each chamber encode separate bacteriocins compared to the DNA molecules in each of the other chambers. Each of the chambers is connected by a valve to a fluidic reservoir. The fluidic reservoir is also connected by a valve to a transcription/translation solution housed in a transcription/translation solution chamber. The device includes a processor configured to open the valve connecting the fluidic reservoir to the transcription/translation solution to allow the transcription/translation solution to flow into the fluidic reservoir, close the valve connecting the fluidic reservoir to the transcription/translation solution to prevent fluid from flowing back into the transcription/translation solution chamber, open valves connecting the fluidic reservoir to chambers housing the selected coding substrates to allow transcription/translation solution to flow from the fluidic reservoir into the chambers housing the selected coding substrates, incubate selected coding substrates the at 37° C. thereby producing bacteriocins from the selected coding substrates, and open one or more valves such as the valves connecting the coding substrates to the fluidic reservoir, to release bacteriocins into the fluidic reservoir and/or a receptacle.

The device is connected electronically or wirelessly to a user input device such as a phone, touchscreen, keyboard, button, mouse, or computer. The processor selects bacteriocins based on user input entered into the user input device, or according to a pre-programmed set of instructions.

Example 4

A device as described herein is used to make a first specified mixture of bacteriocins. The bacteriocins are applied to a transdermal patch that is applied to a subject with a burn. If the burn on the subject does not heal, the device is used to make a second specified mixture of bacteriocins different from the first specified mixture of bacteriocins. The second specified mixture of bacteriocins is then applied to a new transdermal patch that is applied to the burn. Multiple variations of specified mixtures of bacteriocins may be applied to the burn, or to burns of various subjects, depending on whether a particular formulation of bacteriocins is expected to be beneficial for the healing of the burn, or on whether a particular formulation is desired to be tested.

Options

In addition to the items above, the following options are set forth:

1. A method of making bacteriocins, the method comprising expressing a nucleic acid comprising:
   a bacteriocin coding sequence and a second polypeptide coding sequence in a single reading frame, wherein the second polypeptide is a bacteriocin or signal molecule; and
   cleavage site coding sequences disposed between the bacteriocin coding sequence and the second polypeptide coding sequence in the single reading frame, thereby generating a pro-polypeptide comprising the bacteriocin, second polypeptide, and cleavage sites disposed therebetween.

2. The method of option 1, further comprising cleaving the cleavage site, thereby separating the bacteriocin and second polypeptide from each other, and thereby producing a composition comprising the bacteriocin and the second polypeptide.

3. The method of any one of options 1 or 2, wherein the second polypeptide is the bacteriocin.

4. The method of any one of options 1 or 2, wherein the second polypeptide is the signal molecule.

5. The method of any one of options 1-4, wherein the expressing is performed by a microbial cell that does not produce a functional immunity modulator for at least one of the bacteriocins.

6. The method of option 5, wherein the microbial cell does not produce a functional immunity modulator for any of the bacteriocins.

7. The method of any one of options 1-4, wherein the expressing is performed in vitro.

8. The method of any one of options 1-7, wherein at least one of the bacteriocins is inactive when it is part of the pro-polypeptide.

9. The method of any one of options 2-8, further comprising isolating the pro-polypeptide prior to the cleaving.

10. The method of option 9, wherein said isolating comprises affinity purifying the pro-polypeptide, wherein the affinity purification comprises binding an affinity tag encoded by the nucleic acid.

11. The method of any one of options 1-8, wherein the nucleic acid comprises three bacteriocin coding sequences in the single reading frame.

12. The method of any one of options 1-3 or 5-11, wherein at least two of the bacteriocins are different from each other.

13. The method of any one of options 2-12, wherein the composition comprises a desired ratio of bacteriocins, or a desired ratio of signal molecules and bacteriocins.

14. The method of option 13, wherein at least a portion the desired ratio is achieved by a ratio of bacteriocin coding sequences, or bacteriocin and signal molecule coding sequences in the single reading frame of the nucleic acid.

15. The method of any one of options 12-14, wherein the desired ratio is further achieved by a second nucleic acid comprising a ratio of bacteriocins coding sequences and further comprising cleavage sites between the bacteriocin coding sequences.

16. The method of option 15, wherein the desired ratio is achieved by a ratio of bacteriocin coding sequences in the single reading frame of the nucleic acid.

17. The method of any one of options 12-16, wherein the desired ratio of bacteriocins is selected to target an undesired microbial organism or population of undesired microbial organisms, and/or wherein the desired ratio of bacteriocins is selected to balance a population of a microbiome of an animal, a human organ, a plant root, or soil.

18. The method of any one of options 12-16, wherein the desired ratio of bacteriocins and signal molecules is selected to control genetic drift of a target microbial cell, and stimulate growth or production of a producing cell.

19. The method of any one of options 10-18, wherein the desired ratio comprises a ratio of a first bacteriocin to a second bacteriocin of 1:2, 1:3, 1:4, 1:5, 1:6, 1:7, 1:8, 1:9, 1:10, 2:3, 2:5, 2:7, 2:9, 3:4, 3:5, 3:7, 3:8, 3:10, 4:5, 4:7, 4:9, 5:6, 5:7, 5:8, 5:9, 6:7, 7:8, 7:9, 7:10, 8:9, or 9:10, wherein the first bacteriocin is different from the second bacteriocin.

20. The method of any one of options 1-18, wherein the cleavage sites are for a wild-type, variant, or synthetic cleavage enzyme, such as an endopeptidase.

21. The method of any one of options 1-20, wherein the cleavage sites are for a cleavage enzyme selected from the group consisting of: Arg-C proteinase, Asp-N endopeptidase, BNPS-Skatole, Caspase 1, Caspase 2, Caspase 3, Caspase 4, Caspase 5, Caspase 6, Caspase 7, Caspase 8, Caspase 9, Caspase 10, Chymotrypsin-high specificity, Clostripain (Clostridiopeptidase B), CNBr, Enterokinase, Factor Xa, Formic acid, Glutamyl endopeptidase, GranzymeB, Hydroxylamine, Iodosobenzoic acid, LysC, Neutrophil elastase, NTCB (2-nitro-5-thiocyanobenzoic acid), Pepsin (pH1.3), Pepsin (pH>2), Proline-endopeptidase, Proteinase K, Staphylococcal peptidase I, Thermolysin, Thrombin, or Trypsin.

22. The method of any one of options 1-21, wherein the cleavage sites are for a single cleavage enzyme, and wherein the cleavage enzyme does not cleave within the bacteriocins.

23 The method of any one of options 1-22, wherein at least one cleavage site is for a first cleavage enzyme, and another cleavage site is for a second cleavage enzyme, and wherein neither the first nor the second cleavage enzyme cleaves within the bacteriocins.

24. The method of any one of options 1-23, wherein the composition further comprises a signal molecule, and wherein the nucleotide further comprises:
 a coding sequence for a signal molecule in the single reading frame; and
 a cleavage site sequence disposed between the signal molecule and a bacteriocin coding sequence.

25. The method of any one of options 1-2 or 4-24, wherein the signal molecule is selected from the group consisting of: quorum sensing molecules, signal transduction receptor ligands, growth factors, hormones, and cytokines, and wherein the signal molecule can be wild-type, mutant, or synthetic.

26. The method of any one of options 1-25, wherein the pro-polypeptide has a length of no more than about 2000 amino acids.

27. The method of any one of options 1-26, further comprising expressing a second nucleic acid encoding a second pro-polypeptide comprising two bacteriocins and cleavage sites disposed therebetween, wherein the second pro-polypeptide is different from the first pro-polypeptide.

28. The method of any one of options 2-19 or 24-27, wherein cleaving the pro-polypeptide comprises physical treatment of a peptide linker comprised by the cleavage site, wherein the peptide linker is chemical-sensitive or pH sensitive.

29. The method of any one of options 1-28, further comprising chemically modifying the bacteriocins.

30. The method of option 29, wherein the bacteriocins are chemically modified co-translationally.

31. The method of any one of options 2-30, further comprising chemically modifying the bacteriocins following the cleaving.

32. An isolated nucleic acid comprising:
 a bacteriocin coding sequence and a second polypeptide coding sequence in a single reading frame, wherein the second polypeptide is a bacteriocin or a signal molecule; and
 cleavage site coding sequences disposed between the bacteriocin coding sequences and in the single reading frame.

33. The isolated nucleic acid of option 32, wherein the second polypeptide is the bacteriocin.

34. The isolated nucleic acid of option 32, wherein the second polypeptide is the signal molecule.

35. The isolated nucleic acid of any one of options 32-34, wherein the cleavage site coding sequences encode cleavage sites for a cleavage enzyme, and wherein the bacteriocin coding sequences do not comprise cleavage sites for the cleavage enzyme.

35. The isolated nucleic acid of any one of options 32-35, wherein the nucleic acid comprises three bacteriocin coding sequences in the single reading frame.

36. The isolated nucleic acid of any one of options 32-35, wherein the nucleic acid comprises at least 5, 10, 15, or 20 bacteriocin sequences in the single reading frame.

37. The isolated nucleic acid of any one of options 32-36, wherein a cleavage site coding sequence is disposed in frame between any two adjacent bacteriocin and/or signal molecule coding sequences.

38. The isolated nucleic acid of any one of options 32-36, wherein at least two of the bacteriocin sequences encode different bacteriocins from each other.

39. The isolated nucleic acid of option 35, wherein the three bacteriocin sequences are present in a desired ratio or portion of a desired ratio.

40. The isolated nucleic acid of option 39, wherein the desired ratio is selected to target an undesired microbial organism or population of undesired microbial organisms.

41. The isolated nucleic acid of option 39 wherein the desired ratio of bacteriocins is selected to balance a population of a microbiome of an animal, a human organ, a plant root, or soil.

42. The isolated nucleic acid of any one of options 32-41, wherein the cleavage sites are for a wild-type, variant, or synthetic cleavage enzyme, such as an endopeptidase.

43. The isolated nucleic acid of any one of options 32-42, wherein the cleavage sites are for a cleavage enzyme selected from the group consisting of: Arg-C proteinase, Asp-N endopeptidase, BNPS-Skatole, Caspase 1, Caspase 2, Caspase 3, Caspase 4, Caspase 5, Caspase 6, Caspase 7, Caspase 8, Caspase 9, Caspase 10, Chymotrypsin-high specificity, Clostripain (Clostridiopeptidase B), CNBr, Enterokinase, Factor Xa, Formic acid, Glutamyl endopeptidase, GranzymeB, Hydroxylamine, Iodosobenzoic acid, LysC, Neutrophil elastase, NTCB (2-nitro-5-thiocyanobenzoic acid), Pepsin (pH1.3), Pepsin (pH>2), Proline-endopeptidase, Proteinase K, Staphylococcal peptidase I, Thermolysin, Thrombin, or Trypsin.

44. The isolated nucleic acid of any one of options 42-43, wherein a first cleavage site coding sequence encodes a first cleavage site is for a first cleavage enzyme, and wherein a second cleavage site coding sequence encodes a cleavage site for a second cleavage enzyme that is different from the first cleavage enzyme, and wherein the bacteriocins do not comprise a cleavage site for any of the first or second cleavage enzyme.

45. The isolated nucleic acid of any one of options 32-41, wherein the cleavage sites comprise a pH- or chemically-sensitive linker.

46. The isolated nucleic acid of any one of options 32, 33, or 35-44, wherein the isolated nucleic acid further comprises a coding sequence for a signal molecule in the single reading frame, wherein a cleavage site coding sequences is disposed between the coding sequence for signal molecule and an adjacent bacteriocin coding sequence.

47. The isolated nucleic acid of any one of options 32 or 24-46, wherein the signal molecule is selected from the group consisting of: quorum sensing molecules, signal transduction receptor ligands, growth factors, hormones, and cytokines, and wherein the signal molecule can be wild-type, mutant, or synthetic.

48. A microbial cell, comprising a promoter operably linked to the isolated nucleic acid of any one of options 32-47, wherein the isolated microbial cell does not produce a functional immunity modulator for a bacteriocin encoded by the isolated nucleic acid.

49. The microbial cell of option 48, wherein the cell does not produce a functional immunity modulator for any of the bacteriocins encoded by the isolated nucleic acid.

50. An isolated pro-polypeptide comprising:
 two bacteriocins, and/or a bacteriocin and a signal molecule;

cleavage sites disposed between the bacteriocins and/or the bacteriocin and the signal molecule; and
an affinity tag.

51. The isolated pro-polypeptide of option 50, wherein the pro-polypeptide comprises the two bacteriocins.

52. The isolated pro-polypeptide of option 50, wherein the pro-polypeptide comprises the bacteriocin and the signal molecule.

53. The isolated pro-polypeptide of any one of options 50-52, wherein the pro-polypeptide comprises three bacteriocins.

54. The isolated pro-polypeptide of any one of options 50-52, wherein the pro-polypeptide comprises at least 5, 10, 15, or 20 bacteriocins.

55. The isolated pro-polypeptide of any one of options 50, 51, 53, or 54, wherein the pro-polypeptide comprises a signal molecule.

56. The isolated pro-polypeptide of any one of options 50-55, wherein the cleavage sites are for a cleavage enzyme, and wherein the bacteriocin coding sequences do not comprise cleavage sites for the cleavage enzyme.

57. The isolated pro-polypeptide of any one of options 50-55, wherein a cleavage site is for a first cleavage enzyme, and wherein another cleavage site is for a second cleavage enzyme different from the first cleavage enzyme, and wherein the bacteriocins do not comprise a cleavage site for any of the first or second cleavage enzymes.

58. The isolated pro-polypeptide of any one of options 50-57, further comprising a co-translational or post-translational modification.

59. A composition comprising two more bacteriocins in a ratio selected to target a microbial cell or populations of microbial cells,
wherein each of the bacteriocins comprises, at its N-terminus, C-terminus, or N-terminus and C-terminus, a portion of a cleavage sequence that has been cleaved, wherein the portions of cleavage sequences at the N-, C-, or N- and C-termini of the bacteriocins are for cleavage sites of the same or different cleavage enzyme.

60. The composition of option 59, wherein at least some of the bacteriocins further comprise a tag.

61. The composition of option 60, wherein the tag is selected from the group consisting of affinity tags, a signal sequence, or a stability tag.

62. The composition of any one of options 59-61, further comprising a signal molecule in a desired ratio with the bacteriocins, wherein the signal molecule comprises, at its N-terminus, C-terminus, or N-terminus and C-terminus, a portion of a cleavage sequence that has been cleaved, wherein the portions of cleavage sequences at the N-, C-, or N- and C-termini of the signal molecule are for cleavage sites of the same or different cleavage enzymes 63. The composition of any one of options 59-62, wherein the ratio of bacteriocins is selected to target an undesired microbial organism or population of undesired microbial organisms.

64. The composition of any one of options 59-63, wherein the ratio of bacteriocins is selected to balance a population of a microbiome of an animal, a human organ, a plant root, or soil.

65. The composition of option 64, wherein the composition is formulated for topical or oral administration to a human subject.

66. The composition of option 64 or 65, wherein the composition is formulated for use in balancing a population of a microbiome of an animal, a human organ, a plant root, or soil.

67. A method for producing a specified mixture of bacteriocins and/or antimicrobial peptides, the method comprising:
selecting the mixture to comprise two or more different bacteriocins and/or antimicrobial peptides;
in a microfluidic device comprising discrete coding substrates that each encode a bacteriocin or antimicrobial peptide: placing discrete coding substrates that encode the antimicrobial peptides or bacteriocins of the specified mixture in fluid communication with an in vitro transcription/translation solution;
incubating the discrete coding substrates with the in vitro transcription/translation solution, thereby generating antimicrobial peptides and/or bacteriocins encoded by the discrete coding substrates; and
mixing the antimicrobial peptides and/or bacteriocins in the microfluidic device, thereby producing the specified mixture of antimicrobial peptides and/or bacteriocins.

68. The method of option 67, further comprising:
producing two or more submixtures each comprising a subset of the specified mixture of antimicrobial peptides and/or bacteriocins; and
combining the submixtures to produce the specified mixture of antimicrobial peptides and/or bacteriocins.

69. The method of option 67 or 68, wherein selecting further comprises selecting a stoichiometry of the two or more different antimicrobial peptides and/or bacteriocins of the specified mixture.

70. The method of any one of options 68-69, wherein the specified mixture of antimicrobial peptides and/or bacteriocins comprises a specified stoichiometry, and wherein combining the submixtures results in the specified stoichiometry.

71. The method of any one of options 67-70, wherein the discrete coding substrates are comprised within separate chambers.

72. The method of any one of options 67-71, wherein the discrete coding substrates comprise nucleic acids immobilized thereon.

73. The method of any one of options 67-72, wherein discrete coding substrated encoding antimicrobial peptides and/or bacteriocins of the specified mixture, but not other discrete coding substrates, are placed in fludic communication with the in vitro transcription/translation solution.

74. The method of any one of options 67-73, wherein incubating the discrete coding substrates with the in vitro transcription/translation solution comprises flowing the in vitro transcription/translation solution into each chamber.

75. The method of any one of options 67-74, wherein the in vitro transcription/translation solution comprises an in vitro transcription reagent and/or an in vitro translation reagent.

76. The method of any one of options 67-75, wherein placing the discrete coding substrates that encode the antimicrobial peptides and/or bacteriocins of the specified mixture in fluid communication with an in vitro transcription/translation solution comprises (i) opening valves so as to place a source of the in vitro transcription/translation solution in fluid communication with the discrete coding substrates; (ii) closing valves so as to inhibit fluid communication between the source of the in vitro transcription/translation solution and the other discrete coding substrates, or a combination of (i) and (ii).

77. The method of any one of options 67-76, wherein mixing the antimicrobial peptides and/or bacteriocins in the microfluidic device comprises opening a valve to place the discrete coding substrates in fluid communication with a fluidic reservoir, wherein the antimicrobial peptides and/or bacteriocins are mixed in the fluidic reservoir.

78. The method of any one of options 67-77, further comprising screening the mixture of antimicrobial peptides and/or bacteriocins in situ for a desired effect.

79. The method of option 78, wherein the screening is for inhibition of the growth or reproduction of a pathogenic microbial organism in a microbiome of a subject, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract.

80. The method of option 78, wherein the screening is for an absence of deleterious effects of the mixture of antimicrobial peptides and/or bacteriocins on a microbiome of a subject, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract.

81. The method of option 78, wherein said screening is performed in real time.

82. The method of option 78, the screening is for stabilization of an antimicrobial peptide and/or bacteriocin or for destruction of a microbial biofilm.

83. The method of option 82, wherein one or more of the discrete coding substrates encodes an auxiliary protein with anti-protease activity.

84. The method of option 78, wherein the screening is for enhancement of growth or reproduction of a non-pathogenic microbial organism in a microbiome of a subject, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract.

85. The method of option 84, wherein one or more of the discrete coding substrates encodes an auxiliary protein that attracts the non-pathogenic microbial organism, or that enhances growth or reproduction of the non-pathogenic microbial organism in the microbiome of a subject.

86. The method of any one of options 67-85, further comprising delivering the specified mixture of antimicrobial peptides and/or bacteriocins to a wound via a tubing or membrane, thereby cleaning or dressing the wound.

87. A microfluidic device for producing a specified mixture of antimicrobial peptides and/or bacteriocins, the device comprising:
discrete coding substrates that each encode an antimicrobial peptide and/or bacteriocin;
an in vitro transcription/translation solution;
a fluidic reservoir; and
valves each disposed on a fluidic path between a discrete coding substrate and the fluidic reservoir, each valve configured to regulate flow between the discrete coding substrate and the fluidic reservoir, wherein the device is configured to be placed in data communication with a processor configured to:
based on the specified mixture of antimicrobial peptides and/or bacteriocins, configure the valves to place the discrete coding substrates that encode the antimicrobial peptides and/or bacteriocins of the mixture, but not other discrete coding substrates, in fluidic communication with the fluidic reservoir;
permit incubation of the in vitro transcription/translation solution with the discrete coding substrates that encode the antimicrobial peptides and/or bacteriocins of the specified mixture, whereby the antimicrobial peptides and/or bacteriocins of the specified mixture are produced;
permit flow of the antimicrobial peptides and/or bacteriocins through the valves into the fluidic reservoir; and
control flow of fluid in the fluidic reservoir, wherein the flow comprises movement of the antimicrobial peptides and/or bacteriocins in the fluidic reservoir, thereby producing the specified mixture of antimicrobial peptides and/or bacteriocins in the fluidic reservoir.

88. The microfluidic device of option 87, wherein:
the specified mixture of antimicrobial peptides and/or bacteriocins comprises two or more submixtures each comprising a subset of antimicrobial peptides and/or bacteriocins; and
the processor is configured to permit flow of each submixture into the fluidic reservoir, thereby producing the specified mixture of antimicrobial peptides and/or bacteriocins.

89. The microfluidic device of option 88, wherein the specified mixture of antimicrobial peptides and/or bacteriocins comprises a sum of the subsets of antimicrobial peptides and/or bacteriocins in a specified stoichiometry, and wherein combination of the submixtures yields the specified stoichiometry.

90. The microfluidic device of any one of options 87-89, wherein the discrete coding substrates are comprised within separate chambers.

91. The microfluidic device of any one of options 87-90, wherein the discrete coding substrates comprise nucleic acids immobilized thereon.

92. The microfluidic device of option 91, wherein the discrete coding substrates comprise a material or product selected from the group consisting of a chip, bead, nanoparticle, well, membrane, matrix, plastic, metal, glass, polymer, polysaccharide, and paramagnetic compound.

93. The microfluidic device of any one of options 87-92, wherein the in vitro transcription/translation solution comprises an in vitro transcription reagent and/or an in vitro translation reagent.

94. The microfluidic device of any one of options 87-93, wherein the device is portable.

95. The microfluidic device of any one of options 87-94, wherein one or more of the discrete coding substrates encodes an auxiliary protein comprising a protein for stabilization of antimicrobial peptides and/or bacteriocins, a protein with anti-protease activity, or a protein for destruction of a microbial biofilm.

96. The microfluidic device of any one of options 87-95, wherein one or more of the discrete coding substrates encodes an auxiliary protein that attracts a non-pathogenic microbial organism, or that enhances growth or reproduction of the non-pathogenic microbial organism in a microbiome of a subject, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract.

97. The microfluidic device of any one of options 87-96, wherein the fluidic reservoir is configured to be placed in fluid communication with a tissue of a subject.

98. The microfluidic device of any one of option 97, wherein the tissue comprises a microbiome, such as a skin, gut, gastrointestinal tract, mammary gland, placenta, tissue, biofluid, seminal fluid, uterus, vagina, ovarian follicle, lung, saliva, oral cavity, mucosa, conjunctiva, or biliary tract.

99. The microfluidic device of any one of options 87-98, wherein the fluidic reservoir is configured to be placed in fluid communication with a wound of a subject.

100. The microfluidic device of any one of options 97-99, further comprising a fluidic passage such as a tube or membrane through which the fluidic reservoir is in fluid communication with the microbiome or wound, through which the specified mixture of antimicrobial peptides and/or bacteriocins is capable of being delivered to the microbiome or wound.

101. The microfluidic device of any one of options 87-100, wherein each discrete coding substrate encodes a different antimicrobial peptide and/or bacteriocin.

102. The microfluidic device of any one of options 87-102, wherein a discrete coding substrate comprises the isolated nucleic acid of any of options 32-49.

103. The microfluidic device of any one of options 87-102, wherein a discrete coding substrate encodes the isolated pro-polypeptide of any one of options 50-58.

104. The microfluidic device of any one of options 87-103, further comprising the processor.

105. A system comprising:
the microfluidic device of any one of options 87-104, and
a processor configured to:
based on the specified mixture of antimicrobial peptides and/or bacteriocins, configure the valves to place the discrete coding substrates that encode the antimicrobial peptides and/or bacteriocins of the mixture, but not other discrete coding substrates, in fluidic communication with the fluidic reservoir;
permit incubation of the in vitro transcription/translation solution with the discrete coding substrates that encode the antimicrobial peptides and/or bacteriocins of the specified mixture, whereby the antimicrobial peptides and/or bacteriocins of the specified mixture are produced;
permit flow of the antimicrobial peptides and/or bacteriocins through the valves into the fluidic reservoir; and
control flow of fluid in the fluidic reservoir, wherein the flow comprises movement of the antimicrobial peptides and/or bacteriocins in the fluidic reservoir, thereby producing the specified mixture of antimicrobial peptides and/or bacteriocins in the fluidic reservoir.

106. The system of option 105, wherein the microfluidic device is comprised by a cartridge (or is a cartridge), the system comprising a coupling for placing the cartridge in data communication with the processor.

107. The system of any one of options 105-106 further comprising a reservoir of in vitro transcription/translation solution.

108. A microfluidic device for producing a specified mixture of antimicrobial peptides and/or bacteriocins, the device comprising:
discrete coding substrates that each encode an antimicrobial peptide and/or bacteriocin;
valves each disposed on a fluidic path connected to a discrete coding substrate, each valve configured to regulate flow to or from the discrete coding substrate, and wherein the device is configured to be placed in fluid communication with a fluidic reservoir or an in vitro transcription/translation solution.

109. The microfluidic device of option 108 further comprising a fluidic reservoir or an in vitro transcription/translation solution.

110. The method of option 78, wherein the desired effect comprises antimicrobial activity.

111. The method of option 110, further comprising screening 1, 2, 3, 4, 5, 6, 7, 8, 9, or 10 different mixtures against a microbial infection.

112. The method of any one of options 67-86 further comprising delivering the mixture of specified antimicrobial peptides and/or bacteriocins, in combination with a chemical antibiotic and/or a phage antibiotic, to a subject.

113. The method of any one of options 67-86 wherein the in vitro transcription/translation solution is lyophyilized, and further comprising adding water to the in vitro transcription/translation solution.

114. The microfluidic device of any one of claims 87-104, further comprising a reservoir of chemical or phage antibiotics configured to mix with the mixture of specified antimicrobial peptides and/or bacteriocins.

115. The microfluidic device of any one of options 87-104, further comprising an antibiotic comprising a chemical antibiotic and/or a phage.

116. The microfluidic device of any one of options 87-104, wherein the in vitro transcription/translation solution is lyophyilized.

117. The system of any one of options 105-107 further comprising a reservoir of chemical or phage antibiotics configured to mix with the mixture of specified antimicrobial peptides and/or bacteriocins.

118. The system of any one of options 105-107 further comprising an antibiotic comprising a chemical antibiotic and/or a phage.

119. The system of option 107 wherein the in vitro transcription/translation solution is lyophyilized.

120. The method of any one of options 67-86 and 110-113, wherein the method is for making a specified mixture of antimicrobial peptides that does not comprise bacteriocins.

121. The method of any one of options 67-86 and 110-113, wherein the method is for making a specified mixture of bacteriocins that does not comprise antimicrobial peptides.

122. The method of any one of options 67-86 and 110-113, wherein the method is for making a specified mixture of bacteriocins and antimicrobial peptides.

123. The microfluidic device of any one of options 87-104, 108, 109, and 114-116, wherein the device is for producing a specified mixture of bacteriocins that does not comprise antimicrobial peptides.

124. The microfluidic device of any one of options 87-104, 108, 109, and 114-116, wherein the device is for producing a specified mixture of antimicrobial peptides that does not comprise bacteriocins.

125. The microfluidic device of any one of options 87-104, 108, 109, and 114-116, wherein the device is for producing a specified mixture of antimicrobial peptides and bacteriocins.

126. The system of any one of options 105-107 and 117-119, wherein the system is for producing a specified mixture of bacteriocins that does not comprise antimicrobial peptides.

127. The system of any one of options 105-107 and 117-119, wherein the system is for producing a specified mixture of antimicrobial peptides that does not comprise bacteriocins.

128. The system of any one of options 105-107 and 117-119, wherein the system is for producing a specified mixture of antimicrobial peptides and bacteriocins.

In at least some of the embodiments described herein, one or more elements used in an embodiment can interchangeably be used in another embodiment unless such a replacement is not technically feasible. It will be appreciated by those skilled in the art that various other omissions, additions and modifications may be made to the methods and structures described herein without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one of skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed herein. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those of skill in the art. The various aspects and embodiments disclosed herein are for purposes of illustration and are not intended to be limiting, with the true scope and spirit being indicated by the following claims.

What is claimed is:

1. A method for producing a specified mixture of antimicrobial peptides and/or bacteriocins, the method comprising:
in a microfluidic device comprising two or more discrete coding substrates each encoding a different antimicrobial peptide and/or bacteriocin, placing the discrete coding substrates in fluid communication with an in vitro transcription/translation solution;
incubating the discrete coding substrates placed in fluid communication with the in vitro transcription/translation solution, thereby generating antimicrobial peptides and/or bacteriocins encoded by the incubated discrete coding substrates at a stoichiometry defined by a user; and
mixing the generated antimicrobial peptides and/or bacteriocins in the microfluidic device, thereby producing the specified mixture of antimicrobial peptides and/or bacteriocins,
wherein the discrete coding substrates are comprised within separate chambers.

2. The method of claim 1, further comprising:
producing two or more submixtures each comprising a subset of the specified mixture of antimicrobial peptides and/or bacteriocins, wherein at least one of the two or more submixtures comprises two or more different antimicrobial peptides and/or bacteriocins of the specified mixture; and
combining the submixtures to produce the specified mixture of antimicrobial peptides and/or bacteriocins.

3. The method of claim 2, wherein combining the submixtures results in the stoichiometry of the two or more different antimicrobial peptides and/or bacteriocins defined by the user.

4. The method of claim 1, wherein the microfluidic device comprises one or more other discrete coding substrates each encoding an antimicrobial peptide and/or bacteriocin that is not of the specified mixture, and wherein the discrete coding substrates encoding antimicrobial peptides and/or bacteriocins of the specified mixture, but not the one or more other discrete coding substrates, are placed in fluidic communication with the in vitro transcription/translation solution.

5. The method of claim 1, further comprising screening the mixture of antimicrobial peptides and/or bacteriocins in situ for a desired effect.

6. The method of claim 5, wherein the screening is for inhibition of the growth or reproduction of a pathogenic microbial organism in a microbiome of a subject, or for enhancement of growth or reproduction of a non-pathogenic microbial organism in the microbiome of the subject, or for an absence of deleterious effects of the mixture of antimicrobial peptides and/or bacteriocins on the microbiome of the subject.

7. The method of claim 6, wherein one or more of the discrete coding substrates of the microfluidic device encodes an auxiliary protein that attracts the non-pathogenic microbial organism, or that enhances growth or reproduction of the non-pathogenic microbial organism in the microbiome of a subject.

8. The method of claim 5, wherein said screening is performed in real time.

9. The method of claim 5, the screening is for stabilization of antimicrobial peptide and/or bacteriocin, or for destruction of a microbial biofilm.

10. The method of claim 9, wherein one or more of the discrete coding substrates of the microfluidic device encodes an auxiliary protein with anti-protease activity.

11. The method of claim 1, further comprising delivering the specified mixture of antimicrobial peptides and/or bacteriocins to a wound via a tubing or membrane, thereby cleaning or dressing the wound.

12. The method of claim 1, wherein the microfluidic device comprises one or more discrete coding substrates that encodes one or more antimicrobial peptide or bacteriocin that is not of the specified mixture.

13. The method of claim 1, wherein the method comprises placing a subset of the discrete coding substrates of the microfluidic device in fluid communication with the in vitro transcription/translation solution.

14. The method of claim 1, wherein at least one of the two or more discrete coding substrates that encode the antimicrobial peptides and/or bacteriocins of the specified mixture comprises an isolated nucleic acid comprising:
a bacteriocin coding sequence and a second polypeptide coding sequence in a single reading frame, wherein the second polypeptide is a bacteriocin or a signal molecule; and
cleavage site coding sequences disposed between the coding sequences and in the single reading frame,
wherein the method comprises incubating the discrete coding substrates with the in vitro transcription/translation solution, thereby generating a pro-polypeptide comprising the bacteriocin, second polypeptide, and one or more cleavage sites disposed therebetween.

15. The method of claim 14, further comprising cleaving the one or more cleavage sites, thereby separating the bacteriocin and second polypeptide from each other, and thereby producing a composition comprising the bacteriocin and the second polypeptide.

16. The method of claim 15, wherein the discrete coding substrates that encode the antimicrobial peptides and/or bacteriocins of the specified mixture comprise or encode a cleavage enzyme that cleaves at least one of the one or more cleavage sites.

* * * * *